US012529104B2

(12) United States Patent
Suzuki et al.

(10) Patent No.: US 12,529,104 B2
(45) Date of Patent: Jan. 20, 2026

(54) KIT OR DEVICE AND METHOD FOR DETECTING DEMENTIA

(71) Applicants: TORAY INDUSTRIES, INC., Tokyo (JP); NATIONAL CENTER FOR GERIATRICS AND GERONTOLOGY, Obu (JP)

(72) Inventors: Kana Suzuki, Kamakura (JP); Makiko Yoshimoto, Kamakura (JP); Junpei Kawauchi, Kamakura (JP); Hiroko Sudo, Kamakura (JP); Yuho Kida, Kamakura (JP); Satoko Kozono, Kamakura (JP); Satoshi Kondou, Kamakura (JP); Shumpei Niida, Obu (JP); Yuya Asanomi, Obu (JP); Daichi Shigemizu, Obu (JP); Takashi Sakurai, Obu (JP)

(73) Assignees: TORAY INDUSTRIES, INC., Tokyo (JP); NATIONAL CENTER FOR GERIATRICS AND GERONTOLOGY, Obu (JP)

( * ) Notice: Subject to any disclaimer, the term of this patent is extended or adjusted under 35 U.S.C. 154(b) by 1429 days.

(21) Appl. No.: 16/969,328

(22) PCT Filed: Feb. 12, 2019

(86) PCT No.: PCT/JP2019/004832
§ 371 (c)(1),
(2) Date: Aug. 12, 2020

(87) PCT Pub. No.: WO2019/159884
PCT Pub. Date: Aug. 22, 2019

(65) Prior Publication Data

US 2021/0047691 A1 Feb. 18, 2021

(30) Foreign Application Priority Data

Feb. 13, 2018 (JP) ................................ 2018-023283
Apr. 26, 2018 (JP) ................................ 2018-085652
Jul. 24, 2018 (JP) ................................ 2018-138487

(51) Int. Cl.
*C12Q 1/6813* (2018.01)
*C12Q 1/6883* (2018.01)
*G16B 20/20* (2019.01)

(52) U.S. Cl.
CPC ......... *C12Q 1/6883* (2013.01); *C12Q 1/6813* (2013.01); *G16B 20/20* (2019.02); *C12Q 2600/158* (2013.01)

(58) Field of Classification Search
None
See application file for complete search history.

(56) References Cited

U.S. PATENT DOCUMENTS

2013/0184331 A1 7/2013 Roh et al.
2014/0120545 A1 5/2014 Umansky et al.
2014/0206777 A1 7/2014 Goren
2014/0363469 A1* 12/2014 Meyers ................ A61K 39/245 435/236
2014/0378439 A1 12/2014 Dezso et al.
2017/0002348 A1 1/2017 Crary et al.
2017/0130274 A1 5/2017 Kozono et al.
2017/0130275 A1 5/2017 Kondou et al.
2019/0136320 A1* 5/2019 Wojda .................. C12Q 1/6883
2023/0212675 A1 7/2023 Kashimura et al.

FOREIGN PATENT DOCUMENTS

JP 2014-520529 A 8/2014
JP 2015-223165 A 12/2015
JP 2017-184642 A 10/2017
KR 10-2018-0044220 A 5/2018
WO WO 2017/059094 A2 4/2017
WO WO 2017/084770 A1 5/2017
WO WO-2017146653 A1 * 8/2017 ........... C12Q 1/6816
WO WO 2019/048500 A1 3/2019
WO WO 2020/113271 A1 6/2020
WO WO 2021/201092 A1 10/2021

OTHER PUBLICATIONS

Japanese Office Action for Japanese Application No. 2020-500479, dated Jan. 24, 2023.
Sørensen et al., "miRNA Expression Profiles in Cerebrospinal Fluid and Blood of Patients with Alzheimer's Disease and Other Types of Dementia—an Exploratory Study", Translational Neurodegeneration, vol. 5, No. 6, 2016, pp. 1-12.
Partial Supplementary European Search Report for European Application No. 19754972.8, dated Sep. 28, 2021.
Chinese Office Action and Search Report for Chinese Application No. 201980013178.0, dated Jan. 10, 2023.
Jurjević et al., "Decreased Expression of hsa-miR-4274 in Cerebrospinal Fluid of Normal Pressure Hydrocephalus Mimics with Parkinsonian Syndromes." Journal of Alzheimer's Disease, vol. 56, 2017, pp. 317-325.
International Search Report, issued in PCT/JP2019/004832, PCT/ISA/210, dated May 14, 2019.
Kapasi et al., "Impact of Multiple Pathologies on the Threshold for Clinically Overt Dementia", Acta Neuropathol, Aug. 2017, vol. 134, No. 2, pp. 171-186.

(Continued)

*Primary Examiner* — Christopher M Gross
(74) *Attorney, Agent, or Firm* — Birch, Stewart, Kolasch & Birch, LLP

(57) ABSTRACT

An embodiment according to the present invention provides a kit or device for detection of dementia, and a method for detecting dementia. An embodiment according to the present invention relates to: a kit or device for detection of dementia, including a nucleic acid(s) capable of specifically binding to an miRNA(s) or a complementary strand(s) thereof in a sample from a subject; and a method for detecting dementia, including measuring the miRNA(s) in vitro.

5 Claims, 18 Drawing Sheets

Specification includes a Sequence Listing.

(56) References Cited

OTHER PUBLICATIONS

Nagaraj et al., "Profile of 6 microRNA in blood plasma distinguish early stage Alzheimer's disease patients from non-demented subjects", Oncotarget, 2017, vol. 8, No. 10, pp. 16122-16143.

Written Opinion of the International Searching Authority, issued in PCT/JP2019/004832, PCT/ISA/237, dated May 14, 2019.

Extended European Search Report for European Application No. 24217565.1, dated Feb. 28, 2025.

* cited by examiner

A

B

A

B

KIT OR DEVICE AND METHOD FOR DETECTING DEMENTIA

TECHNICAL FIELD

The present invention relates to a kit or device for detection of dementia, comprising a nucleic acid capable of specifically binding to a specific miRNA or a complementary strand thereof, which is used for examining the presence or absence of dementia in a subject, and a method for detecting dementia, comprising measuring the expression level of the miRNA.

BACKGROUND ART

In future estimation of the number of dementia patients and the prevalence in the elderly aged 65 or over, the number of dementia patients in Japan is estimated to reach about 7 million in 2025 (corresponding to ⅕ of the elderly aged 65 or over) while the number was 4.62 million in 2012 (corresponding to ⅐ of the elderly aged 65 or over (a prevalence of 15.0%)) (the 2016 White Paper on Aged Society by Cabinet Office). Meanwhile, it was reported that the cost for medical and nursing care of dementia patients reached 14.5 trillion yen in 2014 (including: medical expenses of 1.9 trillion yen (inpatient expenses of about 970.3 billion yen and outpatient expenses of about 941.2 billion yen), nursing expenses of 6.4 trillion yen (at-home care expenses of about 3.5281 trillion yen and at-facility care expenses of 2.9160 trillion yen), and informal care costs of 6.2 trillion yen) ("Estimation of Social Cost for Dementia" by the research team of the Ministry of Health, Labor and Welfare in May, 2015). The number of dementia patients worldwide will have increased to 74.7 million by 2030 and medical costs for dementia are estimated to reach 240 trillion yen (ADI "World Alzheimer's Report 2015"). Dementia, in general, is a progressive disease and is accompanied by irreversible degeneration of brain neurons. Because no therapeutic drug for dementia is available today, it is critical to test/diagnose dementia and implement an early medical intervention for suppressing progress dementia so as to reduce burden on patients/caregivers and social costs.

Currently, dementia is diagnosed by differential diagnosis including medical history, present symptoms, physical finding, a neuropsychological test, a blood test, imaging test, and the like.

As a method for testing dementia by a neuropsychological test, most internationally widely used is Folstein's "Mini-Mental State Examination" (MMSE). This screening test is most recommended from the viewpoint of sensitivity, specificity, convenience, and past data accumulation. MMSE can simply assess, while the total score is 30, multiple cognitive functions such as orientation, retention, attention/calculation, language function, verbal command response, and figure copying. Generally speaking, when the score is 23 or less, it is determined to be suspected of dementia. However, a high score is sometimes exhibited, depending on education history and/or carrier history, even in a case of dementia. Such an interview method is thus just used for screening and does not give a definite diagnosis.

As a method for testing dementia by imaging, development of diagnostic imaging such as CT, Mill, or PET/SPECT has been in progress. Unfortunately, diagnostic imaging requires special equipment and can thus be implemented by limited medical institutions. In addition, in current diagnostic imaging technology, it is difficult to grasp a difference between a pre-dementia stage and a state in which cognitive functions are normal, etc. Accordingly, different image-reading doctors may give different diagnoses. Thus, there is a disadvantage such as lack of objectivity.

A blood test recommended in the Disease Guideline for Dementia Diagnosis is necessary for exclusion diagnosis of internal diseases, in which dementia and dementia-like symptoms are manifested, during diagnosis of degenerative dementia such as Alzheimer's dementia. However, there is no currently available blood test item that can identify dementia.

The low concentration level of amyloid protein and the high concentration level of tau in cerebrospinal fluid (CSF) are being utilized as surrogate markers for Alzheimer's dementia. However, the test is highly invasive to patients.

Recently, markers have been developed that can diagnose dementia such as Alzheimer's dementia or neurodegenerative disease.

For instance, a report (Non-Patent Literature 1) shows that use of 6 miRNAs (miR-483-5p, miR-486-5p, miR-30b-5p, miR-200a-3p, miR-502-3p, miR-142-3p) included in plasma enables diagnosis of early Alzheimer's included in mild cognitive impairment (MCI), which is a pre-dementia stage. In addition, a report (Patent Literature 1) shows that after subjects with mild dementia were enrolled, they were given a supplement for alleviating dementia symptoms, and expressions of miRNAs in serum before and after the intake were compared to search for dementia markers. 21 markers (hsa-miR-486-5p, hsa-miR-21-5p, hsa-miR-92a-3p, hsa-miR-451a, hsa-let-7b-5p, hsa-miR-126-3p, hsa-miR-25-3p, hsa-miR-10b-5p, hsa-miR-30e-5p, hsa-miR-140-3p, hsa-miR-101-3p, hsa-miR-222-3p, hsa-miR-10a-5p, hsa-miR-221-3p, hsa-miR-375, hsa-miR-30a-5p, hsa-miR-584-5p, hsa-miR-27b-3p, hsa-miR-484, hsa-miR-125a-5p, hsa-miR-93-5p) were extracted.

miR-206 was identified during search of miRNA targets specific to prevention and treatment of neurodegenerative disease, in particular, Alzheimer's disease (Patent Literature 2). Patent Literature 2 reports that this antisense strand caused an increase in the levels of nerve growth factor BDNF and IGF-1 and synapses were found to regenerate in Alzheimer's disease model mice; and this marker was also applicable to diagnosis.

A report (Patent Literature 3) shows that it was found in a try at diagnosis of Alzheimer's disease that Alzheimer's disease could be diagnosed by measuring the expression levels of 67 kinds of miRNAs (e.g., hsa-miR-1296, hsa-miR-424*, hsa-miR-424, hsa-miR-629) in a sample.

A report (Patent Literature 4) shows that measurement of miRNAs (e.g., miR-7, miR-25, miR-26a) in a nerve tissue and/or synapses in body fluid allows for diagnosis and/or treatment monitoring of mild dementia and Alzheimer's disease.

The invention described in Patent Literature 5 aims to treat and prevent Alzheimer's disease and/or neurofibrillary degeneration due to abnormal tau expression. It reports that after search for miRNAs that bind to 3' UTR of tau mRNA and regulate expression of tau the resulting markers (e.g., miR-185-5p, miR-151-5p) for therapeutic purposes were applicable to diagnosis.

A report (Patent Literature 6) shows that vesicles derived from micro-glial cells present in body fluid were isolated and the expression of miRNAs encapsulated therein were analyzed. 36 miRNAs were identified in order to conduct diagnosis, prediction, or treatment monitoring of neurodegenerative disease or the like.

The invention described in Patent Literature 7 ailed to develop a microfluidic device for detecting a microRNA after hybridization. It reports that cancer-, inflammatory disease-, or dementia-related microRNAs in body fluid including blood, serum, and plasma have been detected, as an example of detection, Meanwhile, it has been increasingly evident that dementia is sometimes complicated by many disease types. For instance, in a report where the doctors' diagnosis results had been compared to the corresponding pathological diagnosis results, just 14 (3.13%) of 447 patients diagnosed as Alzheimer's dementia by the doctors had Alzheimer's dementia alone after the pathological diagnosis. 366 patients (81.88%) who had Alzheimer's dementia complicated by vascular dementia and/or Lewy body dementia were also included. In addition, 67 (14.98%) of 477 patients diagnosed as Alzheimer's dementia by the doctors had pathologically neither Alzheimer's dementia nor Alzheimer's dementia complicated by non-Alzheimer's dementia, but had dementia different from Alzheimer's dementia, such as vascular dementia, Lewy body dementia, hippocampal atrophy, and so on (Non-Patent Literature 2).

CITATION LIST

Patent Literature

Patent Literature 1: JP Patent Publication (Kokai) No. 2017-184642
Patent Literature 2: U.S. Patent Application Publication No. 2013/0184331
Patent Literature 3: U.S. Patent Application Publication No. 2014/0206777
Patent Literature 4: U.S. Patent Application Publication No. 2014/0120545
Patent Literature 5: U.S. Patent Application Publication No. 2017/0002348
Patent Literature 6: International Publication No. WO 2017/084770
Patent Literature 7: International Publication No. WO 2017/059094

Non-Patent Literature

Non-Patent Literature 1: Siranjeevi N. et al., Oncotarget, 2017 Feb. 5, vol. 8, No. 10, p. 16122-16143
Non-Patent Literature 2: Alifiya Kapasi et al., Acta Neuropathol, 2017, vol. 134, p. 171-186

SUMMARY OF INVENTION

Problem to be Solved by Invention

Because dementia, in general, is a progressive disease and is accompanied by irreversible degeneration of brain neurons as mentioned above, it is essential to find dementia without misidentification and implement a medical intervention to suppress the progress. To prescribe a progress inhibitor or implement a medical intervention such as "Cognicize" for suppressing the progress, a diagnosis method has been desired that can objectively detect, without misidentification, different disease types of dementia regardless of dementia types.

However, it is uneasy to diagnose dementia as stated above, because used is a subjective diagnosis method in which a difference in diagnosis is large among doctors. In addition, while majority of dementia is a complication type, when only one of dementia types is diagnosed, the other complicated dementia types are neglected, leading to a possibility of loss of treatment opportunities. Thus, markers have been sought that can objectively and comprehensively diagnose each dementia type. However, the markers described in the above Non-Patent Literature 1 and Patent Literatures 1 to 7 cannot be said to exert enough performance as markers for diagnosing dementia as described below.

In Non-Patent Literature 1, only Alzheimer's dementia and early Alzheimer's dementia included in mild dementia (MCI) have been validated. Thus, it is unclear whether any dementia disease type other than Alzheimer's dementia can be detected.

In Patent Literature 1, just MCI, which is a pre-dementia stage, has been validated, and it is unclear whether or not dementia can be detected.

In Patent Literature 2, just Alzheimer's model mice and human brain samples have been examined, and blood samples, which can be collected in a low-invasive manner, have not been examined.

In Patent Literature 3, only Alzheimer's dementia is a target, and it is unclear whether any dementia disease type other than Alzheimer's dementia can be detected.

In Patent Literature 4, it was demonstrated discrimination between MCI and healthy subjects and between MCI and Alzheimer's dementia. However, it was not demonstrated discrimination between healthy subjects and Alzheimer's dementia.

In Patent Literature 5, just brain tissues have been used for validation in Examples, and it is unclear whether or not even blood samples can be likewise used for detection.

In Patent Literature 6, whether or not markers are expressed in micro-glial cells in model mice was examined. However, it is unclear whether or not the markers can be detected using human blood samples.

Patent Literature 7 relates to a diagnostic device using microRNAs in body fluid, and dementia is exemplified together with cancers and inflammatory diseases. Detection of microRNAs by using samples including blood, serum, and plasma is described. However, it is unclear whether or not the markers can be detected using human blood samples because there is no description of Examples.

Collectively, in the past reports regarding dementia markers, samples for just one type of dementia disease were used for validation. Thus, when these markers are used for diagnosis, treatment opportunities may be lost because patients with any other dementia disease type are not found. In addition, in these reports, model mice and/or human brain samples were used for assessment, and validation using human blood was not conducted. As a result, they may be unsuitable for use in diagnosis of dementia.

Further, collection of cerebrospinal fluid as a sample for measurement is not preferable because invasiveness to patients is high. Accordingly, comprehensive dementia markers are desired that allow for detection using blood samples, which can be collected in a low-invasive manner, and can accurately discriminate the presence or absence of dementia. If dementia, in particular, can be found without misidentification, it should be possible to suppress progress of dementia by a medical intervention.

The object of the present invention is to provide a dementia marker that makes it possible to discriminate between dementia and normal cognitive functions (non-dementia) and to diagnose one or more dementia disease types, and to provide a method that makes it possible to objectively and effectively detect the presence or absence of dementia by using a nucleic acid capable of specifically binding to the marker. Specifically, the object is to provide a test method satisfying one or more and preferably all of the 4 points including: 1. there is no difference among medical institutions and among doctors; 2. different dementia types can be comprehensively detected; 3. the detection sensitivity and the specificity for dementia are high; and 4. invasiveness is low.

Means for Solution to Problem

The present inventors have conducted diligent studies to attain the object and completed the present invention by finding novel dementia markers that can be used to detect one or more disease types of dementia selected from Alzheimer's dementia, vascular dementia, Lewy body dementia, normal pressure hydrocephalus, frontotemporal lobar degeneration, or the like.

SUMMARY OF INVENTION

Specifically, the present invention includes the following aspects.

(1) A kit for detection of dementia, comprising nucleic acid(s) capable of specifically binding to one or more polynucleotide(s) selected from the group consisting of dementia markers: miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086, or to complementary strand(s) of the polynucleotide(s).

(2) The kit according to (1), wherein the nucleic acid(s) are polynucleotide(s) selected from the group consisting of the following polynucleotides (a) to (e):

(a) a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 210, 374, 1315 to 1350, and 1435 to 1448, (c) a polynucleotide consisting of a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, and (e) a polynucleotide hybridizing under stringent conditions to any of the polynucleotides (a) to (d).

(3) The kit according to (1) or (2), wherein the kit further comprises nucleic acid(s) capable of specifically binding to one or more polynucleotide(s) selected from the group consisting of other dementia markers: miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-150-3p, miR-423-5p, miR-575, miR-671-5p, miR-939-5p, miR-3665, miR-30d-5p, miR-30b-3p, miR-92a-3p, miR-371b-5p, and miR-486-5p, or to complementary strand(s) of the polynucleotide(s).

(4) The kit according to (3), wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 249, 1351 to 1356, and 1449 to 1453, (h) a polynucleotide consisting of a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, and (j) a polynucleotide hybridizing under stringent conditions to any of the polynucleotides (f) to (i).

(5) The kit according to any one of (1) to (4), wherein the kit further comprises nucleic acid(s) capable of specifically binding to one or more polynucleotide(s) selected from the group consisting of other dementia markers: miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, and miR-6878-3p, or to complementary strand(s) of the polynucleotide(s).

(6) The kit according to (5), wherein the nucleic acid(s) are polynucleotide(s) selected from the group consisting of the following polynucleotides (k) to (o):

(k) a polynucleotide consisting of a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 250 to 373, (m) a polynucleotide consisting of a nucleotide sequence complementary to a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 250 to 373 or a nucleotide sequence derived from the nucleotide sequence by the replacement of u with t, and (o) a polynucleotide hybridizing under stringent conditions to any of the polynucleotides (k) to (n).

(7) The kit according to any one of (1) to (6), wherein the kit further comprises nucleic acid(s) capable of specifically binding to one or more polynucleotide(s) selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p, or to complementary strand(s) of the polynucleotide(s).

(8) The kit according to (7), wherein the nucleic acid(s) are polynucleotide(s) selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(9) A kit for detection or prediction of dementia, comprising nucleic acid(s) I capable of specifically binding to one or more polynucleotide(s) selected from the group consisting of dementia markers: miR-4728-5p, miR-3184-3p, miR-1233-3p, miR-6088, miR-6777-3p, miR-7110-3p, miR-936, miR-6087, miR-1202, miR-4731-3p, miR-4800-5p, miR-6784-3p, miR-4716-5p, miR-6734-3p, miR-6889-3p, miR-6867-3p, miR-3622a-3p, miR-6813-3p, miR-4769-3p, miR-5698, miR-3184-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, and miR-371a-5p, or to complementary strand(s) of the polynucleotide(s), and optionally further comprising nucleic acid(s) II capable of specifically binding to one or more polynucleotide(s) selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p, or to complementary strand(s) of the polynucleotide(s).

(10) The kit according to (9), wherein the nucleic acid(s) I are polynucleotide(s) selected from the group consisting of the following polynucleotides (u) to (y):

(u) a polynucleotide consisting of a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (v) a polynucleotide comprising a nucleotide sequence represented by any of SEQ ID NOs: 3, 8, 15, 26, 34, 40, 53, 69, 99, 101, 107, 109, 112, 125, 128, 133, 191 to 194, 212, and 250 to 374, (w) a polynucleotide consisting of a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (x) a polynucleotide comprising a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, and (y) a polynucleotide hybridizing under stringent conditions to any of the polynucleotides (u) to (x), wherein the nucleic acid(s) II are polynucleotides selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(11) A device for detection of dementia, comprising nucleic acid(s) capable of specifically binding to one or more polynucleotide(s) selected from the group consisting of dementia markers: miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR- 4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086, or to complementary strand(s) of the polynucleotide(s).

(12) The device according to (11), wherein the nucleic acid(s) are polynucleotide(s) selected from the group consisting of the following polynucleotides (a) to (e):

(a) a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 210, 374, 1315 to 1350, and 1435 to 1448, (c) a polynucleotide consisting of a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, and (e) a polynucleotide hybridizing under stringent conditions to any of the polynucleotides (a) to (d).

(13) The device according to (11) or (12), wherein the device further comprises nucleic acid(s) capable of specifically binding to one or more polynucleotide(s) selected from the group consisting of other dementia markers: miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-150-3p, miR-423-5p, miR-575, miR-671-5p, miR-939-5p, miR-3665, miR-30d-5p, miR-30b-3p, miR-92a-3p, miR-371b-5p, and miR-486-5p, or to complementary strand(s) of the polynucleotide(s).

(14) The device according to (13), wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 249, 1351 to 1356, and 1449 to 1453, (h) a polynucleotide consisting of a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, and (j) a polynucleotide hybridizing under stringent conditions to any of the polynucleotides (f) to (i).

(15) The device according to any one of (11) to (14), wherein the device further comprises nucleic acid(s) capable of specifically binding to one or more polynucleotide(s) selected from the group consisting of other dementia markers: miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, and miR-6878-3p, or to complementary strand(s) of the polynucleotide(s).

(16) The device according to (15), wherein the nucleic acid(s) are polynucleotide(s) selected from the group consisting of the following polynucleotides (k) to (o):

(k) a polynucleotide consisting of a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 250 to 373, (m) a polynucleotide consisting of a nucleotide sequence complementary to a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 250 to 373 or a nucleotide sequence derived from the nucleotide sequence by the replacement of u with t, and (o) a polynucleotide hybridizing under stringent conditions to any of the polynucleotides (k) to (n).

(17) The device according to any one of (11) to (16), wherein the device further comprises nucleic acid(s) capable of specifically binding to one or more polynucleotide(s) selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p, or to complementary strand(s) of the polynucleotide(s).

(18) The device according to (17), wherein the nucleic acid(s) are polynucleotide(s) selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(19) A device for detection or prediction of dementia, comprising nucleic acid(s) I capable of specifically binding to one or more polynucleotide(s) selected from the group consisting of dementia markers: miR-4728-5p, miR-3184-3p, miR-1233-3p, miR-6088, miR-6777-3p, miR-7110-3p, miR-936, miR-6087, miR-1202, miR-4731-3p, miR-4800-5p, miR-6784-3p, miR-4716-5p, miR-6734-3p, miR-6889-3p, miR-6867-3p, miR-3622a-3p, miR-6813-3p, miR-4769-3p, miR-5698, miR-3184-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, and miR-371a-5p, or to complementary strand(s) of the polynucleotide(s), and optionally further comprising nucleic acid(s) II capable of specifically binding to one or more polynucleotide(s) selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-

5p, miR-4298, miR-4290, miR-3943, miR-346, and miR-767-3p, or to complementary strand(s) of the polynucleotide(s).

(20) The device according to (19), wherein the nucleic acid(s) I are polynucleotide(s) selected from the group consisting of the following polynucleotides (u) to (y):

(u) a polynucleotide consisting of a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (v) a polynucleotide comprising a nucleotide sequence represented by any of SEQ ID NOs: 3, 8, 15, 26, 34, 40, 53, 69, 99, 101, 107, 109, 112, 125, 128, 133, 191 to 194, 212, and 250 to 374, (w) a polynucleotide consisting of a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (x) a polynucleotide comprising a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, and (y) a polynucleotide hybridizing under stringent conditions to any of the polynucleotides (u) to (x), wherein the nucleic acid(s) II are polynucleotide(s) selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(21) The device according to any one of (11) to (20), wherein the device is a device for measurement by a hybridization technique.

(22) The device according to (21), wherein the hybridization technique is a nucleic acid array technique.

(23) A method for detecting dementia, comprising measuring expression level(s) of one or more polynucleotide(s) selected from the group consisting of dementia markers: miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086 in a sample from a subject; and evaluating in vitro whether or not the subject has dementia using the measured expression level(s).

(24) The method according to (23), comprising plugging the gene expression level(s) of the one or more polynucleotide(s) in the sample from the subject into a discriminant formula capable of discriminating dementia or non-dementia distinctively, wherein the discriminant formula is created by using gene expression levels in samples from subjects known to have dementia and gene expression levels in samples from non-dementia subjects as training samples; and thereby evaluating whether or not the subject has dementia.

(25) The method according to (23) or (24), wherein the expression level(s) of the polynucleotide(s) are measured by using nucleic acid(s) capable of specifically binding to the polynucleotide(s) or to complementary strand(s) of the polynucleotide(s), and wherein the nucleic acid(s) are polynucleotide(s) selected from the group consisting of the following polynucleotides (a) to (e):

(a) a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 210, 374, 1315 to 1350, and 1435 to 1448, (c) a polynucleotide consisting of a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, and (e) a polynucleotide hybridizing under stringent conditions to any of the polynucleotides (a) to (d).

(26) The method according to any one of (23) to (25), further comprising measuring expression level(s) of one or more polynucleotide(s) selected from the group consisting of other dementia markers: miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-150-3p, miR-423-5p, miR-575, miR-671-5p, miR-939-5p, miR-3665, miR-30d-5p, miR-30b-3p, miR-92a-3p, miR-371b-5p, and miR-486-5p.

(27) The method according to (26), wherein the expression level(s) of the polynucleotide(s) are measured by using nucleic acid(s) capable of specifically binding to the polynucleotide(s) or to complementary strand(s) of the polynucleotide(s), and wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 249, 1351 to 1356, and 1449 to 1453, (h) a polynucleotide consisting of a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, and (j) a polynucleotide hybridizing under stringent conditions to any of the polynucleotides (f) to (i).

(28) The method according to any one of (23) to (27), further comprising measuring expression level(s) of one or more polynucleotide(s) selected from the group consisting of other dementia markers: miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, and miR-6878-3p.

(29) The method according to (28), wherein the expression level(s) of the polynucleotide(s) are measured by using nucleic acid(s) capable of specifically binding to the polynucleotide(s) or to complementary strand(s) of the polynucleotide(s), and wherein the nucleic acid(s) are polynucleotide(s) selected from the group consisting of the following polynucleotides (k) to (o):

(k) a polynucleotide consisting of a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 250 to 373, (m) a polynucleotide consisting of a nucleotide sequence complementary to a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 250 to 373 or a nucleotide sequence derived from the nucleotide sequence by the replacement of u with t, and (o) a polynucleotide hybridizing under stringent conditions to any of the polynucleotides (k) to (n).

(30) The method according to any one of (23) to (29), further comprising measuring expression level(s) of one or more polynucleotide(s) selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p.

(31) The method according to (30), wherein the expression level(s) of the polynucleotide(s) are measured by using nucleic acid(s) capable of specifically binding to the polynucleotide(s) or to the complementary strand(s) of the polynucleotide(s), and wherein the nucleic acid (s) are polynucleotide(s) selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(32) A method for detecting or predicting dementia, comprising:

measuring expression level(s) of one or more polynucleotide(s) I selected from the group consisting of dementia markers: miR-4728-5p, miR-3184-3p, miR-1233-3p, miR-6088, miR-6777-3p, miR-7110-3p, miR-936, miR-6087, miR-1202, miR-4731-3p, miR-4800-5p, miR-6784-3p, miR-4716-5p, miR-6734-3p, miR-6889-3p, miR-6867-3p, miR-3622a-3p, miR-6813-3p, miR-4769-3p, miR-5698, miR-3184-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, and miR-371a-5p, further optionally measuring expression level(s) of one or more polynucleotide(s) II selected from the group consisting of other dementia markers: miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p, and evaluating in vitro whether or not the subject has dementia or predicting in vitro the possibility for the subject to develop dementia using the measured expression level(s).

(33) The method according to (32), wherein the expression level(s) of the polynucleotide(s) I are measured by using nucleic acid(s) capable of specifically binding to the polynucleotide(s) I or to complementary strand(s) of the polynucleotide(s), wherein the nucleic acid(s) are polynucleotide(s) selected from the group consisting of the following polynucleotides (u) to (y):

(u) a polynucleotide consisting of a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (v) a polynucleotide comprising a nucleotide sequence represented by any of SEQ ID NOs: 3, 8, 15, 26, 34, 40, 53, 69, 99, 101, 107, 109, 112, 125, 128, 133, 191 to 194, 212, and 250 to 374, (w) a polynucleotide consisting of a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (x) a polynucleotide comprising a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, and (y) a polynucleotide hybridizing under stringent conditions to any of the polynucleotides (u) to (x), wherein the expression level(s) of the polynucleotide(s) II are measured by using nucleic acid(s) capable of specifically binding to the polynucleotide(s) II or to complementary strand(s) of the polynucleotide(s), wherein the nucleic acid(s) are polynucleotide(s) selected from the group consisting of the following polynucleotides (p) to (t):

(p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

(34) The method according to any one of (23) to (33), wherein the expression level(s) of the target gene(s) in the sample from the subject are measured by using the kit according to any one of (1) to (10) or the device according to any one of (11) to (22).

(35) The method according to any one of (23) to (34), wherein the subject is a human.

(36) The method according to any one of (23) to (35), wherein the sample is blood, serum, or plasma.

(1') A kit for detection of dementia, comprising nucleic acid(s) capable of specifically binding to one or more polynucleotide(s) selected from the group consisting of dementia markers: miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p.

(2') The kit according to (1'), wherein the nucleic acid(s) are polynucleotide(s) selected from the group consisting of the following polynucleotides (a) to (e):

(a) a polynucleotide consisting of a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 194 to 210, 374, and 1315 to 1350, (c) a polynucleotide consisting of a nucleotide sequence complementary to a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 194 to 210, 374, and 1315 to 1350 or a nucleotide sequence derived from the nucleotide sequence by the replacement of u with t, and (e) a polynucleotide hybridizing under stringent conditions to any of the polynucleotides (a) to (d).

(3') The kit according to (1') or (2'), wherein the kit further comprises nucleic acid(s) capable of specifically binding to one or more polynucleotide(s) selected from the group consisting of other dementia markers: miR-1225-3p, miR-3184-5p, miR-150-3p, miR-423-5p, miR-575, miR-671-5p, miR-939-5p, and miR-3665.

(4') The kit according to (3'), wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 212 and 1351 to 1356, (h) a polynucleotide consisting of a nucleotide sequence complementary to a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 212 and 1351 to 1356 or a nucleotide sequence derived from the nucleotide sequence by the replacement of u with t, and (j) a polynucleotide hybridizing under stringent conditions to any of the polynucleotides (f) to (i).

(5') A device for detection of dementia, comprising nucleic acid(s) capable of specifically binding to one or more polynucleotide(s) selected from the group consisting of dementia markers: miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p.

(6') The device according to (5'), wherein the nucleic acid(s) are polynucleotide(s) selected from the group consisting of the following polynucleotides (a) to (e):

(a) a polynucleotide consisting of a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 194 to 210, 374, and 1315 to 1350, (c) a polynucleotide consisting of a nucleotide sequence complementary to a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 194 to 210, 374, and 1315 to 1350 or a nucleotide sequence derived from the nucleotide sequence by the replacement of u with t, and (e) a polynucleotide hybridizing under stringent conditions to any of the polynucleotides (a) to (d).

(7') The device according to (5') or (6'), wherein the device further comprises nucleic acid(s) capable of specifically binding to one or more polynucleotide(s) selected from the group consisting of other dementia markers: miR-1225-3p, miR-3184-5p, miR-150-3p, miR-423-5p, miR-575, miR-671-5p, miR-939-5p, and miR-3665.

(8') The device according to (7'), wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 212 and 1351 to 1356, (h) a polynucleotide consisting of a nucleotide sequence complementary to a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 212 and 1351 to 1356 or a nucleotide sequence derived from the nucleotide sequence by the replacement of u with t, and (j) a polynucleotide hybridizing under stringent conditions to any of the polynucleotides (f) to (i).

(9') The device according to any one of (5') to (8'), wherein the device is a device for measurement by a hybridization technique.

(10') The device according to (9'), wherein the hybridization technique is a nucleic acid array technique.

(11') A method for detecting dementia, comprising measuring expression level(s) of target nucleic acid(s) by using the kit according to any one of (1') to (4') or the device according to any one of (5') to (10') including nucleic acid(s) capable of specifically binding to one or more polynucleotide(s) selected from the group consisting of dementia markers: miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p in a sample from a subject; and evaluating in vitro whether or not the subject has dementia using the measured expression level(s) and likewise measured control expression level(s) in a non-dementia sample.

(12') A method for detecting dementia in a subject, comprising measuring expression level(s) of target gene(s) by using the kit according to any one of (1') to (4') or the device according to any one of (5') to (10') including nucleic acid(s) capable of specifically binding to one or more polynucleotide(s) selected from the group consisting of dementia markers: miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p in a sample from the subject; plugging the expression level(s) of the target gene(s) in the sample from the subject into a discriminant formula capable of discriminating dementia or non-dementia distinctively, wherein the discriminant formula is created by using gene expression levels in samples from subjects known to have dementia and gene expression levels in samples from non-dementia subjects as training samples; and thereby evaluating whether or not the subject has dementia.

(13') The method according to (11') or (12'), wherein the nucleic acid(s) are polynucleotide(s) selected from the group consisting of the following polynucleotides (a) to (e):

(a) a polynucleotide consisting of a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 194 to 210, 374, and 1315 to 1350, (c) a polynucleotide consisting of a nucleotide sequence complementary to a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 194 to 210, 374, and 1315 to 1350 or a nucleotide sequence derived from the nucleotide sequence by the replacement of u with t, and (e) a polynucleotide hybridizing under stringent conditions to any of the polynucleotides (a) to (d).

(14') The method according to any one of (11') to (13'), wherein the kit or device further comprises nucleic acid(s) capable of specifically binding to one or more polynucleotide(s) selected from the group consisting of other dementia markers: miR-1225-3p, miR-3184-5p, miR-150-3p, miR-423-5p, miR-575, miR-671-5p, miR-939-5p, and miR-3665.

(15') The method according to (14'), wherein the nucleic acid(s) are polynucleotide(s) selected from the group consisting of the following polynucleotides (f) to (j):

(f) a polynucleotide consisting of a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 212 and 1351 to 1356, (h) a polynucleotide consisting of a nucleotide sequence complementary to a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 212 and 1351 to 1356 or a nucleotide sequence derived from the nucleotide sequence by the replacement of u with t, and (j) a polynucleotide hybridizing under stringent conditions to any of the polynucleotides (f) to (i).

(16') The method according to any one of (11') to (15'), wherein the subject is a human.

(17') The method according to any one of (11') to (16'), wherein the sample is blood, serum, or plasma.

In a preferable aspect of a kit or device for detection of dementia or a method for detecting dementia according to the present invention, a disease type of the dementia may be Alzheimer's dementia, vascular dementia, Lewy body dementia, normal pressure hydrocephalus, frontotemporal lobar degeneration, senile dementia for neurofibrillary tangle type, dementia resulting from diseases (e.g. infectious diseases), alcoholic dementia, vitamin deficiency dementia, or the like, mixed dementia of any of these types, or type-unknown or unspecified dementia.

In another preferable aspect of a kit or device for detection of dementia or a method for detecting dementia according to the present invention, dementia marker miR-4274 is hsa-miR-4274, miR-4272 is hsa-miR-4272, miR-4728-5p is hsa-miR-4728-5p, miR-4443 is hsa-miR-4443, miR-4506 is hsa-miR-4506, miR-6773-5p is hsa-miR-6773-5p, miR-4662a-5p is hsa-miR-4662a-5p, miR-3184-3p is hsa-miR-3184-3p, miR-4281 is hsa-miR-4281, miR-320d is hsa-miR-320d, miR-6729-3p is hsa-miR-6729-3p, miR-5192 is hsa-miR-5192, miR-6853-5p is hsa-miR-6853-5p, miR-1234-3p is hsa-miR-1234-3p, miR-1233-3p is hsa-miR-1233-3p, miR-4539 is hsa-miR-4539, miR-3914 is hsa-miR-3914, miR-4738-5p is hsa-miR-4738-5p, miR-548au-3p is hsa-miR-548au-3p, miR-1539 is hsa-miR-1539, miR-4720-3p is hsa-miR-4720-3p, miR-365b-5p is hsa-miR-365b-5p, miR-4486 is hsa-miR-4486, miR-1227-5p is hsa-miR-1227-5p, miR-4667-5p is hsa-miR-4667-5p, miR-6088 is hsa-miR-6088, miR-6820-5p is hsa-miR-6820-5p, miR-4505 is hsa-miR-4505, miR-548q is hsa-miR-548q, miR-4658 is hsa-miR-4658, miR-450a-5p is hsa-miR-450a-5p, miR-1260b is hsa-miR-1260b, miR-3677-5p is hsa-miR-3677-5p, miR-6777-3p is hsa-miR-6777-3p, miR-6826-3p is hsa-miR-6826-3p, miR-6832-3p is hsa-miR-6832-3p, miR-4725-3p is hsa-miR-4725-3p, miR-7161-3p is hsa-miR-7161-3p, miR-2277-5p is hsa-miR-2277-5p, miR-7110-3p is hsa-miR-7110-3p, miR-4312 is hsa-miR-4312, miR-4461 is hsa-miR-4461, miR-6766-5p is hsa-miR-6766-5p, miR-1266-3p is hsa-miR-1266-3p, miR-6729-5p is hsa-miR-6729-5p, miR-526b-3p is hsa-miR-526b-3p, miR-519e-5p is hsa-miR-519e-5p, miR-512-5p is hsa-miR-512-5p, miR-5088-5p is hsa-miR-5088-5p, miR-1909-3p is hsa-miR-1909-3p, miR-6511a-5p is hsa-miR-6511a-5p, miR-4734 is hsa-miR-4734, miR-936 is hsa-miR-936, miR-1249-3p is hsa-miR-1249-3p, miR-6777-5p is hsa-miR-6777-5p, miR-4487 is hsa-miR-4487, miR-3155a is hsa-miR-3155a, miR-563 is hsa-miR-563, miR-4741 is hsa-miR-4741, miR-6788-5p is hsa-miR-6788-5p, miR-4433b-5p is hsa-miR-4433b-5p, miR-323a-5p is hsa-miR-323a-5p, miR-6811-5p is hsa-miR-6811-5p, miR-6721-5p is hsa-miR-6721-5p, miR-5004-5p is hsa-miR-5004-5p, miR-6509-3p is hsa-miR-6509-3p, miR-648 is hsa-miR-648, miR-3917 is hsa-miR-3917, miR-6087 is hsa-miR-6087, miR-1470 is hsa-miR-1470, miR-586 is hsa-miR-586, miR-3150a-5p is hsa-miR-3150a-5p, miR-105-3p is hsa-miR-105-3p, miR-7973 is hsa-miR-7973, miR-1914-5p is hsa-miR-1914-5p, miR-4749-3p is hsa-miR-4749-3p, miR-15b-5p is hsa-miR-15b-5p, miR-1289 is hsa-miR-1289, miR-4433a-5p is hsa-miR-4433a-5p, miR-3666 is hsa-miR-3666, miR-3186-3p is hsa-miR-3186-3p, miR-4725-5p is hsa-miR-4725-5p, miR-4488 is hsa-miR-4488, miR-4474-3p is hsa-miR-4474-3p, miR-6731-3p is hsa-miR-6731-3p, miR-4640-3p is hsa-miR-4640-3p, miR-202-5p is hsa-miR-202-5p, miR-6816-5p is hsa-miR-6816-5p, miR-638 is hsa-miR-638, miR-6821-5p is hsa-miR- 6821-5p, miR-1247-3p is hsa-miR-1247-3p, miR-6765-5p is hsa-miR-6765-5p, miR-6800-5p is hsa-miR-6800-5p, miR-3928-3p is hsa-miR-3928-3p, miR-3940-5p is hsa-miR-3940-5p, miR-3960 is hsa-miR-3960, miR-6775-5p is hsa-miR-6775-5p, miR-3178 is hsa-miR-3178, miR-1202 is hsa-miR-1202, miR-6790-5p is hsa-miR-6790-5p, miR-4731-3p is hsa-miR-4731-3p, miR-2681-3p is hsa-miR-2681-3p, miR-6758-5p is hsa-miR-6758-5p, miR-8072 is hsa-miR-8072, miR-518d-3p is hsa-miR-518d-3p, miR-3606-3p is hsa-miR-3606-3p, miR-4800-5p is hsa-miR-4800-5p, miR-1292-3p is hsa-miR-1292-3p, miR-6784-3p is hsa-miR-6784-3p, miR-4450 is hsa-miR-4450, miR-6132 is hsa-miR-6132, miR-4716-5p is hsa-miR-4716-5p, miR-6860 is hsa-miR-6860, miR-1268b is hsa-miR-1268b, miR-378d is hsa-miR-378d, miR-4701-5p is hsa-miR-4701-5p, miR-4329 is hsa-miR-4329, miR-185-3p is hsa-miR-185-3p, miR-552-3p is hsa-miR-552-3p, miR-1273g-5p is hsa-miR-1273g-5p, miR-6769b-3p is hsa-miR-6769b-3p, miR-520a-3p is hsa-miR-520a-3p, miR-4524b-5p is hsa-miR-4524b-5p, miR-4291 is hsa-miR-4291, miR-6734-3p is hsa-miR-6734-3p, miR-143-5p is hsa-miR-143-5p, miR-939-3p is hsa-miR-939-3p, miR-6889-3p is hsa-miR-6889-3p, miR-6842-3p is hsa-miR-6842-3p, miR-4511 is hsa-miR-4511, miR-4318 is hsa-miR-4318, miR-4653-5p is hsa-miR-4653-5p, miR-6867-3p is hsa-miR-6867-3p, miR-133b is hsa-miR-133b, miR-3196 is hsa-miR-3196, miR-193b-3p is hsa-miR-193b-3p, miR-3162-3p is hsa-miR-3162-3p, miR-6819-3p is hsa-miR-6819-3p, miR-1908-3p is hsa-miR-1908-3p, miR-6786-5p is hsa-miR-6786-5p, miR-3648 is hsa-miR-3648, miR-4513 is hsa-miR-4513, miR-3652 is hsa-miR-3652, miR-4640-5p is hsa-miR-4640-5p, miR-6871-5p is hsa-miR-6871-5p, miR-7845-5p is hsa-miR-7845-5p, miR-3138 is hsa-miR-3138, miR-6884-5p is hsa-miR-6884-5p, miR-4653-3p is hsa-miR-4653-3p, miR-636 is hsa-miR-636, miR-4652-3p is hsa-miR-4652-3p, miR-6823-5p is hsa-miR-6823-5p, miR-4502 is hsa-miR-4502, miR-7113-5p is hsa-miR-7113-5p, miR-8087 is hsa-miR-8087, miR-7154-3p is hsa-miR-7154-3p, miR-5189-5p is hsa-miR-5189-5p, miR-1253 is hsa-miR-1253, miR-518c-5p is hsa-miR-518c-5p, miR-7151-5p is hsa-miR-7151-5p, miR-3614-3p is hsa-miR-3614-3p, miR-4727-5p is hsa-miR-4727-5p, miR-3682-5p is hsa-miR-3682-5p, miR-5090 is hsa-miR-5090, miR-337-3p is hsa-miR-337-3p, miR-488-5p is hsa-miR-488-5p, miR-100-5p is hsa-miR-100-5p, miR-4520-3p is hsa-miR-4520-3p, miR-373-3p is hsa-miR-373-3p, miR-6499-5p is hsa-miR-6499-5p, miR-3909 is hsa-miR-3909, miR-32-5p is hsa-miR-32-5p, miR-302a-3p is hsa-miR-302a-3p, miR-4686 is hsa-miR-4686, miR-4659a-3p is hsa-miR-4659a-3p, miR-4287 is hsa-miR-4287, miR-1301-5p is hsa-miR-1301-5p, miR-593-3p is hsa-miR-593-3p, miR-517a-3p is hsa-miR-517a-3p, miR-517b-3p is hsa-miR-517b-3p, miR-142-3p is hsa-miR-142-3p, miR-1185-2-3p is hsa-miR-1185-2-3p, miR-602 is hsa-miR-602, miR-527 is hsa-miR-527, miR-518a-5p is hsa-miR-518a-5p, miR-4682 is hsa-miR-4682, miR-28-5p is hsa-miR-28-5p, miR-4252 is hsa-miR-4252, miR-452-5p is hsa-miR-452-5p, miR-525-5p is hsa-miR-525-5p, miR-3622a-3p is hsa-miR-3622a-3p, miR-6813-3p is hsa-miR-6813-3p, miR-4769-3p is hsa-miR-4769-3p, miR-5698 is hsa-miR-5698, miR-1915-3p is hsa-miR-1915-3p, miR-1343-5p is hsa-miR-1343-5p, miR-6861-5p is hsa-miR-6861-5p, miR-6781-5p is hsa-miR-6781-5p, miR-4508 is hsa-miR-4508, miR-6743-5p is hsa-miR-6743-5p, miR-6726-5p is hsa-miR-6726-5p, miR-4525 is hsa-miR-4525, miR-4651 is hsa-miR-4651, miR-6813-5p is hsa-miR-6813-5p, miR-5787 is hsa-miR-5787, miR-1290 is hsa-miR-1290, miR-6075 is hsa-miR-6075, miR-4758-5p is hsa-miR-4758-5p, miR-4690-5p is hsa-miR-4690-5p, miR-762 is hsa-miR-762, miR-1225-3p is hsa-miR-1225-3p, miR-3184-5p is hsa-miR-3184-5p, miR-665 is hsa-miR-665, miR-211-5p is hsa-miR-211-5p, miR-1247-5p is hsa-miR-1247-5p, miR-3656 is hsa-miR-3656, miR-149-5p is hsa-miR-149-5p, miR-744-5p is hsa-miR-744-5p, miR-345-5p is hsa-miR-345-5p, miR-150-5p is hsa-miR-150-5p, miR-191-3p is hsa-miR-191-3p, miR-651-5p is hsa-miR-651-5p, miR-34a-5p is hsa-miR-34a-5p, miR-409-5p is hsa-miR-409-5p, miR-369-5p is hsa-miR-369-5p, miR-1915-5p is hsa-miR-1915-5p, miR-204-5p is hsa-miR-204-5p, miR-137 is hsa-miR-137, miR-382-5p is hsa-miR-382-5p, miR-517-5p is hsa-miR-517-5p, miR-532-5p is hsa-miR-532-5p, miR-22-5p is hsa-miR-22-5p, miR-1237-3p is hsa-miR-1237-3p, miR-1224-3p is hsa-miR-1224-3p, miR-625-3p is hsa-miR-625-3p, miR-328-3p is hsa-miR-328-3p, miR-122-5p is hsa-miR-122-5p, miR-202-3p is hsa-miR-202-3p, miR-4781-5p is hsa-miR-4781-5p, miR-718 is hsa-miR-718, miR-342-3p is hsa-miR-342-3p, miR-26b-3p is hsa-miR-26b-3p, miR-140-3p is hsa-miR-140-3p, miR-200a-3p is hsa-miR-200a-3p, miR-378a-3p is hsa-miR-378a-3p, miR-484 is hsa-miR-484, miR-296-5p is hsa-miR-296-5p, miR-205-5p is hsa-miR-205-5p, miR-431-5p is hsa-miR-431-5p, miR-1471 is hsa-miR-1471, miR-1538 is hsa-miR-1538, miR-449b-3p is hsa-miR-449b-3p, miR-1976 is hsa-miR-1976, miR-4268 is hsa-miR-4268, miR-4279 is hsa-miR-4279, miR-3620-3p is hsa-miR-3620-3p, miR-3944-3p is hsa-miR-3944-3p, miR-3156-3p is hsa-miR-3156-3p, miR-3187-5p is hsa-miR-3187-5p, miR-4685-3p is hsa-miR-4685-3p, miR-4695-3p is hsa-miR-4695-3p, miR-4697-3p is hsa-miR-4697-3p, miR-4713-5p is hsa-miR-4713-5p, miR-4723-3p is hsa-miR-4723-3p, miR-371b-3p is hsa-miR-371b-3p, miR-3151-3p is hsa-miR-3151-3p, miR-3192-3p is hsa-miR-3192-3p, miR-6728-3p is hsa-miR-6728-3p, miR-6736-3p is hsa-miR-6736-3p, miR-6740-3p is hsa-miR-6740-3p, miR-6741-3p is hsa-miR-6741-3p, miR-6743-3p is hsa-miR-6743-3p, miR-6747-3p is hsa-miR-6747-3p, miR-6750-3p is hsa-miR-6750-3p, miR-6754-3p is hsa-miR-6754-3p, miR-6759-3p is hsa-miR-6759-3p, miR-6761-3p is hsa-miR-6761-3p, miR-6762-3p is hsa-miR-6762-3p, miR-6769a-3p is hsa-miR-6769a-3p, miR-6776-3p is hsa-miR-6776-3p, miR-6778-3p is hsa-miR-6778-3p, miR-6779-3p is hsa-miR-6779-3p, miR-6786-3p is hsa-miR-6786-3p, miR-6787-3p is hsa-miR-6787-3p, miR-6792-3p is hsa-miR-6792-3p, miR-6794-3p is hsa-miR-6794-3p, miR-6801-3p is hsa-miR-6801-3p, miR-6802-3p is hsa-miR-6802-3p, miR-6803-3p is hsa-miR-6803-3p, miR-6804-3p is hsa-miR-6804-3p, miR-6810-5p is hsa-miR-6810-5p, miR-6823-3p is hsa-miR-6823-3p, miR-6825-3p is hsa-miR-6825-3p, miR-6829-3p is hsa-miR-6829-3p, miR-6833-3p is hsa-miR-6833-3p, miR-6834-3p is hsa-miR-6834-3p, miR-6780b-3p is hsa-miR-6780b-3p, miR-6845-3p is hsa-miR-6845-3p, miR-6862-3p is hsa-miR-6862-3p, miR-6865-3p is hsa-miR-6865-3p, miR-6870-3p is hsa-miR-6870-3p, miR-6875-3p is hsa-miR-6875-3p, miR-6877-3p is hsa-miR-6877-3p, miR-6879-3p is hsa-miR-6879-3p, miR-6882-3p is hsa-miR-6882-3p, miR-6885-3p is hsa-miR-6885-3p, miR-6886-3p is hsa-miR-6886-3p, miR-6887-3p is hsa-miR-6887-3p, miR-6890-3p is hsa-miR-6890-3p, miR-6893-3p is hsa-miR-6893-3p, miR-6894-3p is hsa-miR-6894-3p, miR-7106-3p is hsa-miR-7106-3p, miR-7109-3p is hsa-miR-7109-3p, miR-7114-3p is hsa-miR-7114-3p, miR-7155-5p is hsa-miR-7155-5p, miR-7160-5p is hsa-miR-7160-5p, miR-615-3p is hsa-miR-615-3p, miR-920 is hsa-miR-920, miR-1825 is hsa-miR-1825, miR-675-3p is hsa-miR-675-3p, miR-1910-5p is hsa-miR-1910-5p, miR-2278 is hsa-miR-2278, miR-2682-3p is hsa-miR-2682-3p, miR-3122 is hsa-miR-3122, miR-3151-5p is hsa-miR-3151-5p, miR-3175 is hsa-miR-3175, miR-4323 is hsa-miR-4323, miR-4326 is hsa-miR-4326, miR-4284 is hsa-miR-4284, miR-3605-3p is hsa-miR-3605-3p, miR-3622b-5p is hsa-miR-3622b-5p, miR-3646 is hsa-miR-3646, miR-3158-5p is hsa-miR-3158-5p, miR-4722-3p is hsa-miR-4722-3p, miR-4728-3p is hsa-miR-4728-3p, miR-4747-3p is hsa-miR-4747-3p, miR-4436b-5p is hsa-miR-4436b-5p, miR-5196-3p is hsa-miR-5196-3p, miR-5589-5p is hsa-miR-5589-5p, miR-345-3p is hsa-miR-345-3p, miR-642b-5p is hsa-miR-642b-5p, miR-6716-3p is hsa-miR-6716-3p, miR-6511b-3p is hsa-miR-6511b-3p, miR-208a-5p is hsa-miR-208a-5p, miR-6726-3p is hsa-miR-6726-3p, miR-6744-5p is hsa-miR-6744-5p, miR-6782-3p is hsa-miR-6782-3p, miR-6789-3p is hsa-miR-6789-3p, miR-6797-3p is hsa-miR-6797-3p, miR-6800-3p is hsa-miR-6800-3p, miR-6806-5p is hsa-miR-6806-5p, miR-6824-3p is hsa-miR-6824-3p, miR-6837-5p is hsa-miR-6837-5p, miR-6846-3p is hsa-miR-6846-3p, miR-6858-3p is hsa-miR-6858-3p, miR-6859-3p is hsa-miR-6859-3p, miR-6861-3p is hsa-miR-6861-3p, miR-6880-3p is hsa-miR-6880-3p, miR-7111-3p is hsa-miR-7111-3p, miR-7152-5p is hsa-miR-7152-5p, miR-642a-5p is hsa-miR-642a-5p, miR-657 is hsa-miR-657, miR-1236-3p is hsa-miR-1236-3p, miR-764 is hsa-miR-764, miR-4314 is hsa-miR-4314, miR-3675-3p is hsa-miR-3675-3p, miR-5703 is hsa-miR-5703, miR-3191-5p is hsa-miR-3191-5p, miR-6511a-3p is hsa-miR-6511a-3p, miR-6809-3p is hsa-miR-6809-3p, miR-6815-5p is hsa-miR-6815-5p, miR-6857-3p is hsa-miR-6857-3p, miR-6878-3p is hsa-miR-6878-3p, miR-371a-5p is hsa-miR-371a-5p, miR-766-3p is hsa-miR-766-3p, miR-1229-3p is hsa-miR-1229-3p, miR-1306-5p is hsa-miR-1306-5p, miR-210-5p is hsa-miR-210-5p, miR-198 is hsa-miR-198, miR-485-3p is hsa-miR-485-3p, miR-668-3p is hsa-miR-668-3p, miR-532-3p is hsa-miR-532-3p, miR-877-3p is hsa-miR-877-3p, miR-1238-3p is hsa-miR-1238-3p, miR-3130-5p is hsa-miR-3130-5p, miR-4298 is hsa-miR-4298, miR-4290 is hsa-miR-4290, miR-3943 is hsa-miR-3943, miR-346 is hsa-miR-346, miR-767-3p is hsa-miR-767-3p, miR-516a-5p is hsa-miR-516a-5p, miR-769-3p is hsa-miR-769-3p, miR-3692-5p is hsa-miR-3692-5p, miR-3945 is hsa-miR-3945, miR-4433a-3p is hsa-miR-4433a-3p, miR-4485-3p is hsa-miR-4485-3p, miR-6831-5p is hsa-miR-6831-5p, miR-519c-5p is hsa-miR-519c-5p, miR-551b-5p is hsa-miR-551b-5p, miR-1343-3p is hsa-miR-1343-3p, miR-4286 is hsa-miR-4286, miR-4634 is hsa-miR-4634, miR-4733-3p is hsa-miR-4733-3p, miR-6086 is hsa-miR-6086, miR-30d-5p is hsa-miR-30d-5p, miR-30b-3p is hsa-miR-30b-3p, miR-92a-3p is hsa-miR-92a-3p, miR-371b-5p is hsa-miR-371b-5p, and miR-486-5p is hsa-miR-486-5p.

In another preferable aspect of a kit or device for detection of dementia or a method for detecting dementia according to the present invention, dementia marker miR-6765-3p is hsa-miR-6765-3p, miR-6784-5p is hsa-miR-6784-5p, miR-5698 is hsa-miR-5698, miR-6778-5p is hsa-miR-6778-5p, miR-1915-3p is hsa-miR-1915-3p, miR-6875-5p is hsa-miR-6875-5p, miR-1343-5p is hsa-miR-1343-5p, miR-4534 is hsa-miR-4534, miR-6861-5p is hsa-miR-6861-5p, miR-4721 is hsa-miR-4721, miR-6756-5p is hsa-miR-6756-5p, miR-615-5p is hsa-miR-615-5p, miR-6727-5p is hsa-miR-6727-5p, miR-6887-5p is hsa-miR-6887-5p, miR-8063 is hsa-miR-8063, miR-6880-5p is hsa-miR-6880-5p, miR-6805-3p is hsa-miR-6805-3p, miR-6781-5p is hsa-miR-6781-5p, miR-4508 is hsa-miR-4508, miR-4726-5p is hsa-miR-4726-5p, miR-4710 is hsa-miR-4710, miR-7111-5p is hsa-miR-7111-5p, miR-3619-3p is hsa-miR-3619-3p, miR-6743-5p is hsa-miR-6743-5p, miR-6795-5p is hsa-miR-6795-5p, miR-6726-5p is hsa-miR-6726-5p, miR-4525 is hsa-miR-4525, miR-1254 is hsa-miR-1254, miR-1233-5p is hsa-miR-1233-5p, miR-4651 is hsa-miR-4651, miR-6836-3p is hsa-miR-6836-3p, miR-6769a-5p is hsa-miR-6769a-5p, miR-6813-5p is hsa-miR-6813-5p, miR-4532 is hsa-miR-4532, miR-365a-5p is hsa-miR-365a-5p, miR-1231 is hsa-miR-1231, miR-5787 is hsa-miR-5787, miR-1290 is hsa-miR-1290, miR-1228-5p is hsa-miR-1228-5p, miR-371a-5p is hsa-miR-371a-5p, miR-4430 is hsa-miR-4430, miR-296-3p is hsa-miR-296-3p, miR-6075 is hsa-miR-6075, miR-1237-5p is hsa-miR-1237-5p, miR-4758-5p is hsa-miR-4758-5p, miR-4690-5p is hsa-miR-4690-5p, miR-4466 is hsa-miR-4466, miR-6789-5p is hsa-miR-6789-5p, miR-4632-5p is hsa-miR-4632-5p, miR-4745-5p is hsa-miR-4745-5p, miR-4665-5p is hsa-miR-4665-5p, miR-6807-5p is hsa-miR-6807-5p, miR-762 is hsa-miR-762, miR-7114-5p is hsa-miR-7114-5p, miR-150-3p is hsa-miR-150-3p, miR-423-5p is hsa-miR-423-5p, miR-575 is hsa-miR-575, miR-671-5p is hsa-miR-671-5p, miR-939-5p is hsa-miR-939-5p, miR-1225-3p is hsa-miR-1225-3p, miR-3184-5p is hsa-miR-3184-5p, and miR-3665 is hsa-miR-3665.

DEFINITION OF TERMS

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 1314, 1315 to 1434, and 1435 to 1505 (e.g., SEQ ID NOs: 194 to 212, 374, 398, 490, 591, 593 to 609, 766, 1015 to 1017, 1019 to 1024, 1026 to 1031, 1285 to 1286, and 1315 to 1434) or a nucleotide sequence derived from the nucleotide sequence by the replacement of u with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID NO) but also a "miRNA" comprising a precursor of the "miRNA" (pre-miRNA or pri-miRNA) and having biological functions equivalent to miRNAs encoded by these, for example, a "miRNA" encoding a congener (i.e., a homolog or an ortholog), a variant such as a genetic polymorph, and a derivative. Such a "miRNA" encoding a precursor, a congener, a variant, or a derivative can be specifically identified using "miRBase" (version 21), and examples thereof can include a "miRNA" having a nucleotide sequence hybridizing under stringent conditions described later to a complementary sequence of any particular nucleotide sequence represented by any of SEQ ID NOs: 1 to 1314, 1315 to 1434, and 1435 to 1505 (e.g., SEQ ID NOs: 194 to 212, 374, 398, 490, 591, 593 to 609, 766, 1015 to 1017, 1019 to 1024, 1026 to 1031, 1285 to 1286, and 1315 to 1434). Note that the "miRBase" (version 21) (http://www.mirbase.org/) is a database on the Web that provides miRNA nucleotide sequences, annotations, and prediction of their target genes. All the miRNAs registered in the "miRBase" have been cloned or limited to miRNAs expressed in vivo and processed. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

In this context, the "complementary polynucleotide" (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 1314, 1315 to 1434, and 1435 to 1505 (e.g., SEQ ID NOs: 194 to 212, 374, 398, 490, 591, 593 to 609, 766, 1015 to 1017, 1019 to 1024, 1026 to 1031, 1285 to 1286, and 1315 to 1434) or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID NO or a nucleotide sequence derived from the nucleotide sequence by the replacement of u with t, or a partial sequence thereof; a variant containing the deletion, substitution, addition, or insertion of one or more nucleotides in a nucleotide sequence of a premature miRNA of the sequence of any of SEQ ID NOs: 1 to 210, 211 to 249, 250 to 374, and 375 to 390, 1315 to 1350, 1351 to 1356, 1435 to 1448, and 1449 to 1453 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by use of a well-known technique such as site-directed mutagenesis or mutagenesis using PCR.

The term "percent (%) identity" used herein can be determined with or without an introduced gap, using a protein or gene search system based on BLAST (https://blast.ncbnlm.nih.gov/Blast.cgi) or FASTA (http://www.genome.jp/tools/fasta/) (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur molecule, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the dementia marker miRNAs described above or to a complementary strand of the polynucleotide is a synthesized or prepared nucleic acid and, for example, includes a "nucleic acid probe" or a "primer", and is utilized directly or indirectly for detecting the presence or absence of dementia in a subject, for diagnosing the presence or absence or the severity of dementia, the presence or absence or the degree of amelioration of dementia, or the therapeutic sensitivity of dementia, or for screening for a candidate substance useful in the prevention, amelioration, or treatment of dementia. The "nucleic acid" includes a nucleotide, an oligonucleotide, and a polynucleotide capable of specifically recognizing and binding to a transcript represented by any of SEQ ID NOs: 1 to 1314, 1315 to 1434, and 1435 to 1505 (e.g., SEQ ID NOs: 194 to 212, 374, 398, 490, 591, 593 to 609, 766, 1015 to 1017, 1019 to 1024, 1026 to 1031, 1285 to 1286, and 1315 to 1434) or a synthetic cDNA nucleic acid thereof, or a complementary strand thereto in vivo, particularly, in a sample such as a body fluid (e.g., blood or urine), in relation to the development of dementia. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing- or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. Meanwhile, the "subject with normal cognitive functions" also means such a mammal, which is an animal without dementia to be detected. The subject with normal cognitive functions is preferably a human.

As used herein, the term "dementia" refers to a state in which once normal cognitive functions are persistently lowered due to acquired brain damage. Generally speaking, dementia is diagnosed when the functions decrease to a level where daily living activity and social activity are impaired.

Dementia, in general, is classified, depending on a cause of disease, into disease types such as Alzheimer's dementia, vascular dementia, Lewy body dementia, normal pressure hydrocephalus, and frontotemporal lobar degeneration. Examples of the "dementia" in the present invention includes: Alzheimer's dementia, vascular dementia, Lewy body dementia, normal pressure hydrocephalus, frontotemporal lobar degeneration, senile dementia of the neurofibrillary tangle type, dementia resulting from other diseases (e.g., infectious diseases) alcoholic dementia or vitamin deficiency dementia or the like. In addition, examples of the "dementia" in the present invention also include mixed dementia of any of these types.

Further, type-unknown or unspecified dementia is also included in the "dementia" in the present invention.

As used herein, the term "Alzheimer's dementia" refers to dementia in which imaging test such as CT, MRI, and PET shows no abnormal structure in the brain, but atrophy of medial temporal lobe is detected, and as a result of which, as a main symptom of cognitive/memory impairment, short-term memory impairment occurs.

As used herein, the term "vascular dementia" refers to dementia which is accompanied by cerebrovascular disease and in which consciousness of disease and judgment is relatively well preserved while cognitive/memory impairment is ununiform or sporadic and memory and mental capacity are decreased.

As used herein, the term "Lewy body dementia" refers to dementia in which cerebral blood flow SPECT or PET imaging shows a decrease in the uptake of dopamine across a transporter in the basal ganglia and which is accompanied by, as a symptom, fluctuating cognitive impairment, hallucination in which a specific detailed event appears repeatedly, and/or parkinsonism.

As used herein, the term "normal pressure hydrocephalus" refers to dementia in which spinal fluid accumulates in the cerebral ventricle and then pressurizes the surrounding brain, causing cognitive function impairment, gait disturbance, and/or dysuria. This dementia can be ameliorated by surgical treatment.

As used herein, the term "frontotemporal lobar degeneration" refers to dementia in which frontal and temporal lobes are apparently atrophied, which causes language disturbance and mental manifestation to be displayed.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows dementia to be detected early and enables an early medical intervention.

The term "specificity" used herein means a value of (the number of true negatives)/(the number of true negatives+the number of false positives). High specificity prevents needless extra examination for subjects with normal cognitive functions misjudged as being dementia patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as dementia develops, as dementia progresses, or as therapeutic effects on dementia are exerted. Specifically, the sample refers to a brain tissue and neurons, a nerve tissue, cerebrospinal fluid, bone marrow aspirate, an organ, skin, and a body fluid such as blood, urine, saliva, sweat, and tissue exudate, serum or plasma prepared from blood, and others such as feces, hair, or the like. The "sample" further refers to a biological sample extracted therefrom, specifically, a gene such as RNA or miRNA.

The term "hsa-miR-4274 gene" or "hsa-miR-4274" used herein includes the hsa-miR-4274 gene (miRBase Accession No. MIMAT0016906) shown in SEQ ID NO: 1, a homolog or an ortholog of a different organism species, and the like. The hsa-miR-4274 gene can be obtained by a method described in Goff L A et al., 2009, PLoS One, Vol. 4, e7192. Also, "hsa-mir-4274" (miRBase Accession No. MI0015884; SEQ ID NO: 391) having a hairpin-like structure is known as a precursor of "hsa-miR-4274."

The term "hsa-miR-4272 gene" or "hsa-miR-4272" used herein includes the hsa-miR-4272 gene (miRBase Accession No. MIMAT0016902) shown in SEQ ID NO: 2, a homolog or an ortholog of a different organism species, and the like. The hsa-miR-4272 gene can be obtained by a method described in Goff L A et al., 2009, PLoS One, Vol. 4, e7192. Also, "hsa-mir-4272" (miRBase Accession No. MI0015880; SEQ ID NO: 392) having a hairpin-like structure is known as a precursor of "hsa-miR-4272."

The term "hsa-miR-4728-5p gene" or "hsa-miR-4728-5p" used herein includes the hsa-miR-4728-5p gene (miRBase Accession No. MIMAT0019849) shown in SEQ ID NO: 3, a homolog or an ortholog of a different organism species, and the like. The hsa-miR-4728-5p gene can be obtained by a method described in Persson H et al., 2011, Cancer Res., Vol. 71, pp. 78-86. Also, "hsa-mir-4728" (miRBase Accession No. MI0017365; SEQ ID NO: 393) having a hairpin-like structure is known as a precursor of "hsa-miR-4728-5p."

The term "hsa-miR-4443 gene" or "hsa-miR-4443" used herein includes the hsa-miR-4443 gene (miRBase Accession No. MIMAT0018961) shown in SEQ ID NO: 4, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786; SEQ ID NO: 394) having a hairpin-like structure is known as a precursor of "hsa-miR-4443."

The term "hsa-miR-4506 gene" or "hsa-miR-4506" used herein includes the hsa-miR-4506 gene (miRBase Accession No. MIMAT0019042) shown in SEQ ID NO: 5, a homolog or an ortholog of a different organism species, and the like. The hsa-miR-4506 gene can be obtained by a method described in Jima D D et al., 2010, Blood, Vol. 116, e118-e127. Also, "hsa-mir-4506" (miRBase Accession No. MI0016869; SEQ ID NO: 395) having a hairpin-like structure is known as a precursor of "hsa-miR-4506."

The term "hsa-miR-6773-5p gene" or "hsa-miR-6773-5p" used herein includes the hsa-miR-6773-5p gene (miRBase Accession No. MIMAT0027446) shown in SEQ ID NO: 6, a homolog or an ortholog of a different organism species, and the like. The hsa-miR-6773-5p gene can be obtained by a method described in Ladewig E et al., 2012, Genome Res., Vol. 22, pp. 1634-1645. Also, "hsa-mir-6773" (miRBase Accession No. MI0022618; SEQ ID NO: 396) having a hairpin-like structure is known as a precursor of "hsa-miR-6773-5p."

The term "hsa-miR-4662a-5p gene" or "hsa-miR-4662a-5p" used herein includes the hsa-miR-4662a-5p gene (miRBase Accession No. MIMAT0019731) shown in SEQ ID NO: 7, a homolog or an ortholog of a different organism species, and the like. The hsa-miR-4662a-5p gene can be obtained by a method described in Persson H et al., 2011, Cancer Res., Vol. 71, pp. 78-86. Also, "hsa-mir-4662a" (miRBase Accession No. MI0017290; SEQ ID NO: 397) having a hairpin-like structure is known as a precursor of "hsa-miR-4662a-5p."

The term "hsa-miR-3184-3p gene" or "hsa-miR-3184-3p" used herein includes the hsa-miR-3184-3p gene (miRBase Accession No. MIMAT0022731) shown in SEQ ID NO: 8, a homolog or an ortholog of a different organism species, and the like. The hsa-miR-3184-3p gene can be obtained by a method described in Stark M S et al., 2010, PLoS One, Vol. 5, e9685. Also, "hsa-mir-3184" (miRBase Accession No. MI0014226; SEQ ID NO: 398) having a hairpin-like structure is known as a precursor of "hsa-miR-3184-3p."

The term "hsa-miR-4281 gene" or "hsa-miR-4281" used herein includes the hsa-miR-4281 gene (miRBase Accession No. MIMAT0016907) shown in SEQ ID NO: 9, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885; SEQ ID NO: 399) having a hairpin-like structure is known as a precursor of "hsa-miR-4281."

The term "hsa-miR-320d gene" or "hsa-miR-320d" used herein includes the hsa-miR-320d gene (miRBase Accession No. MIMAT0006764) shown in SEQ ID NO: 10, a homolog or an ortholog of a different organism species, and the like. The hsa-miR-320d gene can be obtained by a method described in Friedlander M R et al., 2008, Nat. Biotechnol., Vol. 26, 407-415. Also, "hsa-mir-320d-1 and hsa-mir-320d-2" (miRBase Accession Nos. MI0008190 and MI0008192; SEQ ID NOs: 400 and 401) each having a hairpin-like structure are known as precursors of "hsa-miR-320d."

The term "hsa-miR-6729-3p gene" or "hsa-miR-6729-3p" used herein includes the hsa-miR-6729-3p gene (miRBase Accession No. MIMAT0027360) shown in SEQ ID NO: 11, a homolog or an ortholog of a different organism species, and the like. The hsa-miR-6729-3p gene can be obtained by a method described in Ladewig E et al., 2012, Genome Res., Vol. 22, pp. 1634-1645. Also, "hsa-mir-6729" (miRBase Accession No. MI0022574; SEQ ID NO: 402) having a hairpin-like structure is known as a precursor of "hsa-miR-6729-3p."

The term "hsa-miR-5192 gene" or "hsa-miR-5192" used herein includes the hsa-miR-5192 gene (miRBase Accession No. MIMAT0021123) shown in SEQ ID NO: 12, a homolog or an ortholog of a different organism species, and the like. The hsa-miR-5192 gene can be obtained by a method described in Schotte D et al., 2011, Leukemia, Vol. 25, pp. 1389-1399. Also, "hsa-mir-5192" (miRBase Accession No.

MI0018171; SEQ ID NO: 403) having a hairpin-like structure is known as a precursor of "hsa-miR-5192."

The term "hsa-miR-6853-5p gene" or "hsa-miR-6853-5p" used herein includes the hsa-miR-6853-5p gene (miRBase Accession No. MIMAT0027606) shown in SEQ ID NO: 13, a homolog or an ortholog of a different organism species, and the like. The hsa-miR-6853-5p gene can be obtained by a method described in Ladewig E et al., 2012, Genome Res., Vol. 22, pp. 1634-1645. Also, "hsa-mir-6853" (miRBase Accession No. MI0022699; SEQ ID NO: 404) having a hairpin-like structure is known as a precursor of "hsa-miR-6853-5p."

The term "hsa-miR-1234-3p gene" or "hsa-miR-1234-3p" used herein includes the hsa-miR-1234-3p gene (miRBase Accession No. MIMAT0005589) shown in SEQ ID NO: 14, a homolog or an ortholog of a different organism species, and the like. The hsa-miR-1234-3p gene can be obtained by a method described in Berezikov E et al., 2007, Mol. Cell, Vol. 28, pp. 328-336. Also, "hsa-mir-1234" (miRBase Accession No. MI0006324; SEQ ID NO: 405) having a hairpin-like structure is known as a precursor of "hsa-miR-1234-3p."

The term "hsa-miR-1233-3p gene" or "hsa-miR-1233-3p" used herein includes the hsa-miR-1233-3p gene (miRBase Accession No. MIMAT0005588) shown in SEQ ID NO: 15, a homolog or an ortholog of a different organism species, and the like. The hsa-miR-1233-3p gene can be obtained by a method described in Berezikov E et al., 2007, Mol. Cell, Vol. 28, pp. 328-336. Also, "hsa-mir-1233-1 and hsa-mir-1233-2" (miRBase Accession Nos. MI0006323 and MI0015973; SEQ ID NOs: 406 and 407) each having a hairpin-like structure are known as precursors of "hsa-miR-1233-3p."

The term "hsa-miR-4539 gene" or "hsa-miR-4539" used herein includes the hsa-miR-4539 gene (miRBase Accession No. MIMAT0019082) shown in SEQ ID NO: 16, a homolog or an ortholog of a different organism species, and the like. The hsa-miR-4539 gene can be obtained by a method described in Jima D D et al., 2010, Blood, Vol. 116, e118-e127. Also, "hsa-mir-4539" (miRBase Accession No. MI0016910; SEQ ID NO: 408) having a hairpin-like structure is known as a precursor of "hsa-miR-4539."

The term "hsa-miR-3914 gene" or "hsa-miR-3914" used herein includes the hsa-miR-3914 gene (miRBase Accession No. MIMAT0018188) shown in SEQ ID NO: 17, a homolog or an ortholog of a different organism species, and the like. The hsa-miR-3914 gene can be obtained by a method described in Creighton C J et al., 2010, PLoS One, Vol. 5, e9637. Also, "hsa-mir-3914-1 and hsa-mir-3914-2" (miRBase Accession Nos. MI0016419 and MI0016421; SEQ ID NOs: 409 and 410) each having a hairpin-like structure are known as precursors of "hsa-miR-3914."

The term "hsa-miR-4738-5p gene" or "hsa-miR-4738-5p" used herein includes the hsa-miR-4738-5p gene (miRBase Accession No. MIMAT0019866) shown in SEQ ID NO: 18, a homolog or an ortholog of a different organism species, and the like. The hsa-miR-4738-5p gene can be obtained by a method described in Persson H et al., 2011, Cancer Res., Vol. 71, pp. 78-86. Also, "hsa-mir-4738" (miRBase Accession No. MI0017376; SEQ ID NO: 411) having a hairpin-like structure is known as a precursor of "hsa-miR-4738-5p."

The term "hsa-miR-548au-3p gene" or "hsa-miR-548au-3p" used herein includes the hsa-miR-548au-3p gene (miRBase Accession No. MIMAT0022292) shown in SEQ ID NO: 19, a homolog or an ortholog of a different organism species, and the like. The hsa-miR-548au-3p gene can be obtained by a method described in Friedlander M R et al., 2012, Nucleic Acids Res., Vol. 40, pp. 37-52. Also, "hsa-mir-548au" (miRBase Accession No. MI0019145; SEQ ID NO: 412) having a hairpin-like structure is known as a precursor of "hsa-miR-548au-3p."

The term "hsa-miR-1539 gene" or "hsa-miR-1539" used herein includes the hsa-miR-1539 gene (miRBase Accession No. MIMAT0007401) shown in SEQ ID NO: 20, a homolog or an ortholog of a different organism species, and the like. The hsa-miR-1539 gene can be obtained by a method described in Azuma-Mukai, A et al., 2008, Proc. Natl. Acad. Sci. U.S.A., Vol. 105, pp. 7964-7969. Also, "hsa-mir-1539" (miRBase Accession No. MI0007260; SEQ ID NO: 413) having a hairpin-like structure is known as a precursor of "hsa-miR-1539."

The term "hsa-miR-4720-3p gene" or "hsa-miR-4720-3p" used herein includes the hsa-miR-4720-3p gene (miRBase Accession No. MIMAT0019834) shown in SEQ ID NO: 21, a homolog or an ortholog of a different organism species, and the like. The hsa-miR-4720-3p gene can be obtained by a method described in Persson H et al., 2011, Cancer Res., Vol. 71, pp. 78-86. Also, "hsa-mir-4720" (miRBase Accession No. MI0017355; SEQ ID NO: 414) having a hairpin-like structure is known as a precursor of "hsa-miR-4720-3p."

The term "hsa-miR-365b-5p gene" or "hsa-miR-365b-5p" used herein includes the hsa-miR-365b-5p gene (miRBase Accession No. MIMAT0022833) shown in SEQ ID NO: 22, a homolog or an ortholog of a different organism species, and the like. The hsa-miR-365b-5p gene can be obtained by a method described in Xie X et al., 2005, Nature, Vol. 434, pp. 338-345. Also, "hsa-mir-365b" (miRBase Accession No. MI0000769; SEQ ID NO: 415) having a hairpin-like structure is known as a precursor of "hsa-miR-365b-5p."

The term "hsa-miR-4486 gene" or "hsa-miR-4486" used herein includes the hsa-miR-4486 gene (miRBase Accession No. MIMAT0019020) shown in SEQ ID NO: 23, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847; SEQ ID NO: 416) having a hairpin-like structure is known as a precursor of "hsa-miR-4486."

The term "hsa-miR-1227-5p gene" or "hsa-miR-1227-5p" used herein includes the hsa-miR-1227-5p gene (miRBase Accession No. MIMAT0022941) shown in SEQ ID NO: 24, a homolog or an ortholog of a different organism species, and the like. The hsa-miR-1227-5p gene can be obtained by a method described in Berezikov E et al., 2007, Mol. Cell., Vol. 28, pp. 328-336. Also, "hsa-mir-1227" (miRBase Accession No. MI0006316; SEQ ID NO: 417) having a hairpin-like structure is known as a precursor of "hsa-miR-1227-5p."

The term "hsa-miR-4667-5p gene" or "hsa-miR-4667-5p" used herein includes the hsa-miR-4667-5p gene (miRBase Accession No. MIMAT0019743) shown in SEQ ID NO: 25, a homolog or an ortholog of a different organism species, and the like. The hsa-miR-4667-5p gene can be obtained by a method described in Persson H et al., 2011, Cancer Res., Vol. 71, pp. 78-86. Also, "hsa-mir-4667" (miRBase Accession No. MI0017297; SEQ ID NO: 418) having a hairpin-like structure is known as a precursor of "hsa-miR-4667-5p."

The term "hsa-miR-6088 gene" or "hsa-miR-6088" used herein includes the hsa-miR-6088 gene (miRBase Accession No. MIMAT0023713) shown in SEQ ID NO: 26, a homolog or an ortholog of a different organism species, and the like.

The hsa-miR-6088 gene can be obtained by a method described in Yoo J K et al., 2012, Stem Cells Dev., Vol. 21, pp. 2049-2057. Also, “hsa-mir-6088” (miRBase Accession No. MI0020365; SEQ ID NO: 419) having a hairpin-like structure is known as a precursor of “hsa-miR-6088.”

The term “hsa-miR-6820-5p gene” or “hsa-miR-6820-5p” used herein includes the hsa-miR-6820-5p gene (miRBase Accession No. MIMAT0027540) shown in SEQ ID NO: 27, a homolog or an ortholog of a different organism species, and the like. The hsa-miR-6820-5p gene can be obtained by a method described in Ladewig E et al., 2012, Genome Res., Vol. 22, pp. 1634-1645. Also, “hsa-mir-6820” (miRBase Accession No. MI0022665; SEQ ID NO: 420) having a hairpin-like structure is known as a precursor of “hsa-miR-6820-5p.”

The term “hsa-miR-4505 gene” or “hsa-miR-4505” used herein includes the hsa-miR-4505 gene (miRBase Accession No. MIMAT0019041) shown in SEQ ID NO: 28, a homolog or an ortholog of a different organism species, and the like. The hsa-miR-4505 gene can be obtained by a method described in Jima D D et al., 2010, Blood, Vol. 116, e118-e127. Also, “hsa-mir-4505” (miRBase Accession No. MI0016868; SEQ ID NO: 421) having a hairpin-like structure is known as a precursor of “hsa-miR-4505.”

The term “hsa-miR-548q gene” or “hsa-miR-548q” used herein includes the hsa-miR-548q gene (miRBase Accession No. MIMAT0011163) shown in SEQ ID NO: 29, a homolog or an ortholog of a different organism species, and the like. The hsa-miR-548q gene can be obtained by a method described in Wyman S K et al., 2009, PLoS One, Vol. 4, e5311. Also, “hsa-mir-548q” (miRBase Accession No. MI0010637; SEQ ID NO: 422) having a hairpin-like structure is known as a precursor of “hsa-miR-548q.”

The term “hsa-miR-4658 gene” or “hsa-miR-4658” used herein includes the hsa-miR-4658 gene (miRBase Accession No. MIMAT0019725) shown in SEQ ID NO: 30, a homolog or an ortholog of a different organism species, and the like. The hsa-miR-4658 gene can be obtained by a method described in Persson H et al., 2011, Cancer Res., Vol. 71, pp. 78-86. Also, “hsa-mir-4658” (miRBase Accession No. MI0017286; SEQ ID NO: 423) having a hairpin-like structure is known as a precursor of “hsa-miR-4658.”

The term “hsa-miR-450a-5p gene” or “hsa-miR-450a-5p” used herein includes the hsa-miR-450a-5p gene (miRBase Accession No. MIMAT0001545) shown in SEQ ID NO: 31, a homolog or an ortholog of a different organism species, and the like. The hsa-miR-450a-5p gene can be obtained by a method described in Xie X et al., 2005, Nature, Vol. 434, pp. 338-345. Also, “hsa-mir-450a-1 and hsa-mir-450a-2” (miRBase Accession Nos. MI0001652 and MI0003187; SEQ ID NOs: 424 and 425) each having a hairpin-like structure are known as precursors of “hsa-miR-450a-5p.”

The term “hsa-miR-1260b gene” or “hsa-miR-1260b” used herein includes the hsa-miR-1260b gene (miRBase Accession No. MIMAT0015041) shown in SEQ ID NO: 32, a homolog or an ortholog of a different organism species, and the like. The hsa-miR-1260b gene can be obtained by a method described in Stark M S et al., 2010, PLoS One, Vol. 5, e9685. Also, “hsa-mir-1260b” (miRBase Accession No. MI0014197; SEQ ID NO: 426) having a hairpin-like structure is known as a precursor of “hsa-miR-1260b.”

The term “hsa-miR-3677-5p gene” or “hsa-miR-3677-5p” used herein includes the hsa-miR-3677-5p gene (miRBase Accession No. MIMAT0019221) shown in SEQ ID NO: 33, a homolog or an ortholog of a different organism species, and the like. The hsa-miR-3677-5p gene can be obtained by a method described in Vaz C et al., 2010, BMC Genomics, Vol. 11, p. 288. Also, “hsa-mir-3677” (miRBase Accession No. MI0016078; SEQ ID NO: 427) having a hairpin-like structure is known as a precursor of “hsa-miR-3677-5p.”

The term “hsa-miR-6777-3p gene” or “hsa-miR-6777-3p” used herein includes the hsa-miR-6777-3p gene (miRBase Accession No. MIMAT0027455) shown in SEQ ID NO: 34, a homolog or an ortholog of a different organism species, and the like. The hsa-miR-6777-3p gene can be obtained by a method described in Ladewig E et al., 2012, Genome Res., Vol. 22, pp. 1634-1645. Also, “hsa-mir-6777” (miRBase Accession No. MI0022622; SEQ ID NO: 428) having a hairpin-like structure is known as a precursor of “hsa-miR-6777-3p.”

The term “hsa-miR-6826-3p gene” or “hsa-miR-6826-3p” used herein includes the hsa-miR-6826-3p gene (miRBase Accession No. MIMAT0027553) shown in SEQ ID NO: 35, a homolog or an ortholog of a different organism species, and the like. The hsa-miR-6826-3p gene can be obtained by a method described in Ladewig E et al., 2012, Genome Res., Vol. 22, pp. 1634-1645. Also, “hsa-mir-6826” (miRBase Accession No. MI0022671; SEQ ID NO: 429) having a hairpin-like structure is known as a precursor of “hsa-miR-6826-3p.”

The term “hsa-miR-6832-3p gene” or “hsa-miR-6832-3p” used herein includes the hsa-miR-6832-3p gene (miRBase Accession No. MIMAT0027565) shown in SEQ ID NO: 36, a homolog or an ortholog of a different organism species, and the like. The hsa-miR-6832-3p gene can be obtained by a method described in Ladewig E et al., 2012, Genome Res., Vol. 22, pp. 1634-1645. Also, “hsa-mir-6832” (miRBase Accession No. MI0022677; SEQ ID NO: 430) having a hairpin-like structure is known as a precursor of “hsa-miR-6832-3p.”

The term “hsa-miR-4725-3p gene” or “hsa-miR-4725-3p” used herein includes the hsa-miR-4725-3p gene (miRBase Accession No. MIMAT0019844) shown in SEQ ID NO: 37, a homolog or an ortholog of a different organism species, and the like. The hsa-miR-4725-3p gene can be obtained by a method described in Persson H et al., 2011, Cancer Res., Vol. 71, pp. 78-86. Also, “hsa-mir-4725” (miRBase Accession No. MI0017362; SEQ ID NO: 431) having a hairpin-like structure is known as a precursor of “hsa-miR-4725-3p.”

The term “hsa-miR-7161-3p gene” or “hsa-miR-7161-3p” used herein includes the hsa-miR-7161-3p gene (miRBase Accession No. MIMAT0028233) shown in SEQ ID NO: 38, a homolog or an ortholog of a different organism species, and the like. The hsa-miR-7161-3p gene can be obtained by a method described in Meunier J et al., 2013, Genome Res., Vol. 23, pp. 34-45. Also, “hsa-mir-7161” (miRBase Accession No. MI0023619; SEQ ID NO: 432) having a hairpin-like structure is known as a precursor of “hsa-miR-7161-3p.”

The term “hsa-miR-2277-5p gene” or “hsa-miR-2277-5p” used herein includes the hsa-miR-2277-5p gene (miRBase Accession No. MIMAT0017352) shown in SEQ ID NO: 39, a homolog or an ortholog of a different organism species, and the like. The hsa-miR-2277-5p gene can be obtained by a method described in Nygaard S et al., 2009, BMC Med. Genomics, Vol. 2, p. 35. Also, “hsa-mir-2277” (miRBase Accession No. MI0011284; SEQ ID NO: 433) having a hairpin-like structure is known as a precursor of “hsa-miR-2277-5p.”

The term “hsa-miR-7110-3p gene” or “hsa-miR-7110-3p” used herein includes the hsa-miR-7110-3p gene (miRBase Accession No. MIMAT0028118) shown in SEQ ID NO: 40, a homolog or an ortholog of a different organism species, and the like. The hsa-miR-7110-3p gene can be obtained by a method described in Ladewig E et al., 2012, Genome Res., Vol. 22, pp. 1634-1645. Also, "hsa-mir-7110" (miRBase Accession No. MI0022961; SEQ ID NO: 434) having a hairpin-like structure is known as a precursor of "hsa-miR-7110-3p."

The term "hsa-miR-4312 gene" or "hsa-miR-4312" used herein includes the hsa-miR-4312 gene (miRBase Accession No. MIMAT0016864) shown in SEQ ID NO: 41, a homolog or an ortholog of a different organism species, and the like. The hsa-miR-4312 gene can be obtained by a method described in Goff L A et al., 2009, PLoS One, Vol. 4, e7192. Also, "hsa-mir-4312" (miRBase Accession No. MI0015842; SEQ ID NO: 435) having a hairpin-like structure is known as a precursor of "hsa-miR-4312."

The term "hsa-miR-4461 gene" or "hsa-miR-4461" used herein includes the hsa-miR-4461 gene (miRBase Accession No. MIMAT0018983) shown in SEQ ID NO: 42, a homolog or an ortholog of a different organism species, and the like. The hsa-miR-4461 gene can be obtained by a method described in Jima D D et al., 2010, Blood, Vol. 116, e118-e127. Also, "hsa-mir-4461" (miRBase Accession No. MI0016807; SEQ ID NO: 436) having a hairpin-like structure is known as a precursor of "hsa-miR-4461."

The term "hsa-miR-6766-5p gene" or "hsa-miR-6766-5p" used herein includes the hsa-miR-6766-5p gene (miRBase Accession No. MIMAT0027432) shown in SEQ ID NO: 43, a homolog or an ortholog of a different organism species, and the like. The hsa-miR-6766-5p gene can be obtained by a method described in Ladewig E et al., 2012, Genome Res., Vol. 22, pp. 1634-1645. Also, "hsa-mir-6766" (miRBase Accession No. MI0022611; SEQ ID NO: 437) having a hairpin-like structure is known as a precursor of "hsa-miR-6766-5p."

The term "hsa-miR-1266-3p gene" or "hsa-miR-1266-3p" used herein includes the hsa-miR-1266-3p gene (miRBase Accession No. MIMAT0026742) shown in SEQ ID NO: 44, a homolog or an ortholog of a different organism species, and the like. The hsa-miR-1266-3p gene can be obtained by a method described in Morin R D et al., 2008, Genome Res., Vol. 18, pp. 610-621. Also, "hsa-mir-1266" (miRBase Accession No. MI0006403; SEQ ID NO: 438) having a hairpin-like structure is known as a precursor of "hsa-miR-1266-3p."

The term "hsa-miR-6729-5p gene" or "hsa-miR-6729-5p" used herein includes the hsa-miR-6729-5p gene (miRBase Accession No. MIMAT0027359) shown in SEQ ID NO: 45, a homolog or an ortholog of a different organism species, and the like. The hsa-miR-6729-5p gene can be obtained by a method described in Ladewig E et al., 2012, Genome Res., Vol. 22, pp. 1634-1645. Also, "hsa-mir-6729" (miRBase Accession No. MI0022574; SEQ ID NO: 402) having a hairpin-like structure is known as a precursor of "hsa-miR-6729-5p."

The term "hsa-miR-526b-3p gene" or "hsa-miR-526b-3p" used herein includes the hsa-miR-526b-3p gene (miRBase Accession No. MIMAT0002836) shown in SEQ ID NO: 46, a homolog or an ortholog of a different organism species, and the like. The hsa-miR-526b-3p gene can be obtained by a method described in Bentwich I et al., 2005, Nat. Genet., Vol. 37, pp. 766-770. Also, "hsa-mir-526b" (miRBase Accession No. MI0003150; SEQ ID NO: 439) having a hairpin-like structure is known as a precursor of "hsa-miR-526b-3p."

The term "hsa-miR-519e-5p gene" or "hsa-miR-519e-5p" used herein includes the hsa-miR-519e-5p gene (miRBase Accession No. MIMAT0002828) shown in SEQ ID NO: 47, a homolog or an ortholog of a different organism species, and the like. The hsa-miR-519e-5p gene can be obtained by a method described in Bentwich I et al., 2005, Nat. Genet., Vol. 37, pp. 766-770. Also, "hsa-mir-519e" (miRBase Accession No. MI0003145; SEQ ID NO: 440) having a hairpin-like structure is known as a precursor of "hsa-miR-519e-5p."

The term "hsa-miR-512-5p gene" or "hsa-miR-512-5p" used herein includes the hsa-miR-512-5p gene (miRBase Accession No. MIMAT0002822) shown in SEQ ID NO: 48, a homolog or an ortholog of a different organism species, and the like. The hsa-miR-512-5p gene can be obtained by a method described in Bentwich I et al., 2005, Nat. Genet., Vol. 37, pp. 766-770. Also, "hsa-mir-512-1 and hsa-mir-512-2" (miRBase Accession Nos. MI0003140 and MI0003141; SEQ ID NOs: 441 and 442) each having a hairpin-like structure are known as precursors of "hsa-miR-512-5p."

The term "hsa-miR-5088-5p gene" or "hsa-miR-5088-5p" used herein includes the hsa-miR-5088-5p gene (miRBase Accession No. MIMAT0021080) shown in SEQ ID NO: 49, a homolog or an ortholog of a different organism species, and the like. The hsa-miR-5088-5p gene can be obtained by a method described in Ding N et al., 2011, J. Radiat. Res., Vol. 52, pp. 425-432. Also, "hsa-mir-5088" (miRBase Accession No. MI0017977; SEQ ID NO: 443) having a hairpin-like structure is known as a precursor of "hsa-miR-5088-5p."

The term "hsa-miR-1909-3p gene" or "hsa-miR-1909-3p" used herein includes the hsa-miR-1909-3p gene (miRBase Accession No. MIMAT0007883) shown in SEQ ID NO: 50, a homolog or an ortholog of a different organism species, and the like. The hsa-miR-1909-3p gene can be obtained by a method described in Bar M et al., 2008, Stem Cells, Vol. 26, pp. 2496-2505. Also, "hsa-mir-1909" (miRBase Accession No. MI0008330; SEQ ID NO: 444) having a hairpin-like structure is known as a precursor of "hsa-miR-1909-3p."

The term "hsa-miR-6511a-5p gene" or "hsa-miR-6511a-5p" used herein includes the hsa-miR-6511a-5p gene (miRBase Accession No. MIMAT0025478) shown in SEQ ID NO: 51, a homolog or an ortholog of a different organism species, and the like. The hsa-miR-6511a-5p gene can be obtained by a method described in Joyce C E et al., 2011, Hum. Mol. Genet., Vol. 20, pp. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566; SEQ ID NOs: 445, 446, 447, and 448) each having a hairpin-like structure are known as precursors of "hsa-miR-6511a-5p."

The term "hsa-miR-4734 gene" or "hsa-miR-4734" used herein includes the hsa-miR-4734 gene (miRBase Accession No. MIMAT0019859) shown in SEQ ID NO: 52, a homolog or an ortholog of a different organism species, and the like. The hsa-miR-4734 gene can be obtained by a method described in Persson H et al., 2011, Cancer Res., Vol. 71, pp. 78-86. Also, "hsa-mir-4734" (miRBase Accession No. MI0017371; SEQ ID NO: 449) having a hairpin-like structure is known as a precursor of "hsa-miR-4734."

The term "hsa-miR-936 gene" or "hsa-miR-936" used herein includes the hsa-miR-936 gene (miRBase Accession No. MIMAT0004979) shown in SEQ ID NO: 53, a homolog or an ortholog of a different organism species, and the like. The hsa-miR-936 gene can be obtained by a method described in Lui W O et al., 2007, Cancer Res., Vol. 67, pp. 6031-6043. Also, "hsa-mir-936" (miRBase Accession No. MI0005758; SEQ ID NO: 450) having a hairpin-like structure is known as a precursor of "hsa-miR-936."

The term "hsa-miR-1249-3p gene" or "hsa-miR-1249-3p" used herein includes the hsa-miR-1249-3p gene (miRBase Accession No. MIMAT0005901) shown in SEQ ID NO: 54, a homolog or an ortholog of a different organism species, and the like. The hsa-miR-1249-3p gene can be obtained by a method described in Morin R D et al., 2008, Genome Res., Vol. 18, pp. 610-621. Also, "hsa-mir-1249" (miRBase Accession No. MI0006384; SEQ ID NO: 451) having a hairpin-like structure is known as a precursor of "hsa-miR-1249-3p."

The term "hsa-miR-6777-5p gene" or "hsa-miR-6777-5p" used herein includes the hsa-miR-6777-5p gene (miRBase Accession No. MIMAT0027454) shown in SEQ ID NO: 55, a homolog or an ortholog of a different organism species, and the like. The hsa-miR-6777-5p gene can be obtained by a method described in Ladewig E et al., 2012, Genome Res., Vol. 22, pp. 1634-1645. Also, "hsa-mir-6777" (miRBase Accession No. MI0022622; SEQ ID NO: 428) having a hairpin-like structure is known as a precursor of "hsa-miR-6777-5p."

The term "hsa-miR-4487 gene" or "hsa-miR-4487" used herein includes the hsa-miR-4487 gene (miRBase Accession No. MIMAT0019021) shown in SEQ ID NO: 56, a homolog or an ortholog of a different organism species, and the like. The hsa-miR-4487 gene can be obtained by a method described in Jima D D et al., 2010, Blood, Vol. 116, e118-e127. Also, "hsa-mir-4487" (miRBase Accession No. MI0016848; SEQ ID NO: 452) having a hairpin-like structure is known as a precursor of "hsa-miR-4487."

The term "hsa-miR-3155a gene" or "hsa-miR-3155a" used herein includes the hsa-miR-3155a gene (miRBase Accession No. MIMAT0015029) shown in SEQ ID NO: 57, a homolog or an ortholog of a different organism species, and the like. The hsa-miR-3155a gene can be obtained by a method described in Stark M S et al., 2010, PLoS One, Vol. 5, e9685. Also, "hsa-mir-3155a" (miRBase Accession No. MI0014183; SEQ ID NO: 453) having a hairpin-like structure is known as a precursor of "hsa-miR-3155a."

The term "hsa-miR-563 gene" or "hsa-miR-563" used herein includes the hsa-miR-563 gene (miRBase Accession No. MIMAT0003227) shown in SEQ ID NO: 58, a homolog or an ortholog of a different organism species, and the like. The hsa-miR-563 gene can be obtained by a method described in Cummins J M et al., 2006, Proc. Natl. Acad. Sci. U.S.A., Vol. 103, pp. 3687-3692. Also, "hsa-mir-563" (miRBase Accession No. MI0003569; SEQ ID NO: 454) having a hairpin-like structure is known as a precursor of "hsa-miR-563."

The term "hsa-miR-4741 gene" or "hsa-miR-4741" used herein includes the hsa-miR-4741 gene (miRBase Accession No. MIMAT0019871) shown in SEQ ID NO: 59, a homolog or an ortholog of a different organism species, and the like. The hsa-miR-4741 gene can be obtained by a method described in Persson H et al., 2011, Cancer Res., Vol. 71, pp. 78-86. Also, "hsa-mir-4741" (miRBase Accession No. MI0017379; SEQ ID NO: 455) having a hairpin-like structure is known as a precursor of "hsa-miR-4741."

The term "hsa-miR-6788-5p gene" or "hsa-miR-6788-5p" used herein includes the hsa-miR-6788-5p gene (miRBase Accession No. MIMAT0027476) shown in SEQ ID NO: 60, a homolog or an ortholog of a different organism species, and the like. The hsa-miR-6788-5p gene can be obtained by a method described in Ladewig E et al., 2012, Genome Res., Vol. 22, pp. 1634-1645. Also, "hsa-mir-6788" (miRBase Accession No. MI0022633; SEQ ID NO: 456) having a hairpin-like structure is known as a precursor of "hsa-miR-6788-5p."

The term "hsa-miR-4433b-5p gene" or "hsa-miR-4433b-5p" used herein includes the hsa-miR-4433b-5p gene (miRBase Accession No. MIMAT0030413) shown in SEQ ID NO: 61, a homolog or an ortholog of a different organism species, and the like. The hsa-miR-4433b-5p gene can be obtained by a method described in Ple H et al., 2012, PLoS One, Vol. 7, e50746. Also, "hsa-mir-4433b" (miRBase Accession No. MI0025511; SEQ ID NO: 457) having a hairpin-like structure is known as a precursor of "hsa-miR-4433b-5p."

The term "hsa-miR-323a-5p gene" or "hsa-miR-323a-5p" used herein includes the hsa-miR-323a-5p gene (miRBase Accession No. MIMAT0004696) shown in SEQ ID NO: 62, a homolog or an ortholog of a different organism species, and the like. The hsa-miR-323a-5p gene can be obtained by a method described in Kim J et al., 2004, Proc. Natl. Acad. Sci. U.S.A., Vol. 101, pp. 360-365. Also, "hsa-mir-323a" (miRBase Accession No. MI0000807; SEQ ID NO: 458) having a hairpin-like structure is known as a precursor of "hsa-miR-323a-5p."

The term "hsa-miR-6811-5p gene" or "hsa-miR-6811-5p" used herein includes the hsa-miR-6811-5p gene (miRBase Accession No. MIMAT0027522) shown in SEQ ID NO: 63, a homolog or an ortholog of a different organism species, and the like. The hsa-miR-6811-5p gene can be obtained by a method described in Ladewig E et al., 2012, Genome Res., Vol. 22, pp. 1634-1645. Also, "hsa-mir-6811" (miRBase Accession No. MI0022656; SEQ ID NO: 459) having a hairpin-like structure is known as a precursor of "hsa-miR-6811-5p."

The term "hsa-miR-6721-5p gene" or "hsa-miR-6721-5p" used herein includes the hsa-miR-6721-5p gene (miRBase Accession No. MIMAT0025852) shown in SEQ ID NO: 64, a homolog or an ortholog of a different organism species, and the like. The hsa-miR-6721-5p gene can be obtained by a method described in Li Y et al., 2012, Gene, Vol. 497, pp. 330-335. Also, "hsa-mir-6721" (miRBase Accession No. MI0022556; SEQ ID NO: 460) having a hairpin-like structure is known as a precursor of "hsa-miR-6721-5p."

The term "hsa-miR-5004-5p gene" or "hsa-miR-5004-5p" used herein includes the hsa-miR-5004-5p gene (miRBase Accession No. MIMAT0021027) shown in SEQ ID NO: 65, a homolog or an ortholog of a different organism species, and the like. The hsa-miR-5004-5p gene can be obtained by a method described in Hansen T B et al., 2011, RNA Biol., Vol. 8, pp. 378-383. Also, "hsa-mir-5004" (miRBase Accession No. MI0017870; SEQ ID NO: 461) having a hairpin-like structure is known as a precursor of "hsa-miR-5004-5p."

The term "hsa-miR-6509-3p gene" or "hsa-miR-6509-3p" used herein includes the hsa-miR-6509-3p gene (miRBase Accession No. MIMAT0025475) shown in SEQ ID NO: 66, a homolog or an ortholog of a different organism species, and the like. The hsa-miR-6509-3p gene can be obtained by a method described in Joyce C E et al., 2011, Hum. Mol. Genet., Vol. 20, pp. 4025-4040. Also, "hsa-mir-6509" (miRBase Accession No. MI0022221; SEQ ID NO: 462) having a hairpin-like structure is known as a precursor of "hsa-miR-6509-3p."

The term "hsa-miR-648 gene" or "hsa-miR-648" used herein includes the hsa-miR-648 gene (miRBase Accession No. MIMAT0003318) shown in SEQ ID NO: 67, a homolog or an ortholog of a different organism species, and the like. The hsa-miR-648 gene can be obtained by a method described in Cummins J M et al., 2006, Proc. Natl. Acad. Sci. U.S.A., Vol. 103, pp. 3687-3692. Also, "hsa-mir-648"

(miRBase Accession No. MI0003663; SEQ ID NO: 463) having a hairpin-like structure is known as a precursor of "hsa-miR-648."

The term "hsa-miR-3917 gene" or "hsa-miR-3917" used herein includes the hsa-miR-3917 gene (miRBase Accession No. MIMAT0018191) shown in SEQ ID NO: 68, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423; SEQ ID NO: 464) having a hairpin-like structure is known as a precursor of "hsa-miR-3917."

The term "hsa-miR-6087 gene" or "hsa-miR-6087" used herein includes the hsa-miR-6087 gene (miRBase Accession No. MIMAT0023712) shown in SEQ ID NO: 69, a homolog or an ortholog of a different organism species, and the like. The hsa-miR-6087 gene can be obtained by a method described in Yoo J K et al., 2012, Stem Cells Dev., Vol. 21, pp. 2049-2057. Also, "hsa-mir-6087" (miRBase Accession No. MI0020364; SEQ ID NO: 465) having a hairpin-like structure is known as a precursor of "hsa-miR-6087."

The term "hsa-miR-1470 gene" or "hsa-miR-1470" used herein includes the hsa-miR-1470 gene (miRBase Accession No. MIMAT0007348) shown in SEQ ID NO: 70, a homolog or an ortholog of a different organism species, and the like. The hsa-miR-1470 gene can be obtained by a method described in Kawaji H et al., 2008, BMC Genomics, Vol. 9, p. 157. Also, "hsa-mir-1470" (miRBase Accession No. MI0007075; SEQ ID NO: 466) having a hairpin-like structure is known as a precursor of "hsa-miR-1470."

The term "hsa-miR-586 gene" or "hsa-miR-586" used herein includes the hsa-miR-586 gene (miRBase Accession No. MIMAT0003252) shown in SEQ ID NO: 71, a homolog or an ortholog of a different organism species, and the like. The hsa-miR-586 gene can be obtained by a method described in Cummins J M et al., 2006, Proc. Natl. Acad. Sci. U.S.A., Vol. 103, pp. 3687-3692. Also, "hsa-mir-586" (miRBase Accession No. MI0003594; SEQ ID NO: 467) having a hairpin-like structure is known as a precursor of "hsa-miR-586."

The term "hsa-miR-3150a-5p gene" or "hsa-miR-3150a-5p" used herein includes the hsa-miR-3150a-5p gene (miRBase Accession No. MIMAT0019206) shown in SEQ ID NO: 72, a homolog or an ortholog of a different organism species, and the like. The hsa-miR-3150a-5p gene can be obtained by a method described in Stark M S et al., 2010, PLoS One, Vol. 5, e9685. Also, "hsa-mir-3150a" (miRBase Accession No. MI0014177; SEQ ID NO: 468) having a hairpin-like structure is known as a precursor of "hsa-miR-3150a-5p."

The term "hsa-miR-105-3p gene" or "hsa-miR-105-3p" used herein includes the hsa-miR-105-3p gene (miRBase Accession No. MIMAT0004516) shown in SEQ ID NO: 73, a homolog or an ortholog of a different organism species, and the like. The hsa-miR-105-3p gene can be obtained by a method described in Mourelatos Z et al., 2002, Genes Dev., Vol. 16, pp. 720-728. Also, "hsa-mir-105-1 and hsa-mir-105-2" (miRBase Accession Nos. MI0000111 and MI0000112; SEQ ID NOs: 469 and 470) each having a hairpin-like structure are known as precursors of "hsa-miR-105-3p."

The term "hsa-miR-7973 gene" or "hsa-miR-7973" used herein includes the hsa-miR-7973 gene (miRBase Accession No. MIMAT0031176) shown in SEQ ID NO: 74, a homolog or an ortholog of a different organism species, and the like. The hsa-miR-7973 gene can be obtained by a method described in Velthut-Meikas A et al., 2013, Mol. Endocrinol., Vol. 27, pp. 1128-1141. Also, "hsa-mir-7973-1 and hsa-mir-7973-2" (miRBase Accession Nos. MI0025748 and MI0025749; SEQ ID NOs: 471 and 472) each having a hairpin-like structure are known as precursors of "hsa-miR-7973."

The term "hsa-miR-1914-5p gene" or "hsa-miR-1914-5p" used herein includes the hsa-miR-1914-5p gene (miRBase Accession No. MIMAT0007889) shown in SEQ ID NO: 75, a homolog or an ortholog of a different organism species, and the like. The hsa-miR-1914-5p gene can be obtained by a method described in Bar M et al., 2008, Stem Cells, Vol. 26, pp. 2496-2505. Also, "hsa-mir-1914" (miRBase Accession No. MI0008335; SEQ ID NO: 473) having a hairpin-like structure is known as a precursor of "hsa-miR-1914-5p."

The term "hsa-miR-4749-3p gene" or "hsa-miR-4749-3p" used herein includes the hsa-miR-4749-3p gene (miRBase Accession No. MIMAT0019886) shown in SEQ ID NO: 76, a homolog or an ortholog of a different organism species, and the like. The hsa-miR-4749-3p gene can be obtained by a method described in Persson H et al., 2011, Cancer Res., Vol. 71, pp. 78-86. Also, "hsa-mir-4749" (miRBase Accession No. MI0017388; SEQ ID NO: 474) having a hairpin-like structure is known as a precursor of "hsa-miR-4749-3p."

The term "hsa-miR-15b-5p gene" or "hsa-miR-15b-5p" used herein includes the hsa-miR-15b-5p gene (miRBase Accession No. MIMAT0000417) shown in SEQ ID NO: 77, a homolog or an ortholog of a different organism species, and the like. The hsa-miR-15b-5p gene can be obtained by a method described in Lagos-Quintana M et al., 2002, Curr. Biol., Vol. 12, pp. 735-739. Also, "hsa-mir-15b" (miRBase Accession No. MI0000438; SEQ ID NO: 475) having a hairpin-like structure is known as a precursor of "hsa-miR-15b-5p."

The term "hsa-miR-1289 gene" or "hsa-miR-1289" used herein includes the hsa-miR-1289 gene (miRBase Accession No. MIMAT0005879) shown in SEQ ID NO: 78, a homolog or an ortholog of a different organism species, and the like. The hsa-miR-1289 gene can be obtained by a method described in Morin R D et al., 2008, Genome Res., Vol. 18, pp. 610-621. Also, "hsa-mir-1289-1 and hsa-mir-1289-2" (miRBase Accession Nos. MI0006350 and MI0006351; SEQ ID NOs: 476 and 477) each having a hairpin-like structure are known as precursors of "hsa-miR-1289."

The term "hsa-miR-4433a-5p gene" or "hsa-miR-4433a-5p" used herein includes the hsa-miR-4433a-5p gene (miRBase Accession No. MIMAT0020956) shown in SEQ ID NO: 79, a homolog or an ortholog of a different organism species, and the like. The hsa-miR-4433a-5p gene can be obtained by a method described in Jima D D et al., 2010, Blood, Vol. 116, e118-e127. Also, "hsa-mir-4433a" (miRBase Accession No. MI0016773; SEQ ID NO: 478) having a hairpin-like structure is known as a precursor of "hsa-miR-4433a-5p."

The term "hsa-miR-3666 gene" or "hsa-miR-3666" used herein includes the hsa-miR-3666 gene (miRBase Accession No. MIMAT0018088) shown in SEQ ID NO: 80, a homolog or an ortholog of a different organism species, and the like. The hsa-miR-3666 gene can be obtained by a method described in Xie X et al., 2005, Nature, Vol. 434, pp. 338-345. Also, "hsa-mir-3666" (miRBase Accession No. MI0016067; SEQ ID NO: 479) having a hairpin-like structure is known as a precursor of "hsa-miR-3666."

The term "hsa-miR-3186-3p gene" or "hsa-miR-3186-3p" used herein includes the hsa-miR-3186-3p gene (miRBase Accession No. MIMAT0015068) shown in SEQ ID NO: 81, a homolog or an ortholog of a different organism species, and the like. The hsa-miR-3186-3p gene can be obtained by a method described in Creighton C J et al., 2010, PLoS One, Vol. 5, e9637. Also, "hsa-mir-3186" (miRBase Accession No. MI0014229; SEQ ID NO: 480) having a hairpin-like structure is known as a precursor of "hsa-miR-3186-3p."

The term "hsa-miR-4725-5p gene" or "hsa-miR-4725-5p" used herein includes the hsa-miR-4725-5p gene (miRBase Accession No. MIMAT0019843) shown in SEQ ID NO: 82, a homolog or an ortholog of a different organism species, and the like. The hsa-miR-4725-5p gene can be obtained by a method described in Persson H et al., 2011, Cancer Res., Vol. 71, pp. 78-86. Also, "hsa-mir-4725" (miRBase Accession No. MI0017362; SEQ ID NO: 431) having a hairpin-like structure is known as a precursor of "hsa-miR-4725-5p."

The term "hsa-miR-4488 gene" or "hsa-miR-4488" used herein includes the hsa-miR-4488 gene (miRBase Accession No. MIMAT0019022) shown in SEQ ID NO: 83, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849; SEQ ID NO: 481) having a hairpin-like structure is known as a precursor of "hsa-miR-4488."

The term "hsa-miR-4474-3p gene" or "hsa-miR-4474-3p" used herein includes the hsa-miR-4474-3p gene (miRBase Accession No. MIMAT0019001) shown in SEQ ID NO: 84, a homolog or an ortholog of a different organism species, and the like. The hsa-miR-4474-3p gene can be obtained by a method described in Jima D D et al., 2010, Blood, Vol. 116, e118-e127. Also, "hsa-mir-4474" (miRBase Accession No. MI0016826; SEQ ID NO: 482) having a hairpin-like structure is known as a precursor of "hsa-miR-4474-3p."

The term "hsa-miR-6731-3p gene" or "hsa-miR-6731-3p" used herein includes the hsa-miR-6731-3p gene (miRBase Accession No. MIMAT0027364) shown in SEQ ID NO: 85, a homolog or an ortholog of a different organism species, and the like. The hsa-miR-6731-3p gene can be obtained by a method described in Ladewig E et al., 2012, Genome Res., Vol. 22, pp. 1634-1645. Also, "hsa-mir-6731" (miRBase Accession No. MI0022576; SEQ ID NO: 483) having a hairpin-like structure is known as a precursor of "hsa-miR-6731-3p."

The term "hsa-miR-4640-3p gene" or "hsa-miR-4640-3p" used herein includes the hsa-miR-4640-3p gene (miRBase Accession No. MIMAT0019700) shown in SEQ ID NO: 86, a homolog or an ortholog of a different organism species, and the like. The hsa-miR-4640-3p gene can be obtained by a method described in Persson H et al., 2011, Cancer Res., Vol. 71, pp. 78-86. Also, "hsa-mir-4640" (miRBase Accession No. MI0017267; SEQ ID NO: 484) having a hairpin-like structure is known as a precursor of "hsa-miR-4640-3p."

The term "hsa-miR-202-5p gene" or "hsa-miR-202-5p" used herein includes the hsa-miR-202-5p gene (miRBase Accession No. MIMAT0002810) shown in SEQ ID NO: 87, a homolog or an ortholog of a different organism species, and the like. The hsa-miR-202-5p gene can be obtained by a method described in Bentwich I et al., 2005, Nat. Genet., Vol. 37, pp. 766-770. Also, "hsa-mir-202" (miRBase Accession No. MI0003130; SEQ ID NO: 485) having a hairpin-like structure is known as a precursor of "hsa-miR-202-5p."

The term "hsa-miR-6816-5p gene" or "hsa-miR-6816-5p" used herein includes the hsa-miR-6816-5p gene (miRBase Accession No. MIMAT0027532) shown in SEQ ID NO: 88, a homolog or an ortholog of a different organism species, and the like. The hsa-miR-6816-5p gene can be obtained by a method described in Ladewig E et al., 2012, Genome Res., Vol. 22, pp. 1634-1645. Also, "hsa-mir-6816" (miRBase Accession No. MI0022661; SEQ ID NO: 486) having a hairpin-like structure is known as a precursor of "hsa-miR-6816-5p."

The term "hsa-miR-638 gene" or "hsa-miR-638" used herein includes the hsa-miR-638 gene (miRBase Accession No. MIMAT0003308) shown in SEQ ID NO: 89, a homolog or an ortholog of a different organism species, and the like. The hsa-miR-638 gene can be obtained by a method described in Cummins J M et al., 2006, Proc. Natl. Acad. Sci. U.S.A., Vol. 103, pp. 3687-3692. Also, "hsa-mir-638" (miRBase Accession No. MI0003653; SEQ ID NO: 487) having a hairpin-like structure is known as a precursor of "hsa-miR-638."

The term "hsa-miR-6821-5p gene" or "hsa-miR-6821-5p" used herein includes the hsa-miR-6821-5p gene (miRBase Accession No. MIMAT0027542) shown in SEQ ID NO: 90, a homolog or an ortholog of a different organism species, and the like. The hsa-miR-6821-5p gene can be obtained by a method described in Ladewig E et al., 2012, Genome Res., Vol. 22, pp. 1634-1645. Also, "hsa-mir-6821" (miRBase Accession No. MI0022666; SEQ ID NO: 488) having a hairpin-like structure is known as a precursor of "hsa-miR-6821-5p."

The term "hsa-miR-1247-3p gene" or "hsa-miR-1247-3p" used herein includes the hsa-miR-1247-3p gene (miRBase Accession No. MIMAT0022721) shown in SEQ ID NO: 91, a homolog or an ortholog of a different organism species, and the like. The hsa-miR-1247-3p gene can be obtained by a method described in Morin R D et al., 2008, Genome Res., Vol. 18, pp. 610-621. Also, "hsa-mir-1247" (miRBase Accession No. MI0006382; SEQ ID NO: 489) having a hairpin-like structure is known as a precursor of "hsa-miR-1247-3p."

The term "hsa-miR-6765-5p gene" or "hsa-miR-6765-5p" used herein includes the hsa-miR-6765-5p gene (miRBase Accession No. MIMAT0027430) shown in SEQ ID NO: 92, a homolog or an ortholog of a different organism species, and the like. The hsa-miR-6765-5p gene can be obtained by a method described in Ladewig E et al., 2012, Genome Res., Vol. 22, pp. 1634-1645. Also, "hsa-mir-6765" (miRBase Accession No. MI0022610; SEQ ID NO: 490) having a hairpin-like structure is known as a precursor of "hsa-miR-6765-5p."

The term "hsa-miR-6800-5p gene" or "hsa-miR-6800-5p" used herein includes the hsa-miR-6800-5p gene (miRBase Accession No. MIMAT0027500) shown in SEQ ID NO: 93, a homolog or an ortholog of a different organism species, and the like. The hsa-miR-6800-5p gene can be obtained by a method described in Ladewig E et al., 2012, Genome Res., Vol. 22, pp. 1634-1645. Also, "hsa-mir-6800" (miRBase Accession No. MI0022645; SEQ ID NO: 491) having a hairpin-like structure is known as a precursor of "hsa-miR-6800-5p."

The term "hsa-miR-3928-3p gene" or "hsa-miR-3928-3p" used herein includes the hsa-miR-3928-3p gene (miRBase Accession No. MIMAT0018205) shown in SEQ ID NO: 94, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438; SEQ ID NO: 492) having a hairpin-like structure is known as a precursor of "hsa-miR-3928-3p."

The term "hsa-miR-3940-5p gene" or "hsa-miR-3940-5p" used herein includes the hsa-miR-3940-5p gene (miRBase Accession No. MIMAT0019229) shown in SEQ ID NO: 95, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597; SEQ ID NO: 493) having a hairpin-like structure is known as a precursor of "hsa-miR-3940-5p."

The term "hsa-miR-3960 gene" or "hsa-miR-3960" used herein includes the hsa-miR-3960 gene (miRBase Accession No. MIMAT0019337) shown in SEQ ID NO: 96, a homolog or an ortholog of a different organism species, and the like. The hsa-miR-3960 gene can be obtained by a method described in Hu R et al., 2011, J. Biol. Chem., Vol. 286, pp. 12328-12339. Also, "hsa-mir-3960" (miRBase Accession No. MI0016964; SEQ ID NO: 494) having a hairpin-like structure is known as a precursor of "hsa-miR-3960."

The term "hsa-miR-6775-5p gene" or "hsa-miR-6775-5p" used herein includes the hsa-miR-6775-5p gene (miRBase Accession No. MIMAT0027450) shown in SEQ ID NO: 97, a homolog or an ortholog of a different organism species, and the like. The hsa-miR-6775-5p gene can be obtained by a method described in Ladewig E et al., 2012, Genome Res., Vol. 22, pp. 1634-1645. Also, "hsa-mir-6775" (miRBase Accession No. MI0022620; SEQ ID NO: 495) having a hairpin-like structure is known as a precursor of "hsa-miR-6775-5p."

The term "hsa-miR-3178 gene" or "hsa-miR-3178" used herein includes the hsa-miR-3178 gene (miRBase Accession No. MIMAT0015055) shown in SEQ ID NO: 98, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212; SEQ ID NO: 496) having a hairpin-like structure is known as a precursor of "hsa-miR-3178."

The term "hsa-miR-1202 gene" or "hsa-miR-1202" used herein includes the hsa-miR-1202 gene (miRBase Accession No. MIMAT0005865) shown in SEQ ID NO: 99, a homolog or an ortholog of a different organism species, and the like. The hsa-miR-1202 gene can be obtained by a method described in Marton S et al., 2008, Leukemia, Vol. 22, pp. 330-338. Also, "hsa-mir-1202" (miRBase Accession No. MI0006334; SEQ ID NO: 497) having a hairpin-like structure is known as a precursor of "hsa-miR-1202."

The term "hsa-miR-6790-5p gene" or "hsa-miR-6790-5p" used herein includes the hsa-miR-6790-5p gene (miRBase Accession No. MIMAT0027480) shown in SEQ ID NO: 100, a homolog or an ortholog of a different organism species, and the like. The hsa-miR-6790-5p gene can be obtained by a method described in Ladewig E et al., 2012, Genome Res., Vol. 22, pp. 1634-1645. Also, "hsa-mir-6790" (miRBase Accession No. MI0022635; SEQ ID NO: 498) having a hairpin-like structure is known as a precursor of "hsa-miR-6790-5p."

The term "hsa-miR-4731-3p gene" or "hsa-miR-4731-3p" used herein includes the hsa-miR-4731-3p gene (miRBase Accession No. MIMAT0019854) shown in SEQ ID NO: 101, a homolog or an ortholog of a different organism species, and the like. The hsa-miR-4731-3p gene can be obtained by a method described in Persson H et al., 2011, Cancer Res., Vol. 71, pp. 78-86. Also, "hsa-mir-4731" (miRBase Accession No. MI0017368; SEQ ID NO: 499) having a hairpin-like structure is known as a precursor of "hsa-miR-4731-3p."

The term "hsa-miR-2681-3p gene" or "hsa-miR-2681-3p" used herein includes the hsa-miR-2681-3p gene (miRBase Accession No. MIMAT0013516) shown in SEQ ID NO: 102, a homolog or an ortholog of a different organism species, and the like. The hsa-miR-2681-3p gene can be obtained by a method described in Persson H et al., 2011, Cancer Res., Vol. 71, pp. 78-86. Also, "hsa-mir-2681" (miRBase Accession No. MI0012062; SEQ ID NO: 500) having a hairpin-like structure is known as a precursor of "hsa-miR-2681-3p."

The term "hsa-miR-6758-5p gene" or "hsa-miR-6758-5p" used herein includes the hsa-miR-6758-5p gene (miRBase Accession No. MIMAT0027416) shown in SEQ ID NO: 103, a homolog or an ortholog of a different organism species, and the like. The hsa-miR-6758-5p gene can be obtained by a method described in Ladewig E et al., 2012, Genome Res., Vol. 22, pp. 1634-1645. Also, "hsa-mir-6758" (miRBase Accession No. MI0022603; SEQ ID NO: 501) having a hairpin-like structure is known as a precursor of "hsa-miR-6758-5p."

The term "hsa-miR-8072 gene" or "hsa-miR-8072" used herein includes the hsa-miR-8072 gene (miRBase Accession No. MIMAT0030999) shown in SEQ ID NO: 104, a homolog or an ortholog of a different organism species, and the like. The hsa-miR-8072 gene can be obtained by a method described in Wang H J et al., 2013, Shock, Vol. 39, pp. 480-487. Also, "hsa-mir-8072" (miRBase Accession No. MI0025908; SEQ ID NO: 502) having a hairpin-like structure is known as a precursor of "hsa-miR-8072."

The term "hsa-miR-518d-3p gene" or "hsa-miR-518d-3p" used herein includes the hsa-miR-518d-3p gene (miRBase Accession No. MIMAT0002864) shown in SEQ ID NO: 105, a homolog or an ortholog of a different organism species, and the like. The hsa-miR-518d-3p gene can be obtained by a method described in Bentwich I et al., 2005, Nat. Genet., Vol. 37, pp. 766-770. Also, "hsa-mir-518d" (miRBase Accession No. MI0003171; SEQ ID NO: 503) having a hairpin-like structure is known as a precursor of "hsa-miR-518d-3p."

The term "hsa-miR-3606-3p gene" or "hsa-miR-3606-3p" used herein includes the hsa-miR-3606-3p gene (miRBase Accession No. MIMAT0022965) shown in SEQ ID NO: 106, a homolog or an ortholog of a different organism species, and the like. The hsa-miR-3606-3p gene can be obtained by a method described in Witten D et al., 2010, BMC Biol., Vol. 8, p. 58. Also, "hsa-mir-3606" (miRBase Accession No. MI0015996; SEQ ID NO: 504) having a hairpin-like structure is known as a precursor of "hsa-miR-3606-3p."

The term "hsa-miR-4800-5p gene" or "hsa-miR-4800-5p" used herein includes the hsa-miR-4800-5p gene (miRBase Accession No. MIMAT0019978) shown in SEQ ID NO: 107, a homolog or an ortholog of a different organism species, and the like. The hsa-miR-4800-5p gene can be obtained by a method described in Persson H et al., 2011, Cancer Res., Vol. 71, pp. 78-86. Also, "hsa-mir-4800" (miRBase Accession No. MI0017448; SEQ ID NO: 505) having a hairpin-like structure is known as a precursor of "hsa-miR-4800-5p."

The term "hsa-miR-1292-3p gene" or "hsa-miR-1292-3p" used herein includes the hsa-miR-1292-3p gene (miRBase Accession No. MIMAT0022948) shown in SEQ ID NO: 108, a homolog or an ortholog of a different organism species, and the like. The hsa-miR-1292-3p gene can be obtained by a method described in Morin R D et al., 2008, Genome Res., Vol. 18, pp. 610-621. Also, "hsa-mir-1292" (miRBase Accession No. MI0006433; SEQ ID NO: 506) having a hairpin-like structure is known as a precursor of "hsa-miR-1292-3p."

The term "hsa-miR-6784-3p gene" or "hsa-miR-6784-3p" used herein includes the hsa-miR-6784-3p gene (miRBase Accession No. MIMAT0027469) shown in SEQ ID NO: 109, a homolog or an ortholog of a different organism species, and the like. The hsa-miR-6784-3p gene can be obtained by a method described in Ladewig E et al., 2012, Genome Res., Vol. 22, pp. 1634-1645. Also, "hsa-mir-6784" (miRBase Accession No. MI0022629; SEQ ID NO: 507) having a hairpin-like structure is known as a precursor of "hsa-miR-6784-3p."

The term "hsa-miR-4450 gene" or "hsa-miR-4450" used herein includes the hsa-miR-4450 gene (miRBase Accession No. MIMAT0018971) shown in SEQ ID NO: 110, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795; SEQ ID NO: 508) having a hairpin-like structure is known as a precursor of "hsa-miR-4450."

The term "hsa-miR-6132 gene" or "hsa-miR-6132" used herein includes the hsa-miR-6132 gene (miRBase Accession No. MIMAT0024616) shown in SEQ ID NO: 111, a homolog or an ortholog of a different organism species, and the like. The hsa-miR-6132 gene can be obtained by a method described in Dannemann M et al., 2012, Genome Biol. Evol., Vol. 4, pp. 552-564. Also, "hsa-mir-6132" (miRBase Accession No. MI0021277; SEQ ID NO: 509) having a hairpin-like structure is known as a precursor of "hsa-miR-6132."

The term "hsa-miR-4716-5p gene" or "hsa-miR-4716-5p" used herein includes the hsa-miR-4716-5p gene (miRBase Accession No. MIMAT0019826) shown in SEQ ID NO: 112, a homolog or an ortholog of a different organism species, and the like. The hsa-miR-4716-5p gene can be obtained by a method described in Persson H et al., 2011, Cancer Res., Vol. 71, pp. 78-86. Also, "hsa-mir-4716" (miRBase Accession No. MI0017350; SEQ ID NO: 510) having a hairpin-like structure is known as a precursor of "hsa-miR-4716-5p."

The term "hsa-miR-6860 gene" or "hsa-miR-6860" used herein includes the hsa-miR-6860 gene (miRBase Accession No. MIMAT0027622) shown in SEQ ID NO: 113, a homolog or an ortholog of a different organism species, and the like. The hsa-miR-6860 gene can be obtained by a method described in Ladewig E et al., 2012, Genome Res., Vol. 22, pp. 1634-1645. Also, "hsa-mir-6860" (miRBase Accession No. MI0022707; SEQ ID NO: 511) having a hairpin-like structure is known as a precursor of "hsa-miR-6860."

The term "hsa-miR-1268b gene" or "hsa-miR-1268b" used herein includes the hsa-miR-1268b gene (miRBase Accession No. MIMAT0018925) shown in SEQ ID NO: 114, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748; SEQ ID NO: 512) having a hairpin-like structure is known as a precursor of "hsa-miR-1268b."

The term "hsa-miR-378d gene" or "hsa-miR-378d" used herein includes the hsa-miR-378d gene (miRBase Accession No. MIMAT0018926) shown in SEQ ID NO: 115, a homolog or an ortholog of a different organism species, and the like. The hsa-miR-378d gene can be obtained by a method described in Berezikov E et al., 2006, Genome Res., Vol. 16, pp. 1289-1298. Also, "hsa-mir-378d-1 and hsa-mir-378d-2" (miRBase Accession Nos. MI0016749 and MI0003840; SEQ ID NOs: 513 and 514) each having a hairpin-like structure are known as precursors of "hsa-miR-378d."

The term "hsa-miR-4701-5p gene" or "hsa-miR-4701-5p" used herein includes the hsa-miR-4701-5p gene (miRBase Accession No. MIMAT0019798) shown in SEQ ID NO: 116, a homolog or an ortholog of a different organism species, and the like. The hsa-miR-4701-5p gene can be obtained by a method described in Persson H et al., 2011, Cancer Res., Vol. 71, pp. 78-86. Also, "hsa-mir-4701" (miRBase Accession No. MI0017334; SEQ ID NO: 515) having a hairpin-like structure is known as a precursor of "hsa-miR-4701-5p."

The term "hsa-miR-4329 gene" or "hsa-miR-4329" used herein includes the hsa-miR-4329 gene (miRBase Accession No. MIMAT0016923) shown in SEQ ID NO: 117, a homolog or an ortholog of a different organism species, and the like. The hsa-miR-4329 gene can be obtained by a method described in Goff L A et al., 2009, PLoS One, Vol. 4, e7192. Also, "hsa-mir-4329" (miRBase Accession No. MI0015901; SEQ ID NO: 516) having a hairpin-like structure is known as a precursor of "hsa-miR-4329."

The term "hsa-miR-185-3p gene" or "hsa-miR-185-3p" used herein includes the hsa-miR-185-3p gene (miRBase Accession No. MIMAT0004611) shown in SEQ ID NO: 118, a homolog or an ortholog of a different organism species, and the like. The hsa-miR-185-3p gene can be obtained by a method described in Lagos-Quintana M et al., 2003, RNA, Vol. 9, pp. 175-179. Also, "hsa-mir-185" (miRBase Accession No. MI0000482; SEQ ID NO: 517) having a hairpin-like structure is known as a precursor of "hsa-miR-185-3p."

The term "hsa-miR-552-3p gene" or "hsa-miR-552-3p" used herein includes the hsa-miR-552-3p gene (miRBase Accession No. MIMAT0003215) shown in SEQ ID NO: 119, a homolog or an ortholog of a different organism species, and the like. The hsa-miR-552-3p gene can be obtained by a method described in Cummins J M et al., 2006, Proc. Natl. Acad. Sci. U.S.A., Vol. 103, pp. 3687-3692. Also, "hsa-mir-552" (miRBase Accession No. MI0003557; SEQ ID NO: 518) having a hairpin-like structure is known as a precursor of "hsa-miR-552-3p."

The term "hsa-miR-1273g-5p gene" or "hsa-miR-1273g-5p" used herein includes the hsa-miR-1273g-5p gene (miRBase Accession No. MIMAT0020602) shown in SEQ ID NO: 120, a homolog or an ortholog of a different organism species, and the like. The hsa-miR-1273g-5p gene can be obtained by a method described in Reshmi G et al., 2011, Genomics, Vol. 97, pp. 333-340. Also, "hsa-mir-1273g" (miRBase Accession No. MI0018003; SEQ ID NO: 519) having a hairpin-like structure is known as a precursor of "hsa-miR-1273g-5p."

The term "hsa-miR-6769b-3p gene" or "hsa-miR-6769b-3p" used herein includes the hsa-miR-6769b-3p gene (miRBase Accession No. MIMAT0027621) shown in SEQ ID NO: 121, a homolog or an ortholog of a different organism species, and the like. The hsa-miR-6769b-3p gene can be obtained by a method described in Ladewig E et al., 2012, Genome Res., Vol. 22, pp. 1634-1645. Also, "hsa-mir-6769b" (miRBase Accession No. MI0022706; SEQ ID NO: 520) having a hairpin-like structure is known as a precursor of "hsa-miR-6769b-3p."

The term "hsa-miR-520a-3p gene" or "hsa-miR-520a-3p" used herein includes the hsa-miR-520a-3p gene (miRBase Accession No. MIMAT0002834) shown in SEQ ID NO: 122, a homolog or an ortholog of a different organism species, and the like. The hsa-miR-520a-3p gene can be obtained by a method described in Bentwich I et al., 2005, Nat. Genet., Vol. 37, pp. 766-770. Also, “hsa-mir-520a” (miRBase Accession No. MI0003149; SEQ ID NO: 521) having a hairpin-like structure is known as a precursor of “hsa-miR-520a-3p.”

The term “hsa-miR-4524b-5p gene” or “hsa-miR-4524b-5p” used herein includes the hsa-miR-4524b-5p gene (miRBase Accession No. MIMAT0022255) shown in SEQ ID NO: 123, a homolog or an ortholog of a different organism species, and the like. The hsa-miR-4524b-5p gene can be obtained by a method described in Tandon M et al., 2012, Oral Dis., Vol. 18, pp. 127-131. Also, “hsa-mir-4524b” (miRBase Accession No. MI0019114; SEQ ID NO: 522) having a hairpin-like structure is known as a precursor of “hsa-miR-4524b-5p.”

The term “hsa-miR-4291 gene” or “hsa-miR-4291” used herein includes the hsa-miR-4291 gene (miRBase Accession No. MIMAT0016922) shown in SEQ ID NO: 124, a homolog or an ortholog of a different organism species, and the like. The hsa-miR-4291 gene can be obtained by a method described in Goff L A et al., 2009, PLoS One, Vol. 4, e7192. Also, “hsa-mir-4291” (miRBase Accession No. MI0015900; SEQ ID NO: 523) having a hairpin-like structure is known as a precursor of “hsa-miR-4291.”

The term “hsa-miR-6734-3p gene” or “hsa-miR-6734-3p” used herein includes the hsa-miR-6734-3p gene (miRBase Accession No. MIMAT0027370) shown in SEQ ID NO: 125, a homolog or an ortholog of a different organism species, and the like. The hsa-miR-6734-3p gene can be obtained by a method described in Ladewig E et al., 2012, Genome Res., Vol. 22, pp. 1634-1645. Also, “hsa-mir-6734” (miRBase Accession No. MI0022579; SEQ ID NO: 524) having a hairpin-like structure is known as a precursor of “hsa-miR-6734-3p.”

The term “hsa-miR-143-5p gene” or “hsa-miR-143-5p” used herein includes the hsa-miR-143-5p gene (miRBase Accession No. MIMAT0004599) shown in SEQ ID NO: 126, a homolog or an ortholog of a different organism species, and the like. The hsa-miR-143-5p gene can be obtained by a method described in Lagos-Quintana M et al., 2002, Curr. Biol., Vol. 12, pp. 735-739. Also, “hsa-mir-143” (miRBase Accession No. MI0000459; SEQ ID NO: 525) having a hairpin-like structure is known as a precursor of “hsa-miR-143-5p.”

The term “hsa-miR-939-3p gene” or “hsa-miR-939-3p” used herein includes the hsa-miR-939-3p gene (miRBase Accession No. MIMAT0022939) shown in SEQ ID NO: 127, a homolog or an ortholog of a different organism species, and the like. The hsa-miR-939-3p gene can be obtained by a method described in Lui W O et al., 2007, Cancer Res., Vol. 67, pp. 6031-6043. Also, “hsa-mir-939” (miRBase Accession No. MI0005761; SEQ ID NO: 526) having a hairpin-like structure is known as a precursor of “hsa-miR-939-3p.”

The term “hsa-miR-6889-3p gene” or “hsa-miR-6889-3p” used herein includes the hsa-miR-6889-3p gene (miRBase Accession No. MIMAT0027679) shown in SEQ ID NO: 128, a homolog or an ortholog of a different organism species, and the like. The hsa-miR-6889-3p gene can be obtained by a method described in Ladewig E et al., 2012, Genome Res., Vol. 22, pp. 1634-1645. Also, “hsa-mir-6889” (miRBase Accession No. MI0022736; SEQ ID NO: 527) having a hairpin-like structure is known as a precursor of “hsa-miR-6889-3p.”

The term “hsa-miR-6842-3p gene” or “hsa-miR-6842-3p” used herein includes the hsa-miR-6842-3p gene (miRBase Accession No. MIMAT0027587) shown in SEQ ID NO: 129, a homolog or an ortholog of a different organism species, and the like. The hsa-miR-6842-3p gene can be obtained by a method described in Ladewig E et al., 2012, Genome Res., Vol. 22, pp. 1634-1645. Also, “hsa-mir-6842” (miRBase Accession No. MI0022688; SEQ ID NO: 528) having a hairpin-like structure is known as a precursor of “hsa-miR-6842-3p.”

The term “hsa-miR-4511 gene” or “hsa-miR-4511” used herein includes the hsa-miR-4511 gene (miRBase Accession No. MIMAT0019048) shown in SEQ ID NO: 130, a homolog or an ortholog of a different organism species, and the like. The hsa-miR-4511 gene can be obtained by a method described in Jima D D et al., 2010, Blood, Vol. 116, e118-e127. Also, “hsa-mir-4511” (miRBase Accession No. MI0016877; SEQ ID NO: 529) having a hairpin-like structure is known as a precursor of “hsa-miR-4511.”

The term “hsa-miR-4318 gene” or “hsa-miR-4318” used herein includes the hsa-miR-4318 gene (miRBase Accession No. MIMAT0016869) shown in SEQ ID NO: 131, a homolog or an ortholog of a different organism species, and the like. The hsa-miR-4318 gene can be obtained by a method described in Goff L A et al., 2009, PLoS One, Vol. 4, e7192. Also, “hsa-mir-4318” (miRBase Accession No. MI0015847; SEQ ID NO: 530) having a hairpin-like structure is known as a precursor of “hsa-miR-4318.”

The term “hsa-miR-4653-5p gene” or “hsa-miR-4653-5p” used herein includes the hsa-miR-4653-5p gene (miRBase Accession No. MIMAT0019718) shown in SEQ ID NO: 132, a homolog or an ortholog of a different organism species, and the like. The hsa-miR-4653-5p gene can be obtained by a method described in Persson H et al., 2011, Cancer Res., Vol. 71, pp. 78-86. Also, “hsa-mir-4653” (miRBase Accession No. MI0017281; SEQ ID NO: 531) having a hairpin-like structure is known as a precursor of “hsa-miR-4653-5p.”

The term “hsa-miR-6867-3p gene” or “hsa-miR-6867-3p” used herein includes the hsa-miR-6867-3p gene (miRBase Accession No. MIMAT0027635) shown in SEQ ID NO: 133, a homolog or an ortholog of a different organism species, and the like. The hsa-miR-6867-3p gene can be obtained by a method described in Ladewig E et al., 2012, Genome Res., Vol. 22, pp. 1634-1645. Also, “hsa-mir-6867” (miRBase Accession No. MI0022714; SEQ ID NO: 532) having a hairpin-like structure is known as a precursor of “hsa-miR-6867-3p.”

The term “hsa-miR-133b gene” or “hsa-miR-133b” used herein includes the hsa-miR-133b gene (miRBase Accession No. MIMAT0000770) shown in SEQ ID NO: 134, a homolog or an ortholog of a different organism species, and the like. The hsa-miR-133b gene can be obtained by a method described in Lim L P et al., 2003, Science, Vol. 299, p. 1540. Also, “hsa-mir-133b” (miRBase Accession No. MI0000822; SEQ ID NO: 533) having a hairpin-like structure is known as a precursor of “hsa-miR-133b.”

The term “hsa-miR-3196 gene” or “hsa-miR-3196” used herein includes the hsa-miR-3196 gene (miRBase Accession No. MIMAT0015080) shown in SEQ ID NO: 135, a homolog or an ortholog of a different organism species, and the like. The hsa-miR-3196 gene can be obtained by a method described in Stark M S et al., 2010, PLoS One, Vol. 5, e9685. Also, “hsa-mir-3196” (miRBase Accession No. MI0014241; SEQ ID NO: 534) having a hairpin-like structure is known as a precursor of “hsa-miR-3196.”

The term “hsa-miR-193b-3p gene” or “hsa-miR-193b-3p” used herein includes the hsa-miR-193b-3p gene (miRBase Accession No. MIMAT0002819) shown in SEQ ID NO: 136, a homolog or an ortholog of a different organism species, and the like. The hsa-miR-193b-3p gene can be obtained by a method described in Bentwich I et al., 2005, Nat. Genet., Vol. 37, pp. 766-770. Also, “hsa-mir-193b” (miRBase Accession No. MI0003137; SEQ ID NO: 535) having a hairpin-like structure is known as a precursor of “hsa-miR-193b-3p.”

The term “hsa-miR-3162-3p gene” or “hsa-miR-3162-3p” used herein includes the hsa-miR-3162-3p gene (miRBase Accession No. MIMAT0019213) shown in SEQ ID NO: 137, a homolog or an ortholog of a different organism species, and the like. The hsa-miR-3162-3p gene can be obtained by a method described in Stark M S et al., 2010, PLoS One, Vol. 5, e9685. Also, “hsa-mir-3162” (miRBase Accession No. MI0014192; SEQ ID NO: 536) having a hairpin-like structure is known as a precursor of “hsa-miR-3162-3p.”

The term “hsa-miR-6819-3p gene” or “hsa-miR-6819-3p” used herein includes the hsa-miR-6819-3p gene (miRBase Accession No. MIMAT0027539) shown in SEQ ID NO: 138, a homolog or an ortholog of a different organism species, and the like. The hsa-miR-6819-3p gene can be obtained by a method described in Ladewig E et al., 2012, Genome Res., Vol. 22, pp. 1634-1645. Also, “hsa-mir-6819” (miRBase Accession No. MI0022664; SEQ ID NO: 537) having a hairpin-like structure is known as a precursor of “hsa-miR-6819-3p.”

The term “hsa-miR-1908-3p gene” or “hsa-miR-1908-3p” used herein includes the hsa-miR-1908-3p gene (miRBase Accession No. MIMAT0026916) shown in SEQ ID NO: 139, a homolog or an ortholog of a different organism species, and the like. The hsa-miR-1908-3p gene can be obtained by a method described in Bar M et al., 2008, Stem Cells, Vol. 26, pp. 2496-2505. Also, “hsa-mir-1908” (miRBase Accession No. MI0008329; SEQ ID NO: 538) having a hairpin-like structure is known as a precursor of “hsa-miR-1908-3p.”

The term “hsa-miR-6786-5p gene” or “hsa-miR-6786-5p” used herein includes the hsa-miR-6786-5p gene (miRBase Accession No. MIMAT0027472) shown in SEQ ID NO: 140, a homolog or an ortholog of a different organism species, and the like. The hsa-miR-6786-5p gene can be obtained by a method described in Ladewig E et al., 2012, Genome Res., Vol. 22, pp. 1634-1645. Also, “hsa-mir-6786” (miRBase Accession No. MI0022631; SEQ ID NO: 539) having a hairpin-like structure is known as a precursor of “hsa-miR-6786-5p.”

The term “hsa-miR-3648 gene” or “hsa-miR-3648” used herein includes the hsa-miR-3648 gene (miRBase Accession No. MIMAT0018068) shown in SEQ ID NO: 141, a homolog or an ortholog of a different organism species, and the like. The hsa-miR-3648 gene can be obtained by a method described in Meiri E et al., 2010, Nucleic Acids Res., Vol. 38, p. 6234-6246. Also, “hsa-mir-3648-1 and hsa-mir-3648-2” (miRBase Accession Nos. MI0016048 and MI0031512; SEQ ID NOs: 540 and 541) each having a hairpin-like structure are known as precursors of “hsa-miR-3648.”

The term “hsa-miR-4513 gene” or “hsa-miR-4513” used herein includes the hsa-miR-4513 gene (miRBase Accession No. MIMAT0019050) shown in SEQ ID NO: 142, a homolog or an ortholog of a different organism species, and the like. The hsa-miR-4513 gene can be obtained by a method described in Jima D D et al., 2010, Blood, Vol. 116, e118-e127. Also, “hsa-mir-4513” (miRBase Accession No. MI0016879; SEQ ID NO: 542) having a hairpin-like structure is known as a precursor of “hsa-miR-4513.”

The term “hsa-miR-3652 gene” or “hsa-miR-3652” used herein includes the hsa-miR-3652 gene (miRBase Accession No. MIMAT0018072) shown in SEQ ID NO: 143, a homolog or an ortholog of a different organism species, and the like. The hsa-miR-3652 gene can be obtained by a method described in Meiri E et al., 2010, Nucleic Acids Res., Vol. 38, p. 6234-6246. Also, “hsa-mir-3652” (miRBase Accession No. MI0016052; SEQ ID NO: 543) having a hairpin-like structure is known as a precursor of “hsa-miR-3652.”

The term “hsa-miR-4640-5p gene” or “hsa-miR-4640-5p” used herein includes the hsa-miR-4640-5p gene (miRBase Accession No. MIMAT0019699) shown in SEQ ID NO: 144, a homolog or an ortholog of a different organism species, and the like. The hsa-miR-4640-5p gene can be obtained by a method described in Persson H et al., 2011, Cancer Res., Vol. 71, pp. 78-86. Also, “hsa-mir-4640” (miRBase Accession No. MI0017267; SEQ ID NO: 484) having a hairpin-like structure is known as a precursor of “hsa-miR-4640-5p.”

The term “hsa-miR-6871-5p gene” or “hsa-miR-6871-5p” used herein includes the hsa-miR-6871-5p gene (miRBase Accession No. MIMAT0027642) shown in SEQ ID NO: 145, a homolog or an ortholog of a different organism species, and the like. The hsa-miR-6871-5p gene can be obtained by a method described in Ladewig E et al., 2012, Genome Res., Vol. 22, pp. 1634-1645. Also, “hsa-mir-6871” (miRBase Accession No. MI0022718; SEQ ID NO: 544) having a hairpin-like structure is known as a precursor of “hsa-miR-6871-5p.”

The term “hsa-miR-7845-5p gene” or “hsa-miR-7845-5p” used herein includes the hsa-miR-7845-5p gene (miRBase Accession No. MIMAT0030420) shown in SEQ ID NO: 146, a homolog or an ortholog of a different organism species, and the like. The hsa-miR-7845-5p gene can be obtained by a method described in Ple H et al., 2012, PLoS One, Vol. 7, e50746. Also, “hsa-mir-7845” (miRBase Accession No. MI0025515; SEQ ID NO: 545) having a hairpin-like structure is known as a precursor of “hsa-miR-7845-5p.”

The term “hsa-miR-3138 gene” or “hsa-miR-3138” used herein includes the hsa-miR-3138 gene (miRBase Accession No. MIMAT0015006) shown in SEQ ID NO: 147, a homolog or an ortholog of a different organism species, and the like. The hsa-miR-3138 gene can be obtained by a method described in Creighton C J et al., 2010, PLoS One, Vol. 5, e9637. Also, “hsa-mir-3138” (miRBase Accession No. MI0014161; SEQ ID NO: 546) having a hairpin-like structure is known as a precursor of “hsa-miR-3138.”

The term “hsa-miR-6884-5p gene” or “hsa-miR-6884-5p” used herein includes the hsa-miR-6884-5p gene (miRBase Accession No. MIMAT0027668) shown in SEQ ID NO: 148, a homolog or an ortholog of a different organism species, and the like. The hsa-miR-6884-5p gene can be obtained by a method described in Ladewig E et al., 2012, Genome Res., Vol. 22, pp. 1634-1645. Also, “hsa-mir-6884” (miRBase Accession No. MI0022731; SEQ ID NO: 547) having a hairpin-like structure is known as a precursor of “hsa-miR-6884-5p.”

The term “hsa-miR-4653-3p gene” or “hsa-miR-4653-3p” used herein includes the hsa-miR-4653-3p gene (miRBase Accession No. MIMAT0019719) shown in SEQ ID NO: 149, a homolog or an ortholog of a different organism species, and the like. The hsa-miR-4653-3p gene can be obtained by a method described in Persson H et al., 2011, Cancer Res., Vol. 71, pp. 78-86. Also, “hsa-mir-4653”

(miRBase Accession No. MI0017281; SEQ ID NO: 531) having a hairpin-like structure is known as a precursor of "hsa-miR-4653-3p."

The term "hsa-miR-636 gene" or "hsa-miR-636" used herein includes the hsa-miR-636 gene (miRBase Accession No. MIMAT0003306) shown in SEQ ID NO: 150, a homolog or an ortholog of a different organism species, and the like. The hsa-miR-636 gene can be obtained by a method described in Cummins J M et al., 2006, Proc. Natl. Acad. Sci. U.S.A., Vol. 103, pp. 3687-3692. Also, "hsa-mir-636" (miRBase Accession No. MI0003651; SEQ ID NO: 548) having a hairpin-like structure is known as a precursor of "hsa-miR-636."

The term "hsa-miR-4652-3p gene" or "hsa-miR-4652-3p" used herein includes the hsa-miR-4652-3p gene (miRBase Accession No. MIMAT0019717) shown in SEQ ID NO: 151, a homolog or an ortholog of a different organism species, and the like. The hsa-miR-4652-3p gene can be obtained by a method described in Persson H et al., 2011, Cancer Res., Vol. 71, pp. 78-86. Also, "hsa-mir-4652" (miRBase Accession No. MI0017280; SEQ ID NO: 549) having a hairpin-like structure is known as a precursor of "hsa-miR-4652-3p."

The term "hsa-miR-6823-5p gene" or "hsa-miR-6823-5p" used herein includes the hsa-miR-6823-5p gene (miRBase Accession No. MIMAT0027546) shown in SEQ ID NO: 152, a homolog or an ortholog of a different organism species, and the like. The hsa-miR-6823-5p gene can be obtained by a method described in Ladewig E et al., 2012, Genome Res., Vol. 22, pp. 1634-1645. Also, "hsa-mir-6823" (miRBase Accession No. MI0022668; SEQ ID NO: 550) having a hairpin-like structure is known as a precursor of "hsa-miR-6823-5p."

The term "hsa-miR-4502 gene" or "hsa-miR-4502" used herein includes the hsa-miR-4502 gene (miRBase Accession No. MIMAT0019038) shown in SEQ ID NO: 153, a homolog or an ortholog of a different organism species, and the like. The hsa-miR-4502 gene can be obtained by a method described in Jima D D et al., 2010, Blood, Vol. 116, e118-e127. Also, "hsa-mir-4502" (miRBase Accession No. MI0016865; SEQ ID NO: 551) having a hairpin-like structure is known as a precursor of "hsa-miR-4502."

The term "hsa-miR-7113-5p gene" or "hsa-miR-7113-5p" used herein includes the hsa-miR-7113-5p gene (miRBase Accession No. MIMAT0028123) shown in SEQ ID NO: 154, a homolog or an ortholog of a different organism species, and the like. The hsa-miR-7113-5p gene can be obtained by a method described in Ladewig E et al., 2012, Genome Res., Vol. 22, pp. 1634-1645. Also, "hsa-mir-7113" (miRBase Accession No. MI0022964; SEQ ID NO: 552) having a hairpin-like structure is known as a precursor of "hsa-miR-7113-5p."

The term "hsa-miR-8087 gene" or "hsa-miR-8087" used herein includes the hsa-miR-8087 gene (miRBase Accession No. MIMAT0031014) shown in SEQ ID NO: 155, a homolog or an ortholog of a different organism species, and the like. The hsa-miR-8087 gene can be obtained by a method described in Wang H J et al., 2013, Shock, Vol. 39, pp. 480-487. Also, "hsa-mir-8087" (miRBase Accession No. MI0025923; SEQ ID NO: 553) having a hairpin-like structure is known as a precursor of "hsa-miR-8087."

The term "hsa-miR-7154-3p gene" or "hsa-miR-7154-3p" used herein includes the hsa-miR-7154-3p gene (miRBase Accession No. MIMAT0028219) shown in SEQ ID NO: 156, a homolog or an ortholog of a different organism species, and the like. The hsa-miR-7154-3p gene can be obtained by a method described in Meunier J et al., 2013, Genome Res., Vol. 23, pp. 34-45. Also, "hsa-mir-7154" (miRBase Accession No. MI0023614; SEQ ID NO: 554) having a hairpin-like structure is known as a precursor of "hsa-miR-7154-3p."

The term "hsa-miR-5189-5p gene" or "hsa-miR-5189-5p" used herein includes the hsa-miR-5189-5p gene (miRBase Accession No. MIMAT0021120) shown in SEQ ID NO: 157, a homolog or an ortholog of a different organism species, and the like. The hsa-miR-5189-5p gene can be obtained by a method described in Schotte D et al., 2011, Leukemia, Vol. 25, pp. 1389-1399. Also, "hsa-mir-5189" (miRBase Accession No. MI0018168; SEQ ID NO: 555) having a hairpin-like structure is known as a precursor of "hsa-miR-5189-5p."

The term "hsa-miR-1253 gene" or "hsa-miR-1253" used herein includes the hsa-miR-1253 gene (miRBase Accession No. MIMAT0005904) shown in SEQ ID NO: 158, a homolog or an ortholog of a different organism species, and the like. The hsa-miR-1253 gene can be obtained by a method described in Morin R D et al., 2008, Genome Res., Vol. 18, pp. 610-621. Also, "hsa-mir-1253" (miRBase Accession No. MI0006387; SEQ ID NO: 556) having a hairpin-like structure is known as a precursor of "hsa-miR-1253."

The term "hsa-miR-518c-5p gene" or "hsa-miR-518c-5p" used herein includes the hsa-miR-518c-5p gene (miRBase Accession No. MIMAT0002847) shown in SEQ ID NO: 159, a homolog or an ortholog of a different organism species, and the like. The hsa-miR-518c-5p gene can be obtained by a method described in Bentwich I et al., 2005, Nat. Genet., Vol. 37, pp. 766-770. Also, "hsa-mir-518c" (miRBase Accession No. MI0003159; SEQ ID NO: 557) having a hairpin-like structure is known as a precursor of "hsa-miR-518c-5p."

The term "hsa-miR-7151-5p gene" or "hsa-miR-7151-5p" used herein includes the hsa-miR-7151-5p gene (miRBase Accession No. MIMAT0028212) shown in SEQ ID NO: 160, a homolog or an ortholog of a different organism species, and the like. The hsa-miR-7151-5p gene can be obtained by a method described in Meunier J et al., 2013, Genome Res., Vol. 23, pp. 34-45. Also, "hsa-mir-7151" (miRBase Accession No. MI0023611; SEQ ID NO: 558) having a hairpin-like structure is known as a precursor of "hsa-miR-7151-5p."

The term "hsa-miR-3614-3p gene" or "hsa-miR-3614-3p" used herein includes the hsa-miR-3614-3p gene (miRBase Accession No. MIMAT0017993) shown in SEQ ID NO: 161, a homolog or an ortholog of a different organism species, and the like. The hsa-miR-3614-3p gene can be obtained by a method described in Witten D et al., 2010, BMC Biol., Vol. 8, p. 58. Also, "hsa-mir-3614" (miRBase Accession No. MI0016004; SEQ ID NO: 559) having a hairpin-like structure is known as a precursor of "hsa-miR-3614-3p."

The term "hsa-miR-4727-5p gene" or "hsa-miR-4727-5p" used herein includes the hsa-miR-4727-5p gene (miRBase Accession No. MIMAT0019847) shown in SEQ ID NO: 162, a homolog or an ortholog of a different organism species, and the like. The hsa-miR-4727-5p gene can be obtained by a method described in Persson H et al., 2011, Cancer Res., Vol. 71, pp. 78-86. Also, "hsa-mir-4727" (miRBase Accession No. MI0017364; SEQ ID NO: 560) having a hairpin-like structure is known as a precursor of "hsa-miR-4727-5p."

The term "hsa-miR-3682-5p gene" or "hsa-miR-3682-5p" used herein includes the hsa-miR-3682-5p gene (miRBase Accession No. MIMAT0019222) shown in SEQ ID NO:

163, a homolog or an ortholog of a different organism species, and the like. The hsa-miR-3682-5p gene can be obtained by a method described in Vaz C et al., 2010, BMC Genomics, Vol. 11, p. 288. Also, "hsa-mir-3682" (miRBase Accession No. MI0016083; SEQ ID NO: 561) having a hairpin-like structure is known as a precursor of "hsa-miR-3682-5p."

The term "hsa-miR-5090 gene" or "hsa-miR-5090" used herein includes the hsa-miR-5090 gene (miRBase Accession No. MIMAT0021082) shown in SEQ ID NO: 164, a homolog or an ortholog of a different organism species, and the like. The hsa-miR-5090 gene can be obtained by a method described in Ding N et al., 2011, J. Radiat. Res., Vol. 52, pp. 425-432. Also, "hsa-mir-5090" (miRBase Accession No. MI0017979; SEQ ID NO: 562) having a hairpin-like structure is known as a precursor of "hsa-miR-5090."

The term "hsa-miR-337-3p gene" or "hsa-miR-337-3p" used herein includes the hsa-miR-337-3p gene (miRBase Accession No. MIMAT0000754) shown in SEQ ID NO: 165, a homolog or an ortholog of a different organism species, and the like. The hsa-miR-337-3p gene can be obtained by a method described in Kim J et al., 2004, Proc. Natl. Acad. Sci. U.S.A., Vol. 101, pp. 360-365. Also, "hsa-mir-337" (miRBase Accession No. MI0000806; SEQ ID NO: 563) having a hairpin-like structure is known as a precursor of "hsa-miR-337-3p."

The term "hsa-miR-488-5p gene" or "hsa-miR-488-5p" used herein includes the hsa-miR-488-5p gene (miRBase Accession No. MIMAT0002804) shown in SEQ ID NO: 166, a homolog or an ortholog of a different organism species, and the like. The hsa-miR-488-5p gene can be obtained by a method described in Bentwich I et al., 2005, Nat. Genet., Vol. 37, pp. 766-770. Also, "hsa-mir-488" (miRBase Accession No. MI0003123; SEQ ID NO: 564) having a hairpin-like structure is known as a precursor of "hsa-miR-488-5p."

The term "hsa-miR-100-5p gene" or "hsa-miR-100-5p" used herein includes the hsa-miR-100-5p gene (miRBase Accession No. MIMAT0000098) shown in SEQ ID NO: 167, a homolog or an ortholog of a different organism species, and the like. The hsa-miR-100-5p gene can be obtained by a method described in Mourelatos Z et al., 2002, Genes Dev., Vol. 16, pp. 720-728. Also, "hsa-mir-100" (miRBase Accession No. MI0000102; SEQ ID NO: 565) having a hairpin-like structure is known as a precursor of "hsa-miR-100-5p."

The term "hsa-miR-4520-3p gene" or "hsa-miR-4520-3p" used herein includes the hsa-miR-4520-3p gene (miRBase Accession No. MIMAT0019057) shown in SEQ ID NO: 168, a homolog or an ortholog of a different organism species, and the like. The hsa-miR-4520-3p gene can be obtained by a method described in Jima D D et al., 2010, Blood, Vol. 116, e118-e127. Also, "hsa-mir-4520-1" (miRBase Accession No. MI0016886; SEQ ID NO: 566) having a hairpin-like structure is known as a precursor of "hsa-miR-4520-3p."

The term "hsa-miR-373-3p gene" or "hsa-miR-373-3p" used herein includes the hsa-miR-373-3p gene (miRBase Accession No. MIMAT0000726) shown in SEQ ID NO: 169, a homolog or an ortholog of a different organism species, and the like. The hsa-miR-373-3p gene can be obtained by a method described in Suh M R et al., 2004, Dev. Biol., Vol. 270, pp. 488-498. Also, "hsa-mir-373" (miRBase Accession No. MI0000781; SEQ ID NO: 567) having a hairpin-like structure is known as a precursor of "hsa-miR-373-3p."

The term "hsa-miR-6499-5p gene" or "hsa-miR-6499-5p" used herein includes the hsa-miR-6499-5p gene (miRBase Accession No. MIMAT0025450) shown in SEQ ID NO: 170, a homolog or an ortholog of a different organism species, and the like. The hsa-miR-6499-5p gene can be obtained by a method described in Joyce C E et al., 2011, Hum. Mol. Genet., Vol. 20, pp. 4025-4040. Also, "hsa-mir-6499" (miRBase Accession No. MI0022209; SEQ ID NO: 568) having a hairpin-like structure is known as a precursor of "hsa-miR-6499-5p."

The term "hsa-miR-3909 gene" or "hsa-miR-3909" used herein includes the hsa-miR-3909 gene (miRBase Accession No. MIMAT0018183) shown in SEQ ID NO: 171, a homolog or an ortholog of a different organism species, and the like. The hsa-miR-3909 gene can be obtained by a method described in Creighton C J et al., 2010, PLoS One, Vol. 5, e9637. Also, "hsa-mir-3909" (miRBase Accession No. MI0016413; SEQ ID NO: 569) having a hairpin-like structure is known as a precursor of "hsa-miR-3909."

The term "hsa-miR-32-5p gene" or "hsa-miR-32-5p" used herein includes the hsa-miR-32-5p gene (miRBase Accession No. MIMAT0000090) shown in SEQ ID NO: 172, a homolog or an ortholog of a different organism species, and the like. The hsa-miR-32-5p gene can be obtained by a method described in Lagos-Quintana M et al., 2001, Science, Vol. 294, pp. 853-858. Also, "hsa-mir-32" (miRBase Accession No. MI0000090; SEQ ID NO: 570) having a hairpin-like structure is known as a precursor of "hsa-miR-3909."

The term "hsa-miR-302a-3p gene" or "hsa-miR-302a-3p" used herein includes the hsa-miR-302a-3p gene (miRBase Accession No. MIMAT0000684) shown in SEQ ID NO: 173, a homolog or an ortholog of a different organism species, and the like. The hsa-miR-302a-3p gene can be obtained by a method described in Houbaviy H B et al., 2003, Dev. Cell., Vol. 5, pp. 351-358. Also, "hsa-mir-302a" (miRBase Accession No. MI0000738; SEQ ID NO: 571) having a hairpin-like structure is known as a precursor of "hsa-miR-302a-3p."

The term "hsa-miR-4686 gene" or "hsa-miR-4686" used herein includes the hsa-miR-4686 gene (miRBase Accession No. MIMAT0019773) shown in SEQ ID NO: 174, a homolog or an ortholog of a different organism species, and the like. The hsa-miR-4686 gene can be obtained by a method described in Persson H et al., 2011, Cancer Res., Vol. 71, pp. 78-86. Also, "hsa-mir-4686" (miRBase Accession No. MI0017318; SEQ ID NO: 572) having a hairpin-like structure is known as a precursor of "hsa-miR-4686."

The term "hsa-miR-4659a-3p gene" or "hsa-miR-4659a-3p" used herein includes the hsa-miR-4659a-3p gene (miRBase Accession No. MIMAT0019727) shown in SEQ ID NO: 175, a homolog or an ortholog of a different organism species, and the like. The hsa-miR-4659a-3p gene can be obtained by a method described in Persson H et al., 2011, Cancer Res., Vol. 71, pp. 78-86. Also, "hsa-mir-4659a" (miRBase Accession No. MI0017287; SEQ ID NO: 573) having a hairpin-like structure is known as a precursor of "hsa-miR-4659a-3p."

The term "hsa-miR-4287 gene" or "hsa-miR-4287" used herein includes the hsa-miR-4287 gene (miRBase Accession No. MIMAT0016917) shown in SEQ ID NO: 176, a homolog or an ortholog of a different organism species, and the like. The hsa-miR-4287 gene can be obtained by a method described in Goff L A et al., 2009, PLoS One, Vol. 4, e7192. Also, "hsa-mir-4287" (miRBase Accession No. MI0015895; SEQ ID NO: 574) having a hairpin-like structure is known as a precursor of "hsa-miR-4287."

The term "hsa-miR-1301-5p gene" or "hsa-miR-1301-5p" used herein includes the hsa-miR-1301-5p gene (miRBase Accession No. MIMAT0026639) shown in SEQ ID NO: 177, a homolog or an ortholog of a different organism species, and the like. The hsa-miR-1301-5p gene can be obtained by a method described in Berezikov E et al., 2006, Genome Res., Vol. 16, pp. 1289-1298. Also, "hsa-mir-1301" (miRBase Accession No. MI0003815; SEQ ID NO: 575) having a hairpin-like structure is known as a precursor of "hsa-miR-1301-5p."

The term "hsa-miR-593-3p gene" or "hsa-miR-593-3p" used herein includes the hsa-miR-593-3p gene (miRBase Accession No. MIMAT0004802) shown in SEQ ID NO: 178, a homolog or an ortholog of a different organism species, and the like. The hsa-miR-593-3p gene can be obtained by a method described in Cummins J M et al., 2006, Proc. Natl. Acad. Sci. U.S.A., Vol. 103, pp. 3687-3692. Also, "hsa-mir-593" (miRBase Accession No. MI0003605; SEQ ID NO: 576) having a hairpin-like structure is known as a precursor of "hsa-miR-593-3p."

The term "hsa-miR-517a-3p gene" or "hsa-miR-517a-3p" used herein includes the hsa-miR-517a-3p gene (miRBase Accession No. MIMAT0002852) shown in SEQ ID NO: 179, a homolog or an ortholog of a different organism species, and the like. The hsa-miR-517a-3p gene can be obtained by a method described in Bentwich I et al., 2005, Nat. Genet., Vol. 37, pp. 766-770. Also, "hsa-mir-517a" (miRBase Accession No. MI0003161; SEQ ID NO: 577) having a hairpin-like structure is known as a precursor of "hsa-miR-593-3p."

The term "hsa-miR-517b-3p gene" or "hsa-miR-517b-3p" used herein includes the hsa-miR-517b-3p gene (miRBase Accession No. MIMAT0002857) shown in SEQ ID NO: 180, a homolog or an ortholog of a different organism species, and the like. The hsa-miR-517b-3p gene can be obtained by a method described in Bentwich I et al., 2005, Nat. Genet., Vol. 37, pp. 766-770. Also, "hsa-mir-517b" (miRBase Accession No. MI0003165; SEQ ID NO: 578) having a hairpin-like structure is known as a precursor of "hsa-miR-517b-3p."

The term "hsa-miR-142-3p gene" or "hsa-miR-142-3p" used herein includes the hsa-miR-142-3p gene (miRBase Accession No. MIMAT0000434) shown in SEQ ID NO: 181, a homolog or an ortholog of a different organism species, and the like. The hsa-miR-142-3p gene can be obtained by a method described in Lagos-Quintana M et al., 2002, Curr. Biol., Vol. 12, pp. 735-739. Also, "hsa-mir-142" (miRBase Accession No. MI0000458; SEQ ID NO: 579) having a hairpin-like structure is known as a precursor of "hsa-miR-142-3p."

The term "hsa-miR-1185-2-3p gene" or "hsa-miR-1185-2-3p" used herein includes the hsa-miR-1185-2-3p gene (miRBase Accession No. MIMAT0022713) shown in SEQ ID NO: 182, a homolog or an ortholog of a different organism species, and the like. The hsa-miR-1185-2-3p gene can be obtained by a method described in Berezikov E et al., 2006, Genome Res., Vol. 16, pp. 1289-1298. Also, "hsa-mir-1185-2" (miRBase Accession No. MI0003821; SEQ ID NO: 580) having a hairpin-like structure is known as a precursor of "hsa-miR-1185-2-3p."

The term "hsa-miR-602 gene" or "hsa-miR-602" used herein includes the hsa-miR-602 gene (miRBase Accession No. MIMAT0003270) shown in SEQ ID NO: 183, a homolog or an ortholog of a different organism species, and the like. The hsa-miR-602 gene can be obtained by a method described in Cummins J M et al., 2006, Proc. Natl. Acad. Sci. U.S.A., Vol. 103, pp. 3687-3692. Also, "hsa-mir-602" (miRBase Accession No. MI0003615; SEQ ID NO: 581) having a hairpin-like structure is known as a precursor of "hsa-miR-1185-2-3p."

The term "hsa-miR-527 gene" or "hsa-miR-527" used herein includes the hsa-miR-527 gene (miRBase Accession No. MIMAT0002862) shown in SEQ ID NO: 184, a homolog or an ortholog of a different organism species, and the like. The hsa-miR-527 gene can be obtained by a method described in Bentwich I et al., 2005, Nat. Genet., Vol. 37, pp. 766-770. Also, "hsa-mir-527" (miRBase Accession No. MI0003179; SEQ ID NO: 582) having a hairpin-like structure is known as a precursor of "hsa-miR-527."

The term "hsa-miR-518a-5p gene" or "hsa-miR-518a-5p" used herein includes the hsa-miR-518a-5p gene (miRBase Accession No. MIMAT0005457) shown in SEQ ID NO: 185, a homolog or an ortholog of a different organism species, and the like. The hsa-miR-518a-5p gene can be obtained by a method described in Bentwich I et al., 2005, Nat. Genet., Vol. 37, pp. 766-770. Also, "hsa-mir-518a-1 and hsa-mir-518a-2" (miRBase Accession Nos. MI0003170 and MI0003173; SEQ ID NOs: 583 and 584) each having a hairpin-like structure are known as precursors of "hsa-miR-518a-5p."

The term "hsa-miR-4682 gene" or "hsa-miR-4682" used herein includes the hsa-miR-4682 gene (miRBase Accession No. MIMAT0019767) shown in SEQ ID NO: 186, a homolog or an ortholog of a different organism species, and the like. The hsa-miR-4682 gene can be obtained by a method described in Persson H et al., 2011, Cancer Res., Vol. 71, pp. 78-86. Also, "hsa-mir-4682" (miRBase Accession No. MI0017314; SEQ ID NO: 585) having a hairpin-like structure is known as a precursor of "hsa-miR-4682."

The term "hsa-miR-28-5p gene" or "hsa-miR-28-5p" used herein includes the hsa-miR-28-5p gene (miRBase Accession No. MIMAT0000085) shown in SEQ ID NO: 187, a homolog or an ortholog of a different organism species, and the like. The hsa-miR-28-5p gene can be obtained by a method described in Lagos-Quintana M et al., 2001, Science, Vol. 294, pp. 853-858. Also, "hsa-mir-28" (miRBase Accession No. MI0000086; SEQ ID NO: 586) having a hairpin-like structure is known as a precursor of "hsa-miR-28-5p."

The term "hsa-miR-4252 gene" or "hsa-miR-4252" used herein includes the hsa-miR-4252 gene (miRBase Accession No. MIMAT0016886) shown in SEQ ID NO: 188, a homolog or an ortholog of a different organism species, and the like. The hsa-miR-4252 gene can be obtained by a method described in Goff L A et al., 2009, PLoS One, Vol. 4, e7192. Also, "hsa-mir-4252" (miRBase Accession No. MI0015864; SEQ ID NO: 587) having a hairpin-like structure is known as a precursor of "hsa-miR-4252."

The term "hsa-miR-452-5p gene" or "hsa-miR-452-5p" used herein includes the hsa-miR-452-5p gene (miRBase Accession No. MIMAT0001635) shown in SEQ ID NO: 189, a homolog or an ortholog of a different organism species, and the like. The hsa-miR-452-5p gene can be obtained by a method described in Altuvia Y et al., 2005, Nucleic Acids Res., Vol. 33, pp. 2697-2706. Also, "hsa-mir-452" (miRBase Accession No. MI0001733; SEQ ID NO: 588) having a hairpin-like structure is known as a precursor of "hsa-miR-452-5p."

The term "hsa-miR-525-5p gene" or "hsa-miR-525-5p" used herein includes the hsa-miR-525-5p gene (miRBase Accession No. MIMAT0002838) shown in SEQ ID NO: 190, a homolog or an ortholog of a different organism species, and the like. The hsa-miR-525-5p gene can be obtained by a method described in Bentwich I et al., 2005, Nat. Genet., Vol. 37, pp. 766-770. Also, “hsa-mir-525” (miRBase Accession No. MI0003152; SEQ ID NO: 589) having a hairpin-like structure is known as a precursor of “hsa-miR-525-5p.”

The term “hsa-miR-3622a-3p gene” or “hsa-miR-3622a-3p” used herein includes the hsa-miR-3622a-3p gene (miRBase Accession No. MIMAT0018004) shown in SEQ ID NO: 191, a homolog or an ortholog of a different organism species, and the like. The hsa-miR-3622a-3p gene can be obtained by a method described in Witten D et al., 2010, BMC Biol., Vol. 8, p. 58. Also, “hsa-mir-3622a” (miRBase Accession No. MI0016013; SEQ ID NO: 590) having a hairpin-like structure is known as a precursor of “hsa-miR-3622a-3p.”

The term “hsa-miR-6813-3p gene” or “hsa-miR-6813-3p” used herein includes the hsa-miR-6813-3p gene (miRBase Accession No. MIMAT0027527) shown in SEQ ID NO: 192, a homolog or an ortholog of a different organism species, and the like. The hsa-miR-6813-3p gene can be obtained by a method described in Ladewig E et al., 2012, Genome Res., Vol. 22, pp. 1634-1645. Also, “hsa-mir-6813” (miRBase Accession No. MI0022658; SEQ ID NO: 591) having a hairpin-like structure is known as a precursor of “hsa-miR-6813-3p.”

The term “hsa-miR-4769-3p gene” or “hsa-miR-4769-3p” used herein includes the hsa-miR-4769-3p gene (miRBase Accession No. MIMAT0019923) shown in SEQ ID NO: 193, a homolog or an ortholog of a different organism species, and the like. The hsa-miR-4769-3p gene can be obtained by a method described in Persson H et al., 2011, Cancer Res., Vol. 71, pp. 78-86. Also, “hsa-mir-4769” (miRBase Accession No. MI0017410; SEQ ID NO: 592) having a hairpin-like structure is known as a precursor of “hsa-miR-4769-3p.”

The term “hsa-miR-5698 gene” or “hsa-miR-5698” used herein includes the hsa-miR-5698 gene (miRBase Accession No. MIMAT0022491) shown in SEQ ID NO: 194, a homolog or an ortholog of a different organism species, and the like. The hsa-miR-5698 gene can be obtained by a method described in Watahiki A et al., 2011, PLoS One, Vol. 6, e24950. Also, “hsa-mir-5698” (miRBase Accession No. MI0019305; SEQ ID NO: 593) having a hairpin-like structure is known as a precursor of “hsa-miR-5698.”

The term “hsa-miR-1915-3p gene” or “hsa-miR-1915-3p” used herein includes the hsa-miR-1915-3p gene (miRBase Accession No. MIMAT0007892) shown in SEQ ID NO: 195, a homolog or an ortholog of a different organism species, and the like. The hsa-miR-1915-3p gene can be obtained by a method described in Bar M et al., 2008, Stem Cells, Vol. 26, pp. 2496-2505. Also, “hsa-mir-1915” (miRBase Accession No. MI0008336; SEQ ID NO: 594) having a hairpin-like structure is known as a precursor of “hsa-miR-1915-3p.”

The term “hsa-miR-1343-5p gene” or “hsa-miR-1343-5p” used herein includes the hsa-miR-1343-5p gene (miRBase Accession No. MIMAT0027038) shown in SEQ ID NO: 196, a homolog or an ortholog of a different organism species, and the like. The hsa-miR-1343-5p gene can be obtained by a method described in Persson H et al., 2011, Cancer Res., Vol. 71, pp. 78-86. Also, “hsa-mir-1343” (miRBase Accession No. MI0017320; SEQ ID NO: 595) having a hairpin-like structure is known as a precursor of “hsa-miR-1343-5p.”

The term “hsa-miR-6861-5p gene” or “hsa-miR-6861-5p” used herein includes the hsa-miR-6861-5p gene (miRBase Accession No. MIMAT0027623) shown in SEQ ID NO: 197, a homolog or an ortholog of a different organism species, and the like. The hsa-miR-6861-5p gene can be obtained by a method described in Ladewig E et al., 2012, Genome Res., Vol. 22, pp. 1634-1645. Also, “hsa-mir-6861” (miRBase Accession No. MI0022708; SEQ ID NO: 596) having a hairpin-like structure is known as a precursor of “hsa-miR-6861-5p.”

The term “hsa-miR-6781-5p gene” or “hsa-miR-6781-5p” used herein includes the hsa-miR-6781-5p gene (miRBase Accession No. MIMAT0027462) shown in SEQ ID NO: 198, a homolog or an ortholog of a different organism species, and the like. The hsa-miR-6781-5p gene can be obtained by a method described in Ladewig E et al., 2012, Genome Res., Vol. 22, pp. 1634-1645. Also, “hsa-mir-6781” (miRBase Accession No. MI0022626; SEQ ID NO: 597) having a hairpin-like structure is known as a precursor of “hsa-miR-6781-5p.”

The term “hsa-miR-4508 gene” or “hsa-miR-4508” used herein includes the hsa-miR-4508 gene (miRBase Accession No. MIMAT0019045) shown in SEQ ID NO: 199, a homolog or an ortholog of a different organism species, and the like. The hsa-miR-4508 gene can be obtained by a method described in Jima D D et al., 2010, Blood, Vol. 116, e118-e127. Also, “hsa-mir-4508” (miRBase Accession No. MI0016872; SEQ ID NO: 598) having a hairpin-like structure is known as a precursor of “hsa-miR-4508.”

The term “hsa-miR-6743-5p gene” or “hsa-miR-6743-5p” used herein includes the hsa-miR-6743-5p gene (miRBase Accession No. MIMAT0027387) shown in SEQ ID NO: 200, a homolog or an ortholog of a different organism species, and the like. The hsa-miR-6743-5p gene can be obtained by a method described in Ladewig E et al., 2012, Genome Res., Vol. 22, pp. 1634-1645. Also, “hsa-mir-6743” (miRBase Accession No. MI0022588; SEQ ID NO: 599) having a hairpin-like structure is known as a precursor of “hsa-miR-6743-5p.”

The term “hsa-miR-6726-5p gene” or “hsa-miR-6726-5p” used herein includes the hsa-miR-6726-5p gene (miRBase Accession No. MIMAT0027353) shown in SEQ ID NO: 201, a homolog or an ortholog of a different organism species, and the like. The hsa-miR-6726-5p gene can be obtained by a method described in Ladewig E et al., 2012, Genome Res., Vol. 22, pp. 1634-1645. Also, “hsa-mir-6726” (miRBase Accession No. MI0022571; SEQ ID NO: 600) having a hairpin-like structure is known as a precursor of “hsa-miR-6726-5p.”

The term “hsa-miR-4525 gene” or “hsa-miR-4525” used herein includes the hsa-miR-4525 gene (miRBase Accession No. MIMAT0019064) shown in SEQ ID NO: 202, a homolog or an ortholog of a different organism species, and the like. The hsa-miR-4525 gene can be obtained by a method described in Jima D D et al., 2010, Blood, Vol. 116, e118-e127. Also, “hsa-mir-4525” (miRBase Accession No. MI0016892; SEQ ID NO: 601) having a hairpin-like structure is known as a precursor of “hsa-miR-4525.”

The term “hsa-miR-4651 gene” or “hsa-miR-4651” used herein includes the hsa-miR-4651 gene (miRBase Accession No. MIMAT0019715) shown in SEQ ID NO: 203, a homolog or an ortholog of a different organism species, and the like. The hsa-miR-4651 gene can be obtained by a method described in Persson H et al., 2011, Cancer Res., Vol. 71, pp. 78-86. Also, “hsa-mir-4651” (miRBase Accession No. MI0017279; SEQ ID NO: 602) having a hairpin-like structure is known as a precursor of “hsa-miR-4651.”

The term “hsa-miR-6813-5p gene” or “hsa-miR-6813-5p” used herein includes the hsa-miR-6813-5p gene (miRBase Accession No. MIMAT0027526) shown in SEQ ID NO: 204, a homolog or an ortholog of a different organism species, and the like. The hsa-miR-6813-5p gene can be obtained by a method described in Ladewig E et al., 2012, Genome Res., Vol. 22, pp. 1634-1645. Also, “hsa-mir-6813” (miRBase Accession No. MI0022658; SEQ ID NO: 591) having a hairpin-like structure is known as a precursor of “hsa-miR-6813-5p.”

The term “hsa-miR-5787 gene” or “hsa-miR-5787” used herein includes the hsa-miR-5787 gene (miRBase Accession No. MIMAT0023252) shown in SEQ ID NO: 205, a homolog or an ortholog of a different organism species, and the like. The hsa-miR-5787 gene can be obtained by a method described in Yoo H et al., 2011, Biochem. Biophys. Res. Commun., Vol. 415, pp. 567-572. Also, “hsa-mir-5787” (miRBase Accession No. MI0019797; SEQ ID NO: 603) having a hairpin-like structure is known as a precursor of “hsa-miR-5787.”

The term “hsa-miR-1290 gene” or “hsa-miR-1290” used herein includes the hsa-miR-1290 gene (miRBase Accession No. MIMAT0005880) shown in SEQ ID NO: 206, a homolog or an ortholog of a different organism species, and the like. The hsa-miR-1290 gene can be obtained by a method described in Morin R D et al., 2008, Genome Res., Vol. 18, pp. 610-621. Also, “hsa-mir-1290” (miRBase Accession No. MI0006352; SEQ ID NO: 604) having a hairpin-like structure is known as a precursor of “hsa-miR-1290.”

The term “hsa-miR-6075 gene” or “hsa-miR-6075” used herein includes the hsa-miR-6075 gene (miRBase Accession No. MIMAT0023700) shown in SEQ ID NO: 207, a homolog or an ortholog of a different organism species, and the like. The hsa-miR-6075 gene can be obtained by a method described in Voellenkle C et al., 2012, RNA, Vol. 18, p. 472-484. Also, “hsa-mir-6075” (miRBase Accession No. MI0020352; SEQ ID NO: 605) having a hairpin-like structure is known as a precursor of “hsa-miR-6075.”

The term “hsa-miR-4758-5p gene” or “hsa-miR-4758-5p” used herein includes the hsa-miR-4758-5p gene (miRBase Accession No. MIMAT0019903) shown in SEQ ID NO: 208, a homolog or an ortholog of a different organism species, and the like. The hsa-miR-4758-5p gene can be obtained by a method described in Persson H et al., 2011, Cancer Res., Vol. 71, pp. 78-86. Also, “hsa-mir-4758” (miRBase Accession No. MI0017399; SEQ ID NO: 606) having a hairpin-like structure is known as a precursor of “hsa-miR-4758-5p.”

The term “hsa-miR-4690-5p gene” or “hsa-miR-4690-5p” used herein includes the hsa-miR-4690-5p gene (miRBase Accession No. MIMAT0019779) shown in SEQ ID NO: 209, a homolog or an ortholog of a different organism species, and the like. The hsa-miR-4690-5p gene can be obtained by a method described in Persson H et al., 2011, Cancer Res., Vol. 71, pp. 78-86. Also, “hsa-mir-4690” (miRBase Accession No. MI0017323; SEQ ID NO: 607) having a hairpin-like structure is known as a precursor of “hsa-miR-4690-5p.”

The term “hsa-miR-762 gene” or “hsa-miR-762” used herein includes the hsa-miR-762 gene (miRBase Accession No. MIMAT0010313) shown in SEQ ID NO: 210, a homolog or an ortholog of a different organism species, and the like. The hsa-miR-762 gene can be obtained by a method described in Berezikov E et al., 2006, Genome Res., Vol. 16, pp. 1289-1298. Also, “hsa-mir-762” (miRBase Accession No. MI0003892; SEQ ID NO: 608) having a hairpin-like structure is known as a precursor of “hsa-miR-762.”

The term “hsa-miR-1225-3p gene” or “hsa-miR-1225-3p” used herein includes the hsa-miR-1225-3p gene (miRBase Accession No. MIMAT0005573) shown in SEQ ID NO: 211, a homolog or an ortholog of a different organism species, and the like. The hsa-miR-1225-3p gene can be obtained by a method described in Berezikov E et al., 2007, Mol. Cell, Vol. 28, pp. 328-336. Also, “hsa-mir-1225” (miRBase Accession No. MI0006311; SEQ ID NO: 609) having a hairpin-like structure is known as a precursor of “hsa-miR-1225-3p.”

The term “hsa-miR-3184-5p gene” or “hsa-miR-3184-5p” used herein includes the hsa-miR-3184-5p gene (miRBase Accession No. MIMAT0015064) shown in SEQ ID NO: 212, a homolog or an ortholog of a different organism species, and the like. The hsa-miR-3184-5p gene can be obtained by a method described in Stark M S et al., 2010, PLoS One, Vol. 5, e9685. Also, “hsa-mir-3184” (miRBase Accession No. MI0014226; SEQ ID NO: 398) having a hairpin-like structure is known as a precursor of “hsa-miR-3184-5p.”

The term “hsa-miR-665 gene” or “hsa-miR-665” used herein includes the hsa-miR-665 gene (miRBase Accession No. MIMAT0004952) shown in SEQ ID NO: 213, a homolog or an ortholog of a different organism species, and the like. The hsa-miR-665 gene can be obtained by a method described in Berezikov E et al., 2006, Genome Res., Vol. 16, pp. 1289-1298. Also, “hsa-mir-665” (miRBase Accession No. MI0005563; SEQ ID NO: 610) having a hairpin-like structure is known as a precursor of “hsa-miR-665.”

The term “hsa-miR-211-5p gene” or “hsa-miR-211-5p” used herein includes the hsa-miR-211-5p gene (miRBase Accession No. MIMAT0000268) shown in SEQ ID NO: 214, a homolog or an ortholog of a different organism species, and the like. The hsa-miR-211-5p gene can be obtained by a method described in Lim L P et al., 2003, Science, Vol. 299, p. 1540. Also, “hsa-mir-211” (miRBase Accession No. MI0000287; SEQ ID NO: 611) having a hairpin-like structure is known as a precursor of “hsa-miR-211-5p.”

The term “hsa-miR-1247-5p gene” or “hsa-miR-1247-5p” used herein includes the hsa-miR-1247-5p gene (miRBase Accession No. MIMAT0005899) shown in SEQ ID NO: 215, a homolog or an ortholog of a different organism species, and the like. The hsa-miR-1247-5p gene can be obtained by a method described in Morin R D et al., 2008, Genome Res., Vol. 18, pp. 610-621. Also, “hsa-mir-1247” (miRBase Accession No. MI0006382; SEQ ID NO: 489) having a hairpin-like structure is known as a precursor of “hsa-miR-1247-5p.”

The term “hsa-miR-3656 gene” or “hsa-miR-3656” used herein includes the hsa-miR-3656 gene (miRBase Accession No. MIMAT0018076) shown in SEQ ID NO: 216, a homolog or an ortholog of a different organism species, and the like. The hsa-miR-3656 gene can be obtained by a method described in Meiri E et al., 2010, Nucleic Acids Res., Vol. 38, p. 6234-6246. Also, “hsa-mir-3656” (miRBase Accession No. MI0016056; SEQ ID NO: 612) having a hairpin-like structure is known as a precursor of “hsa-miR-3656.”

The term “hsa-miR-149-5p gene” or “hsa-miR-149-5p” used herein includes the hsa-miR-149-5p gene (miRBase Accession No. MIMAT0000450) shown in SEQ ID NO: 217, a homolog or an ortholog of a different organism species, and the like. The hsa-miR-149-5p gene can be obtained by a method described in Lagos-Quintana M et al., 2002, Curr. Biol., Vol. 12, pp. 735-739. Also, “hsa-mir-149” (miRBase Accession No. MI0000478; SEQ ID NO: 613) having a hairpin-like structure is known as a precursor of “hsa-miR-149-5p.”

The term "hsa-miR-744-5p gene" or "hsa-miR-744-5p" used herein includes the hsa-miR-744-5p gene (miRBase Accession No. MIMAT0004945) shown in SEQ ID NO: 218, a homolog or an ortholog of a different organism species, and the like. The hsa-miR-744-5p gene can be obtained by a method described in Berezikov E et al., 2006, Genome Res., Vol. 16, pp. 1289-1298. Also, "hsa-mir-744" (miRBase Accession No. MI0005559; SEQ ID NO: 614) having a hairpin-like structure is known as a precursor of "hsa-miR-744-5p."

The term "hsa-miR-345-5p gene" or "hsa-miR-345-5p" used herein includes the hsa-miR-345-5p gene (miRBase Accession No. MIMAT0000772) shown in SEQ ID NO: 219, a homolog or an ortholog of a different organism species, and the like. The hsa-miR-345-5p gene can be obtained by a method described in Kim J et al., 2004, Proc. Natl. Acad. Sci. U.S.A., Vol. 101, pp. 360-365. Also, "hsa-mir-345" (miRBase Accession No. MI0000825; SEQ ID NO: 615) having a hairpin-like structure is known as a precursor of "hsa-miR-345-5p."

The term "hsa-miR-150-5p gene" or "hsa-miR-150-5p" used herein includes the hsa-miR-150-5p gene (miRBase Accession No. MIMAT0000451) shown in SEQ ID NO: 220, a homolog or an ortholog of a different organism species, and the like. The hsa-miR-150-5p gene can be obtained by a method described in Lagos-Quintana M et al., 2002, Curr. Biol., Vol. 12, pp. 735-739. Also, "hsa-mir-150" (miRBase Accession No. MI0000479; SEQ ID NO: 616) having a hairpin-like structure is known as a precursor of "hsa-miR-150-5p."

The term "hsa-miR-191-3p gene" or "hsa-miR-191-3p" used herein includes the hsa-miR-191-3p gene (miRBase Accession No. MIMAT0001618) shown in SEQ ID NO: 221, a homolog or an ortholog of a different organism species, and the like. The hsa-miR-191-3p gene can be obtained by a method described in Lagos-Quintana M et al., 2003, RNA, Vol. 9, pp. 175-179. Also, "hsa-mir-191" (miRBase Accession No. MI0000465; SEQ ID NO: 617) having a hairpin-like structure is known as a precursor of "hsa-miR-191-3p."

The term "hsa-miR-651-5p gene" or "hsa-miR-651-5p" used herein includes the hsa-miR-651-5p gene (miRBase Accession No. MIMAT0003321) shown in SEQ ID NO: 222, a homolog or an ortholog of a different organism species, and the like. The hsa-miR-651-5p gene can be obtained by a method described in Cummins J M et al., 2006, Proc. Natl. Acad. Sci., U.S.A., Vol. 103, pp. 3687-3692. Also, "hsa-mir-651" (miRBase Accession No. MI0003666; SEQ ID NO: 618) having a hairpin-like structure is known as a precursor of "hsa-miR-651-5p."

The term "hsa-miR-34a-5p gene" or "hsa-miR-34a-5p" used herein includes the hsa-miR-34a-5p gene (miRBase Accession No. MIMAT0000255) shown in SEQ ID NO: 223, a homolog or an ortholog of a different organism species, and the like. The hsa-miR-34a-5p gene can be obtained by a method described in Dostie J et al., 2003, RNA, Vol. 9, pp. 180-186. Also, "hsa-mir-34a" (miRBase Accession No. MI0000268; SEQ ID NO: 619) having a hairpin-like structure is known as a precursor of "hsa-miR-34a-5p."

The term "hsa-miR-409-5p gene" or "hsa-miR-409-5p" used herein includes the hsa-miR-409-5p gene (miRBase Accession No. MIMAT0001638) shown in SEQ ID NO: 224, a homolog or an ortholog of a different organism species, and the like. The hsa-miR-409-5p gene can be obtained by a method described in Altuvia Y et al., 2005, Nucleic Acids Res., Vol. 33, pp. 2697-2706. Also, "hsa-mir-409" (miRBase Accession No. MI0001735; SEQ ID NO: 620) having a hairpin-like structure is known as a precursor of "hsa-miR-409-5p."

The term "hsa-miR-369-5p gene" or "hsa-miR-369-5p" used herein includes the hsa-miR-369-5p gene (miRBase Accession No. MIMAT0001621) shown in SEQ ID NO: 225, a homolog or an ortholog of a different organism species, and the like. The hsa-miR-369-5p gene can be obtained by a method described in Suh M R et al., 2004, Dev. Biol., Vol. 270, pp. 488-498. Also, "hsa-mir-369" (miRBase Accession No. MI0000777; SEQ ID NO: 621) having a hairpin-like structure is known as a precursor of "hsa-miR-369-5p."

The term "hsa-miR-1915-5p gene" or "hsa-miR-1915-5p" used herein includes the hsa-miR-1915-5p gene (miRBase Accession No. MIMAT0007891) shown in SEQ ID NO: 226, a homolog or an ortholog of a different organism species, and the like. The hsa-miR-1915-5p gene can be obtained by a method described in Bar M et al., 2008, Stem Cells, Vol. 26, pp. 2496-2505. Also, "hsa-mir-1915" (miRBase Accession No. MI0008336; SEQ ID NO: 594) having a hairpin-like structure is known as a precursor of "hsa-miR-1915-5p."

The term "hsa-miR-204-5p gene" or "hsa-miR-204-5p" used herein includes the hsa-miR-204-5p gene (miRBase Accession No. MIMAT0000265) shown in SEQ ID NO: 227, a homolog or an ortholog of a different organism species, and the like. The hsa-miR-204-5p gene can be obtained by a method described in Lim L P et al., 2003, Science, Vol. 299, p. 1540. Also, "hsa-mir-204" (miRBase Accession No. MI0000284; SEQ ID NO: 622) having a hairpin-like structure is known as a precursor of "hsa-miR-204-5p."

The term "hsa-miR-137 gene" or "hsa-miR-137" used herein includes the hsa-miR-137 gene (miRBase Accession No. MIMAT0000429) shown in SEQ ID NO: 228, a homolog or an ortholog of a different organism species, and the like. The hsa-miR-137 gene can be obtained by a method described in Lagos-Quintana M et al., 2002, Curr. Biol., Vol. 12, pp. 735-739. Also, "hsa-mir-137" (miRBase Accession No. MI0000454; SEQ ID NO: 623) having a hairpin-like structure is known as a precursor of "hsa-miR-137."

The term "hsa-miR-382-5p gene" or "hsa-miR-382-5p" used herein includes the hsa-miR-382-5p gene (miRBase Accession No. MIMAT0000737) shown in SEQ ID NO: 229, a homolog or an ortholog of a different organism species, and the like. The hsa-miR-382-5p gene can be obtained by a method described in Altuvia Y et al., 2005, Nucleic Acids Res., Vol. 33, pp. 2697-2706. Also, "hsa-mir-382" (miRBase Accession No. MI0000790; SEQ ID NO: 624) having a hairpin-like structure is known as a precursor of "hsa-miR-382-5p."

The term "hsa-miR-517-5p gene" or "hsa-miR-517-5p" used herein includes the hsa-miR-517-5p gene (miRBase Accession No. MIMAT0002851) shown in SEQ ID NO: 230, a homolog or an ortholog of a different organism species, and the like. The hsa-miR-517-5p gene can be obtained by a method described in Bentwich I et al., 2005, Nat. Genet., Vol. 37, pp. 766-770. Also, "hsa-mir-517c" (miRBase Accession No. MI0003174; SEQ ID NO: 625) having a hairpin-like structure is known as a precursor of "hsa-miR-517-5p."

The term "hsa-miR-532-5p gene" or "hsa-miR-532-5p" used herein includes the hsa-miR-532-5p gene (miRBase Accession No. MIMAT0002888) shown in SEQ ID NO: 231, a homolog or an ortholog of a different organism species, and the like. The hsa-miR-532-5p gene can be obtained by a method described in Lagos-Quintana M et al., 2001, Science, Vol. 294, pp. 853-858. Also, "hsa-mir-532" (miRBase Accession No. MI0003205; SEQ ID NO: 626) having a hairpin-like structure is known as a precursor of "hsa-miR-532-5p."

The term "hsa-miR-22-5p gene" or "hsa-miR-22-5p" used herein includes the hsa-miR-22-5p gene (miRBase Accession No. MIMAT0004495) shown in SEQ ID NO: 232, a homolog or an ortholog of a different organism species, and the like. The hsa-miR-22-5p gene can be obtained by a method described in Berezikov E et al., 2007, Mol. Cell, Vol. 28, pp. 328-336. Also, "hsa-mir-22" (miRBase Accession No. MI0000078; SEQ ID NO: 627) having a hairpin-like structure is known as a precursor of "hsa-miR-22-5p."

The term "hsa-miR-1237-3p gene" or "hsa-miR-1237-3p" used herein includes the hsa-miR-1237-3p gene (miRBase Accession No. MIMAT0005592) shown in SEQ ID NO: 233, a homolog or an ortholog of a different organism species, and the like. The hsa-miR-1237-3p gene can be obtained by a method described in Berezikov E et al., 2006, Genome Res., Vol. 16, pp. 1289-1298. Also, "hsa-mir-1237" (miRBase Accession No. MI0006327; SEQ ID NO: 628) having a hairpin-like structure is known as a precursor of "hsa-miR-1237-3p."

The term "hsa-miR-1224-3p gene" or "hsa-miR-1224-3p" used herein includes the hsa-miR-1224-3p gene (miRBase Accession No. MIMAT0005459) shown in SEQ ID NO: 234, a homolog or an ortholog of a different organism species, and the like. The hsa-miR-1224-3p gene can be obtained by a method described in Cummins J M et al., 2006, Proc. Natl. Acad. Sci. U.S.A., Vol. 103, pp. 3687-3692. Also, "hsa-mir-1224" (miRBase Accession No. MI0003764; SEQ ID NO: 629) having a hairpin-like structure is known as a precursor of "hsa-miR-1224-3p."

The term "hsa-miR-625-3p gene" or "hsa-miR-625-3p" used herein includes the hsa-miR-625-3p gene (miRBase Accession No. MIMAT0004808) shown in SEQ ID NO: 235, a homolog or an ortholog of a different organism species, and the like. The hsa-miR-625-3p gene can be obtained by a method described in Kim J et al., 2004, Proc. Natl. Acad. Sci., U.S.A. Vol. 101, pp. 360-365. Also, "hsa-mir-625" (miRBase Accession No. MI0003639; SEQ ID NO: 630) having a hairpin-like structure is known as a precursor of "hsa-miR-625-3p."

The term "hsa-miR-328-3p gene" or "hsa-miR-328-3p" used herein includes the hsa-miR-328-3p gene (miRBase Accession No. MIMAT0000752) shown in SEQ ID NO: 236, a homolog or an ortholog of a different organism species, and the like. The hsa-miR-328-3p gene can be obtained by a method described in Lagos-Quintana M et al., 2002, Curr. Biol., Vol. 12, pp. 735-739. Also, "hsa-mir-328" (miRBase Accession No. MI0000804; SEQ ID NO: 631) having a hairpin-like structure is known as a precursor of "hsa-miR-328-3p."

The term "hsa-miR-122-5p gene" or "hsa-miR-122-5p" used herein includes the hsa-miR-122-5p gene (miRBase Accession No. MIMAT0000421) shown in SEQ ID NO: 237, a homolog or an ortholog of a different organism species, and the like. The hsa-miR-122-5p gene can be obtained by a method described in Bentwich I et al., 2005, Nat. Genet., Vol. 37, pp. 766-770. Also, "hsa-mir-122" (miRBase Accession No. MI0000442; SEQ ID NO: 632) having a hairpin-like structure is known as a precursor of "hsa-miR-122-5p."

The term "hsa-miR-202-3p gene" or "hsa-miR-202-3p" used herein includes the hsa-miR-202-3p gene (miRBase Accession No. MIMAT0002811) shown in SEQ ID NO: 238, a homolog or an ortholog of a different organism species, and the like. The hsa-miR-202-3p gene can be obtained by a method described in Persson H et al., 2011, Cancer Res., Vol. 71, pp. 78-86. Also, "hsa-mir-202" (miRBase Accession No. MI0003130; SEQ ID NO: 485) having a hairpin-like structure is known as a precursor of "hsa-miR-202-3p."

The term "hsa-miR-4781-5p gene" or "hsa-miR-4781-5p" used herein includes the hsa-miR-4781-5p gene (miRBase Accession No. MIMAT0019942) shown in SEQ ID NO: 239, a homolog or an ortholog of a different organism species, and the like. The hsa-miR-4781-5p gene can be obtained by a method described in Artzi S et al., 2008, BMC Bioinformatics, Vol. 9, p. 39. Also, "hsa-mir-4781" (miRBase Accession No. MI0017426; SEQ ID NO: 633) having a hairpin-like structure is known as a precursor of "hsa-miR-4781-5p."

The term "hsa-miR-718 gene" or "hsa-miR-718" used herein includes the hsa-miR-718 gene (miRBase Accession No. MIMAT0012735) shown in SEQ ID NO: 240, a homolog or an ortholog of a different organism species, and the like. The hsa-miR-718 gene can be obtained by a method described in Kim J et al., 2004, Proc. Natl. Acad. Sci. U.S.A., Vol. 101, pp. 360-365. Also, "hsa-mir-718" (miRBase Accession No. MI0012489; SEQ ID NO: 634) having a hairpin-like structure is known as a precursor of "hsa-miR-718."

The term "hsa-miR-342-3p gene" or "hsa-miR-342-3p" used herein includes the hsa-miR-342-3p gene (miRBase Accession No. MIMAT0000753) shown in SEQ ID NO: 241, a homolog or an ortholog of a different organism species, and the like. The hsa-miR-342-3p gene can be obtained by a method described in Lagos-Quintana M et al., 2001, Science, Vol. 294, pp. 853-858. Also, "hsa-mir-342" (miRBase Accession No. MI0000805; SEQ ID NO: 635) having a hairpin-like structure is known as a precursor of "hsa-miR-342-3p."

The term "hsa-miR-26b-3p gene" or "hsa-miR-26b-3p" used herein includes the hsa-miR-26b-3p gene (miRBase Accession No. MIMAT0004500) shown in SEQ ID NO: 242, a homolog or an ortholog of a different organism species, and the like. The hsa-miR-26b-3p gene can be obtained by a method described in Lagos-Quintana M et al., 2002, Curr. Biol., Vol. 12, pp. 735-739. Also, "hsa-mir-26b" (miRBase Accession No. MI0000084; SEQ ID NO: 636) having a hairpin-like structure is known as a precursor of "hsa-miR-26b-3p."

The term "hsa-miR-140-3p gene" or "hsa-miR-140-3p" used herein includes the hsa-miR-140-3p gene (miRBase Accession No. MIMAT0004597) shown in SEQ ID NO: 243, a homolog or an ortholog of a different organism species, and the like. The hsa-miR-140-3p gene can be obtained by a method described in Lagos-Quintana M et al., 2003, RNA, Vol. 9, pp. 175-179. Also, "hsa-mir-140" (miRBase Accession No. MI0000456; SEQ ID NO: 637) having a hairpin-like structure is known as a precursor of "hsa-miR-140-3p."

The term "hsa-miR-200a-3p gene" or "hsa-miR-200a-3p" used herein includes the hsa-miR-200a-3p gene (miRBase Accession No. MIMAT0000682) shown in SEQ ID NO: 244, a homolog or an ortholog of a different organism species, and the like. The hsa-miR-200a-3p gene can be obtained by a method described in Kasashima K et al., 2004, Biochem. Biophys. Res. Commun., Vol. 322, pp. 403-410. Also, "hsa-mir-200a" (miRBase Accession No. MI0000737;

SEQ ID NO: 638) having a hairpin-like structure is known as a precursor of “hsa-miR-200a-3p.”

The term “hsa-miR-378a-3p gene” or “hsa-miR-378a-3p” used herein includes the hsa-miR-378a-3p gene (miRBase Accession No. MIMAT0000732) shown in SEQ ID NO: 245, a homolog or an ortholog of a different organism species, and the like. The hsa-miR-378a-3p gene can be obtained by a method described in Fu H et al., 2005, FEBS Lett., Vol. 579, pp. 3849-3854. Also, “hsa-mir-378a” (miRBase Accession No. MI0000786; SEQ ID NO: 639) having a hairpin-like structure is known as a precursor of “hsa-miR-378a-3p.”

The term “hsa-miR-484 gene” or “hsa-miR-484” used herein includes the hsa-miR-484 gene (miRBase Accession No. MIMAT0002174) shown in SEQ ID NO: 246, a homolog or an ortholog of a different organism species, and the like. The hsa-miR-484 gene can be obtained by a method described in Houbaviy H B et al., 2003, Dev. Cell., Vol. 5, pp. 351-358. Also, “hsa-mir-484” (miRBase Accession No. MI0002468; SEQ ID NO: 640) having a hairpin-like structure is known as a precursor of “hsa-miR-484.”

The term “hsa-miR-296-5p gene” or “hsa-miR-296-5p” used herein includes the hsa-miR-296-5p gene (miRBase Accession No. MIMAT0000690) shown in SEQ ID NO: 247, a homolog or an ortholog of a different organism species, and the like. The hsa-miR-296-5p gene can be obtained by a method described in Lim L P et al., 2003, Science, Vol. 299, p. 1540. Also, “hsa-mir-296” (miRBase Accession No. MI0000747; SEQ ID NO: 641) having a hairpin-like structure is known as a precursor of “hsa-miR-296-5p.”

The term “hsa-miR-205-5p gene” or “hsa-miR-205-5p” used herein includes the hsa-miR-205-5p gene (miRBase Accession No. MIMAT0000266) shown in SEQ ID NO: 248, a homolog or an ortholog of a different organism species, and the like. The hsa-miR-205-5p gene can be obtained by a method described in Altuvia Y et al., 2005, Nucleic Acids Res., Vol. 33, pp. 2697-2706. Also, “hsa-mir-205” (miRBase Accession No. MI0000285; SEQ ID NO: 642) having a hairpin-like structure is known as a precursor of “hsa-miR-205-5p.”

The term “hsa-miR-431-5p gene” or “hsa-miR-431-5p” used herein includes the hsa-miR-431-5p gene (miRBase Accession No. MIMAT0001625) shown in SEQ ID NO: 249, a homolog or an ortholog of a different organism species, and the like. The hsa-miR-431-5p gene can be obtained by a method described in Kawaji H et al., 2008, BMC Genomics, Vol. 9, p. 157. Also, “hsa-mir-431” (miRBase Accession No. MI0001721; SEQ ID NO: 643) having a hairpin-like structure is known as a precursor of “hsa-miR-431-5p.”

The term “hsa-miR-1471 gene” or “hsa-miR-1471” used herein includes the hsa-miR-1471 gene (miRBase Accession No. MIMAT0007349) shown in SEQ ID NO: 250, a homolog or an ortholog of a different organism species, and the like. The hsa-miR-1471 gene can be obtained by a method described in Azuma, Mukai, A et al., 2008, Proc. Natl. Acad. Sci. U.S.A., Vol. 105, pp. 7964-7969. Also, “hsa-mir-1471” (miRBase Accession No. MI0007076; SEQ ID NO: 644) having a hairpin-like structure is known as a precursor of “hsa-miR-1471.”

The term “hsa-miR-1538 gene” or “hsa-miR-1538” used herein includes the hsa-miR-1538 gene (miRBase Accession No. MIMAT0007400) shown in SEQ ID NO: 251, a homolog or an ortholog of a different organism species, and the like. The hsa-miR-1538 gene can be obtained by a method described in Cummins J M et al., 2006, Proc. Natl. Acad. Sci. U.S.A., Vol. 103, pp. 3687-3692. Also, “hsa-mir-1538” (miRBase Accession No. MI0007259; SEQ ID NO: 645) having a hairpin-like structure is known as a precursor of “hsa-miR-1538.”

The term “hsa-miR-449b-3p gene” or “hsa-miR-449b-3p” used herein includes the hsa-miR-449b-3p gene (miRBase Accession No. MIMAT0009203) shown in SEQ ID NO: 252, a homolog or an ortholog of a different organism species, and the like. The hsa-miR-449b-3p gene can be obtained by a method described in Schotte D et al., 2009, Leukemia, Vol. 23, pp. 313-322. Also, “hsa-mir-449b” (miRBase Accession No. MI0003673; SEQ ID NO: 646) having a hairpin-like structure is known as a precursor of “hsa-miR-449b-3p.”

The term “hsa-miR-1976 gene” or “hsa-miR-1976” used herein includes the hsa-miR-1976 gene (miRBase Accession No. MIMAT0009451) shown in SEQ ID NO: 253, a homolog or an ortholog of a different organism species, and the like. The hsa-miR-1976 gene can be obtained by a method described in Goff L A et al., 2009, PLoS One, Vol. 4, e7192. Also, “hsa-mir-1976” (miRBase Accession No. MI0009986; SEQ ID NO: 647) having a hairpin-like structure is known as a precursor of “hsa-miR-1976.”

The term “hsa-miR-4268 gene” or “hsa-miR-4268” used herein includes the hsa-miR-4268 gene (miRBase Accession No. MIMAT0016896) shown in SEQ ID NO: 254, a homolog or an ortholog of a different organism species, and the like. The hsa-miR-4268 gene can be obtained by a method described in Goff L A et al., 2009, PLoS One, Vol. 4, e7192. Also, “hsa-mir-4268” (miRBase Accession No. MI0015874; SEQ ID NO: 648) having a hairpin-like structure is known as a precursor of “hsa-miR-4268.”

The term “hsa-miR-4279 gene” or “hsa-miR-4279” used herein includes the hsa-miR-4279 gene (miRBase Accession No. MIMAT0016909) shown in SEQ ID NO: 255, a homolog or an ortholog of a different organism species, and the like. The hsa-miR-4279 gene can be obtained by a method described in Witten D et al., 2010, BMC Biol., Vol. 8, p. 58. Also, “hsa-mir-4279” (miRBase Accession No. MI0015887; SEQ ID NO: 649) having a hairpin-like structure is known as a precursor of “hsa-miR-4279.”

The term “hsa-miR-3620-3p gene” or “hsa-miR-3620-3p” used herein includes the hsa-miR-3620-3p gene (miRBase Accession No. MIMAT0018001) shown in SEQ ID NO: 256, a homolog or an ortholog of a different organism species, and the like. The hsa-miR-3620-3p gene can be obtained by a method described in Witten D et al., 2010, BMC Biol., Vol. 8, p. 58. Also, “hsa-mir-3620” (miRBase Accession No. MI0016011; SEQ ID NO: 650) having a hairpin-like structure is known as a precursor of “hsa-miR-3620-3p.”

The term “hsa-miR-3944-3p gene” or “hsa-miR-3944-3p” used herein includes the hsa-miR-3944-3p gene (miRBase Accession No. MIMAT0018360) shown in SEQ ID NO: 257, a homolog or an ortholog of a different organism species, and the like. The hsa-miR-3944-3p gene can be obtained by a method described in Liao J Y et al., 2010, PLoS One, Vol. 5, e10563. Also, “hsa-mir-3944” (miRBase Accession No. MI0016601; SEQ ID NO: 651) having a hairpin-like structure is known as a precursor of “hsa-miR-3944-3p.”

The term “hsa-miR-3156-3p gene” or “hsa-miR-3156-3p” used herein includes the hsa-miR-3156-3p gene (miRBase Accession No. MIMAT0019209) shown in SEQ ID NO: 258, a homolog or an ortholog of a different organism species, and the like. The hsa-miR-3156-3p gene can be obtained by a method described in Stark M S et al., 2010, PLoS One, Vol. 5, e9685. Also, "hsa-mir-3156-1 and hsa-mir-3156-2" (miRBase Accession Nos. MI0014184 and MI0014230; SEQ ID NOs: 652 and 653) each having a hairpin-like structure are known as precursors of "hsa-miR-3156-3p."

The term "hsa-miR-3187-5p gene" or "hsa-miR-3187-5p" used herein includes the hsa-miR-3187-5p gene (miRBase Accession No. MIMAT0019216) shown in SEQ ID NO: 259, a homolog or an ortholog of a different organism species, and the like. The hsa-miR-318'7-5p gene can be obtained by a method described in Stark M S et al., 2010, PLoS One, Vol. 5, e9685. Also, "hsa-mir-3187" (miRBase Accession No. MI0014231; SEQ ID NO: 654) having a hairpin-like structure is known as a precursor of "hsa-miR-3187-5p."

The term "hsa-miR-4685-3p gene" or "hsa-miR-4685-3p" used herein includes the hsa-miR-4685-3p gene (miRBase Accession No. MIMAT0019772) shown in SEQ ID NO: 260, a homolog or an ortholog of a different organism species, and the like. The hsa-miR-4685-3p gene can be obtained by a method described in Persson H et al., 2011, Cancer Res., Vol. 71, pp. 78-86. Also, "hsa-mir-4685" (miRBase Accession No. MI0017317; SEQ ID NO: 655) having a hairpin-like structure is known as a precursor of "hsa-miR-4685-3p."

The term "hsa-miR-4695-3p gene" or "hsa-miR-4695-3p" used herein includes the hsa-miR-4695-3p gene (miRBase Accession No. MIMAT0019789) shown in SEQ ID NO: 261, a homolog or an ortholog of a different organism species, and the like. The hsa-miR-4695-3p gene can be obtained by a method described in Persson H et al., 2011, Cancer Res., Vol. 71, pp. 78-86. Also, "hsa-mir-4695" (miRBase Accession No. MI0017328; SEQ ID NO: 656) having a hairpin-like structure is known as a precursor of "hsa-miR-4695-3p."

The term "hsa-miR-4697-3p gene" or "hsa-miR-4697-3p" used herein includes the hsa-miR-4697-3p gene (miRBase Accession No. MIMAT0019792) shown in SEQ ID NO: 262, a homolog or an ortholog of a different organism species, and the like. The hsa-miR-4697-3p gene can be obtained by a method described in Persson H et al., 2011, Cancer Res., Vol. 71, pp. 78-86. Also, "hsa-mir-4697" (miRBase Accession No. MI0017330; SEQ ID NO: 657) having a hairpin-like structure is known as a precursor of "hsa-miR-4697-3p."

The term "hsa-miR-4713-5p gene" or "hsa-miR-4713-5p" used herein includes the hsa-miR-4713-5p gene (miRBase Accession No. MIMAT0019820) shown in SEQ ID NO: 263, a homolog or an ortholog of a different organism species, and the like. The hsa-miR-4713-5p gene can be obtained by a method described in Persson H et al., 2011, Cancer Res., Vol. 71, pp. 78-86. Also, "hsa-mir-4713" (miRBase Accession No. MI0017347; SEQ ID NO: 658) having a hairpin-like structure is known as a precursor of "hsa-miR-4713-5p."

The term "hsa-miR-4723-3p gene" or "hsa-miR-4723-3p" used herein includes the hsa-miR-4723-3p gene (miRBase Accession No. MIMAT0019839) shown in SEQ ID NO: 264, a homolog or an ortholog of a different organism species, and the like. The hsa-miR-4723-3p gene can be obtained by a method described in Persson H et al., 2011, Cancer Res., Vol. 71, pp. 78-86. Also, "hsa-mir-4723" (miRBase Accession No. MI0017359; SEQ ID NO: 659) having a hairpin-like structure is known as a precursor of "hsa-miR-4723-3p."

The term "hsa-miR-371b-3p gene" or "hsa-miR-371b-3p" used herein includes the hsa-miR-371b-3p gene (miRBase Accession No. MIMAT0019893) shown in SEQ ID NO: 265, a homolog or an ortholog of a different organism species, and the like. The hsa-miR-371b-3p gene can be obtained by a method described in Persson H et al., 2011, Cancer Res., Vol. 71, pp. 78-86. Also, "hsa-mir-371b" (miRBase Accession No. MI0017393; SEQ ID NO: 660) having a hairpin-like structure is known as a precursor of "hsa-miR-371b-3p."

The term "hsa-miR-3151-3p gene" or "hsa-miR-3151-3p" used herein includes the hsa-miR-3151-3p gene (miRBase Accession No. MIMAT0027026) shown in SEQ ID NO: 266, a homolog or an ortholog of a different organism species, and the like. The hsa-miR-3151-3p gene can be obtained by a method described in Stark M S et al., 2010, PLoS One, Vol. 5, e9685. Also, "hsa-mir-3151" (miRBase Accession No. MI0014178; SEQ ID NO: 661) having a hairpin-like structure is known as a precursor of "hsa-miR-3151-3p."

The term "hsa-miR-3192-3p gene" or "hsa-miR-3192-3p" used herein includes the hsa-miR-3192-3p gene (miRBase Accession No. MIMAT0027027) shown in SEQ ID NO: 267, a homolog or an ortholog of a different organism species, and the like. The hsa-miR-3192-3p gene can be obtained by a method described in Stark M S et al., 2010, PLoS One, Vol. 5, e9685. Also, "hsa-mir-3192" (miRBase Accession No. MI0014237; SEQ ID NO: 662) having a hairpin-like structure is known as a precursor of "hsa-miR-3192-3p."

The term "hsa-miR-6728-3p gene" or "hsa-miR-6728-3p" used herein includes the hsa-miR-6728-3p gene (miRBase Accession No. MIMAT0027358) shown in SEQ ID NO: 268, a homolog or an ortholog of a different organism species, and the like. The hsa-miR-6728-3p gene can be obtained by a method described in Ladewig E et al., 2012, Genome Res., Vol. 22, pp. 1634-1645. Also, "hsa-mir-6728" (miRBase Accession No. MI0022573; SEQ ID NO: 663) having a hairpin-like structure is known as a precursor of "hsa-miR-6728-3p."

The term "hsa-miR-6736-3p gene" or "hsa-miR-6736-3p" used herein includes the hsa-miR-6736-3p gene (miRBase Accession No. MIMAT0027374) shown in SEQ ID NO: 269, a homolog or an ortholog of a different organism species, and the like. The hsa-miR-6736-3p gene can be obtained by a method described in Ladewig E et al., 2012, Genome Res., Vol. 22, pp. 1634-1645. Also, "hsa-mir-6736" (miRBase Accession No. MI0022581; SEQ ID NO: 664) having a hairpin-like structure is known as a precursor of "hsa-miR-6736-3p."

The term "hsa-miR-6740-3p gene" or "hsa-miR-6740-3p" used herein includes the hsa-miR-6740-3p gene (miRBase Accession No. MIMAT0027382) shown in SEQ ID NO: 270, a homolog or an ortholog of a different organism species, and the like. The hsa-miR-6740-3p gene can be obtained by a method described in Ladewig E et al., 2012, Genome Res., Vol. 22, pp. 1634-1645. Also, "hsa-mir-6740" (miRBase Accession No. MI0022585; SEQ ID NO: 665) having a hairpin-like structure is known as a precursor of "hsa-miR-6740-3p."

The term "hsa-miR-6741-3p gene" or "hsa-miR-6741-3p" used herein includes the hsa-miR-6741-3p gene (miRBase Accession No. MIMAT0027384) shown in SEQ ID NO: 271, a homolog or an ortholog of a different organism species, and the like. The hsa-miR-6741-3p gene can be obtained by a method described in Ladewig E et al., 2012, Genome Res., Vol. 22, pp. 1634-1645. Also, "hsa-mir-6741"

(miRBase Accession No. MI0022586; SEQ ID NO: 666) having a hairpin-like structure is known as a precursor of "hsa-miR-6741-3p."

The term "hsa-miR-6743-3p gene" or "hsa-miR-6743-3p" used herein includes the hsa-miR-6743-3p gene (miRBase Accession No. MIMAT0027388) shown in SEQ ID NO: 272, a homolog or an ortholog of a different organism species, and the like. The hsa-miR-6743-3p gene can be obtained by a method described in Ladewig E et al., 2012, Genome Res., Vol. 22, pp. 1634-1645. Also, "hsa-mir-6743" (miRBase Accession No. MI0022588; SEQ ID NO: 599) having a hairpin-like structure is known as a precursor of "hsa-miR-6743-3p."

The term "hsa-miR-6747-3p gene" or "hsa-miR-6747-3p" used herein includes the hsa-miR-6747-3p gene (miRBase Accession No. MIMAT0027395) shown in SEQ ID NO: 273, a homolog or an ortholog of a different organism species, and the like. The hsa-miR-6747-3p gene can be obtained by a method described in Ladewig E et al., 2012, Genome Res., Vol. 22, pp. 1634-1645. Also, "hsa-mir-6747" (miRBase Accession No. MI0022592; SEQ ID NO: 667) having a hairpin-like structure is known as a precursor of "hsa-miR-6747-3p."

The term "hsa-miR-6750-3p gene" or "hsa-miR-6750-3p" used herein includes the hsa-miR-6750-3p gene (miRBase Accession No. MIMAT0027401) shown in SEQ ID NO: 274, a homolog or an ortholog of a different organism species, and the like. The hsa-miR-6750-3p gene can be obtained by a method described in Ladewig E et al., 2012, Genome Res., Vol. 22, pp. 1634-1645. Also, "hsa-mir-6750" (miRBase Accession No. MI0022595; SEQ ID NO: 668) having a hairpin-like structure is known as a precursor of "hsa-miR-6747-3p."

The term "hsa-miR-6754-3p gene" or "hsa-miR-6754-3p" used herein includes the hsa-miR-6754-3p gene (miRBase Accession No. MIMAT0027409) shown in SEQ ID NO: 275, a homolog or an ortholog of a different organism species, and the like. The hsa-miR-6754-3p gene can be obtained by a method described in Ladewig E et al., 2012, Genome Res., Vol. 22, pp. 1634-1645. Also, "hsa-mir-6754" (miRBase Accession No. MI0022599; SEQ ID NO: 669) having a hairpin-like structure is known as a precursor of "hsa-miR-6754-3p."

The term "hsa-miR-6759-3p gene" or "hsa-miR-6759-3p" used herein includes the hsa-miR-6759-3p gene (miRBase Accession No. MIMAT0027419) shown in SEQ ID NO: 276, a homolog or an ortholog of a different organism species, and the like. The hsa-miR-6759-3p gene can be obtained by a method described in Ladewig E et al., 2012, Genome Res., Vol. 22, pp. 1634-1645. Also, "hsa-mir-6759" (miRBase Accession No. MI0022604; SEQ ID NO: 670) having a hairpin-like structure is known as a precursor of "hsa-miR-6759-3p."

The term "hsa-miR-6761-3p gene" or "hsa-miR-6761-3p" used herein includes the hsa-miR-6761-3p gene (miRBase Accession No. MIMAT0027423) shown in SEQ ID NO: 277, a homolog or an ortholog of a different organism species, and the like. The hsa-miR-6761-3p gene can be obtained by a method described in Ladewig E et al., 2012, Genome Res., Vol. 22, pp. 1634-1645. Also, "hsa-mir-6761" (miRBase Accession No. MI0022606; SEQ ID NO: 671) having a hairpin-like structure is known as a precursor of "hsa-miR-6761-3p."

The term "hsa-miR-6762-3p gene" or "hsa-miR-6762-3p" used herein includes the hsa-miR-6762-3p gene (miRBase Accession No. MIMAT0027425) shown in SEQ ID NO: 278, a homolog or an ortholog of a different organism species, and the like. The hsa-miR-6762-3p gene can be obtained by a method described in Ladewig E et al., 2012, Genome Res., Vol. 22, pp. 1634-1645. Also, "hsa-mir-6762" (miRBase Accession No. MI0022607; SEQ ID NO: 672) having a hairpin-like structure is known as a precursor of "hsa-miR-6762-3p."

The term "hsa-miR-6769a-3p gene" or "hsa-miR-6769a-3p" used herein includes the hsa-miR-6769a-3p gene (miRBase Accession No. MIMAT0027439) shown in SEQ ID NO: 279, a homolog or an ortholog of a different organism species, and the like. The hsa-miR-6769a-3p gene can be obtained by a method described in Ladewig E et al., 2012, Genome Res., Vol. 22, pp. 1634-1645. Also, "hsa-mir-6769a" (miRBase Accession No. MI0022614; SEQ ID NO: 673) having a hairpin-like structure is known as a precursor of "hsa-miR-6769a-3p."

The term "hsa-miR-6776-3p gene" or "hsa-miR-6776-3p" used herein includes the hsa-miR-6776-3p gene (miRBase Accession No. MIMAT0027453) shown in SEQ ID NO: 280, a homolog or an ortholog of a different organism species, and the like. The hsa-miR-6776-3p gene can be obtained by a method described in Ladewig E et al., 2012, Genome Res., Vol. 22, pp. 1634-1645. Also, "hsa-mir-6776" (miRBase Accession No. MI0022621; SEQ ID NO: 674) having a hairpin-like structure is known as a precursor of "hsa-miR-6776-3p."

The term "hsa-miR-6778-3p gene" or "hsa-miR-6778-3p" used herein includes the hsa-miR-6778-3p gene (miRBase Accession No. MIMAT0027457) shown in SEQ ID NO: 281, a homolog or an ortholog of a different organism species, and the like. The hsa-miR-6778-3p gene can be obtained by a method described in Ladewig E et al., 2012, Genome Res., Vol. 22, pp. 1634-1645. Also, "hsa-mir-6778" (miRBase Accession No. MI0022623; SEQ ID NO: 675) having a hairpin-like structure is known as a precursor of "hsa-miR-6778-3p."

The term "hsa-miR-6779-3p gene" or "hsa-miR-6779-3p" used herein includes the hsa-miR-6779-3p gene (miRBase Accession No. MIMAT0027459) shown in SEQ ID NO: 282, a homolog or an ortholog of a different organism species, and the like. The hsa-miR-6779-3p gene can be obtained by a method described in Ladewig E et al., 2012, Genome Res., Vol. 22, pp. 1634-1645. Also, "hsa-mir-6779" (miRBase Accession No. MI0022624; SEQ ID NO: 676) having a hairpin-like structure is known as a precursor of "hsa-miR-6779-3p."

The term "hsa-miR-6786-3p gene" or "hsa-miR-6786-3p" used herein includes the hsa-miR-6786-3p gene (miRBase Accession No. MIMAT0027473) shown in SEQ ID NO: 283, a homolog or an ortholog of a different organism species, and the like. The hsa-miR-6786-3p gene can be obtained by a method described in Ladewig E et al., 2012, Genome Res., Vol. 22, pp. 1634-1645. Also, "hsa-mir-6786" (miRBase Accession No. MI0022631; SEQ ID NO: 539) having a hairpin-like structure is known as a precursor of "hsa-miR-6786-3p."

The term "hsa-miR-6787-3p gene" or "hsa-miR-6787-3p" used herein includes the hsa-miR-6787-3p gene (miRBase Accession No. MIMAT0027475) shown in SEQ ID NO: 284, a homolog or an ortholog of a different organism species, and the like. The hsa-miR-6787-3p gene can be obtained by a method described in Ladewig E et al., 2012, Genome Res., Vol. 22, pp. 1634-1645. Also, "hsa-mir-6787" (miRBase Accession No. MI0022632; SEQ ID NO: 677) having a hairpin-like structure is known as a precursor of "hsa-miR-6787-3p."

The term "hsa-miR-6792-3p gene" or "hsa-miR-6792-3p" used herein includes the hsa-miR-6792-3p gene (miRBase Accession No. MIMAT0027485) shown in SEQ ID NO: 285, a homolog or an ortholog of a different organism species, and the like. The hsa-miR-6792-3p gene can be obtained by a method described in Ladewig E et al., 2012, Genome Res., Vol. 22, pp. 1634-1645. Also, "hsa-mir-6792" (miRBase Accession No. MI0022637; SEQ ID NO: 678) having a hairpin-like structure is known as a precursor of "hsa-miR-6792-3p."

The term "hsa-miR-6794-3p gene" or "hsa-miR-6794-3p" used herein includes the hsa-miR-6794-3p gene (miRBase Accession No. MIMAT0027489) shown in SEQ ID NO: 286, a homolog or an ortholog of a different organism species, and the like. The hsa-miR-6794-3p gene can be obtained by a method described in Ladewig E et al., 2012, Genome Res., Vol. 22, pp. 1634-1645. Also, "hsa-mir-6794" (miRBase Accession No. MI0022639; SEQ ID NO: 679) having a hairpin-like structure is known as a precursor of "hsa-miR-6794-3p."

The term "hsa-miR-6801-3p gene" or "hsa-miR-6801-3p" used herein includes the hsa-miR-6801-3p gene (miRBase Accession No. MIMAT0027503) shown in SEQ ID NO: 287, a homolog or an ortholog of a different organism species, and the like. The hsa-miR-6801-3p gene can be obtained by a method described in Ladewig E et al., 2012, Genome Res., Vol. 22, pp. 1634-1645. Also, "hsa-mir-6801" (miRBase Accession No. MI0022646; SEQ ID NO: 680) having a hairpin-like structure is known as a precursor of "hsa-miR-6801-3p."

The term "hsa-miR-6802-3p gene" or "hsa-miR-6802-3p" used herein includes the hsa-miR-6802-3p gene (miRBase Accession No. MIMAT0027505) shown in SEQ ID NO: 288, a homolog or an ortholog of a different organism species, and the like. The hsa-miR-6802-3p gene can be obtained by a method described in Ladewig E et al., 2012, Genome Res., Vol. 22, pp. 1634-1645. Also, "hsa-mir-6802" (miRBase Accession No. MI0022647; SEQ ID NO: 681) having a hairpin-like structure is known as a precursor of "hsa-miR-6802-3p."

The term "hsa-miR-6803-3p gene" or "hsa-miR-6803-3p" used herein includes the hsa-miR-6803-3p gene (miRBase Accession No. MIMAT0027507) shown in SEQ ID NO: 289, a homolog or an ortholog of a different organism species, and the like. The hsa-miR-6803-3p gene can be obtained by a method described in Ladewig E et al., 2012, Genome Res., Vol. 22, pp. 1634-1645. Also, "hsa-mir-6803" (miRBase Accession No. MI0022648; SEQ ID NO: 682) having a hairpin-like structure is known as a precursor of "hsa-miR-6803-3p."

The term "hsa-miR-6804-3p gene" or "hsa-miR-6804-3p" used herein includes the hsa-miR-6804-3p gene (miRBase Accession No. MIMAT0027509) shown in SEQ ID NO: 290, a homolog or an ortholog of a different organism species, and the like. The hsa-miR-6804-3p gene can be obtained by a method described in Ladewig E et al., 2012, Genome Res., Vol. 22, pp. 1634-1645. Also, "hsa-mir-6804" (miRBase Accession No. MI0022649; SEQ ID NO: 683) having a hairpin-like structure is known as a precursor of "hsa-miR-6804-3p."

The term "hsa-miR-6810-5p gene" or "hsa-miR-6810-5p" used herein includes the hsa-miR-6810-5p gene (miRBase Accession No. MIMAT0027520) shown in SEQ ID NO: 291, a homolog or an ortholog of a different organism species, and the like. The hsa-miR-6810-5p gene can be obtained by a method described in Ladewig E et al., 2012, Genome Res., Vol. 22, pp. 1634-1645. Also, "hsa-mir-6810" (miRBase Accession No. MI0022655; SEQ ID NO: 684) having a hairpin-like structure is known as a precursor of "hsa-miR-6810-5p."

The term "hsa-miR-6823-3p gene" or "hsa-miR-6823-3p" used herein includes the hsa-miR-6823-3p gene (miRBase Accession No. MIMAT0027547) shown in SEQ ID NO: 292, a homolog or an ortholog of a different organism species, and the like. The hsa-miR-6823-3p gene can be obtained by a method described in Ladewig E et al., 2012, Genome Res., Vol. 22, pp. 1634-1645. Also, "hsa-mir-6823" (miRBase Accession No. MI0022668; SEQ ID NO: 550) having a hairpin-like structure is known as a precursor of "hsa-miR-6823-3p."

The term "hsa-miR-6825-3p gene" or "hsa-miR-6825-3p" used herein includes the hsa-miR-6825-3p gene (miRBase Accession No. MIMAT0027551) shown in SEQ ID NO: 293, a homolog or an ortholog of a different organism species, and the like. The hsa-miR-6825-3p gene can be obtained by a method described in Ladewig E et al., 2012, Genome Res., Vol. 22, pp. 1634-1645. Also, "hsa-mir-6825" (miRBase Accession No. MI0022670; SEQ ID NO: 685) having a hairpin-like structure is known as a precursor of "hsa-miR-6825-3p."

The term "hsa-miR-6829-3p gene" or "hsa-miR-6829-3p" used herein includes the hsa-miR-6829-3p gene (miRBase Accession No. MIMAT0027559) shown in SEQ ID NO: 294, a homolog or an ortholog of a different organism species, and the like. The hsa-miR-6829-3p gene can be obtained by a method described in Ladewig E et al., 2012, Genome Res., Vol. 22, pp. 1634-1645. Also, "hsa-mir-6829" (miRBase Accession No. MI0022674; SEQ ID NO: 686) having a hairpin-like structure is known as a precursor of "hsa-miR-6829-3p."

The term "hsa-miR-6833-3p gene" or "hsa-miR-6833-3p" used herein includes the hsa-miR-6833-3p gene (miRBase Accession No. MIMAT0027567) shown in SEQ ID NO: 295, a homolog or an ortholog of a different organism species, and the like. The hsa-miR-6833-3p gene can be obtained by a method described in Ladewig E et al., 2012, Genome Res., Vol. 22, pp. 1634-1645. Also, "hsa-mir-6833" (miRBase Accession No. MI0022678; SEQ ID NO: 687) having a hairpin-like structure is known as a precursor of "hsa-miR-6833-3p."

The term "hsa-miR-6834-3p gene" or "hsa-miR-6834-3p" used herein includes the hsa-miR-6834-3p gene (miRBase Accession No. MIMAT0027569) shown in SEQ ID NO: 296, a homolog or an ortholog of a different organism species, and the like. The hsa-miR-6834-3p gene can be obtained by a method described in Ladewig E et al., 2012, Genome Res., Vol. 22, pp. 1634-1645. Also, "hsa-mir-6834" (miRBase Accession No. MI0022679; SEQ ID NO: 688) having a hairpin-like structure is known as a precursor of "hsa-miR-6834-3p."

The term "hsa-miR-6780b-3p gene" or "hsa-miR-6780b-3p" used herein includes the hsa-miR-6780b-3p gene (miRBase Accession No. MIMAT0027573) shown in SEQ ID NO: 297, a homolog or an ortholog of a different organism species, and the like. The hsa-miR-6780b-3p gene can be obtained by a method described in Ladewig E et al., 2012, Genome Res., Vol. 22, pp. 1634-1645. Also, "hsa-mir-6780b" (miRBase Accession No. MI0022681; SEQ ID NO: 689) having a hairpin-like structure is known as a precursor of "hsa-miR-6780b-3p."

The term "hsa-miR-6845-3p gene" or "hsa-miR-6845-3p" used herein includes the hsa-miR-6845-3p gene (miRBase Accession No. MIMAT0027591) shown in SEQ ID NO: 298, a homolog or an ortholog of a different organism species, and the like. The hsa-miR-6845-3p gene can be obtained by a method described in Ladewig E et al., 2012, Genome Res., Vol. 22, pp. 1634-1645. Also, “hsa-mir-6845” (miRBase Accession No. MI0022691; SEQ ID NO: 690) having a hairpin-like structure is known as a precursor of “hsa-miR-6845-3p.”

The term “hsa-miR-6862-3p gene” or “hsa-miR-6862-3p” used herein includes the hsa-miR-6862-3p gene (miRBase Accession No. MIMAT0027626) shown in SEQ ID NO: 299, a homolog or an ortholog of a different organism species, and the like. The hsa-miR-6862-3p gene can be obtained by a method described in Ladewig E et al., 2012, Genome Res., Vol. 22, pp. 1634-1645. Also, “hsa-mir-6862-1 and hsa-mir-6862-2” (miRBase Accession Nos. MI0022709 and MI0026415; SEQ ID NOs: 691 and 692) each having a hairpin-like structure are known as precursors of “hsa-miR-6862-3p.”

The term “hsa-miR-6865-3p gene” or “hsa-miR-6865-3p” used herein includes the hsa-miR-6865-3p gene (miRBase Accession No. MIMAT0027631) shown in SEQ ID NO: 300, a homolog or an ortholog of a different organism species, and the like. The hsa-miR-6865-3p gene can be obtained by a method described in Ladewig E et al., 2012, Genome Res., Vol. 22, pp. 1634-1645. Also, “hsa-mir-6865” (miRBase Accession No. MI0022712; SEQ ID NO: 693) having a hairpin-like structure is known as a precursor of “hsa-miR-6865-3p.”

The term “hsa-miR-6870-3p gene” or “hsa-miR-6870-3p” used herein includes the hsa-miR-6870-3p gene (miRBase Accession No. MIMAT0027641) shown in SEQ ID NO: 301, a homolog or an ortholog of a different organism species, and the like. The hsa-miR-6870-3p gene can be obtained by a method described in Ladewig E et al., 2012, Genome Res., Vol. 22, pp. 1634-1645. Also, “hsa-mir-6870” (miRBase Accession No. MI0022717; SEQ ID NO: 694) having a hairpin-like structure is known as a precursor of “hsa-miR-6870-3p.”

The term “hsa-miR-6875-3p gene” or “hsa-miR-6875-3p” used herein includes the hsa-miR-6875-3p gene (miRBase Accession No. MIMAT0027651) shown in SEQ ID NO: 302, a homolog or an ortholog of a different organism species, and the like. The hsa-miR-6875-3p gene can be obtained by a method described in Ladewig E et al., 2012, Genome Res., Vol. 22, pp. 1634-1645. Also, “hsa-mir-6875” (miRBase Accession No. MI0022722; SEQ ID NO: 695) having a hairpin-like structure is known as a precursor of “hsa-miR-6875-3p.”

The term “hsa-miR-6877-3p gene” or “hsa-miR-6877-3p” used herein includes the hsa-miR-6877-3p gene (miRBase Accession No. MIMAT0027655) shown in SEQ ID NO: 303, a homolog or an ortholog of a different organism species, and the like. The hsa-miR-6877-3p gene can be obtained by a method described in Ladewig E et al., 2012, Genome Res., Vol. 22, pp. 1634-1645. Also, “hsa-mir-6877” (miRBase Accession No. MI0022724; SEQ ID NO: 696) having a hairpin-like structure is known as a precursor of “hsa-miR-6877-3p.”

The term “hsa-miR-6879-3p gene” or “hsa-miR-6879-3p” used herein includes the hsa-miR-6879-3p gene (miRBase Accession No. MIMAT0027659) shown in SEQ ID NO: 304, a homolog or an ortholog of a different organism species, and the like. The hsa-miR-6879-3p gene can be obtained by a method described in Ladewig E et al., 2012, Genome Res., Vol. 22, pp. 1634-1645. Also, “hsa-mir-6879” (miRBase Accession No. MI0022726; SEQ ID NO: 697) having a hairpin-like structure is known as a precursor of “hsa-miR-6879-3p.”

The term “hsa-miR-6882-3p gene” or “hsa-miR-6882-3p” used herein includes the hsa-miR-6882-3p gene (miRBase Accession No. MIMAT0027665) shown in SEQ ID NO: 305, a homolog or an ortholog of a different organism species, and the like. The hsa-miR-6882-3p gene can be obtained by a method described in Ladewig E et al., 2012, Genome Res., Vol. 22, pp. 1634-1645. Also, “hsa-mir-6882” (miRBase Accession No. MI0022729; SEQ ID NO: 698) having a hairpin-like structure is known as a precursor of “hsa-miR-6882-3p.”

The term “hsa-miR-6885-3p gene” or “hsa-miR-6885-3p” used herein includes the hsa-miR-6885-3p gene (miRBase Accession No. MIMAT0027671) shown in SEQ ID NO: 306, a homolog or an ortholog of a different organism species, and the like. The hsa-miR-6885-3p gene can be obtained by a method described in Ladewig E et al., 2012, Genome Res., Vol. 22, pp. 1634-1645. Also, “hsa-mir-6885” (miRBase Accession No. MI0022732; SEQ ID NO: 699) having a hairpin-like structure is known as a precursor of “hsa-miR-6885-3p.”

The term “hsa-miR-6886-3p gene” or “hsa-miR-6886-3p” used herein includes the hsa-miR-6886-3p gene (miRBase Accession No. MIMAT0027673) shown in SEQ ID NO: 307, a homolog or an ortholog of a different organism species, and the like. The hsa-miR-6886-3p gene can be obtained by a method described in Ladewig E et al., 2012, Genome Res., Vol. 22, pp. 1634-1645. Also, “hsa-mir-6886” (miRBase Accession No. MI0022733; SEQ ID NO: 700) having a hairpin-like structure is known as a precursor of “hsa-miR-6886-3p.”

The term “hsa-miR-6887-3p gene” or “hsa-miR-6887-3p” used herein includes the hsa-miR-6887-3p gene (miRBase Accession No. MIMAT0027675) shown in SEQ ID NO: 308, a homolog or an ortholog of a different organism species, and the like. The hsa-miR-6887-3p gene can be obtained by a method described in Ladewig E et al., 2012, Genome Res., Vol. 22, pp. 1634-1645. Also, “hsa-mir-6887” (miRBase Accession No. MI0022734; SEQ ID NO: 701) having a hairpin-like structure is known as a precursor of “hsa-miR-6887-3p.”

The term “hsa-miR-6890-3p gene” or “hsa-miR-6890-3p” used herein includes the hsa-miR-6890-3p gene (miRBase Accession No. MIMAT0027681) shown in SEQ ID NO: 309, a homolog or an ortholog of a different organism species, and the like. The hsa-miR-6890-3p gene can be obtained by a method described in Ladewig E et al., 2012, Genome Res., Vol. 22, pp. 1634-1645. Also, “hsa-mir-6890” (miRBase Accession No. MI0022737; SEQ ID NO: 702) having a hairpin-like structure is known as a precursor of “hsa-miR-6890-3p.”

The term “hsa-miR-6893-3p gene” or “hsa-miR-6893-3p” used herein includes the hsa-miR-6893-3p gene (miRBase Accession No. MIMAT0027687) shown in SEQ ID NO: 310, a homolog or an ortholog of a different organism species, and the like. The hsa-miR-6893-3p gene can be obtained by a method described in Ladewig E et al., 2012, Genome Res., Vol. 22, pp. 1634-1645. Also, “hsa-mir-6893” (miRBase Accession No. MI0022740; SEQ ID NO: 703) having a hairpin-like structure is known as a precursor of “hsa-miR-6893-3p.”

The term “hsa-miR-6894-3p gene” or “hsa-miR-6894-3p” used herein includes the hsa-miR-6894-3p gene (miRBase Accession No. MIMAT0027689) shown in SEQ ID NO: 311, a homolog or an ortholog of a different organism species, and the like. The hsa-miR-6894-3p gene can be obtained by a method described in Ladewig E et al., 2012, Genome Res., Vol. 22, pp. 1634-1645. Also, “hsa-mir-6894”

(miRBase Accession No. MI0022741; SEQ ID NO: 704) having a hairpin-like structure is known as a precursor of "hsa-miR-6894-3p."

The term "hsa-miR-7106-3p gene" or "hsa-miR-7106-3p" used herein includes the hsa-miR-7106-3p gene (miRBase Accession No. MIMAT0028110) shown in SEQ ID NO: 312, a homolog or an ortholog of a different organism species, and the like. The hsa-miR-7106-3p gene can be obtained by a method described in Ladewig E et al., 2012, Genome Res., Vol. 22, pp. 1634-1645. Also, "hsa-mir-7106" (miRBase Accession No. MI0022957; SEQ ID NO: 705) having a hairpin-like structure is known as a precursor of "hsa-miR-7106-3p."

The term "hsa-miR-7109-3p gene" or "hsa-miR-7109-3p" used herein includes the hsa-miR-7109-3p gene (miRBase Accession No. MIMAT0028116) shown in SEQ ID NO: 313, a homolog or an ortholog of a different organism species, and the like. The hsa-miR-7109-3p gene can be obtained by a method described in Ladewig E et al., 2012, Genome Res., Vol. 22, pp. 1634-1645. Also, "hsa-mir-7109" (miRBase Accession No. MI0022960; SEQ ID NO: 706) having a hairpin-like structure is known as a precursor of "hsa-miR-7109-3p."

The term "hsa-miR-7114-3p gene" or "hsa-miR-7114-3p" used herein includes the hsa-miR-7114-3p gene (miRBase Accession No. MIMAT0028126) shown in SEQ ID NO: 314, a homolog or an ortholog of a different organism species, and the like. The hsa-miR-7114-3p gene can be obtained by a method described in Ladewig E et al., 2012, Genome Res., Vol. 22, pp. 1634-1645. Also, "hsa-mir-7114" (miRBase Accession No. MI0022965; SEQ ID NO: 707) having a hairpin-like structure is known as a precursor of "hsa-miR-7114-3p."

The term "hsa-miR-7155-5p gene" or "hsa-miR-7155-5p" used herein includes the hsa-miR-7155-5p gene (miRBase Accession No. MIMAT0028220) shown in SEQ ID NO: 315, a homolog or an ortholog of a different organism species, and the like. The hsa-miR-7155-5p gene can be obtained by a method described in Meunier J et al., 2013, Genome Res., Vol. 23, pp. 34-45. Also, "hsa-mir-7155" (miRBase Accession No. MI0023615; SEQ ID NO: 708) having a hairpin-like structure is known as a precursor of "hsa-miR-7155-5p."

The term "hsa-miR-7160-5p gene" or "hsa-miR-7160-5p" used herein includes the hsa-miR-7160-5p gene (miRBase Accession No. MIMAT0028230) shown in SEQ ID NO: 316, a homolog or an ortholog of a different organism species, and the like. The hsa-miR-7160-5p gene can be obtained by a method described in Meunier J et al., 2013, Genome Res., Vol. 23, pp. 34-45. Also, "hsa-mir-7160" (miRBase Accession No. MI0023621; SEQ ID NO: 709) having a hairpin-like structure is known as a precursor of "hsa-miR-7160-5p."

The term "hsa-miR-615-3p gene" or "hsa-miR-615-3p" used herein includes the hsa-miR-615-3p gene (miRBase Accession No. MIMAT0003283) shown in SEQ ID NO: 317, a homolog or an ortholog of a different organism species, and the like. The hsa-miR-615-3p gene can be obtained by a method described in Cummins J M et al., 2006, Proc. Natl. Acad. Sci. U.S.A., Vol. 103, pp. 3687-3692. Also, "hsa-mir-615" (miRBase Accession No. MI0003628; SEQ ID NO: 710) having a hairpin-like structure is known as a precursor of "hsa-miR-615-3p."

The term "hsa-miR-920 gene" or "hsa-miR-920" used herein includes the hsa-miR-920 gene (miRBase Accession No. MIMAT0004970) shown in SEQ ID NO: 318, a homolog or an ortholog of a different organism species, and the like. The hsa-miR-920 gene can be obtained by a method described in Novotny G W et al., 2007, Int. J. Androl., Vol. 30, pp. 316-326. Also, "hsa-mir-920" (miRBase Accession No. MI0005712; SEQ ID NO: 711) having a hairpin-like structure is known as a precursor of "hsa-miR-920."

The term "hsa-miR-1825 gene" or "hsa-miR-1825" used herein includes the hsa-miR-1825 gene (miRBase Accession No. MIMAT0006765) shown in SEQ ID NO: 319, a homolog or an ortholog of a different organism species, and the like. The hsa-miR-1825 gene can be obtained by a method described in Friedlander M R et al., 2008, Nat. Biotechnol., Vol. 26, pp. 407-415. Also, "hsa-mir-1825" (miRBase Accession No. MI0008193; SEQ ID NO: 712) having a hairpin-like structure is known as a precursor of "hsa-miR-1825."

The term "hsa-miR-675-3p gene" or "hsa-miR-675-3p" used herein includes the hsa-miR-675-3p gene (miRBase Accession No. MIMAT0006790) shown in SEQ ID NO: 320, a homolog or an ortholog of a different organism species, and the like. The hsa-miR-675-3p gene can be obtained by a method described in Cai X et al., 2007, RNA, Vol. 13, pp. 313-316. Also, "hsa-mir-675" (miRBase Accession No. MI0005416; SEQ ID NO: 713) having a hairpin-like structure is known as a precursor of "hsa-miR-675-3p."

The term "hsa-miR-1910-5p gene" or "hsa-miR-1910-5p" used herein includes the hsa-miR-1910-5p gene (miRBase Accession No. MIMAT0007884) shown in SEQ ID NO: 321, a homolog or an ortholog of a different organism species, and the like. The hsa-miR-1910-5p gene can be obtained by a method described in Bar M et al., 2008, Stem Cells, Vol. 26, pp. 2496-2505. Also, "hsa-mir-1910" (miRBase Accession No. MI0008331; SEQ ID NO: 714) having a hairpin-like structure is known as a precursor of "hsa-miR-1910-5p."

The term "hsa-miR-2278 gene" or "hsa-miR-2278" used herein includes the hsa-miR-2278 gene (miRBase Accession No. MIMAT0011778) shown in SEQ ID NO: 322, a homolog or an ortholog of a different organism species, and the like. The hsa-miR-2278 gene can be obtained by a method described in Nygaard S et al., 2009, BMC Med. Genomics, Vol. 2, p. 35. Also, "hsa-mir-2278" (miRBase Accession No. MI0011285; SEQ ID NO: 715) having a hairpin-like structure is known as a precursor of "hsa-miR-2278."

The term "hsa-miR-2682-3p gene" or "hsa-miR-2682-3p" used herein includes the hsa-miR-2682-3p gene (miRBase Accession No. MIMAT0013518) shown in SEQ ID NO: 323, a homolog or an ortholog of a different organism species, and the like. The hsa-miR-2682-3p gene can be obtained by a method described in Creighton C J et al., 2010, PLoS One, Vol. 5, e9637. Also, "hsa-mir-2682" (miRBase Accession No. MI0012063; SEQ ID NO: 716) having a hairpin-like structure is known as a precursor of "hsa-miR-2682-3p."

The term "hsa-miR-3122 gene" or "hsa-miR-3122" used herein includes the hsa-miR-3122 gene (miRBase Accession No. MIMAT0014984) shown in SEQ ID NO: 324, a homolog or an ortholog of a different organism species, and the like. The hsa-miR-3122 gene can be obtained by a method described in Stark M S et al., 2010, PLoS One, Vol. 5, e9685. Also, "hsa-mir-3122" (miRBase Accession No. MI0014138; SEQ ID NO: 717) having a hairpin-like structure is known as a precursor of "hsa-miR-3122."

The term "hsa-miR-3151-5p gene" or "hsa-miR-3151-5p" used herein includes the hsa-miR-3151-5p gene (miRBase Accession No. MIMAT0015024) shown in SEQ ID NO: 325, a homolog or an ortholog of a different organism species, and the like. The hsa-miR-3151-5p gene can be obtained by a method described in Stark M S et al., 2010, PLoS One, Vol. 5, e9685. Also, “hsa-mir-3151” (miRBase Accession No. MI0014178; SEQ ID NO: 661) having a hairpin-like structure is known as a precursor of “hsa-miR-3151-5p.”

The term “hsa-miR-3175 gene” or “hsa-miR-3175” used herein includes the hsa-miR-3175 gene (miRBase Accession No. MIMAT0015052) shown in SEQ ID NO: 326, a homolog or an ortholog of a different organism species, and the like. The hsa-miR-3175 gene can be obtained by a method described in Creighton C J et al., 2010, PLoS One, Vol. 5, e9637. Also, “hsa-mir-3175” (miRBase Accession No. MI0014209; SEQ ID NO: 718) having a hairpin-like structure is known as a precursor of “hsa-miR-3175.”

The term “hsa-miR-4323 gene” or “hsa-miR-4323” used herein includes the hsa-miR-4323 gene (miRBase Accession No. MIMAT0016875) shown in SEQ ID NO: 327, a homolog or an ortholog of a different organism species, and the like. The hsa-miR-4323 gene can be obtained by a method described in Goff L A et al., 2009, PLoS One, Vol. 4, e7192. Also, “hsa-mir-4323” (miRBase Accession No. MI0015853; SEQ ID NO: 719) having a hairpin-like structure is known as a precursor of “hsa-miR-4323.”

The term “hsa-miR-4326 gene” or “hsa-miR-4326” used herein includes the hsa-miR-4326 gene (miRBase Accession No. MIMAT0016888) shown in SEQ ID NO: 328, a homolog or an ortholog of a different organism species, and the like. The hsa-miR-4326 gene can be obtained by a method described in Goff L A et al., 2009, PLoS One, Vol. 4, e7192. Also, “hsa-mir-4326” (miRBase Accession No. MI0015866; SEQ ID NO: 720) having a hairpin-like structure is known as a precursor of “hsa-miR-4326.”

The term “hsa-miR-4284 gene” or “hsa-miR-4284” used herein includes the hsa-miR-4284 gene (miRBase Accession No. MIMAT0016915) shown in SEQ ID NO: 329, a homolog or an ortholog of a different organism species, and the like. The hsa-miR-4284 gene can be obtained by a method described in Goff L A et al., 2009, PLoS One, Vol. 4, e7192. Also, “hsa-mir-4284” (miRBase Accession No. MI0015893; SEQ ID NO: 721) having a hairpin-like structure is known as a precursor of “hsa-miR-4284.”

The term “hsa-miR-3605-3p gene” or “hsa-miR-3605-3p” used herein includes the hsa-miR-3605-3p gene (miRBase Accession No. MIMAT0017982) shown in SEQ ID NO: 330, a homolog or an ortholog of a different organism species, and the like. The hsa-miR-3605-3p gene can be obtained by a method described in Creighton C J et al., 2010, PLoS One, Vol. 5, e9637. Also, “hsa-mir-3605” (miRBase Accession No. MI0015995; SEQ ID NO: 722) having a hairpin-like structure is known as a precursor of “hsa-miR-3605-3p.”

The term “hsa-miR-3622b-5p gene” or “hsa-miR-3622b-5p” used herein includes the hsa-miR-3622b-5p gene (miRBase Accession No. MIMAT0018005) shown in SEQ ID NO: 331, a homolog or an ortholog of a different organism species, and the like. The hsa-miR-3622b-5p gene can be obtained by a method described in Witten D et al., 2010, BMC Biol., Vol. 8, p. 58. Also, “hsa-mir-3622b” (miRBase Accession No. MI0016014; SEQ ID NO: 723) having a hairpin-like structure is known as a precursor of “hsa-miR-3622b-5p.”

The term “hsa-miR-3646 gene” or “hsa-miR-3646” used herein includes the hsa-miR-3646 gene (miRBase Accession No. MIMAT0018065) shown in SEQ ID NO: 332, a homolog or an ortholog of a different organism species, and the like. The hsa-miR-3646 gene can be obtained by a method described in Meiri E et al., 2010, Nucleic Acids Res., Vol. 38, pp. 6234-6246. Also, “hsa-mir-3646” (miRBase Accession No. MI0016046; SEQ ID NO: 724) having a hairpin-like structure is known as a precursor of “hsa-miR-3646.”

The term “hsa-miR-3158-5p gene” or “hsa-miR-3158-5p” used herein includes the hsa-miR-3158-5p gene (miRBase Accession No. MIMAT0019211) shown in SEQ ID NO: 333, a homolog or an ortholog of a different organism species, and the like. The hsa-miR-3158-5p gene can be obtained by a method described in Creighton C J et al., 2010, PLoS One, Vol. 5, e9637. Also, “hsa-mir-3158-1 and hsa-mir-3158-2” (miRBase Accession Nos. MI0014186 and MI0014187; SEQ ID NOs: 725 and 726) each having a hairpin-like structure are known as precursors of “hsa-miR-3158-5p.”

The term “hsa-miR-4722-3p gene” or “hsa-miR-4722-3p” used herein includes the hsa-miR-4722-3p gene (miRBase Accession No. MIMAT0019837) shown in SEQ ID NO: 334, a homolog or an ortholog of a different organism species, and the like. The hsa-miR-4722-3p gene can be obtained by a method described in Persson H et al., 2011, Cancer Res., Vol. 71, pp. 78-86. Also, “hsa-mir-4722” (miRBase Accession No. MI0017357; SEQ ID NO: 727) having a hairpin-like structure is known as a precursor of “hsa-miR-4722-3p.”

The term “hsa-miR-4728-3p gene” or “hsa-miR-4728-3p” used herein includes the hsa-miR-4728-3p gene (miRBase Accession No. MIMAT0019850) shown in SEQ ID NO: 335, a homolog or an ortholog of a different organism species, and the like. The hsa-miR-4728-3p gene can be obtained by a method described in Persson H et al., 2011, Cancer Res., Vol. 71, pp. 78-86. Also, “hsa-mir-4728” (miRBase Accession No. MI0017365; SEQ ID NO: 393) having a hairpin-like structure is known as a precursor of “hsa-miR-4728-3p.”

The term “hsa-miR-4747-3p gene” or “hsa-miR-4747-3p” used herein includes the hsa-miR-4747-3p gene (miRBase Accession No. MIMAT0019883) shown in SEQ ID NO: 336, a homolog or an ortholog of a different organism species, and the like. The hsa-miR-4747-3p gene can be obtained by a method described in Persson H et al., 2011, Cancer Res., Vol. 71, pp. 78-86. Also, “hsa-mir-4747” (miRBase Accession No. MI0017386; SEQ ID NO: 728) having a hairpin-like structure is known as a precursor of “hsa-miR-4747-3p.”

The term “hsa-miR-4436b-5p gene” or “hsa-miR-4436b-5p” used herein includes the hsa-miR-4436b-5p gene (miRBase Accession No. MIMAT0019940) shown in SEQ ID NO: 337, a homolog or an ortholog of a different organism species, and the like. The hsa-miR-4436b-5p gene can be obtained by a method described in Persson H et al., 2011, Cancer Res., Vol. 71, pp. 78-86. Also, “hsa-mir-4436b-1 and hsa-mir-4436b-2” (miRBase Accession Nos. MI0017425 and MI0019110; SEQ ID NOs: 729 and 730) each having a hairpin-like structure are known as precursors of “hsa-miR-4436b-5p.”

The term “hsa-miR-5196-3p gene” or “hsa-miR-5196-3p” used herein includes the hsa-miR-5196-3p gene (miRBase Accession No. MIMAT0021129) shown in SEQ ID NO: 338, a homolog or an ortholog of a different organism species, and the like. The hsa-miR-5196-3p gene can be obtained by a method described in Schotte D et al., 2011, Leukemia, Vol. 25, pp. 1389-1399. Also, “hsa-mir-5196” (miRBase Accession No. MI0018175; SEQ ID NO: 731) having a hairpin-like structure is known as a precursor of “hsa-miR-4436b-5p.”

The term "hsa-miR-5589-5p gene" or "hsa-miR-5589-5p" used herein includes the hsa-miR-5589-5p gene (miRBase Accession No. MIMAT0022297) shown in SEQ ID NO: 339, a homolog or an ortholog of a different organism species, and the like. The hsa-miR-5589-5p gene can be obtained by a method described in Friedlander M R et al., 2012, Nucleic Acids Res., Vol. 40, pp. 37-52. Also, "hsa-mir-5589" (miRBase Accession No. MI0019148; SEQ ID NO: 732) having a hairpin-like structure is known as a precursor of "hsa-miR-5589-5p."

The term "hsa-miR-345-3p gene" or "hsa-miR-345-3p" used herein includes the hsa-miR-345-3p gene (miRBase Accession No. MIMAT0022698) shown in SEQ ID NO: 340, a homolog or an ortholog of a different organism species, and the like. The hsa-miR-345-3p gene can be obtained by a method described in Kim J et al., 2004, Proc. Natl. Acad. Sci. U.S.A., Vol. 101, pp. 360-365. Also, "hsa-mir-345" (miRBase Accession No. MI0000825; SEQ ID NO: 615) having a hairpin-like structure is known as a precursor of "hsa-miR-345-3p."

The term "hsa-miR-642b-5p gene" or "hsa-miR-642b-5p" used herein includes the hsa-miR-642b-5p gene (miRBase Accession No. MIMAT0022736) shown in SEQ ID NO: 341, a homolog or an ortholog of a different organism species, and the like. The hsa-miR-642b-5p gene can be obtained by a method described in Witten D et al., 2010, BMC Biol., Vol. 8, p. 58. Also, "hsa-mir-642b" (miRBase Accession No. MI0016685; SEQ ID NO: 733) having a hairpin-like structure is known as a precursor of "hsa-miR-642b-5p."

The term "hsa-miR-6716-3p gene" or "hsa-miR-6716-3p" used herein includes the hsa-miR-6716-3p gene (miRBase Accession No. MIMAT0025845) shown in SEQ ID NO: 342, a homolog or an ortholog of a different organism species, and the like. The hsa-miR-6716-3p gene can be obtained by a method described in Li Y et al., 2012, Gene, Vol. 497, pp. 330-335. Also, "hsa-mir-6716" (miRBase Accession No. MI0022550; SEQ ID NO: 734) having a hairpin-like structure is known as a precursor of "hsa-miR-6716-3p."

The term "hsa-miR-6511b-3p gene" or "hsa-miR-6511b-3p" used herein includes the hsa-miR-6511b-3p gene (miRBase Accession No. MIMAT0025848) shown in SEQ ID NO: 343, a homolog or an ortholog of a different organism species, and the like. The hsa-miR-6511b-3p gene can be obtained by a method described in Li Y et al., 2012, Gene, Vol. 497, pp. 330-335. Also, "hsa-mir-6511b-1 and hsa-mir-6511b-2" (miRBase Accession Nos. MI0022552 and MI0023431; SEQ ID NOs: 735 and 736) each having a hairpin-like structure are known as precursors of "hsa-miR-6511b-3p."

The term "hsa-miR-208a-5p gene" or "hsa-miR-208a-5p" used herein includes the hsa-miR-208a-5p gene (miRBase Accession No. MIMAT0026474) shown in SEQ ID NO: 344, a homolog or an ortholog of a different organism species, and the like. The hsa-miR-208a-5p gene can be obtained by a method described in Lagos-Quintana M et al., 2003, RNA, Vol. 9, pp. 175-179. Also, "hsa-mir-208a" (miRBase Accession No. MI0000251; SEQ ID NO: 737) having a hairpin-like structure is known as a precursor of "hsa-miR-208a-5p."

The term "hsa-miR-6726-3p gene" or "hsa-miR-6726-3p" used herein includes the hsa-miR-6726-3p gene (miRBase Accession No. MIMAT0027354) shown in SEQ ID NO: 345, a homolog or an ortholog of a different organism species, and the like. The hsa-miR-6726-3p gene can be obtained by a method described in Ladewig E et al., 2012, Genome Res., Vol. 22, pp. 1634-1645. Also, "hsa-mir-6726" (miRBase Accession No. MI0022571; SEQ ID NO: 600) having a hairpin-like structure is known as a precursor of "hsa-miR-6726-3p."

The term "hsa-miR-6744-5p gene" or "hsa-miR-6744-5p" used herein includes the hsa-miR-6744-5p gene (miRBase Accession No. MIMAT0027389) shown in SEQ ID NO: 346, a homolog or an ortholog of a different organism species, and the like. The hsa-miR-6744-5p gene can be obtained by a method described in Ladewig E et al., 2012, Genome Res., Vol. 22, pp. 1634-1645. Also, "hsa-mir-6744" (miRBase Accession No. MI0022589; SEQ ID NO: 738) having a hairpin-like structure is known as a precursor of "hsa-miR-6744-5p."

The term "hsa-miR-6782-3p gene" or "hsa-miR-6782-3p" used herein includes the hsa-miR-6782-3p gene (miRBase Accession No. MIMAT0027465) shown in SEQ ID NO: 347, a homolog or an ortholog of a different organism species, and the like. The hsa-miR-6782-3p gene can be obtained by a method described in Ladewig E et al., 2012, Genome Res., Vol. 22, pp. 1634-1645. Also, "hsa-mir-6782" (miRBase Accession No. MI0022627; SEQ ID NO: 739) having a hairpin-like structure is known as a precursor of "hsa-miR-6782-3p."

The term "hsa-miR-6789-3p gene" or "hsa-miR-6789-3p" used herein includes the hsa-miR-6789-3p gene (miRBase Accession No. MIMAT0027479) shown in SEQ ID NO: 348, a homolog or an ortholog of a different organism species, and the like. The hsa-miR-6789-3p gene can be obtained by a method described in Ladewig E et al., 2012, Genome Res., Vol. 22, pp. 1634-1645. Also, "hsa-mir-6789" (miRBase Accession No. MI0022634; SEQ ID NO: 740) having a hairpin-like structure is known as a precursor of "hsa-miR-6789-3p."

The term "hsa-miR-6797-3p gene" or "hsa-miR-6797-3p" used herein includes the hsa-miR-6797-3p gene (miRBase Accession No. MIMAT0027495) shown in SEQ ID NO: 349, a homolog or an ortholog of a different organism species, and the like. The hsa-miR-6797-3p gene can be obtained by a method described in Ladewig E et al., 2012, Genome Res., Vol. 22, pp. 1634-1645. Also, "hsa-mir-6797" (miRBase Accession No. MI0022642; SEQ ID NO: 741) having a hairpin-like structure is known as a precursor of "hsa-miR-6797-3p."

The term "hsa-miR-6800-3p gene" or "hsa-miR-6800-3p" used herein includes the hsa-miR-6800-3p gene (miRBase Accession No. MIMAT0027501) shown in SEQ ID NO: 350, a homolog or an ortholog of a different organism species, and the like. The hsa-miR-6800-3p gene can be obtained by a method described in Ladewig E et al., 2012, Genome Res., Vol. 22, pp. 1634-1645. Also, "hsa-mir-6800" (miRBase Accession No. MI0022645; SEQ ID NO: 491) having a hairpin-like structure is known as a precursor of "hsa-miR-6800-3p."

The term "hsa-miR-6806-5p gene" or "hsa-miR-6806-5p" used herein includes the hsa-miR-6806-5p gene (miRBase Accession No. MIMAT0027512) shown in SEQ ID NO: 351, a homolog or an ortholog of a different organism species, and the like. The hsa-miR-6806-5p gene can be obtained by a method described in Ladewig E et al., 2012, Genome Res., Vol. 22, pp. 1634-1645. Also, "hsa-mir-6806" (miRBase Accession No. MI0022651; SEQ ID NO: 742) having a hairpin-like structure is known as a precursor of "hsa-miR-6806-5p."

The term "hsa-miR-6824-3p gene" or "hsa-miR-6824-3p" used herein includes the hsa-miR-6824-3p gene (miRBase Accession No. MIMAT0027549) shown in SEQ ID NO:

352, a homolog or an ortholog of a different organism species, and the like. The hsa-miR-6824-3p gene can be obtained by a method described in Ladewig E et al., 2012, Genome Res., Vol. 22, pp. 1634-1645. Also, "hsa-mir-6824" (miRBase Accession No. MI0022669; SEQ ID NO: 743) having a hairpin-like structure is known as a precursor of "hsa-miR-6824-3p."

The term "hsa-miR-6837-5p gene" or "hsa-miR-6837-5p" used herein includes the hsa-miR-6837-5p gene (miRBase Accession No. MIMAT0027576) shown in SEQ ID NO: 353, a homolog or an ortholog of a different organism species, and the like. The hsa-miR-6837-5p gene can be obtained by a method described in Ladewig E et al., 2012, Genome Res., Vol. 22, pp. 1634-1645. Also, "hsa-mir-6837" (miRBase Accession No. MI0022683; SEQ ID NO: 744) having a hairpin-like structure is known as a precursor of "hsa-miR-6837-5p."

The term "hsa-miR-6846-3p gene" or "hsa-miR-6846-3p" used herein includes the hsa-miR-6846-3p gene (miRBase Accession No. MIMAT0027593) shown in SEQ ID NO: 354, a homolog or an ortholog of a different organism species, and the like. The hsa-miR-6846-3p gene can be obtained by a method described in Ladewig E et al., 2012, Genome Res., Vol. 22, pp. 1634-1645. Also, "hsa-mir-6846" (miRBase Accession No. MI0022692; SEQ ID NO: 745) having a hairpin-like structure is known as a precursor of "hsa-miR-6846-3p."

The term "hsa-miR-6858-3p gene" or "hsa-miR-6858-3p" used herein includes the hsa-miR-6858-3p gene (miRBase Accession No. MIMAT0027617) shown in SEQ ID NO: 355, a homolog or an ortholog of a different organism species, and the like. The hsa-miR-6858-3p gene can be obtained by a method described in Ladewig E et al., 2012, Genome Res., Vol. 22, pp. 1634-1645. Also, "hsa-mir-6858" (miRBase Accession No. MI0022704; SEQ ID NO: 746) having a hairpin-like structure is known as a precursor of "hsa-miR-6858-3p."

The term "hsa-miR-6859-3p gene" or "hsa-miR-6859-3p" used herein includes the hsa-miR-6859-3p gene (miRBase Accession No. MIMAT0027619) shown in SEQ ID NO: 356, a homolog or an ortholog of a different organism species, and the like. The hsa-miR-6859-3p gene can be obtained by a method described in Ladewig E et al., 2012, Genome Res., Vol. 22, pp. 1634-1645. Also, "hsa-mir-6859-1, hsa-mir-6859-2, hsa-mir-6859-3, and hsa-mir-6859-4" (miRBase Accession Nos. MI0022705, MI0026420, MI0026421, and MI0031521; SEQ ID NOs: 747, 748, 749, and 750) each having a hairpin-like structure are known as precursors of "hsa-miR-6858-3p."

The term "hsa-miR-6861-3p gene" or "hsa-miR-6861-3p" used herein includes the hsa-miR-6861-3p gene (miRBase Accession No. MIMAT0027624) shown in SEQ ID NO: 357, a homolog or an ortholog of a different organism species, and the like. The hsa-miR-6861-3p gene can be obtained by a method described in Ladewig E et al., 2012, Genome Res., Vol. 22, pp. 1634-1645. Also, "hsa-mir-6861" (miRBase Accession No. MI0022708; SEQ ID NO: 596) having a hairpin-like structure is known as a precursor of "hsa-miR-6861-3p."

The term "hsa-miR-6880-3p gene" or "hsa-miR-6880-3p" used herein includes the hsa-miR-6880-3p gene (miRBase Accession No. MIMAT0027661) shown in SEQ ID NO: 358, a homolog or an ortholog of a different organism species, and the like. The hsa-miR-6880-3p gene can be obtained by a method described in Ladewig E et al., 2012, Genome Res., Vol. 22, pp. 1634-1645. Also, "hsa-mir-6880" (miRBase Accession No. MI0022727; SEQ ID NO: 751) having a hairpin-like structure is known as a precursor of "hsa-miR-6880-3p."

The term "hsa-miR-7111-3p gene" or "hsa-miR-7111-3p" used herein includes the hsa-miR-7111-3p gene (miRBase Accession No. MIMAT0028120) shown in SEQ ID NO: 359, a homolog or an ortholog of a different organism species, and the like. The hsa-miR-7111-3p gene can be obtained by a method described in Ladewig E et al., 2012, Genome Res., Vol. 22, pp. 1634-1645. Also, "hsa-mir-7111" (miRBase Accession No. MI0022962; SEQ ID NO: 752) having a hairpin-like structure is known as a precursor of "hsa-miR-7111-3p."

The term "hsa-miR-7152-5p gene" or "hsa-miR-7152-5p" used herein includes the hsa-miR-7152-5p gene (miRBase Accession No. MIMAT0028214) shown in SEQ ID NO: 360, a homolog or an ortholog of a different organism species, and the like. The hsa-miR-7152-5p gene can be obtained by a method described in Meunier J et al., 2013, Genome Res., Vol. 23, pp. 34-45. Also, "hsa-mir-7152" (miRBase Accession No. MI0023612; SEQ ID NO: 753) having a hairpin-like structure is known as a precursor of "hsa-miR-7152-5p."

The term "hsa-miR-642a-5p gene" or "hsa-miR-642a-5p" used herein includes the hsa-miR-642a-5p gene (miRBase Accession No. MIMAT0003312) shown in SEQ ID NO: 361, a homolog or an ortholog of a different organism species, and the like. The hsa-miR-642a-5p gene can be obtained by a method described in Cummins J M et al., 2006, Proc. Natl. Acad. Sci. U.S.A., Vol. 103, pp. 3687-3692. Also, "hsa-mir-642a" (miRBase Accession No. MI0003657; SEQ ID NO: 754) having a hairpin-like structure is known as a precursor of "hsa-miR-642a-5p."

The term "hsa-miR-657 gene" or "hsa-miR-657" used herein includes the hsa-miR-657 gene (miRBase Accession No. MIMAT0003335) shown in SEQ ID NO: 362, a homolog or an ortholog of a different organism species, and the like. The hsa-miR-657 gene can be obtained by a method described in Cummins J M et al., 2006, Proc. Natl. Acad. Sci. U.S.A., Vol. 103, pp. 3687-3692. Also, "hsa-mir-657" (miRBase Accession No. MI0003681; SEQ ID NO: 755) having a hairpin-like structure is known as a precursor of "hsa-miR-657."

The term "hsa-miR-1236-3p gene" or "hsa-miR-1236-3p" used herein includes the hsa-miR-1236-3p gene (miRBase Accession No. MIMAT0005591) shown in SEQ ID NO: 363, a homolog or an ortholog of a different organism species, and the like. The hsa-miR-1236-3p gene can be obtained by a method described in Berezikov E et al., 2007, Mol. Cell, Vol. 28, pp. 328-336. Also, "hsa-mir-1236" (miRBase Accession No. MI0006326; SEQ ID NO: 756) having a hairpin-like structure is known as a precursor of "hsa-miR-1236-3p."

The term "hsa-miR-764 gene" or "hsa-miR-764" used herein includes the hsa-miR-764 gene (miRBase Accession No. MIMAT0010367) shown in SEQ ID NO: 364, a homolog or an ortholog of a different organism species, and the like. The hsa-miR-764 gene can be obtained by a method described in Berezikov E et al., 2006, Genome Res., Vol. 16, pp. 1289-1298. Also, "hsa-mir-764" (miRBase Accession No. MI0003944; SEQ ID NO: 757) having a hairpin-like structure is known as a precursor of "hsa-miR-764."

The term "hsa-miR-4314 gene" or "hsa-miR-4314" used herein includes the hsa-miR-4314 gene (miRBase Accession No. MIMAT0016868) shown in SEQ ID NO: 365, a homolog or an ortholog of a different organism species, and the like. The hsa-miR-4314 gene can be obtained by a method described in Goff L A et al., 2009, PLoS One, Vol. 4, e7192. Also, "hsa-mir-4314" (miRBase Accession No. MI0015846; SEQ ID NO: 758) having a hairpin-like structure is known as a precursor of "hsa-miR-4314."

The term "hsa-miR-3675-3p gene" or "hsa-miR-3675-3p" used herein includes the hsa-miR-3675-3p gene (miRBase Accession No. MIMAT0018099) shown in SEQ ID NO: 366, a homolog or an ortholog of a different organism species, and the like. The hsa-miR-3675-3p gene can be obtained by a method described in Vaz C et al., 2010, BMC Genomics, Vol. 11, p. 288. Also, "hsa-mir-3675" (miRBase Accession No. MI0016076; SEQ ID NO: 759) having a hairpin-like structure is known as a precursor of "hsa-miR-3675-3p."

The term "hsa-miR-5703 gene" or "hsa-miR-5703" used herein includes the hsa-miR-5703 gene (miRBase Accession No. MIMAT0022496) shown in SEQ ID NO: 367, a homolog or an ortholog of a different organism species, and the like. The hsa-miR-5703 gene can be obtained by a method described in Watahiki A et al., 2011, PLoS One, Vol. 6, e24950. Also, "hsa-mir-5703" (miRBase Accession No. MI0019310; SEQ ID NO: 760) having a hairpin-like structure is known as a precursor of "hsa-miR-5703."

The term "hsa-miR-3191-5p gene" or "hsa-miR-3191-5p" used herein includes the hsa-miR-3191-5p gene (miRBase Accession No. MIMAT0022732) shown in SEQ ID NO: 368, a homolog or an ortholog of a different organism species, and the like. The hsa-miR-3191-5p gene can be obtained by a method described in Stark M S et al., 2010, PLoS One, Vol. 5, e9685. Also, "hsa-mir-3191" (miRBase Accession No. MI0014236; SEQ ID NO: 761) having a hairpin-like structure is known as a precursor of "hsa-miR-3191-5p."

The term "hsa-miR-6511a-3p gene" or "hsa-miR-6511a-3p" used herein includes the hsa-miR-6511a-3p gene (miRBase Accession No. MIMAT0025479) shown in SEQ ID NO: 369, a homolog or an ortholog of a different organism species, and the like. The hsa-miR-6511a-3p gene can be obtained by a method described in Joyce C E et al., 2011, Hum. Mol. Genet., Vol. 20, pp. 4025-4040. Also, "hsa-mir-6511a-1" (miRBase Accession No. MI0022223; SEQ ID NO: 445) having a hairpin-like structure is known as a precursor of "hsa-miR-6511a-3p."

The term "hsa-miR-6809-3p gene" or "hsa-miR-6809-3p" used herein includes the hsa-miR-6809-3p gene (miRBase Accession No. MIMAT0027519) shown in SEQ ID NO: 370, a homolog or an ortholog of a different organism species, and the like. The hsa-miR-6809-3p gene can be obtained by a method described in Ladewig E et al., 2012, Genome Res., Vol. 22, pp. 1634-1645. Also, "hsa-mir-6809" (miRBase Accession No. MI0022654; SEQ ID NO: 762) having a hairpin-like structure is known as a precursor of "hsa-miR-6809-3p."

The term "hsa-miR-6815-5p gene" or "hsa-miR-6815-5p" used herein includes the hsa-miR-6815-5p gene (miRBase Accession No. MIMAT0027530) shown in SEQ ID NO: 371, a homolog or an ortholog of a different organism species, and the like. The hsa-miR-6815-5p gene can be obtained by a method described in Ladewig E et al., 2012, Genome Res., Vol. 22, pp. 1634-1645. Also, "hsa-mir-6815" (miRBase Accession No. MI0022660; SEQ ID NO: 763) having a hairpin-like structure is known as a precursor of "hsa-miR-6815-5p."

The term "hsa-miR-6857-3p gene" or "hsa-miR-6857-3p" used herein includes the hsa-miR-6857-3p gene (miRBase Accession No. MIMAT0027615) shown in SEQ ID NO: 372, a homolog or an ortholog of a different organism species, and the like. The hsa-miR-6857-3p gene can be obtained by a method described in Ladewig E et al., 2012, Genome Res., Vol. 22, pp. 1634-1645. Also, "hsa-mir-6857" (miRBase Accession No. MI0022703; SEQ ID NO: 764) having a hairpin-like structure is known as a precursor of "hsa-miR-6857-3p."

The term "hsa-miR-6878-3p gene" or "hsa-miR-6878-3p" used herein includes the hsa-miR-6878-3p gene (miRBase Accession No. MIMAT0027657) shown in SEQ ID NO: 373, a homolog or an ortholog of a different organism species, and the like. The hsa-miR-6878-3p gene can be obtained by a method described in Ladewig E et al., 2012, Genome Res., Vol. 22, pp. 1634-1645. Also, "hsa-mir-6878" (miRBase Accession No. MI0022725; SEQ ID NO: 765) having a hairpin-like structure is known as a precursor of "hsa-miR-6878-3p."

The term "hsa-miR-371a-5p gene" or "hsa-miR-371a-5p" used herein includes the hsa-miR-371a-5p gene (miRBase Accession No. MIMAT0004687) shown in SEQ ID NO: 374, a homolog or an ortholog of a different organism species, and the like. The hsa-miR-371a-5p gene can be obtained by a method described in Suh M R et al., 2004, Dev. Biol., Vol. 270, pp. 488-498. Also, "hsa-mir-371a" (miRBase Accession No. MI0000779; SEQ ID NO: 766) having a hairpin-like structure is known as a precursor of "hsa-miR-371a-5p."

The term "hsa-miR-766-3p gene" or "hsa-miR-766-3p" used herein includes the hsa-miR-766-3p gene (miRBase Accession No. MIMAT0003888) shown in SEQ ID NO: 375, a homolog or an ortholog of a different organism species, and the like. The hsa-miR-766-3p gene can be obtained by a method described in Berezikov E et al., 2006, Genome Res., Vol. 16, pp. 1289-1298. Also, "hsa-mir-766" (miRBase Accession No. MI0003836; SEQ ID NO: 767) having a hairpin-like structure is known as a precursor of "hsa-miR-766-3p."

The term "hsa-miR-1229-3p gene" or "hsa-miR-1229-3p" used herein includes the hsa-miR-1229-3p gene (miRBase Accession No. MIMAT0005584) shown in SEQ ID NO: 376, a homolog or an ortholog of a different organism species, and the like. The hsa-miR-1229-3p gene can be obtained by a method described in Berezikov E et al., 2007, Mol. Cell, Vol. 28, pp. 328-336. Also, "hsa-mir-1229" (miRBase Accession No. MI0006319; SEQ ID NO: 768) having a hairpin-like structure is known as a precursor of "hsa-miR-1229-3p."

The term "hsa-miR-1306-5p gene" or "hsa-miR-1306-5p" used herein includes the hsa-miR-1306-5p gene (miRBase Accession No. MIMAT0022726) shown in SEQ ID NO: 377, a homolog or an ortholog of a different organism species, and the like. The hsa-miR-1306-5p gene can be obtained by a method described in Morin R D et al., 2008, Genome Res., Vol. 18, pp. 610-621. Also, "hsa-mir-1306" (miRBase Accession No. MI0006443; SEQ ID NO: 769) having a hairpin-like structure is known as a precursor of "hsa-miR-1306-5p."

The term "hsa-miR-210-5p gene" or "hsa-miR-210-5p" used herein includes the hsa-miR-210-5p gene (miRBase Accession No. MIMAT0026475) shown in SEQ ID NO: 378, a homolog or an ortholog of a different organism species, and the like. The hsa-miR-210-5p gene can be obtained by a method described in Lim L P et al., 2003, Science, Vol. 299, p. 1540. Also, "hsa-mir-210" (miRBase Accession No. MI0000286; SEQ ID NO: 770) having a hairpin-like structure is known as a precursor of "hsa-miR-210-5p."

The term "hsa-miR-198 gene" or "hsa-miR-198" used herein includes the hsa-miR-198 gene (miRBase Accession No. MIMAT0000228) shown in SEQ ID NO: 379, a homolog or an ortholog of a different organism species, and the like. The hsa-miR-198 gene can be obtained by a method described in Lagos-Quintana M et al., 2003, RNA, Vol. 9, pp. 175-179. Also, "hsa-mir-198" (miRBase Accession No. MI0000240; SEQ ID NO: 771) having a hairpin-like structure is known as a precursor of "hsa-miR-198."

The term "hsa-miR-485-3p gene" or "hsa-miR-485-3p" used herein includes the hsa-miR-485-3p gene (miRBase Accession No. MIMAT0002176) shown in SEQ ID NO: 380, a homolog or an ortholog of a different organism species, and the like. The hsa-miR-485-3p gene can be obtained by a method described in Bentwich I et al., 2005, Nat. Genet., Vol. 37, pp. 766-770. Also, "hsa-mir-485" (miRBase Accession No. MI0002469; SEQ ID NO: 772) having a hairpin-like structure is known as a precursor of "hsa-miR-485-3p."

The term "hsa-miR-668-3p gene" or "hsa-miR-668-3p" used herein includes the hsa-miR-668-3p gene (miRBase Accession No. MIMAT0003881) shown in SEQ ID NO: 381, a homolog or an ortholog of a different organism species, and the like. The hsa-miR-668-3p gene can be obtained by a method described in Berezikov E et al., 2006, Genome Res., Vol. 16, pp. 1289-1298. Also, "hsa-mir-668" (miRBase Accession No. MI0003761; SEQ ID NO: 773) having a hairpin-like structure is known as a precursor of "hsa-miR-668-3p."

The term "hsa-miR-532-3p gene" or "hsa-miR-532-3p" used herein includes the hsa-miR-532-3p gene (miRBase Accession No. MIMAT0004780) shown in SEQ ID NO: 382, a homolog or an ortholog of a different organism species, and the like. The hsa-miR-532-3p gene can be obtained by a method described in Lagos-Quintana M et al., 2001, Science, Vol. 294, pp. 853-858. Also, "hsa-mir-532" (miRBase Accession No. MI0003205; SEQ ID NO: 626) having a hairpin-like structure is known as a precursor of "hsa-miR-532-3p."

The term "hsa-miR-877-3p gene" or "hsa-miR-877-3p" used herein includes the hsa-miR-877-3p gene (miRBase Accession No. MIMAT0004950) shown in SEQ ID NO: 383, a homolog or an ortholog of a different organism species, and the like. The hsa-miR-877-3p gene can be obtained by a method described in Berezikov E et al., 2006, Genome Res., Vol. 16, pp. 1289-1298. Also, "hsa-mir-877" (miRBase Accession No. MI0005561; SEQ ID NO: 774) having a hairpin-like structure is known as a precursor of "hsa-miR-877-3p."

The term "hsa-miR-1238-3p gene" or "hsa-miR-1238-3p" used herein includes the hsa-miR-1238-3p gene (miRBase Accession No. MIMAT0005593) shown in SEQ ID NO: 384, a homolog or an ortholog of a different organism species, and the like. The hsa-miR-1238-3p gene can be obtained by a method described in Berezikov E et al., 2007, Mol. Cell, Vol. 28, pp. 328-336. Also, "hsa-mir-1238" (miRBase Accession No. MI0006328; SEQ ID NO: 775) having a hairpin-like structure is known as a precursor of "hsa-miR-1238-3p."

The term "hsa-miR-3130-5p gene" or "hsa-miR-3130-5p" used herein includes the hsa-miR-3130-5p gene (miRBase Accession No. MIMAT0014995) shown in SEQ ID NO: 385, a homolog or an ortholog of a different organism species, and the like. The hsa-miR-3130-5p gene can be obtained by a method described in Creighton C J et al., 2010, PLoS One, Vol. 5, e9637. Also, "hsa-mir-3130-1 and hsa-mir-3130-2" (miRBase Accession Nos. MI0014147 and MI0014148; SEQ ID NOs: 776 and 777) each having a hairpin-like structure are known as precursors of "hsa-miR-3130-5p."

The term "hsa-miR-4298 gene" or "hsa-miR-4298" used herein includes the hsa-miR-4298 gene (miRBase Accession No. MIMAT0016852) shown in SEQ ID NO: 386, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830; SEQ ID NO: 778) having a hairpin-like structure is known as a precursor of "hsa-miR-4298."

The term "hsa-miR-4290 gene" or "hsa-miR-4290" used herein includes the hsa-miR-4290 gene (miRBase Accession No. MIMAT0016921) shown in SEQ ID NO: 387, a homolog or an ortholog of a different organism species, and the like. The hsa-miR-4290 gene can be obtained by a method described in Goff L A et al., 2009, PLoS One, Vol. 4, e7192. Also, "hsa-mir-4290" (miRBase Accession No. MI0015899; SEQ ID NO: 779) having a hairpin-like structure is known as a precursor of "hsa-miR-4290."

The term "hsa-miR-3943 gene" or "hsa-miR-3943" used herein includes the hsa-miR-3943 gene (miRBase Accession No. MIMAT0018359) shown in SEQ ID NO: 388, a homolog or an ortholog of a different organism species, and the like. The hsa-miR-3943 gene can be obtained by a method described in Liao J Y et al., 2010, PLoS One, Vol. 5, e10563. Also, "hsa-mir-3943" (miRBase Accession No. MI0016600; SEQ ID NO: 780) having a hairpin-like structure is known as a precursor of "hsa-miR-3943."

The term "hsa-miR-346 gene" or "hsa-miR-346" used herein includes the hsa-miR-346 gene (miRBase Accession No. MIMAT0000773) shown in SEQ ID NO: 389, a homolog or an ortholog of a different organism species, and the like. The hsa-miR-346 gene can be obtained by a method described in Kim J et al., 2004, Proc. Natl. Acad. Sci. U.S.A., Vol. 101, pp. 360-365. Also, "hsa-mir-346" (miRBase Accession No. MI0000826; SEQ ID NO: 781) having a hairpin-like structure is known as a precursor of "hsa-miR-346."

The term "hsa-miR-767-3p gene" or "hsa-miR-767-3p" used herein includes the hsa-miR-767-3p gene (miRBase Accession No. MIMAT0003883) shown in SEQ ID NO: 390, a homolog or an ortholog of a different organism species, and the like. The hsa-miR-767-3p gene can be obtained by a method described in Berezikov E et al., 2006, Genome Res., Vol. 16, pp. 1289-1298. Also, "hsa-mir-767" (miRBase Accession No. MI0003763; SEQ ID NO: 782) having a hairpin-like structure is known as a precursor of "hsa-miR-767-3p."

The term "hsa-miR-6765-3p gene" or "hsa-miR-6765-3p" used herein includes the hsa-miR-6765-3p gene (miRBase Accession No. MIMAT0027431) shown in SEQ ID NO: 1315, a homolog or an ortholog of a different organism species, and the like. The hsa-miR-6765-3p gene can be obtained by a method described in Ladewig E et al., 2012, Genome Res., Vol. 22, pp. 1634-1645. Also, "hsa-mir-6765" (miRBase Accession No. MI0022610; SEQ ID NO: 490) having a hairpin-like structure is known as a precursor of "hsa-miR-6765-3p."

The term "hsa-miR-6784-5p gene" or "hsa-miR-6784-5p" used herein includes the hsa-miR-6784-5p gene (miRBase Accession No. MIMAT0027468) shown in SEQ ID NO: 1316, a homolog or an ortholog of a different organism species, and the like. The hsa-miR-6784-5p gene can be obtained by a method described in Ladewig E et al., 2012, Genome Res., Vol. 22, pp. 1634-1645. Also, "hsa-mir-6784"

(miRBase Accession No. MI0022629; SEQ ID NO: 1357) having a hairpin-like structure is known as a precursor of "hsa-miR-6784-5p."

The term "hsa-miR-6778-5p gene" or "hsa-miR-6778-5p" used herein includes the hsa-miR-6778-5p gene (miRBase Accession No. MIMAT0027456) shown in SEQ ID NO: 1317, a homolog or an ortholog of a different organism species, and the like. The hsa-miR-6778-5p gene can be obtained by a method described in Ladewig E et al., 2012, Genome Res., Vol. 22, pp. 1634-1645. Also, "hsa-mir-6778" (miRBase Accession No. MI0022623; SEQ ID NO: 1358) having a hairpin-like structure is known as a precursor of "hsa-miR-6778-5p."

The term "hsa-miR-6875-5p gene" or "hsa-miR-6875-5p" used herein includes the hsa-miR-6875-5p gene (miRBase Accession No. MIMAT0027650) shown in SEQ ID NO: 1318, a homolog or an ortholog of a different organism species, and the like. The hsa-miR-6875-5p gene can be obtained by a method described in Ladewig E et al., 2012, Genome Res., Vol. 22, pp. 1634-1645. Also, "hsa-mir-6875" (miRBase Accession No. MI0022722; SEQ ID NO: 1359) having a hairpin-like structure is known as a precursor of "hsa-miR-6875-5p."

The term "hsa-miR-4534 gene" or "hsa-miR-4534" used herein includes the hsa-miR-4534 gene (miRBase Accession No. MIMAT0019073) shown in SEQ ID NO: 1319, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901; SEQ ID NO: 1360) having a hairpin-like structure is known as a precursor of "hsa-miR-4534."

The term "hsa-miR-4721 gene" or "hsa-miR-4721" used herein includes the hsa-miR-4721 gene (miRBase Accession No. MIMAT0019835) shown in SEQ ID NO: 1320, a homolog or an ortholog of a different organism species, and the like. The hsa-miR-4721 gene can be obtained by a method described in Persson H et al., 2011, Cancer Res., Vol. 71, pp. 78-86. Also, "hsa-mir-4721" (miRBase Accession No. MI0017356; SEQ ID NO: 1361) having a hairpin-like structure is known as a precursor of "hsa-miR-4721."

The term "hsa-miR-6756-5p gene" or "hsa-miR-6756-5p" used herein includes the hsa-miR-6756-5p gene (miRBase Accession No. MIMAT0027412) shown in SEQ ID NO: 1321, a homolog or an ortholog of a different organism species, and the like. The hsa-miR-6756-5p gene can be obtained by a method described in Ladewig E et al., 2012, Genome Res., Vol. 22, pp. 1634-1645. Also, "hsa-mir-6756" (miRBase Accession No. MI0022601; SEQ ID NO: 1362) having a hairpin-like structure is known as a precursor of "hsa-miR-6756-5p."

The term "hsa-miR-615-5p gene" or "hsa-miR-615-5p" used herein includes the hsa-miR-615-5p gene (miRBase Accession No. MIMAT0004804) shown in SEQ ID NO: 1322, a homolog or an ortholog of a different organism species, and the like. The hsa-miR-615-5p gene can be obtained by a method described in Cummins J M et al., 2006, Proc. Natl. Acad. Sci. U.S.A., Vol. 103, pp. 3687-3692. Also, "hsa-mir-615" (miRBase Accession No. MI0003628; SEQ ID NO: 1363) having a hairpin-like structure is known as a precursor of "hsa-miR-615-5p."

The term "hsa-miR-6727-5p gene" or "hsa-miR-6727-5p" used herein includes the hsa-miR-6727-5p gene (miRBase Accession No. MIMAT0027355) shown in SEQ ID NO: 1323, a homolog or an ortholog of a different organism species, and the like. The hsa-miR-6727-5p gene can be obtained by a method described in Ladewig E et al., 2012, Genome Res., Vol. 22, pp. 1634-1645. Also, "hsa-mir-6727" (miRBase Accession No. MI0022572; SEQ ID NO: 1364) having a hairpin-like structure is known as a precursor of "hsa-miR-6727-5p."

The term "hsa-miR-6887-5p gene" or "hsa-miR-6887-5p" used herein includes the hsa-miR-6887-5p gene (miRBase Accession No. MIMAT0027674) shown in SEQ ID NO: 1324, a homolog or an ortholog of a different organism species, and the like. The hsa-miR-6887-5p gene can be obtained by a method described in Ladewig E et al., 2012, Genome Res., Vol. 22, pp. 1634-1645. Also, "hsa-mir-6887" (miRBase Accession No. MI0022734; SEQ ID NO: 1365) having a hairpin-like structure is known as a precursor of "hsa-miR-6887-5p."

The term "hsa-miR-8063 gene" or "hsa-miR-8063" used herein includes the hsa-miR-8063 gene (miRBase Accession No. MIMAT0030990) shown in SEQ ID NO: 1325, a homolog or an ortholog of a different organism species, and the like. The hsa-miR-8063 gene can be obtained by a method described in Wang H J et al., 2013, Shock, Vol. 39, pp. 480-487. Also, "hsa-mir-8063" (miRBase Accession No. MI0025899; SEQ ID NO: 1366) having a hairpin-like structure is known as a precursor of "hsa-miR-8063."

The term "hsa-miR-6880-5p gene" or "hsa-miR-6880-5p" used herein includes the hsa-miR-6880-5p gene (miRBase Accession No. MIMAT0027660) shown in SEQ ID NO: 1326, a homolog or an ortholog of a different organism species, and the like. The hsa-miR-6880-5p gene can be obtained by a method described in Ladewig E et al., 2012, Genome Res., Vol. 22, pp. 1634-1645. Also, "hsa-mir-6880" (miRBase Accession No. MI0022727; SEQ ID NO: 1367) having a hairpin-like structure is known as a precursor of "hsa-miR-6880-5p."

The term "hsa-miR-6805-3p gene" or "hsa-miR-6805-3p" used herein includes the hsa-miR-6805-3p gene (miRBase Accession No. MIMAT0027511) shown in SEQ ID NO: 1327, a homolog or an ortholog of a different organism species, and the like. The hsa-miR-6805-3p gene can be obtained by a method described in Ladewig E et al., 2012, Genome Res., Vol. 22, pp. 1634-1645. Also, "hsa-mir-6805" (miRBase Accession No. MI0022650; SEQ ID NO: 1368) having a hairpin-like structure is known as a precursor of "hsa-miR-6805-3p."

The term "hsa-miR-4726-5p gene" or "hsa-miR-4726-5p" used herein includes the hsa-miR-4726-5p gene (miRBase Accession No. MIMAT0019845) shown in SEQ ID NO: 1328, a homolog or an ortholog of a different organism species, and the like. The hsa-miR-4726-5p gene can be obtained by a method described in Persson H et al., 2011, Cancer Res., Vol. 71, pp. 78-86. Also, "hsa-mir-4726" (miRBase Accession No. MI0017363; SEQ ID NO: 1369) having a hairpin-like structure is known as a precursor of "hsa-miR-4726-5p."

The term "hsa-miR-4710 gene" or "hsa-miR-4710" used herein includes the hsa-miR-4710 gene (miRBase Accession No. MIMAT0019815) shown in SEQ ID NO: 1329, a homolog or an ortholog of a different organism species, and the like. The hsa-miR-4710 gene can be obtained by a method described in Persson H et al., 2011, Cancer Res., Vol. 71, pp. 78-86. Also, "hsa-mir-4710" (miRBase Accession No. MI0017344; SEQ ID NO: 1370) having a hairpin-like structure is known as a precursor of "hsa-miR-4710."

The term "hsa-miR-7111-5p gene" or "hsa-miR-7111-5p" used herein includes the hsa-miR-7111-5p gene (miRBase Accession No. MIMAT0028119) shown in SEQ ID NO: 1330, a homolog or an ortholog of a different organism species, and the like. The hsa-miR-7111-5p gene can be obtained by a method described in Ladewig E et al., 2012, Genome Res., Vol. 22, pp. 1634-1645. Also, “hsa-mir-7111” (miRBase Accession No. MI0022962; SEQ ID NO: 1371) having a hairpin-like structure is known as a precursor of “hsa-miR-7111-5p.”

The term “hsa-miR-3619-3p gene” or “hsa-miR-3619-3p” used herein includes the hsa-miR-3619-3p gene (miRBase Accession No. MIMAT0019219) shown in SEQ ID NO: 1331, a homolog or an ortholog of a different organism species, and the like. The hsa-miR-3619-3p gene can be obtained by a method described in Witten D et al., 2010, BMC Biol., Vol. 8, p. 58. Also, “hsa-mir-3619” (miRBase Accession No. MI0016009; SEQ ID NO: 1372) having a hairpin-like structure is known as a precursor of “hsa-miR-3619-3p.”

The term “hsa-miR-6795-5p gene” or “hsa-miR-6795-5p” used herein includes the hsa-miR-6795-5p gene (miRBase Accession No. MIMAT0027490) shown in SEQ ID NO: 1332, a homolog or an ortholog of a different organism species, and the like. The hsa-miR-6795-5p gene can be obtained by a method described in Ladewig E et al., 2012, Genome Res., Vol. 22, pp. 1634-1645. Also, “hsa-mir-6795” (miRBase Accession No. MI0022640; SEQ ID NO: 1373) having a hairpin-like structure is known as a precursor of “hsa-miR-6795-5p.”

The term “hsa-miR-1254 gene” or “hsa-miR-1254” used herein includes the hsa-miR-1254 gene (miRBase Accession No. MIMAT0005905) shown in SEQ ID NO: 1333, a homolog or an ortholog of a different organism species, and the like. The hsa-miR-1254 gene can be obtained by a method described in Morin R D et al., 2008, Genome Res., Vol. 18, pp. 610-621. Also, “hsa-mir-1254-1 and hsa-mir-1254-2” (miRBase Accession Nos. MI0006388 and MI0016747; SEQ ID NOs: 1374 and 1375) each having a hairpin-like structure are known as precursors of “hsa-miR-1254.”

The term “hsa-miR-1233-5p gene” or “hsa-miR-1233-5p” used herein includes the hsa-miR-1233-5p gene (miRBase Accession No. MIMAT0022943) shown in SEQ ID NO: 1334, a homolog or an ortholog of a different organism species, and the like. The hsa-miR-1233-5p gene can be obtained by a method described in Berezikov E et al., 2007, Mol. Cell, Vol. 28, pp. 328-336. Also, “hsa-mir-1233-1 and hsa-mir-1233-2” (miRBase Accession Nos. MI0006323 and MI0015973; SEQ ID NOs: 1376 and 1377) each having a hairpin-like structure are known as precursors of “hsa-miR-1233-5p.”

The term “hsa-miR-6836-3p gene” or “hsa-miR-6836-3p” used herein includes the hsa-miR-6836-3p gene (miRBase Accession No. MIMAT0027575) shown in SEQ ID NO: 1335, a homolog or an ortholog of a different organism species, and the like. The hsa-miR-6836-3p gene can be obtained by a method described in Ladewig E et al., 2012, Genome Res., Vol. 22, pp. 1634-1645. Also, “hsa-mir-6836” (miRBase Accession No. MI0022682; SEQ ID NO: 1378) having a hairpin-like structure is known as a precursor of “hsa-miR-6836-3p.”

The term “hsa-miR-6769a-5p gene” or “hsa-miR-6769a-5p” used herein includes the hsa-miR-6769a-5p gene (miRBase Accession No. MIMAT0027438) shown in SEQ ID NO: 1336, a homolog or an ortholog of a different organism species, and the like. The hsa-miR-6769a-5p gene can be obtained by a method described in Ladewig E et al., 2012, Genome Res., Vol. 22, pp. 1634-1645. Also, “hsa-mir-6769a” (miRBase Accession No. MI0022614; SEQ ID NO: 1379) having a hairpin-like structure is known as a precursor of “hsa-miR-6769a-5p.”

The term “hsa-miR-4532 gene” or “hsa-miR-4532” used herein includes the hsa-miR-4532 gene (miRBase Accession No. MIMAT0019071) shown in SEQ ID NO: 1337, a homolog or an ortholog of a different organism species, and the like. The hsa-miR-4532 gene can be obtained by a method described in Jima D D et al., 2010, Blood, Vol. 116, e118-e127. Also, “hsa-mir-4532” (miRBase Accession No. MI0016899; SEQ ID NO: 1380) having a hairpin-like structure is known as a precursor of “hsa-miR-4532.”

The term “hsa-miR-365a-5p gene” or “hsa-miR-365a-5p” used herein includes the hsa-miR-365a-5p gene (miRBase Accession No. MIMAT0009199) shown in SEQ ID NO: 1338, a homolog or an ortholog of a different organism species, and the like. The hsa-miR-365a-5p gene can be obtained by a method described in Xie X et al., 2005, Nature, Vol. 434, pp. 338-345. Also, “hsa-mir-365a” (miRBase Accession No. MI0000767; SEQ ID NO: 1381) having a hairpin-like structure is known as a precursor of “hsa-miR-365a-5p.”

The term “hsa-miR-1231 gene” or “hsa-miR-1231” used herein includes the hsa-miR-1231 gene (miRBase Accession No. MIMAT0005586) shown in SEQ ID NO: 1339, a homolog or an ortholog of a different organism species, and the like. The hsa-miR-1231 gene can be obtained by a method described in Berezikov E et al., 2007, Mol. Cell, Vol. 28, pp. 328-336. Also, “hsa-mir-1231” (miRBase Accession No. MI0006321; SEQ ID NO: 1382) having a hairpin-like structure is known as a precursor of “hsa-miR-1231.”

The term “hsa-miR-1228-5p gene” or “hsa-miR-1228-5p” used herein includes the hsa-miR-1228-5p gene (miRBase Accession No. MIMAT0005582) shown in SEQ ID NO: 1340, a homolog or an ortholog of a different organism species, and the like. The hsa-miR-1228-5p gene can be obtained by a method described in Berezikov E et al., 2007, Mol. Cell, Vol. 28, pp. 328-336. Also, “hsa-mir-1228” (miRBase Accession No. MI0006318; SEQ ID NO: 1383) having a hairpin-like structure is known as a precursor of “hsa-miR-1228-5p.”

The term “hsa-miR-4430 gene” or “hsa-miR-4430” used herein includes the hsa-miR-4430 gene (miRBase Accession No. MIMAT0018945) shown in SEQ ID NO: 1341, a homolog or an ortholog of a different organism species, and the like. The hsa-miR-4430 gene can be obtained by a method described in Jima D D et al., 2010, Blood, Vol. 116, e118-e127. Also, “hsa-mir-4430” (miRBase Accession No. MI0016769; SEQ ID NO: 1384) having a hairpin-like structure is known as a precursor of “hsa-miR-4430.”

The term “hsa-miR-296-3p gene” or “hsa-miR-296-3p” used herein includes the hsa-miR-296-3p gene (miRBase Accession No. MIMAT0004679) shown in SEQ ID NO: 1342, a homolog or an ortholog of a different organism species, and the like. The hsa-miR-296-3p gene can be obtained by a method described in Houbaviy H B et al., 2003, Dev. Cell, Vol. 5, pp. 351-358. Also, “hsa-mir-296” (miRBase Accession No. MI0000747; SEQ ID NO: 1385) having a hairpin-like structure is known as a precursor of “hsa-miR-296-3p.”

The term “hsa-miR-1237-5p gene” or “hsa-miR-1237-5p” used herein includes the hsa-miR-1237-5p gene (miRBase Accession No. MIMAT0022946) shown in SEQ ID NO: 1343, a homolog or an ortholog of a different organism species, and the like. The hsa-miR-1237-5p gene can be obtained by a method described in Berezikov E et al., 2007, Mol. Cell, Vol. 28, pp. 328-336. Also, “hsa-mir-1237” (miRBase Accession No. MI0006327; SEQ ID NO: 1386) having a hairpin-like structure is known as a precursor of “hsa-miR-1237-5p.”

The term "hsa-miR-4466 gene" or "hsa-miR-4466" used herein includes the hsa-miR-4466 gene (miRBase Accession No. MIMAT0018993) shown in SEQ ID NO: 1344, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817; SEQ ID NO: 1387) having a hairpin-like structure is known as a precursor of "hsa-miR-4466."

The term "hsa-miR-6789-5p gene" or "hsa-miR-6789-5p" used herein includes the hsa-miR-6789-5p gene (miRBase Accession No. MIMAT0027478) shown in SEQ ID NO: 1345, a homolog or an ortholog of a different organism species, and the like. The hsa-miR-6789-5p gene can be obtained by a method described in Ladewig E et al., 2012, Genome Res., Vol. 22, pp. 1634-1645. Also, "hsa-mir-6789" (miRBase Accession No. MI0022634; SEQ ID NO: 1388) having a hairpin-like structure is known as a precursor of "hsa-miR-6789-5p."

The term "hsa-miR-4632-5p gene" or "hsa-miR-4632-5p" used herein includes the hsa-miR-4632-5p gene (miRBase Accession No. MIMAT0022977) shown in SEQ ID NO: 1346, a homolog or an ortholog of a different organism species, and the like. The hsa-miR-4632-5p gene can be obtained by a method described in Persson H et al., 2011, Cancer Res., Vol. 71, pp. 78-86. Also, "hsa-mir-4632" (miRBase Accession No. MI0017259; SEQ ID NO: 1389) having a hairpin-like structure is known as a precursor of "hsa-miR-4632-5p."

The term "hsa-miR-4745-5p gene" or "hsa-miR-4745-5p" used herein includes the hsa-miR-4745-5p gene (miRBase Accession No. MIMAT0019878) shown in SEQ ID NO: 1347, a homolog or an ortholog of a different organism species, and the like. The hsa-miR-4745-5p gene can be obtained by a method described in Persson H et al., 2011, Cancer Res., Vol. 71, pp. 78-86. Also, "hsa-mir-4745" (miRBase Accession No. MI0017384; SEQ ID NO: 1390) having a hairpin-like structure is known as a precursor of "hsa-miR-4745-5p."

The term "hsa-miR-4665-5p gene" or "hsa-miR-4665-5p" used herein includes the hsa-miR-4665-5p gene (miRBase Accession No. MIMAT0019739) shown in SEQ ID NO: 1348, a homolog or an ortholog of a different organism species, and the like. The hsa-miR-4665-5p gene can be obtained by a method described in Persson H et al., 2011, Cancer Res., Vol. 71, pp. 78-86. Also, "hsa-mir-4665" (miRBase Accession No. MI0017295; SEQ ID NO: 1391) having a hairpin-like structure is known as a precursor of "hsa-miR-4665-5p."

The term "hsa-miR-6807-5p gene" or "hsa-miR-6807-5p" used herein includes the hsa-miR-6807-5p gene (miRBase Accession No. MIMAT0027514) shown in SEQ ID NO: 1349, a homolog or an ortholog of a different organism species, and the like. The hsa-miR-6807-5p gene can be obtained by a method described in Ladewig E et al., 2012, Genome Res., Vol. 22, pp. 1634-1645. Also, "hsa-mir-6807" (miRBase Accession No. MI0022652; SEQ ID NO: 1392) having a hairpin-like structure is known as a precursor of "hsa-miR-6807-5p."

The term "hsa-miR-7114-5p gene" or "hsa-miR-7114-5p" used herein includes the hsa-miR-7114-5p gene (miRBase Accession No. MIMAT0028125) shown in SEQ ID NO: 1350, a homolog or an ortholog of a different organism species, and the like. The hsa-miR-7114-5p gene can be obtained by a method described in Ladewig E et al., 2012, Genome Res., Vol. 22, pp. 1634-1645. Also, "hsa-mir-7114" (miRBase Accession No. MI0022965; SEQ ID NO: 1393) having a hairpin-like structure is known as a precursor of "hsa-miR-7114-5p."

The term "hsa-miR-150-3p gene" or "hsa-miR-150-3p" used herein includes the hsa-miR-150-3p gene (miRBase Accession No. MIMAT0004610) shown in SEQ ID NO: 1351, a homolog or an ortholog of a different organism species, and the like. The hsa-miR-150-3p gene can be obtained by a method described in Lagos-Quintana M et al., 2002, Curr. Biol., Vol. 12, pp. 735-739. Also, "hsa-mir-150" (miRBase Accession No. MI0000479; SEQ ID NO: 1394) having a hairpin-like structure is known as a precursor of "hsa-miR-150-3p."

The term "hsa-miR-423-5p gene" or "hsa-miR-423-5p" used herein includes the hsa-miR-423-5p gene (miRBase Accession No. MIMAT0004748) shown in SEQ ID NO: 1352, a homolog or an ortholog of a different organism species, and the like. The hsa-miR-423-5p gene can be obtained by a method described in Kasashima K et al., 2004, Biochem. Biophys. Res. Commun., Vol. 322, pp. 403-410. Also, "hsa-mir-423" (miRBase Accession No. MI0001445; SEQ ID NO: 1395) having a hairpin-like structure is known as a precursor of "hsa-miR-423-5p."

The term "hsa-miR-575 gene" or "hsa-miR-575" used herein includes the hsa-miR-575 gene (miRBase Accession No. MIMAT0003240) shown in SEQ ID NO: 1353, a homolog or an ortholog of a different organism species, and the like. The hsa-miR-575 gene can be obtained by a method described in Cummins J M et al., 2006, Proc. Natl. Acad. Sci. U.S.A., Vol. 103, pp. 3687-3692. Also, "hsa-mir-575" (miRBase Accession No. MI0003582; SEQ ID NO: 1396) having a hairpin-like structure is known as a precursor of "hsa-miR-575."

The term "hsa-miR-671-5p gene" or "hsa-miR-671-5p" used herein includes the hsa-miR-671-5p gene (miRBase Accession No. MIMAT0003880) shown in SEQ ID NO: 1354, a homolog or an ortholog of a different organism species, and the like. The hsa-miR-671-5p gene can be obtained by a method described in Berezikov E et al., 2006, Genome Res., Vol. 16, pp. 1289-1298. Also, "hsa-mir-671" (miRBase Accession No. MI0003760; SEQ ID NO: 1397) having a hairpin-like structure is known as a precursor of "hsa-miR-671-5p."

The term "hsa-miR-939-5p gene" or "hsa-miR-939-5p" used herein includes the hsa-miR-939-5p gene (miRBase Accession No. MIMAT0004982) shown in SEQ ID NO: 1355, a homolog or an ortholog of a different organism species, and the like. The hsa-miR-939-5p gene can be obtained by a method described in Lui W O et al., 2007, Cancer Res., Vol. 67, pp. 6031-6043. Also, "hsa-mir-939" (miRBase Accession No. MI0005761; SEQ ID NO: 1398) having a hairpin-like structure is known as a precursor of "hsa-miR-939-5p."

The term "hsa-miR-3665 gene" or "hsa-miR-3665" used herein includes the hsa-miR-3665 gene (miRBase Accession No. MIMAT0018087) shown in SEQ ID NO: 1356, a homolog or an ortholog of a different organism species, and the like. The hsa-miR-3665 gene can be obtained by a method described in Xie X et al., 2005, Nature, Vol. 434, pp. 338-345. Also, "hsa-mir-3665" (miRBase Accession No. MI0016066; SEQ ID NO: 1399) having a hairpin-like structure is known as a precursor of "hsa-miR-3665."

The term "hsa-miR-516a-5p gene" or "hsa-miR-516a-5p" used herein includes the hsa-miR-516a-5p gene (miRBase Accession No. MIMAT0004770) shown in SEQ ID NO: 1435, a homolog or an ortholog of a different organism species, and the like. The hsa-miR-516a-5p gene can be obtained by a method described in Bentwich I et al., 2005, Nat. Genet., Vol. 37, pp. 766-770. Also, "hsa-miR-516a-1" (miRBase Accession No. MI0003180; SEQ ID NO: 1454) having a hairpin-like structure is known as a precursor of "hsa-miR-516a-5p."

The term "hsa-miR-769-3p gene" or "hsa-miR-769-3p" used herein includes the hsa-miR-769-3p gene (miRBase Accession No. MIMAT0003887) shown in SEQ ID NO: 1436, a homolog or an ortholog of a different organism species, and the like. The hsa-miR-769-3p gene can be obtained by a method described in Berezikov E et al., 2006, Genome Res., Vol. 16, pp. 1289-1298. Also, "hsa-miR-769-3p" (miRBase Accession No. MI0003834; SEQ ID NO: 1465) having a hairpin-like structure is known as a precursor of "hsa-miR-769-3p."

The term "hsa-miR-3692-5p gene" or "hsa-miR-3692-5p" used herein includes the hsa-miR-3692-5p gene (miRBase Accession No. MIMAT0018121) shown in SEQ ID NO: 1437, a homolog or an ortholog of a different organism species, and the like. The hsa-miR-3692-5p gene can be obtained by a method described in Vaz C et al., 2010, BMC Genomics, Vol. 11, p. 288. Also, "hsa-miR-3692-5p" (miRBase Accession No. MI0016093; SEQ ID NO: 1456) having a hairpin-like structure is known as a precursor of "hsa-miR-3692-5p."

The term "hsa-miR-3945 gene" or "hsa-miR-3945" used herein includes the hsa-miR-3945 gene (miRBase Accession No. MIMAT0018361) shown in SEQ ID NO: 1438, a homolog or an ortholog of a different organism species, and the like. The hsa-miR-3945 gene can be obtained by a method described in Liao J Y et al., 2010, PLoS One, Vol. 5, e10563. Also, "hsa-miR-3945" (miRBase Accession No. MI0016602; SEQ ID NO: 1457) having a hairpin-like structure is known as a precursor of "hsa-miR-3945."

The term "hsa-miR-4433a-3p gene" or "hsa-miR-4433a-3p" used herein includes the hsa-miR-4433a-3p gene (miRBase Accession No. MIMAT0018949) shown in SEQ ID NO: 1439, a homolog or an ortholog of a different organism species, and the like. The hsa-miR-4433a-3p gene can be obtained by a method described in Jima D D et al., 2010, Blood, Vol. 116, e118-e127. Also, "hsa-miR-4433a-3p" (miRBase Accession No. MI0016773; SEQ ID NO: 1458) having a hairpin-like structure is known as a precursor of "hsa-miR-4433a-3p."

The term "hsa-miR-4485-3p gene" or "hsa-miR-4485-3p" used herein includes the hsa-miR-4485-3p gene (miRBase Accession No. MIMAT0019019) shown in SEQ ID NO: 1440, a homolog or an ortholog of a different organism species, and the like. The hsa-miR-4485-3p gene can be obtained by a method described in Jima D D et al., 2010, Blood, Vol. 116, e118-e127. Also, "hsa-miR-4485-3p" (miRBase Accession No. MI0016846; SEQ ID NO: 1459) having a hairpin-like structure is known as a precursor of "hsa-miR-4485-3p."

The term "hsa-miR-6831-5p gene" or "hsa-miR-6831-5p" used herein includes the hsa-miR-6831-5p gene (miRBase Accession No. MIMAT0027562) shown in SEQ ID NO: 1441, a homolog or an ortholog of a different organism species, and the like. The hsa-miR-6831-5p gene can be obtained by a method described in Ladewig E et al., 2012, Genome Res., Vol. 22, pp. 1634-1645. Also, "hsa-miR-6831-5p" (miRBase Accession No. MI0022676; SEQ ID NO: 1460) having a hairpin-like structure is known as a precursor of "hsa-miR-6831-5p."

The term "hsa-miR-519c-5p gene" or "hsa-miR-519c-5p" used herein includes the hsa-miR-519c-5p gene (miRBase Accession No. MIMAT0002831) shown in SEQ ID NO: 1442, a homolog or an ortholog of a different organism species, and the like. The hsa-miR-519c-5p gene can be obtained by a method described in Bentwich I et al., 2005, Nat. Genet., Vol. 37, pp. 766-770. Also, "hsa-miR-519c-5p" (miRBase Accession No. MI0003148; SEQ ID NO: 1461) having a hairpin-like structure is known as a precursor of "hsa-miR-519c-5p."

The term "hsa-miR-551b-5p gene" or "hsa-miR-551b-5p" used herein includes the hsa-miR-551b-5p gene (miRBase Accession No. MIMAT0004794) shown in SEQ ID NO: 1443, a homolog or an ortholog of a different organism species, and the like. The hsa-miR-551b-5p gene can be obtained by a method described in Cummins J M et al., 2006, Proc. Natl. Acad. Sci. U.S.A., Vol. 103, pp. 3687-3692. Also, "hsa-miR-551b-5p" (miRBase Accession No. MI0003575; SEQ ID NO: 1462) having a hairpin-like structure is known as a precursor of "hsa-miR-551b-5p."

The term "hsa-miR-1343-3p gene" or "hsa-miR-1343-3p" used herein includes the hsa-miR-1343-3p gene (miRBase Accession No. MIMAT0019776) shown in SEQ ID NO: 1444, a homolog or an ortholog of a different organism species, and the like. The hsa-miR-1343-3p gene can be obtained by a method described in Persson H et al., 2011, Cancer Res., Vol. 71, pp. 78-86. Also, "hsa-miR-1343-3p" (miRBase Accession No. MI0017320; SEQ ID NO: 1463) having a hairpin-like structure is known as a precursor of "hsa-miR-1343-3p."

The term "hsa-miR-4286 gene" or "hsa-miR-4286" used herein includes the hsa-miR-4286 gene (miRBase Accession No. MIMAT0016916) shown in SEQ ID NO: 1445, a homolog or an ortholog of a different organism species, and the like. The hsa-miR-4286 gene can be obtained by a method described in Goff L A et al., 2009, PLoS One, Vol. 4, e7192. Also, "hsa-miR-4286" (miRBase Accession No. MI0015894; SEQ ID NO: 1464) having a hairpin-like structure is known as a precursor of "hsa-miR-4286."

The term "hsa-miR-4634 gene" or "hsa-miR-4634" used herein includes the hsa-miR-4634 gene (miRBase Accession No. MIMAT0019691) shown in SEQ ID NO: 1446, a homolog or an ortholog of a different organism species, and the like. The hsa-miR-4634 gene can be obtained by a method described in Persson H et al., 2011, Cancer Res., Vol. 71, pp. 78-86. Also, "hsa-miR-4634" (miRBase Accession No. MI0017261; SEQ ID NO: 1465) having a hairpin-like structure is known as a precursor of "hsa-miR-4634."

The term "hsa-miR-4733-3p gene" or "hsa-miR-4733-3p" used herein includes the hsa-miR-4733-3p gene (miRBase Accession No. MIMAT0019858) shown in SEQ ID NO: 1447, a homolog or an ortholog of a different organism species, and the like. The hsa-miR-4733-3p gene can be obtained by a method described in Persson H et al., 2011, Cancer Res., Vol. 71, pp. 78-86. Also, "hsa-miR-4733-3p" (miRBase Accession No. MI0017370; SEQ ID NO: 1466) having a hairpin-like structure is known as a precursor of "hsa-miR-4733-3p."

The term "hsa-miR-6086 gene" or "hsa-miR-6086" used herein includes the hsa-miR-6086 gene (miRBase Accession No. MIMAT0023711) shown in SEQ ID NO: 1448, a homolog or an ortholog of a different organism species, and the like. The hsa-miR-6086 gene can be obtained by a method described in Yoo J K et al., 2012, Stem Cells Dev., Vol. 21, pp. 2049-2057. Also, "hsa-miR-6086" (miRBase Accession No. MI0020363; SEQ ID NO: 1467) having a hairpin-like structure is known as a precursor of "hsa-miR-6086."

The term "hsa-miR-30d-5p gene" or "hsa-miR-30d-5p" used herein includes the hsa-miR-30d-5p gene (miRBase Accession No. MIMAT0000245) shown in SEQ ID NO: 1449, a homolog or an ortholog of a different organism species, and the like. The hsa-miR-30d-5p gene can be obtained by a method described in Lagos-Quintana M et al., 2002, Curr. Biol., Vol. 12, pp. 735-739. Also, "hsa-miR-30d-5p" (miRBase Accession No. MI0000255; SEQ ID NO: 1468) having a hairpin-like structure is known as a precursor of "hsa-miR-30d-5p."

The term "hsa-miR-30b-3p gene" or "hsa-miR-30b-3p" used herein includes the hsa-miR-30b-3p gene (miRBase Accession No. MIMAT0004589) shown in SEQ ID NO: 1450, a homolog or an ortholog of a different organism species, and the like. The hsa-miR-30b-3p gene can be obtained by a method described in Lagos-Quintana M et al., 2002, Curr. Biol., Vol. 12, pp. 735-739. Also, "hsa-miR-30b-3p" (miRBase Accession No. MI0000441; SEQ ID NO: 1469) having a hairpin-like structure is known as a precursor of "hsa-miR-30b-3p."

The term "hsa-miR-92a-3p gene" or "hsa-miR-92a-3p" used herein includes the hsa-miR-92a-3p gene (miRBase Accession No. MIMAT0000092) shown in SEQ ID NO: 1451, a homolog or an ortholog of a different organism species, and the like. The hsa-miR-92a-3p gene can be obtained by a method described in Mourelatos Z et al., 2002, Genes Dev., Vol. 16, pp. 720-728. Also, "hsa-miR-92a-3p" (miRBase Accession No. MI0000093; SEQ ID NO: 1470) having a hairpin-like structure is known as a precursor of "hsa-miR-92a-3p."

The term "hsa-miR-371b-5p gene" or "hsa-miR-371b-5p" used herein includes the hsa-miR-371b-5p gene (miRBase Accession No. MIMAT0019892) shown in SEQ ID NO: 1452, a homolog or an ortholog of a different organism species, and the like. The hsa-miR-371b-5p gene can be obtained by a method described in Persson H et al., 2011, Cancer Res., Vol. 71, pp. 78-86. Also, "hsa-miR-371b-5p" (miRBase Accession No. MI0017393; SEQ ID NO: 1471) having a hairpin-like structure is known as a precursor of "hsa-miR-371b-5p."

The term "hsa-miR-486-5p gene" or "hsa-miR-486-5p" used herein includes the hsa-miR-486-5p gene (miRBase Accession No. MIMAT0002177) shown in SEQ ID NO: 1453, a homolog or an ortholog of a different organism species, and the like. The hsa-miR-486-5p gene can be obtained by a method described in Fu H et al., 2005, FEBS Lett., Vol. 579, pp. 3849-3854. Also, "hsa-miR-486-5p" (miRBase Accession No. MI0002470; SEQ ID NO: 1472) having a hairpin-like structure is known as a precursor of "hsa-miR-486-5p."

A mature miRNA may become a variant due to the sequence cleaved shorter or longer by one to several flanking nucleotides, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase (version 21) shows the nucleotide sequences represented by any of SEQ ID NOs: 1 to 210, 211 to 249, 250 to 374, and 375 to 390 as well as a large number of the nucleotide sequence variants and fragments represented by any of SEQ ID NOs: 783 to 1314, called isomiRs. These variants can also be obtained as miRNAs having a nucleotide sequence represented by any of SEQ ID NOs: 1 to 210, 211 to 249, 250 to 374, and 375 to 390. Specifically, among the variants of polynucleotides consisting of the nucleotide sequence represented by any of SEQ ID NOs: 3, 4, 5, 6, 7, 8, 10, 11, 12, 13, 15, 16, 17, 19, 22, 23, 25, 26, 28, 29, 30, 31, 32, 33, 34, 35, 36, 37, 39, 40, 41, 44, 47, 48, 49, 50, 51, 52, 54, 56, 57, 59, 60, 61, 62, 63, 64, 65, 66, 67, 68, 69, 70, 71, 72, 73, 75, 77, 78, 79, 81, 82, 83, 84, 85, 86, 87, 89, 91, 94, 95, 96, 98, 99, 100, 101, 102, 103, 105, 107, 109, 111, 112, 113, 114, 115, 116, 118, 119, 121, 122, 125, 126, 127, 128, 129, 130, 133, 134, 135, 136, 137, 138, 139, 141, 142, 143, 144, 145, 147, 148, 149, 150, 151, 152, 153, 154, 157, 158, 159, 161, 162, 163, 164, 165, 166, 167, 168, 169, 170, 171, 172, 173, 175, 177, 179, 180, 181, 182, 185, 187, 189, 190, 191, 192, 194, 195, 199, 202, 203, 205, 206, 208, 209, 213, 214, 215, 216, 217, 218, 219, 220, 221, 222, 223, 224, 225, 226, 227, 228, 229, 230, 231, 232, 233, 234, 235, 236, 237, 238, 239, 241, 242, 243, 244, 245, 246, 247, 248, 249, 251, 252, 253, 255, 256, 257, 259, 260, 261, 262, 263, 264, 265, 268, 269, 270, 271, 272, 273, 274, 275, 276, 277, 278, 279, 280, 281, 282, 283, 284, 286, 287, 288, 289, 290, 291, 292, 293, 295, 296, 297, 298, 299, 300, 301, 302, 303, 304, 305, 306, 307, 308, 309, 310, 311, 312, 313, 314, 315, 316, 317, 320, 321, 322, 323, 324, 325, 326, 327, 328, 329, 330, 331, 332, 333, 335, 338, 340, 341, 342, 343, 345, 347, 348, 349, 350, 352, 353, 354, 355, 356, 357, 359, 361, 362, 363, 367, 368, 369, 371, 372, 373, 374, 375, 376, 377, 378, 379, 380, 381, 382, 383, 385, 386, 388, 389, and 390 or a nucleotide sequence derived from the nucleotide sequence by the replacement of u with t according to the present invention, polynucleotides represented by SEQ ID NOs: 241 and 243 are included as the longest variants registered in miRBase (version 21), polynucleotides having sequences represented by SEQ ID NOs: 4, 25, 26, 68, 69, 70, 83, 91, 96, 99, 114, 135, 141, 182, 199, 202, 205, 206, 208, 213, 218, 235, 350, and 386 are also included as the shortest variants, in the same manner. In addition to these variants and fragments, a large number of isomiR polynucleotides of SEQ ID NOs: 1 to 210, 211 to 249, 250 to 374, and 375 to 390 registered in the miRBase are included. Further, polynucleotides represented by any of SEQ ID NOs: 391 to 782, which are their respective precursors are included as polynucleotides comprising nucleotide sequences represented by any of SEQ ID NOs: 1 to 210, 211 to 249, 250 to 374, and 375 to 390.

The miRBase (version 21) shows the nucleotide sequences represented by any of SEQ ID NOs: 194 to 210, 374, and 1315 to 1350, and 211 to 212 and 1351 to 1356 as well as a large number of the nucleotide sequence variants and fragments represented by any of SEQ ID NOs: 1015 to 1017, 1019 to 1024, 1026 to 1031, 1285 to 1286, and 1400 to 1434, called isomiRs. These variants can also be obtained as miRNAs having a nucleotide sequence represented by any of SEQ ID NOs: 194 to 210, 374, and 1315 to 1350, and 211 to 212 and 1351 to 1356. Specifically, among the variants of polynucleotides consisting of the nucleotide sequence represented by any of SEQ ID NOs: 194, 195, 1320, 1322, 199, 1328, 1329, 202, 1333, 1334, 203, 1337, 1338, 205, 206, 1340, 374, 1341, 1342, 1343, 208, 209, 1344, 1346, 1347, 1348, 1351, 1352, 1354, 1355, and 1356 or a nucleotide sequence derived from the nucleotide sequence by the replacement of u with t according to the present invention, a polynucleotide represented by SEQ ID NO: 1427 are included as the longest variants registered in miRBase (version 21). polynucleotides having sequences represented by SEQ ID NOs: 1017, 1020, 1405, 1022, 1407, 1409, 1411, 1024, 1027, 1415, 1417, 1418, 1419, 1029, 1421, 1428, 1430, 1432, and 1434 are also included as the shortest variants in the same manner. In addition to these variants and fragments, a large number of isomiR polynucleotides of SEQ ID NOs: 194 to 210, 374, and 1315 to 1350, and 211 to 212 and 1351 to 1356 registered in the miRBase are included. Further, polynucleotides represented by any of SEQ ID NOs: 398, 490, 591, 593 to 609, 766, and 1357 to 1399, which are their respective precursors are included as the polynucleotides comprising nucleotide sequences represented by any of SEQ ID NOs: 194 to 210, 374, and 1315 to 1350, and 211 to 212 and 1351 to 1356.

In addition, the miRBase (version 21) shows the nucleotide sequences represented by SEQ ID NOs: 1435 to 1448 and 1449 to 1453 as well as a large number of the nucleotide sequence variants and fragments represented by any of SEQ ID NOs: 1473 to 1505, called isomiRs. These variants can also be obtained as miRNAs having a nucleotide sequence represented by any of SEQ ID NOs: 1435 to 1448 and 1449 to 1453. Specifically, among the variants of polynucleotides consisting of the nucleotide sequence represented by any of SEQ ID NOs: 1435, 1436, 1437, 1438, 1439, 1440, 1441, 1442, 1443, 1444, 1445, 1447, 1449, 1450, 1451, 1452, and 1453 or a nucleotide sequence derived from the nucleotide sequence by the replacement of u with t according to the present invention, a polynucleotide represented by SEQ ID NO: 1496 is included as the longest variant registered in miRBase (version 21), Also, polynucleotides having sequences represented by SEQ ID NOs: 1494, 1501, and 1505 also included as the shortest variants in the same manner. In addition to these variants and fragments, a large number of isomiR polynucleotides of SEQ ID NOs: 1435 to 1448 and 1449 to 1453 registered in the miRBase are included. Further, polynucleotides represented by any of SEQ ID NOs: 1454 to 1467 and 1468 to 1472, which are their respective precursors are included as the polynucleotide comprising a nucleotide sequence represented by any of SEQ ID NOs: 1435 to 1448 and 1449 to 1453.

The names and miRBase Accession Nos. (registration numbers) of the genes represented by SEQ ID NOs: 1 to 1314 and 1435 to 1505 are shown in Table 1-1.

In addition, the names and miRBase Accession Nos. (registration numbers) of the genes represented by SEQ ID NOs: 1315 to 1434 are shown in Table 1-2.

As used herein, the term "capable of specifically binding" means that the nucleic acid probe or the primer used in the present invention binds to a specific target nucleic acid and cannot substantially bind to other nucleic acids.

TABLE 1-1

| SEQ ID NO | Name of gene | Accession No. of miRBase |
|---|---|---|
| 1 | hsa-miR-4274 | MIMAT0016906 |
| 2 | hsa-miR-4272 | MIMAT0016902 |
| 3 | hsa-miR-4728-5p | MIMAT0019849 |
| 4 | hsa-miR-4443 | MIMAT0018961 |
| 5 | hsa-miR-4506 | MIMAT0019042 |
| 6 | hsa-miR-6773-5p | MIMAT0027446 |
| 7 | hsa-miR-4662a-5p | MIMAT0019731 |
| 8 | hsa-miR-3184-3p | MIMAT0022731 |
| 9 | hsa-miR-4281 | MIMAT0016907 |
| 10 | hsa-miR-320d | MIMAT0006764 |
| 11 | hsa-miR-6729-3p | MIMAT0027360 |
| 12 | hsa-miR-5192 | MIMAT0021123 |
| 13 | hsa-miR-6853-5p | MIMAT0027606 |
| 14 | hsa-miR-1234-3p | MIMAT0005589 |
| 15 | hsa-miR-1233-3p | MIMAT0005588 |
| 16 | hsa-miR-4539 | MIMAT0019082 |
| 17 | hsa-miR-3914 | MIMAT0018188 |
| 18 | hsa-miR-4738-5p | MIMAT0019866 |
| 19 | hsa-miR-548au-3p | MIMAT0022292 |
| 20 | hsa-miR-1539 | MIMAT0007401 |
| 21 | hsa-miR-4720-3p | MIMAT0019834 |
| 22 | hsa-miR-365b-5p | MIMAT0022833 |
| 23 | hsa-miR-4486 | MIMAT0019020 |
| 24 | hsa-miR-1227-5p | MIMAT0022941 |
| 25 | hsa-miR-4667-5p | MIMAT0019743 |
| 26 | hsa-miR-6088 | MIMAT0023713 |

TABLE 1-1-continued

| SEQ ID NO | Name of gene | Accession No. of miRBase |
|---|---|---|
| 27 | hsa-miR-6820-5p | MIMAT0027540 |
| 28 | hsa-miR-4505 | MIMAT0019041 |
| 29 | hsa-miR-548q | MIMAT0011163 |
| 30 | hsa-miR-4658 | MIMAT0019725 |
| 31 | hsa-miR-450a-5p | MIMAT0001545 |
| 32 | hsa-miR-1260b | MIMAT0015041 |
| 33 | hsa-miR-3677-5p | MIMAT0019221 |
| 34 | hsa-miR-6777-3p | MIMAT0027455 |
| 35 | hsa-miR-6826-3p | MIMAT0027553 |
| 36 | hsa-miR-6832-3p | MIMAT0027565 |
| 37 | hsa-miR-4725-3p | MIMAT0019844 |
| 38 | hsa-miR-7161-3p | MIMAT0028233 |
| 39 | hsa-miR-2277-5p | MIMAT0017352 |
| 40 | hsa-miR-7110-3p | MIMAT0028118 |
| 41 | hsa-miR-4312 | MIMAT0016864 |
| 42 | hsa-miR-4461 | MIMAT0018983 |
| 43 | hsa-miR-6766-5p | MIMAT0027432 |
| 44 | hsa-miR-1266-3p | MIMAT0026742 |
| 45 | hsa-miR-6729-5p | MIMAT0027359 |
| 46 | hsa-miR-526b-3p | MIMAT0002836 |
| 47 | hsa-miR-519e-5p | MIMAT0002828 |
| 48 | hsa-miR-512-5p | MIMAT0002822 |
| 49 | hsa-miR-5088-5p | MIMAT0021080 |
| 50 | hsa-miR-1909-3p | MIMAT0007883 |
| 51 | hsa-miR-6511a-5p | MIMAT0025478 |
| 52 | hsa-miR-4734 | MIMAT0019859 |
| 53 | hsa-miR-936 | MIMAT0004979 |
| 54 | hsa-miR-1249-3p | MIMAT0005901 |
| 55 | hsa-miR-6777-5p | MIMAT0027454 |
| 56 | hsa-miR-4487 | MIMAT0019021 |
| 57 | hsa-miR-3155a | MIMAT0015029 |
| 58 | hsa-miR-563 | MIMAT0003227 |
| 59 | hsa-miR-4741 | MIMAT0019871 |
| 60 | hsa-miR-6788-5p | MIMAT0027476 |
| 61 | hsa-miR-4433b-5p | MIMAT0030413 |
| 62 | hsa-miR-323a-5p | MIMAT0004696 |
| 63 | hsa-miR-6811-5p | MIMAT0027522 |
| 64 | hsa-miR-6721-5p | MIMAT0025852 |
| 65 | hsa-miR-5004-5p | MIMAT0021027 |
| 66 | hsa-miR-6509-3p | MIMAT0025475 |
| 67 | hsa-miR-648 | MIMAT0003318 |
| 68 | hsa-miR-3917 | MIMAT0018191 |
| 69 | hsa-miR-6087 | MIMAT0023712 |
| 70 | hsa-miR-1470 | MIMAT0007348 |
| 71 | hsa-miR-586 | MIMAT0003252 |
| 72 | hsa-miR-3150a-5p | MIMAT0019206 |
| 73 | hsa-miR-105-3p | MIMAT0004516 |
| 74 | hsa-miR-7973 | MIMAT0031176 |
| 75 | hsa-miR-1914-5p | MIMAT0007889 |
| 76 | hsa-miR-4749-3p | MIMAT0019886 |
| 77 | hsa-miR-15b-5p | MIMAT0000417 |
| 78 | hsa-miR-1289 | MIMAT0005879 |
| 79 | hsa-miR-4433a-5p | MIMAT0020956 |
| 80 | hsa-miR-3666 | MIMAT0018088 |
| 81 | hsa-miR-3186-3p | MIMAT0015068 |
| 82 | hsa-miR-4725-5p | MIMAT0019843 |
| 83 | hsa-miR-4488 | MIMAT0019022 |
| 84 | hsa-miR-4474-3p | MIMAT0019001 |
| 85 | hsa-miR-6731-3p | MIMAT0027364 |
| 86 | hsa-miR-4640-3p | MIMAT0019700 |
| 87 | hsa-miR-202-5p | MIMAT0002810 |
| 88 | hsa-miR-6816-5p | MIMAT0027532 |
| 89 | hsa-miR-638 | MIMAT0003308 |
| 90 | hsa-miR-6821-5p | MIMAT0027542 |
| 91 | hsa-miR-1247-3p | MIMAT0022721 |
| 92 | hsa-miR-6765-5p | MIMAT0027430 |
| 93 | hsa-miR-6800-5p | MIMAT0027500 |
| 94 | hsa-miR-3928-3p | MIMAT0018205 |
| 95 | hsa-miR-3940-5p | MIMAT0019229 |
| 96 | hsa-miR-3960 | MIMAT0019337 |
| 97 | hsa-miR-6775-5p | MIMAT0027450 |
| 98 | hsa-miR-3178 | MIMAT0015055 |
| 99 | hsa-miR-1202 | MIMAT0005865 |
| 100 | hsa-miR-6790-5p | MIMAT0027480 |
| 101 | hsa-miR-4731-3p | MIMAT0019854 |
| 102 | hsa-miR-2681-3p | MIMAT0013516 |
| 103 | hsa-miR-6758-5p | MIMAT0027416 |

TABLE 1-1-continued

| SEQ ID NO | Name of gene | Accession No. of miRBase |
|---|---|---|
| 104 | hsa-miR-8072 | MIMAT0030999 |
| 105 | hsa-miR-518d-3p | MIMAT0002864 |
| 106 | hsa-miR-3606-3p | MIMAT0022965 |
| 107 | hsa-miR-4800-5p | MIMAT0019978 |
| 108 | hsa-miR-1292-3p | MIMAT0022948 |
| 109 | hsa-miR-6784-3p | MIMAT0027469 |
| 110 | hsa-miR-4450 | MIMAT0018971 |
| 111 | hsa-miR-6132 | MIMAT0024616 |
| 112 | hsa-miR-4716-5p | MIMAT0019826 |
| 113 | hsa-miR-6860 | MIMAT0027622 |
| 114 | hsa-miR-1268b | MIMAT0018925 |
| 115 | hsa-miR-378d | MIMAT0018926 |
| 116 | hsa-miR-4701-5p | MIMAT0019798 |
| 117 | hsa-miR-4329 | MIMAT0016923 |
| 118 | hsa-miR-185-3p | MIMAT0004611 |
| 119 | hsa-miR-552-3p | MIMAT0003215 |
| 120 | hsa-miR-1273g-5p | MIMAT0020602 |
| 121 | hsa-miR-6769b-3p | MIMAT0027621 |
| 122 | hsa-miR-520a-3p | MIMAT0002834 |
| 123 | hsa-miR-4524b-5p | MIMAT0022255 |
| 124 | hsa-miR-4291 | MIMAT0016922 |
| 125 | hsa-miR-6734-3p | MIMAT0027370 |
| 126 | hsa-miR-143-5p | MIMAT0004599 |
| 127 | hsa-miR-939-3p | MIMAT0022939 |
| 128 | hsa-miR-6889-3p | MIMAT0027679 |
| 129 | hsa-miR-6842-3p | MIMAT0027587 |
| 130 | hsa-miR-4511 | MIMAT0019048 |
| 131 | hsa-miR-4318 | MIMAT0016869 |
| 132 | hsa-miR-4653-5p | MIMAT0019718 |
| 133 | hsa-miR-6867-3p | MIMAT0027635 |
| 134 | hsa-miR-133b | MIMAT0000770 |
| 135 | hsa-miR-3196 | MIMAT0015080 |
| 136 | hsa-miR-193b-3p | MIMAT0002819 |
| 137 | hsa-miR-3162-3p | MIMAT0019213 |
| 138 | hsa-miR-6819-3p | MIMAT0027539 |
| 139 | hsa-miR-1908-3p | MIMAT0026916 |
| 140 | hsa-miR-6786-5p | MIMAT0027472 |
| 141 | hsa-miR-3648 | MIMAT0018068 |
| 142 | hsa-miR-4513 | MIMAT0019050 |
| 143 | hsa-miR-3652 | MIMAT0018072 |
| 144 | hsa-miR-4640-5p | MIMAT0019699 |
| 145 | hsa-miR-6871-5p | MIMAT0027642 |
| 146 | hsa-miR-7845-5p | MIMAT0030420 |
| 147 | hsa-miR-3138 | MIMAT0015006 |
| 148 | hsa-miR-6884-5p | MIMAT0027668 |
| 149 | hsa-miR-4653-3p | MIMAT0019719 |
| 150 | hsa-miR-636 | MIMAT0003306 |
| 151 | hsa-miR-4652-3p | MIMAT0019717 |
| 152 | hsa-miR-6823-5p | MIMAT0027546 |
| 153 | hsa-miR-4502 | MIMAT0019038 |
| 154 | hsa-miR-7113-5p | MIMAT0028123 |
| 155 | hsa-miR-8087 | MIMAT0031014 |
| 156 | hsa-miR-7154-3p | MIMAT0028219 |
| 157 | hsa-miR-5189-5p | MIMAT0021120 |
| 158 | hsa-miR-1253 | MIMAT0005904 |
| 159 | hsa-miR-518c-5p | MIMAT0002847 |
| 160 | hsa-miR-7151-5p | MIMAT0028212 |
| 161 | hsa-miR-3614-3p | MIMAT0017993 |
| 162 | hsa-miR-4727-5p | MIMAT0019847 |
| 163 | hsa-miR-3682-5p | MIMAT0019222 |
| 164 | hsa-miR-5090 | MIMAT0021082 |
| 165 | hsa-miR-337-3p | MIMAT0000754 |
| 166 | hsa-miR-488-5p | MIMAT0002804 |
| 167 | hsa-miR-100-5p | MIMAT0000098 |
| 168 | hsa-miR-4520-3p | MIMAT0019057 |
| 169 | hsa-miR-373-3p | MIMAT0000726 |
| 170 | hsa-miR-6499-5p | MIMAT0025450 |
| 171 | hsa-miR-3909 | MIMAT0018183 |
| 172 | hsa-miR-32-5p | MIMAT0000090 |
| 173 | hsa-miR-302a-3p | MIMAT0000684 |
| 174 | hsa-miR-4686 | MIMAT0019773 |
| 175 | hsa-miR-4659a-3p | MIMAT0019727 |
| 176 | hsa-miR-4287 | MIMAT0016917 |
| 177 | hsa-miR-1301-5p | MIMAT0026639 |
| 178 | hsa-miR-593-3p | MIMAT0004802 |
| 179 | hsa-miR-517a-3p | MIMAT0002852 |
| 180 | hsa-miR-517b-3p | MIMAT0002857 |

TABLE 1-1-continued

| SEQ ID NO | Name of gene | Accession No. of miRBase |
|---|---|---|
| 181 | hsa-miR-142-3p | MIMAT0000434 |
| 182 | hsa-miR-1185-2-3p | MIMAT0022713 |
| 183 | hsa-miR-602 | MIMAT0003270 |
| 184 | hsa-miR-527 | MIMAT0002862 |
| 185 | hsa-miR-518a-5p | MIMAT0005457 |
| 186 | hsa-miR-4682 | MIMAT0019767 |
| 187 | hsa-miR-28-5p | MIMAT0000085 |
| 188 | hsa-miR-4252 | MIMAT0016886 |
| 189 | hsa-miR-452-5p | MIMAT0001635 |
| 190 | hsa-miR-525-5p | MIMAT0002838 |
| 191 | hsa-miR-3622a-3p | MIMAT0018004 |
| 192 | hsa-miR-6813-3p | MIMAT0027527 |
| 193 | hsa-miR-4769-3p | MIMAT0019923 |
| 194 | hsa-miR-5698 | MIMAT0022491 |
| 195 | hsa-miR-1915-3p | MIMAT0007892 |
| 196 | hsa-miR-1343-5p | MIMAT0027038 |
| 197 | hsa-miR-6861-5p | MIMAT0027623 |
| 198 | hsa-miR-6781-5p | MIMAT0027462 |
| 199 | hsa-miR-4508 | MIMAT0019045 |
| 200 | hsa-miR-6743-5p | MIMAT0027387 |
| 201 | hsa-miR-6726-5p | MIMAT0027353 |
| 202 | hsa-miR-4525 | MIMAT0019064 |
| 203 | hsa-miR-4651 | MIMAT0019715 |
| 204 | hsa-miR-6813-5p | MIMAT0027526 |
| 205 | hsa-miR-5787 | MIMAT0023252 |
| 206 | hsa-miR-1290 | MIMAT0005880 |
| 207 | hsa-miR-6075 | MIMAT0023700 |
| 208 | hsa-miR-4758-5p | MIMAT0019903 |
| 209 | hsa-miR-4690-5p | MIMAT0019779 |
| 210 | hsa-miR-762 | MIMAT0010313 |
| 211 | hsa-miR-1225-3p | MIMAT0005573 |
| 212 | hsa-miR-3184-5p | MIMAT0015064 |
| 213 | hsa-miR-665 | MIMAT0004952 |
| 214 | hsa-miR-211-5p | MIMAT0000268 |
| 215 | hsa-miR-1247-5p | MIMAT0005899 |
| 216 | hsa-miR-3656 | MIMAT0018076 |
| 217 | hsa-miR-149-5p | MIMAT0000450 |
| 218 | hsa-miR-744-5p | MIMAT0004945 |
| 219 | hsa-miR-345-5p | MIMAT0000772 |
| 220 | hsa-miR-150-5p | MIMAT0000451 |
| 221 | hsa-miR-191-3p | MIMAT0001618 |
| 222 | hsa-miR-651-5p | MIMAT0003321 |
| 223 | hsa-miR-34a-5p | MIMAT0000255 |
| 224 | hsa-miR-409-5p | MIMAT0001638 |
| 225 | hsa-miR-369-5p | MIMAT0001621 |
| 226 | hsa-miR-1915-5p | MIMAT0007891 |
| 227 | hsa-miR-204-5p | MIMAT0000265 |
| 228 | hsa-miR-137 | MIMAT0000429 |
| 229 | hsa-miR-382-5p | MIMAT0000737 |
| 230 | hsa-miR-517-5p | MIMAT0002851 |
| 231 | hsa-miR-532-5p | MIMAT0002888 |
| 232 | hsa-miR-22-5p | MIMAT0004495 |
| 233 | hsa-miR-1237-3p | MIMAT0005592 |
| 234 | hsa-miR-1224-3p | MIMAT0005459 |
| 235 | hsa-miR-625-3p | MIMAT0004808 |
| 236 | hsa-miR-328-3p | MIMAT0000752 |
| 237 | hsa-miR-122-5p | MIMAT0000421 |
| 238 | hsa-miR-202-3p | MIMAT0002811 |
| 239 | hsa-miR-4781-5p | MIMAT0019942 |
| 240 | hsa-miR-718 | MIMAT0012735 |
| 241 | hsa-miR-342-3p | MIMAT0000753 |
| 242 | hsa-miR-26b-3p | MIMAT0004500 |
| 243 | hsa-miR-140-3p | MIMAT0004597 |
| 244 | hsa-miR-200a-3p | MIMAT0000682 |
| 245 | hsa-miR-378a-3p | MIMAT0000732 |
| 246 | hsa-miR-484 | MIMAT0002174 |
| 247 | hsa-miR-296-5p | MIMAT0000690 |
| 248 | hsa-miR-205-5p | MIMAT0000266 |
| 249 | hsa-miR-431-5p | MIMAT0001625 |
| 250 | hsa-miR-1471 | MIMAT0007349 |
| 251 | hsa-miR-1538 | MIMAT0007400 |
| 252 | hsa-miR-449b-3p | MIMAT0009203 |
| 253 | hsa-miR-1976 | MIMAT0009451 |
| 254 | hsa-miR-4268 | MIMAT0016896 |
| 255 | hsa-miR-4279 | MIMAT0016909 |
| 256 | hsa-miR-3620-3p | MIMAT0018001 |
| 257 | hsa-miR-3944-3p | MIMAT0018360 |

TABLE 1-1-continued

| SEQ ID NO | Name of gene | Accession No. of miRBase |
|---|---|---|
| 258 | hsa-miR-3156-3p | MIMAT0019209 |
| 259 | hsa-miR-3187-5p | MIMAT0019216 |
| 260 | hsa-miR-4685-3p | MIMAT0019772 |
| 261 | hsa-miR-4695-3p | MIMAT0019789 |
| 262 | hsa-miR-4697-3p | MIMAT0019792 |
| 263 | hsa-miR-4713-5p | MIMAT0019820 |
| 264 | hsa-miR-4723-3p | MIMAT0019839 |
| 265 | hsa-miR-371b-3p | MIMAT0019893 |
| 266 | hsa-miR-3151-3p | MIMAT0027026 |
| 267 | hsa-miR-3192-3p | MIMAT0027027 |
| 268 | hsa-miR-6728-3p | MIMAT0027358 |
| 269 | hsa-miR-6736-3p | MIMAT0027374 |
| 270 | hsa-miR-6740-3p | MIMAT0027382 |
| 271 | hsa-miR-6741-3p | MIMAT0027384 |
| 272 | hsa-miR-6743-3p | MIMAT0027388 |
| 273 | hsa-miR-6747-3p | MIMAT0027395 |
| 274 | hsa-miR-6750-3p | MIMAT0027401 |
| 275 | hsa-miR-6754-3p | MIMAT0027409 |
| 276 | hsa-miR-6759-3p | MIMAT0027419 |
| 277 | hsa-miR-6761-3p | MIMAT0027423 |
| 278 | hsa-miR-6762-3p | MIMAT0027425 |
| 279 | hsa-miR-6769a-3p | MIMAT0027439 |
| 280 | hsa-miR-6776-3p | MIMAT0027453 |
| 281 | hsa-miR-6778-3p | MIMAT0027457 |
| 282 | hsa-miR-6779-3p | MIMAT0027459 |
| 283 | hsa-miR-6786-3p | MIMAT0027473 |
| 284 | hsa-miR-6787-3p | MIMAT0027475 |
| 285 | hsa-miR-6792-3p | MIMAT0027485 |
| 286 | hsa-miR-6794-3p | MIMAT0027489 |
| 287 | hsa-miR-6801-3p | MIMAT0027503 |
| 288 | hsa-miR-6802-3p | MIMAT0027505 |
| 289 | hsa-miR-6803-3p | MIMAT0027507 |
| 290 | hsa-miR-6804-3p | MIMAT0027509 |
| 291 | hsa-miR-6810-5p | MIMAT0027520 |
| 292 | hsa-miR-6823-3p | MIMAT0027547 |
| 293 | hsa-miR-6825-3p | MIMAT0027551 |
| 294 | hsa-miR-6829-3p | MIMAT0027559 |
| 295 | hsa-miR-6833-3p | MIMAT0027567 |
| 296 | hsa-miR-6834-3p | MIMAT0027569 |
| 297 | hsa-miR-6780b-3p | MIMAT0027573 |
| 298 | hsa-miR-6845-3p | MIMAT0027591 |
| 299 | hsa-miR-6862-3p | MIMAT0027626 |
| 300 | hsa-miR-6865-3p | MIMAT0027631 |
| 301 | hsa-miR-6870-3p | MIMAT0027641 |
| 302 | hsa-miR-6875-3p | MIMAT0027651 |
| 303 | hsa-miR-6877-3p | MIMAT0027655 |
| 304 | hsa-miR-6879-3p | MIMAT0027659 |
| 305 | hsa-miR-6882-3p | MIMAT0027665 |
| 306 | hsa-miR-6885-3p | MIMAT0027671 |
| 307 | hsa-miR-6886-3p | MIMAT0027673 |
| 308 | hsa-miR-6887-3p | MIMAT0027675 |
| 309 | hsa-miR-6890-3p | MIMAT0027681 |
| 310 | hsa-miR-6893-3p | MIMAT0027687 |
| 311 | hsa-miR-6894-3p | MIMAT0027689 |
| 312 | hsa-miR-7106-3p | MIMAT0028110 |
| 313 | hsa-miR-7109-3p | MIMAT0028116 |
| 314 | hsa-miR-7114-3p | MIMAT0028126 |
| 315 | hsa-miR-7155-5p | MIMAT0028220 |
| 316 | hsa-miR-7160-5p | MIMAT0028230 |
| 317 | hsa-miR-615-3p | MIMAT0003283 |
| 318 | hsa-miR-920 | MIMAT0004970 |
| 319 | hsa-miR-1825 | MIMAT0006765 |
| 320 | hsa-miR-675-3p | MIMAT0006790 |
| 321 | hsa-miR-1910-5p | MIMAT0007884 |
| 322 | hsa-miR-2278 | MIMAT0011778 |
| 323 | hsa-miR-2682-3p | MIMAT0013518 |
| 324 | hsa-miR-3122 | MIMAT0014984 |
| 325 | hsa-miR-3151-5p | MIMAT0015024 |
| 326 | hsa-miR-3175 | MIMAT0015052 |
| 327 | hsa-miR-4323 | MIMAT0016875 |
| 328 | hsa-miR-4326 | MIMAT0016888 |
| 329 | hsa-miR-4284 | MIMAT0016915 |
| 330 | hsa-miR-3605-3p | MIMAT0017982 |
| 331 | hsa-miR-3622b-5p | MIMAT0018005 |
| 332 | hsa-miR-3646 | MIMAT0018065 |
| 333 | hsa-miR-3158-5p | MIMAT0019211 |
| 334 | hsa-miR-4722-3p | MIMAT0019837 |

TABLE 1-1-continued

| SEQ ID NO | Name of gene | Accession No. of miRBase |
|---|---|---|
| 335 | hsa-miR-4728-3p | MIMAT0019850 |
| 336 | hsa-miR-4747-3p | MIMAT0019883 |
| 337 | hsa-miR-4436b-5p | MIMAT0019940 |
| 338 | hsa-miR-5196-3p | MIMAT0021129 |
| 339 | hsa-miR-5589-5p | MIMAT0022297 |
| 340 | hsa-miR-345-3p | MIMAT0022698 |
| 341 | hsa-miR-642b-5p | MIMAT0022736 |
| 342 | hsa-miR-6716-3p | MIMAT0025845 |
| 343 | hsa-miR-6511b-3p | MIMAT0025848 |
| 344 | hsa-miR-208a-5p | MIMAT0026474 |
| 345 | hsa-miR-6726-3p | MIMAT0027354 |
| 346 | hsa-miR-6744-5p | MIMAT0027389 |
| 347 | hsa-miR-6782-3p | MIMAT0027465 |
| 348 | hsa-miR-6789-3p | MIMAT0027479 |
| 349 | hsa-miR-6797-3p | MIMAT0027495 |
| 350 | hsa-miR-6800-3p | MIMAT0027501 |
| 351 | hsa-miR-6806-5p | MIMAT0027512 |
| 352 | hsa-miR-6824-3p | MIMAT0027549 |
| 353 | hsa-miR-6837-5p | MIMAT0027576 |
| 354 | hsa-miR-6846-3p | MIMAT0027593 |
| 355 | hsa-miR-6858-3p | MIMAT0027617 |
| 356 | hsa-miR-6859-3p | MIMAT0027619 |
| 357 | hsa-miR-6861-3p | MIMAT0027624 |
| 358 | hsa-miR-6880-3p | MIMAT0027661 |
| 359 | hsa-miR-7111-3p | MIMAT0028120 |
| 360 | hsa-miR-7152-5p | MIMAT0028214 |
| 361 | hsa-miR-642a-5p | MIMAT0003312 |
| 362 | hsa-miR-657 | MIMAT0003335 |
| 363 | hsa-miR-1236-3p | MIMAT0005591 |
| 364 | hsa-miR-764 | MIMAT0010367 |
| 365 | hsa-miR-4314 | MIMAT0016868 |
| 366 | hsa-miR-3675-3p | MIMAT0018099 |
| 367 | hsa-miR-5703 | MIMAT0022496 |
| 368 | hsa-miR-3191-5p | MIMAT0022732 |
| 369 | hsa-miR-6511a-3p | MIMAT0025479 |
| 370 | hsa-miR-6809-3p | MIMAT0027519 |
| 371 | hsa-miR-6815-5p | MIMAT0027530 |
| 372 | hsa-miR-6857-3p | MIMAT0027615 |
| 373 | hsa-miR-6878-3p | MIMAT0027657 |
| 374 | hsa-miR-371a-5p | MIMAT0004687 |
| 375 | hsa-miR-766-3p | MIMAT0003888 |
| 376 | hsa-miR-1229-3p | MIMAT0005584 |
| 377 | hsa-miR-1306-5p | MIMAT0022726 |
| 378 | hsa-miR-210-5p | MIMAT0026475 |
| 379 | hsa-miR-198 | MIMAT0000228 |
| 380 | hsa-miR-485-3p | MIMAT0002176 |
| 381 | hsa-miR-668-3p | MIMAT0003881 |
| 382 | hsa-miR-532-3p | MIMAT0004780 |
| 383 | hsa-miR-877-3p | MIMAT0004950 |
| 384 | hsa-miR-1238-3p | MIMAT0005593 |
| 385 | hsa-miR-3130-5p | MIMAT0014995 |
| 386 | hsa-miR-4298 | MIMAT0016852 |
| 387 | hsa-miR-4290 | MIMAT0016921 |
| 388 | hsa-miR-3943 | MIMAT0018359 |
| 389 | hsa-miR-346 | MIMAT0000773 |
| 390 | hsa-miR-767-3p | MIMAT0003883 |
| 391 | hsa-mir-4274 | MI0015884 |
| 392 | hsa-mir-4272 | MI0015880 |
| 393 | hsa-mir-4728 | MI0017365 |
| 394 | hsa-mir-4443 | MI0016786 |
| 395 | hsa-mir-4506 | MI0016869 |
| 396 | hsa-mir-6773 | MI0022618 |
| 397 | hsa-mir-4662a | MI0017290 |
| 398 | hsa-mir-3184 | MI0014226 |
| 399 | hsa-mir-4281 | MI0015885 |
| 400 | hsa-mir-320d-1 | MI0008190 |
| 401 | hsa-mir-320d-2 | MI0008192 |
| 402 | hsa-mir-6729 | MI0022574 |
| 403 | hsa-mir-5192 | MI0018171 |
| 404 | hsa-mir-6853 | MI0022699 |
| 405 | hsa-mir-1234 | MI0006324 |
| 406 | hsa-mir-1233-1 | MI0006323 |
| 407 | hsa-mir-1233-2 | MI0015973 |
| 408 | hsa-mir-4539 | MI0016910 |
| 409 | hsa-mir-3914-1 | MI0016419 |
| 410 | hsa-mir-3914-2 | MI0016421 |
| 411 | hsa-mir-4738 | MI0017376 |

TABLE 1-1-continued

| SEQ ID NO | Name of gene | Accession No. of miRBase |
|---|---|---|
| 412 | hsa-mir-548au | MI0019145 |
| 413 | hsa-mir-1539 | MI0007260 |
| 414 | hsa-mir-4720 | MI0017355 |
| 415 | hsa-mir-365b | MI0000769 |
| 416 | hsa-mir-4486 | MI0016847 |
| 417 | hsa-mir-1227 | MI0006316 |
| 418 | hsa-mir-4667 | MI0017297 |
| 419 | hsa-mir-6088 | MI0020365 |
| 420 | hsa-mir-6820 | MI0022665 |
| 421 | hsa-mir-4505 | MI0016868 |
| 422 | hsa-mir-548q | MI0010637 |
| 423 | hsa-mir-4658 | MI0017286 |
| 424 | hsa-mir-450a-1 | MI0001652 |
| 425 | hsa-mir-450a-2 | MI0003187 |
| 426 | hsa-mir-1260b | MI0014197 |
| 427 | hsa-mir-3677 | MI0016078 |
| 428 | hsa-mir-6777 | MI0022622 |
| 429 | hsa-mir-6826 | MI0022671 |
| 430 | hsa-mir-6832 | MI0022677 |
| 431 | hsa-mir-4725 | MI0017362 |
| 432 | hsa-mir-7161 | MI0023619 |
| 433 | hsa-mir-2277 | MI0011284 |
| 434 | hsa-mir-7110 | MI0022961 |
| 435 | hsa-mir-4312 | MI0015842 |
| 436 | hsa-mir-4461 | MI0016807 |
| 437 | hsa-mir-6766 | MI0022611 |
| 438 | hsa-mir-1266 | MI0006403 |
| 439 | hsa-mir-526b | MI0003150 |
| 440 | hsa-mir-519e | MI0003145 |
| 441 | hsa-mir-512-1 | MI0003140 |
| 442 | hsa-mir-512-2 | MI0003141 |
| 443 | hsa-mir-5088 | MI0017977 |
| 444 | hsa-mir-1909 | MI0008330 |
| 445 | hsa-mir-6511a-1 | MI0022223 |
| 446 | hsa-mir-6511a-2 | MI0023564 |
| 447 | hsa-mir-6511a-3 | MI0023565 |
| 448 | hsa-mir-6511a-4 | MI0023566 |
| 449 | hsa-mir-4734 | MI0017371 |
| 450 | hsa-mir-936 | MI0005758 |
| 451 | hsa-mir-1249 | MI0006384 |
| 452 | hsa-mir-4487 | MI0016848 |
| 453 | hsa-mir-3155a | MI0014183 |
| 454 | hsa-mir-563 | MI0003569 |
| 455 | hsa-mir-4741 | MI0017379 |
| 456 | hsa-mir-6788 | MI0022633 |
| 457 | hsa-mir-4433b | MI0025511 |
| 458 | hsa-mir-323a | MI0000807 |
| 459 | hsa-mir-6811 | MI0022656 |
| 460 | hsa-mir-6721 | MI0022556 |
| 461 | hsa-mir-5004 | MI0017870 |
| 462 | hsa-mir-6509 | MI0022221 |
| 463 | hsa-mir-648 | MI0003663 |
| 464 | hsa-mir-3917 | MI0016423 |
| 465 | hsa-mir-6087 | MI0020364 |
| 466 | hsa-mir-1470 | MI0007075 |
| 467 | hsa-mir-586 | MI0003594 |
| 468 | hsa-mir-3150a | MI0014177 |
| 469 | hsa-mir-105-1 | MI0000111 |
| 470 | hsa-mir-105-2 | MI0000112 |
| 471 | hsa-mir-7973-1 | MI0025748 |
| 472 | hsa-mir-7973-2 | MI0025749 |
| 473 | hsa-mir-1914 | MI0008335 |
| 474 | hsa-mir-4749 | MI0017388 |
| 475 | hsa-mir-15b | MI0000438 |
| 476 | hsa-mir-1289-1 | MI0006350 |
| 477 | hsa-mir-1289-2 | MI0006351 |
| 478 | hsa-mir-4433a | MI0016773 |
| 479 | hsa-mir-3666 | MI0016067 |
| 480 | hsa-mir-3186 | MI0014229 |
| 481 | hsa-mir-4488 | MI0016849 |
| 482 | hsa-mir-4474 | MI0016826 |
| 483 | hsa-mir-6731 | MI0022576 |
| 484 | hsa-mir-4640 | MI0017267 |
| 485 | hsa-mir-202 | MI0003130 |
| 486 | hsa-mir-6816 | MI0022661 |
| 487 | hsa-mir-638 | MI0003653 |
| 488 | hsa-mir-6821 | MI0022666 |

TABLE 1-1-continued

| SEQ ID NO | Name of gene | Accession No. of miRBase |
|---|---|---|
| 489 | hsa-mir-1247 | MI0006382 |
| 490 | hsa-mir-6765 | MI0022610 |
| 491 | hsa-mir-6800 | MI0022645 |
| 492 | hsa-mir-3928 | MI0016438 |
| 493 | hsa-mir-3940 | MI0016597 |
| 494 | hsa-mir-3960 | MI0016964 |
| 495 | hsa-mir-6775 | MI0022620 |
| 496 | hsa-mir-3178 | MI0014212 |
| 497 | hsa-mir-1202 | MI0006334 |
| 498 | hsa-mir-6790 | MI0022635 |
| 499 | hsa-mir-4731 | MI0017368 |
| 500 | hsa-mir-2681 | MI0012062 |
| 501 | hsa-mir-6758 | MI0022603 |
| 502 | hsa-mir-8072 | MI0025908 |
| 503 | hsa-mir-518d | MI0003171 |
| 504 | hsa-mir-3606 | MI0015996 |
| 505 | hsa-mir-4800 | MI0017448 |
| 506 | hsa-mir-1292 | MI0006433 |
| 507 | hsa-mir-6784 | MI0022629 |
| 508 | hsa-mir-4450 | MI0016795 |
| 509 | hsa-mir-6132 | MI0021277 |
| 510 | hsa-mir-4716 | MI0017350 |
| 511 | hsa-mir-6860 | MI0022707 |
| 512 | hsa-mir-1268b | MI0016748 |
| 513 | hsa-mir-378d-2 | MI0003840 |
| 514 | hsa-mir-378d-1 | MI0016749 |
| 515 | hsa-mir-4701 | MI0017334 |
| 516 | hsa-mir-4329 | MI0015901 |
| 517 | hsa-mir-185 | MI0000482 |
| 518 | hsa-mir-552 | MI0003557 |
| 519 | hsa-mir-1273g | MI0018003 |
| 520 | hsa-mir-6769b | MI0022706 |
| 521 | hsa-mir-520a | MI0003149 |
| 522 | hsa-mir-4524b | MI0019114 |
| 523 | hsa-mir-4291 | MI0015900 |
| 524 | hsa-mir-6734 | MI0022579 |
| 525 | hsa-mir-143 | MI0000459 |
| 526 | hsa-mir-939 | MI0005761 |
| 527 | hsa-mir-6889 | MI0022736 |
| 528 | hsa-mir-6842 | MI0022688 |
| 529 | hsa-mir-4511 | MI0016877 |
| 530 | hsa-mir-4318 | MI0015847 |
| 531 | hsa-mir-4653 | MI0017281 |
| 532 | hsa-mir-6867 | MI0022714 |
| 533 | hsa-mir-133b | MI0000822 |
| 534 | hsa-mir-3196 | MI0014241 |
| 535 | hsa-mir-193b | MI0003137 |
| 536 | hsa-mir-3162 | MI0014192 |
| 537 | hsa-mir-6819 | MI0022664 |
| 538 | hsa-mir-1908 | MI0008329 |
| 539 | hsa-mir-6786 | MI0022631 |
| 540 | hsa-mir-3648-1 | MI0016048 |
| 541 | hsa-mir-3648-2 | MI0031512 |
| 542 | hsa-mir-4513 | MI0016879 |
| 543 | hsa-mir-3652 | MI0016052 |
| 544 | hsa-mir-6871 | MI0022718 |
| 545 | hsa-mir-7845 | MI0025515 |
| 546 | hsa-mir-3138 | MI0014161 |
| 547 | hsa-mir-6884 | MI0022731 |
| 548 | hsa-mir-636 | MI0003651 |
| 549 | hsa-mir-4652 | MI0017280 |
| 550 | hsa-mir-6823 | MI0022668 |
| 551 | hsa-mir-4502 | MI0016865 |
| 552 | hsa-mir-7113 | MI0022964 |
| 553 | hsa-mir-8087 | MI0025923 |
| 554 | hsa-mir-7154 | MI0023614 |
| 555 | hsa-mir-5189 | MI0018168 |
| 556 | hsa-mir-1253 | MI0006387 |
| 557 | hsa-mir-518c | MI0003159 |
| 558 | hsa-mir-7151 | MI0023611 |
| 559 | hsa-mir-3614 | MI0016004 |
| 560 | hsa-mir-4727 | MI0017364 |
| 561 | hsa-mir-3682 | MI0016083 |
| 562 | hsa-mir-5090 | MI0017979 |
| 563 | hsa-mir-337 | MI0000806 |
| 564 | hsa-mir-488 | MI0003123 |
| 565 | hsa-mir-100 | MI0000102 |

TABLE 1-1-continued

| SEQ ID NO | Name of gene | Accession No. of miRBase |
|---|---|---|
| 566 | hsa-mir-4520-1 | MI0016886 |
| 567 | hsa-mir-373 | MI0000781 |
| 568 | hsa-mir-6499 | MI0022209 |
| 569 | hsa-mir-3909 | MI0016413 |
| 570 | hsa-mir-32 | MI0000090 |
| 571 | hsa-mir-302a | MI0000738 |
| 572 | hsa-mir-4686 | MI0017318 |
| 573 | hsa-mir-4659a | MI0017287 |
| 574 | hsa-mir-4287 | MI0015895 |
| 575 | hsa-mir-1301 | MI0003815 |
| 576 | hsa-mir-593 | MI0003605 |
| 577 | hsa-mir-517a | MI0003161 |
| 578 | hsa-mir-517b | MI0003165 |
| 579 | hsa-mir-142 | MI0000458 |
| 580 | hsa-mir-1185-2 | MI0003821 |
| 581 | hsa-mir-602 | MI0003615 |
| 582 | hsa-mir-527 | MI0003179 |
| 583 | hsa-mir-518a-1 | MI0003170 |
| 584 | hsa-mir-518a-2 | MI0003173 |
| 585 | hsa-mir-4682 | MI0017314 |
| 586 | hsa-mir-28 | MI0000086 |
| 587 | hsa-mir-4252 | MI0015864 |
| 588 | hsa-mir-452 | MI0001733 |
| 589 | hsa-mir-525 | MI0003152 |
| 590 | hsa-mir-3622a | MI0016013 |
| 591 | hsa-mir-6813 | MI0022658 |
| 592 | hsa-mir-4769 | MI0017410 |
| 593 | hsa-mir-5698 | MI0019305 |
| 594 | hsa-mir-1915 | MI0008336 |
| 595 | hsa-mir-1343 | MI0017320 |
| 596 | hsa-mir-6861 | MI0022708 |
| 597 | hsa-mir-6781 | MI0022626 |
| 598 | hsa-mir-4508 | MI0016872 |
| 599 | hsa-mir-6743 | MI0022588 |
| 600 | hsa-mir-6726 | MI0022571 |
| 601 | hsa-mir-4525 | MI0016892 |
| 602 | hsa-mir-4651 | MI0017279 |
| 603 | hsa-mir-5787 | MI0019797 |
| 604 | hsa-mir-1290 | MI0006352 |
| 605 | hsa-mir-6075 | MI0020352 |
| 606 | hsa-mir-4758 | MI0017399 |
| 607 | hsa-mir-4690 | MI0017323 |
| 608 | hsa-mir-762 | MI0003892 |
| 609 | hsa-mir-1225 | MI0006311 |
| 610 | hsa-mir-665 | MI0005563 |
| 611 | hsa-mir-211 | MI0000287 |
| 612 | hsa-mir-3656 | MI0016056 |
| 613 | hsa-mir-149 | MI0000478 |
| 614 | hsa-mir-744 | MI0005559 |
| 615 | hsa-mir-345 | MI0000825 |
| 616 | hsa-mir-150 | MI0000479 |
| 617 | hsa-mir-191 | MI0000465 |
| 618 | hsa-mir-651 | MI0003666 |
| 619 | hsa-mir-34a | MI0000268 |
| 620 | hsa-mir-409 | MI0001735 |
| 621 | hsa-mir-369 | MI0000777 |
| 622 | hsa-mir-204 | MI0000284 |
| 623 | hsa-mir-137 | MI0000454 |
| 624 | hsa-mir-382 | MI0000790 |
| 625 | hsa-mir-517c | MI0003174 |
| 626 | hsa-mir-532 | MI0003205 |
| 627 | hsa-mir-22 | MI0000078 |
| 628 | hsa-mir-1237 | MI0006327 |
| 629 | hsa-mir-1224 | MI0003764 |
| 630 | hsa-mir-625 | MI0003639 |
| 631 | hsa-mir-328 | MI0000804 |
| 632 | hsa-mir-122 | MI0000442 |
| 633 | hsa-mir-4781 | MI0017426 |
| 634 | hsa-mir-718 | MI0012489 |
| 635 | hsa-mir-342 | MI0000805 |
| 636 | hsa-mir-26b | MI0000084 |
| 637 | hsa-mir-140 | MI0000456 |
| 638 | hsa-mir-200a | MI0000737 |
| 639 | hsa-mir-378a | MI0000786 |
| 640 | hsa-mir-484 | MI0002468 |
| 641 | hsa-mir-296 | MI0000747 |
| 642 | hsa-mir-205 | MI0000285 |
| 643 | hsa-mir-431 | MI0001721 |
| 644 | hsa-mir-1471 | MI0007076 |
| 645 | hsa-mir-1538 | MI0007259 |
| 646 | hsa-mir-449b | MI0003673 |
| 647 | hsa-mir-1976 | MI0009986 |
| 648 | hsa-mir-4268 | MI0015874 |
| 649 | hsa-mir-4279 | MI0015887 |
| 650 | hsa-mir-3620 | MI0016011 |
| 651 | hsa-mir-3944 | MI0016601 |
| 652 | hsa-mir-3156-1 | MI0014184 |
| 653 | hsa-mir-3156-2 | MI0014230 |
| 654 | hsa-mir-3187 | MI0014231 |
| 655 | hsa-mir-4685 | MI0017317 |
| 656 | hsa-mir-4695 | MI0017328 |
| 657 | hsa-mir-4697 | MI0017330 |
| 658 | hsa-mir-4713 | MI0017347 |
| 659 | hsa-mir-4723 | MI0017359 |
| 660 | hsa-mir-371b | MI0017393 |
| 661 | hsa-mir-3151 | MI0014178 |
| 662 | hsa-mir-3192 | MI0014237 |
| 663 | hsa-mir-6728 | MI0022573 |
| 664 | hsa-mir-6736 | MI0022581 |
| 665 | hsa-mir-6740 | MI0022585 |
| 666 | hsa-mir-6741 | MI0022586 |
| 667 | hsa-mir-6747 | MI0022592 |
| 668 | hsa-mir-6750 | MI0022595 |
| 669 | hsa-mir-6754 | MI0022599 |
| 670 | hsa-mir-6759 | MI0022604 |
| 671 | hsa-mir-6761 | MI0022606 |
| 672 | hsa-mir-6762 | MI0022607 |
| 673 | hsa-mir-6769a | MI0022614 |
| 674 | hsa-mir-6776 | MI0022621 |
| 675 | hsa-mir-6778 | MI0022623 |
| 676 | hsa-mir-6779 | MI0022624 |
| 677 | hsa-mir-6787 | MI0022632 |
| 678 | hsa-mir-6792 | MI0022637 |
| 679 | hsa-mir-6794 | MI0022639 |
| 680 | hsa-mir-6801 | MI0022646 |
| 681 | hsa-mir-6802 | MI0022647 |
| 682 | hsa-mir-6803 | MI0022648 |
| 683 | hsa-mir-6804 | MI0022649 |
| 684 | hsa-mir-6810 | MI0022655 |
| 685 | hsa-mir-6825 | MI0022670 |
| 686 | hsa-mir-6829 | MI0022674 |
| 687 | hsa-mir-6833 | MI0022678 |
| 688 | hsa-mir-6834 | MI0022679 |
| 689 | hsa-mir-6780b | MI0022681 |
| 690 | hsa-mir-6845 | MI0022691 |
| 691 | hsa-mir-6862-1 | MI0022709 |
| 692 | hsa-mir-6862-2 | MI0026415 |
| 693 | hsa-mir-6865 | MI0022712 |
| 694 | hsa-mir-6870 | MI0022717 |
| 695 | hsa-mir-6875 | MI0022722 |
| 696 | hsa-mir-6877 | MI0022724 |
| 697 | hsa-mir-6879 | MI0022726 |
| 698 | hsa-mir-6882 | MI0022729 |
| 699 | hsa-mir-6885 | MI0022732 |
| 700 | hsa-mir-6886 | MI0022733 |
| 701 | hsa-mir-6887 | MI0022734 |
| 702 | hsa-mir-6890 | MI0022737 |
| 703 | hsa-mir-6893 | MI0022740 |
| 704 | hsa-mir-6894 | MI0022741 |
| 705 | hsa-mir-7106 | MI0022957 |
| 706 | hsa-mir-7109 | MI0022960 |
| 707 | hsa-mir-7114 | MI0022965 |
| 708 | hsa-mir-7155 | MI0023615 |
| 709 | hsa-mir-7160 | MI0023621 |
| 710 | hsa-mir-615 | MI0003628 |
| 711 | hsa-mir-920 | MI0005712 |
| 712 | hsa-mir-1825 | MI0008193 |
| 713 | hsa-mir-675 | MI0005416 |
| 714 | hsa-mir-1910 | MI0008331 |
| 715 | hsa-mir-2278 | MI0011285 |
| 716 | hsa-mir-2682 | MI0012063 |
| 717 | hsa-mir-3122 | MI0014138 |
| 718 | hsa-mir-3175 | MI0014209 |
| 719 | hsa-mir-4323 | MI0015853 |

TABLE 1-1-continued

| SEQ ID NO | Name of gene | Accession No. of miRBase |
|---|---|---|
| 720 | hsa-mir-4326 | MI0015866 |
| 721 | hsa-mir-4284 | MI0015893 |
| 722 | hsa-mir-3605 | MI0015995 |
| 723 | hsa-mir-3622b | MI0016014 |
| 724 | hsa-mir-3646 | MI0016046 |
| 725 | hsa-mir-3158-1 | MI0014186 |
| 726 | hsa-mir-3158-2 | MI0014187 |
| 727 | hsa-mir-4722 | MI0017357 |
| 728 | hsa-mir-4747 | MI0017386 |
| 729 | hsa-mir-4436b-1 | MI0017425 |
| 730 | hsa-mir-4436b-2 | MI0019110 |
| 731 | hsa-mir-5196 | MI0018175 |
| 732 | hsa-mir-5589 | MI0019148 |
| 733 | hsa-mir-642b | MI0016685 |
| 734 | hsa-mir-6716 | MI0022550 |
| 735 | hsa-mir-6511b-1 | MI0022552 |
| 736 | hsa-mir-6511b-2 | MI0023431 |
| 737 | hsa-mir-208a | MI0000251 |
| 738 | hsa-mir-6744 | MI0022589 |
| 739 | hsa-mir-6782 | MI0022627 |
| 740 | hsa-mir-6789 | MI0022634 |
| 741 | hsa-mir-6797 | MI0022642 |
| 742 | hsa-mir-6806 | MI0022651 |
| 743 | hsa-mir-6824 | MI0022669 |
| 744 | hsa-mir-6837 | MI0022683 |
| 745 | hsa-mir-6846 | MI0022692 |
| 746 | hsa-mir-6858 | MI0022704 |
| 747 | hsa-mir-6859-1 | MI0022705 |
| 748 | hsa-mir-6859-2 | MI0026420 |
| 749 | hsa-mir-6859-3 | MI0026421 |
| 750 | hsa-mir-6859-4 | MI0031521 |
| 751 | hsa-mir-6880 | MI0022727 |
| 752 | hsa-mir-7111 | MI0022962 |
| 753 | hsa-mir-7152 | MI0023612 |
| 754 | hsa-mir-642a | MI0003657 |
| 755 | hsa-mir-657 | MI0003681 |
| 756 | hsa-mir-1236 | MI0006326 |
| 757 | hsa-mir-764 | MI0003944 |
| 758 | hsa-mir-4314 | MI0015846 |
| 759 | hsa-mir-3675 | MI0016076 |
| 760 | hsa-mir-5703 | MI0019310 |
| 761 | hsa-mir-3191 | MI0014236 |
| 762 | hsa-mir-6809 | MI0022654 |
| 763 | hsa-mir-6815 | MI0022660 |
| 764 | hsa-mir-6857 | MI0022703 |
| 765 | hsa-mir-6878 | MI0022725 |
| 766 | hsa-mir-371a | MI0000779 |
| 767 | hsa-mir-766 | MI0003836 |
| 768 | hsa-mir-1229 | MI0006319 |
| 769 | hsa-mir-1306 | MI0006443 |
| 770 | hsa-mir-210 | MI0000286 |
| 771 | hsa-mir-198 | MI0000240 |
| 772 | hsa-mir-485 | MI0002469 |
| 773 | hsa-mir-668 | MI0003761 |
| 774 | hsa-mir-877 | MI0005561 |
| 775 | hsa-mir-1238 | MI0006328 |
| 776 | hsa-mir-3130-1 | MI0014147 |
| 777 | hsa-mir-3130-2 | MI0014148 |
| 778 | hsa-mir-4298 | MI0015830 |
| 779 | hsa-mir-4290 | MI0015899 |
| 780 | hsa-mir-3943 | MI0016600 |
| 781 | hsa-mir-346 | MI0000826 |
| 782 | hsa-mir-767 | MI0003763 |
| 783 | isomiR sequence 1 of SEQ ID NO: 3 | — |
| 784 | isomiR sequence 2 of SEQ ID NO: 3 | — |
| 785 | isomiR sequence 1 of SEQ ID NO: 4 | — |
| 786 | isomiR sequence 2 of SEQ ID NO: 4 | — |
| 787 | isomiR sequence 1 of SEQ ID NO: 5 | — |
| 788 | isomiR sequence 2 of SEQ ID NO: 5 | — |
| 789 | isomiR sequence 1 of SEQ ID NO: 6 | — |
| 790 | isomiR sequence 2 of SEQ ID NO: 6 | — |
| 791 | isomiR sequence 1 of SEQ ID NO: 7 | — |
| 792 | isomiR sequence 1 of SEQ ID NO: 8 | — |
| 793 | isomiR sequence 1 of SEQ ID NO: 10 | — |
| 794 | isomiR sequence 2 of SEQ ID NO: 10 | — |
| 795 | isomiR sequence 1 of SEQ ID NO: 11 | — |
| 796 | isomiR sequence 1 of SEQ ID NO: 12 | — |
| 797 | isomiR sequence 1 of SEQ ID NO: 13 | — |
| 798 | isomiR sequence 1 of SEQ ID NO: 15 | — |
| 799 | isomiR sequence 2 of SEQ ID NO: 15 | — |
| 800 | isomiR sequence 1 of SEQ ID NO: 16 | — |
| 801 | isomiR sequence 1 of SEQ ID NO: 17 | — |
| 802 | isomiR sequence 1 of SEQ ID NO: 19 | — |
| 803 | isomiR sequence 1 of SEQ ID NO: 22 | — |
| 804 | isomiR sequence 2 of SEQ ID NO: 22 | — |
| 805 | isomiR sequence 1 of SEQ ID NO: 23 | — |
| 806 | isomiR sequence 1 of SEQ ID NO: 25 | — |
| 807 | isomiR sequence 2 of SEQ ID NO: 25 | — |
| 808 | isomiR sequence 1 of SEQ ID NO: 26 | — |
| 809 | isomiR sequence 2 of SEQ ID NO: 26 | — |
| 810 | isomiR sequence 1 of SEQ ID NO: 28 | — |
| 811 | isomiR sequence 1 of SEQ ID NO: 29 | — |
| 812 | isomiR sequence 2 of SEQ ID NO: 29 | — |
| 813 | isomiR sequence 1 of SEQ ID NO: 30 | — |
| 814 | isomiR sequence 1 of SEQ ID NO: 31 | — |
| 815 | isomiR sequence 2 of SEQ ID NO: 31 | — |
| 816 | isomiR sequence 1 of SEQ ID NO: 32 | — |
| 817 | isomiR sequence 2 of SEQ ID NO: 32 | — |
| 818 | isomiR sequence 1 of SEQ ID NO: 33 | — |
| 819 | isomiR sequence 1 of SEQ ID NO: 34 | — |
| 820 | isomiR sequence 1 of SEQ ID NO: 35 | — |
| 821 | isomiR sequence 1 of SEQ ID NO: 36 | — |
| 822 | isomiR sequence 1 of SEQ ID NO: 37 | — |
| 823 | isomiR sequence 2 of SEQ ID NO: 37 | — |
| 824 | isomiR sequence 1 of SEQ ID NO: 39 | — |
| 825 | isomiR sequence 2 of SEQ ID NO: 39 | — |
| 826 | isomiR sequence 1 of SEQ ID NO: 40 | — |
| 827 | isomiR sequence 2 of SEQ ID NO: 40 | — |
| 828 | isomiR sequence 1 of SEQ ID NO: 41 | — |
| 829 | isomiR sequence 1 of SEQ ID NO: 44 | — |
| 830 | isomiR sequence 1 of SEQ ID NO: 47 | — |
| 831 | isomiR sequence 1 of SEQ ID NO: 48 | — |
| 832 | isomiR sequence 1 of SEQ ID NO: 49 | — |
| 833 | isomiR sequence 2 of SEQ ID NO: 49 | — |
| 834 | isomiR sequence 1 of SEQ ID NO: 50 | — |
| 835 | isomiR sequence 2 of SEQ ID NO: 50 | — |
| 836 | isomiR sequence 1 of SEQ ID NO: 51 | — |
| 837 | isomiR sequence 2 of SEQ ID NO: 51 | — |
| 838 | isomiR sequence 1 of SEQ ID NO: 52 | — |
| 839 | isomiR sequence 1 of SEQ ID NO: 54 | — |
| 840 | isomiR sequence 2 of SEQ ID NO: 54 | — |
| 841 | isomiR sequence 1 of SEQ ID NO: 56 | — |
| 842 | isomiR sequence 2 of SEQ ID NO: 56 | — |
| 843 | isomiR sequence 1 of SEQ ID NO: 57 | — |
| 844 | isomiR sequence 2 of SEQ ID NO: 57 | — |
| 845 | isomiR sequence 1 of SEQ ID NO: 59 | — |
| 846 | isomiR sequence 2 of SEQ ID NO: 59 | — |
| 847 | isomiR sequence 1 of SEQ ID NO: 60 | — |
| 848 | isomiR sequence 2 of SEQ ID NO: 60 | — |
| 849 | isomiR sequence 1 of SEQ ID NO: 61 | — |
| 850 | isomiR sequence 2 of SEQ ID NO: 61 | — |
| 851 | isomiR sequence 1 of SEQ ID NO: 62 | — |
| 852 | isomiR sequence 2 of SEQ ID NO: 62 | — |
| 853 | isomiR sequence 1 of SEQ ID NO: 63 | — |
| 854 | isomiR sequence 2 of SEQ ID NO: 63 | — |
| 855 | isomiR sequence 1 of SEQ ID NO: 64 | — |
| 856 | isomiR sequence 2 of SEQ ID NO: 64 | — |
| 857 | isomiR sequence 1 of SEQ ID NO: 65 | — |
| 858 | isomiR sequence 1 of SEQ ID NO: 66 | — |
| 859 | isomiR sequence 1 of SEQ ID NO: 67 | — |
| 860 | isomiR sequence 1 of SEQ ID NO: 68 | — |
| 861 | isomiR sequence 2 of SEQ ID NO: 68 | — |
| 862 | isomiR sequence 1 of SEQ ID NO: 69 | — |
| 863 | isomiR sequence 2 of SEQ ID NO: 69 | — |
| 864 | isomiR sequence 1 of SEQ ID NO: 70 | — |
| 865 | isomiR sequence 1 of SEQ ID NO: 71 | — |
| 866 | isomiR sequence 1 of SEQ ID NO: 72 | — |
| 867 | isomiR sequence 2 of SEQ ID NO: 72 | — |
| 868 | isomiR sequence 1 of SEQ ID NO: 73 | — |
| 869 | isomiR sequence 2 of SEQ ID NO: 73 | — |
| 870 | isomiR sequence 1 of SEQ ID NO: 75 | — |
| 871 | isomiR sequence 1 of SEQ ID NO: 77 | — |
| 872 | isomiR sequence 2 of SEQ ID NO: 77 | — |
| 873 | isomiR sequence 1 of SEQ ID NO: 78 | — |

TABLE 1-1-continued

| SEQ ID NO | Name of gene | Accession No. of miRBase |
|---|---|---|
| 874 | isomiR sequence 1 of SEQ ID NO: 79 | — |
| 875 | isomiR sequence 1 of SEQ ID NO: 81 | — |
| 876 | isomiR sequence 2 of SEQ ID NO: 81 | — |
| 877 | isomiR sequence 1 of SEQ ID NO: 82 | — |
| 878 | isomiR sequence 1 of SEQ ID NO: 83 | — |
| 879 | isomiR sequence 2 of SEQ ID NO: 83 | — |
| 880 | isomiR sequence 1 of SEQ ID NO: 84 | — |
| 881 | isomiR sequence 1 of SEQ ID NO: 85 | — |
| 882 | isomiR sequence 1 of SEQ ID NO: 86 | — |
| 883 | isomiR sequence 1 of SEQ ID NO: 87 | — |
| 884 | isomiR sequence 2 of SEQ ID NO: 87 | — |
| 885 | isomiR sequence 1 of SEQ ID NO: 89 | — |
| 886 | isomiR sequence 2 of SEQ ID NO: 89 | — |
| 887 | isomiR sequence 1 of SEQ ID NO: 91 | — |
| 888 | isomiR sequence 2 of SEQ ID NO: 91 | — |
| 889 | isomiR sequence 1 of SEQ ID NO: 94 | — |
| 890 | isomiR sequence 2 of SEQ ID NO: 94 | — |
| 891 | isomiR sequence 1 of SEQ ID NO: 95 | — |
| 892 | isomiR sequence 2 of SEQ ID NO: 95 | — |
| 893 | isomiR sequence 1 of SEQ ID NO: 96 | — |
| 894 | isomiR sequence 2 of SEQ ID NO: 96 | — |
| 895 | isomiR sequence 1 of SEQ ID NO: 98 | — |
| 896 | isomiR sequence 2 of SEQ ID NO: 98 | — |
| 897 | isomiR sequence 1 of SEQ ID NO: 99 | — |
| 898 | isomiR sequence 1 of SEQ ID NO: 100 | — |
| 899 | isomiR sequence 1 of SEQ ID NO: 101 | — |
| 900 | isomiR sequence 1 of SEQ ID NO: 102 | — |
| 901 | isomiR sequence 1 of SEQ ID NO: 103 | — |
| 902 | isomiR sequence 2 of SEQ ID NO: 103 | — |
| 903 | isomiR sequence 1 of SEQ ID NO: 105 | — |
| 904 | isomiR sequence 1 of SEQ ID NO: 107 | — |
| 905 | isomiR sequence 1 of SEQ ID NO: 109 | — |
| 906 | isomiR sequence 1 of SEQ ID NO: 111 | — |
| 907 | isomiR sequence 1 of SEQ ID NO: 112 | — |
| 908 | isomiR sequence 2 of SEQ ID NO: 112 | — |
| 909 | isomiR sequence 1 of SEQ ID NO: 113 | — |
| 910 | isomiR sequence 1 of SEQ ID NO: 114 | — |
| 911 | isomiR sequence 2 of SEQ ID NO: 114 | — |
| 912 | isomiR sequence 1 of SEQ ID NO: 115 | — |
| 913 | isomiR sequence 2 of SEQ ID NO: 115 | — |
| 914 | isomiR sequence 1 of SEQ ID NO: 116 | — |
| 915 | isomiR sequence 2 of SEQ ID NO: 116 | — |
| 916 | isomiR sequence 1 of SEQ ID NO: 118 | — |
| 917 | isomiR sequence 2 of SEQ ID NO: 118 | — |
| 918 | isomiR sequence 1 of SEQ ID NO: 119 | — |
| 919 | isomiR sequence 1 of SEQ ID NO: 121 | — |
| 920 | isomiR sequence 1 of SEQ ID NO: 122 | — |
| 921 | isomiR sequence 1 of SEQ ID NO: 125 | — |
| 922 | isomiR sequence 1 of SEQ ID NO: 126 | — |
| 923 | isomiR sequence 2 of SEQ ID NO: 126 | — |
| 924 | isomiR sequence 1 of SEQ ID NO: 127 | — |
| 925 | isomiR sequence 2 of SEQ ID NO: 127 | — |
| 926 | isomiR sequence 1 of SEQ ID NO: 128 | — |
| 927 | isomiR sequence 1 of SEQ ID NO: 129 | — |
| 928 | isomiR sequence 1 of SEQ ID NO: 130 | — |
| 929 | isomiR sequence 2 of SEQ ID NO: 130 | — |
| 930 | isomiR sequence 1 of SEQ ID NO: 133 | — |
| 931 | isomiR sequence 1 of SEQ ID NO: 134 | — |
| 932 | isomiR sequence 2 of SEQ ID NO: 134 | — |
| 933 | isomiR sequence 1 of SEQ ID NO: 135 | — |
| 934 | isomiR sequence 2 of SEQ ID NO: 135 | — |
| 935 | isomiR sequence 1 of SEQ ID NO: 136 | — |
| 936 | isomiR sequence 2 of SEQ ID NO: 136 | — |
| 937 | isomiR sequence 1 of SEQ ID NO: 137 | — |
| 938 | isomiR sequence 1 of SEQ ID NO: 138 | — |
| 939 | isomiR sequence 1 of SEQ ID NO: 139 | — |
| 940 | isomiR sequence 2 of SEQ ID NO: 139 | — |
| 941 | isomiR sequence 1 of SEQ ID NO: 141 | — |
| 942 | isomiR sequence 2 of SEQ ID NO: 141 | — |
| 943 | isomiR sequence 1 of SEQ ID NO: 142 | — |
| 944 | isomiR sequence 2 of SEQ ID NO: 142 | — |
| 945 | isomiR sequence 1 of SEQ ID NO: 143 | — |
| 946 | isomiR sequence 2 of SEQ ID NO: 143 | — |
| 947 | isomiR sequence 1 of SEQ ID NO: 144 | — |
| 948 | isomiR sequence 2 of SEQ ID NO: 144 | — |
| 949 | isomiR sequence 1 of SEQ ID NO: 145 | — |
| 950 | isomiR sequence 2 of SEQ ID NO: 145 | — |

TABLE 1-1-continued

| SEQ ID NO | Name of gene | Accession No. of miRBase |
|---|---|---|
| 951 | isomiR sequence 1 of SEQ ID NO: 147 | — |
| 952 | isomiR sequence 2 of SEQ ID NO: 147 | — |
| 953 | isomiR sequence 1 of SEQ ID NO: 148 | — |
| 954 | isomiR sequence 2 of SEQ ID NO: 148 | — |
| 955 | isomiR sequence 1 of SEQ ID NO: 149 | — |
| 956 | isomiR sequence 2 of SEQ ID NO: 149 | — |
| 957 | isomiR sequence 1 of SEQ ID NO: 150 | — |
| 958 | isomiR sequence 2 of SEQ ID NO: 150 | — |
| 959 | isomiR sequence 1 of SEQ ID NO: 151 | — |
| 960 | isomiR sequence 2 of SEQ ID NO: 151 | — |
| 961 | isomiR sequence 1 of SEQ ID NO: 152 | — |
| 962 | isomiR sequence 2 of SEQ ID NO: 152 | — |
| 963 | isomiR sequence 1 of SEQ ID NO: 153 | — |
| 964 | isomiR sequence 2 of SEQ ID NO: 153 | — |
| 965 | isomiR sequence 1 of SEQ ID NO: 154 | — |
| 966 | isomiR sequence 2 of SEQ ID NO: 154 | — |
| 967 | isomiR sequence 1 of SEQ ID NO: 157 | — |
| 968 | isomiR sequence 2 of SEQ ID NO: 157 | — |
| 969 | isomiR sequence 1 of SEQ ID NO: 158 | — |
| 970 | isomiR sequence 1 of SEQ ID NO: 159 | — |
| 971 | isomiR sequence 1 of SEQ ID NO: 161 | — |
| 972 | isomiR sequence 2 of SEQ ID NO: 161 | — |
| 973 | isomiR sequence 1 of SEQ ID NO: 162 | — |
| 974 | isomiR sequence 1 of SEQ ID NO: 163 | — |
| 975 | isomiR sequence 2 of SEQ ID NO: 163 | — |
| 976 | isomiR sequence 1 of SEQ ID NO: 164 | — |
| 977 | isomiR sequence 2 of SEQ ID NO: 164 | — |
| 978 | isomiR sequence 1 of SEQ ID NO: 165 | — |
| 979 | isomiR sequence 2 of SEQ ID NO: 165 | — |
| 980 | isomiR sequence 1 of SEQ ID NO: 166 | — |
| 981 | isomiR sequence 1 of SEQ ID NO: 167 | — |
| 982 | isomiR sequence 2 of SEQ ID NO: 167 | — |
| 983 | isomiR sequence 1 of SEQ ID NO: 168 | — |
| 984 | isomiR sequence 2 of SEQ ID NO: 168 | — |
| 985 | isomiR sequence 1 of SEQ ID NO: 169 | — |
| 986 | isomiR sequence 1 of SEQ ID NO: 170 | — |
| 987 | isomiR sequence 2 of SEQ ID NO: 170 | — |
| 988 | isomiR sequence 1 of SEQ ID NO: 171 | — |
| 989 | isomiR sequence 2 of SEQ ID NO: 171 | — |
| 990 | isomiR sequence 1 of SEQ ID NO: 172 | — |
| 991 | isomiR sequence 2 of SEQ ID NO: 172 | — |
| 992 | isomiR sequence 1 of SEQ ID NO: 173 | — |
| 993 | isomiR sequence 2 of SEQ ID NO: 173 | — |
| 994 | isomiR sequence 1 of SEQ ID NO: 175 | — |
| 995 | isomiR sequence 2 of SEQ ID NO: 175 | — |
| 996 | isomiR sequence 1 of SEQ ID NO: 177 | — |
| 997 | isomiR sequence 2 of SEQ ID NO: 177 | — |
| 998 | isomiR sequence 1 of SEQ ID NO: 179 | — |
| 999 | isomiR sequence 2 of SEQ ID NO: 179 | — |
| 1000 | isomiR sequence 1 of SEQ ID NO: 180 | — |
| 1001 | isomiR sequence 2 of SEQ ID NO: 180 | — |
| 1002 | isomiR sequence 1 of SEQ ID NO: 181 | — |
| 1003 | isomiR sequence 2 of SEQ ID NO: 181 | — |
| 1004 | isomiR sequence 1 of SEQ ID NO: 182 | — |
| 1005 | isomiR sequence 2 of SEQ ID NO: 182 | — |
| 1006 | isomiR sequence 1 of SEQ ID NO: 185 | — |
| 1007 | isomiR sequence 1 of SEQ ID NO: 187 | — |
| 1008 | isomiR sequence 2 of SEQ ID NO: 187 | — |
| 1009 | isomiR sequence 1 of SEQ ID NO: 189 | — |
| 1010 | isomiR sequence 2 of SEQ ID NO: 189 | — |
| 1011 | isomiR sequence 1 of SEQ ID NO: 190 | — |
| 1012 | isomiR sequence 1 of SEQ ID NO: 191 | — |
| 1013 | isomiR sequence 2 of SEQ ID NO: 191 | — |
| 1014 | isomiR sequence 1 of SEQ ID NO: 192 | — |
| 1015 | isomiR sequence 1 of SEQ ID NO: 194 | — |
| 1016 | isomiR sequence 2 of SEQ ID NO: 194 | — |
| 1017 | isomiR sequence 1 of SEQ ID NO: 195 | — |
| 1018 | isomiR sequence 2 of SEQ ID NO: 195 | — |
| 1019 | isomiR sequence 1 of SEQ ID NO: 199 | — |
| 1020 | isomiR sequence 2 of SEQ ID NO: 199 | — |
| 1021 | isomiR sequence 1 of SEQ ID NO: 202 | — |
| 1022 | isomiR sequence 2 of SEQ ID NO: 202 | — |
| 1023 | isomiR sequence 1 of SEQ ID NO: 203 | — |
| 1024 | isomiR sequence 1 of SEQ ID NO: 205 | — |
| 1025 | isomiR sequence 2 of SEQ ID NO: 205 | — |
| 1026 | isomiR sequence 1 of SEQ ID NO: 206 | — |
| 1027 | isomiR sequence 2 of SEQ ID NO: 206 | — |

TABLE 1-1-continued

| SEQ ID NO | Name of gene | Accession No. of miRBase |
| --- | --- | --- |
| 1028 | isomiR sequence 1 of SEQ ID NO: 208 | — |
| 1029 | isomiR sequence 2 of SEQ ID NO: 208 | — |
| 1030 | isomiR sequence 1 of SEQ ID NO: 209 | — |
| 1031 | isomiR sequence 2 of SEQ ID NO: 209 | — |
| 1032 | isomiR sequence 1 of SEQ ID NO: 213 | — |
| 1033 | isomiR sequence 2 of SEQ ID NO: 213 | — |
| 1034 | isomiR sequence 1 of SEQ ID NO: 214 | — |
| 1035 | isomiR sequence 2 of SEQ ID NO: 214 | — |
| 1036 | isomiR sequence 1 of SEQ ID NO: 215 | — |
| 1037 | isomiR sequence 2 of SEQ ID NO: 215 | — |
| 1038 | isomiR sequence 1 of SEQ ID NO: 216 | — |
| 1039 | isomiR sequence 2 of SEQ ID NO: 216 | — |
| 1040 | isomiR sequence 1 of SEQ ID NO: 217 | — |
| 1041 | isomiR sequence 2 of SEQ ID NO: 217 | — |
| 1042 | isomiR sequence 1 of SEQ ID NO: 218 | — |
| 1043 | isomiR sequence 2 of SEQ ID NO: 218 | — |
| 1044 | isomiR sequence 1 of SEQ ID NO: 219 | — |
| 1045 | isomiR sequence 2 of SEQ ID NO: 219 | — |
| 1046 | isomiR sequence 1 of SEQ ID NO: 220 | — |
| 1047 | isomiR sequence 2 of SEQ ID NO: 220 | — |
| 1048 | isomiR sequence 1 of SEQ ID NO: 221 | — |
| 1049 | isomiR sequence 2 of SEQ ID NO: 221 | — |
| 1050 | isomiR sequence 1 of SEQ ID NO: 222 | — |
| 1051 | isomiR sequence 2 of SEQ ID NO: 222 | — |
| 1052 | isomiR sequence 1 of SEQ ID NO: 223 | — |
| 1053 | isomiR sequence 1 of SEQ ID NO: 223 | — |
| 1054 | isomiR sequence 1 of SEQ ID NO: 224 | — |
| 1055 | isomiR sequence 2 of SEQ ID NO: 224 | — |
| 1056 | isomiR sequence 1 of SEQ ID NO: 225 | — |
| 1057 | isomiR sequence 2 of SEQ ID NO: 225 | — |
| 1058 | isomiR sequence 1 of SEQ ID NO: 226 | — |
| 1059 | isomiR sequence 2 of SEQ ID NO: 226 | — |
| 1060 | isomiR sequence 1 of SEQ ID NO: 227 | — |
| 1061 | isomiR sequence 2 of SEQ ID NO: 227 | — |
| 1062 | isomiR sequence 1 of SEQ ID NO: 228 | — |
| 1063 | isomiR sequence 2 of SEQ ID NO: 228 | — |
| 1064 | isomiR sequence 1 of SEQ ID NO: 229 | — |
| 1065 | isomiR sequence 2 of SEQ ID NO: 229 | — |
| 1066 | isomiR sequence 1 of SEQ ID NO: 230 | — |
| 1067 | isomiR sequence 1 of SEQ ID NO: 231 | — |
| 1068 | isomiR sequence 2 of SEQ ID NO: 231 | — |
| 1069 | isomiR sequence 1 of SEQ ID NO: 232 | — |
| 1070 | isomiR sequence 2 of SEQ ID NO: 232 | — |
| 1071 | isomiR sequence 1 of SEQ ID NO: 233 | — |
| 1072 | isomiR sequence 2 of SEQ ID NO: 233 | — |
| 1073 | isomiR sequence 1 of SEQ ID NO: 234 | — |
| 1074 | isomiR sequence 2 of SEQ ID NO: 234 | — |
| 1075 | isomiR sequence 1 of SEQ ID NO: 235 | — |
| 1076 | isomiR sequence 2 of SEQ ID NO: 235 | — |
| 1077 | isomiR sequence 1 of SEQ ID NO: 236 | — |
| 1078 | isomiR sequence 2 of SEQ ID NO: 236 | — |
| 1079 | isomiR sequence 1 of SEQ ID NO: 237 | — |
| 1080 | isomiR sequence 2 of SEQ ID NO: 237 | — |
| 1081 | isomiR sequence 1 of SEQ ID NO: 238 | — |
| 1082 | isomiR sequence 2 of SEQ ID NO: 238 | — |
| 1083 | isomiR sequence 1 of SEQ ID NO: 239 | — |
| 1084 | isomiR sequence 2 of SEQ ID NO: 239 | — |
| 1085 | isomiR sequence 1 of SEQ ID NO: 241 | — |
| 1086 | isomiR sequence 2 of SEQ ID NO: 241 | — |
| 1087 | isomiR sequence 1 of SEQ ID NO: 242 | — |
| 1088 | isomiR sequence 2 of SEQ ID NO: 242 | — |
| 1089 | isomiR sequence 1 of SEQ ID NO: 243 | — |
| 1090 | isomiR sequence 2 of SEQ ID NO: 243 | — |
| 1091 | isomiR sequence 1 of SEQ ID NO: 244 | — |
| 1092 | isomiR sequence 2 of SEQ ID NO: 244 | — |
| 1093 | isomiR sequence 1 of SEQ ID NO: 245 | — |
| 1094 | isomiR sequence 2 of SEQ ID NO: 245 | — |
| 1095 | isomiR sequence 1 of SEQ ID NO: 246 | — |
| 1096 | isomiR sequence 2 of SEQ ID NO: 246 | — |
| 1097 | isomiR sequence 1 of SEQ ID NO: 247 | — |
| 1098 | isomiR sequence 2 of SEQ ID NO: 247 | — |
| 1099 | isomiR sequence 1 of SEQ ID NO: 248 | — |
| 1100 | isomiR sequence 2 of SEQ ID NO: 248 | — |
| 1101 | isomiR sequence 1 of SEQ ID NO: 249 | — |
| 1102 | isomiR sequence 2 of SEQ ID NO: 249 | — |
| 1103 | isomiR sequence 1 of SEQ ID NO: 251 | — |
| 1104 | isomiR sequence 2 of SEQ ID NO: 251 | — |

TABLE 1-1-continued

| SEQ ID NO | Name of gene | Accession No. of miRBase |
| --- | --- | --- |
| 1105 | isomiR sequence 1 of SEQ ID NO: 252 | — |
| 1106 | isomiR sequence 2 of SEQ ID NO: 252 | — |
| 1107 | isomiR sequence 1 of SEQ ID NO: 253 | — |
| 1108 | isomiR sequence 2 of SEQ ID NO: 253 | — |
| 1109 | isomiR sequence 1 of SEQ ID NO: 255 | — |
| 1110 | isomiR sequence 1 of SEQ ID NO: 256 | — |
| 1111 | isomiR sequence 2 of SEQ ID NO: 256 | — |
| 1112 | isomiR sequence 1 of SEQ ID NO: 257 | — |
| 1113 | isomiR sequence 2 of SEQ ID NO: 257 | — |
| 1114 | isomiR sequence 1 of SEQ ID NO: 259 | — |
| 1115 | isomiR sequence 2 of SEQ ID NO: 259 | — |
| 1116 | isomiR sequence 1 of SEQ ID NO: 260 | — |
| 1117 | isomiR sequence 2 of SEQ ID NO: 260 | — |
| 1118 | isomiR sequence 1 of SEQ ID NO: 261 | — |
| 1119 | isomiR sequence 2 of SEQ ID NO: 261 | — |
| 1120 | isomiR sequence 1 of SEQ ID NO: 262 | — |
| 1121 | isomiR sequence 2 of SEQ ID NO: 262 | — |
| 1122 | isomiR sequence 1 of SEQ ID NO: 263 | — |
| 1123 | isomiR sequence 2 of SEQ ID NO: 263 | — |
| 1124 | isomiR sequence 1 of SEQ ID NO: 264 | — |
| 1125 | isomiR sequence 2 of SEQ ID NO: 264 | — |
| 1126 | isomiR sequence 1 of SEQ ID NO: 265 | — |
| 1127 | isomiR sequence 1 of SEQ ID NO: 268 | — |
| 1128 | isomiR sequence 1 of SEQ ID NO: 269 | — |
| 1129 | isomiR sequence 2 of SEQ ID NO: 269 | — |
| 1130 | isomiR sequence 1 of SEQ ID NO: 270 | — |
| 1131 | isomiR sequence 2 of SEQ ID NO: 270 | — |
| 1132 | isomiR sequence 1 of SEQ ID NO: 271 | — |
| 1133 | isomiR sequence 2 of SEQ ID NO: 271 | — |
| 1134 | isomiR sequence 1 of SEQ ID NO: 272 | — |
| 1135 | isomiR sequence 2 of SEQ ID NO: 272 | — |
| 1136 | isomiR sequence 1 of SEQ ID NO: 273 | — |
| 1137 | isomiR sequence 2 of SEQ ID NO: 273 | — |
| 1138 | isomiR sequence 1 of SEQ ID NO: 274 | — |
| 1139 | isomiR sequence 2 of SEQ ID NO: 274 | — |
| 1140 | isomiR sequence 1 of SEQ ID NO: 275 | — |
| 1141 | isomiR sequence 2 of SEQ ID NO: 275 | — |
| 1142 | isomiR sequence 1 of SEQ ID NO: 276 | — |
| 1143 | isomiR sequence 1 of SEQ ID NO: 277 | — |
| 1144 | isomiR sequence 2 of SEQ ID NO: 277 | — |
| 1145 | isomiR sequence 1 of SEQ ID NO: 278 | — |
| 1146 | isomiR sequence 2 of SEQ ID NO: 278 | — |
| 1147 | isomiR sequence 1 of SEQ ID NO: 279 | — |
| 1148 | isomiR sequence 1 of SEQ ID NO: 280 | — |
| 1149 | isomiR sequence 2 of SEQ ID NO: 280 | — |
| 1150 | isomiR sequence 1 of SEQ ID NO: 281 | — |
| 1151 | isomiR sequence 2 of SEQ ID NO: 281 | — |
| 1152 | isomiR sequence 1 of SEQ ID NO: 282 | — |
| 1153 | isomiR sequence 2 of SEQ ID NO: 282 | — |
| 1154 | isomiR sequence 1 of SEQ ID NO: 283 | — |
| 1155 | isomiR sequence 2 of SEQ ID NO: 283 | — |
| 1156 | isomiR sequence 1 of SEQ ID NO: 284 | — |
| 1157 | isomiR sequence 2 of SEQ ID NO: 284 | — |
| 1158 | isomiR sequence 1 of SEQ ID NO: 286 | — |
| 1159 | isomiR sequence 2 of SEQ ID NO: 286 | — |
| 1160 | isomiR sequence 1 of SEQ ID NO: 287 | — |
| 1161 | isomiR sequence 2 of SEQ ID NO: 287 | — |
| 1162 | isomiR sequence 1 of SEQ ID NO: 288 | — |
| 1163 | isomiR sequence 2 of SEQ ID NO: 288 | — |
| 1164 | isomiR sequence 1 of SEQ ID NO: 289 | — |
| 1165 | isomiR sequence 2 of SEQ ID NO: 289 | — |
| 1166 | isomiR sequence 1 of SEQ ID NO: 290 | — |
| 1167 | isomiR sequence 1 of SEQ ID NO: 291 | — |
| 1168 | isomiR sequence 2 of SEQ ID NO: 291 | — |
| 1169 | isomiR sequence 1 of SEQ ID NO: 292 | — |
| 1170 | isomiR sequence 1 of SEQ ID NO: 293 | — |
| 1171 | isomiR sequence 2 of SEQ ID NO: 293 | — |
| 1172 | isomiR sequence 1 of SEQ ID NO: 295 | — |
| 1173 | isomiR sequence 2 of SEQ ID NO: 295 | — |
| 1174 | isomiR sequence 1 of SEQ ID NO: 296 | — |
| 1175 | isomiR sequence 2 of SEQ ID NO: 296 | — |
| 1176 | isomiR sequence 1 of SEQ ID NO: 297 | — |
| 1177 | isomiR sequence 2 of SEQ ID NO: 297 | — |
| 1178 | isomiR sequence 1 of SEQ ID NO: 298 | — |
| 1179 | isomiR sequence 1 of SEQ ID NO: 299 | — |
| 1180 | isomiR sequence 2 of SEQ ID NO: 299 | — |
| 1181 | isomiR sequence 1 of SEQ ID NO: 300 | — |

TABLE 1-1-continued

| SEQ ID NO | Name of gene | Accession No. of miRBase |
|---|---|---|
| 1182 | isomiR sequence 2 of SEQ ID NO: 300 | — |
| 1183 | isomiR sequence 1 of SEQ ID NO: 301 | — |
| 1184 | isomiR sequence 1 of SEQ ID NO: 302 | — |
| 1185 | isomiR sequence 2 of SEQ ID NO: 302 | — |
| 1186 | isomiR sequence 1 of SEQ ID NO: 303 | — |
| 1187 | isomiR sequence 1 of SEQ ID NO: 304 | — |
| 1188 | isomiR sequence 2 of SEQ ID NO: 304 | — |
| 1189 | isomiR sequence 1 of SEQ ID NO: 305 | — |
| 1190 | isomiR sequence 2 of SEQ ID NO: 305 | — |
| 1191 | isomiR sequence 1 of SEQ ID NO: 306 | — |
| 1192 | isomiR sequence 2 of SEQ ID NO: 306 | — |
| 1193 | isomiR sequence 1 of SEQ ID NO: 307 | — |
| 1194 | isomiR sequence 1 of SEQ ID NO: 308 | — |
| 1195 | isomiR sequence 2 of SEQ ID NO: 308 | — |
| 1196 | isomiR sequence 1 of SEQ ID NO: 309 | — |
| 1197 | isomiR sequence 1 of SEQ ID NO: 310 | — |
| 1198 | isomiR sequence 1 of SEQ ID NO: 311 | — |
| 1199 | isomiR sequence 2 of SEQ ID NO: 311 | — |
| 1200 | isomiR sequence 1 of SEQ ID NO: 312 | — |
| 1201 | isomiR sequence 1 of SEQ ID NO: 313 | — |
| 1202 | isomiR sequence 2 of SEQ ID NO: 313 | — |
| 1203 | isomiR sequence 1 of SEQ ID NO: 314 | — |
| 1204 | isomiR sequence 2 of SEQ ID NO: 314 | — |
| 1205 | isomiR sequence 1 of SEQ ID NO: 315 | — |
| 1206 | isomiR sequence 1 of SEQ ID NO: 316 | — |
| 1207 | isomiR sequence 2 of SEQ ID NO: 316 | — |
| 1208 | isomiR sequence 1 of SEQ ID NO: 317 | — |
| 1209 | isomiR sequence 2 of SEQ ID NO: 317 | — |
| 1210 | isomiR sequence 1 of SEQ ID NO: 320 | — |
| 1211 | isomiR sequence 2 of SEQ ID NO: 320 | — |
| 1212 | isomiR sequence 1 of SEQ ID NO: 321 | — |
| 1213 | isomiR sequence 2 of SEQ ID NO: 321 | — |
| 1214 | isomiR sequence 1 of SEQ ID NO: 322 | — |
| 1215 | isomiR sequence 2 of SEQ ID NO: 322 | — |
| 1216 | isomiR sequence 1 of SEQ ID NO: 323 | — |
| 1217 | isomiR sequence 2 of SEQ ID NO: 323 | — |
| 1218 | isomiR sequence 1 of SEQ ID NO: 324 | — |
| 1219 | isomiR sequence 2 of SEQ ID NO: 324 | — |
| 1220 | isomiR sequence 1 of SEQ ID NO: 325 | — |
| 1221 | isomiR sequence 2 of SEQ ID NO: 325 | — |
| 1222 | isomiR sequence 1 of SEQ ID NO: 326 | — |
| 1223 | isomiR sequence 2 of SEQ ID NO: 326 | — |
| 1224 | isomiR sequence 1 of SEQ ID NO: 327 | — |
| 1225 | isomiR sequence 1 of SEQ ID NO: 328 | — |
| 1226 | isomiR sequence 2 of SEQ ID NO: 328 | — |
| 1227 | isomiR sequence 1 of SEQ ID NO: 329 | — |
| 1228 | isomiR sequence 2 of SEQ ID NO: 329 | — |
| 1229 | isomiR sequence 1 of SEQ ID NO: 330 | — |
| 1230 | isomiR sequence 2 of SEQ ID NO: 330 | — |
| 1231 | isomiR sequence 1 of SEQ ID NO: 331 | — |
| 1232 | isomiR sequence 1 of SEQ ID NO: 332 | — |
| 1233 | isomiR sequence 1 of SEQ ID NO: 333 | — |
| 1234 | isomiR sequence 2 of SEQ ID NO: 333 | — |
| 1235 | isomiR sequence 1 of SEQ ID NO: 335 | — |
| 1236 | isomiR sequence 2 of SEQ ID NO: 335 | — |
| 1237 | isomiR sequence 1 of SEQ ID NO: 338 | — |
| 1238 | isomiR sequence 2 of SEQ ID NO: 338 | — |
| 1239 | isomiR sequence 1 of SEQ ID NO: 340 | — |
| 1240 | isomiR sequence 2 of SEQ ID NO: 340 | — |
| 1241 | isomiR sequence 1 of SEQ ID NO: 341 | — |
| 1242 | isomiR sequence 2 of SEQ ID NO: 341 | — |
| 1243 | isomiR sequence 1 of SEQ ID NO: 342 | — |
| 1244 | isomiR sequence 2 of SEQ ID NO: 342 | — |
| 1245 | isomiR sequence 1 of SEQ ID NO: 343 | — |
| 1246 | isomiR sequence 2 of SEQ ID NO: 343 | — |
| 1247 | isomiR sequence 1 of SEQ ID NO: 345 | — |
| 1248 | isomiR sequence 2 of SEQ ID NO: 345 | — |
| 1249 | isomiR sequence 1 of SEQ ID NO: 347 | — |
| 1250 | isomiR sequence 2 of SEQ ID NO: 347 | — |
| 1251 | isomiR sequence 1 of SEQ ID NO: 348 | — |
| 1252 | isomiR sequence 2 of SEQ ID NO: 348 | — |
| 1253 | isomiR sequence 1 of SEQ ID NO: 349 | — |
| 1254 | isomiR sequence 2 of SEQ ID NO: 349 | — |
| 1255 | isomiR sequence 1 of SEQ ID NO: 350 | — |
| 1256 | isomiR sequence 1 of SEQ ID NO: 352 | — |
| 1257 | isomiR sequence 2 of SEQ ID NO: 352 | — |
| 1258 | isomiR sequence 1 of SEQ ID NO: 353 | — |

TABLE 1-1-continued

| SEQ ID NO | Name of gene | Accession No. of miRBase |
|---|---|---|
| 1259 | isomiR sequence 2 of SEQ ID NO: 353 | — |
| 1260 | isomiR sequence 1 of SEQ ID NO: 354 | — |
| 1261 | isomiR sequence 1 of SEQ ID NO: 355 | — |
| 1262 | isomiR sequence 2 of SEQ ID NO: 355 | — |
| 1263 | isomiR sequence 1 of SEQ ID NO: 356 | — |
| 1264 | isomiR sequence 2 of SEQ ID NO: 356 | — |
| 1265 | isomiR sequence 1 of SEQ ID NO: 357 | — |
| 1266 | isomiR sequence 2 of SEQ ID NO: 357 | — |
| 1267 | isomiR sequence 1 of SEQ ID NO: 359 | — |
| 1268 | isomiR sequence 2 of SEQ ID NO: 359 | — |
| 1269 | isomiR sequence 1 of SEQ ID NO: 361 | — |
| 1270 | isomiR sequence 2 of SEQ ID NO: 361 | — |
| 1271 | isomiR sequence 1 of SEQ ID NO: 362 | — |
| 1272 | isomiR sequence 1 of SEQ ID NO: 363 | — |
| 1273 | isomiR sequence 2 of SEQ ID NO: 363 | — |
| 1274 | isomiR sequence 1 of SEQ ID NO: 367 | — |
| 1275 | isomiR sequence 2 of SEQ ID NO: 367 | — |
| 1276 | isomiR sequence 1 of SEQ ID NO: 368 | — |
| 1277 | isomiR sequence 2 of SEQ ID NO: 368 | — |
| 1278 | isomiR sequence 1 of SEQ ID NO: 369 | — |
| 1279 | isomiR sequence 2 of SEQ ID NO: 369 | — |
| 1280 | isomiR sequence 1 of SEQ ID NO: 371 | — |
| 1281 | isomiR sequence 2 of SEQ ID NO: 371 | — |
| 1282 | isomiR sequence 1 of SEQ ID NO: 372 | — |
| 1283 | isomiR sequence 2 of SEQ ID NO: 372 | — |
| 1284 | isomiR sequence 1 of SEQ ID NO: 373 | — |
| 1285 | isomiR sequence 1 of SEQ ID NO: 374 | — |
| 1286 | isomiR sequence 2 of SEQ ID NO: 374 | — |
| 1287 | isomiR sequence 1 of SEQ ID NO: 375 | — |
| 1288 | isomiR sequence 2 of SEQ ID NO: 375 | — |
| 1289 | isomiR sequence 1 of SEQ ID NO: 376 | — |
| 1290 | isomiR sequence 2 of SEQ ID NO: 376 | — |
| 1291 | isomiR sequence 1 of SEQ ID NO: 377 | — |
| 1292 | isomiR sequence 2 of SEQ ID NO: 377 | — |
| 1293 | isomiR sequence 1 of SEQ ID NO: 378 | — |
| 1294 | isomiR sequence 2 of SEQ ID NO: 378 | — |
| 1295 | isomiR sequence 1 of SEQ ID NO: 379 | — |
| 1296 | isomiR sequence 2 of SEQ ID NO: 379 | — |
| 1297 | isomiR sequence 1 of SEQ ID NO: 380 | — |
| 1298 | isomiR sequence 2 of SEQ ID NO: 380 | — |
| 1299 | isomiR sequence 1 of SEQ ID NO: 381 | — |
| 1300 | isomiR sequence 2 of SEQ ID NO: 381 | — |
| 1301 | isomiR sequence 1 of SEQ ID NO: 382 | — |
| 1302 | isomiR sequence 2 of SEQ ID NO: 382 | — |
| 1303 | isomiR sequence 1 of SEQ ID NO: 383 | — |
| 1304 | isomiR sequence 2 of SEQ ID NO: 383 | — |
| 1305 | isomiR sequence 1 of SEQ ID NO: 385 | — |
| 1306 | isomiR sequence 2 of SEQ ID NO: 385 | — |
| 1307 | isomiR sequence 1 of SEQ ID NO: 386 | — |
| 1308 | isomiR sequence 2 of SEQ ID NO: 386 | — |
| 1309 | isomiR sequence 1 of SEQ ID NO: 388 | — |
| 1310 | isomiR sequence 2 of SEQ ID NO: 388 | — |
| 1311 | isomiR sequence 1 of SEQ ID NO: 389 | — |
| 1312 | isomiR sequence 2 of SEQ ID NO: 389 | — |
| 1313 | isomiR sequence 1 of SEQ ID NO: 390 | — |
| 1314 | isomiR sequence 2 of SEQ ID NO: 390 | — |
| 1435 | hsa-miR-516a-5p | MIMAT0004770 |
| 1436 | hsa-miR-769-3p | MIMAT0003887 |
| 1437 | hsa-miR-3692-5p | MIMAT0018121 |
| 1438 | hsa-miR-3945 | MIMAT0018361 |
| 1439 | hsa-miR-4433a-3p | MIMAT0018949 |
| 1440 | hsa-miR-4485-3p | MIMAT0019019 |
| 1441 | hsa-miR-6831-5p | MIMAT0027562 |
| 1442 | hsa-miR-519c-5p | MIMAT0002831 |
| 1443 | hsa-miR-551b-5p | MIMAT0004794 |
| 1444 | hsa-miR-1343-3p | MIMAT0019776 |
| 1445 | hsa-miR-4286 | MIMAT0016916 |
| 1446 | hsa-miR-4634 | MIMAT0019691 |
| 1447 | hsa-miR-4733-3p | MIMAT0019858 |
| 1448 | hsa-miR-6086 | MIMAT0023711 |
| 1449 | hsa-miR-30d-5p | MIMAT0000245 |
| 1450 | hsa-miR-30b-3p | MIMAT0004589 |
| 1451 | hsa-miR-92a-3p | MIMAT0000092 |
| 1452 | hsa-miR-371b-5p | MIMAT0019892 |
| 1453 | hsa-miR-486-5p | MIMAT0002177 |
| 1454 | hsa-mir-516a-1 | MI0003180 |
| 1455 | hsa-mir-769 | MI0003834 |

TABLE 1-1-continued

| SEQ ID NO | Name of gene | Accession No. of miRBase |
|---|---|---|
| 1456 | hsa-mir-3692 | MI0016093 |
| 1457 | hsa-mir-3945 | MI0016602 |
| 1458 | hsa-mir-4433a | MI0016773 |
| 1459 | hsa-mir-4485 | MI0016846 |
| 1460 | hsa-mir-6831 | MI0022676 |
| 1461 | hsa-mir-519c | MI0003148 |
| 1462 | hsa-mir-551b | MI0003575 |
| 1463 | hsa-mir-1343 | MI0017320 |
| 1464 | hsa-mir-4286 | MI0015894 |
| 1465 | hsa-mir-4634 | MI0017261 |
| 1466 | hsa-mir-4733 | MI0017370 |
| 1467 | hsa-mir-6086 | MI0020363 |
| 1468 | hsa-mir-30d | MI0000255 |
| 1469 | hsa-mir-30b | MI0000441 |
| 1470 | hsa-mir-92a-1 | MI0000093 |
| 1471 | hsa-mir-371b | MI0017393 |
| 1472 | hsa-mir-486-1 | MI0002470 |
| 1473 | isomiR sequence 1 of SEQ ID NO: 1435 | — |
| 1474 | isomiR sequence 2 of SEQ ID NO: 1435 | — |
| 1475 | isomiR sequence 1 of SEQ ID NO: 1436 | — |
| 1476 | isomiR sequence 2 of SEQ ID NO: 1436 | — |
| 1477 | isomiR sequence 1 of SEQ ID NO: 1438 | — |
| 1478 | isomiR sequence 2 of SEQ ID NO: 1438 | — |
| 1479 | isomiR sequence 1 of SEQ ID NO: 1439 | — |
| 1480 | isomiR sequence 2 of SEQ ID NO: 1439 | — |
| 1481 | isomiR sequence 1 of SEQ ID NO: 1440 | — |
| 1482 | isomiR sequence 2 of SEQ ID NO: 1440 | |
| 1483 | isomiR sequence 1 of SEQ ID NO: 1441 | — |
| 1484 | isomiR sequence 2 of SEQ ID NO: 1441 | — |
| 1485 | isomiR sequence 1 of SEQ ID NO: 1446 | — |
| 1486 | isomiR sequence 2 of SEQ ID NO: 1446 | — |
| 1487 | isomiR sequence 1 of SEQ ID NO: 1448 | — |
| 1488 | isomiR sequence 2 of SEQ ID NO: 1448 | — |
| 1489 | isomiR sequence 1 of SEQ ID NO: 1449 | — |
| 1490 | isomiR sequence 2 of SEQ ID NO: 1449 | — |
| 1491 | isomiR sequence 1 of SEQ ID NO: 1451 | — |
| 1492 | isomiR sequence 2 of SEQ ID NO: 1451 | — |
| 1493 | isomiR sequence 1 of SEQ ID NO: 1452 | — |
| 1494 | isomiR sequence 2 of SEQ ID NO: 1452 | — |
| 1495 | isomiR sequence 1 of SEQ ID NO: 1455 | — |
| 1496 | isomiR sequence 1 of SEQ ID NO: 1458 | — |
| 1497 | isomiR sequence 2 of SEQ ID NO: 1458 | — |
| 1498 | isomiR sequence 1 of SEQ ID NO: 1460 | — |
| 1499 | isomiR sequence 2 of SEQ ID NO: 1460 | — |
| 1500 | isomiR sequence 1 of SEQ ID NO: 1461 | — |
| 1501 | isomiR sequence 2 of SEQ ID NO: 1461 | — |
| 1502 | isomiR sequence 1 of SEQ ID NO: 1462 | — |
| 1503 | isomiR sequence 2 of SEQ ID NO: 1462 | — |
| 1504 | isomiR sequence 1 of SEQ ID NO: 1463 | — |
| 1505 | isomiR sequence 2 of SEQ ID NO: 1463 | — |

TABLE 1-2

| SEQ ID NO | Name of gene | Accession No. of miRBase |
|---|---|---|
| 1315 | hsa-miR-6765-3p | MIMAT0027431 |
| 1316 | hsa-miR-6784-5p | MIMAT0027468 |
| 194 | hsa-miR-5698 | MIMAT0022491 |
| 1317 | hsa-miR-6778-5p | MIMAT0027456 |
| 195 | hsa-miR-1915-3p | MIMAT0007892 |
| 1318 | hsa-miR-6875-5p | MIMAT0027650 |
| 196 | hsa-miR-1343-5p | MIMAT0027038 |
| 1319 | hsa-miR-4534 | MIMAT0019073 |
| 197 | hsa-miR-6861-5p | MIMAT0027623 |
| 1320 | hsa-miR-4721 | MIMAT0019835 |
| 1321 | hsa-miR-6756-5p | MIMAT0027412 |
| 1322 | hsa-miR-615-5p | MIMAT0004804 |
| 1323 | hsa-miR-6727-5p | MIMAT0027355 |
| 1324 | hsa-miR-6887-5p | MIMAT0027674 |
| 1325 | hsa-miR-8063 | MIMAT0030990 |
| 1326 | hsa-miR-6880-5p | MIMAT0027660 |
| 1327 | hsa-miR-6805-3p | MIMAT0027511 |
| 198 | hsa-miR-6781-5p | MIMAT0027462 |

TABLE 1-2-continued

| SEQ ID NO | Name of gene | Accession No. of miRBase |
|---|---|---|
| 199 | hsa-miR-4508 | MIMAT0019045 |
| 1328 | hsa-miR-4726-5p | MIMAT0019845 |
| 1329 | hsa-miR-4710 | MIMAT0019815 |
| 1330 | hsa-miR-7111-5p | MIMAT0028119 |
| 1331 | hsa-miR-3619-3p | MIMAT0019219 |
| 200 | hsa-miR-6743-5p | MIMAT0027387 |
| 1332 | hsa-miR-6795-5p | MIMAT0027490 |
| 201 | hsa-miR-6726-5p | MIMAT0027353 |
| 202 | hsa-miR-4525 | MIMAT0019064 |
| 1333 | hsa-miR-1254 | MIMAT0005905 |
| 1334 | hsa-miR-1233-5p | MIMAT0022943 |
| 203 | hsa-miR-4651 | MIMAT0019715 |
| 1335 | hsa-miR-6836-3p | MIMAT0027575 |
| 1336 | hsa-miR-6769a-5p | MIMAT0027438 |
| 204 | hsa-miR-6813-5p | MIMAT0027526 |
| 1337 | hsa-miR-4532 | MIMAT0019071 |
| 1338 | hsa-miR-365a-5p | MIMAT0009199 |
| 1339 | hsa-miR-1231 | MIMAT0005586 |
| 205 | hsa-miR-5787 | MIMAT0023252 |
| 206 | hsa-miR-1290 | MIMAT0005880 |
| 1340 | hsa-miR-1228-5p | MIMAT0005582 |
| 374 | hsa-miR-371a-5p | MIMAT0004687 |
| 1341 | hsa-miR-4430 | MIMAT0018945 |
| 1342 | hsa-miR-296-3p | MIMAT0004679 |
| 207 | hsa-miR-6075 | MIMAT0023700 |
| 1343 | hsa-miR-1237-5p | MIMAT0022946 |
| 208 | hsa-miR-4758-5p | MIMAT0019903 |
| 209 | hsa-miR-4690-5p | MIMAT0019779 |
| 1344 | hsa-miR-4466 | MIMAT0018993 |
| 1345 | hsa-miR-6789-5p | MIMAT0027478 |
| 1346 | hsa-miR-4632-5p | MIMAT0022977 |
| 1347 | hsa-miR-4745-5p | MIMAT0019878 |
| 1348 | hsa-miR-4665-5p | MIMAT0019739 |
| 1349 | hsa-miR-6807-5p | MIMAT0027514 |
| 210 | hsa-miR-762 | MIMAT0010313 |
| 1350 | hsa-miR-7114-5p | MIMAT0028125 |
| 1351 | hsa-miR-150-3p | MIMAT0004610 |
| 1352 | hsa-miR-423-5p | MIMAT0004748 |
| 1353 | hsa-miR-575 | MIMAT0003240 |
| 1354 | hsa-miR-671-5p | MIMAT0003880 |
| 1355 | hsa-miR-939-5p | MIMAT0004982 |
| 211 | hsa-miR-1225-3p | MIMAT0005573 |
| 212 | hsa-miR-3184-5p | MIMAT0015064 |
| 1356 | hsa-miR-3665 | MIMAT0018087 |
| 490 | hsa-mir-6765 | MI0022610 |
| 1357 | hsa-mir-6784 | MI0022629 |
| 593 | hsa-mir-5698 | MI0019305 |
| 1358 | hsa-mir-6778 | MI0022623 |
| 594 | hsa-mir-1915 | MI0008336 |
| 1359 | hsa-mir-6875 | MI0022722 |
| 595 | hsa-mir-1343 | MI0017320 |
| 1360 | hsa-mir-4534 | MI0016901 |
| 596 | hsa-mir-6861 | MI0022708 |
| 1361 | hsa-mir-4721 | MI0017356 |
| 1362 | hsa-mir-6756 | MI0022601 |
| 1363 | hsa-mir-615 | MI0003628 |
| 1364 | hsa-mir-6727 | MI0022572 |
| 1365 | hsa-mir-6887 | MI0022734 |
| 1366 | hsa-mir-8063 | MI0025899 |
| 1367 | hsa-mir-6880 | MI0022727 |
| 1368 | hsa-mir-6805 | MI0022650 |
| 597 | hsa-mir-6781 | MI0022626 |
| 598 | hsa-mir-4508 | MI0016872 |
| 1369 | hsa-mir-4726 | MI0017363 |
| 1370 | hsa-mir-4710 | MI0017344 |
| 1371 | hsa-mir-7111 | MI0022962 |
| 1372 | hsa-mir-3619 | MI0016009 |
| 599 | hsa-mir-6743 | MI0022588 |
| 1373 | hsa-mir-6795 | MI0022640 |
| 600 | hsa-mir-6726 | MI0022571 |
| 601 | hsa-mir-4525 | MI0016892 |
| 1374 | hsa-mir-1254-1 | MI0006388 |
| 1375 | hsa-mir-1254-2 | MI0016747 |
| 1376 | hsa-mir-1233-1 | MI0006323 |
| 1377 | hsa-mir-1233-2 | MI0015973 |
| 602 | hsa-mir-4651 | MI0017279 |
| 1378 | hsa-mir-6836 | MI0022682 |

TABLE 1-2-continued

| SEQ ID NO | Name of gene | Accession No. of miRBase |
|---|---|---|
| 1379 | hsa-mir-6769a | MI0022614 |
| 591 | hsa-mir-6813 | MI0022658 |
| 1380 | hsa-mir-4532 | MI0016899 |
| 1381 | hsa-mir-365a | MI0000767 |
| 1382 | hsa-mir-1231 | MI0006321 |
| 603 | hsa-mir-5787 | MI0019797 |
| 604 | hsa-mir-1290 | MI0006352 |
| 1383 | hsa-mir-1228 | MI0006318 |
| 766 | hsa-mir-371a | MI0000779 |
| 1384 | hsa-mir-4430 | MI0016769 |
| 1385 | hsa-mir-296 | MI0000747 |
| 605 | hsa-mir-6075 | MI0020352 |
| 1386 | hsa-mir-1237 | MI0006327 |
| 606 | hsa-mir-4758 | MI0017399 |
| 607 | hsa-mir-4690 | MI0017323 |
| 1387 | hsa-mir-4466 | MI0016817 |
| 1388 | hsa-mir-6789 | MI0022634 |
| 1389 | hsa-mir-4632 | MI0017259 |
| 1390 | hsa-mir-4745 | MI0017384 |
| 1391 | hsa-mir-4665 | MI0017295 |
| 1392 | hsa-mir-6807 | MI0022652 |
| 608 | hsa-mir-762 | MI0003892 |
| 1393 | hsa-mir-7114 | MI0022965 |
| 1394 | hsa-mir-150 | MI0000479 |
| 1395 | hsa-mir-423 | MI0001445 |
| 1396 | hsa-mir-575 | MI0003582 |
| 1397 | hsa-mir-671 | MI0003760 |
| 1398 | hsa-mir-939 | MI0005761 |
| 609 | hsa-mir-1225 | MI0006311 |
| 398 | hsa-mir-3184 | MI0014226 |
| 1399 | hsa-mir-3665 | MI0016066 |
| 1015 | isomiR sequence 1 of SEQ ID NO: 194 | — |
| 1016 | isomiR sequence 2 of SEQ ID NO: 194 | — |
| 1017 | isomiR sequence 2 of SEQ ID NO: 195 | — |
| 1400 | isomiR sequence 1 of SEQ ID NO: 1320 | — |
| 1401 | isomiR sequence 1 of SEQ ID NO: 1322 | — |
| 1402 | isomiR sequence 2 of SEQ ID NO: 1322 | — |
| 1019 | isomiR sequence 1 of SEQ ID NO: 199 | — |
| 1020 | isomiR sequence 2 of SEQ ID NO: 199 | — |
| 1403 | isomiR sequence 1 of SEQ ID NO: 1328 | — |
| 1404 | isomiR sequence 2 of SEQ ID NO: 1328 | — |
| 1405 | isomiR sequence 2 of SEQ ID NO: 1329 | — |
| 1021 | isomiR sequence 1 of SEQ ID NO: 202 | — |
| 1022 | isomiR sequence 2 of SEQ ID NO: 202 | — |
| 1406 | isomiR sequence 1 of SEQ ID NO: 1333 | — |
| 1407 | isomiR sequence 2 of SEQ ID NO: 1333 | — |
| 1408 | isomiR sequence 1 of SEQ ID NO: 1334 | — |
| 1409 | isomiR sequence 2 of SEQ ID NO: 1334 | — |
| 1023 | isomiR sequence 1 of SEQ ID NO: 203 | — |
| 1410 | isomiR sequence 1 of SEQ ID NO: 1337 | — |
| 1411 | isomiR sequence 2 of SEQ ID NO: 1337 | — |
| 1412 | isomiR sequence 1 of SEQ ID NO: 1338 | — |
| 1413 | isomiR sequence 2 of SEQ ID NO: 1338 | — |
| 1024 | isomiR sequence 2 of SEQ ID NO: 205 | — |
| 1026 | isomiR sequence 1 of SEQ ID NO: 206 | — |
| 1027 | isomiR sequence 2 of SEQ ID NO: 206 | — |
| 1414 | isomiR sequence 1 of SEQ ID NO: 1340 | — |
| 1415 | isomiR sequence 2 of SEQ ID NO: 1340 | — |
| 1285 | isomiR sequence 1 of SEQ ID NO: 374 | — |
| 1286 | isomiR sequence 2 of SEQ ID NO: 374 | — |
| 1416 | isomiR sequence 1 of SEQ ID NO: 1341 | — |
| 1417 | isomiR sequence 2 of SEQ ID NO: 1341 | — |
| 1418 | isomiR sequence 2 of SEQ ID NO: 1342 | — |
| 1419 | isomiR sequence 2 of SEQ ID NO: 1343 | — |
| 1028 | isomiR sequence 1 of SEQ ID NO: 208 | — |
| 1029 | isomiR sequence 2 of SEQ ID NO: 208 | — |
| 1030 | isomiR sequence 1 of SEQ ID NO: 209 | — |
| 1031 | isomiR sequence 2 of SEQ ID NO: 209 | — |
| 1420 | isomiR sequence 1 of SEQ ID NO: 1344 | — |
| 1421 | isomiR sequence 2 of SEQ ID NO: 1344 | — |
| 1422 | isomiR sequence 2 of SEQ ID NO: 1346 | — |
| 1423 | isomiR sequence 2 of SEQ ID NO: 1347 | — |
| 1424 | isomiR sequence 2 of SEQ ID NO: 1348 | — |
| 1425 | isomiR sequence 1 of SEQ ID NO: 1351 | — |
| 1426 | isomiR sequence 2 of SEQ ID NO: 1351 | — |
| 1427 | isomiR sequence 1 of SEQ ID NO: 1352 | — |
| 1428 | isomiR sequence 2 of SEQ ID NO: 1352 | — |
| 1429 | isomiR sequence 1 of SEQ ID NO: 1354 | — |
| 1430 | isomiR sequence 2 of SEQ ID NO: 1354 | — |
| 1431 | isomiR sequence 1 of SEQ ID NO: 1355 | — |
| 1432 | isomiR sequence 2 of SEQ ID NO: 1355 | — |
| 1433 | isomiR sequence 1 of SEQ ID NO: 1356 | — |
| 1434 | isomiR sequence 2 of SEQ ID NO: 1356 | — |

The present specification encompasses the contents disclosed in Japanese Patent Application Nos. 2018-023283, 2018-085652, and 2018-138487 from which the present application claims priority.

Advantageous Effect of Invention

The present invention makes it possible to detect a wide range of disease types of dementia comprehensively with high accuracy (or AUC), sensitivity, and specificity, thereby discriminating between dementia and normal cognitive functions (non-dementia). Use of a nucleic acid capable of specifically binding to a dementia marker in the present invention enables the disease type of dementia to be detected easily and objectively without causing a difference among physicians and/or among facilities of medical institutions. For instance, using the measured value(s) for the expression level(s) of at least one or several miRNAs in blood, serum, and/or plasma that can be collected less invasively from a subject as an indicator(s), whether or not the subject has dementia can be detected easily.

BRIEF DESCRIPTION OF THE DRAWINGS

FIG. 2A is a plot of discriminant scores for Alzheimer's dementia as obtained in Example 1-1; FIG. 2B is a plot of discriminant scores for vascular dementia as obtained in Example 1-2; and FIG. 2C is a plot of discriminant scores for Lewy body dementia as obtained in Example 1-3.

FIG. 13A is a plot of discriminant scores for Alzheimer's dementia as obtained in Example 9-1; FIG. 13B is a plot of discriminant scores for vascular dementia as obtained in Example 9-2; and FIG. 13C is a plot of discriminant scores for Lewy body dementia as obtained in Example 9-3.

In FIG. 17A, 42 miRNA markers obtained in Example 15 were used and in FIG. 17B, 51 miRNA markers obtained in Example 20 were used to calculate the sensitivity as the ordinate and the specificity as the abscissa expressed in ROC curves.

FIG. 18A is a plot of discriminant scores in validation cohorts in which 44 miRNA markers obtained in Example 24 were used. In FIG. 18B, 44 miRNA markers obtained in Example 24 were used to calculate the sensitivity as the ordinate and the specificity as the abscissa expressed in the ROC curve.

DESCRIPTION OF EMBODIMENTS

Figure 1:
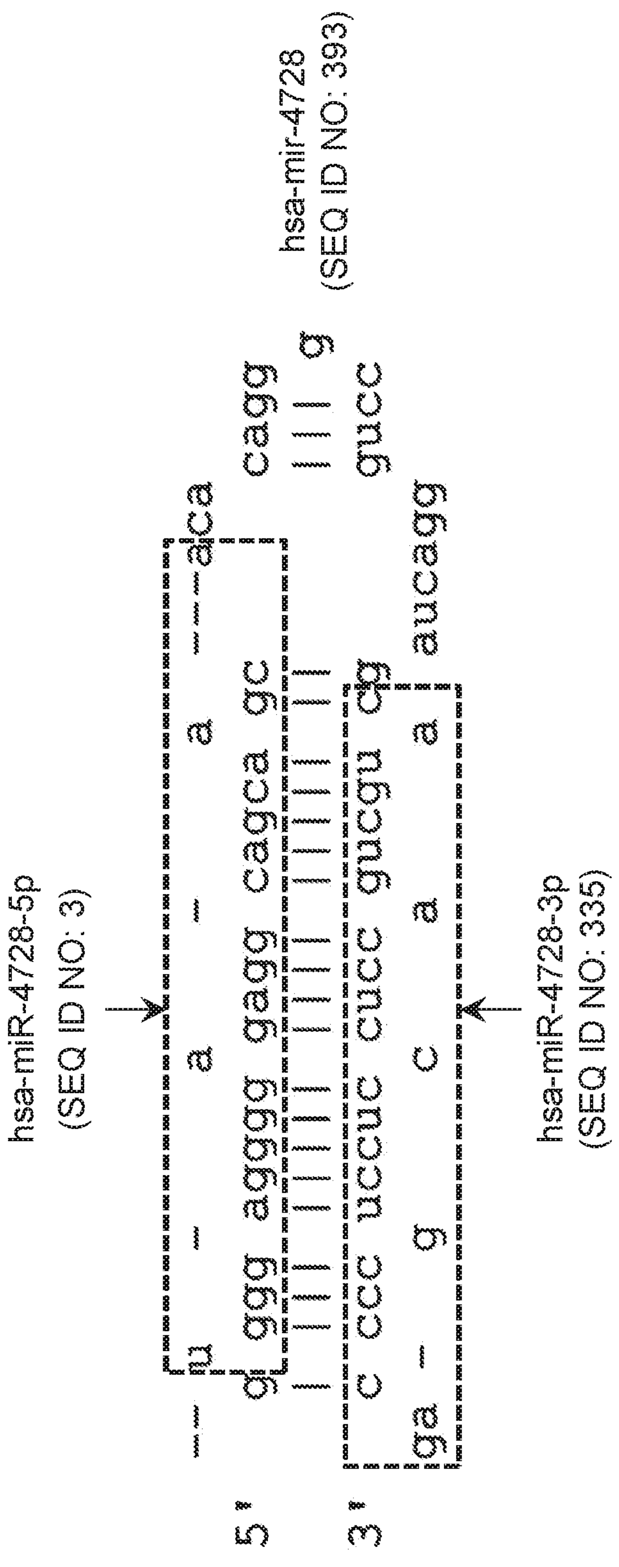
FIG. 1 illustrates the relationship between the nucleotide sequences of hsa-miR-4728-5p represented by SEQ ID NO: 3 and hsa-miR-4728-3p represented by SEQ ID NO: 335, which are generated from a precursor hsa-mir-4728 represented by SEQ ID NO: 393.

Hereinafter, the present invention will be further described in detail.

1. Target Nucleic Acids for Dementia

The major target nucleic acids as dementia markers for detecting dementia or the presence or absence of dementia by using the nucleic acid probes or primers for detection of dementia as defined above according to the present invention include at least one miRNA selected from the group consisting of (i) miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086. Further, it is possible to preferably use, as target nucleic acid(s), other dementia marker(s) that can be combined with these miRNAs (i), specifically 1, 2, 3 or more, 10 or more, preferably 3 to 30 miRNAs selected from the group consisting of (ii) miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR- 431-5p, miR-150-3p, miR-423-5p, miR-575, miR-671-5p, miR-939-5p, miR-3665, miR-30d-5p, miR-30b-3p, miR-92a-3p, miR-371b-5p, and miR-486-5p. In addition to the above miRNAs (i) to (ii) or aside from the above miRNAs (i) to (ii), it is possible to preferably use, as target nucleic acid(s), 1, 2, 3 or more, 10 or more, preferably 3 to 110 miRNAs selected from the group consisting of (iii) miR-4728-5p, miR-3184-3p, miR-1233-3p, miR-6088, miR-6777-3p, miR-7110-3p, miR-936, miR-6087, miR-1202, miR-4731-3p, miR-4800-5p, miR-6784-3p, miR-4716-5p, miR-6734-3p, miR-6889-3p, miR-6867-3p, miR-3622a-3p, miR-6813-3p, miR-4769-3p, miR-5698, miR-3184-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, and miR-6878-3p. Also, it is possible to preferably use, as target nucleic acid(s), other dementia marker(s) that can be combined with these miRNAs (i) to (iii), specifically, 1, 2, 3 or more, 10 or more, preferably 3 to 110 miRNAs selected from the group consisting of (iv) miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p.

Above miRNAs include any human genes containing any nucleotide sequence represented by any of SEQ ID NOs: 1 to 210, 211 to 249, 250 to 374, 375 to 390, 1315 to 1350, 1351 to 1356, 1435 to 1448, and 1449 to 1453 (i.e., respective miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-

5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, miR-371a-5p, miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346 or miR-767-3p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p, miR-150-3p, miR-423-5p, miR-575, miR-671-5p, miR-939-5p, miR-3665, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, miR-6086, miR-30d-5p, miR-30b-3p, miR-92a-3p, miR-371b-5p, and miR-486-5p), any congener thereof, any transcript thereof, and any variant or derivative thereof. Here, the gene, congener, transcript, variant, and derivative are as defined above.

Preferable target nucleic acid(s) is any human gene containing any nucleotide sequence represented by any of SEQ ID NOs: 1 to 210, 211 to 249, 250 to 374, and 375 to 390, 1315 to 1350, 1351 to 1356, 1435 to 1448, and 1449 to 1453 or any transcript thereof and more preferably is the corresponding transcript(s), i.e. miRNA(s) and any precursor RNA such as pri-miRNA or pre-miRNA thereof.

Additionally, in one embodiment, the major target nucleic acids as dementia markers for detecting dementia or the presence or absence of dementia by using the nucleic acid probes or primers for detection of dementia as defined above according to the present invention include at least one miRNA selected from the group consisting of miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p. Further, it is possible to include other dementia markers that can be combined with these miRNAs, specifically 1, 2, 3 or more, 10 or more, preferably 20 to 60, and more preferably 40 to 55 miRNAs selected from the group consisting of miR-1225-3p, miR-3184-5p, miR-150-3p, miR-423-5p, miR-575, miR-671-5p, miR-939-5p, and miR-3665.

The above miRNAs include, for instance, any human genes containing any nucleotide sequences represented by any of SEQ ID NOs: 194 to 210, 374, and 1315 to 1350, and 211 to 212, and 1351 to 1356 (i.e., respective miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, and miR-1225-3p, miR-3184-5p, miR-150-3p, miR-423-5p, miR-575, miR-671-5p, miR-939-5p, and miR-3665), any congener thereof, any transcript thereof, and/or any variant or derivative thereof. Here, the gene, congener, transcript, variant, and derivative are as defined above.

In one embodiment, the target nucleic acid(s) is any human gene containing any nucleotide sequence represented by any of SEQ ID NOs: 194 to 210, 374, and 1315 to 1350, and 211 to 212, and 1351 to 1356 or any transcript thereof and more preferably is the corresponding transcript(s), namely miRNA(s) and any precursor RNA such as pri-miRNA or pre-miRNA thereof.

The first target gene is the hsa-miR-4274 gene, a congener thereof, a transcript thereof, or a variant or derivative thereof. None of the previously known reports show that change in the expression of the gene or the transcript thereof can serve as a marker for dementia.

The second target gene is the hsa-miR-4272 gene, a congener thereof, a transcript thereof, or a variant or derivative thereof. None of the previously known reports show that change in the expression of the gene or the transcript thereof can serve as a marker for dementia.

The third target gene is the hsa-miR-4728-5p gene, a congener thereof, a transcript thereof, or a variant or derivative thereof. None of the previously known reports show that change in the expression of the gene or the transcript thereof can serve as a marker for dementia.

The 4th target gene is the hsa-miR-4443 gene, a congener thereof, a transcript thereof, or a variant or derivative thereof. None of the previously known reports show that change in the expression of the gene or the transcript thereof can serve as a marker for dementia.

The 5th target gene is the hsa-miR-4506 gene, a congener thereof, a transcript thereof, or a variant or derivative thereof. None of the previously known reports show that change in the expression of the gene or the transcript thereof can serve as a marker for dementia.

The 6th target gene is the hsa-miR-6773-5p gene, a congener thereof, a transcript thereof, or a variant or derivative thereof. None of the previously known reports show that change in the expression of the gene or the transcript thereof can serve as a marker for dementia.

The 7th target gene is the hsa-miR-4662a-5p gene, a congener thereof, a transcript thereof, or a variant or derivative thereof. None of the previously known reports show that change in the expression of the gene or the transcript thereof can serve as a marker for dementia.

The 8th target gene is the hsa-miR-3184-3p gene, a congener thereof, a transcript thereof, or a variant or derivative thereof. None of the previously known reports show that change in the expression of the gene or the transcript thereof can serve as a marker for dementia.

The 9th target gene is the hsa-miR-4281 gene, a congener thereof, a transcript thereof, or a variant or derivative thereof. None of the previously known reports show that change in the expression of the gene or the transcript thereof can serve as a marker for dementia.

The 10th target gene is the hsa-miR-320d gene, a congener thereof, a transcript thereof, or a variant or derivative thereof. None of the previously known reports show that change in the expression of the gene or the transcript thereof can serve as a marker for dementia.

The 11th target gene is the hsa-miR-6729-3p gene, a congener thereof, a transcript thereof, or a variant or derivative thereof. None of the previously known reports show that change in the expression of the gene or the transcript thereof can serve as a marker for dementia.

The 12th target gene is the hsa-miR-5192 gene, a congener thereof, a transcript thereof, or a variant or derivative thereof. None of the previously known reports show that change in the expression of the gene or the transcript thereof can serve as a marker for dementia.

The 13th target gene is the hsa-miR-6853-5p gene, a congener thereof, a transcript thereof, or a variant or derivative thereof. None of the previously known reports show that change in the expression of the gene or the transcript thereof can serve as a marker for dementia.

The 14th target gene is the hsa-miR-1234-3p gene, a congener thereof, a transcript thereof, or a variant or derivative thereof. None of the previously known reports show that change in the expression of the gene or the transcript thereof can serve as a marker for dementia.

The 15th target gene is the hsa-miR-1233-3p gene, a congener thereof, a transcript thereof, or a variant or derivative thereof. None of the previously known reports show that change in the expression of the gene or the transcript thereof can serve as a marker for dementia.

The 16th target gene is the hsa-miR-4539 gene, a congener thereof, a transcript thereof, or a variant or derivative thereof. None of the previously known reports show that change in the expression of the gene or the transcript thereof can serve as a marker for dementia.

The 17th target gene is the hsa-miR-3914 gene, a congener thereof, a transcript thereof, or a variant or derivative thereof. None of the previously known reports show that change in the expression of the gene or the transcript thereof can serve as a marker for dementia.

The 18th target gene is the hsa-miR-4738-5p gene, a congener thereof, a transcript thereof, or a variant or derivative thereof. None of the previously known reports show that change in the expression of the gene or the transcript thereof can serve as a marker for dementia.

The 19th target gene is the hsa-miR-548au-3p gene, a congener thereof, a transcript thereof, or a variant or derivative thereof. None of the previously known reports show that change in the expression of the gene or the transcript thereof can serve as a marker for dementia.

The 20th target gene is the hsa-miR-1539 gene, a congener thereof, a transcript thereof, or a variant or derivative thereof. None of the previously known reports show that change in the expression of the gene or the transcript thereof can serve as a marker for dementia.

The 21st target gene is the hsa-miR-4720-3p gene, a congener thereof, a transcript thereof, or a variant or derivative thereof. None of the previously known reports show that change in the expression of the gene or the transcript thereof can serve as a marker for dementia.

The 22nd target gene is the hsa-miR-365b-5p gene, a congener thereof, a transcript thereof, or a variant or derivative thereof. None of the previously known reports show that change in the expression of the gene or the transcript thereof can serve as a marker for dementia.

The 23rd target gene is the hsa-miR-4486 gene, a congener thereof, a transcript thereof, or a variant or derivative thereof. None of the previously known reports show that change in the expression of the gene or the transcript thereof can serve as a marker for dementia.

The 24th target gene is the hsa-miR-1227-5p gene, a congener thereof, a transcript thereof, or a variant or derivative thereof. None of the previously known reports show that change in the expression of the gene or the transcript thereof can serve as a marker for dementia.

The 25th target gene is the hsa-miR-4667-5p gene, a congener thereof, a transcript thereof, or a variant or derivative thereof. None of the previously known reports show that change in the expression of the gene or the transcript thereof can serve as a marker for dementia.

The 26th target gene is the hsa-miR-6088 gene, a congener thereof, a transcript thereof, or a variant or derivative thereof. None of the previously known reports show that change in the expression of the gene or the transcript thereof can serve as a marker for dementia.

The 27th target gene is the hsa-miR-6820-5p gene, a congener thereof, a transcript thereof, or a variant or derivative thereof. None of the previously known reports show that change in the expression of the gene or the transcript thereof can serve as a marker for dementia.

The 28th target gene is the hsa-miR-4505 gene, a congener thereof, a transcript thereof, or a variant or derivative thereof. None of the previously known reports show that change in the expression of the gene or the transcript thereof can serve as a marker for dementia.

The 29th target gene is the hsa-miR-548q gene, a congener thereof, a transcript thereof, or a variant or derivative thereof. None of the previously known reports show that change in the expression of the gene or the transcript thereof can serve as a marker for dementia.

The 30th target gene is the hsa-miR-4658 gene, a congener thereof, a transcript thereof, or a variant or derivative thereof. None of the previously known reports show that change in the expression of the gene or the transcript thereof can serve as a marker for dementia.

The 31st target gene is the hsa-miR-450a-5p gene, a congener thereof, a transcript thereof, or a variant or derivative thereof. None of the previously known reports show that change in the expression of the gene or the transcript thereof can serve as a marker for dementia.

The 32nd target gene is the hsa-miR-1260b gene, a congener thereof, a transcript thereof, or a variant or derivative thereof. None of the previously known reports show that change in the expression of the gene or the transcript thereof can serve as a marker for dementia.

The 33rd target gene is the hsa-miR-3677-5p gene, a congener thereof, a transcript thereof, or a variant or derivative thereof. None of the previously known reports show that change in the expression of the gene or the transcript thereof can serve as a marker for dementia.

The 34th target gene is the hsa-miR-6777-3p gene, a congener thereof, a transcript thereof, or a variant or derivative thereof. None of the previously known reports show that change in the expression of the gene or the transcript thereof can serve as a marker for dementia.

The 35th target gene is the hsa-miR-6826-3p gene, a congener thereof, a transcript thereof, or a variant or derivative thereof. None of the previously known reports show that change in the expression of the gene or the transcript thereof can serve as a marker for dementia.

The 36th target gene is the hsa-miR-6832-3p gene, a congener thereof, a transcript thereof, or a variant or derivative thereof. None of the previously known reports show that change in the expression of the gene or the transcript thereof can serve as a marker for dementia.

The 37th target gene is the hsa-miR-4725-3p gene, a congener thereof, a transcript thereof, or a variant or derivative thereof. None of the previously known reports show that change in the expression of the gene or the transcript thereof can serve as a marker for dementia.

The 38th target gene is the hsa-miR-7161-3p gene, a congener thereof, a transcript thereof, or a variant or derivative thereof. None of the previously known reports show that change in the expression of the gene or the transcript thereof can serve as a marker for dementia.

The 39th target gene is the hsa-miR-2277-5p gene, a congener thereof, a transcript thereof, or a variant or derivative thereof. None of the previously known reports show that change in the expression of the gene or the transcript thereof can serve as a marker for dementia.

The 40th target gene is the hsa-miR-7110-3p gene, a congener thereof, a transcript thereof, or a variant or derivative thereof. None of the previously known reports show that change in the expression of the gene or the transcript thereof can serve as a marker for dementia.

The 41st target gene is the hsa-miR-4312 gene, a congener thereof, a transcript thereof, or a variant or derivative thereof. None of the previously known reports show that change in the expression of the gene or the transcript thereof can serve as a marker for dementia.

The 42nd target gene is the hsa-miR-4461 gene, a congener thereof, a transcript thereof, or a variant or derivative thereof. None of the previously known reports show that change in the expression of the gene or the transcript thereof can serve as a marker for dementia.

The 43rd target gene is the hsa-miR-6766-5p gene, a congener thereof, a transcript thereof, or a variant or derivative thereof. None of the previously known reports show that change in the expression of the gene or the transcript thereof can serve as a marker for dementia.

The 44th target gene is the hsa-miR-1266-3p gene, a congener thereof, a transcript thereof, or a variant or derivative thereof. None of the previously known reports show that change in the expression of the gene or the transcript thereof can serve as a marker for dementia.

The 45th target gene is the hsa-miR-6729-5p gene, a congener thereof, a transcript thereof, or a variant or derivative thereof. None of the previously known reports show that change in the expression of the gene or the transcript thereof can serve as a marker for dementia.

The 46th target gene is the hsa-miR-526b-3p gene, a congener thereof, a transcript thereof, or a variant or derivative thereof. None of the previously known reports show that change in the expression of the gene or the transcript thereof can serve as a marker for dementia.

The 47th target gene is the hsa-miR-519e-5p gene, a congener thereof, a transcript thereof, or a variant or derivative thereof. None of the previously known reports show that change in the expression of the gene or the transcript thereof can serve as a marker for dementia.

The 48th target gene is the hsa-miR-512-5p gene, a congener thereof, a transcript thereof, or a variant or derivative thereof. None of the previously known reports show that change in the expression of the gene or the transcript thereof can serve as a marker for dementia.

The 49th target gene is the hsa-miR-5088-5p gene, a congener thereof, a transcript thereof, or a variant or derivative thereof. None of the previously known reports show that change in the expression of the gene or the transcript thereof can serve as a marker for dementia.

The 50th target gene is the hsa-miR-1909-3p gene, a congener thereof, a transcript thereof, or a variant or derivative thereof. None of the previously known reports show that change in the expression of the gene or the transcript thereof can serve as a marker for dementia.

The 51st target gene is the hsa-miR-6511a-5p gene, a congener thereof, a transcript thereof, or a variant or derivative thereof. None of the previously known reports show that change in the expression of the gene or the transcript thereof can serve as a marker for dementia.

The 52nd target gene is the hsa-miR-4734 gene, a congener thereof, a transcript thereof, or a variant or derivative thereof. None of the previously known reports show that change in the expression of the gene or the transcript thereof can serve as a marker for dementia.

The 53rd target gene is the hsa-miR-936 gene, a congener thereof, a transcript thereof, or a variant or derivative thereof. None of the previously known reports show that change in the expression of the gene or the transcript thereof can serve as a marker for dementia.

The 54th target gene is the hsa-miR-1249-3p gene, a congener thereof, a transcript thereof, or a variant or derivative thereof. None of the previously known reports show that change in the expression of the gene or the transcript thereof can serve as a marker for dementia.

The 55th target gene is the hsa-miR-6777-5p gene, a congener thereof, a transcript thereof, or a variant or derivative thereof. None of the previously known reports show that change in the expression of the gene or the transcript thereof can serve as a marker for dementia.

The 56th target gene is the hsa-miR-4487 gene, a congener thereof, a transcript thereof, or a variant or derivative thereof. None of the previously known reports show that change in the expression of the gene or the transcript thereof can serve as a marker for dementia.

The 57th target gene is the hsa-miR-3155a gene, a congener thereof, a transcript thereof, or a variant or derivative thereof. None of the previously known reports show that change in the expression of the gene or the transcript thereof can serve as a marker for dementia.

The 58th target gene is the hsa-miR-563 gene, a congener thereof, a transcript thereof, or a variant or derivative thereof. None of the previously known reports show that change in the expression of the gene or the transcript thereof can serve as a marker for dementia.

The 59th target gene is the hsa-miR-4741 gene, a congener thereof, a transcript thereof, or a variant or derivative thereof. None of the previously known reports show that change in the expression of the gene or the transcript thereof can serve as a marker for dementia.

The 60th target gene is the hsa-miR-6788-5p gene, a congener thereof, a transcript thereof, or a variant or derivative thereof. None of the previously known reports show that change in the expression of the gene or the transcript thereof can serve as a marker for dementia.

The 61st target gene is the hsa-miR-4433b-5p gene, a congener thereof, a transcript thereof, or a variant or derivative thereof. None of the previously known reports show that change in the expression of the gene or the transcript thereof can serve as a marker for dementia.

The 62nd target gene is the hsa-miR-323a-5p gene, a congener thereof, a transcript thereof, or a variant or derivative thereof. None of the previously known reports show that change in the expression of the gene or the transcript thereof can serve as a marker for dementia.

The 63rd target gene is the hsa-miR-6811-5p gene, a congener thereof, a transcript thereof, or a variant or derivative thereof. None of the previously known reports show that change in the expression of the gene or the transcript thereof can serve as a marker for dementia.

The 64th target gene is the hsa-miR-6721-5p gene, a congener thereof, a transcript thereof, or a variant or derivative thereof. None of the previously known reports show that change in the expression of the gene or the transcript thereof can serve as a marker for dementia.

The 65th target gene is the hsa-miR-5004-5p gene, a congener thereof, a transcript thereof, or a variant or derivative thereof. None of the previously known reports show that change in the expression of the gene or the transcript thereof can serve as a marker for dementia.

The 66th target gene is the hsa-miR-6509-3p gene, a congener thereof, a transcript thereof, or a variant or derivative thereof. None of the previously known reports show that change in the expression of the gene or the transcript thereof can serve as a marker for dementia.

The 67th target gene is the hsa-miR-648 gene, a congener thereof, a transcript thereof, or a variant or derivative thereof. None of the previously known reports show that change in the expression of the gene or the transcript thereof can serve as a marker for dementia.

The 68th target gene is the hsa-miR-3917 gene, a congener thereof, a transcript thereof, or a variant or derivative thereof. None of the previously known reports show that change in the expression of the gene or the transcript thereof can serve as a marker for dementia.

The 69th target gene is the hsa-miR-6087 gene, a congener thereof, a transcript thereof, or a variant or derivative thereof. None of the previously known reports show that change in the expression of the gene or the transcript thereof can serve as a marker for dementia.

The 70th target gene is the hsa-miR-1470 gene, a congener thereof, a transcript thereof, or a variant or derivative thereof. None of the previously known reports show that change in the expression of the gene or the transcript thereof can serve as a marker for dementia.

The 71st target gene is the hsa-miR-586 gene, a congener thereof, a transcript thereof, or a variant or derivative thereof. None of the previously known reports show that change in the expression of the gene or the transcript thereof can serve as a marker for dementia.

The 72nd target gene is the hsa-miR-3150a-5p gene, a congener thereof, a transcript thereof, or a variant or derivative thereof. None of the previously known reports show that change in the expression of the gene or the transcript thereof can serve as a marker for dementia.

The 73rd target gene is the hsa-miR-105-3p gene, a congener thereof, a transcript thereof, or a variant or derivative thereof. None of the previously known reports show that change in the expression of the gene or the transcript thereof can serve as a marker for dementia.

The 74th target gene is the hsa-miR-7973 gene, a congener thereof, a transcript thereof, or a variant or derivative thereof. None of the previously known reports show that change in the expression of the gene or the transcript thereof can serve as a marker for dementia.

The 75th target gene is the hsa-miR-1914-5p gene, a congener thereof, a transcript thereof, or a variant or derivative thereof. None of the previously known reports show that change in the expression of the gene or the transcript thereof can serve as a marker for dementia.

The 76th target gene is the hsa-miR-4749-3p gene, a congener thereof, a transcript thereof, or a variant or derivative thereof. None of the previously known reports show that change in the expression of the gene or the transcript thereof can serve as a marker for dementia.

The 77th target gene is the hsa-miR-15b-5p gene, a congener thereof, a transcript thereof, or a variant or derivative thereof. None of the previously known reports show that change in the expression of the gene or the transcript thereof can serve as a marker for dementia.

The 78th target gene is the hsa-miR-1289 gene, a congener thereof, a transcript thereof, or a variant or derivative thereof. None of the previously known reports show that change in the expression of the gene or the transcript thereof can serve as a marker for dementia.

The 79th target gene is the hsa-miR-4433a-5p gene, a congener thereof, a transcript thereof, or a variant or derivative thereof. None of the previously known reports show that change in the expression of the gene or the transcript thereof can serve as a marker for dementia.

The 80th target gene is the hsa-miR-3666 gene, a congener thereof, a transcript thereof, or a variant or derivative thereof. None of the previously known reports show that change in the expression of the gene or the transcript thereof can serve as a marker for dementia.

The 81st target gene is the hsa-miR-3186-3p gene, a congener thereof, a transcript thereof, or a variant or derivative thereof. None of the previously known reports show that change in the expression of the gene or the transcript thereof can serve as a marker for dementia.

The 82nd target gene is the hsa-miR-4725-5p gene, a congener thereof, a transcript thereof, or a variant or derivative thereof. None of the previously known reports show that change in the expression of the gene or the transcript thereof can serve as a marker for dementia.

The 83rd target gene is the hsa-miR-4488 gene, a congener thereof, a transcript thereof, or a variant or derivative thereof. None of the previously known reports show that change in the expression of the gene or the transcript thereof can serve as a marker for dementia.

The 84th target gene is the hsa-miR-4474-3p gene, a congener thereof, a transcript thereof, or a variant or derivative thereof. None of the previously known reports show that change in the expression of the gene or the transcript thereof can serve as a marker for dementia.

The 85th target gene is the hsa-miR-6731-3p gene, a congener thereof, a transcript thereof, or a variant or derivative thereof. None of the previously known reports show that change in the expression of the gene or the transcript thereof can serve as a marker for dementia.

The 86th target gene is the hsa-miR-4640-3p gene, a congener thereof, a transcript thereof, or a variant or derivative thereof. None of the previously known reports show that change in the expression of the gene or the transcript thereof can serve as a marker for dementia.

The 87th target gene is the hsa-miR-202-5p gene, a congener thereof, a transcript thereof, or a variant or derivative thereof. None of the previously known reports show that change in the expression of the gene or the transcript thereof can serve as a marker for dementia.

The 88th target gene is the hsa-miR-6816-5p gene, a congener thereof, a transcript thereof, or a variant or derivative thereof. None of the previously known reports show that change in the expression of the gene or the transcript thereof can serve as a marker for dementia.

The 89th target gene is the hsa-miR-638 gene, a congener thereof, a transcript thereof, or a variant or derivative thereof. None of the previously known reports show that change in the expression of the gene or the transcript thereof can serve as a marker for dementia.

The 90th target gene is the hsa-miR-6821-5p gene, a congener thereof, a transcript thereof, or a variant or derivative thereof. None of the previously known reports show that change in the expression of the gene or the transcript thereof can serve as a marker for dementia.

The 91st target gene is the hsa-miR-1247-3p gene, a congener thereof, a transcript thereof, or a variant or derivative thereof. None of the previously known reports show that change in the expression of the gene or the transcript thereof can serve as a marker for dementia.

The 92nd target gene is the hsa-miR-6765-5p gene, a congener thereof, a transcript thereof, or a variant or derivative thereof. None of the previously known reports show that change in the expression of the gene or the transcript thereof can serve as a marker for dementia.

The 93rd target gene is the hsa-miR-6800-5p gene, a congener thereof, a transcript thereof, or a variant or derivative thereof. None of the previously known reports show that change in the expression of the gene or the transcript thereof can serve as a marker for dementia.

The 94th target gene is the hsa-miR-3928-3p gene, a congener thereof, a transcript thereof, or a variant or derivative thereof. None of the previously known reports show that change in the expression of the gene or the transcript thereof can serve as a marker for dementia.

The 95th target gene is the hsa-miR-3940-5p gene, a congener thereof, a transcript thereof, or a variant or derivative thereof. None of the previously known reports show that change in the expression of the gene or the transcript thereof can serve as a marker for dementia.

The 96th target gene is the hsa-miR-3960 gene, a congener thereof, a transcript thereof, or a variant or derivative thereof. None of the previously known reports show that change in the expression of the gene or the transcript thereof can serve as a marker for dementia.

The 97th target gene is the hsa-miR-6775-5p gene, a congener thereof, a transcript thereof, or a variant or derivative thereof. None of the previously known reports show that change in the expression of the gene or the transcript thereof can serve as a marker for dementia.

The 98th target gene is the hsa-miR-3178 gene, a congener thereof, a transcript thereof, or a variant or derivative thereof. None of the previously known reports show that change in the expression of the gene or the transcript thereof can serve as a marker for dementia.

The 99th target gene is the hsa-miR-1202 gene, a congener thereof, a transcript thereof, or a variant or derivative thereof. None of the previously known reports show that change in the expression of the gene or the transcript thereof can serve as a marker for dementia.

The 100th target gene is the hsa-miR-6790-5p gene, a congener thereof, a transcript thereof, or a variant or derivative thereof. None of the previously known reports show that change in the expression of the gene or the transcript thereof can serve as a marker for dementia.

The 101st target gene is the hsa-miR-4731-3p gene, a congener thereof, a transcript thereof, or a variant or derivative thereof. None of the previously known reports show that change in the expression of the gene or the transcript thereof can serve as a marker for dementia.

The 102nd target gene is the hsa-miR-2681-3p gene, a congener thereof, a transcript thereof, or a variant or derivative thereof. None of the previously known reports show that change in the expression of the gene or the transcript thereof can serve as a marker for dementia.

The 103rd target gene is the hsa-miR-6758-5p gene, a congener thereof, a transcript thereof, or a variant or derivative thereof. None of the previously known reports show that change in the expression of the gene or the transcript thereof can serve as a marker for dementia.

The 104th target gene is the hsa-miR-8072 gene, a congener thereof, a transcript thereof, or a variant or derivative thereof. None of the previously known reports show that change in the expression of the gene or the transcript thereof can serve as a marker for dementia.

The 105th target gene is the hsa-miR-518d-3p gene, a congener thereof, a transcript thereof, or a variant or derivative thereof. None of the previously known reports show that change in the expression of the gene or the transcript thereof can serve as a marker for dementia.

The 106th target gene is the hsa-miR-3606-3p gene, a congener thereof, a transcript thereof, or a variant or derivative thereof. None of the previously known reports show that change in the expression of the gene or the transcript thereof can serve as a marker for dementia.

The 107th target gene is the hsa-miR-4800-5p gene, a congener thereof, a transcript thereof, or a variant or derivative thereof. None of the previously known reports show that change in the expression of the gene or the transcript thereof can serve as a marker for dementia.

The 108th target gene is the hsa-miR-1292-3p gene, a congener thereof, a transcript thereof, or a variant or derivative thereof. None of the previously known reports show that change in the expression of the gene or the transcript thereof can serve as a marker for dementia.

The 109th target gene is the hsa-miR-6784-3p gene, a congener thereof, a transcript thereof, or a variant or derivative thereof. None of the previously known reports show that change in the expression of the gene or the transcript thereof can serve as a marker for dementia.

The 110th target gene is the hsa-miR-4450 gene, a congener thereof, a transcript thereof, or a variant or derivative thereof. None of the previously known reports show that change in the expression of the gene or the transcript thereof can serve as a marker for dementia.

The 111st target gene is the hsa-miR-6132 gene, a congener thereof, a transcript thereof, or a variant or derivative thereof. None of the previously known reports show that change in the expression of the gene or the transcript thereof can serve as a marker for dementia.

The 112nd target gene is the hsa-miR-4716-5p gene, a congener thereof, a transcript thereof, or a variant or derivative thereof. None of the previously known reports show that change in the expression of the gene or the transcript thereof can serve as a marker for dementia.

The 113rd target gene is the hsa-miR-6860 gene, a congener thereof, a transcript thereof, or a variant or derivative thereof. None of the previously known reports show that change in the expression of the gene or the transcript thereof can serve as a marker for dementia.

The 114th target gene is the hsa-miR-1268b gene, a congener thereof, a transcript thereof, or a variant or derivative thereof. None of the previously known reports show that change in the expression of the gene or the transcript thereof can serve as a marker for dementia.

The 115th target gene is the hsa-miR-378d gene, a congener thereof, a transcript thereof, or a variant or derivative thereof. None of the previously known reports show that change in the expression of the gene or the transcript thereof can serve as a marker for dementia.

The 116th target gene is the hsa-miR-4701-5p gene, a congener thereof, a transcript thereof, or a variant or derivative thereof. None of the previously known reports show that change in the expression of the gene or the transcript thereof can serve as a marker for dementia.

The 117th target gene is the hsa-miR-4329 gene, a congener thereof, a transcript thereof, or a variant or derivative thereof. None of the previously known reports show that change in the expression of the gene or the transcript thereof can serve as a marker for dementia.

The 118th target gene is the hsa-miR-185-3p gene, a congener thereof, a transcript thereof, or a variant or derivative thereof. None of the previously known reports show that change in the expression of the gene or the transcript thereof can serve as a marker for dementia.

The 119th target gene is the hsa-miR-552-3p gene, a congener thereof, a transcript thereof, or a variant or derivative thereof. None of the previously known reports show that change in the expression of the gene or the transcript thereof can serve as a marker for dementia.

The 120th target gene is the hsa-miR-1273g-5p gene, a congener thereof, a transcript thereof, or a variant or derivative thereof. None of the previously known reports show that change in the expression of the gene or the transcript thereof can serve as a marker for dementia.

The 121st target gene is the hsa-miR-6769b-3p gene, a congener thereof, a transcript thereof, or a variant or derivative thereof. None of the previously known reports show that change in the expression of the gene or the transcript thereof can serve as a marker for dementia.

The 122nd target gene is the hsa-miR-520a-3p gene, a congener thereof, a transcript thereof, or a variant or derivative thereof. None of the previously known reports show that change in the expression of the gene or the transcript thereof can serve as a marker for dementia.

The 123rd target gene is the hsa-miR-4524b-5p gene, a congener thereof, a transcript thereof, or a variant or derivative thereof. None of the previously known reports show that change in the expression of the gene or the transcript thereof can serve as a marker for dementia.

The 124th target gene is the hsa-miR-4291 gene, a congener thereof, a transcript thereof, or a variant or derivative thereof. None of the previously known reports show that change in the expression of the gene or the transcript thereof can serve as a marker for dementia.

The 125th target gene is the hsa-miR-6734-3p gene, a congener thereof, a transcript thereof, or a variant or derivative thereof. None of the previously known reports show that change in the expression of the gene or the transcript thereof can serve as a marker for dementia.

The 126th target gene is the hsa-miR-143-5p gene, a congener thereof, a transcript thereof, or a variant or derivative thereof. None of the previously known reports show that change in the expression of the gene or the transcript thereof can serve as a marker for dementia.

The 127th target gene is the hsa-miR-939-3p gene, a congener thereof, a transcript thereof, or a variant or derivative thereof. None of the previously known reports show that change in the expression of the gene or the transcript thereof can serve as a marker for dementia.

The 128th target gene is the hsa-miR-6889-3p gene, a congener thereof, a transcript thereof, or a variant or derivative thereof. None of the previously known reports show that change in the expression of the gene or the transcript thereof can serve as a marker for dementia.

The 129th target gene is the hsa-miR-6842-3p gene, a congener thereof, a transcript thereof, or a variant or derivative thereof. None of the previously known reports show that change in the expression of the gene or the transcript thereof can serve as a marker for dementia.

The 130th target gene is the hsa-miR-4511 gene, a congener thereof, a transcript thereof, or a variant or derivative thereof. None of the previously known reports show that change in the expression of the gene or the transcript thereof can serve as a marker for dementia.

The 131st target gene is the hsa-miR-4318 gene, a congener thereof, a transcript thereof, or a variant or derivative thereof. None of the previously known reports show that change in the expression of the gene or the transcript thereof can serve as a marker for dementia.

The 132nd target gene is the hsa-miR-4653-5p gene, a congener thereof, a transcript thereof, or a variant or derivative thereof. None of the previously known reports show that change in the expression of the gene or the transcript thereof can serve as a marker for dementia.

The 133rd target gene is the hsa-miR-6867-3p gene, a congener thereof, a transcript thereof, or a variant or derivative thereof. None of the previously known reports show that change in the expression of the gene or the transcript thereof can serve as a marker for dementia.

The 134th target gene is the hsa-miR-133b gene, a congener thereof, a transcript thereof, or a variant or derivative thereof. None of the previously known reports show that change in the expression of the gene or the transcript thereof can serve as a marker for dementia.

The 135th target gene is the hsa-miR-3196 gene, a congener thereof, a transcript thereof, or a variant or derivative thereof. None of the previously known reports show that change in the expression of the gene or the transcript thereof can serve as a marker for dementia.

The 136th target gene is the hsa-miR-193b-3p gene, a congener thereof, a transcript thereof, or a variant or derivative thereof. None of the previously known reports show that change in the expression of the gene or the transcript thereof can serve as a marker for dementia.

The 137th target gene is the hsa-miR-3162-3p gene, a congener thereof, a transcript thereof, or a variant or derivative thereof. None of the previously known reports show that change in the expression of the gene or the transcript thereof can serve as a marker for dementia.

The 138th target gene is the hsa-miR-6819-3p gene, a congener thereof, a transcript thereof, or a variant or derivative thereof. None of the previously known reports show that change in the expression of the gene or the transcript thereof can serve as a marker for dementia.

The 139th target gene is the hsa-miR-1908-3p gene, a congener thereof, a transcript thereof, or a variant or derivative thereof. None of the previously known reports show that change in the expression of the gene or the transcript thereof can serve as a marker for dementia.

The 140th target gene is the hsa-miR-6786-5p gene, a congener thereof, a transcript thereof, or a variant or derivative thereof. None of the previously known reports show that change in the expression of the gene or the transcript thereof can serve as a marker for dementia.

The 141st target gene is the hsa-miR-3648 gene, a congener thereof, a transcript thereof, or a variant or derivative thereof. None of the previously known reports show that change in the expression of the gene or the transcript thereof can serve as a marker for dementia.

The 142nd target gene is the hsa-miR-4513 gene, a congener thereof, a transcript thereof, or a variant or derivative thereof. None of the previously known reports show that change in the expression of the gene or the transcript thereof can serve as a marker for dementia.

The 143rd target gene is the hsa-miR-3652 gene, a congener thereof, a transcript thereof, or a variant or derivative thereof. None of the previously known reports show that change in the expression of the gene or the transcript thereof can serve as a marker for dementia.

The 144th target gene is the hsa-miR-4640-5p gene, a congener thereof, a transcript thereof, or a variant or derivative thereof. None of the previously known reports show that change in the expression of the gene or the transcript thereof can serve as a marker for dementia.

The 145th target gene is the hsa-miR-6871-5p gene, a congener thereof, a transcript thereof, or a variant or derivative thereof. None of the previously known reports show that change in the expression of the gene or the transcript thereof can serve as a marker for dementia.

The 146th target gene is the hsa-miR-7845-5p gene, a congener thereof, a transcript thereof, or a variant or derivative thereof. None of the previously known reports show that change in the expression of the gene or the transcript thereof can serve as a marker for dementia.

The 147th target gene is the hsa-miR-3138 gene, a congener thereof, a transcript thereof, or a variant or derivative thereof. None of the previously known reports show that change in the expression of the gene or the transcript thereof can serve as a marker for dementia.

The 148th target gene is the hsa-miR-6884-5p gene, a congener thereof, a transcript thereof, or a variant or derivative thereof. None of the previously known reports show that change in the expression of the gene or the transcript thereof can serve as a marker for dementia.

The 149th target gene is the hsa-miR-4653-3p gene, a congener thereof, a transcript thereof, or a variant or derivative thereof. None of the previously known reports show that change in the expression of the gene or the transcript thereof can serve as a marker for dementia.

The 150th target gene is the hsa-miR-636 gene, a congener thereof, a transcript thereof, or a variant or derivative thereof. None of the previously known reports show that change in the expression of the gene or the transcript thereof can serve as a marker for dementia.

The 151st target gene is the hsa-miR-4652-3p gene, a congener thereof, a transcript thereof, or a variant or derivative thereof. None of the previously known reports show that change in the expression of the gene or the transcript thereof can serve as a marker for dementia.

The 152nd target gene is the hsa-miR-6823-5p gene, a congener thereof, a transcript thereof, or a variant or derivative thereof. None of the previously known reports show that change in the expression of the gene or the transcript thereof can serve as a marker for dementia.

The 153rd target gene is the hsa-miR-4502 gene, a congener thereof, a transcript thereof, or a variant or derivative thereof. None of the previously known reports show that change in the expression of the gene or the transcript thereof can serve as a marker for dementia.

The 154th target gene is the hsa-miR-7113-5p gene, a congener thereof, a transcript thereof, or a variant or derivative thereof. None of the previously known reports show that change in the expression of the gene or the transcript thereof can serve as a marker for dementia.

The 155th target gene is the hsa-miR-8087 gene, a congener thereof, a transcript thereof, or a variant or derivative thereof. None of the previously known reports show that change in the expression of the gene or the transcript thereof can serve as a marker for dementia.

The 156th target gene is the hsa-miR-7154-3p gene, a congener thereof, a transcript thereof, or a variant or derivative thereof. None of the previously known reports show that change in the expression of the gene or the transcript thereof can serve as a marker for dementia.

The 157th target gene is the hsa-miR-5189-5p gene, a congener thereof, a transcript thereof, or a variant or derivative thereof. None of the previously known reports show that change in the expression of the gene or the transcript thereof can serve as a marker for dementia.

The 158th target gene is the hsa-miR-1253 gene, a congener thereof, a transcript thereof, or a variant or derivative thereof. None of the previously known reports show that change in the expression of the gene or the transcript thereof can serve as a marker for dementia.

The 159th target gene is the hsa-miR-518c-5p gene, a congener thereof, a transcript thereof, or a variant or derivative thereof. None of the previously known reports show that change in the expression of the gene or the transcript thereof can serve as a marker for dementia.

The 160th target gene is the hsa-miR-7151-5p gene, a congener thereof, a transcript thereof, or a variant or derivative thereof. None of the previously known reports show that change in the expression of the gene or the transcript thereof can serve as a marker for dementia.

The 161st target gene is the hsa-miR-3614-3p gene, a congener thereof, a transcript thereof, or a variant or derivative thereof. None of the previously known reports show that change in the expression of the gene or the transcript thereof can serve as a marker for dementia.

The 162nd target gene is the hsa-miR-4727-5p gene, a congener thereof, a transcript thereof, or a variant or derivative thereof. None of the previously known reports show that change in the expression of the gene or the transcript thereof can serve as a marker for dementia.

The 163rd target gene is the hsa-miR-3682-5p gene, a congener thereof, a transcript thereof, or a variant or derivative thereof. None of the previously known reports show that change in the expression of the gene or the transcript thereof can serve as a marker for dementia.

The 164th target gene is the hsa-miR-5090 gene, a congener thereof, a transcript thereof, or a variant or derivative thereof. None of the previously known reports show that change in the expression of the gene or the transcript thereof can serve as a marker for dementia.

The 165th target gene is the hsa-miR-337-3p gene, a congener thereof, a transcript thereof, or a variant or derivative thereof. None of the previously known reports show that change in the expression of the gene or the transcript thereof can serve as a marker for dementia.

The 166th target gene is the hsa-miR-488-5p gene, a congener thereof, a transcript thereof, or a variant or derivative thereof. None of the previously known reports show that change in the expression of the gene or the transcript thereof can serve as a marker for dementia.

The 167th target gene is the hsa-miR-100-5p gene, a congener thereof, a transcript thereof, or a variant or derivative thereof. None of the previously known reports show that change in the expression of the gene or the transcript thereof can serve as a marker for dementia.

The 168th target gene is the hsa-miR-4520-3p gene, a congener thereof, a transcript thereof, or a variant or derivative thereof. None of the previously known reports show that change in the expression of the gene or the transcript thereof can serve as a marker for dementia.

The 169th target gene is the hsa-miR-373-3p gene, a congener thereof, a transcript thereof, or a variant or derivative thereof. None of the previously known reports show that change in the expression of the gene or the transcript thereof can serve as a marker for dementia.

The 170th target gene is the hsa-miR-6499-5p gene, a congener thereof, a transcript thereof, or a variant or derivative thereof. None of the previously known reports show that change in the expression of the gene or the transcript thereof can serve as a marker for dementia.

The 171st target gene is the hsa-miR-3909 gene, a congener thereof, a transcript thereof, or a variant or derivative thereof. None of the previously known reports show that change in the expression of the gene or the transcript thereof can serve as a marker for dementia.

The 172nd target gene is the hsa-miR-32-5p gene, a congener thereof, a transcript thereof, or a variant or derivative thereof. None of the previously known reports show that change in the expression of the gene or the transcript thereof can serve as a marker for dementia.

The 173rd target gene is the hsa-miR-302a-3p gene, a congener thereof, a transcript thereof, or a variant or derivative thereof. None of the previously known reports show that change in the expression of the gene or the transcript thereof can serve as a marker for dementia.

The 174th target gene is the hsa-miR-4686 gene, a congener thereof, a transcript thereof, or a variant or derivative thereof. None of the previously known reports show that change in the expression of the gene or the transcript thereof can serve as a marker for dementia.

The 175th target gene is the hsa-miR-4659a-3p gene, a congener thereof, a transcript thereof, or a variant or derivative thereof. None of the previously known reports show that change in the expression of the gene or the transcript thereof can serve as a marker for dementia.

The 176th target gene is the hsa-miR-4287 gene, a congener thereof, a transcript thereof, or a variant or derivative thereof. None of the previously known reports show that change in the expression of the gene or the transcript thereof can serve as a marker for dementia.

The 177th target gene is the hsa-miR-1301-5p gene, a congener thereof, a transcript thereof, or a variant or derivative thereof. None of the previously known reports show that change in the expression of the gene or the transcript thereof can serve as a marker for dementia.

The 178th target gene is the hsa-miR-593-3p gene, a congener thereof, a transcript thereof, or a variant or derivative thereof. None of the previously known reports show that change in the expression of the gene or the transcript thereof can serve as a marker for dementia.

The 179th target gene is the hsa-miR-517a-3p gene, a congener thereof, a transcript thereof, or a variant or derivative thereof. None of the previously known reports show that change in the expression of the gene or the transcript thereof can serve as a marker for dementia.

The 180th target gene is the hsa-miR-517b-3p gene, a congener thereof, a transcript thereof, or a variant or derivative thereof. None of the previously known reports show that change in the expression of the gene or the transcript thereof can serve as a marker for dementia.

The 181st target gene is the hsa-miR-142-3p gene, a congener thereof, a transcript thereof, or a variant or derivative thereof. None of the previously known reports show that change in the expression of the gene or the transcript thereof can serve as a marker for dementia.

The 182nd target gene is the hsa-miR-1185-2-3p gene, a congener thereof, a transcript thereof, or a variant or derivative thereof. None of the previously known reports show that change in the expression of the gene or the transcript thereof can serve as a marker for dementia.

The 183rd target gene is the hsa-miR-602 gene, a congener thereof, a transcript thereof, or a variant or derivative thereof. None of the previously known reports show that change in the expression of the gene or the transcript thereof can serve as a marker for dementia.

The 184th target gene is the hsa-miR-527 gene, a congener thereof, a transcript thereof, or a variant or derivative thereof. None of the previously known reports show that change in the expression of the gene or the transcript thereof can serve as a marker for dementia.

The 185th target gene is the hsa-miR-518a-5p gene, a congener thereof, a transcript thereof, or a variant or derivative thereof. None of the previously known reports show that change in the expression of the gene or the transcript thereof can serve as a marker for dementia.

The 186th target gene is the hsa-miR-4682 gene, a congener thereof, a transcript thereof, or a variant or derivative thereof. None of the previously known reports show that change in the expression of the gene or the transcript thereof can serve as a marker for dementia.

The 187th target gene is the hsa-miR-28-5p gene, a congener thereof, a transcript thereof, or a variant or derivative thereof. None of the previously known reports show that change in the expression of the gene or the transcript thereof can serve as a marker for dementia.

The 188th target gene is the hsa-miR-4252 gene, a congener thereof, a transcript thereof, or a variant or derivative thereof. None of the previously known reports show that change in the expression of the gene or the transcript thereof can serve as a marker for dementia.

The 189th target gene is the hsa-miR-452-5p gene, a congener thereof, a transcript thereof, or a variant or derivative thereof. None of the previously known reports show that change in the expression of the gene or the transcript thereof can serve as a marker for dementia.

The 190th target gene is the hsa-miR-525-5p gene, a congener thereof, a transcript thereof, or a variant or derivative thereof. None of the previously known reports show that change in the expression of the gene or the transcript thereof can serve as a marker for dementia.

The 191st target gene is the hsa-miR-3622a-3p gene, a congener thereof, a transcript thereof, or a variant or derivative thereof. None of the previously known reports show that change in the expression of the gene or the transcript thereof can serve as a marker for dementia.

The 192nd target gene is the hsa-miR-6813-3p gene, a congener thereof, a transcript thereof, or a variant or derivative thereof. None of the previously known reports show that change in the expression of the gene or the transcript thereof can serve as a marker for dementia.

The 193rd target gene is the hsa-miR-4769-3p gene, a congener thereof, a transcript thereof, or a variant or derivative thereof. None of the previously known reports show that change in the expression of the gene or the transcript thereof can serve as a marker for dementia.

The 194th target gene is the hsa-miR-5698 gene, a congener thereof, a transcript thereof, or a variant or derivative thereof. None of the previously known reports show that change in the expression of the gene or the transcript thereof can serve as a marker for dementia.

The 195th target gene is the hsa-miR-1915-3p gene, a congener thereof, a transcript thereof, or a variant or derivative thereof. None of the previously known reports show that change in the expression of the gene or the transcript thereof can serve as a marker for dementia.

The 196th target gene is the hsa-miR-1343-5p gene, a congener thereof, a transcript thereof, or a variant or derivative thereof. None of the previously known reports show that change in the expression of the gene or the transcript thereof can serve as a marker for dementia.

The 197th target gene is the hsa-miR-6861-5p gene, a congener thereof, a transcript thereof, or a variant or derivative thereof. None of the previously known reports show that change in the expression of the gene or the transcript thereof can serve as a marker for dementia.

The 198th target gene is the hsa-miR-6781-5p gene, a congener thereof, a transcript thereof, or a variant or derivative thereof. None of the previously known reports show that change in the expression of the gene or the transcript thereof can serve as a marker for dementia.

The 199th target gene is the hsa-miR-4508 gene, a congener thereof, a transcript thereof, or a variant or derivative thereof. None of the previously known reports show that change in the expression of the gene or the transcript thereof can serve as a marker for dementia.

The 200th target gene is the hsa-miR-6743-5p gene, a congener thereof, a transcript thereof, or a variant or derivative thereof. None of the previously known reports show that change in the expression of the gene or the transcript thereof can serve as a marker for dementia.

The 201st target gene is the hsa-miR-6726-5p gene, a congener thereof, a transcript thereof, or a variant or derivative thereof. None of the previously known reports show that change in the expression of the gene or the transcript thereof can serve as a marker for dementia.

The 202nd target gene is the hsa-miR-4525 gene, a congener thereof, a transcript thereof, or a variant or derivative thereof. None of the previously known reports show that change in the expression of the gene or the transcript thereof can serve as a marker for dementia.

The 203rd target gene is the hsa-miR-4651 gene, a congener thereof, a transcript thereof, or a variant or derivative thereof. None of the previously known reports show that change in the expression of the gene or the transcript thereof can serve as a marker for dementia.

The 204th target gene is the hsa-miR-6813-5p gene, a congener thereof, a transcript thereof, or a variant or derivative thereof. None of the previously known reports show that change in the expression of the gene or the transcript thereof can serve as a marker for dementia.

The 205th target gene is the hsa-miR-5787 gene, a congener thereof, a transcript thereof, or a variant or derivative thereof. None of the previously known reports show that change in the expression of the gene or the transcript thereof can serve as a marker for dementia.

The 206th target gene is the hsa-miR-1290 gene, a congener thereof, a transcript thereof, or a variant or derivative thereof. None of the previously known reports show that change in the expression of the gene or the transcript thereof can serve as a marker for dementia.

The 207th target gene is the hsa-miR-6075 gene, a congener thereof, a transcript thereof, or a variant or derivative thereof. None of the previously known reports show that change in the expression of the gene or the transcript thereof can serve as a marker for dementia.

The 208th target gene is the hsa-miR-4758-5p gene, a congener thereof, a transcript thereof, or a variant or derivative thereof. None of the previously known reports show that change in the expression of the gene or the transcript thereof can serve as a marker for dementia.

The 209th target gene is the hsa-miR-4690-5p gene, a congener thereof, a transcript thereof, or a variant or derivative thereof. None of the previously known reports show that change in the expression of the gene or the transcript thereof can serve as a marker for dementia.

The 210th target gene is the hsa-miR-762 gene, a congener thereof, a transcript thereof, or a variant or derivative thereof. None of the previously known reports show that change in the expression of the gene or the transcript thereof can serve as a marker for dementia.

The 211st target gene is the hsa-miR-1225-3p gene, a congener thereof, a transcript thereof, or a variant or derivative thereof. The previously known report shows that change in the expression of the gene or the transcript thereof can serve as a marker for dementia (Patent Literature 5).

The 212nd target gene is the hsa-miR-3184-5p gene, a congener thereof, a transcript thereof, or a variant or derivative thereof. The previously known report shows that change in the expression of the gene or the transcript thereof can serve as a marker for dementia (Patent Literature 5).

The 213rd target gene is the hsa-miR-665 gene, a congener thereof, a transcript thereof, or a variant or derivative thereof. The previously known report shows that change in the expression of the gene or the transcript thereof can serve as a marker for dementia (Patent Literature 3).

The 214th target gene is the hsa-miR-211-5p gene, a congener thereof, a transcript thereof, or a variant or derivative thereof. The previously known report shows that change in the expression of the gene or the transcript thereof can serve as a marker for dementia (U.S. Patent Application Publication No. 2005/0261218).

The 215th target gene is the hsa-miR-1247-5p gene, a congener thereof, a transcript thereof, or a variant or derivative thereof. The previously known report shows that change in the expression of the gene or the transcript thereof can serve as a marker for dementia (Patent Literature 5).

The 216th target gene is the hsa-miR-3656 gene, a congener thereof, a transcript thereof, or a variant or derivative thereof. The previously known report shows that change in the expression of the gene or the transcript thereof can serve as a marker for dementia (Patent Literature 7).

The 217th target gene is the hsa-miR-149-5p gene, a congener thereof, a transcript thereof, or a variant or derivative thereof. The previously known report shows that change in the expression of the gene or the transcript thereof can serve as a marker for dementia (Patent Literature 5).

The 218th target gene is the hsa-miR-744-5p gene, a congener thereof, a transcript thereof, or a variant or derivative thereof. The previously known report shows that change in the expression of the gene or the transcript thereof can serve as a marker for dementia (Patent Literature 6).

The 219th target gene is the hsa-miR-345-5p gene, a congener thereof, a transcript thereof, or a variant or derivative thereof. The previously known report shows that change in the expression of the gene or the transcript thereof can serve as a marker for dementia (Patent Literature 3).

The 220th target gene is the hsa-miR-150-5p gene, a congener thereof, a transcript thereof, or a variant or derivative thereof. The previously known report shows that change in the expression of the gene or the transcript thereof can serve as a marker for dementia (Patent Literature 7).

The 221st target gene is the hsa-miR-191-3p gene, a congener thereof, a transcript thereof, or a variant or derivative thereof. The previously known report shows that change in the expression of the gene or the transcript thereof can serve as a marker for dementia (Patent Literature 2).

The 222nd target gene is the hsa-miR-651-5p gene, a congener thereof, a transcript thereof, or a variant or derivative thereof. The previously known report shows that change in the expression of the gene or the transcript thereof can serve as a marker for dementia (U.S. Patent Application Publication No. 2014/0303025).

The 223rd target gene is the hsa-miR-34a-5p gene, a congener thereof, a transcript thereof, or a variant or derivative thereof. The previously known report shows that change in the expression of the gene or the transcript thereof can serve as a marker for dementia (U.S. Patent Application Publication No. 2013/0040303).

The 224th target gene is the hsa-miR-409-5p gene, a congener thereof, a transcript thereof, or a variant or derivative thereof. The previously known report shows that change in the expression of the gene or the transcript thereof can serve as a marker for dementia (Patent Literature 5).

The 225th target gene is the hsa-miR-369-5p gene, a congener thereof, a transcript thereof, or a variant or derivative thereof. The previously known report shows that change in the expression of the gene or the transcript thereof can serve as a marker for dementia (Patent Literature 5).

The 226th target gene is the hsa-miR-1915-5p gene, a congener thereof, a transcript thereof, or a variant or derivative thereof. The previously known report shows that change in the expression of the gene or the transcript thereof can serve as a marker for dementia (Patent Literature 5).

The 227th target gene is the hsa-miR-204-5p gene, a congener thereof, a transcript thereof, or a variant or derivative thereof. The previously known report shows that change in the expression of the gene or the transcript thereof can serve as a marker for dementia (Patent Literature 5).

The 228th target gene is the hsa-miR-137 gene, a congener thereof, a transcript thereof, or a variant or derivative thereof. The previously known report shows that change in the expression of the gene or the transcript thereof can serve as a marker for dementia (Patent Literature 4).

The 229th target gene is the hsa-miR-382-5p gene, a congener thereof, a transcript thereof, or a variant or derivative thereof. The previously known report shows that change in the expression of the gene or the transcript thereof can serve as a marker for dementia (Patent Literature 3).

The 230th target gene is the hsa-miR-517-5p gene, a congener thereof, a transcript thereof, or a variant or derivative thereof. The previously known report shows that change in the expression of the gene or the transcript thereof can serve as a marker for dementia (U.S. Patent Application Publication No. 2013/0040303).

The 231st target gene is the hsa-miR-532-5p gene, a congener thereof, a transcript thereof, or a variant or derivative thereof. The previously known report shows that change in the expression of the gene or the transcript thereof can serve as a marker for dementia (U.S. Patent Application Publication No. 2016/0273040).

The 232nd target gene is the hsa-miR-22-5p gene, a congener thereof, a transcript thereof, or a variant or derivative thereof. The previously known report shows that change in the expression of the gene or the transcript thereof can serve as a marker for dementia (International Publication No. WO 2017/186719).

The 233rd target gene is the hsa-miR-1237-3p gene, a congener thereof, a transcript thereof, or a variant or derivative thereof. The previously known report shows that change in the expression of the gene or the transcript thereof can serve as a marker for dementia (Patent Literature 5).

The 234th target gene is the hsa-miR-1224-3p gene, a congener thereof, a transcript thereof, or a variant or derivative thereof. The previously known report shows that change in the expression of the gene or the transcript thereof can serve as a marker for dementia (Patent Literature 5).

The 235th target gene is the hsa-miR-625-3p gene, a congener thereof, a transcript thereof, or a variant or derivative thereof. The previously known report shows that change in the expression of the gene or the transcript thereof can serve as a marker for dementia (Patent Literature 1).

The 236th target gene is the hsa-miR-328-3p gene, a congener thereof, a transcript thereof, or a variant or derivative thereof. The previously known report shows that change in the expression of the gene or the transcript thereof can serve as a marker for dementia (Patent Literature 7).

The 237th target gene is the hsa-miR-122-5p gene, a congener thereof, a transcript thereof, or a variant or derivative thereof. The previously known report shows that change in the expression of the gene or the transcript thereof can serve as a marker for dementia (Patent Literature 7).

The 238th target gene is the hsa-miR-202-3p gene, a congener thereof, a transcript thereof, or a variant or derivative thereof. The previously known report shows that change in the expression of the gene or the transcript thereof can serve as a marker for dementia (Patent Literature 7).

The 239th target gene is the hsa-miR-4781-5p gene, a congener thereof, a transcript thereof, or a variant or derivative thereof. The previously known report shows that change in the expression of the gene or the transcript thereof can serve as a marker for dementia (U.S. Patent Application Publication No. 2016/0273040).

The 240th target gene is the hsa-miR-718 gene, a congener thereof, a transcript thereof, or a variant or derivative thereof. The previously known report shows that change in the expression of the gene or the transcript thereof can serve as a marker for dementia (Patent Literature 5).

The 241st target gene is the hsa-miR-342-3p gene, a congener thereof, a transcript thereof, or a variant or derivative thereof. The previously known report shows that change in the expression of the gene or the transcript thereof can serve as a marker for dementia (Patent Literature 3).

The 242nd target gene is the hsa-miR-26b-3p gene, a congener thereof, a transcript thereof, or a variant or derivative thereof. The previously known report shows that change in the expression of the gene or the transcript thereof can serve as a marker for dementia (Satoh J., et al., Biomark Insights., 2015, vol. 10, pp. 21-23).

The 243rd target gene is the hsa-miR-140-3p gene, a congener thereof, a transcript thereof, or a variant or derivative thereof. The previously known report shows that change in the expression of the gene or the transcript thereof can serve as a marker for dementia (Patent Literature 1).

The 244th target gene is the hsa-miR-200a-3p gene, a congener thereof, a transcript thereof, or a variant or derivative thereof. The previously known report shows that change in the expression of the gene or the transcript thereof can serve as a marker for dementia (International Publication No. WO 2017/186719).

The 245th target gene is the hsa-miR-378a-3p gene, a congener thereof, a transcript thereof, or a variant or derivative thereof. The previously known report shows that change in the expression of the gene or the transcript thereof can serve as a marker for dementia (Patent Literature 5).

The 246th target gene is the hsa-miR-484 gene, a congener thereof, a transcript thereof, or a variant or derivative thereof. The previously known report shows that change in the expression of the gene or the transcript thereof can serve as a marker for dementia (Patent Literature 1).

The 247th target gene is the hsa-miR-296-5p gene, a congener thereof, a transcript thereof, or a variant or derivative thereof. The previously known report shows that change in the expression of the gene or the transcript thereof can serve as a marker for dementia (Patent Literature 5).

The 248th target gene is the hsa-miR-205-5p gene, a congener thereof, a transcript thereof, or a variant or derivative thereof. The previously known report shows that change in the expression of the gene or the transcript thereof can serve as a marker for dementia (Patent Literature 7).

The 249th target gene is the hsa-miR-431-5p gene, a congener thereof, a transcript thereof, or a variant or derivative thereof. The previously known report shows that change in the expression of the gene or the transcript thereof can serve as a marker for dementia (Patent Literature 7).

The 250th target gene is the hsa-miR-1471 gene, a congener thereof, a transcript thereof, or a variant or derivative thereof. None of the previously known reports show that change in the expression of the gene or the transcript thereof can serve as a marker for dementia.

The 251st target gene is the hsa-miR-1538 gene, a congener thereof, a transcript thereof, or a variant or derivative thereof. None of the previously known reports show that change in the expression of the gene or the transcript thereof can serve as a marker for dementia.

The 252nd target gene is the hsa-miR-449b-3p gene, a congener thereof, a transcript thereof, or a variant or derivative thereof. None of the previously known reports show that change in the expression of the gene or the transcript thereof can serve as a marker for dementia.

The 253rd target gene is the hsa-miR-1976 gene, a congener thereof, a transcript thereof, or a variant or derivative thereof. None of the previously known reports show that change in the expression of the gene or the transcript thereof can serve as a marker for dementia.

The 254th target gene is the hsa-miR-4268 gene, a congener thereof, a transcript thereof, or a variant or derivative thereof. None of the previously known reports show that change in the expression of the gene or the transcript thereof can serve as a marker for dementia.

The 255th target gene is the hsa-miR-4279 gene, a congener thereof, a transcript thereof, or a variant or derivative thereof. None of the previously known reports show that change in the expression of the gene or the transcript thereof can serve as a marker for dementia.

The 256th target gene is the hsa-miR-3620-3p gene, a congener thereof, a transcript thereof, or a variant or derivative thereof. None of the previously known reports show that change in the expression of the gene or the transcript thereof can serve as a marker for dementia.

The 257th target gene is the hsa-miR-3944-3p gene, a congener thereof, a transcript thereof, or a variant or derivative thereof. None of the previously known reports show that change in the expression of the gene or the transcript thereof can serve as a marker for dementia.

The 258th target gene is the hsa-miR-3156-3p gene, a congener thereof, a transcript thereof, or a variant or derivative thereof. None of the previously known reports show that change in the expression of the gene or the transcript thereof can serve as a marker for dementia.

The 259th target gene is the hsa-miR-3187-5p gene, a congener thereof, a transcript thereof, or a variant or derivative thereof. None of the previously known reports show that change in the expression of the gene or the transcript thereof can serve as a marker for dementia.

The 260th target gene is the hsa-miR-4685-3p gene, a congener thereof, a transcript thereof, or a variant or derivative thereof. None of the previously known reports show that change in the expression of the gene or the transcript thereof can serve as a marker for dementia.

The 261st target gene is the hsa-miR-4695-3p gene, a congener thereof, a transcript thereof, or a variant or derivative thereof. None of the previously known reports show that change in the expression of the gene or the transcript thereof can serve as a marker for dementia.

The 262nd target gene is the hsa-miR-4697-3p gene, a congener thereof, a transcript thereof, or a variant or derivative thereof. None of the previously known reports show that change in the expression of the gene or the transcript thereof can serve as a marker for dementia.

The 263rd target gene is the hsa-miR-4713-5p gene, a congener thereof, a transcript thereof, or a variant or derivative thereof. None of the previously known reports show that change in the expression of the gene or the transcript thereof can serve as a marker for dementia.

The 264th target gene is the hsa-miR-4723-3p gene, a congener thereof, a transcript thereof, or a variant or derivative thereof. None of the previously known reports show that change in the expression of the gene or the transcript thereof can serve as a marker for dementia.

The 265th target gene is the hsa-miR-371b-3p gene, a congener thereof, a transcript thereof, or a variant or derivative thereof. None of the previously known reports show that change in the expression of the gene or the transcript thereof can serve as a marker for dementia.

The 266th target gene is the hsa-miR-3151-3p gene, a congener thereof, a transcript thereof, or a variant or derivative thereof. None of the previously known reports show that change in the expression of the gene or the transcript thereof can serve as a marker for dementia.

The 267th target gene is the hsa-miR-3192-3p gene, a congener thereof, a transcript thereof, or a variant or derivative thereof. None of the previously known reports show that change in the expression of the gene or the transcript thereof can serve as a marker for dementia.

The 268th target gene is the hsa-miR-6728-3p gene, a congener thereof, a transcript thereof, or a variant or derivative thereof. None of the previously known reports show that change in the expression of the gene or the transcript thereof can serve as a marker for dementia.

The 269th target gene is the hsa-miR-6736-3p gene, a congener thereof, a transcript thereof, or a variant or derivative thereof. None of the previously known reports show that change in the expression of the gene or the transcript thereof can serve as a marker for dementia.

The 270th target gene is the hsa-miR-6740-3p gene, a congener thereof, a transcript thereof, or a variant or derivative thereof. None of the previously known reports show that change in the expression of the gene or the transcript thereof can serve as a marker for dementia.

The 271st target gene is the hsa-miR-6741-3p gene, a congener thereof, a transcript thereof, or a variant or derivative thereof. None of the previously known reports show that change in the expression of the gene or the transcript thereof can serve as a marker for dementia.

The 272nd target gene is the hsa-miR-6743-3p gene, a congener thereof, a transcript thereof, or a variant or derivative thereof. None of the previously known reports show that change in the expression of the gene or the transcript thereof can serve as a marker for dementia.

The 273rd target gene is the hsa-miR-6747-3p gene, a congener thereof, a transcript thereof, or a variant or derivative thereof. None of the previously known reports show that change in the expression of the gene or the transcript thereof can serve as a marker for dementia.

The 274th target gene is the hsa-miR-6750-3p gene, a congener thereof, a transcript thereof, or a variant or derivative thereof. None of the previously known reports show that change in the expression of the gene or the transcript thereof can serve as a marker for dementia.

The 275th target gene is the hsa-miR-6754-3p gene, a congener thereof, a transcript thereof, or a variant or derivative thereof. None of the previously known reports show that change in the expression of the gene or the transcript thereof can serve as a marker for dementia.

The 276th target gene is the hsa-miR-6759-3p gene, a congener thereof, a transcript thereof, or a variant or derivative thereof. None of the previously known reports show that change in the expression of the gene or the transcript thereof can serve as a marker for dementia.

The 277th target gene is the hsa-miR-6761-3p gene, a congener thereof, a transcript thereof, or a variant or derivative thereof. None of the previously known reports show that change in the expression of the gene or the transcript thereof can serve as a marker for dementia.

The 278th target gene is the hsa-miR-6762-3p gene, a congener thereof, a transcript thereof, or a variant or derivative thereof. None of the previously known reports show that change in the expression of the gene or the transcript thereof can serve as a marker for dementia.

The 279th target gene is the hsa-miR-6769a-3p gene, a congener thereof, a transcript thereof, or a variant or derivative thereof. None of the previously known reports show that change in the expression of the gene or the transcript thereof can serve as a marker for dementia.

The 280th target gene is the hsa-miR-6776-3p gene, a congener thereof, a transcript thereof, or a variant or derivative thereof. None of the previously known reports show that change in the expression of the gene or the transcript thereof can serve as a marker for dementia.

The 281st target gene is the hsa-miR-6778-3p gene, a congener thereof, a transcript thereof, or a variant or derivative thereof. None of the previously known reports show that change in the expression of the gene or the transcript thereof can serve as a marker for dementia.

The 282nd target gene is the hsa-miR-6779-3p gene, a congener thereof, a transcript thereof, or a variant or derivative thereof. None of the previously known reports show that change in the expression of the gene or the transcript thereof can serve as a marker for dementia.

The 283rd target gene is the hsa-miR-6786-3p gene, a congener thereof, a transcript thereof, or a variant or derivative thereof. None of the previously known reports show that change in the expression of the gene or the transcript thereof can serve as a marker for dementia.

The 284th target gene is the hsa-miR-6787-3p gene, a congener thereof, a transcript thereof, or a variant or derivative thereof. None of the previously known reports show that change in the expression of the gene or the transcript thereof can serve as a marker for dementia.

The 285th target gene is the hsa-miR-6792-3p gene, a congener thereof, a transcript thereof, or a variant or derivative thereof. None of the previously known reports show that change in the expression of the gene or the transcript thereof can serve as a marker for dementia.

The 286th target gene is the hsa-miR-6794-3p gene, a congener thereof, a transcript thereof, or a variant or derivative thereof. None of the previously known reports show that change in the expression of the gene or the transcript thereof can serve as a marker for dementia.

The 287th target gene is the hsa-miR-6801-3p gene, a congener thereof, a transcript thereof, or a variant or derivative thereof. None of the previously known reports show that change in the expression of the gene or the transcript thereof can serve as a marker for dementia.

The 288th target gene is the hsa-miR-6802-3p gene, a congener thereof, a transcript thereof, or a variant or derivative thereof. None of the previously known reports show that change in the expression of the gene or the transcript thereof can serve as a marker for dementia.

The 289th target gene is the hsa-miR-6803-3p gene, a congener thereof, a transcript thereof, or a variant or derivative thereof. None of the previously known reports show that change in the expression of the gene or the transcript thereof can serve as a marker for dementia.

The 290th target gene is the hsa-miR-6804-3p gene, a congener thereof, a transcript thereof, or a variant or derivative thereof. None of the previously known reports show that change in the expression of the gene or the transcript thereof can serve as a marker for dementia.

The 291st target gene is the hsa-miR-6810-5p gene, a congener thereof, a transcript thereof, or a variant or derivative thereof. None of the previously known reports show that change in the expression of the gene or the transcript thereof can serve as a marker for dementia.

The 292nd target gene is the hsa-miR-6823-3p gene, a congener thereof, a transcript thereof, or a variant or derivative thereof. None of the previously known reports show that change in the expression of the gene or the transcript thereof can serve as a marker for dementia.

The 293rd target gene is the hsa-miR-6825-3p gene, a congener thereof, a transcript thereof, or a variant or derivative thereof. None of the previously known reports show that change in the expression of the gene or the transcript thereof can serve as a marker for dementia.

The 294th target gene is the hsa-miR-6829-3p gene, a congener thereof, a transcript thereof, or a variant or derivative thereof. None of the previously known reports show that change in the expression of the gene or the transcript thereof can serve as a marker for dementia.

The 295th target gene is the hsa-miR-6833-3p gene, a congener thereof, a transcript thereof, or a variant or derivative thereof. None of the previously known reports show that change in the expression of the gene or the transcript thereof can serve as a marker for dementia.

The 296th target gene is the hsa-miR-6834-3p gene, a congener thereof, a transcript thereof, or a variant or derivative thereof. None of the previously known reports show that change in the expression of the gene or the transcript thereof can serve as a marker for dementia.

The 297th target gene is the hsa-miR-6780b-3p gene, a congener thereof, a transcript thereof, or a variant or derivative thereof. None of the previously known reports show that change in the expression of the gene or the transcript thereof can serve as a marker for dementia.

The 298th target gene is the hsa-miR-6845-3p gene, a congener thereof, a transcript thereof, or a variant or derivative thereof. None of the previously known reports show that change in the expression of the gene or the transcript thereof can serve as a marker for dementia.

The 299th target gene is the hsa-miR-6862-3p gene, a congener thereof, a transcript thereof, or a variant or derivative thereof. None of the previously known reports show that change in the expression of the gene or the transcript thereof can serve as a marker for dementia.

The 300th target gene is the hsa-miR-6865-3p gene, a congener thereof, a transcript thereof, or a variant or derivative thereof. None of the previously known reports show that change in the expression of the gene or the transcript thereof can serve as a marker for dementia.

The 301st target gene is the hsa-miR-6870-3p gene, a congener thereof, a transcript thereof, or a variant or derivative thereof. None of the previously known reports show that change in the expression of the gene or the transcript thereof can serve as a marker for dementia.

The 302nd target gene is the hsa-miR-6875-3p gene, a congener thereof, a transcript thereof, or a variant or derivative thereof. None of the previously known reports show that change in the expression of the gene or the transcript thereof can serve as a marker for dementia.

The 303rd target gene is the hsa-miR-6877-3p gene, a congener thereof, a transcript thereof, or a variant or derivative thereof. None of the previously known reports show that change in the expression of the gene or the transcript thereof can serve as a marker for dementia.

The 304th target gene is the hsa-miR-6879-3p gene, a congener thereof, a transcript thereof, or a variant or derivative thereof. None of the previously known reports show that change in the expression of the gene or the transcript thereof can serve as a marker for dementia.

The 305th target gene is the hsa-miR-6882-3p gene, a congener thereof, a transcript thereof, or a variant or derivative thereof. None of the previously known reports show that change in the expression of the gene or the transcript thereof can serve as a marker for dementia.

The 306th target gene is the hsa-miR-6885-3p gene, a congener thereof, a transcript thereof, or a variant or derivative thereof. None of the previously known reports show that change in the expression of the gene or the transcript thereof can serve as a marker for dementia.

The 307th target gene is the hsa-miR-6886-3p gene, a congener thereof, a transcript thereof, or a variant or derivative thereof. None of the previously known reports show that change in the expression of the gene or the transcript thereof can serve as a marker for dementia.

The 308th target gene is the hsa-miR-6887-3p gene, a congener thereof, a transcript thereof, or a variant or derivative thereof. None of the previously known reports show that change in the expression of the gene or the transcript thereof can serve as a marker for dementia.

The 309th target gene is the hsa-miR-6890-3p gene, a congener thereof, a transcript thereof, or a variant or derivative thereof. None of the previously known reports show that change in the expression of the gene or the transcript thereof can serve as a marker for dementia.

The 310th target gene is the hsa-miR-6893-3p gene, a congener thereof, a transcript thereof, or a variant or derivative thereof. None of the previously known reports show that change in the expression of the gene or the transcript thereof can serve as a marker for dementia.

The 311st target gene is the hsa-miR-6894-3p gene, a congener thereof, a transcript thereof, or a variant or derivative thereof. None of the previously known reports show that change in the expression of the gene or the transcript thereof can serve as a marker for dementia.

The 312nd target gene is the hsa-miR-7106-3p gene, a congener thereof, a transcript thereof, or a variant or derivative thereof. None of the previously known reports show that change in the expression of the gene or the transcript thereof can serve as a marker for dementia.

The 313rd target gene is the hsa-miR-7109-3p gene, a congener thereof, a transcript thereof, or a variant or derivative thereof. None of the previously known reports show that change in the expression of the gene or the transcript thereof can serve as a marker for dementia.

The 314th target gene is the hsa-miR-7114-3p gene, a congener thereof, a transcript thereof, or a variant or derivative thereof. None of the previously known reports show that change in the expression of the gene or the transcript thereof can serve as a marker for dementia.

The 315th target gene is the hsa-miR-7155-5p gene, a congener thereof, a transcript thereof, or a variant or derivative thereof. None of the previously known reports show that change in the expression of the gene or the transcript thereof can serve as a marker for dementia.

The 316th target gene is the hsa-miR-7160-5p gene, a congener thereof, a transcript thereof, or a variant or derivative thereof. None of the previously known reports show that change in the expression of the gene or the transcript thereof can serve as a marker for dementia.

The 317th target gene is the hsa-miR-615-3p gene, a congener thereof, a transcript thereof, or a variant or derivative thereof. None of the previously known reports show that change in the expression of the gene or the transcript thereof can serve as a marker for dementia.

The 318th target gene is the hsa-miR-920 gene, a congener thereof, a transcript thereof, or a variant or derivative thereof. None of the previously known reports show that change in the expression of the gene or the transcript thereof can serve as a marker for dementia.

The 319th target gene is the hsa-miR-1825 gene, a congener thereof, a transcript thereof, or a variant or derivative thereof. None of the previously known reports show that change in the expression of the gene or the transcript thereof can serve as a marker for dementia.

The 320th target gene is the hsa-miR-675-3p gene, a congener thereof, a transcript thereof, or a variant or derivative thereof. None of the previously known reports show that change in the expression of the gene or the transcript thereof can serve as a marker for dementia.

The 321st target gene is the hsa-miR-1910-5p gene, a congener thereof, a transcript thereof, or a variant or derivative thereof. None of the previously known reports show that change in the expression of the gene or the transcript thereof can serve as a marker for dementia.

The 322nd target gene is the hsa-miR-2278 gene, a congener thereof, a transcript thereof, or a variant or derivative thereof. None of the previously known reports show that change in the expression of the gene or the transcript thereof can serve as a marker for dementia.

The 323rd target gene is the hsa-miR-2682-3p gene, a congener thereof, a transcript thereof, or a variant or derivative thereof. None of the previously known reports show that change in the expression of the gene or the transcript thereof can serve as a marker for dementia.

The 324th target gene is the hsa-miR-3122 gene, a congener thereof, a transcript thereof, or a variant or derivative thereof. None of the previously known reports show that change in the expression of the gene or the transcript thereof can serve as a marker for dementia.

The 325th target gene is the hsa-miR-3151-5p gene, a congener thereof, a transcript thereof, or a variant or derivative thereof. None of the previously known reports show that change in the expression of the gene or the transcript thereof can serve as a marker for dementia.

The 326th target gene is the hsa-miR-3175 gene, a congener thereof, a transcript thereof, or a variant or derivative thereof. None of the previously known reports show that change in the expression of the gene or the transcript thereof can serve as a marker for dementia.

The 327th target gene is the hsa-miR-4323 gene, a congener thereof, a transcript thereof, or a variant or derivative thereof. None of the previously known reports show that change in the expression of the gene or the transcript thereof can serve as a marker for dementia.

The 328th target gene is the hsa-miR-4326 gene, a congener thereof, a transcript thereof, or a variant or derivative thereof. None of the previously known reports show that change in the expression of the gene or the transcript thereof can serve as a marker for dementia.

The 329th target gene is the hsa-miR-4284 gene, a congener thereof, a transcript thereof, or a variant or derivative thereof. None of the previously known reports show that change in the expression of the gene or the transcript thereof can serve as a marker for dementia.

The 330th target gene is the hsa-miR-3605-3p gene, a congener thereof, a transcript thereof, or a variant or derivative thereof. None of the previously known reports show that change in the expression of the gene or the transcript thereof can serve as a marker for dementia.

The 331st target gene is the hsa-miR-3622b-5p gene, a congener thereof, a transcript thereof, or a variant or derivative thereof. None of the previously known reports show that change in the expression of the gene or the transcript thereof can serve as a marker for dementia.

The 332nd target gene is the hsa-miR-3646 gene, a congener thereof, a transcript thereof, or a variant or derivative thereof. None of the previously known reports show that change in the expression of the gene or the transcript thereof can serve as a marker for dementia.

The 333rd target gene is the hsa-miR-3158-5p gene, a congener thereof, a transcript thereof, or a variant or derivative thereof. None of the previously known reports show that change in the expression of the gene or the transcript thereof can serve as a marker for dementia.

The 334th target gene is the hsa-miR-4722-3p gene, a congener thereof, a transcript thereof, or a variant or derivative thereof. None of the previously known reports show that change in the expression of the gene or the transcript thereof can serve as a marker for dementia.

The 335th target gene is the hsa-miR-4728-3p gene, a congener thereof, a transcript thereof, or a variant or derivative thereof. None of the previously known reports show that change in the expression of the gene or the transcript thereof can serve as a marker for dementia.

The 336th target gene is the hsa-miR-4747-3p gene, a congener thereof, a transcript thereof, or a variant or derivative thereof. None of the previously known reports show that change in the expression of the gene or the transcript thereof can serve as a marker for dementia.

The 337th target gene is the hsa-miR-4436b-5p gene, a congener thereof, a transcript thereof, or a variant or derivative thereof. None of the previously known reports show that change in the expression of the gene or the transcript thereof can serve as a marker for dementia.

The 338th target gene is the hsa-miR-5196-3p gene, a congener thereof, a transcript thereof, or a variant or derivative thereof. None of the previously known reports show that change in the expression of the gene or the transcript thereof can serve as a marker for dementia.

The 339th target gene is the hsa-miR-5589-5p gene, a congener thereof, a transcript thereof, or a variant or derivative thereof. None of the previously known reports show that change in the expression of the gene or the transcript thereof can serve as a marker for dementia.

The 340th target gene is the hsa-miR-345-3p gene, a congener thereof, a transcript thereof, or a variant or derivative thereof. None of the previously known reports show that change in the expression of the gene or the transcript thereof can serve as a marker for dementia.

The 341st target gene is the hsa-miR-642b-5p gene, a congener thereof, a transcript thereof, or a variant or derivative thereof. None of the previously known reports show that change in the expression of the gene or the transcript thereof can serve as a marker for dementia.

The 342nd target gene is the hsa-miR-6716-3p gene, a congener thereof, a transcript thereof, or a variant or derivative thereof. None of the previously known reports show that change in the expression of the gene or the transcript thereof can serve as a marker for dementia.

The 343rd target gene is the hsa-miR-6511b-3p gene, a congener thereof, a transcript thereof, or a variant or derivative thereof. None of the previously known reports show that change in the expression of the gene or the transcript thereof can serve as a marker for dementia.

The 344th target gene is the hsa-miR-208a-5p gene, a congener thereof, a transcript thereof, or a variant or derivative thereof. None of the previously known reports show that change in the expression of the gene or the transcript thereof can serve as a marker for dementia.

The 345th target gene is the hsa-miR-6726-3p gene, a congener thereof, a transcript thereof, or a variant or derivative thereof. None of the previously known reports show that change in the expression of the gene or the transcript thereof can serve as a marker for dementia.

The 346th target gene is the hsa-miR-6744-5p gene, a congener thereof, a transcript thereof, or a variant or derivative thereof. None of the previously known reports show that change in the expression of the gene or the transcript thereof can serve as a marker for dementia.

The 347th target gene is the hsa-miR-6782-3p gene, a congener thereof, a transcript thereof, or a variant or derivative thereof. None of the previously known reports show that change in the expression of the gene or the transcript thereof can serve as a marker for dementia.

The 348th target gene is the hsa-miR-6789-3p gene, a congener thereof, a transcript thereof, or a variant or derivative thereof. None of the previously known reports show that change in the expression of the gene or the transcript thereof can serve as a marker for dementia.

The 349th target gene is the hsa-miR-6797-3p gene, a congener thereof, a transcript thereof, or a variant or derivative thereof. None of the previously known reports show that change in the expression of the gene or the transcript thereof can serve as a marker for dementia.

The 350th target gene is the hsa-miR-6800-3p gene, a congener thereof, a transcript thereof, or a variant or derivative thereof. None of the previously known reports show that change in the expression of the gene or the transcript thereof can serve as a marker for dementia.

The 351st target gene is the hsa-miR-6806-5p gene, a congener thereof, a transcript thereof, or a variant or derivative thereof. None of the previously known reports show that change in the expression of the gene or the transcript thereof can serve as a marker for dementia.

The 352nd target gene is the hsa-miR-6824-3p gene, a congener thereof, a transcript thereof, or a variant or derivative thereof. None of the previously known reports show that change in the expression of the gene or the transcript thereof can serve as a marker for dementia.

The 353rd target gene is the hsa-miR-6837-5p gene, a congener thereof, a transcript thereof, or a variant or derivative thereof. None of the previously known reports show that change in the expression of the gene or the transcript thereof can serve as a marker for dementia.

The 354th target gene is the hsa-miR-6846-3p gene, a congener thereof, a transcript thereof, or a variant or derivative thereof. None of the previously known reports show that change in the expression of the gene or the transcript thereof can serve as a marker for dementia.

The 355th target gene is the hsa-miR-6858-3p gene, a congener thereof, a transcript thereof, or a variant or derivative thereof. None of the previously known reports show that change in the expression of the gene or the transcript thereof can serve as a marker for dementia.

The 356th target gene is the hsa-miR-6859-3p gene, a congener thereof, a transcript thereof, or a variant or derivative thereof. None of the previously known reports show that change in the expression of the gene or the transcript thereof can serve as a marker for dementia.

The 357th target gene is the hsa-miR-6861-3p gene, a congener thereof, a transcript thereof, or a variant or derivative thereof. None of the previously known reports show that change in the expression of the gene or the transcript thereof can serve as a marker for dementia.

The 358th target gene is the hsa-miR-6880-3p gene, a congener thereof, a transcript thereof, or a variant or derivative thereof. None of the previously known reports show that change in the expression of the gene or the transcript thereof can serve as a marker for dementia.

The 359th target gene is the hsa-miR-7111-3p gene, a congener thereof, a transcript thereof, or a variant or derivative thereof. None of the previously known reports show that change in the expression of the gene or the transcript thereof can serve as a marker for dementia.

The 360th target gene is the hsa-miR-7152-5p gene, a congener thereof, a transcript thereof, or a variant or derivative thereof. None of the previously known reports show that change in the expression of the gene or the transcript thereof can serve as a marker for dementia.

The 361st target gene is the hsa-miR-642a-5p gene, a congener thereof, a transcript thereof, or a variant or derivative thereof. None of the previously known reports show that change in the expression of the gene or the transcript thereof can serve as a marker for dementia.

The 362nd target gene is the hsa-miR-657 gene, a congener thereof, a transcript thereof, or a variant or derivative thereof. None of the previously known reports show that change in the expression of the gene or the transcript thereof can serve as a marker for dementia.

The 363rd target gene is the hsa-miR-1236-3p gene, a congener thereof, a transcript thereof, or a variant or derivative thereof. None of the previously known reports show that change in the expression of the gene or the transcript thereof can serve as a marker for dementia.

The 364th target gene is the hsa-miR-764 gene, a congener thereof, a transcript thereof, or a variant or derivative thereof. None of the previously known reports show that change in the expression of the gene or the transcript thereof can serve as a marker for dementia.

The 365th target gene is the hsa-miR-4314 gene, a congener thereof, a transcript thereof, or a variant or derivative thereof. None of the previously known reports show that change in the expression of the gene or the transcript thereof can serve as a marker for dementia.

The 366th target gene is the hsa-miR-3675-3p gene, a congener thereof, a transcript thereof, or a variant or derivative thereof. None of the previously known reports show that change in the expression of the gene or the transcript thereof can serve as a marker for dementia.

The 367th target gene is the hsa-miR-5703 gene, a congener thereof, a transcript thereof, or a variant or derivative thereof. None of the previously known reports show that change in the expression of the gene or the transcript thereof can serve as a marker for dementia.

The 368th target gene is the hsa-miR-3191-5p gene, a congener thereof, a transcript thereof, or a variant or derivative thereof. None of the previously known reports show that change in the expression of the gene or the transcript thereof can serve as a marker for dementia.

The 369th target gene is the hsa-miR-6511a-3p gene, a congener thereof, a transcript thereof, or a variant or derivative thereof. None of the previously known reports show that change in the expression of the gene or the transcript thereof can serve as a marker for dementia.

The 370th target gene is the hsa-miR-6809-3p gene, a congener thereof, a transcript thereof, or a variant or derivative thereof. None of the previously known reports show that change in the expression of the gene or the transcript thereof can serve as a marker for dementia.

The 371st target gene is the hsa-miR-6815-5p gene, a congener thereof, a transcript thereof, or a variant or derivative thereof. None of the previously known reports show that change in the expression of the gene or the transcript thereof can serve as a marker for dementia.

The 372nd target gene is the hsa-miR-6857-3p gene, a congener thereof, a transcript thereof, or a variant or derivative thereof. None of the previously known reports show that change in the expression of the gene or the transcript thereof can serve as a marker for dementia.

The 373rd target gene is the hsa-miR-6878-3p gene, a congener thereof, a transcript thereof, or a variant or derivative thereof. None of the previously known reports show that change in the expression of the gene or the transcript thereof can serve as a marker for dementia.

The 374th target gene is the hsa-miR-371a-5p gene, a congener thereof, a transcript thereof, or a variant or derivative thereof. None of the previously known reports show that change in the expression of the gene or the transcript thereof can serve as a marker for dementia.

The 375th target gene is the hsa-miR-766-3p gene, a congener thereof, a transcript thereof, or a variant or derivative thereof. The previously known report shows that change in the expression of the gene or the transcript thereof can serve as a marker for dementia (Patent Literature 5).

The 376th target gene is the hsa-miR-1229-3p gene, a congener thereof, a transcript thereof, or a variant or derivative thereof. The previously known report shows that change in the expression of the gene or the transcript thereof can serve as a marker for dementia (Patent Literature 7).

The 377th target gene is the hsa-miR-1306-5p gene, a congener thereof, a transcript thereof, or a variant or derivative thereof. The previously known report shows that change in the expression of the gene or the transcript thereof can serve as a marker for dementia (Patent Literature 6).

The 378th target gene is the hsa-miR-210-5p gene, a congener thereof, a transcript thereof, or a variant or derivative thereof. The previously known report shows that change in the expression of the gene or the transcript thereof can serve as a marker for dementia (Patent Literature 5).

The 379th target gene is the hsa-miR-198 gene, a congener thereof, a transcript thereof, or a variant or derivative thereof. The previously known report shows that change in the expression of the gene or the transcript thereof can serve as a marker for dementia (Patent Literature 7).

The 380th target gene is the hsa-miR-485-3p gene, a congener thereof, a transcript thereof, or a variant or derivative thereof. The previously known report shows that change in the expression of the gene or the transcript thereof can serve as a marker for dementia (Patent Literature 7).

The 381st target gene is the hsa-miR-668-3p gene, a congener thereof, a transcript thereof, or a variant or derivative thereof. The previously known report shows that change in the expression of the gene or the transcript thereof can serve as a marker for dementia (Patent Literature 4).

The 382nd target gene is the hsa-miR-532-3p gene, a congener thereof, a transcript thereof, or a variant or derivative thereof. The previously known report shows that change in the expression of the gene or the transcript thereof can serve as a marker for dementia (Patent Literature 5).

The 383rd target gene is the hsa-miR-877-3p gene, a congener thereof, a transcript thereof, or a variant or derivative thereof. The previously known report shows that change in the expression of the gene or the transcript thereof can serve as a marker for dementia (Patent Literature 5).

The 384th target gene is the hsa-miR-1238-3p gene, a congener thereof, a transcript thereof, or a variant or derivative thereof. The previously known report shows that change in the expression of the gene or the transcript thereof can serve as a marker for dementia (Patent Literature 2).

The 385th target gene is the hsa-miR-3130-5p gene, a congener thereof, a transcript thereof, or a variant or derivative thereof. The previously known report shows that change in the expression of the gene or the transcript thereof can serve as a marker for dementia (Patent Literature 5).

The 386th target gene is the hsa-miR-4298 gene, a congener thereof, a transcript thereof, or a variant or derivative thereof. The previously known report shows that change in the expression of the gene or the transcript thereof can serve as a marker for dementia (Patent Literature 5).

The 387th target gene is the hsa-miR-4290 gene, a congener thereof, a transcript thereof, or a variant or derivative thereof. The previously known report shows that change in the expression of the gene or the transcript thereof can serve as a marker for dementia (Patent Literature 5).

The 388th target gene is the hsa-miR-3943 gene, a congener thereof, a transcript thereof, or a variant or derivative thereof. The previously known report shows that change in the expression of the gene or the transcript thereof can serve as a marker for dementia (Patent Literature 5).

The 389th target gene is the hsa-miR-346 gene, a congener thereof, a transcript thereof, or a variant or derivative thereof. The previously known report shows that change in the expression of the gene or the transcript thereof can serve as a marker for dementia (Patent Literature 3).

The 390th target gene is the hsa-miR-767-3p gene, a congener thereof, a transcript thereof, or a variant or derivative thereof. The previously known report shows that change in the expression of the gene or the transcript thereof can serve as a marker for dementia (Patent Literature 5).

The 391st target gene is the hsa-miR-6765-3p gene, a congener thereof, a transcript thereof, or a variant or derivative thereof. None of the previously known reports show that change in the expression of the gene or the transcript thereof can serve as a marker for dementia.

The 392nd target gene is the hsa-miR-6784-5p gene, a congener thereof, a transcript thereof, or a variant or derivative thereof. None of the previously known reports show that change in the expression of the gene or the transcript thereof can serve as a marker for dementia.

The 393rd target gene is the hsa-miR-6778-5p gene, a congener thereof, a transcript thereof, or a variant or derivative thereof. None of the previously known reports show that change in the expression of the gene or the transcript thereof can serve as a marker for dementia.

The 394th target gene is the hsa-miR-6875-5p gene, a congener thereof, a transcript thereof, or a variant or derivative thereof. None of the previously known reports show that change in the expression of the gene or the transcript thereof can serve as a marker for dementia.

The 395th target gene is the hsa-miR-4534 gene, a congener thereof, a transcript thereof, or a variant or derivative thereof. None of the previously known reports show that change in the expression of the gene or the transcript thereof can serve as a marker for dementia.

The 396th target gene is the hsa-miR-4721 gene, a congener thereof, a transcript thereof, or a variant or derivative thereof. None of the previously known reports show that change in the expression of the gene or the transcript thereof can serve as a marker for dementia.

The 397th target gene is the hsa-miR-6756-5p gene, a congener thereof, a transcript thereof, or a variant or derivative thereof. None of the previously known reports show that change in the expression of the gene or the transcript thereof can serve as a marker for dementia.

The 398th target gene is the hsa-miR-615-5p gene, a congener thereof, a transcript thereof, or a variant or derivative thereof. None of the previously known reports show that change in the expression of the gene or the transcript thereof can serve as a marker for dementia.

The 399th target gene is the hsa-miR-6727-5p gene, a congener thereof, a transcript thereof, or a variant or derivative thereof. None of the previously known reports show that change in the expression of the gene or the transcript thereof can serve as a marker for dementia.

The 400th target gene is the hsa-miR-6887-5p gene, a congener thereof, a transcript thereof, or a variant or derivative thereof. None of the previously known reports show that change in the expression of the gene or the transcript thereof can serve as a marker for dementia.

The 401st target gene is the hsa-miR-8063 gene, a congener thereof, a transcript thereof, or a variant or derivative thereof. None of the previously known reports show that change in the expression of the gene or the transcript thereof can serve as a marker for dementia.

The 402nd target gene is the hsa-miR-6880-5p gene, a congener thereof, a transcript thereof, or a variant or derivative thereof. None of the previously known reports show that change in the expression of the gene or the transcript thereof can serve as a marker for dementia.

The 403rd target gene is the hsa-miR-6805-3p gene, a congener thereof, a transcript thereof, or a variant or derivative thereof. None of the previously known reports show that change in the expression of the gene or the transcript thereof can serve as a marker for dementia.

The 404th target gene is the hsa-miR-4726-5p gene, a congener thereof, a transcript thereof, or a variant or derivative thereof. None of the previously known reports show that change in the expression of the gene or the transcript thereof can serve as a marker for dementia.

The 405th target gene is the hsa-miR-4710 gene, a congener thereof, a transcript thereof, or a variant or derivative thereof. None of the previously known reports show that change in the expression of the gene or the transcript thereof can serve as a marker for dementia.

The 406th target gene is the hsa-miR-7111-5p gene, a congener thereof, a transcript thereof, or a variant or derivative thereof. None of the previously known reports show that change in the expression of the gene or the transcript thereof can serve as a marker for dementia.

The 407th target gene is the hsa-miR-3619-3p gene, a congener thereof, a transcript thereof, or a variant or derivative thereof. None of the previously known reports show that change in the expression of the gene or the transcript thereof can serve as a marker for dementia.

The 408th target gene is the hsa-miR-6795-5p gene, a congener thereof, a transcript thereof, or a variant or derivative thereof. None of the previously known reports show that change in the expression of the gene or the transcript thereof can serve as a marker for dementia.

The 409th target gene is the hsa-miR-1254 gene, a congener thereof, a transcript thereof, or a variant or derivative thereof. None of the previously known reports show that change in the expression of the gene or the transcript thereof can serve as a marker for dementia.

The 410th target gene is the hsa-miR-1233-5p gene, a congener thereof, a transcript thereof, or a variant or derivative thereof. None of the previously known reports show that change in the expression of the gene or the transcript thereof can serve as a marker for dementia.

The 411st target gene is the hsa-miR-6836-3p gene, a congener thereof, a transcript thereof, or a variant or derivative thereof. None of the previously known reports show that change in the expression of the gene or the transcript thereof can serve as a marker for dementia.

The 412nd target gene is the hsa-miR-6769a-5p gene, a congener thereof, a transcript thereof, or a variant or derivative thereof. None of the previously known reports show that change in the expression of the gene or the transcript thereof can serve as a marker for dementia.

The 413rd target gene is the hsa-miR-4532 gene, a congener thereof, a transcript thereof, or a variant or derivative thereof. None of the previously known reports show that change in the expression of the gene or the transcript thereof can serve as a marker for dementia.

The 414th target gene is the hsa-miR-365a-5p gene, a congener thereof, a transcript thereof, or a variant or derivative thereof. None of the previously known reports show that change in the expression of the gene or the transcript thereof can serve as a marker for dementia.

The 415th target gene is the hsa-miR-1231 gene, a congener thereof, a transcript thereof, or a variant or derivative thereof. None of the previously known reports show that change in the expression of the gene or the transcript thereof can serve as a marker for dementia.

The 416th target gene is the hsa-miR-1228-5p gene, a congener thereof, a transcript thereof, or a variant or derivative thereof. None of the previously known reports show that change in the expression of the gene or the transcript thereof can serve as a marker for dementia.

The 417th target gene is the hsa-miR-4430 gene, a congener thereof, a transcript thereof, or a variant or derivative thereof. None of the previously known reports show that change in the expression of the gene or the transcript thereof can serve as a marker for dementia.

The 418th target gene is the hsa-miR-296-3p gene, a congener thereof, a transcript thereof, or a variant or derivative thereof. None of the previously known reports show that change in the expression of the gene or the transcript thereof can serve as a marker for dementia.

The 419th target gene is the hsa-miR-1237-5p gene, a congener thereof, a transcript thereof, or a variant or derivative thereof. None of the previously known reports show that change in the expression of the gene or the transcript thereof can serve as a marker for dementia.

The 420th target gene is the hsa-miR-4466 gene, a congener thereof, a transcript thereof, or a variant or derivative thereof. None of the previously known reports show that change in the expression of the gene or the transcript thereof can serve as a marker for dementia.

The 421st target gene is the hsa-miR-6789-5p gene, a congener thereof, a transcript thereof, or a variant or derivative thereof. None of the previously known reports show that change in the expression of the gene or the transcript thereof can serve as a marker for dementia.

The 422nd target gene is the hsa-miR-4632-5p gene, a congener thereof, a transcript thereof, or a variant or derivative thereof. None of the previously known reports show that change in the expression of the gene or the transcript thereof can serve as a marker for dementia.

The 423rd target gene is the hsa-miR-4745-5p gene, a congener thereof, a transcript thereof, or a variant or derivative thereof. None of the previously known reports show that change in the expression of the gene or the transcript thereof can serve as a marker for dementia.

The 424th target gene is the hsa-miR-4665-5p gene, a congener thereof, a transcript thereof, or a variant or derivative thereof. None of the previously known reports show that change in the expression of the gene or the transcript thereof can serve as a marker for dementia.

The 425th target gene is the hsa-miR-6807-5p gene, a congener thereof, a transcript thereof, or a variant or derivative thereof. None of the previously known reports show that change in the expression of the gene or the transcript thereof can serve as a marker for dementia.

The 426th target gene is the hsa-miR-7114-5p gene, a congener thereof, a transcript thereof, or a variant or derivative thereof. None of the previously known reports show that change in the expression of the gene or the transcript thereof can serve as a marker for dementia.

The 427th target gene is the hsa-miR-150-3p gene, a congener thereof, a transcript thereof, or a variant or derivative thereof. The previously known report shows that change in the expression of the gene or the transcript thereof can serve as a marker for dementia (Patent Literature 1).

The 428th target gene is the hsa-miR-423-5p gene, a congener thereof, a transcript thereof, or a variant or derivative thereof. The previously known report shows that change in the expression of the gene or the transcript thereof can serve as a marker for dementia (Patent Literature 1).

The 429th target gene is the hsa-miR-575 gene, a congener thereof, a transcript thereof, or a variant or derivative thereof. The previously known report shows that change in the expression of the gene or the transcript thereof can serve as a marker for dementia (Patent Literature 2).

The 430th target gene is the hsa-miR-671-5p gene, a congener thereof, a transcript thereof, or a variant or derivative thereof. The previously known report shows that change in the expression of the gene or the transcript thereof can serve as a marker for dementia (Patent Literature 3).

The 431st target gene is the hsa-miR-939-5p gene, a congener thereof, a transcript thereof, or a variant or derivative thereof. The previously known report shows that change in the expression of the gene or the transcript thereof can serve as a marker for dementia (Patent Literature 4).

The 432nd target gene is the hsa-miR-3665 gene, a congener thereof, a transcript thereof, or a variant or derivative thereof. The previously known report shows that change in the expression of the gene or the transcript thereof can serve as a marker for dementia (Patent Literature 5).

The 433rd target gene is the hsa-miR-516a-5p gene, a congener thereof, a transcript thereof, or a variant or derivative thereof. None of the previously known reports show that change in the expression of the gene or the transcript thereof can serve as a marker for dementia.

The 434th target gene is the hsa-miR-769-3p gene, a congener thereof, a transcript thereof, or a variant or derivative thereof. None of the previously known reports show that change in the expression of the gene or the transcript thereof can serve as a marker for dementia.

The 435th target gene is the hsa-miR-3692-5p gene, a congener thereof, a transcript thereof, or a variant or derivative thereof. None of the previously known reports show that change in the expression of the gene or the transcript thereof can serve as a marker for dementia.

The 436th target gene is the hsa-miR-3945 gene, a congener thereof, a transcript thereof, or a variant or derivative thereof. None of the previously known reports show that change in the expression of the gene or the transcript thereof can serve as a marker for dementia.

The 437th target gene is the hsa-miR-4433a-3p gene, a congener thereof, a transcript thereof, or a variant or derivative thereof. None of the previously known reports show that change in the expression of the gene or the transcript thereof can serve as a marker for dementia.

The 438th target gene is the hsa-miR-4485-3p gene, a congener thereof, a transcript thereof, or a variant or derivative thereof. None of the previously known reports show that change in the expression of the gene or the transcript thereof can serve as a marker for dementia.

The 439th target gene is the hsa-miR-6831-5p gene, a congener thereof, a transcript thereof, or a variant or derivative thereof. None of the previously known reports show that change in the expression of the gene or the transcript thereof can serve as a marker for dementia.

The 440th target gene is the hsa-miR-519c-5p gene, a congener thereof, a transcript thereof, or a variant or derivative thereof. None of the previously known reports show that change in the expression of the gene or the transcript thereof can serve as a marker for dementia.

The 441st target gene is the hsa-miR-551b-5p gene, a congener thereof, a transcript thereof, or a variant or derivative thereof. None of the previously known reports show that change in the expression of the gene or the transcript thereof can serve as a marker for dementia.

The 442nd target gene is the hsa-miR-1343-3p gene, a congener thereof, a transcript thereof, or a variant or derivative thereof. None of the previously known reports show that change in the expression of the gene or the transcript thereof can serve as a marker for dementia.

The 443rd target gene is the hsa-miR-4286 gene, a congener thereof, a transcript thereof, or a variant or derivative thereof. None of the previously known reports show that change in the expression of the gene or the transcript thereof can serve as a marker for dementia.

The 444th target gene is the hsa-miR-4634 gene, a congener thereof, a transcript thereof, or a variant or derivative thereof. None of the previously known reports show that change in the expression of the gene or the transcript thereof can serve as a marker for dementia.

The 445th target gene is the hsa-miR-4733-3p gene, a congener thereof, a transcript thereof, or a variant or derivative thereof. None of the previously known reports show that change in the expression of the gene or the transcript thereof can serve as a marker for dementia.

The 446th target gene is the hsa-miR-6086 gene, a congener thereof, a transcript thereof, or a variant or derivative thereof. None of the previously known reports show that change in the expression of the gene or the transcript thereof can serve as a marker for dementia.

The 447th target gene is the hsa-miR-30d-5p gene, a congener thereof, a transcript thereof, or a variant or derivative thereof. The previously known report shows that change in the expression of the gene or the transcript thereof can serve as a marker for dementia (U.S. Patent Application Publication No. 2010/279292).

The 448th target gene is the hsa-miR-30b-3p gene, a congener thereof, a transcript thereof, or a variant or derivative thereof. The previously known report shows that change in the expression of the gene or the transcript thereof can serve as a marker for dementia (U.S. Patent Application Publication No. 2010/279292).

The 449th target gene is the hsa-miR-92a-3p gene, a congener thereof, a transcript thereof, or a variant or derivative thereof. The previously known report shows that change in the expression of the gene or the transcript thereof can serve as a marker for dementia (Patent Literature 1).

The 450th target gene is the hsa-miR-371b-5p gene, a congener thereof, a transcript thereof, or a variant or derivative thereof. The previously known report shows that change in the expression of the gene or the transcript thereof can serve as a marker for dementia (Schipper H M et al., Gene Regulation and Systems Biology, 2007, vol. 1, pp. 263-74).

The 451st target gene is the hsa-miR-486-5p gene, a congener thereof, a transcript thereof, or a variant or derivative thereof. The previously known report shows that change in the expression of the gene or the transcript thereof can serve as a marker for dementia (Patent Literature 1).

In one embodiment, the present invention relates to a marker(s) for detecting dementia or diagnosing dementia, which comprises at least one selected from the above target nucleic acid(s).

In one embodiment, the present invention relates to use of at least one selected from the above target nucleic acid(s) for detecting dementia or diagnosing dementia.

In one embodiment, the present invention relates to a marker(s) for predicting dementia, which comprises at least one target nucleic acid selected from the group of the above (iii).

In one embodiment, the present invention relates to use of at least one target nucleic acid which is selected from the group of the above (iii), for predicting dementia.

2. Nucleic acid Probe(s) or Primer(s) for Detection of Dementia

A nucleic acid probe(s) or primer(s) capable of being used for detection of dementia or diagnosis of dementia according to the present invention enables qualitative and/or quantitative measurement of the presence, expression level(s), or abundance of target nucleic acid(s) for dementia: human-derived miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR- 3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, miR-6086, miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-150-3p, miR-423-5p, miR-575, miR-671-5p, miR-939-5p and miR-3665, miR-30d-5p, miR-30b-3p, miR-92a-3p, miR-371b-5p, miR-486-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346 or miR-767-3p, or any combination thereof, any congener thereof, any transcript thereof, or any variant or derivative thereof.

In one embodiment, a nucleic acid probe(s) or primer(s) capable of being used for detection of dementia or diagnosis of dementia enables qualitative and/or quantitative measurement of the presence, expression level(s), or abundance of target nucleic acid(s) for dementia: human-derived miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, miR-150-3p, miR-423-5p, miR-575, miR-671-5p, miR-939-5p, miR-1225-3p, miR-3184-5p, or miR-3665, or any combination thereof, any congener thereof, any transcript thereof, or any variant or derivative thereof.

The expression level(s) of the above target nucleic acid(s) in samples (herein also referred to as “dementia subject samples”) from patients having dementia (herein also referred to as “dementia patients”) may be increased or decreased (hereinafter, also referred to as an “increase/decrease”), depending on the kind(s) of the target nucleic acid(s), than samples (herein also referred to as “non-dementia subject samples”) from subjects with normal cognitive functions who do not have dementia (herein also referred to as “non-dementia subjects,” which includes patients who do not have dementia, but have diseases other than dementia). Thus, a kit or device of the present invention can be effectively used for detection of dementia by measuring the expression level(s) of the above target nucleic acid(s) in body fluid derived from a subject (e.g., a human) suspected of having dementia and in body fluids derived from non-dementia subjects and then comparing the expression level(s) therebetween.

A nucleic acid probe(s) or primer(s) capable of being used in the present invention is a nucleic acid probe(s) capable of specifically binding to a polynucleotide(s) consisting of a nucleotide sequence(s) represented by at least one selected from SEQ ID NOs: 1 to 210, 374, 1315 to 1350, and 1435 to 1448 or to a complementary strand(s) of the polynucleotide(s), or a primer(s) for amplifying a polynucleotide(s)

consisting of a nucleotide sequence(s) represented by at least one selected from SEQ ID NOs: 1 to 210, 374, 1315 to 1350, and 1435 to 1448.

The nucleic acid probes or primers capable of being used in the present invention may further comprise a nucleic acid probe(s) capable of specifically binding to a polynucleotide(s) consisting of a nucleotide sequence(s) represented by at least one selected from SEQ ID NOs: 211 to 249, and 1351 to 1356, and 1449 to 1453 or to a complementary strand(s) of the polynucleotide(s), or a primer(s) for amplifying a polynucleotide(s) consisting of a nucleotide sequence(s) represented by at least one selected from SEQ ID NOs: 211 to 249, and 1351 to 1356, and 1449 to 1453.

A nucleic acid probe(s) or primer(s) capable of being used in the present invention is or may further comprise a nucleic acid probe(s) capable of specifically binding to a polynucleotide(s) consisting of a nucleotide sequence(s) represented by at least one selected from SEQ ID NOs: 250 to 373 or to a complementary strand(s) of the polynucleotide(s), or a primer(s) for amplifying a polynucleotide(s) consisting of a nucleotide sequence(s) represented by at least one selected from SEQ ID NOs: 250 to 373.

The nucleic acid probes or primers capable of being used in the present invention may further comprise a nucleic acid probe(s) capable of specifically binding to a polynucleotide(s) consisting of a nucleotide sequence(s) represented by at least one selected from SEQ ID NOs: 375 to 390 or to a complementary strand(s) of the polynucleotide(s), or a primer(s) for amplifying a polynucleotide(s) consisting of a nucleotide sequence(s) represented by at least one selected from SEQ ID NOs: 375 to 390.

In a preferred embodiment of the method according to preferred embodiment the present invention, the above nucleic acid probe(s) or primer(s) includes any combination of one or more polynucleotides selected from a group of polynucleotides comprising a nucleotide sequence(s) represented by any of SEQ ID NOs: 1 to 1314, 1315 to 1434, and 1435 to 1505 and a nucleotide sequence(s) derived from the nucleotide sequence(s) by the replacement of u with t and a group of polynucleotides complementary thereto, a group of polynucleotides hybridizing under stringent conditions (described below) to DNA comprising a nucleotide sequence(s) complementary to the former nucleotide sequence(s) and a group of polynucleotides complementary thereto, and a group of polynucleotides comprising 15 or more, preferably 17 or more consecutive nucleotides in the nucleotide sequence(s) of these polynucleotide groups. These polynucleotides can be used as nucleic acid probes and primers for detecting target nucleic acids, namely the above dementia markers.

Further, specific examples of the nucleic acid probe(s) or primer(s) capable of being used in the present invention include one or more polynucleotides selected from the group consisting of any of the following polynucleotides (a) to (e):

(a) a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 210, 374, 1315 to 1350, and 1435 to 1448, (c) a polynucleotide consisting of a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, and (e) a polynucleotide hybridizing under stringent conditions to any of the polynucleotides (a) to (d).

In addition to at least one polynucleotide selected from any of the above polynucleotides (a) to (e), the nucleic acid probe(s) or primer(s) capable of being used in the present invention can further comprise a polynucleotide represented by any of the following (f) to (j), (k) to (o), and (p) to (t):

(f) a polynucleotide consisting of a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 249, 1351 to 1356, and 1449 to 1453, (h) a polynucleotide consisting of a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, and (j) a polynucleotide hybridizing under stringent conditions to any of the polynucleotides (f) to (i), (k) a polynucleotide consisting of a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 250 to 373, (m) a polynucleotide consisting of a nucleotide sequence complementary to a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 250 to 373 or a nucleotide sequence derived from the nucleotide sequence by the replacement of u with t, and (o) a polynucleotide hybridizing under stringent conditions to any of the polynucleotides (k) to (n), (p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

Further, examples of the nucleic acid probe(s) or primer(s) capable of being used in the present invention include one or more polynucleotides, which may be optionally combined with a polynucleotide represented by any of the above (p) to (s), selected from the group consisting of any of the following polynucleotides (u) to (y):

(u) a polynucleotide consisting of a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (v) a polynucleotide comprising a nucleotide sequence represented by any of SEQ ID NOs: 3, 8, 15, 26, 34, 40, 53, 69, 99, 101, 107, 109, 112, 125, 128, 133, 191 to 194, 212, and 250 to 374, (w) a polynucleotide consisting of a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, a variant thereof, a derivative thereof, or a fragment thereof comprising 15 or more consecutive nucleotides, (x) a polynucleotide comprising a nucleotide sequence complementary to a nucleotide sequence represented by any of SEQ ID NOs: 3, 8, 15, 26, 34, 40, 53, 69, 99, 101, 107, 109, 112, 125, 128, 133, 191 to 194, 212, and 250 to 374 or a nucleotide sequence derived from the nucleotide sequence by the replacement of u with t, and (y) a polynucleotide hybridizing under stringent conditions to any of the polynucleotides (u) to (x).

In one embodiment, a nucleic acid probe(s) or primer(s) capable of being used in the present invention is a nucleic acid probe(s) capable of specifically binding to a polynucleotide(s) consisting of a nucleotide sequence(s) represented by at least one selected from SEQ ID NOs: 194 to 210, 374, 1315 to 1350, and 1435 to 1448 or to a complementary strand(s) of the polynucleotide(s), or a primer(s) for amplifying a polynucleotide(s) consisting of a nucleotide sequence(s) represented by at least one selected from SEQ ID NOs: 194 to 210, 374, 1315 to 1350, and 1435 to 1448.

A nucleic acid probe(s) or primer(s) capable of being used in the present invention is a nucleic acid probe(s) capable of specifically binding to a polynucleotide(s) consisting of a nucleotide sequence(s) represented by at least one selected from SEQ ID NOs: 211 to 212, 1351 to 1356, and 1449 to 1453 or to a complementary strand(s) of the polynucleotide(s), or a primer(s) for amplifying a polynucleotide(s) consisting of a nucleotide sequence(s) represented by at least one selected from SEQ ID NOs: 211 to 212, 1351 to 1356, and 1449 to 1453.

In a preferred embodiment of the method according to the present invention, the above nucleic acid probe(s) or primer(s) comprises any combination of one or more polynucleotides selected from a group of polynucleotides comprising a nucleotide sequence(s) represented by any of SEQ ID NOs: 194 to 212, 374, 398, 490, 591, 593 to 609, 766, 1015 to 1017, 1019 to 1024, 1026 to 1031, 1285 to 1286, and 1315 to 1434 and a nucleotide sequence(s) derived from the nucleotide sequence(s) by the replacement of u with t and a group of polynucleotides complementary thereto, a group of polynucleotides hybridizing under stringent conditions (described below) to DNA comprising a nucleotide sequence(s) complementary to the former nucleotide sequence(s) and a group of polynucleotides complementary thereto, and a group of polynucleotides comprising 15 or more, preferably 17 or more consecutive nucleotides in the nucleotide sequence(s) of these polynucleotide groups. These polynucleotides can be used as nucleic acid probes and primers for detecting target nucleic acids, namely the above dementia markers.

In one embodiment, examples of the nucleic acid probe(s) or primer(s) capable of being used in the present invention include one or more polynucleotides selected from the group consisting of any of the following polynucleotides (a) to (e):

(a) a polynucleotide consisting of a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 194 to 210, 374, and 1315 to 1350, (c) a polynucleotide consisting of a nucleotide sequence complementary to a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 194 to 210, 374, and 1315 to 1350 or a nucleotide sequence derived from the nucleotide sequence by the replacement of u with t, and (e) a polynucleotide hybridizing under stringent conditions to any of the polynucleotides (a) to (d).

In one embodiment, in addition to at least one polynucleotide selected from any of the above polynucleotides (a) to (e), the nucleic acid probe(s) or primer(s) capable of being used in the present invention may further comprise a polynucleotide represented by any of the following (f) to (j):

(f) a polynucleotide consisting of a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 212 and 1351 to 1356, (h) a polynucleotide consisting of a nucleotide sequence complementary to a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 212 and 1351 to 1356 or a nucleotide sequence derived from the nucleotide sequence by the replacement of u with t, and (j) a polynucleotide hybridizing under stringent conditions to any of the polynucleotides (f) to (i).

The above polynucleotides or fragments thereof used in the present invention may each be DNA or RNA.

The above polynucleotide(s) capable of being used in the present invention may be prepared using a general technique such as DNA recombination technology, a PCR method, or a method using an automated DNA/RNA synthesizer.

As the DNA recombination technology or the PCR method, it is possible to use techniques described in, for instance, Ausubel et al., Current Protocols in Molecular Biology, John Willey & Sons, US (1993); and Sambrook et al., Molecular Cloning A Laboratory Manual, Cold Spring Harbor Laboratory Press, US (1989).

The human-derived miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, miR-371a-5p, miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346 and miR-767-3p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, miR-6086, miR-30d-5p, miR-30b-3p, miR-92a-3p, miR- 371b-5p, and miR-486-5p, which are represented by SEQ ID NOs: 1 to 210, 211 to 249, 250 to 374, 375 to 390, 1315 to 1350, 1435 to 1448, and 1449 to 1453, are known, and methods for obtaining them are also known, as described above. Therefore, a polynucleotide that can be used as a nucleic acid probe or a primer in the present invention can be produced via cloning the gene.

Moreover, the followings are also known, and methods for obtaining them are also known, as described above: human-derived hsa-mir-4274, hsa-mir-4272, hsa-mir-4728, hsa-mir-4443, hsa-mir-4506, hsa-mir-6773, hsa-mir-4662a, hsa-mir-3184, hsa-mir-4281, hsa-mir-320d-1, hsa-mir-320d-2, hsa-mir-6729, hsa-mir-5192, hsa-mir-6853, hsa-mir-1234, hsa-mir-1233-1, hsa-mir-1233-2, hsa-mir-4539, hsa-mir-3914-1, hsa-mir-3914-2, hsa-mir-4738, hsa-mir-548au, hsa-mir-1539, hsa-mir-4720, hsa-mir-365b, hsa-mir-4486, hsa-mir-1227, hsa-mir-4667, hsa-mir-6088, hsa-mir-6820, hsa-mir-4505, hsa-mir-548q, hsa-mir-4658, hsa-mir-450a-1, hsa-mir-450a-2, hsa-mir-1260b, hsa-mir-3677, hsa-mir-6777, hsa-mir-6826, hsa-mir-6832, hsa-mir-4725, hsa-mir-7161, hsa-mir-2277, hsa-mir-7110, hsa-mir-4312, hsa-mir-4461, hsa-mir-6766, hsa-mir-1266, hsa-mir-526b, hsa-mir-519e, hsa-mir-512-1, hsa-mir-512-2, hsa-mir-5088, hsa-mir-1909, hsa-mir-6511a-1, hsa-mir-6511a-2, hsa-mir-6511a-3, hsa-mir-6511a-4, hsa-mir-4734, hsa-mir-936, hsa-mir-1249, hsa-mir-4487, hsa-mir-3155a, hsa-mir-563, hsa-mir-4741, hsa-mir-6788, hsa-mir-4433b, hsa-mir-323a, hsa-mir-6811, hsa-mir-6721, hsa-mir-5004, hsa-mir-6509, hsa-mir-648, hsa-mir-3917, hsa-mir-6087, hsa-mir-1470, hsa-mir-586, hsa-mir-3150a, hsa-mir-105-1, hsa-mir-105-2, hsa-mir-7973-1, hsa-mir-7973-2, hsa-mir-1914, hsa-mir-4749, hsa-mir-15b, hsa-mir-1289-1, hsa-mir-1289-2, hsa-mir-4433a, hsa-mir-3666, hsa-mir-3186, hsa-mir-4488, hsa-mir-4474, hsa-mir-6731, hsa-mir-4640, hsa-mir-202, hsa-mir-6816, hsa-mir-638, hsa-mir-6821, hsa-mir-1247, hsa-mir-6765, hsa-mir-6800, hsa-mir-3928, hsa-mir-3940, hsa-mir-3960, hsa-mir-6775, hsa-mir-3178, hsa-mir-1202, hsa-mir-6790, hsa-mir-4731, hsa-mir-2681, hsa-mir-6758, hsa-mir-8072, hsa-mir-518d, hsa-mir-3606, hsa-mir-4800, hsa-mir-1292, hsa-mir-6784, hsa-mir-4450, hsa-mir-6132, hsa-mir-4716, hsa-mir-6860, hsa-mir-1268b, hsa-mir-378d-2, hsa-mir-378d-1, hsa-mir-4701, hsa-mir-4329, hsa-mir-185, hsa-mir-552, hsa-mir-1273g, hsa-mir-6769b, hsa-mir-520a, hsa-mir-4524b, hsa-mir-4291, hsa-mir-6734, hsa-mir-143, hsa-mir-939, hsa-mir-6889, hsa-mir-6842, hsa-mir-4511, hsa-mir-4318, hsa-mir-4653, hsa-mir-6867, hsa-mir-133b, hsa-mir-3196, hsa-mir-193b, hsa-mir-3162, hsa-mir-6819, hsa-mir-1908, hsa-mir-6786, hsa-mir-3648-1, hsa-mir-3648-2, hsa-mir-4513, hsa-mir-3652, hsa-mir-6871, hsa-mir-7845, hsa-mir-3138, hsa-mir-6884, hsa-mir-636, hsa-mir-4652, hsa-mir-6823, hsa-mir-4502, hsa-mir-7113, hsa-mir-8087, hsa-mir-7154, hsa-mir-5189, hsa-mir-1253, hsa-mir-518c, hsa-mir-7151, hsa-mir-3614, hsa-mir-4727, hsa-mir-3682, hsa-mir-5090, hsa-mir-337, hsa-mir-488, hsa-mir-100, hsa-mir-4520-1, hsa-mir-373, hsa-mir-6499, hsa-mir-3909, hsa-mir-32, hsa-mir-302a, hsa-mir-4686, hsa-mir-4659a, hsa-mir-4287, hsa-mir-1301, hsa-mir-593, hsa-mir-517a, hsa-mir-517b, hsa-mir-142, hsa-mir-1185-2, hsa-mir-602, hsa-mir-527, hsa-mir-518a-1, hsa-mir-518a-2, hsa-mir-4682, hsa-mir-28, hsa-mir-4252, hsa-mir-452, hsa-mir-525, hsa-mir-3622a, hsa-mir-6813, hsa-mir-4769, hsa-mir-5698, hsa-mir-1915, hsa-mir-1343, hsa-mir-6861, hsa-mir-6781, hsa-mir-4508, hsa-mir-6743, hsa-mir-6726, hsa-mir-4525, hsa-mir-4651, hsa-mir-5787, hsa-mir-1290, hsa-mir-6075, hsa-mir-4758, hsa-mir-4690, hsa-mir-762, hsa-mir-1225, hsa-mir-665, hsa-mir-211, hsa-mir-3656, hsa-mir-149, hsa-mir-744, hsa-mir-345, hsa-mir-150, hsa-mir-191, hsa-mir-651, hsa-mir-34a, hsa-mir-409, hsa-mir-369, hsa-mir-204, hsa-mir-137, hsa-mir-382, hsa-mir-517c, hsa-mir-532, hsa-mir-22, hsa-mir-1237, hsa-mir-1224, hsa-mir-625, hsa-mir-328, hsa-mir-122, hsa-mir-4781, hsa-mir-718, hsa-mir-342, hsa-mir-26b, hsa-mir-140, hsa-mir-200a, hsa-mir-378a, hsa-mir-484, hsa-mir-296, hsa-mir-205, hsa-mir-431, hsa-mir-1471, hsa-mir-1538, hsa-mir-449b, hsa-mir-1976, hsa-mir-4268, hsa-mir-4279, hsa-mir-3620, hsa-mir-3944, hsa-mir-3156-1, hsa-mir-3156-2, hsa-mir-3187, hsa-mir-4685, hsa-mir-4695, hsa-mir-4697, hsa-mir-4713, hsa-mir-4723, hsa-mir-371b, hsa-mir-3151, hsa-mir-3192, hsa-mir-6728, hsa-mir-6736, hsa-mir-6740, hsa-mir-6741, hsa-mir-6747, hsa-mir-6750, hsa-mir-6754, hsa-mir-6759, hsa-mir-6761, hsa-mir-6762, hsa-mir-6769a, hsa-mir-6776, hsa-mir-6778, hsa-mir-6779, hsa-mir-6787, hsa-mir-6792, hsa-mir-6794, hsa-mir-6801, hsa-mir-6802, hsa-mir-6803, hsa-mir-6804, hsa-mir-6810, hsa-mir-6825, hsa-mir-6829, hsa-mir-6833, hsa-mir-6834, hsa-mir-6780b, hsa-mir-6845, hsa-mir-6862-1, hsa-mir-6862-2, hsa-mir-6865, hsa-mir-6870, hsa-mir-6875, hsa-mir-6877, hsa-mir-6879, hsa-mir-6882, hsa-mir-6885, hsa-mir-6886, hsa-mir-6887, hsa-mir-6890, hsa-mir-6893, hsa-mir-6894, hsa-mir-7106, hsa-mir-7109, hsa-mir-7114, hsa-mir-7155, hsa-mir-7160, hsa-mir-615, hsa-mir-920, hsa-mir-1825, hsa-mir-675, hsa-mir-1910, hsa-mir-2278, hsa-mir-2682, hsa-mir-3122, hsa-mir-3175, hsa-mir-4323, hsa-mir-4326, hsa-mir-4284, hsa-mir-3605, hsa-mir-3622b, hsa-mir-3646, hsa-mir-3158-1, hsa-mir-3158-2, hsa-mir-4722, hsa-mir-4747, hsa-mir-4436b-1, hsa-mir-4436b-2, hsa-mir-5196, hsa-mir-5589, hsa-mir-642b, hsa-mir-6716, hsa-mir-6511b-1, hsa-mir-6511b-2, hsa-mir-208a, hsa-mir-6744, hsa-mir-6782, hsa-mir-6789, hsa-mir-6797, hsa-mir-6806, hsa-mir-6824, hsa-mir-6837, hsa-mir-6846, hsa-mir-6858, hsa-mir-6859-1, hsa-mir-6859-2, hsa-mir-6859-3, hsa-mir-6859-4, hsa-mir-6880, hsa-mir-7111, hsa-mir-7152, hsa-mir-642a, hsa-mir-657, hsa-mir-1236, hsa-mir-764, hsa-mir-4314, hsa-mir-3675, hsa-mir-5703, hsa-mir-3191, hsa-mir-6809, hsa-mir-6815, hsa-mir-6857, hsa-mir-6878, hsa-mir-371a, hsa-mir-766, hsa-mir-1229, hsa-mir-1306, hsa-mir-210, hsa-mir-198, hsa-mir-485, hsa-mir-668, hsa-mir-877, hsa-mir-1238, hsa-mir-3130-1, hsa-mir-3130-2, hsa-mir-4298, hsa-mir-4290, hsa-mir-3943, hsa-mir-346, hsa-mir-767, hsa-mir-516a-1, hsa-mir-769, hsa-mir-3692, hsa-mir-3945, hsa-mir-4433a, hsa-mir-4485, hsa-mir-6831, hsa-mir-519c, hsa-mir-551b, hsa-mir-1343, hsa-mir-4286, hsa-mir-4634, hsa-mir-4733, hsa-mir-6086, hsa-mir-30d, hsa-mir-30b, hsa-mir-92a-1, hsa-mir-371b, hsa-mir-486-1, isomiR sequence 1 of SEQ ID NO: 3, isomiR sequence 2 of SEQ ID NO: 3, isomiR sequence 1 of SEQ ID NO: 4, isomiR sequence 2 of SEQ ID NO: 4, isomiR sequence 1 of SEQ ID NO: 5, isomiR sequence 2 of SEQ ID NO: 5, isomiR sequence 1 of SEQ ID NO: 6, isomiR sequence 2 of SEQ ID NO: 6, isomiR sequence 1 of SEQ ID NO: 7, isomiR sequence 1 of SEQ ID NO: 8, isomiR sequence 1 of SEQ ID NO: 10, isomiR sequence 2 of SEQ ID NO: 10, isomiR sequence 1 of SEQ ID NO: 11, isomiR sequence 1 of SEQ ID NO: 12, isomiR sequence 1 of SEQ ID NO: 13, isomiR sequence 1 of SEQ ID NO: 15, isomiR sequence 2 of SEQ ID NO: 15, isomiR sequence 1 of SEQ ID NO: 16, isomiR sequence 1 of SEQ ID NO: 17, isomiR sequence 1 of SEQ ID NO: 19, isomiR sequence 1 of SEQ ID NO: 22, isomiR sequence 2 of SEQ ID NO: 22, isomiR sequence 1 of SEQ ID NO: 23, isomiR sequence 1 of SEQ ID NO: 25, isomiR sequence 2 of SEQ ID NO: 25, isomiR sequence 1 of SEQ ID NO: 26, isomiR sequence 2 of SEQ ID NO: 26, isomiR sequence 1 of SEQ ID NO: 28, isomiR sequence 1 of SEQ ID NO: 29, isomiR sequence 2 of SEQ ID NO: 29, isomiR sequence 1 of SEQ ID NO: 30, isomiR sequence 1 of SEQ ID NO: 31, isomiR sequence 2 of SEQ ID NO: 31, isomiR sequence 1 of SEQ ID NO: 32, isomiR sequence 2 of SEQ ID NO: 32, isomiR sequence 1 of SEQ ID NO: 33, isomiR sequence 1 of SEQ ID NO: 34, isomiR sequence 1 of SEQ ID NO: 35, isomiR sequence 1 of SEQ ID NO: 36, isomiR sequence 1 of SEQ ID NO: 37, isomiR sequence 2 of SEQ ID NO: 37, isomiR sequence 1 of SEQ ID NO: 39, isomiR sequence 2 of SEQ ID NO: 39, isomiR sequence 1 of SEQ ID NO: 40, isomiR sequence 2 of SEQ ID NO: 40, isomiR sequence 1 of SEQ ID NO: 41, isomiR sequence 1 of SEQ ID NO: 44, isomiR sequence 1 of SEQ ID NO: 47, isomiR sequence 1 of SEQ ID NO: 48, isomiR sequence 1 of SEQ ID NO: 49, isomiR sequence 2 of SEQ ID NO: 49, isomiR sequence 1 of SEQ ID NO: 50, isomiR sequence 2 of SEQ ID NO: 50, isomiR sequence 1 of SEQ ID NO: 51, isomiR sequence 2 of SEQ ID NO: 51, isomiR sequence 1 of SEQ ID NO: 52, isomiR sequence 1 of SEQ ID NO: 54, isomiR sequence 2 of SEQ ID NO: 54, isomiR sequence 1 of SEQ ID NO: 56, isomiR sequence 2 of SEQ ID NO: 56, isomiR sequence 1 of SEQ ID NO: 57, isomiR sequence 2 of SEQ ID NO: 57, isomiR sequence 1 of SEQ ID NO: 59, isomiR sequence 2 of SEQ ID NO: 59, isomiR sequence 1 of SEQ ID NO: 60, isomiR sequence 2 of SEQ ID NO: 60, isomiR sequence 1 of SEQ ID NO: 61, isomiR sequence 2 of SEQ ID NO: 61, isomiR sequence 1 of SEQ ID NO: 62, isomiR sequence 2 of SEQ ID NO: 62, isomiR sequence 1 of SEQ ID NO: 63, isomiR sequence 2 of SEQ ID NO: 63, isomiR sequence 1 of SEQ ID NO: 64, isomiR sequence 2 of SEQ ID NO: 64, isomiR sequence 1 of SEQ ID NO: 65, isomiR sequence 1 of SEQ ID NO: 66, isomiR sequence 1 of SEQ ID NO: 67, isomiR sequence 1 of SEQ ID NO: 68, isomiR sequence 2 of SEQ ID NO: 68, isomiR sequence 1 of SEQ ID NO: 69, isomiR sequence 2 of SEQ ID NO: 69, isomiR sequence 1 of SEQ ID NO: 70, isomiR sequence 1 of SEQ ID NO: 71, isomiR sequence 1 of SEQ ID NO: 72, isomiR sequence 2 of SEQ ID NO: 72, isomiR sequence 1 of SEQ ID NO: 73, isomiR sequence 2 of SEQ ID NO: 73, isomiR sequence 1 of SEQ ID NO: 75, isomiR sequence 1 of SEQ ID NO: 77, isomiR sequence 2 of SEQ ID NO: 77, isomiR sequence 1 of SEQ ID NO: 78, isomiR sequence 1 of SEQ ID NO: 79, isomiR sequence 1 of SEQ ID NO: 81, isomiR sequence 2 of SEQ ID NO: 81, isomiR sequence 1 of SEQ ID NO: 82, isomiR sequence 1 of SEQ ID NO: 83, isomiR sequence 2 of SEQ ID NO: 83, isomiR sequence 1 of SEQ ID NO: 84, isomiR sequence 1 of SEQ ID NO: 85, isomiR sequence 1 of SEQ ID NO: 86, isomiR sequence 1 of SEQ ID NO: 87, isomiR sequence 2 of SEQ ID NO: 87, isomiR sequence 1 of SEQ ID NO: 89, isomiR sequence 2 of SEQ ID NO: 89, isomiR sequence 1 of SEQ ID NO: 91, isomiR sequence 2 of SEQ ID NO: 91, isomiR sequence 1 of SEQ ID NO: 94, isomiR sequence 2 of SEQ ID NO: 94, isomiR sequence 1 of SEQ ID NO: 95, isomiR sequence 2 of SEQ ID NO: 95, isomiR sequence 1 of SEQ ID NO: 96, isomiR sequence 2 of SEQ ID NO: 96, isomiR sequence 1 of SEQ ID NO: 98, isomiR sequence 2 of SEQ ID NO: 98, isomiR sequence 1 of SEQ ID NO: 99, isomiR sequence 1 of SEQ ID NO: 100, isomiR sequence 1 of SEQ ID NO: 101, isomiR sequence 1 of SEQ ID NO: 102, isomiR sequence 1 of SEQ ID NO: 103, isomiR sequence 2 of SEQ ID NO: 103, isomiR sequence 1 of SEQ ID NO: 105, isomiR sequence 1 of SEQ ID NO: 107, isomiR sequence 1 of SEQ ID NO: 109, isomiR sequence 1 of SEQ ID NO: 111, isomiR sequence 1 of SEQ ID NO: 112, isomiR sequence 2 of SEQ ID NO: 112, isomiR sequence 1 of SEQ ID NO: 113, isomiR sequence 1 of SEQ ID NO: 114, isomiR sequence 2 of SEQ ID NO: 114, isomiR sequence 1 of SEQ ID NO: 115, isomiR sequence 2 of SEQ ID NO: 115, isomiR sequence 1 of SEQ ID NO: 116, isomiR sequence 2 of SEQ ID NO: 116, isomiR sequence 1 of SEQ ID NO: 118, isomiR sequence 2 of SEQ ID NO: 118, isomiR sequence 1 of SEQ ID NO: 119, isomiR sequence 1 of SEQ ID NO: 121, isomiR sequence 1 of SEQ ID NO: 122, isomiR sequence 1 of SEQ ID NO: 125, isomiR sequence 1 of SEQ ID NO: 126, isomiR sequence 2 of SEQ ID NO: 126, isomiR sequence 1 of SEQ ID NO: 127, isomiR sequence 2 of SEQ ID NO: 127, isomiR sequence 1 of SEQ ID NO: 128, isomiR sequence 1 of SEQ ID NO: 129, isomiR sequence 1 of SEQ ID NO: 130, isomiR sequence 2 of SEQ ID NO: 130, isomiR sequence 1 of SEQ ID NO: 133, isomiR sequence 1 of SEQ ID NO: 134, isomiR sequence 2 of SEQ ID NO: 134, isomiR sequence 1 of SEQ ID NO: 135, isomiR sequence 2 of SEQ ID NO: 135, isomiR sequence 1 of SEQ ID NO: 136, isomiR sequence 2 of SEQ ID NO: 136, isomiR sequence 1 of SEQ ID NO: 137, isomiR sequence 1 of SEQ ID NO: 138, isomiR sequence 1 of SEQ ID NO: 139, isomiR sequence 2 of SEQ ID NO: 139, isomiR sequence 1 of SEQ ID NO: 141, isomiR sequence 2 of SEQ ID NO: 141, isomiR sequence 1 of SEQ ID NO: 142, isomiR sequence 2 of SEQ ID NO: 142, isomiR sequence 1 of SEQ ID NO: 143, isomiR sequence 2 of SEQ ID NO: 143, isomiR sequence 1 of SEQ ID NO: 144, isomiR sequence 2 of SEQ ID NO: 144, isomiR sequence 1 of SEQ ID NO: 145, isomiR sequence 2 of SEQ ID NO: 145, isomiR sequence 1 of SEQ ID NO: 147, isomiR sequence 2 of SEQ ID NO: 147, isomiR sequence 1 of SEQ ID NO: 148, isomiR sequence 2 of SEQ ID NO: 148, isomiR sequence 1 of SEQ ID NO: 149, isomiR sequence 2 of SEQ ID NO: 149, isomiR sequence 1 of SEQ ID NO: 150, isomiR sequence 2 of SEQ ID NO: 150, isomiR sequence 1 of SEQ ID NO: 151, isomiR sequence 2 of SEQ ID NO: 151, isomiR sequence 1 of SEQ ID NO: 152, isomiR sequence 2 of SEQ ID NO: 152, isomiR sequence 1 of SEQ ID NO: 153, isomiR sequence 2 of SEQ ID NO: 153, isomiR sequence 1 of SEQ ID NO: 154, isomiR sequence 2 of SEQ ID NO: 154, isomiR sequence 1 of SEQ ID NO: 157, isomiR sequence 2 of SEQ ID NO: 157, isomiR sequence 1 of SEQ ID NO: 158, isomiR sequence 1 of SEQ ID NO: 159, isomiR sequence 1 of SEQ ID NO: 161, isomiR sequence 2 of SEQ ID NO: 161, isomiR sequence 1 of SEQ ID NO: 162, isomiR sequence 1 of SEQ ID NO: 163, isomiR sequence 2 of SEQ ID NO: 163, isomiR sequence 1 of SEQ ID NO: 164, isomiR sequence 2 of SEQ ID NO: 164, isomiR sequence 1 of SEQ ID NO: 165, isomiR sequence 2 of SEQ ID NO: 165, isomiR sequence 1 of SEQ ID NO: 166, isomiR sequence 1 of SEQ ID NO: 167, isomiR sequence 2 of SEQ ID NO: 167, isomiR sequence 1 of SEQ ID NO: 168, isomiR sequence 2 of SEQ ID NO: 168, isomiR sequence 1 of SEQ ID NO: 169, isomiR sequence 1 of SEQ ID NO: 170, isomiR sequence 2 of SEQ ID NO: 170, isomiR sequence 1 of SEQ ID NO: 171, isomiR sequence 2 of SEQ ID NO: 171, isomiR sequence 1 of SEQ ID NO: 172, isomiR sequence 2 of SEQ ID NO: 172, isomiR sequence 1 of SEQ ID NO: 173, isomiR sequence 2 of SEQ ID NO: 173, isomiR sequence 1 of SEQ ID NO: 175, isomiR sequence 2 of SEQ ID NO: 175, isomiR sequence 1 of SEQ ID NO: 177, isomiR sequence 2 of SEQ ID NO: 177, isomiR sequence 1 of SEQ ID NO: 179, isomiR sequence 2 of SEQ ID NO: 179, isomiR sequence 1 of SEQ ID NO: 180, isomiR sequence 2 of SEQ ID NO: 180, isomiR sequence 1 of SEQ ID NO: 181, isomiR sequence 2 of SEQ ID NO: 181, isomiR sequence 1 of SEQ ID NO: 182, isomiR sequence 2 of SEQ ID NO: 182, isomiR sequence 1 of SEQ ID NO: 185, isomiR sequence 1 of SEQ ID NO: 187, isomiR sequence 2 of SEQ ID NO: 187, isomiR sequence 1 of SEQ ID NO: 189, isomiR sequence 2 of SEQ ID NO: 189, isomiR sequence 1 of SEQ ID NO: 190, isomiR sequence 1 of SEQ ID NO: 191, isomiR sequence 2 of SEQ ID NO: 191, isomiR sequence 1 of SEQ ID NO: 192, isomiR sequence 1 of SEQ ID NO: 194, isomiR sequence 2 of SEQ ID NO: 194, isomiR sequence 1 of SEQ ID NO: 195, isomiR sequence 2 of SEQ ID NO: 195, isomiR sequence 1 of SEQ ID NO: 199, isomiR sequence 2 of SEQ ID NO: 199, isomiR sequence 1 of SEQ ID NO: 202, isomiR sequence 2 of SEQ ID NO: 202, isomiR sequence 1 of SEQ ID NO: 203, isomiR sequence 1 of SEQ ID NO: 205, isomiR sequence 2 of SEQ ID NO: 205, isomiR sequence 1 of SEQ ID NO: 206, isomiR sequence 2 of SEQ ID NO: 206, isomiR sequence 1 of SEQ ID NO: 208, isomiR sequence 2 of SEQ ID NO: 208, isomiR sequence 1 of SEQ ID NO: 209, isomiR sequence 2 of SEQ ID NO: 209, isomiR sequence 1 of SEQ ID NO: 213, isomiR sequence 2 of SEQ ID NO: 213, isomiR sequence 1 of SEQ ID NO: 214, isomiR sequence 2 of SEQ ID NO: 214, isomiR sequence 1 of SEQ ID NO: 215, isomiR sequence 2 of SEQ ID NO: 215, isomiR sequence 1 of SEQ ID NO: 216, isomiR sequence 2 of SEQ ID NO: 216, isomiR sequence 1 of SEQ ID NO: 217, isomiR sequence 2 of SEQ ID NO: 217, isomiR sequence 1 of SEQ ID NO: 218, isomiR sequence 2 of SEQ ID NO: 218, isomiR sequence 1 of SEQ ID NO: 219, isomiR sequence 2 of SEQ ID NO: 219, isomiR sequence 1 of SEQ ID NO: 220, isomiR sequence 2 of SEQ ID NO: 220, isomiR sequence 1 of SEQ ID NO: 221, isomiR sequence 2 of SEQ ID NO: 221, isomiR sequence 1 of SEQ ID NO: 222, isomiR sequence 2 of SEQ ID NO: 222, isomiR sequence 1 of SEQ ID NO: 223, isomiR sequence 2 of SEQ ID NO: 223, isomiR sequence 1 of SEQ ID NO: 224, isomiR sequence 2 of SEQ ID NO: 224, isomiR sequence 1 of SEQ ID NO: 225, isomiR sequence 2 of SEQ ID NO: 225, isomiR sequence 1 of SEQ ID NO: 226, isomiR sequence 2 of SEQ ID NO: 226, isomiR sequence 1 of SEQ ID NO: 227, isomiR sequence 2 of SEQ ID NO: 227, isomiR sequence 1 of SEQ ID NO: 228, isomiR sequence 2 of SEQ ID NO: 228, isomiR sequence 1 of SEQ ID NO: 229, isomiR sequence 2 of SEQ ID NO: 229, isomiR sequence 1 of SEQ ID NO: 230, isomiR sequence 1 of SEQ ID NO: 231, isomiR sequence 2 of SEQ ID NO: 231, isomiR sequence 1 of SEQ ID NO: 232, isomiR sequence 2 of SEQ ID NO: 232, isomiR sequence 1 of SEQ ID NO: 233, isomiR sequence 2 of SEQ ID NO: 233, isomiR sequence 1 of SEQ ID NO: 234, isomiR sequence 2 of SEQ ID NO: 234, isomiR sequence 1 of SEQ ID NO: 235, isomiR sequence 2 of SEQ ID NO: 235, isomiR sequence 1 of SEQ ID NO: 236, isomiR sequence 2 of SEQ ID NO: 236, isomiR sequence 1 of SEQ ID NO: 237, isomiR sequence 2 of SEQ ID NO: 237, isomiR sequence 1 of SEQ ID NO: 238, isomiR sequence 2 of SEQ ID NO: 238, isomiR sequence 1 of SEQ ID NO: 239, isomiR sequence 2 of SEQ ID NO: 239, isomiR sequence 1 of SEQ ID NO: 241, isomiR sequence 2 of SEQ ID NO: 241, isomiR sequence 1 of SEQ ID NO: 242, isomiR sequence 2 of SEQ ID NO: 242, isomiR sequence 1 of SEQ ID NO: 243, isomiR sequence 2 of SEQ ID NO: 243, isomiR sequence 1 of SEQ ID NO: 244, isomiR sequence 2 of SEQ ID NO: 244, isomiR sequence 1 of SEQ ID NO: 245, isomiR sequence 2 of SEQ ID NO: 245, isomiR sequence 1 of SEQ ID NO: 246, isomiR sequence 2 of SEQ ID NO: 246, isomiR sequence 1 of SEQ ID NO: 247, isomiR sequence 2 of SEQ ID NO: 247, isomiR sequence 1 of SEQ ID NO: 248, isomiR sequence 2 of SEQ ID NO: 248, isomiR sequence 1 of SEQ ID NO: 249, isomiR sequence 2 of SEQ ID NO: 249, isomiR sequence 1 of SEQ ID NO: 251, isomiR sequence 2 of SEQ ID NO: 251, isomiR sequence 1 of SEQ ID NO: 252, isomiR sequence 2 of SEQ ID NO: 252, isomiR sequence 1 of SEQ ID NO: 253, isomiR sequence 2 of SEQ ID NO: 253, isomiR sequence 1 of SEQ ID NO: 255, isomiR sequence 1 of SEQ ID NO: 256, isomiR sequence 2 of SEQ ID NO: 256, isomiR sequence 1 of SEQ ID NO: 257, isomiR sequence 2 of SEQ ID NO: 257, isomiR sequence 1 of SEQ ID NO: 259, isomiR sequence 2 of SEQ ID NO: 259, isomiR sequence 1 of SEQ ID NO: 260, isomiR sequence 2 of SEQ ID NO: 260, isomiR sequence 1 of SEQ ID NO: 261, isomiR sequence 2 of SEQ ID NO: 261, isomiR sequence 1 of SEQ ID NO: 262, isomiR sequence 2 of SEQ ID NO: 262, isomiR sequence 1 of SEQ ID NO: 263, isomiR sequence 2 of SEQ ID NO: 263, isomiR sequence 1 of SEQ ID NO: 264, isomiR sequence 2 of SEQ ID NO: 264, isomiR sequence 1 of SEQ ID NO: 265, isomiR sequence 1 of SEQ ID NO: 268, isomiR sequence 1 of SEQ ID NO: 269, isomiR sequence 2 of SEQ ID NO: 269, isomiR sequence 1 of SEQ ID NO: 270, isomiR sequence 2 of SEQ ID NO: 270, isomiR sequence 1 of SEQ ID NO: 271, isomiR sequence 2 of SEQ ID NO: 271, isomiR sequence 1 of SEQ ID NO: 272, isomiR sequence 2 of SEQ ID NO: 272, isomiR sequence 1 of SEQ ID NO: 273, isomiR sequence 2 of SEQ ID NO: 273, isomiR sequence 1 of SEQ ID NO: 274, isomiR sequence 2 of SEQ ID NO: 274, isomiR sequence 1 of SEQ ID NO: 275, isomiR sequence 2 of SEQ ID NO: 275, isomiR sequence 1 of SEQ ID NO: 276, isomiR sequence 1 of SEQ ID NO: 277, isomiR sequence 2 of SEQ ID NO: 277, isomiR sequence 1 of SEQ ID NO: 278, isomiR sequence 2 of SEQ ID NO: 278, isomiR sequence 1 of SEQ ID NO: 279, isomiR sequence 1 of SEQ ID NO: 280, isomiR sequence 2 of SEQ ID NO: 280, isomiR sequence 1 of SEQ ID NO: 281, isomiR sequence 2 of SEQ ID NO: 281, isomiR sequence 1 of SEQ ID NO: 282, isomiR sequence 2 of SEQ ID NO: 282, isomiR sequence 1 of SEQ ID NO: 283, isomiR sequence 2 of SEQ ID NO: 283, isomiR sequence 1 of SEQ ID NO: 284, isomiR sequence 2 of SEQ ID NO: 284, isomiR sequence 1 of SEQ ID NO: 286, isomiR sequence 2 of SEQ ID NO: 286, isomiR sequence 1 of SEQ ID NO: 287, isomiR sequence 2 of SEQ ID NO: 287, isomiR sequence 1 of SEQ ID NO: 288, isomiR sequence 2 of SEQ ID NO: 288, isomiR sequence 1 of SEQ ID NO: 289, isomiR sequence 2 of SEQ ID NO: 289, isomiR sequence 1 of SEQ ID NO: 290, isomiR sequence 1 of SEQ ID NO: 291, isomiR sequence 2 of SEQ ID NO: 291, isomiR sequence 1 of SEQ ID NO: 292, isomiR sequence 1 of SEQ ID NO: 293, isomiR sequence 2 of SEQ ID NO: 293, isomiR sequence 1 of SEQ ID NO: 295, isomiR sequence 2 of SEQ ID NO: 295, isomiR sequence 1 of SEQ ID NO: 296, isomiR sequence 2 of SEQ ID NO: 296, isomiR sequence 1 of SEQ ID NO: 297, isomiR sequence 2 of SEQ ID NO: 297, isomiR sequence 1 of SEQ ID NO: 298, isomiR sequence 1 of SEQ ID NO: 299, isomiR sequence 2 of SEQ ID NO: 299, isomiR sequence 1 of SEQ ID NO: 300, isomiR sequence 2 of SEQ ID NO: 300, isomiR sequence 1 of SEQ ID NO: 301, isomiR sequence 1 of SEQ ID NO: 302, isomiR sequence 2 of SEQ ID NO: 302, isomiR sequence 1 of SEQ ID NO: 303, isomiR sequence 1 of SEQ ID NO: 304, isomiR sequence 2 of SEQ ID NO: 304, isomiR sequence 1 of SEQ ID NO: 305, isomiR sequence 2 of SEQ ID NO: 305, isomiR sequence 1 of SEQ ID NO: 306, isomiR sequence 2 of SEQ ID NO: 306, isomiR sequence 1 of SEQ ID NO: 307, isomiR sequence 1 of SEQ ID NO: 308, isomiR sequence 2 of SEQ ID NO: 308, isomiR sequence 1 of SEQ ID NO: 309, isomiR sequence 1 of SEQ ID NO: 310, isomiR sequence 1 of SEQ ID NO: 311, isomiR sequence 2 of SEQ ID NO: 311, isomiR sequence 1 of SEQ ID NO: 312, isomiR sequence 1 of SEQ ID NO: 313, isomiR sequence 2 of SEQ ID NO: 313, isomiR sequence 1 of SEQ ID NO: 314, isomiR sequence 2 of SEQ ID NO: 314, isomiR sequence 1 of SEQ ID NO: 315, isomiR sequence 1 of SEQ ID NO: 316, isomiR sequence 2 of SEQ ID NO: 316, isomiR sequence 1 of SEQ ID NO: 317, isomiR sequence 2 of SEQ ID NO: 317, isomiR sequence 1 of SEQ ID NO: 320, isomiR sequence 2 of SEQ ID NO: 320, isomiR sequence 1 of SEQ ID NO: 321, isomiR sequence 2 of SEQ ID NO: 321, isomiR sequence 1 of SEQ ID NO: 322, isomiR sequence 2 of SEQ ID NO: 322, isomiR sequence 1 of SEQ ID NO: 323, isomiR sequence 2 of SEQ ID NO: 323, isomiR sequence 1 of SEQ ID NO: 324, isomiR sequence 2 of SEQ ID NO: 324, isomiR sequence 1 of SEQ ID NO: 325, isomiR sequence 2 of SEQ ID NO: 325, isomiR sequence 1 of SEQ ID NO: 326, isomiR sequence 2 of SEQ ID NO: 326, isomiR sequence 1 of SEQ ID NO: 327, isomiR sequence 1 of SEQ ID NO: 328, isomiR sequence 2 of SEQ ID NO: 328, isomiR sequence 1 of SEQ ID NO: 329, isomiR sequence 2 of SEQ ID NO: 329, isomiR sequence 1 of SEQ ID NO: 330, isomiR sequence 2 of SEQ ID NO: 330, isomiR sequence 1 of SEQ ID NO: 331, isomiR sequence 1 of SEQ ID NO: 332, isomiR sequence 1 of SEQ ID NO: 333, isomiR sequence 2 of SEQ ID NO: 333, isomiR sequence 1 of SEQ ID NO: 335, isomiR sequence 2 of SEQ ID NO: 335, isomiR sequence 1 of SEQ ID NO: 338, isomiR sequence 2 of SEQ ID NO: 338, isomiR sequence 1 of SEQ ID NO: 340, isomiR sequence 2 of SEQ ID NO: 340, isomiR sequence 1 of SEQ ID NO: 341, isomiR sequence 2 of SEQ ID NO: 341, isomiR sequence 1 of SEQ ID NO: 342, isomiR sequence 2 of SEQ ID NO: 342, isomiR sequence 1 of SEQ ID NO: 343, isomiR sequence 2 of SEQ ID NO: 343, isomiR sequence 1 of SEQ ID NO: 345, isomiR sequence 2 of SEQ ID NO: 345, isomiR sequence 1 of SEQ ID NO: 347, isomiR sequence 2 of SEQ ID NO: 347, isomiR sequence 1 of SEQ ID NO: 348, isomiR sequence 2 of SEQ ID NO: 348, isomiR sequence 1 of SEQ ID NO: 349, isomiR sequence 2 of SEQ ID NO: 349, isomiR sequence 1 of SEQ ID NO: 350, isomiR sequence 1 of SEQ ID NO: 352, isomiR sequence 2 of SEQ ID NO: 352, isomiR sequence 1 of SEQ ID NO: 353, isomiR sequence 2 of SEQ ID NO: 353, isomiR sequence 1 of SEQ ID NO: 354, isomiR sequence 1 of SEQ ID NO: 355, isomiR sequence 2 of SEQ ID NO: 355, isomiR sequence 1 of SEQ ID NO: 356, isomiR sequence 2 of SEQ ID NO: 356, isomiR sequence 1 of SEQ ID NO: 357, isomiR sequence 2 of SEQ ID NO: 357, isomiR sequence 1 of SEQ ID NO: 359, isomiR sequence 2 of SEQ ID NO: 359, isomiR sequence 1 of SEQ ID NO: 361, isomiR sequence 2 of SEQ ID NO: 361, isomiR sequence 1 of SEQ ID NO: 362, isomiR sequence 1 of SEQ ID NO: 363, isomiR sequence 2 of SEQ ID NO: 363, isomiR sequence 1 of SEQ ID NO: 367, isomiR sequence 2 of SEQ ID NO: 367, isomiR sequence 1 of SEQ ID NO: 368, isomiR sequence 2 of SEQ ID NO: 368, isomiR sequence 1 of SEQ ID NO: 369, isomiR sequence 2 of SEQ ID NO: 369, isomiR sequence 1 of SEQ ID NO: 371, isomiR sequence 2 of SEQ ID NO: 371, isomiR sequence 1 of SEQ ID NO: 372, isomiR sequence 2 of SEQ ID NO: 372, isomiR sequence 1 of SEQ ID NO: 373, isomiR sequence 1 of SEQ ID NO: 374, isomiR sequence 2 of SEQ ID NO: 374, isomiR sequence 1 of SEQ ID NO: 375, isomiR sequence 2 of SEQ ID NO: 375, isomiR sequence 1 of SEQ ID NO: 376, isomiR sequence 2 of SEQ ID NO: 376, isomiR sequence 1 of SEQ ID NO: 377, isomiR sequence 2 of SEQ ID NO: 377, isomiR sequence 1 of SEQ ID NO: 378, isomiR sequence 2 of SEQ ID NO: 378, isomiR sequence 1 of SEQ ID NO: 379, isomiR sequence 2 of SEQ ID NO: 379, isomiR sequence 1 of SEQ ID NO: 380, isomiR sequence 2 of SEQ ID NO: 380, isomiR sequence 1 of SEQ ID NO: 381, isomiR sequence 2 of SEQ ID NO: 381, isomiR sequence 1 of SEQ ID NO: 382, isomiR sequence 2 of SEQ ID NO: 382, isomiR sequence 1 of SEQ ID NO: 383, isomiR sequence 2 of SEQ ID NO: 383, isomiR sequence 1 of SEQ ID NO: 385, isomiR sequence 2 of SEQ ID NO: 385, isomiR sequence 1 of SEQ ID NO: 386, isomiR sequence 2 of SEQ ID NO: 386, isomiR sequence 1 of SEQ ID NO: 388, isomiR sequence 2 of SEQ ID NO: 388, isomiR sequence 1 of SEQ ID NO: 389, isomiR sequence 2 of SEQ ID NO: 389, isomiR sequence 1 of SEQ ID NO: 390, isomiR sequence 2 of SEQ ID NO: 390, isomiR sequence 1 of SEQ ID NO: 1435, isomiR sequence 2 of SEQ ID NO: 1435, isomiR sequence 1 of SEQ ID NO: 1436, isomiR sequence 2 of SEQ ID NO: 1436, isomiR sequence 1 of SEQ ID NO: 1438, isomiR sequence 2 of SEQ ID NO: 1438, isomiR sequence 1 of SEQ ID NO: 1439, isomiR sequence 2 of SEQ ID NO: 1439, isomiR sequence 1 of SEQ ID NO: 1440, isomiR sequence 2 of SEQ ID NO: 1440, isomiR sequence 1 of SEQ ID NO: 1441, isomiR sequence 2 of SEQ ID NO: 1441, isomiR sequence 1 of SEQ ID NO: 1446, isomiR sequence 2 of SEQ ID NO: 1446, isomiR sequence 1 of SEQ ID NO: 1448, isomiR sequence 2 of SEQ ID NO: 1448, isomiR sequence 1 of SEQ ID NO: 1449, isomiR sequence 2 of SEQ ID NO: 1449, isomiR sequence 1 of SEQ ID NO: 1451, isomiR sequence 2 of SEQ ID NO: 1451, isomiR sequence 1 of SEQ ID NO: 1452, isomiR sequence 2 of SEQ ID NO: 1452, isomiR sequence 1 of SEQ ID NO: 1455, isomiR sequence 1 of SEQ ID NO: 1458, isomiR sequence 2 of SEQ ID NO: 1458, isomiR sequence 1 of SEQ ID NO: 1460, isomiR sequence 2 of SEQ ID NO: 1460, isomiR sequence 1 of SEQ ID NO: 1461, isomiR sequence 2 of SEQ ID NO: 1461, isomiR sequence 1 of SEQ ID NO: 1462, isomiR sequence 2 of SEQ ID NO: 1462, isomiR sequence 1 of SEQ ID NO: 1463, and isomiR sequence 2 of SEQ ID NO: 1463, which are represented by SEQ ID NOs: 391 to 1314 and 1454 to 1472. Therefore, a polynucleotide that can be used as a nucleic acid probe or a primer in the present invention can be produced via cloning the gene.

Furthermore, the followings are also known, and methods for obtaining them are also known, as described above: human-derived hsa-miR-6765-3p, hsa-miR-6784-5p, hsa-miR-6778-5p, hsa-miR-6875-5p, hsa-miR-4534, hsa-miR-4721, hsa-miR-6756-5p, hsa-miR-615-5p, hsa-miR-6727-5p, hsa-miR-6887-5p, hsa-miR-8063, hsa-miR-6880-5p, hsa-miR-6805-3p, hsa-miR-4726-5p, hsa-miR-4710, hsa-miR-7111-5p, hsa-miR-3619-3p, hsa-miR-6795-5p, hsa-miR-1254, hsa-miR-1233-5p, hsa-miR-6836-3p, hsa-miR-6769a-5p, hsa-miR-4532, hsa-miR-365a-5p, hsa-miR-1231, hsa-miR-1228-5p, hsa-miR-4430, hsa-miR-296-3p, hsa-miR-1237-5p, hsa-miR-4466, hsa-miR-6789-5p, hsa-miR-4632-5p, hsa-miR-4745-5p, hsa-miR-4665-5p, hsa-miR-6807-5p, hsa-miR-7114-5p, hsa-miR-150-3p, hsa-miR-423-5p, hsa-miR-575, hsa-miR-671-5p, hsa-miR-939-5p, hsa-miR-3665, hsa-mir-6784, hsa-mir-6778, hsa-mir-6875, hsa-mir-4534, hsa-mir-4721, hsa-mir-6756, hsa-mir-615, hsa-mir-6727, hsa-mir-6887, hsa-mir-8063, hsa-mir-6880, hsa-mir-6805, hsa-mir-4726, hsa-mir-4710, hsa-mir-7111, hsa-mir-3619, hsa-mir-6795, hsa-mir-1254-1, hsa-mir-1254-2, hsa-mir-1233-1, hsa-mir-1233-2, hsa-mir-6836, hsa-mir-6769a, hsa-mir-4532, hsa-mir-365a, hsa-mir-1231, hsa-mir-1228, hsa-mir-4430, hsa-mir-296, hsa-mir-1237, hsa-mir-4466, hsa-mir-6789, hsa-mir-4632, hsa-mir-4745, hsa-mir-4665, hsa-mir-6807, hsa-mir-7114, hsa-mir-150, hsa-mir-423, hsa-mir-575, hsa-mir-671, hsa-mir-939, hsa-mir-3665, isomiR example-1 of SEQ ID NO: 1320, isomiR example-1 of SEQ ID NO: 1322, isomiR example-2 of SEQ ID NO: 1322, isomiR example-1 of SEQ ID NO: 1328, isomiR example-2 of SEQ ID NO: 1328, isomiR example-2 of SEQ ID NO: 1329, isomiR example-1 of SEQ ID NO: 1333, isomiR example-2 of SEQ ID NO: 1333, isomiR example-1 of SEQ ID NO: 1334, isomiR example-2 of SEQ ID NO: 1334, isomiR example-1 of SEQ ID NO: 1337, isomiR example-2 of SEQ ID NO: 1337, isomiR example-1 of SEQ ID NO: 1338, isomiR example-2 of SEQ ID NO: 1338, isomiR example-1 of SEQ ID NO: 1340, isomiR example-2 of SEQ ID NO: 1340, isomiR example-1 of SEQ ID NO: 1341, isomiR example-2 of SEQ ID NO: 1341, isomiR example-2 of SEQ ID NO: 1342, isomiR example-2 of SEQ ID NO: 1343, isomiR example-1 of SEQ ID NO: 1344, isomiR example-2 of SEQ ID NO: 1344, isomiR example-2 of SEQ ID NO: 1346, isomiR example-2 of SEQ ID NO: 1347, isomiR example-2 of SEQ ID NO: 1348, isomiR example-1 of SEQ ID NO: 1351, isomiR example-2 of SEQ ID NO: 1351, isomiR example-1 of SEQ ID NO: 1352, isomiR example-2 of SEQ ID NO: 1352, isomiR example-1 of SEQ ID NO: 1354, isomiR example-2 of SEQ ID NO: 1354, isomiR example-1 of SEQ ID NO: 1355, isomiR example-2 of SEQ ID NO: 1355, isomiR example-1 of SEQ ID NO: 1356, and isomiR example-2 of SEQ ID NO: 1356, which are represented by SEQ ID NOs: 1351 to 1434. Therefore, a polynucleotide that can be used as a nucleic acid probe or a primer in the present invention can be produced via cloning the gene.

Such a nucleic acid probe(s) or primer(s) may be chemically synthesized using an automated DNA synthesizer. A phosphoramidite process is commonly used for this synthesis, and this process can be used to automatically synthesize a single-stranded DNA with up to about 100 nucleotides in length. The automated DNA synthesizer is commercially available from, for instance, Polygen, Inc., ABI, Inc., or Applied BioSystems, Inc.

Alternatively, a polynucleotide(s) of the present invention may be prepared by cDNA cloning. For the cDNA cloning technology, a microRNA Cloning Kit Wako, for instance, can be utilized.

The sequence of a nucleic acid probe or primer for detection of a polynucleotide consisting of a nucleotide sequence represented by any of SEQ ID NOs: 1 to 210, 211 to 249, 250 to 374, 375 to 390, 1435 to 1448, and 1449 to 1453 is not present in vivo as an miRNA or any precursor thereof. For instance, the nucleotide sequences represented by SEQ ID NO: 3 and miR-4728-5p are generated from the precursor represented by SEQ ID NO: 393. This precursor has a hairpin-like structure as shown in FIG. 1, and the nucleotide sequences represented by SEQ ID NO: 3 and miR-4728-5p have mismatch nucleotides therebetween. Accordingly, a nucleotide sequence perfectly complementary to the nucleotide sequence represented by SEQ ID NO: 3 or miR-4728-5p is not naturally occurring in vivo. Thus, the nucleic acid probe(s) or primer(s) for detecting a nucleotide sequence represented by any of SEQ ID NOs: 1 to 210, 211 to 249, 250 to 374, 375 to 390, 1435 to 1448, and 1449 to 1453 may have an artificial nucleotide sequence not present in vivo.

Figure 14:
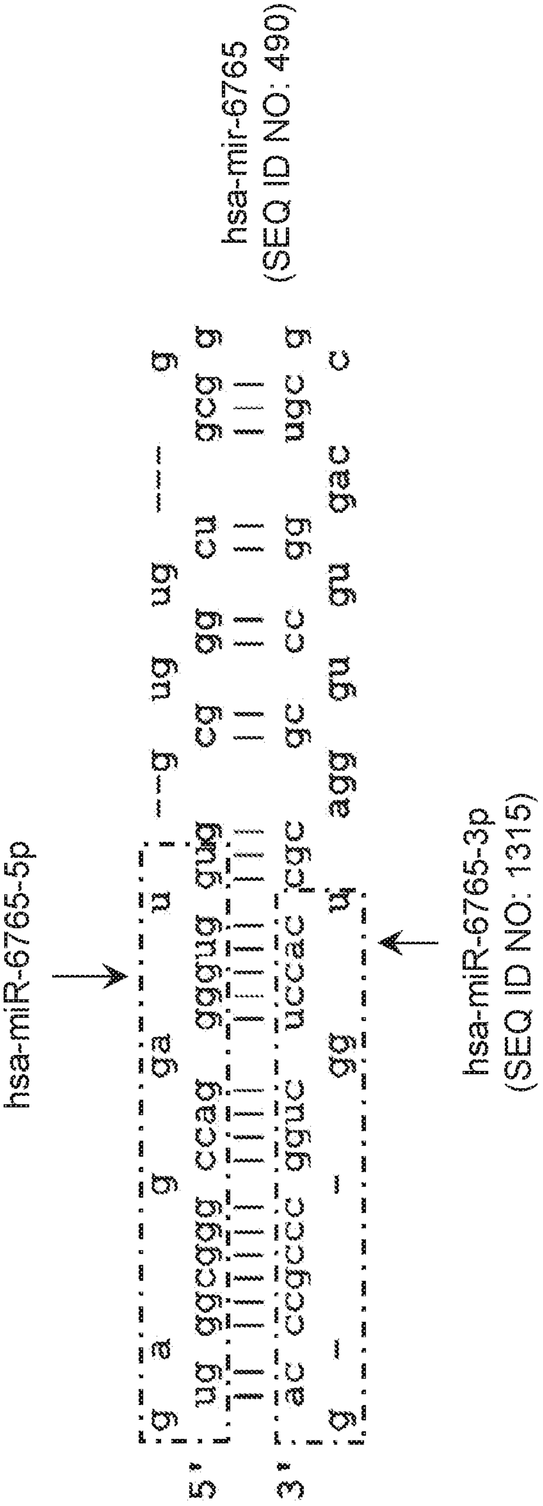
FIG. 14 illustrates the relationship between the nucleotide sequences of hsa-miR-6765-5p and hsa-miR-6765-3p represented by SEQ ID NO: 1315, which are generated from a precursor hsa-mir-6765 represented by SEQ ID NO: 490.

In addition, for instance, the nucleotide sequences represented by SEQ ID NO: 1315 and miR-6765-5p are generated from the precursor represented by SEQ ID NO: 490. This precursor has a hairpin-like structure as shown in FIG. 14, and the nucleotide sequences represented by SEQ ID NO: 1315 and miR-6765-5p have mismatch nucleotides therebetween. Accordingly, a nucleotide sequence perfectly complementary to the nucleotide sequence represented by SEQ ID NO: 1315 or miR-6765-5p is not naturally occurring in vivo. Thus, the nucleic acid probe(s) or primer(s) for detecting a nucleotide sequence represented by any of SEQ ID NOs: 194 to 210, 374, and 1315 to 1350 and 211 to 212, and 1351 to 1356 may have an artificial nucleotide sequence not present in vivo.

3. Kit or Device for Detection of Dementia

The present invention provides a kit or device for detection of dementia, comprising one or more polynucleotide(s) (which may include any variant(s), fragment(s), or derivative(s)) capable of being used as a nucleic acid probe(s) or primer(s) for measuring a target nucleic acid(s) as a dementia marker(s) in the present invention.

A target nucleic acid(s) as a dementia marker(s) according to the present invention is preferably at least one selected from the following group A.

Group A:

miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR-6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086.

An additional target nucleic acid(s) capable of being optionally used for the measurement is preferably selected from the following group B, C, or D.

Group B:

miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, miR-431-5p, miR-150-3p, miR-423-5p, miR-575, miR-671-5p, miR-939-5p and miR-3665, miR-30d-5p, miR-30b-3p, miR-92a-3p, miR-371b-5p, and miR-486-5p.

Group C:

miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p.

Group D:

miR-766-3p, miR-1229-3p, miR-1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, miR-767-3p.

In one embodiment, a target nucleic acid(s) as a dementia marker(s) according to the present invention is at least one selected from the following group E.

Group E:

at least one polynucleotide selected from the group consisting of miR-4728-5p, miR-3184-3p, miR-1233-3p, miR-6088, miR-6777-3p, miR-7110-3p, miR-936, miR-6087, miR-1202, miR-4731-3p, miR-4800-5p, miR-6784-3p, miR-4716-5p, miR-6734-3p, miR-6889-3p, miR-6867-3p, miR-3622a-3p, miR-6813-3p, miR-4769-3p, miR-5698, miR-3184-5p, miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, miR-6878-3p, and miR-371a-5p.

The target nucleic acid(s) selected from group E may be used in combination with one or more target nucleic acids arbitrarily selected from the group A, B, and D.

The target nucleic acid(s) selected from group E can be used for prediction of dementia in addition to detection of dementia. The term "prediction of dementia" used herein means predicting the possibility that a subject without currently having dementia will have dementia in the future. The detection or prediction of dementia may be distinctively carried out using different thresholds (e.g., a lower threshold for prediction than for detection) or carried out by using the same threshold (such that a subject without dementia detected is determined to be likely to have dementia). The prediction of dementia is useful because it enables a prophylactic treatment for dementia to be implemented in a subject who has been determined to be likely to have dementia.

A kit or device of the present invention comprises a nucleic acid(s) capable of specifically binding to the above target nucleic acid(s) as dementia marker(s), preferably, at least one polynucleotide selected from the polynucleotides described in the above groups or a variant thereof.

Specifically, a kit or device of the present invention may comprise at least one of a polynucleotide comprising (or consisting of) a nucleotide sequence represented by any of SEQ ID NOs: 1 to 210, 211 to 249, 250 to 374, 375 to 390, 1315 to 1350, 1351 to 1356, 1435 to 1448, and 1449 to 1453 or a nucleotide sequence derived from the nucleotide sequence by the replacement of u with t or a polynucleotide comprising (consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

A fragment(s) that can be comprised in a kit or device of the present invention may be, for instance, one or more polynucleotides and preferably at least two polynucleotides selected from the group consisting of the following (1) to (8):

(1) a polynucleotide comprising a sequence of 15 or more consecutive nucleotides in a nucleotide sequence derived from the nucleotide sequence represented by any of SEQ ID NOs: 1 to 210 by the replacement of u with t or in a complementary sequence thereof;

(2) a polynucleotide comprising a sequence of 15 or more consecutive nucleotides in a nucleotide sequence derived from the nucleotide sequence represented by any of SEQ ID NOs: 211 to 249 by the replacement of u with t or in a complementary sequence thereof;

(3) a polynucleotide comprising a sequence of 15 or more consecutive nucleotides in a nucleotide sequence derived from the nucleotide sequence represented by any of SEQ ID NOs: 250 to 374 by the replacement of u with t or in a complementary sequence thereof;

(4) a polynucleotide comprising a sequence of 15 or more consecutive nucleotides in a nucleotide sequence derived from the nucleotide sequence represented by any of SEQ ID NOs: 375 to 390 by the replacement of u with t or in a complementary sequence thereof;

(5) a polynucleotide comprising a sequence of 15 or more consecutive nucleotides in a nucleotide sequence derived from the nucleotide sequence represented by any of SEQ ID NOs: 391 to 782 by the replacement of u with t or in a complementary sequence thereof;

(6) a polynucleotide comprising a sequence of 15 or more consecutive nucleotides in a nucleotide sequence derived from the nucleotide sequence represented by any of SEQ ID NOs: 783 to 1314 by the replacement of u with t or in a complementary sequence thereof;

(7) a polynucleotide comprising a sequence of 15 or more consecutive nucleotides in a nucleotide sequence derived from the nucleotide sequence represented by any of SEQ ID NOs: 1315 to 1434 by the replacement of u with t or in a complementary sequence thereof; and (8) a polynucleotide comprising a sequence of 15 or more consecutive nucleotides in a nucleotide sequence derived from the nucleotide sequence represented by any of SEQ ID NOs: 1434 to 1505 by the replacement of u with t or in a complementary sequence thereof.

In a preferred embodiment, the polynucleotide is a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising a sequence of 15 or more, preferably 17 or more, and more preferably 19 or more consecutive nucleotides of any of the polynucleotides.

In addition, in a preferred embodiment, the polynucleotide is a polynucleotide consisting of a nucleotide sequence represented by any of SEQ ID NOs: 1 to 210, 211 to 249, 250 to 374, and 375 to 390, 391 to 782, 783 to 1314, 1315 to 1350, 1351 to 1356, 1435 to 1448, 1449 to 1453, and 1454 to 1505 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, the fragment may be a polynucleotide comprising 15 or more, preferably 17 or more, and more preferably 19 or more consecutive nucleotides.

In the present invention, the size of the polynucleotide fragment is represented by the number of nucleotides in a range of, for instance, from 15 to less than the total number of consecutive nucleotides in the nucleotide sequence of each polynucleotide, from 17 to less than the total number of nucleotides in the sequence, or from 19 to less than the total number of nucleotides in the sequence.

Specific examples of a combination of the above polynucleotides as target nucleic acids in a kit or device of the present invention include a combination of 1, 2, 3, 4, 5, 6, 7, 8, 9, 10, or more polynucleotides selected from polynucleotides consisting of nucleotide sequences represented by SEQ ID NOs: 1 to 210, 211 to 249, 250 to 374, and 375 to 390, 1435 to 1448, and 1449 to 1453 listed in Table 1-1 (provided that at least one selected from polynucleotides consisting of nucleotide sequences represented by SEQ ID NOs: 1 to 210 and 250 to 374 is included). This is just an example and all the other various possible combinations are included in the present invention.

As a combination of target nucleic acids in a kit or device for discriminating between dementia patients and non-dementia subjects in the present invention, for instance, it is desirable to combine two or more polynucleotides listed in Table 1-1 (provided that at least one selected from polynucleotides consisting of nucleotide sequences represented by SEQ ID NOs: 1 to 210 and 250 to 374 is included). Specific examples include any combination of at least 2 and preferably 3 to 110 polynucleotides selected from polynucleotides consisting of nucleotide sequences represented by SEQ ID NOs: 1 to 210, 211 to 249, 250 to 374, 375 to 390, 1315 to 1350, 1351 to 1356, 1435 to 1448, and 1449 to 1453, provided that at least one selected from polynucleotides consisting of nucleotide sequences represented by SEQ ID NOs: 1 to 210 is included.

The following shows, as non-limiting examples, combinations comprising the above polynucleotide(s) as a target nucleic acid(s). For instance, the target nucleic acids may be combined as follows.

As a combination of target nucleic acids in a kit or device for discriminating between Alzheimer's dementia patients and non-dementia subjects in the present invention, it is desirable to combine 2 or more and preferably 3 to 110 polynucleotides listed in Table 1-1 (provided that at least one selected from polynucleotides consisting of nucleotide sequences represented by SEQ ID NOs: 1 to 210 and 250 to 374 is included). Specific examples include any combination of 2 or more polynucleotides selected from polynucleotides consisting of nucleotide sequences represented by SEQ ID NOs: 1 to 23, 26, 34, 40, 47, 49, 54, 63, 72, 77, 78, 83, 87, 90, 91, 99, 101, 104, 133, 145, 146, 152 to 156, 191, 192 and 194, 200, 206, 212, 214, 215, 250 to 316, and 375 to 378. Preferred examples include any combination of 2 or more polynucleotides selected from polynucleotides consisting of nucleotide sequences represented by SEQ ID NOs: 1 to 13, 15, 16, 18 to 20, 23, 26, 49, 72, 77, 83, 101, 152, 153, 155, 156, 192 and 194, 200, 214, and 215.

In addition, as a combination of target nucleic acids in a kit or device for discriminating between vascular dementia patients and non-dementia subjects in the present invention, for instance, it is desirable to combine 2 or more and preferably 3 to 30 polynucleotides listed in Table 1-1 (provided that at least one selected from polynucleotides consisting of nucleotide sequences represented by SEQ ID NOs: 1 to 210 is included). Specific examples include any combination of 2 or more polynucleotides selected from polynucleotides consisting of nucleotide sequences represented by SEQ ID NOs: 3, 4, 8, 15, 16, 23 to 45, 59, 69, 79, 80, 83, 88, 89, 91, 99, 101, 109, 110 to 112, 125, 133, 140, 141, 191 to 193 and 194, 197, 199, 201, 203, 204, 206 to 209, 214, 216 to 218, 233, 252, 255, 258, 261 to 264, 266, 267, 271, 277, 278, 282, 284, 287, 289, 290, 293, 294, 297, 298, 301, 303, 306, 307, 310, 312 to 314, 320, 321, 323, 327, 329, 335, 336, 338, 342, 343, 345, 348, 349, 351, 352, 354, 359, 361 to 373, 375, 376, 380 to 383, 385, and 387 to 390. Preferred examples include any combination of 2 or more polynucleotides selected from polynucleotides consisting of nucleotide sequences represented by SEQ ID NOs: 3, 4, 8, 16, 23 to 30, 32, 34, 36, 37, 42, 43, 45, 79, 88, 89, 99, 111, 125 and 194, 197, 199, 201, 203, 204, 206, 207, 214, and 216 to 218.

In addition, as a combination of target nucleic acids in a kit or device for discriminating between Lewy body dementia patients and non-dementia subjects in the present invention, for instance, it is desirable to combine 2 or more and preferably 3 to 30 polynucleotides listed in Table 1-1 (provided that at least one selected from polynucleotides consisting of nucleotide sequences represented by SEQ ID NOs: 1 to 210 is included). Specific examples include any combination of 2 or more polynucleotides selected from polynucleotides consisting of nucleotide sequences represented by SEQ ID NOs: 1, 3, 4, 8, 11, 13, 15, 16, 26, 29, 30, 32 to 34, 36, 37, 45 to 68, 83, 87, 90 to 99, 101, 107, 109, 112 to 114, 116, 128, 133, 134, 157 to 159, 191, 192 and 194, 196, 197, 200, 204, 206, 207, 209, 210, 214, 216, 218 to 222, 234, 247, 250, 253 to 258, 261, 262, 264 to 267, 271, 277, 279, 282, 283, 284, 287, 289, 290, 293, 294, 298, 299, 301 to 303, 306, 308, 310, 312 to 314, 316 to 360, 374 to 377, and 379 to 388. Preferred examples include any combination of 2 or more polynucleotides selected from polynucleotides consisting of nucleotide sequences represented by SEQ ID NOs: 3, 4, 8, 11, 13, 16, 26, 29, 32, 36, 37, 45 to 49, 52 to 55, 60, 64, 68, 91, 116, 134 and 194, 197, 200, 207, 209, 214, 216, 219, 220, 221, and 247.

In addition, as a combination of target nucleic acids in a kit or device for discriminating between normal pressure hydrocephalus patients and non-dementia subjects in the present invention, for instance, it is desirable to combine 2 or more and preferably 3 to 30 polynucleotides listed in Table 1-1 (provided that at least one selected from polynucleotides consisting of nucleotide sequences represented by SEQ ID NOs: 1 to 210 is included). Specific examples include any combination of 2 or more polynucleotides selected from polynucleotides consisting of nucleotide sequences represented by SEQ ID NOs: 1, 3, 8, 10, 11, 16, 26, 30, 34, 37, 41, 43, 45, 49, 52 to 54, 60, 66, 75, 76, 83 to 86, 88, 94, 98, 99, 104, 116, 134, 136, 139 to 144, 150, 151, 176, 183 to 190 and 195, 200, 203, 205, 211, 212, 214, 215, 220, 225, 226, 230, 234, 240, 245, and 246. Preferred examples include any combination of 2 or more polynucleotides selected from polynucleotides consisting of nucleotide sequences represented by SEQ ID NOs: 1, 3, 8, 10, 11, 16, 26, 30, 34, 37, 41, 45, 49, 52, 54, 60, 66, 75, 76, 83 to 85, 88, 94, 104, 136, 140, 151, 176, 184 to 186 and 203, 211, 212, 220, 226, 230, 234, and 245.

In addition, as a combination of target nucleic acids in a kit or device for discriminating between frontotemporal lobar degeneration patients and non-dementia subjects in the present invention, for instance, it is desirable to combine 2 or more and preferably 3 to 30 polynucleotides listed in Table 1-1 (provided that at least one selected from polynucleotides consisting of nucleotide sequences represented by SEQ ID NOs: 1 to 210 is included). Specific examples include any combination of 2 or more polynucleotides selected from polynucleotides consisting of nucleotide sequences represented by SEQ ID NOs: 3, 10, 13, 24, 26, 29, 30, 33, 37, 43, 49, 53, 69 to 74, 81 to 83, 94, 98, 99, 115 to 117, 120, 121, 125, 128, 133, 135, 147 to 149, 153, 160 to 182, 191, 193 and 197, 200, 202, 213, 217, 223 to 225, 227, 228, 236, 238, 241 to 243, 248, and 249. Preferred examples include any combination of 2 or more polynucleotides selected from polynucleotides consisting of nucleotide sequences represented by SEQ ID NOs: 3, 10, 13, 24, 26, 29, 30, 33, 37, 43, 69 to 74, 82, 98, 99, 116, 117, 120, 121, 125, 147, 148, 161 to 163, 166, 167, 169, 175, 176 and 197, 200, 202, 223 to 225, 227, 236, 241, 242, 248, and 249.

In addition, as a combination of target nucleic acids in a kit or device for discriminating between Alzheimer's dementia patients and non-dementia subjects or for predicting Alzheimer's dementia patients in the present invention, for instance, it is desirable to combine SEQ ID NOs: 8, 15, 34, 40, 133, 191, 212, 250 to 316, and 375 to 378.

In addition, as a combination of target nucleic acids in a kit or device for discriminating between vascular dementia patients and non-dementia subjects in the present invention, for instance, it is desirable to combine SEQ ID NOs: 3, 8, 15, 26, 34, 69, 99, 101, 109, 112, 125, 133, 191 to 194, 252, 255, 258, 261 to 264, 266, 267, 271, 277, 278, 282, 284, 287, 289, 290, 293, 294, 297, 298, 301, 303, 306, 307, 310, 312 to 314, 320, 321, 323, 327, 329, 335, 336, 338, 342, 343, 345, 348, 349, 351, 352, 354, 359, 361 to 373 and 375, 376, 380 to 383, 385, and 387 to 390.

In addition, as a combination of target nucleic acids in a kit or device for discriminating between Lewy body dementia patients and non-dementia subjects in the present invention, for instance, it is desirable to combine SEQ ID NOs: 3, 8, 15, 26, 34, 53, 99, 101, 107, 109, 112, 128, 133, 191, 192, 194, 250, 253 to 258, 261, 262, 264 to 267, 271, 277, 279, 282 to 284, 287, 289, 290, 293, 294, 298, 299, 301 to 303, 306, 308, 310, 312 to 314, 316 to 360 and 374 to 377, and 379 to 388.

In one embodiment, a target nucleic acid(s) as a dementia marker(s) according to the present invention is preferably at least one selected from the following group A'.

Group A':

miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, miR-7114-5p.

In one embodiment, an additional target nucleic acid(s) capable of being optionally used for the measurement is preferably selected from the following group B'.

Group B':

miR-1225-3p, miR-3184-5p, miR-150-3p, miR-423-5p, miR-575, miR-671-5p, miR-939-5p, miR-3665.

In one embodiment, a kit or device of the present invention comprises a nucleic acid(s) capable of specifically binding to the above target nucleic acids as dementia markers, preferably at least one polynucleotide selected from the polynucleotides described in the above two groups or a variant thereof.

In one embodiment, a kit or device of the present invention may comprise at least one of a polynucleotide comprising (or consisting of) a nucleotide sequence represented by any of SEQ ID NOs: 194 to 210, 374, and 1315 to 1350, and 211 to 212, and 1351 to 1356 or a nucleotide sequence derived from the nucleotide sequence by the replacement of u with t or a polynucleotide comprising (or consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

In one embodiment, a fragment(s) that can be comprised in a kit or device of the present invention may be, for instance, one or more polynucleotides and preferably at least two polynucleotides selected from the group consisting of the following (1) to (4):

(1) a polynucleotide comprising a sequence of 15 or more consecutive nucleotides in a nucleotide sequence derived from the nucleotide sequence represented by any of SEQ ID NOs: 194 to 210, 374, and 1315 to 1350 by the replacement of u with t or in a complementary sequence thereof;

(2) a polynucleotide comprising a sequence of 15 or more consecutive nucleotides in a nucleotide sequence derived from the nucleotide sequence represented by any of SEQ ID NOs: 211 to 212 and 1351 to 1356 by the replacement of u with t or in a complementary sequence thereof;

(3) a polynucleotide comprising a sequence of 15 or more consecutive nucleotides in a nucleotide sequence derived from the nucleotide sequence represented by any of SEQ ID NOs: 398, 490, 591, 593 to 609, and 1357 to 1399 by the replacement of u with t or in a complementary sequence thereof; and (4) a polynucleotide comprising a sequence of 15 or more consecutive nucleotides in a nucleotide sequence derived from the nucleotide sequence represented by any of SEQ ID NOs: 1015 to 1017, 1019 to 1024, 1026 to 1031, 1285 to 1286, and 1400 to 1434 by the replacement of u with t or in a complementary sequence thereof.

In a preferred embodiment, the polynucleotide is a polynucleotide consisting of a nucleotide sequence represented by any of SEQ ID NOs: 194 to 210, 374, and 1315 to 1350 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising a sequence of 15 or more, preferably 17 or more, and more preferably 19 or more consecutive nucleotides of any of the polynucleotides.

In addition, in a preferred embodiment, the polynucleotide is a polynucleotide consisting of a nucleotide sequence represented by any of SEQ ID NOs: 211 to 212 and 1351 to 1356, 398, 490, 591, 593 to 609, 1357 to 1399, 1015 to 1017, 1019 to 1024, 1026 to 1031, 1285 to 1286, and 1400 to 1434 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, the fragment may be a polynucleotide comprising 15 or more, preferably 17 or more, and more preferably 19 or more consecutive nucleotides.

In the present invention, the size of the polynucleotide fragment is represented by the number of nucleotides in a range of, for instance, from 15 to less than the total number of consecutive nucleotides in the nucleotide sequence of each polynucleotide, from 17 to less than the total number of nucleotides in the sequence, or from 19 to less than the total number of nucleotides in the sequence.

Specific examples of a combination of the above polynucleotides as target nucleic acids in a kit or device of the present invention include a combination of 1, 2, 3, 4, 5, 6, 7, 8, 9, 10, or more polynucleotides selected from polynucleotides consisting of nucleotide sequences represented by SEQ ID NOs: 194 to 210, 374, and 1315 to 1350, and 211 to 212, and 1351 to 1356 listed in Table 1-2 (provided that at least one selected from polynucleotides consisting of nucleotide sequences represented by SEQ ID NOs: 194 to 210, 374, and 1315 to 1350 is included). This is just an example and all the other various possible combinations are included in the present invention.

As a combination of target nucleic acids in a kit or device for discriminating between dementia patients and non-dementia subjects in the present invention, for instance, it is desirable to combine two or more polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2, preferably 20 to 60, and more preferably 40 to 55 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of nucleotide sequences represented by SEQ ID NOs: 194 to 210, 374, and 1315 to 1350 is included.

The following shows, as non-limiting examples, combinations comprising the above polynucleotide(s) as a target nucleic acid(s). Examples of a combination of target nucleic acids include any combination comprising a polynucleotide consisting of SEQ ID NO: 1315. Examples of a combination of two target nucleic acids include any combination comprising two polynucleotides consisting of SEQ ID NOs: 1317 and 195. Examples of a combination of three target nucleic acids include any combination comprising three polynucleotides consisting of SEQ ID NOs: 1315, 1316, and 194. Examples of a combination of 20 target nucleic acids include any combination comprising 20 polynucleotides consisting of SEQ ID NOs: 1315, 1316, 194, 195, 1318, 1319, 197, 1320 to 1325, 199, 1331, 200, 1335, 1352, 1354, and 1356; or of SEQ ID NOs: 1315, 1316, 194, 195, 197, 1321, 1322, 1326, 1327, 199, 1331, 200, 202, 1333, 1335, 206, 1349, 1352, 1355, and 212. Examples of a combination of 42 target nucleic acids include any combination comprising 42 polynucleotides consisting of SEQ ID NOs: 194 to 205, 1315 to 1339, 1352 to 1355, and 1356. Examples of a combination of 51 target nucleic acids include any combination comprising 51 polynucleotides consisting of SEQ ID NOs: 1315, 1316, 194, 195, 1318, 1319, 197, 1321 to 1323, 1326, 1327, 198, 199, 1329, 1331, 200, 202, 1333, 203, 1335, 204 to 212, 374, and 1337 to 1356.

In addition, as a combination of target nucleic acids in a kit or device for discriminating between Alzheimer's dementia patients and non-dementia subjects in the present invention, it is desirable to combine 2 or more, preferably 20 to 60, and more preferably 40 to 55 polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of nucleotide sequences represented by SEQ ID NOs: 194 to 210, 374, and 1315 to 1350 is included.

In addition, as a combination of target nucleic acids in a kit or device for discriminating between vascular dementia patients and non-dementia subjects in the present invention, it is desirable to combine 2 or more, preferably 20 to 60, and more preferably 40 to 55 polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of nucleotide sequences represented by SEQ ID NOs: 194 to 210, 374, and 1315 to 1350 is included.

In addition, as a combination of target nucleic acids in a kit or device for discriminating between Lewy body dementia patients and non-dementia subjects in the present invention, it is desirable to combine 2 or more, preferably 20 to 60, and more preferably 40 to 55 polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of a nucleotide sequence represented by SEQ ID NOs: 194 to 210, 374, and 1315 to 1350 is included.

In addition, as a combination of target nucleic acids in a kit or device for discriminating between normal pressure hydrocephalus patients and non-dementia subjects in the present invention, it is desirable to combine 2 or more, preferably 20 to 60, and more preferably 40 to 55 polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of nucleotide sequences represented by SEQ ID NOs: 194 to 210, 374, and 1315 to 1350 is included.

In addition, as a combination of target nucleic acids in a kit or device for discriminating between frontotemporal lobar degeneration patients and non-dementia subjects in the present invention, it is desirable to combine 2 or more, preferably 20 to 60, and more preferably 40 to 55 polynucleotides listed in Table 1-2 (provided that at least one selected from polynucleotides consisting of nucleotide sequences represented by SEQ ID NOs: 194 to 210, 374, and 1315 to 1350 is included). Specific examples include any combination of at least 2 polynucleotides selected from polynucleotides consisting of nucleotide sequences represented by SEQ ID NOs: 194 to 210, 374, and 1315 to 1350, and 211 to 212, and 1351 to 1356, provided that at least one selected from polynucleotides consisting of nucleotide sequences represented by SEQ ID NOs: 194 to 210, 374, and 1315 to 1350 is included.

A kit or device of the present invention may comprise, in addition to the above-described polynucleotide(s) in the present invention (which may include any variant(s), fragment(s), or derivative(s)), a polynucleotide(s) known to be able to detect dementia or a polynucleotide(s) that will be discovered in the future.

The kit or device of the present invention may be used in combination with, in addition to the above-described polynucleotides according to the present invention, a known marker(s) for detection of dementia, such as amyloid β-protein or tau protein, and/or an imaging test, such as PET, that visualizes the marker(s).

The kit of the present invention may be used in combination with, in addition to the above-described polynucleotides according to the present invention, a neuropsychological examination or test such as MMSE.

These polynucleotides, or variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention may be a device for measuring a dementia marker(s), in which nucleic acids such as the above-described polynucleotide(s), variant(s), derivative(s), or fragment(s) thereof according to the present invention are, for instance, bonded or attached onto a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or device of the present invention comprises nucleic acids capable of specifically binding to at least one, preferably at least two, more preferably at least three, most preferably at least five to all polynucleotides selected from the above-mentioned dementia marker miRNAs of the group A, or to a complementary strand(s) of the polynucleotide(s), respectively. The kit or device of the present invention can optionally further comprise nucleic acids capable of specifically binding to at least one, preferably at least two, more preferably at least three, most preferably at least five to all polynucleotides selected from the above-mentioned dementia marker miRNAs of the group B, or to a complementary strand(s) of the polynucleotide(s), respectively.

The kit or device of the present invention can be used for detecting dementia as described in Section 4 below.

4. Method for Detecting Dementia

The present invention relates to a method for detecting dementia, comprising measuring, in vitro, an expression level(s) of 1 or more, 2 or more, 3 or more, 10 or more, preferably 3 to 30, or 3 to 110 genes comprising target gene(s) selected from group A (optionally in combination with target gene(s) selected from groups B to D) or target gene(s) selected from group E (optionally in combination with target gene(s) selected from group A, B, or D) in a sample as described in the Section "3. Kit or Device for Detection of Dementia"; and evaluating in vitro whether or not a subject has dementia using the measured expression level(s) (and optionally a control expression level(s) in a healthy subject(s) as likewise measured). In the method, it is possible to determine that a subject has dementia by using the expression level(s) of the above-mentioned genes in a sample from a subject suspected of having dementia and control expression levels of the genes in samples from non-dementia subjects, e.g., if there is a difference in the expression level(s) of the target nucleic acid(s) in the samples when comparing the expression level(s) between the subjects, in which the sample(s) may be, for instance, blood, serum, plasma or the like collected from the subject suspected of having dementia and the non-dementia subjects.

In addition, the present invention relates to a method for predicting dementia, comprising measuring, in vitro, an expression level(s) of 1 or more, 2 or more, 3 or more, 10 or more, preferably 3 to 30, or 3 to 110 genes comprising target gene(s) selected from group E (optionally in combination with target gene(s) selected from group A, B, or D) as described in the Section "3. Kit or Device for Detection of Dementia"; and predicting in vitro the possibility for a subject to develop dementia in the future by using the measured expression level(s) (and optionally control expression level(s) in healthy subjects as likewise measured). In the method, it is possible to predict that a subject is likely to have dementia by using the expression level(s) of the above-mentioned genes in a sample from a subject with the possibility of developing dementia in the future and control expression levels of the genes in samples from non-dementia subjects, e.g., if there is a difference in the expression level(s) of the target nucleic acid(s) in the samples when comparing the expression level(s) between the subjects, in which the samples may be, for instance, blood, serum, plasma or the like collected from the subject with the possibility of developing dementia in the future and the non-dementia subjects.

In one embodiment, the present invention provides a method for detecting dementia, comprising: measuring in vitro an expression level(s) of 1 or more, 2 or more, 3 or more, 10 or more, preferably 20 to 60, and more preferably 40 to 55 genes selected from genes including dementia-derived genes represented by miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p, and miR-7114-5p and optionally further comprising dementia-derived genes represented by miR-1225-3p, miR-3184-5p, miR-150-3p, miR-423-5p, miR-575, miR-671-5p, miR-939-5p, and miR-3665 in a sample by using a kit or device (comprising the above nucleic acid(s) capable of being used in the present invention) according to the present invention as described in the above Section 3; and determining that a subject has dementia by using the expression level(s) of the above-mentioned genes in a sample from a subject suspected of having dementia and control expression levels of the genes in samples from non-dementia subjects, e.g., if there is a difference in the expression level(s) of the target nucleic acid(s) in the samples when comparing both the expression level(s) between the subject(s), in which the sample(s) may be, for instance, blood, serum, plasma or the like collected from the subject suspected of having dementia and the non-dementia subjects.

The above-mentioned method of the present invention enables less-invasive, highly sensitive and specific early diagnosis of at least one dementia selected from Alzheimer's dementia, vascular dementia, Lewy body dementia, normal pressure hydrocephalus, frontotemporal lobar degeneration, senile dementia of the neurofibrillary tangle type, dementia resulting from other diseases (e.g., infectious diseases), alcoholic dementia, vitamin deficiency dementia, or the like, mixed dementia of any of these types, or type-unknown or unspecified dementia. This allows for an early medical intervention and suppression of disease progression and further makes it possible to monitor exacerbation of the disease and monitor effectiveness of surgical treatment or medication.

For the method for extracting the dementia-derived gene(s) from the sample such as blood, serum, or plasma according to the present invention, it is particularly preferred to add a reagent for RNA extraction in 3D-Gene (registered trademark) RNA extraction reagent from liquid sample kit (Toray Industries, Inc., Japan) for preparation of a sample. Alternatively, a general acidic phenol method (acid guanidinium-phenol-chloroform (AGPC)) may be used, or Trizol (registered trademark) (Life Technologies Corp.) may be used. Alternatively, for preparation of a sample, a reagent for RNA extraction containing acidic phenol, such as Trizol (Life Technologies Corp.) or Isogen (Nippon Gene Co., Ltd., Japan) may be added. Alternatively, a kit such as miRNeasy (registered trademark) Mini Kit (Qiagen N.V.) may be used. However, the method according to the present invention is not limited thereto.

The present invention also provides use of a dementia-derived miRNA gene(s) in a sample from a subject for in vitro detection of an expression product(s) thereof.

The present invention also provides use of the kit or the device of the present invention for detecting in vitro an expression product(s) of a dementia-derived miRNA gene(s) in a sample from a subject.

A technique to be used for carrying out the method of the present invention is not limited and, for instance, the kit or device of the present invention (comprising the above nucleic acid(s) capable of being used in the present invention) as described in the above Section 3 may be used for carrying out the method.

In the method of the present invention, the kit or device described above comprising a single polynucleotide or any possible combination of polynucleotides that can be used in the present invention as described above, can be used.

In the detection or (genetic) diagnosis of dementia according to the present invention, a polynucleotide(s) contained in the kit or device of the present invention can be used as a probe(s) or a primer(s). In the case of using the polynucleotide(s) as a primer(s), TaqMan (registered trademark) MicroRNA Assays from Life Technologies Corp., miScript PCR System from Qiagen N.V., or the like can be used. However, though the method according to the present invention is not limited thereto.

In the method of the present invention, measurement of the gene expression levels can be performed according to a routine technique of a method known in the art for specifically detecting particular genes, for example, a hybridization technique such as Northern blot, Southern blot, in situ hybridization, Northern hybridization, or Southern hybridization; a quantitative amplification technique such as quantitative RT-PCR; or a method with a next-generation sequencer. A body fluid such as blood, serum, plasma, or urine from a subject is collected as a sample to be assayed depending on the type of the detection method to be used. Alternatively, total RNA prepared from such a body fluid by the method described above may be used, and various polynucleotides including cDNA prepared from the RNA may be used.

The method of the present invention is useful for the diagnosis of dementia or the detection of the presence or absence of dementia. Specifically, the detection of dementia according to the present invention can be performed by detecting in vitro an expression level(s) of a gene(s) which is detected using the nucleic acid probe(s) or the primer(s) contained in the kit or the device according to the present invention, in a sample such as blood, serum, plasma, or urine from a subject suspected of having dementia. If the expression level(s) of a polynucleotide(s) consisting of a nucleotide sequence(s) represented by at least one selected from SEQ ID NOs: 1 to 210, 374, 1315 to 1350, and 1435 to 1448 and optionally a nucleotide sequence(s) represented by one or more of SEQ ID NOs: 211 to 249, 1351 to 1356, and 1449 to 1453, or optionally a nucleotide sequence(s) represented by at least one selected from SEQ ID NOs: 250 to 373, and optionally a nucleotide sequence(s) represented by one or more selected from SEQ ID NOs: 375 to 390 in a sample such as blood, serum, plasma, or urine of a subject suspected of having dementia, is statistically significantly higher compared to an expression level(s) thereof in a sample such as blood, serum, or plasma, or urine of a subject without dementia, the former subject can be evaluated as having dementia.

In one embodiment, if the expression level(s) of a polynucleotide(s) consisting of a nucleotide sequence(s) represented by at least one selected from SEQ ID NOs: 194 to 210, 374, and 1315 to 1350 and optionally a nucleotide sequence(s) represented by one or more selected from SEQ ID NOs: 211 to 212 and 1351 to 1356 in a sample such as blood, serum, plasma, or urine of a subject suspected of having dementia, is statistically significantly higher compared to an expression level(s) thereof in a sample such as blood, serum, or plasma, or urine of a subject without dementia, the former subject can be evaluated as having dementia.

Regarding the method of the present invention, the method for detecting the absence of dementia or the presence of dementia for a sample from a subject comprises collecting a body fluid such as blood, serum, plasma, or urine of the subject, and measuring the expression level(s) of the target gene(s) (or target nucleic acid(s)) contained therein using one or more polynucleotides (including variant(s), fragment(s), or derivative(s)) selected from the groups of polynucleotides according to the present invention, thereby evaluating the presence or absence of dementia or detecting dementia. The method for detecting dementia according to the present invention can also be used to evaluate or diagnose, for example, the presence or absence of amelioration of the disease or the degree of amelioration thereof in a dementia patient when a dementia-related therapeutic drug which is known in the art or on a development stage (including Aricept, GE Aricept, memantine, galantamine, rivastigmine, and combination drugs thereof, as non-limiting examples) is administered to the patient for treatment or amelioration of the disease.

The method of the present invention may comprise, for example, the following steps (a), (b), and (c):

(a) contacting in vitro a sample from a subject with a polynucleotide(s) contained in a kit or device of the present invention;
(b) measuring an expression level(s) of target nucleic acid(s) in the sample using the polynucleotide(s) as a nucleic acid probe(s) or primer(s); and
(c) evaluating the presence or absence of dementia (or mutant protein(s)) in the subject on the basis of the measurement results in step (b).

In a preferred embodiment of the method according to the present invention, the present invention provides a method for detecting dementia, comprising measuring an expression level(s) of a target nucleic acid(s) in a sample from a subject using a nucleic acid(s) capable of specifically binding to 1, preferably 2 or more, 3 or more, 10 or more, and more preferably 3 to 30 polynucleotides selected from the group consisting of miR-4274, miR-4272, miR-4728-5p, miR-4443, miR-4506, miR-6773-5p, miR-4662a-5p, miR-3184-3p, miR-4281, miR-320d, miR-6729-3p, miR-5192, miR-6853-5p, miR-1234-3p, miR-1233-3p, miR-4539, miR-3914, miR-4738-5p, miR-548au-3p, miR-1539, miR-4720-3p, miR-365b-5p, miR-4486, miR-1227-5p, miR-4667-5p, miR-6088, miR-6820-5p, miR-4505, miR-548q, miR-4658, miR-450a-5p, miR-1260b, miR-3677-5p, miR-6777-3p, miR-6826-3p, miR-6832-3p, miR-4725-3p, miR-7161-3p, miR-2277-5p, miR-7110-3p, miR-4312, miR-4461, miR-6766-5p, miR-1266-3p, miR-6729-5p, miR-526b-3p, miR-519e-5p, miR-512-5p, miR-5088-5p, miR-1909-3p, miR-6511a-5p, miR-4734, miR-936, miR-1249-3p, miR-6777-5p, miR-4487, miR-3155a, miR-563, miR-4741, miR-6788-5p, miR-4433b-5p, miR-323a-5p, miR-6811-5p, miR-6721-5p, miR-5004-5p, miR-6509-3p, miR-648, miR-3917, miR-6087, miR-1470, miR-586, miR-3150a-5p, miR-105-3p, miR-7973, miR-1914-5p, miR-4749-3p, miR-15b-5p, miR-1289, miR-4433a-5p, miR-3666, miR-3186-3p, miR-4725-5p, miR-4488, miR-4474-3p, miR-6731-3p, miR-4640-3p, miR-202-5p, miR-6816-5p, miR-638, miR-6821-5p, miR-1247-3p, miR-6765-5p, miR-6800-5p, miR-3928-3p, miR-3940-5p, miR-3960, miR-6775-5p, miR-3178, miR-1202, miR-6790-5p, miR-4731-3p, miR-2681-3p, miR-6758-5p, miR-8072, miR-518d-3p, miR-3606-3p, miR-4800-5p, miR-1292-3p, miR-6784-3p, miR-4450, miR-6132, miR-4716-5p, miR-6860, miR-1268b, miR-378d, miR-4701-5p, miR-4329, miR-185-3p, miR-552-3p, miR-1273g-5p, miR-6769b-3p, miR-520a-3p, miR-4524b-5p, miR-4291, miR- 6734-3p, miR-143-5p, miR-939-3p, miR-6889-3p, miR-6842-3p, miR-4511, miR-4318, miR-4653-5p, miR-6867-3p, miR-133b, miR-3196, miR-193b-3p, miR-3162-3p, miR-6819-3p, miR-1908-3p, miR-6786-5p, miR-3648, miR-4513, miR-3652, miR-4640-5p, miR-6871-5p, miR-7845-5p, miR-3138, miR-6884-5p, miR-4653-3p, miR-636, miR-4652-3p, miR-6823-5p, miR-4502, miR-7113-5p, miR-8087, miR-7154-3p, miR-5189-5p, miR-1253, miR-518c-5p, miR-7151-5p, miR-3614-3p, miR-4727-5p, miR-3682-5p, miR-5090, miR-337-3p, miR-488-5p, miR-100-5p, miR-4520-3p, miR-373-3p, miR-6499-5p, miR-3909, miR-32-5p, miR-302a-3p, miR-4686, miR-4659a-3p, miR-4287, miR-1301-5p, miR-593-3p, miR-517a-3p, miR-517b-3p, miR-142-3p, miR-1185-2-3p, miR-602, miR-527, miR-518a-5p, miR-4682, miR-28-5p, miR-4252, miR-452-5p, miR-525-5p, miR-3622a-3p, miR-6813-3p, and miR-4769-3p, miR-5698, miR-1915-3p, miR-1343-5p, miR-6861-5p, miR-6781-5p, miR-4508, miR-6743-5p, miR-6726-5p, miR-4525, miR-4651, miR-6813-5p, miR-5787, miR-1290, miR-6075, miR-4758-5p, miR-4690-5p, miR-762, miR-371a-5p, miR-6765-3p, miR-6784-5p, miR-6778-5p, miR-6875-5p, miR-4534, miR-4721, miR-6756-5p, miR-615-5p, miR-6727-5p, miR-6887-5p, miR-8063, miR-6880-5p, miR-6805-3p, miR-4726-5p, miR-4710, miR-7111-5p, miR-3619-3p, miR-6795-5p, miR-1254, miR-1233-5p, miR-6836-3p, miR-6769a-5p, miR-4532, miR-365a-5p, miR-1231, miR-1228-5p, miR-4430, miR-296-3p, miR-1237-5p, miR-4466, miR-6789-5p, miR-4632-5p, miR-4745-5p, miR-4665-5p, miR-6807-5p and miR-7114-5p, miR-516a-5p, miR-769-3p, miR-3692-5p, miR-3945, miR-4433a-3p, miR-4485-3p, miR-6831-5p, miR-519c-5p, miR-551b-5p, miR-1343-3p, miR-4286, miR-4634, miR-4733-3p, and miR-6086, or to a complementary strand(s) of the polynucleotide(s); and evaluating in vitro whether or not the subject has dementia by using the measured expression level(s) and a control expression level(s) in a subject(s) without dementia as likewise measured.

The term "evaluating" as used herein is evaluation support based on results of in vitro examination, not physician's judgment.

As described above, in a preferred embodiment of the method according to the present invention, miR-5698 is hsa-miR-5698, miR-1915-3p is hsa-miR-1915-3p, miR-1343-5p is hsa-miR-1343-5p, miR-6861-5p is hsa-miR-6861-5p, miR-6781-5p is hsa-miR-6781-5p, miR-4508 is hsa-miR-4508, miR-6743-5p is hsa-miR-6743-5p, miR-6726-5p is hsa-miR-6726-5p, miR-4525 is hsa-miR-4525, miR-4651 is hsa-miR-4651, miR-6813-5p is hsa-miR-6813-5p, miR-5787 is hsa-miR-5787, miR-1290 is hsa-miR-1290, miR-6075 is hsa-miR-6075, miR-4758-5p is hsa-miR-4758-5p, miR-4690-5p is hsa-miR-4690-5p, miR-762 is hsa-miR-762, miR-4274 is hsa-miR-4274, miR-4272 is hsa-miR-4272, miR-4728-5p is hsa-miR-4728-5p, miR-4443 is hsa-miR-4443, miR-4506 is hsa-miR-4506, miR-6773-5p is hsa-miR-6773-5p, miR-4662a-5p is hsa-miR-4662a-5p, miR-3184-3p is hsa-miR-3184-3p, miR-4281 is hsa-miR-4281, miR-320d is hsa-miR-320d, miR-6729-3p is hsa-miR-6729-3p, miR-5192 is hsa-miR-5192, miR-6853-5p is hsa-miR-6853-5p, miR-1234-3p is hsa-miR-1234-3p, miR-1233-3p is hsa-miR-1233-3p, miR-4539 is hsa-miR-4539, miR-3914 is hsa-miR-3914, miR-4738-5p is hsa-miR-4738-5p, miR-548au-3p is hsa-miR-548au-3p, miR-1539 is hsa-miR-1539, miR-4720-3p is hsa-miR-4720-3p, miR-365b-5p is hsa-miR-365b-5p, miR-4486 is hsa-miR-4486, miR-1227-5p is hsa-miR-1227-5p, miR-4667-5p is hsa-miR-4667-5p, miR-6088 is hsa-miR-6088, miR-6820-5p is hsa-miR-6820-5p, miR-4505 is hsa-miR-4505, miR-548q is hsa-miR-548q, miR-4658 is hsa-miR-4658, miR-450a-5p is hsa-miR-450a-5p, miR-1260b is hsa-miR-1260b, miR-3677-5p is hsa-miR-3677-5p, miR-6777-3p is hsa-miR-6777-3p, miR-6826-3p is hsa-miR-6826-3p, miR-6832-3p is hsa-miR-6832-3p, miR-4725-3p is hsa-miR-4725-3p, miR-7161-3p is hsa-miR-7161-3p, miR-2277-5p is hsa-miR-2277-5p, miR-7110-3p is hsa-miR-7110-3p, miR-4312 is hsa-miR-4312, miR-4461 is hsa-miR-4461, miR-6766-5p is hsa-miR-6766-5p, miR-1266-3p is hsa-miR-1266-3p, miR-6729-5p is hsa-miR-6729-5p, miR-526b-3p is hsa-miR-526b-3p, miR-519e-5p is hsa-miR-519e-5p, miR-512-5p is hsa-miR-512-5p, miR-5088-5p is hsa-miR-5088-5p, miR-1909-3p is hsa-miR-1909-3p, miR-6511a-5p is hsa-miR-6511a-5p, miR-4734 is hsa-miR-4734, miR-936 is hsa-miR-936, miR-1249-3p is hsa-miR-1249-3p, miR-6777-5p is hsa-miR-6777-5p, miR-4487 is hsa-miR-4487, miR-3155a is hsa-miR-3155a, miR-563 is hsa-miR-563, miR-4741 is hsa-miR-4741, miR-6788-5p is hsa-miR-6788-5p, miR-4433b-5p is hsa-miR-4433b-5p, miR-323a-5p is hsa-miR-323a-5p, miR-6811-5p is hsa-miR-6811-5p, miR-6721-5p is hsa-miR-6721-5p, miR-5004-5p is hsa-miR-5004-5p, miR-6509-3p is hsa-miR-6509-3p, miR-648 is hsa-miR-648, miR-3917 is hsa-miR-3917, miR-6087 is hsa-miR-6087, miR-1470 is hsa-miR-1470, miR-586 is hsa-miR-586, miR-3150a-5p is hsa-miR-3150a-5p, miR-105-3p is hsa-miR-105-3p, miR-7973 is hsa-miR-7973, miR-1914-5p is hsa-miR-1914-5p, miR-4749-3p is hsa-miR-4749-3p, miR-15b-5p is hsa-miR-15b-5p, miR-1289 is hsa-miR-1289, miR-4433a-5p is hsa-miR-4433a-5p, miR-3666 is hsa-miR-3666, miR-3186-3p is hsa-miR-3186-3p, miR-4725-5p is hsa-miR-4725-5p, miR-4488 is hsa-miR-4488, miR-4474-3p is hsa-miR-4474-3p, miR-6731-3p is hsa-miR-6731-3p, miR-4640-3p is hsa-miR-4640-3p, miR-202-5p is hsa-miR-202-5p, miR-6816-5p is hsa-miR-6816-5p, miR-638 is hsa-miR-638, miR-6821-5p is hsa-miR-6821-5p, miR-1247-3p is hsa-miR-1247-3p, miR-6765-5p is hsa-miR-6765-5p, miR-6800-5p is hsa-miR-6800-5p, miR-3928-3p is hsa-miR-3928-3p, miR-3940-5p is hsa-miR-3940-5p, miR-3960 is hsa-miR-3960, miR-6775-5p is hsa-miR-6775-5p, miR-3178 is hsa-miR-3178, miR-1202 is hsa-miR-1202, miR-6790-5p is hsa-miR-6790-5p, miR-4731-3p is hsa-miR-4731-3p, miR-2681-3p is hsa-miR-2681-3p, miR-6758-5p is hsa-miR-6758-5p, miR-8072 is hsa-miR-8072, miR-518d-3p is hsa-miR-518d-3p, miR-3606-3p is hsa-miR-3606-3p, miR-4800-5p is hsa-miR-4800-5p, miR-1292-3p is hsa-miR-1292-3p, miR-6784-3p is hsa-miR-6784-3p, miR-4450 is hsa-miR-4450, miR-6132 is hsa-miR-6132, miR-4716-5p is hsa-miR-4716-5p, miR-6860 is hsa-miR-6860, miR-1268b is hsa-miR-1268b, miR-378d is hsa-miR-378d, miR-4701-5p is hsa-miR-4701-5p, miR-4329 is hsa-miR-4329, miR-185-3p is hsa-miR-185-3p, miR-552-3p is hsa-miR-552-3p, miR-1273g-5p is hsa-miR-1273g-5p, miR-6769b-3p is hsa-miR-6769b-3p, miR-520a-3p is hsa-miR-520a-3p, miR-4524b-5p is hsa-miR-4524b-5p, miR-4291 is hsa-miR-4291, miR-6734-3p is hsa-miR-6734-3p, miR-143-5p is hsa-miR-143-5p, miR-939-3p is hsa-miR-939-3p, miR-6889-3p is hsa-miR-6889-3p, miR-6842-3p is hsa-miR-6842-3p, miR-4511 is hsa-miR-4511, miR-4318 is hsa-miR-4318, miR-4653-5p is hsa-miR-4653-5p, miR-6867-3p is hsa-miR-6867-3p, miR-133b is hsa-miR-133b, miR-3196 is hsa-miR-3196, miR-193b-3p is hsa-miR-193b-3p, miR-3162-3p is hsa-miR-3162-3p, miR-6819-3p is hsa-miR-6819-3p, miR-1908-3p is hsa-miR-1908-3p, miR-6786-5p is hsa-miR-6786-5p, miR-3648 is hsa-miR-3648, miR-4513 is hsa-miR-4513, miR-3652 is hsa-miR-3652, miR-4640-5p is hsa-miR-4640-5p, miR-6871-5p is hsa-miR-6871-5p, miR-7845-5p is hsa-miR-7845-5p, miR-3138 is hsa-miR-3138, miR-6884-5p is hsa-miR-6884-5p, miR-4653-3p is hsa-miR-4653-3p, miR-636 is hsa-miR-636, miR-4652-3p is hsa-miR-4652-3p, miR-6823-5p is hsa-miR-6823-5p, miR-4502 is hsa-miR-4502, miR-7113-5p is hsa-miR-7113-5p, miR-8087 is hsa-miR-8087, miR-7154-3p is hsa-miR-7154-3p, miR-5189-5p is hsa-miR-5189-5p, miR-1253 is hsa-miR-1253, miR-518c-5p is hsa-miR-518c-5p, miR-7151-5p is hsa-miR-7151-5p, miR-3614-3p is hsa-miR-3614-3p, miR-4727-5p is hsa-miR-4727-5p, miR-3682-5p is hsa-miR-3682-5p, miR-5090 is hsa-miR-5090, miR-337-3p is hsa-miR-337-3p, miR-488-5p is hsa-miR-488-5p, miR-100-5p is hsa-miR-100-5p, miR-4520-3p is hsa-miR-4520-3p, miR-373-3p is hsa-miR-373-3p, miR-6499-5p is hsa-miR-6499-5p, miR-3909 is hsa-miR-3909, miR-32-5p is hsa-miR-32-5p, miR-302a-3p is hsa-miR-302a-3p, miR-4686 is hsa-miR-4686, miR-4659a-3p is hsa-miR-4659a-3p, miR-4287 is hsa-miR-4287, miR-1301-5p is hsa-miR-1301-5p, miR-593-3p is hsa-miR-593-3p, miR-517a-3p is hsa-miR-517a-3p, miR-517b-3p is hsa-miR-517b-3p, miR-142-3p is hsa-miR-142-3p, miR-1185-2-3p is hsa-miR-1185-2-3p, miR-602 is hsa-miR-602, miR-527 is hsa-miR-527, miR-518a-5p is hsa-miR-518a-5p, miR-4682 is hsa-miR-4682, miR-28-5p is hsa-miR-28-5p, miR-4252 is hsa-miR-4252, miR-452-5p is hsa-miR-452-5p, miR-525-5p is hsa-miR-525-5p, miR-3622a-3p is hsa-miR-3622a-3p, miR-6813-3p is hsa-miR-6813-3p, miR-4769-3p is hsa-miR-4769-3p, miR-371a-5p is hsa-miR-371a-5p, miR-6765-3p is hsa-miR-6765-3p, miR-6784-5p is hsa-miR-6784-5p, miR-6778-5p is hsa-miR-6778-5p, miR-6875-5p is hsa-miR-6875-5p, miR-4534 is hsa-miR-4534, miR-4721 is hsa-miR-4721, miR-6756-5p is hsa-miR-6756-5p, miR-615-5p is hsa-miR-615-5p, miR-6727-5p is hsa-miR-6727-5p, miR-6887-5p is hsa-miR-6887-5p, miR-8063 is hsa-miR-8063, miR-6880-5p is hsa-miR-6880-5p, miR-6805-3p is hsa-miR-6805-3p, miR-4726-5p is hsa-miR-4726-5p, miR-4710 is hsa-miR-4710, miR-7111-5p is hsa-miR-7111-5p, miR-3619-3p is hsa-miR-3619-3p, miR-6795-5p is hsa-miR-6795-5p, miR-1254 is hsa-miR-1254, miR-1233-5p is hsa-miR-1233-5p, miR-6836-3p is hsa-miR-6836-3p, miR-6769a-5p is hsa-miR-6769a-5p, miR-4532 is hsa-miR-4532, miR-365a-5p is hsa-miR-365a-5p, miR-1231 is hsa-miR-1231, miR-1228-5p is hsa-miR-1228-5p, miR-4430 is hsa-miR-4430, miR-296-3p is hsa-miR-296-3p, miR-1237-5p is hsa-miR-1237-5p, miR-4466 is hsa-miR-4466, miR-6789-5p is hsa-miR-6789-5p, miR-4632-5p is hsa-miR-4632-5p, miR-4745-5p is hsa-miR-4745-5p, miR-4665-5p is hsa-miR-4665-5p, miR-6807-5p is hsa-miR-6807-5p, miR-7114-5p is hsa-miR-7114-5p, miR-516a-5p is hsa-miR-516a-5p, miR-769-3p is hsa-miR-769-3p, miR-3692-5p is hsa-miR-3692-5p, miR-3945 is hsa-miR-3945, miR-4433a-3p is hsa-miR-4433a-3p, miR-4485-3p is hsa-miR-4485-3p, miR-6831-5p is hsa-miR-6831-5p, miR-519c-5p is hsa-miR-519c-5p, miR-551b-5p is hsa-miR-551b-5p, miR-1343-3p is hsa-miR-1343-3p, miR-4286 is hsa-miR-4286, miR-4634 is hsa-miR-4634, miR-4733-3p is hsa-miR-4733-3p, and miR-6086 is hsa-miR-6086.

In addition, in a preferred embodiment of the method according to the present invention, a nucleic acid(s) (specifically, a probe(s) or primer(s)) is selected from the group consisting of polynucleotides shown in any of the following group (a) to (e):

(a) a polynucleotide consisting of a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 210, 374, 1315 to 1350, and 1435 to 1448, (c) a polynucleotide consisting of a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 210, 374, 1315 to 1350, and 1435 to 1448 or a nucleotide sequence derived from the nucleotide sequence by the replacement of u with t, and (e) a polynucleotide hybridizing under stringent conditions to any of the polynucleotides (a) to (d).

A target nucleic acid(s) in the method of the present invention may further comprise at least one polynucleotide selected from the group consisting of miR-1225-3p, miR-3184-5p, miR-665, miR-211-5p, miR-1247-5p, miR-3656, miR-149-5p, miR-744-5p, miR-345-5p, miR-150-5p, miR-191-3p, miR-651-5p, miR-34a-5p, miR-409-5p, miR-369-5p, miR-1915-5p, miR-204-5p, miR-137, miR-382-5p, miR-517-5p, miR-532-5p, miR-22-5p, miR-1237-3p, miR-1224-3p, miR-625-3p, miR-328-3p, miR-122-5p, miR-202-3p, miR-4781-5p, miR-718, miR-342-3p, miR-26b-3p, miR-140-3p, miR-200a-3p, miR-378a-3p, miR-484, miR-296-5p, miR-205-5p, and miR-431-5p, miR-150-3p, miR-423-5p, miR-575, miR-671-5p, miR-939-5p, and miR-3665, miR-30d-5p, miR-30b-3p, miR-92a-3p, miR-371b-5p, miR-486-5p, or miR-1471, miR-1538, miR-449b-3p, miR-1976, miR-4268, miR-4279, miR-3620-3p, miR-3944-3p, miR-3156-3p, miR-3187-5p, miR-4685-3p, miR-4695-3p, miR-4697-3p, miR-4713-5p, miR-4723-3p, miR-371b-3p, miR-3151-3p, miR-3192-3p, miR-6728-3p, miR-6736-3p, miR-6740-3p, miR-6741-3p, miR-6743-3p, miR-6747-3p, miR-6750-3p, miR-6754-3p, miR-6759-3p, miR-6761-3p, miR-6762-3p, miR-6769a-3p, miR-6776-3p, miR-6778-3p, miR-6779-3p, miR-6786-3p, miR-6787-3p, miR-6792-3p, miR-6794-3p, miR-6801-3p, miR-6802-3p, miR-6803-3p, miR-6804-3p, miR-6810-5p, miR-6823-3p, miR-6825-3p, miR-6829-3p, miR-6833-3p, miR-6834-3p, miR-6780b-3p, miR-6845-3p, miR-6862-3p, miR-6865-3p, miR-6870-3p, miR-6875-3p, miR-6877-3p, miR-6879-3p, miR-6882-3p, miR-6885-3p, miR-6886-3p, miR-6887-3p, miR-6890-3p, miR-6893-3p, miR-6894-3p, miR-7106-3p, miR-7109-3p, miR-7114-3p, miR-7155-5p, miR-7160-5p, miR-615-3p, miR-920, miR-1825, miR-675-3p, miR-1910-5p, miR-2278, miR-2682-3p, miR-3122, miR-3151-5p, miR-3175, miR-4323, miR-4326, miR-4284, miR-3605-3p, miR-3622b-5p, miR-3646, miR-3158-5p, miR-4722-3p, miR-4728-3p, miR-4747-3p, miR-4436b-5p, miR-5196-3p, miR-5589-5p, miR-345-3p, miR-642b-5p, miR-6716-3p, miR-6511b-3p, miR-208a-5p, miR-6726-3p, miR-6744-5p, miR-6782-3p, miR-6789-3p, miR-6797-3p, miR-6800-3p, miR-6806-5p, miR-6824-3p, miR-6837-5p, miR-6846-3p, miR-6858-3p, miR-6859-3p, miR-6861-3p, miR-6880-3p, miR-7111-3p, miR-7152-5p, miR-642a-5p, miR-657, miR-1236-3p, miR-764, miR-4314, miR-3675-3p, miR-5703, miR-3191-5p, miR-6511a-3p, miR-6809-3p, miR-6815-5p, miR-6857-3p, and miR-6878-3p, or miR-766-3p, miR-1229-3p, miR- 1306-5p, miR-210-5p, miR-198, miR-485-3p, miR-668-3p, miR-532-3p, miR-877-3p, miR-1238-3p, miR-3130-5p, miR-4298, miR-4290, miR-3943, miR-346, and miR-767-3p or a nucleic acid(s) capable of specifically binding to the polynucleotide(s).

In a preferred embodiment of the method according to the present invention, miR-1225-3p is hsa-miR-1225-3p, miR-3184-5p is hsa-miR-3184-5p, miR-665 is hsa-miR-665, miR-211-5p is hsa-miR-211-5p, miR-1247-5p is hsa-miR-1247-5p, miR-3656 is hsa-miR-3656, miR-149-5p is hsa-miR-149-5p, miR-744-5p is hsa-miR-744-5p, miR-345-5p is hsa-miR-345-5p, miR-150-5p is hsa-miR-150-5p, miR-191-3p is hsa-miR-191-3p, miR-651-5p is hsa-miR-651-5p, miR-34a-5p is hsa-miR-34a-5p, miR-409-5p is hsa-miR-409-5p, miR-369-5p is hsa-miR-369-5p, miR-1915-5p is hsa-miR-1915-5p, miR-204-5p is hsa-miR-204-5p, miR-137 is hsa-miR-137, miR-382-5p is hsa-miR-382-5p, miR-517-5p is hsa-miR-517-5p, miR-532-5p is hsa-miR-532-5p, miR-22-5p is hsa-miR-22-5p, miR-1237-3p is hsa-miR-1237-3p, miR-1224-3p is hsa-miR-1224-3p, miR-625-3p is hsa-miR-625-3p, miR-328-3p is hsa-miR-328-3p, miR-122-5p is hsa-miR-122-5p, miR-202-3p is hsa-miR-202-3p, miR-4781-5p is hsa-miR-4781-5p, miR-718 is hsa-miR-718, miR-342-3p is hsa-miR-342-3p, miR-26b-3p is hsa-miR-26b-3p, miR-140-3p is hsa-miR-140-3p, miR-200a-3p is hsa-miR-200a-3p, miR-378a-3p is hsa-miR-378a-3p, miR-484 is hsa-miR-484, miR-296-5p is hsa-miR-296-5p, miR-205-5p is hsa-miR-205-5p, miR-431-5p is hsa-miR-431-5p, miR-150-3p is hsa-miR-150-3p, miR-423-5p is hsa-miR-423-5p, miR-575 is hsa-miR-575, miR-671-5p is hsa-miR-671-5p, miR-939-5p is hsa-miR-939-5p, miR-3665 is hsa-miR-3665, miR-30d-5p is hsa-miR-30d-5p, miR-30b-3p is hsa-miR-30b-3p, miR-92a-3p is hsa-miR-92a-3p, miR-371b-5p is hsa-miR-371b-5p, miR-486-5p is hsa-miR-486-5p, miR-1471 is hsa-miR-1471, miR-1538 is hsa-miR-1538, miR-449b-3p is hsa-miR-449b-3p, miR-1976 is hsa-miR-1976, miR-4268 is hsa-miR-4268, miR-4279 is hsa-miR-4279, miR-3620-3p is hsa-miR-3620-3p, miR-3944-3p is hsa-miR-3944-3p, miR-3156-3p is hsa-miR-3156-3p, miR-3187-5p is hsa-miR-3187-5p, miR-4685-3p is hsa-miR-4685-3p, miR-4695-3p is hsa-miR-4695-3p, miR-4697-3p is hsa-miR-4697-3p, miR-4713-5p is hsa-miR-4713-5p, miR-4723-3p is hsa-miR-4723-3p, miR-371b-3p is hsa-miR-371b-3p, miR-3151-3p is hsa-miR-3151-3p, miR-3192-3p is hsa-miR-3192-3p, miR-6728-3p is hsa-miR-6728-3p, miR-6736-3p is hsa-miR-6736-3p, miR-6740-3p is hsa-miR-6740-3p, miR-6741-3p is hsa-miR-6741-3p, miR-6743-3p is hsa-miR-6743-3p, miR-6747-3p is hsa-miR-6747-3p, miR-6750-3p is hsa-miR-6750-3p, miR-6754-3p is hsa-miR-6754-3p, miR-6759-3p is hsa-miR-6759-3p, miR-6761-3p is hsa-miR-6761-3p, miR-6762-3p is hsa-miR-6762-3p, miR-6769a-3p is hsa-miR-6769a-3p, miR-6776-3p is hsa-miR-6776-3p, miR-6778-3p is hsa-miR-6778-3p, miR-6779-3p is hsa-miR-6779-3p, miR-6786-3p is hsa-miR-6786-3p, miR-6787-3p is hsa-miR-6787-3p, miR-6792-3p is hsa-miR-6792-3p, miR-6794-3p is hsa-miR-6794-3p, miR-6801-3p is hsa-miR-6801-3p, miR-6802-3p is hsa-miR-6802-3p, miR-6803-3p is hsa-miR-6803-3p, miR-6804-3p is hsa-miR-6804-3p, miR-6810-5p is hsa-miR-6810-5p, miR-6823-3p is hsa-miR-6823-3p, miR-6825-3p is hsa-miR-6825-3p, miR-6829-3p is hsa-miR-6829-3p, miR-6833-3p is hsa-miR-6833-3p, miR-6834-3p is hsa-miR-6834-3p, miR-6780b-3p is hsa-miR-6780b-3p, miR-6845-3p is hsa-miR-6845-3p, miR-6862-3p is hsa-miR-6862-3p, miR-6865-3p is hsa-miR-6865-3p, miR-6870-3p is hsa-miR-6870-3p, miR-6875-3p is hsa-miR-6875-3p, miR-6877-3p is hsa-miR-6877-3p, miR-6879-3p is hsa-miR-6879-3p, miR-6882-3p is hsa-miR-6882-3p, miR-6885-3p is hsa-miR-6885-3p, miR-6886-3p is hsa-miR-6886-3p, miR-6887-3p is hsa-miR-6887-3p, miR-6890-3p is hsa-miR-6890-3p, miR-6893-3p is hsa-miR-6893-3p, miR-6894-3p is hsa-miR-6894-3p, miR-7106-3p is hsa-miR-7106-3p, miR-7109-3p is hsa-miR-7109-3p, miR-7114-3p is hsa-miR-7114-3p, miR-7155-5p is hsa-miR-7155-5p, miR-7160-5p is hsa-miR-7160-5p, miR-615-3p is hsa-miR-615-3p, miR-920 is hsa-miR-920, miR-1825 is hsa-miR-1825, miR-675-3p is hsa-miR-675-3p, miR-1910-5p is hsa-miR-1910-5p, miR-2278 is hsa-miR-2278, miR-2682-3p is hsa-miR-2682-3p, miR-3122 is hsa-miR-3122, miR-3151-5p is hsa-miR-3151-5p, miR-3175 is hsa-miR-3175, miR-4323 is hsa-miR-4323, miR-4326 is hsa-miR-4326, miR-4284 is hsa-miR-4284, miR-3605-3p is hsa-miR-3605-3p, miR-3622b-5p is hsa-miR-3622b-5p, miR-3646 is hsa-miR-3646, miR-3158-5p is hsa-miR-3158-5p, miR-4722-3p is hsa-miR-4722-3p, miR-4728-3p is hsa-miR-4728-3p, miR-4747-3p is hsa-miR-4747-3p, miR-4436b-5p is hsa-miR-4436b-5p, miR-5196-3p is hsa-miR-5196-3p, miR-5589-5p is hsa-miR-5589-5p, miR-345-3p is hsa-miR-345-3p, miR-642b-5p is hsa-miR-642b-5p, miR-6716-3p is hsa-miR-6716-3p, miR-6511b-3p is hsa-miR-6511b-3p, miR-208a-5p is hsa-miR-208a-5p, miR-6726-3p is hsa-miR-6726-3p, miR-6744-5p is hsa-miR-6744-5p, miR-6782-3p is hsa-miR-6782-3p, miR-6789-3p is hsa-miR-6789-3p, miR-6797-3p is hsa-miR-6797-3p, miR-6800-3p is hsa-miR-6800-3p, miR-6806-5p is hsa-miR-6806-5p, miR-6824-3p is hsa-miR-6824-3p, miR-6837-5p is hsa-miR-6837-5p, miR-6846-3p is hsa-miR-6846-3p, miR-6858-3p is hsa-miR-6858-3p, miR-6859-3p is hsa-miR-6859-3p, miR-6861-3p is hsa-miR-6861-3p, miR-6880-3p is hsa-miR-6880-3p, miR-7111-3p is hsa-miR-7111-3p, miR-7152-5p is hsa-miR-7152-5p, miR-642a-5p is hsa-miR-642a-5p, miR-657 is hsa-miR-657, miR-1236-3p is hsa-miR-1236-3p, miR-764 is hsa-miR-764, miR-4314 is hsa-miR-4314, miR-3675-3p is hsa-miR-3675-3p, miR-5703 is hsa-miR-5703, miR-3191-5p is hsa-miR-3191-5p, miR-6511a-3p is hsa-miR-6511a-3p, miR-6809-3p is hsa-miR-6809-3p, miR-6815-5p is hsa-miR-6815-5p, miR-6857-3p is hsa-miR-6857-3p, miR-6878-3p is hsa-miR-6878-3p, miR-766-3p is hsa-miR-766-3p, miR-1229-3p is hsa-miR-1229-3p, miR-1306-5p is hsa-miR-1306-5p, miR-210-5p is hsa-miR-210-5p, miR-198 is hsa-miR-198, miR-485-3p is hsa-miR-485-3p, miR-668-3p is hsa-miR-668-3p, miR-532-3p is hsa-miR-532-3p, miR-877-3p is hsa-miR-877-3p, miR-1238-3p is hsa-miR-1238-3p, miR-3130-5p is hsa-miR-3130-5p, miR-4298 is hsa-miR-4298, miR-4290 is hsa-miR-4290, miR-3943 is hsa-miR-3943, miR-346 is hsa-miR-346, and miR-767-3p is hsa-miR-767-3p.

Further, in one embodiment, the expression level(s) of the polynucleotide(s) are measured by using nucleic acid(s) capable of specifically binding to the polynucleotide(s) or to the complementary strand(s) of the polynucleotide(s), and the nucleic acid(s) are polynucleotide(s) selected from the group consisting of the following polynucleotides (f) to (j), (k) to (o), and (p) to (t):

(f) a polynucleotide consisting of a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 249, 1351 to 1356, and 1449 to 1453, (h) a polynucleotide consisting of a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 249, 1351 to 1356, and 1449 to 1453 or a nucleotide sequence derived from the nucleotide sequence by the replacement of u with t, and (j) a polynucleotide hybridizing under stringent conditions to any of the polynucleotides (f) to (i), (k) a polynucleotide consisting of a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 250 to 373, (m) a polynucleotide consisting of a nucleotide sequence complementary to a nucleotide sequence represented by any of SEQ ID NOs: 250 to 373 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 250 to 373 or a nucleotide sequence derived from the nucleotide sequence by the replacement of u with t, and (o) a polynucleotide hybridizing under stringent conditions to any of the polynucleotides (k) to (n), and (p) a polynucleotide consisting of a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (q) a polynucleotide comprising a nucleotide sequence represented by any of SEQ ID NOs: 375 to 390, (r) a polynucleotide consisting of a nucleotide sequence complementary to a nucleotide sequence represented by any of SEQ ID NOs: 375 to 390 or a nucleotide sequence derived from the nucleotide sequence by the replacement of u with t, a variant thereof, a derivative thereof, or a fragment thereof comprising 15 or more consecutive nucleotides, (s) a polynucleotide comprising a nucleotide sequence complementary to a nucleotide sequence represented by any of SEQ ID NOs: 375 to 390 or a nucleotide sequence derived from the nucleotide sequence by the replacement of u with t, and (t) a polynucleotide hybridizing under stringent conditions to any of the polynucleotides (p) to (s).

In one embodiment of the method according to the present invention, the present invention provides a method for detecting dementia, comprising measuring an expression level(s) of a target nucleic acid(s) in a sample from a subject by using a nucleic acid(s) capable of specifically binding to 1, preferably 2 or more, 3 or more, 10 or more, more preferably 20 to 60, and still more preferably 40 to 55 polynucleotides selected from the group consisting of miR-6765-3p, miR-6784-5p, miR-5698, miR-6778-5p, miR-1915-3p, miR-6875-5p, miR-1343-5p, miR-4534, miR-6861-5p, miR-4721, miR-6756-5p, miR-615-5p, miR-6727-5p, miR-6887-5p, miR-8063, miR-6880-5p, miR-6805-3p, miR-6781-5p, miR-4508, miR-4726-5p, miR-4710, miR-7111-5p, miR-3619-3p, miR-6743-5p, miR-6795-5p, miR-6726-5p, miR-4525, miR-1254, miR-1233-5p, miR-4651, miR-6836-3p, miR-6769a-5p, miR-6813-5p, miR-4532, miR-365a-5p, miR-1231, miR-5787, miR-1290, miR-1228-5p, miR-371a-5p, miR-4430, miR-296-3p, miR-6075, miR-1237-5p, miR-4758-5p, miR-4690-5p, miR-4466, miR-6789-5p, miR-4632-5p, miR-4745-5p, miR-4665-5p, miR-6807-5p, miR-762, and miR-7114-5p; and evaluating in vitro whether or not the subject has dementia by using the measured expression level(s) and a control expression level (s) in a subject(s) without dementia as likewise measured.

In an embodiment of the method according to the present invention, miR-6765-3p is hsa-miR-6765-3p, miR-6784-5p is hsa-miR-6784-5p, miR-5698 is hsa-miR-5698, miR-6778-5p is hsa-miR-6778-5p, miR-1915-3p is hsa-miR-1915-3p, miR-6875-5p is hsa-miR-6875-5p, miR-1343-5p is hsa-miR-1343-5p, miR-4534 is hsa-miR-4534, miR-6861-5p is hsa-miR-6861-5p, miR-4721 is hsa-miR-4721, miR-6756-5p is hsa-miR-6756-5p, miR-615-5p is hsa-miR-615-5p, miR-6727-5p is hsa-miR-6727-5p, miR-6887-5p is hsa-miR-6887-5p, miR-8063 is hsa-miR-8063, miR-6880-5p is hsa-miR-6880-5p, miR-6805-3p is hsa-miR-6805-3p, miR-6781-5p is hsa-miR-6781-5p, miR-4508 is hsa-miR-4508, miR-4726-5p is hsa-miR-4726-5p, miR-4710 is hsa-miR-4710, miR-7111-5p is hsa-miR-7111-5p, miR-3619-3p is hsa-miR-3619-3p, miR-6743-5p is hsa-miR-6743-5p, miR-6795-5p is hsa-miR-6795-5p, miR-6726-5p is hsa-miR-6726-5p, miR-4525 is hsa-miR-4525, miR-1254 is hsa-miR-1254, miR-1233-5p is hsa-miR-1233-5p, miR-4651 is hsa-miR-4651, miR-6836-3p is hsa-miR-6836-3p, miR-6769a-5p is hsa-miR-6769a-5p, miR-6813-5p is hsa-miR-6813-5p, miR-4532 is hsa-miR-4532, miR-365a-5p is hsa-miR-365a-5p, miR-1231 is hsa-miR-1231, miR-5787 is hsa-miR-5787, miR-1290 is hsa-miR-1290, miR-1228-5p is hsa-miR-1228-5p, miR-371a-5p is hsa-miR-371a-5p, miR-4430 is hsa-miR-4430, miR-296-3p is hsa-miR-296-3p, miR-6075 is hsa-miR-6075, miR-1237-5p is hsa-miR-1237-5p, miR-4758-5p is hsa-miR-4758-5p, miR-4690-5p is hsa-miR-4690-5p, miR-4466 is hsa-miR-4466, miR-6789-5p is hsa-miR-6789-5p, miR-4632-5p is hsa-miR-4632-5p, miR-4745-5p is hsa-miR-4745-5p, miR-4665-5p is hsa-miR-4665-5p, miR-6807-5p is hsa-miR-6807-5p, miR-762 is hsa-miR-762, and miR-7114-5p is hsa-miR-7114-5p.

In addition, in one embodiment of the method according to the present invention, a nucleic acid(s) (specifically, a probe(s) or primer(s)) is a polynucleotide(s) selected from the group consisting of polynucleotides shown in any of the following group (a) to (e):

(a) a polynucleotide consisting of a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 194 to 210, 374, and 1315 to 1350, (c) a polynucleotide consisting of a nucleotide sequence complementary to a nucleotide sequence represented by any of SEQ ID NOs: 194 to 210, 374, and 1315 to 1350 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 194 to 210, 374, and 1315 to 1350 or a nucleotide sequence derived from the nucleotide sequence by the replacement of u with t, and (e) a polynucleotide hybridizing under stringent conditions to any of the polynucleotides (a) to (d).

In one embodiment, a target nucleic acid(s) in a method according to the present invention may further comprise a nucleic acid(s) capable of specifically binding to at least one polynucleotide selected from the group consisting of miR-1225-3p, miR-3184-5p, miR-150-3p, miR-423-5p, miR-575, miR-671-5p, miR-939-5p, and miR-3665.

In one embodiment of the method according to the present invention, miR-150-3p is hsa-miR-150-3p, miR-423-5p is hsa-miR-423-5p, miR-575 is hsa-miR-575, miR-671-5p is hsa-miR-671-5p, miR-939-5p is hsa-miR-939-5p, miR-1225-3p is hsa-miR-1225-3p, miR-3184-5p is hsa-miR-3184-5p, and miR-3665 is hsa-miR-3665.

Further, in one embodiment of the method according to the present invention, the nucleic acid(s) is a polynucleotide (s) selected from the group consisting of polynucleotides shown in any of the following group (f) to (j):

(f) a polynucleotide consisting of a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 211 to 212 and 1351 to 1356, (h) a polynucleotide consisting of a nucleotide sequence complementary to a nucleotide sequence represented by any of SEQ ID NOs: 211 to 212 and 1351 to 1356 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 211 to 212 and 1351 to 1356 or a nucleotide sequence derived from the nucleotide sequence by the replacement of u with t, and (j) a polynucleotide hybridizing under stringent conditions to any of the polynucleotides (f) to (i).

Examples of the sample used in the method of the present invention can include samples prepared from living tissues (preferably brain tissues or nerve tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed depending on the type of the sample to be measured.

In the case of using RNA as an analyte, the method for detecting dementia (abnormal protein) can comprise, for example, the following steps (a), (b), and (c):

(a) binding RNA prepared from a sample from a subject (wherein, for example, the 3' end of the RNA may be polyadenylated for quantitative RT-PCR in step (b) or any sequence may be added to one or both ends of the RNA by ligation) or a complementary polynucleotides (cDNA) transcribed from the RNA to a polynucleotide(s) in the kit of the present invention;

(b) measuring the sample-derived RNA or the cDNA synthesized from the RNA, which has been bound to the polynucleotide(s), by hybridization using the polynucleotide(s) as a nucleic acid probe(s) or by quantitative RT-PCR using the polynucleotide(s) as a primer(s); and (c) evaluating the presence or absence of dementia (or dementia-derived gene(s)) on the basis of the measurement results of step (b).

For example, various hybridization methods can be used for measuring the expression level(s) of a target gene(s) according to the present invention. For example, Northern blot, Southern blot, DNA chip analysis, in situ hybridization, Northern hybridization, or Southern hybridization can be used as such a hybridization method. PCR such as quantitative RT-PCR or next-generation sequencing can also be used in combination with a hybridization method, or as an alternative thereof.

In the case of using the Northern blot, the presence or absence of expression of each gene or the expression level thereof in the RNA can be detected or measured by using, for example, the nucleic acid probe(s) that can be used in the present invention. Specific examples thereof can include a method which comprises labeling the nucleic acid probe (or a complementary strand) with a radioisotope ($^{32}$P, $^{33}$P, $^{35}$S, etc.), a fluorescent material, or the like, hybridizing the labeled product with the living tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by using, for example, the primer(s) that can be used in the present invention. Specific examples thereof can include a method which comprises recovering the living tissue-derived RNA from a subject, polyadenylating the 3'-end, preparing cDNAs from the polyadenylated RNA according to a routine method, and performing PCR according to a routine method by hybridizing a pair of primers (consisting of a positive strand and a reverse strand each binding to the cDNA) which could be contained in the kit or device for detection of the present invention with the cDNA such that the region of each target gene marker can be amplified with the cDNA as a template, to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA with a labeled nucleic acid probe for detection.

In the case of using the nucleic acid array analysis, an RNA chip or a DNA chip in which the kit or device for detection in the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene (registered trademark) Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene (registered trademark) scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2)") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% homology to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCl, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan (registered trademark) MicroRNA Assays (Life Technologies Corp.), LNA (registered trademark)-based MicroRNA PCR (Exiqon), or Ncode (registered trademark) miRNA qRT-PCT kit (Invitrogen Corp.) may be used.

In the method of the present invention, measurement of the gene expression level(s) may be performed with a sequencer, in addition to hybridization methods described above. In use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specifically designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p. 308 and Int. Neurourol. J., 2016, 20 (Suppl. 2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be amplified or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene(s) having a gene expression level of $2^6$, preferably $2^8$, more preferably $2^{10}$ or larger in 20% or more, preferably 50% or more, more preferably 80% or more of the number of measurement samples can be selected as the analyte(s). Examples of the normalization of the gene expression level include, but are not limited to, global normalization and quantile normalization (Bolstad, B. M. et al., 2003, Bioinformatics, Vol. 19, p. 185-193).

The present invention also provides a method for detecting dementia (or assisting the detection thereof) in a subject, comprising measuring a target genes or gene expression levels in a sample from the subject; and assigning the expression levels of the target genes in the sample from the subject to a discriminant (discriminant function), which is prepared using gene expression levels of a sample(s) from a subject(s) (or a patient(s)) known to have dementia and a sample(s) from a subject(s) without dementia, as a training sample(s), and which can distinguishably discriminate the presence or absence of dementia, thereby evaluating the presence or absence of dementia.

Specifically, the present invention further provides the method comprising a first step of measuring in vitro expression levels of target genes, which are known to determine or evaluate whether a subject has dementia and/or not, in a plurality of samples; a second step of preparing a discriminant using the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether or not the subject has dementia on the basis of the results obtained from the discriminant. The above target genes are those that can be detected, for example, by the polynucleotides, the polynucleotides contained in the kit or chip, and variants thereof or fragments thereof.

The discriminant herein can be prepared by use of any discriminant analysis method, based on which a discriminant that distinguishably discriminates the presence or absence of dementia can be prepared, such as linear discriminant analysis such as Fisher's discriminant analysis, nonlinear discriminant analysis based on the Mahalanobis' distance, neural network, Support Vector Machine (SVM) such as C-SVC, logistic regression analysis (especially, logistic regression analysis using the LASSO (Least Absolute Shrinkage and Selection Operator) method, ridge regression, or logistic regression using elastic net and multiple logistic regression using principal component analysis), k-nearest neighbor method, or decision tree, though the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and $w_0$ represents a constant term.

Formula 1

$$f(x) = w_0 + \sum_{i=1}^{n} w_i x_i$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, μ represents an average input, $n_g$ represents the number of data belonging to class g, and $\mu_g$ represents an average input of the data belonging to class g. The numerator and the denominator are the interclass variance and the intraclass variance, respectively, when each of data is projected in the direction of the vector w. Discriminant coefficient wi is determined by maximizing this ratio (Takafumi Kanamori et al., "Pattern Recognition", KYORITSU SHUPPAN CO., LTD. (Tokyo, Japan) (2009); Richard O. et al., Pattern Classification, Second Edition., Wiley-Interscience, 2000).

Formula 2

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)}$$

$$\text{subject to } \mu = \sum_{i=1}^{n} \frac{x_i}{n},\ \mu_g = \sum_{i:u_i=g}^{n} \frac{x_i}{n_g}.$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

Formula 3

$$D(x, \mu) = \{(x-\mu)' S^{-1} (x-\mu)\}^{\frac{1}{2}}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, an RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of dementia patients and a group of subjects without dementia. Diagnostic brain imaging (e.g., MRI, CT, SPECT) can be used as a reference of determining whether or not a subject has dementia.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_{a} \frac{1}{2} a^T Q a - e^T a$$

$$\text{subject to } y^T a = 0,\ 0 \le a_i \le C,\ i = 1, \ldots, l,$$

Formula 4

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \operatorname{sgn}\left(\sum_{i=1}^{l} y_i a_i K(x_i, x) + b\right)$$

Formula 5

For example, an RBF kernel defined by Formula 6 can be used as the kernel function. In this formula, x represents a support vector, and y represents a kernel parameter for adjusting the complexity of the hyperplane.

$$K(x_i,x_j)=\exp(-r\|x_i-x_j\|^2),\ r<0$$

Formula 6

Logistic regression is a multivariate analysis method in which one category variable (binary variable) is used as an objective variable to predict the probability of occurrence by using multiple explanatory variables, and is expressed in the following formula 7.

$$\log\text{it}(\text{prob}(y_i=1))=\beta_0+\Sigma_{j=1}^{P}\beta_j\chi_j$$

Formula 7

The LASSO (Least Absolute Shrinkage and Selection Operator) method is one of techniques for selecting and adjusting variables when multiple observed variables are present, and was proposed by Tibshirani (Tibshirani R., 1996, J R Stat Soc Ser B, vol. 58, p 267-88). Ridge regression is the oldest regularization technique, and was proposed by Hoerl (Hoerl, A. E., 1970, Technometrics., vol. 12, p. 55-67). Elastic net refers to a model in which the LASSO method and ridge regression is linearly combined and was proposed by Zou (Zou, H., 2005, J R Stat Soc Ser B, vol. 67, p. 301-320). The LASSO method is characterized in that when regression coefficients are estimated, penalties are imposed, so that overfitting to a model is reduced and some of the regression coefficients are then estimated as 0. In ridge regression, coefficients in a model can be estimated and even if the explanatory variable is larger than the number of samples, the variable larger than the number of samples can be selected. When there is a strong correlation between explanatory variables, only one of the variables with a high correlation remains in the LASSO method and the rest are estimated to 0. By contrast, in ridge regression, both can be selected. In elastic net, explanatory variables that have a high correlation and are difficult to be selected in the LASSO method can be properly selected to create a model with reduced dimensions. In logistic regression using the LASSO method, regression coefficients are estimated so as to maximize a log-likelihood function expressed in Formula 8.

$$\frac{1}{N}\sum_{i=1}^{N}\left(y_i(\beta_0 + x_j^T\beta) - \log\left(1 + e^{(\beta_0 + x_j^T\beta)}\right)\right) - \lambda\sum_{j=1}^{P}|\beta_j|$$

Formula 8

Principal component analysis method is a technique in which correlation between variables of quantitative data described using many variables is excluded and analysis is conducted, with as small information loss as possible, by converging into a small number of synthetic variables without any correlation, and was proposed by Pearson (PEARSON, K., 1901, Philosophical Magazine, series 6, vol. 2(11), p 559-572) and Hotelling (HOTELLING, H., 1933, Journal of Educational Psychology, vol. 24, p 417-441, p 498-520). The degree of contribution to a certain data point can be expressed by principal component scores obtained after the principal component analysis.

The method of the present invention can comprise, for example, the following steps (a), (b), and (c):

(a) measuring an expression level(s) of a target gene(s) in samples already known to be from dementia patients and to be from subjects without dementia, using polynucleotide(s), a kit, or a DNA chip for detection according to the present invention;

(b) preparing the discriminants of Formulas 1 to 3, 5 and 6 described above from the measurement values of the expression level(s) measured in step (a); and (c) measuring an expression level(s) of the target gene(s) in a sample from a subject using the polynucleotide(s), the kit, or the DNA chip for diagnosis (detection) according to the present invention, and assigning the obtained measurement value(s) to the discriminants prepared in step (b), and determining or evaluating whether or not the subject has dementia on the basis of the obtained results, or evaluating the expression level (s) derived from a dementia patient by comparison with a control from a subject(s) without dementia.

In this context, in the discriminants of Formulas 1 to 3, 5 and 6, x represents an explanatory variable and includes a value obtained by measuring a polynucleotide(s) selected from the polynucleotides described in Section 2 above, or a fragment thereof. Specifically, the explanatory variable of the present invention for discriminating between a dementia patient(s) and subject(s) without dementia is a gene expression level(s) selected from, for example, the following:

gene expression level(s) in sera of a dementia patient and a subject without dementia as measured by any DNA comprising 15 or more consecutive nucleotides in the nucleotide sequence represented by any of SEQ ID NOs: 1 to 210, 211 to 249, 250 to 374, 375 to 390, 1315 to 1350, 1351 to 1356, 1435 to 1448, and 1449 to 1453 or in a complementary sequence thereof.

In addition, in one embodiment, an explanatory variable for discriminating between the subjects is a gene expression level(s) selected from, for instance, the following:

gene expression level(s) in sera of a dementia patient and a subject without dementia as measured by any DNA comprising 15 or more consecutive nucleotides in the nucleotide sequence represented by any of SEQ ID NOs: 194 to 210, 374, and 1315 to 1350, and 211 to 212, and 1351 to 1356 or in a complementary sequence thereof.

As described above, for the method for determining or evaluating whether or not a subject has dementia using a sample from the subject, it is necessary to use a discriminant employing one or more gene expression levels as an explanatory variable(s). In particular, for enhancing the accuracy of the discriminant using a single gene expression level alone, it is necessary to use a gene having a clear difference in the expression level between two groups consisting of a group of dementia patients and a group of subjects with normal cognitive functions, in a discriminant.

Specifically, the gene that is used for an explanatory variable of a discriminant is preferably determined as follows. First, using comprehensive gene expression levels of a group of dementia patients and comprehensive gene expression levels of a group of test subjects without dementia, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a group of dementia patients and gene expression levels of a group of test subjects without dementia may be calculated to select a gene that is used for an explanatory variable in a discriminant. Alternatively, ROC curves may be prepared using gene expression levels of a group of dementia patients and a group of test subjects without dementia, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). To the discriminant, the gene expression level of another independent dementia patient or a test subject without dementia is assigned as an explanatory variable to calculate discrimination results of the group to which the independent dementia patient or the test subject without dementia belongs. Specifically, the gene set for diagnosis found and the discriminant constructed using the gene set for diagnosis can be evaluated in an independent sample cohort to find more universal gene set for diagnosis that can detect dementia and a more universal method for discriminating dementia.

In preparing a discriminant using expression levels of a plurality of genes as an explanatory variable, it is not necessary to select a gene having a clear difference in expression level between the group of dementia patients and the group of test subjects without dementia as described above. Specifically, if expression levels of a plurality of genes are used in combination even though the expression levels of individual genes do not clearly differ, a discriminant having high discriminant performance can be obtained, as the case may be. Because of this, it is possible to utilize a method of directly searching for a discriminant having high discriminant performance without beforehand selecting the gene to be employed in the discriminant.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for diagnosis or detection of a disease as being useful for diagnosing and treating dementia, a method for detecting dementia using the polynucleotide(s), and a kit and device for detecting dementia, comprising the polynucleotide(s).

A gene set for diagnosis may be set as, for instance, any combination selected from a group of one or more polynucleotides based on a nucleotide sequence(s) represented by any of SEQ ID NOs: 1 to 210 as described above, and optionally further comprising at least one polynucleotide based on a nucleotide sequence(s) represented by any of SEQ ID NOs: 194 to 210, 211 to 249, 250 to 374, and 375 to 390. Then, a discriminant is constructed using the expression levels of the gene set for diagnosis in samples from dementia patients as a result of tissue diagnosis and samples from subjects without dementia. As a result, whether or not a subject, from which an unknown sample is provided, has dementia can be discriminated by measuring expression levels of the gene set for diagnosis in the unknown sample.

In one embodiment, a gene set for diagnosis is set as any combination selected from a group of one or more polynucleotides based on a nucleotide sequence(s) represented by any of SEQ ID NOs: 194 to 210, 374, and 1315 to 1350 as described above and optionally further comprising at least one polynucleotide based on a nucleotide sequence(s) represented by any of SEQ ID NOs: 211 to 212 and 1351 to 1356. Then, a discriminant is constructed using the expression levels of the gene set for diagnosis in samples from dementia patients as a result of tissue diagnosis and samples from subjects without dementia. As a result, whether or not a subject, from which an unknown sample is provided, has dementia can be discriminated by measuring expression levels of the gene set for diagnosis in the unknown sample.

EXAMPLES

The present invention is described further specifically with reference to Examples below. However, the scope of the present invention is not intended to be limited by these Examples.

Reference Example 1

<Collection of Samples>

Sera were collected using VENOJECT II vacuum blood collecting tube VP-AS109K60 (Terumo Corp. (Japan)) from a total of 1,606 people including 1,496 dementia patients (patients having diagnosed definitely as dementia by doctors) and 110 non-dementia subjects after obtainment of informed consent (Table 2).

TABLE 2

| | Subject's disease type | Number of samples | |
|---|---|---|---|
| Dementia patients | 1 Alzheimer's dementia | 1147 | 1496 |
| | 2 Vascular dementia | 80 | |
| | 3 Lewy body dementia | 159 | |
| | 4 Frontotemporal lobar degeneration | 40 | |
| | 5 Normal pressure hydrocephalus | 70 | |
| Non-dementia subjects | 6 Subjects with normal cognitive functions | | 110 |
| Total | | | 1606 |

Each disease type number corresponds to the same numeral on the abscissa in FIGS. 2 to 12.

<Extraction of Total RNA>

Total RNA was obtained, using a reagent for RNA extraction in 3D-Gene (registered trademark) RNA extraction reagent from liquid sample kit (Toray Industries, Inc. (Japan)) according to the protocol provided by the manufacturer, from 300 μL of the serum sample obtained from each of the total of 1,606 people <Measurement of Gene Expression Level>

MiRNA in the total RNA, which was obtained from the serum sample of each of the total of 1,606 people, was fluorescently labeled by use of 3D-Gene (registered trademark) miRNA Labeling kit (Toray Industries, Inc.) according to the protocol provided by the manufacturer. The oligo DNA chip used was 3D-Gene (registered trademark) Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene (registered trademark) scanner (Toray Industries, Inc.) to obtain images. Fluorescence intensity on the image was digitized using 3D-Gene (registered trademark) Extraction (Toray Industries, Inc.). The digitized fluorescence intensity was converted to a logarithmic value having a base of 2 and used as a gene expression level, from which a blank value was subtracted. A missing value was replaced with a signal value 0.1.

As a result, the comprehensive gene expression levels of the miRNAs in the sera were obtained for the above 1,606 people. Subsequently, samples used for discriminant analysis of dementia were extracted. First, dementia patients were assigned to a positive group and non-dementia subjects were assigned to a negative group. Next, each cohort was sorted into a training cohort and a validation cohort as described in each Example below. Calculation and statistical analysis using the digitized gene expression levels of the miRNAs were carried out using R language 3.3.1 (R Core Team (2016) R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

Example 1

In Example 1, analysis was conducted by logistic regression using the LASSO method.

Example 1-1: Search for Alzheimer's Dementia Markers

To search for markers that can discriminate between patients with Alzheimer's dementia, a type of dementia and non-dementia subjects, 75 samples from the respective Alzheimer's dementia patients or non-dementia subjects were sorted into a training cohort (B in Table 3-1) and the rest samples were sorted into a validation cohort (C in Table 3-1).

TABLE 3-1

| Subject's disease type | | | A. All samples | Example 1-1 B. Training samples | Example 1-1 C. Validation samples | Example 1-2 D. Training samples | Example 1-2 E. Validation samples |
|---|---|---|---|---|---|---|---|
| Dementia patients | 1 | Alzheimer's dementia | 1147 1496 | 75 | 1072 | — | — |
| | 2 | Vascular dementia | 80 | — | — | 50 | 30 |
| | 3 | Lewy body dementia | 159 | — | — | — | — |
| | 4 | Frontotemporal lobar degeneration | 40 | — | — | — | — |
| | 5 | Normal pressure hydrocephalus | 70 | — | — | — | — |
| Non-dementia subjects | 6 | Subjects with normal cognitive functions | 110 | 75 | 35 | 50 | 60 |
| | | Total | 1606 | | | | |

Each disease type number corresponds to the same numeral on the abscissa in FIGS. 2 to 12.

TABLE 3-2

| Subject's disease type | | | A. All samples | Example 1-3 F Training samples | Example 1-3 G. Validation samples | Example 1-4 H. Training samples | Example 1-4 I. Validation samples |
|---|---|---|---|---|---|---|---|
| Dementia patients | 1 | Alzheimer's dementia | 1147 1496 | — | — | — | — |
| | 2 | Vascular dementia | 80 | 54 | 26 | — | — |
| | 3 | Lewy body dementia | 159 | — | — | 75 | 84 |
| | 4 | Frontotemporal lobar degeneration | 40 | — | — | — | — |
| | 5 | Normal pressure hydrocephalus | 70 | — | — | — | — |
| Non-dementia subjects | 6 | Subjects with normal cognitive functions | 110 | 74 | 36 | 75 | 35 |
| | | Total | 1606 | | | | |

Each disease type number corresponds to the same numeral on the abscissa in FIGS. 2 to 12.

TABLE 3-3

| Subject's disease type | | | A. All samples | Example 1-5 J Training samples | Example 1-5 K Validation samples | Example 1-6 L. Training samples | Example 1-6 M Validation samples |
|---|---|---|---|---|---|---|---|
| Dementia patients | 1 | Alzheimer's dementia | 1147 1496 | — | — | — | — |
| | 2 | Vascular dementia | 80 | — | — | — | — |
| | 3 | Lewy body dementia | 159 | 106 | 53 | — | — |
| | 4 | Frontotemporal lobar degeneration | 40 | — | — | 30 | 10 |
| | 5 | Normal pressure hydrocephalus | 70 | — | — | — | — |
| Non-dementia subjects | 6 | Subjects with normal cognitive functions | 110 | 74 | 36 | 30 | 80 |
| | | Total | 1606 | | | | |

Each disease type number corresponds to the same numeral on the abscissa in FIGS. 2 to 12.

TABLE 3-4

| Subject's disease type | | A. All samples | Example 1-7 N Training samples | Example 1-7 O Validation samples | Example 1-8 P. Training samples | Example 1-8 Q Validation samples |
|---|---|---|---|---|---|---|
| Dementia patients | 1 Alzheimer's dementia | 1147 1496 | — | — | — | — |
| | 2 Vascular dementia | 80 | — | — | — | — |
| | 3 Lewy body dementia | 159 | — | — | — | — |
| | 4 Frontotemporal lobar degeneration | 40 | — | — | — | — |
| | 5 Normal pressure hydrocephalus | 70 | 50 | 20 | 47 | 23 |
| Non-dementia subjects | 6 Subjects with normal cognitive functions | 110 | 50 | 60 | 74 | 36 |
| | Total | 1606 | | | | |

Each disease type number corresponds to the same numeral on the abscissa in FIGS. 2 to 12.

Meanwhile, in this Example, a discriminant formula with six gene markers was prepared using the above training cohort, and discriminant performance was then evaluated in the above validation cohort.

Specifically, first, miRNA expression levels obtained in the above Reference Example 1 were together normalized in accordance with quantile normalization. Further, in order to obtain a more highly reliable diagnostic marker, only 317 genes having a gene expression level of $2^6$ or more in 50% or more samples in either one of a group of dementia patients or a group of non-dementia subjects were analyzed. Next, a combination of the measurement values for the gene expression levels of 6 out of 317 miRNAs was subjected to logistic regression to construct a discriminant formula for discriminating the presence or absence of dementia. Further, this constructed discriminant formula was used to calculate the accuracy, the sensitivity, and the specificity in the validation cohort. Then, discriminant performance was validated in independent samples.

This resulted in a discriminant formula with an accuracy of 76%, a sensitivity of 77%, and a specificity of 49% in the validation cohort when the 6 miRNAs designated in Table 4 were used as discriminant markers (Table 4).

Example 1-2: Search for Vascular Dementia Markers—1

To search for markers that can discriminate between patients with vascular dementia, a type of dementia and non-dementia subjects, 50 samples from the respective vascular dementia patients or non-dementia subjects were sorted into a training cohort (D in Table 3-1) and the rest samples were sorted into a validation cohort (E in Table 3-1).

Like Example 1-1, a combination of 13 miRNAs was used to construct a discriminant formula for discriminating the presence or absence of dementia, and the discriminant formula was validated.

This resulted in a discriminant formula with an accuracy of 79%, a sensitivity of 87%, and a specificity of 75% in the validation cohort when the 13 miRNAs designated in Table 4 were used as discriminant markers (Table 4).

Example 1-3: Search for Vascular Dementia Markers—2

In order to sort as many samples as possible into a training cohort and search for markers with high accuracy, about ⅔ of samples from the respective vascular dementia patients or non-dementia subjects were sorted into a training cohort (F in Table 3-2) and the rest samples were sorted into a validation cohort (G in Table 3-2).

Like Example 1-1, a combination of 17 miRNAs was used to construct a discriminant formula for discriminating the presence or absence of dementia, and the discriminant formula was validated.

This resulted in a discriminant formula with an accuracy of 84%, a sensitivity of 73%, and a specificity of 92% in the validation cohort when the 17 miRNAs designated in Table 4 were used as discriminant markers (Table 4).

Sorting many samples into the training cohort resulted in the increased accuracy by 5% and the increased specificity by 17% compared to those in Example 1-2. However, because the number of positive samples was less than the number of negative samples in the training cohort, the sensitivity was decreased by 14%.

Example 1-4: Search for Lewy Body Dementia Markers—1

To search for markers that can discriminate between patients with Lewy body dementia, a type of dementia and non-dementia subjects, 75 samples from the respective Lewy body dementia patients or non-dementia subjects were sorted into a training cohort (H in Table 3-2) and the rest samples were sorted into a validation cohort (I in Table 3-2).

Like Example 1-1, a combination of 4 miRNAs was used to construct a discriminant formula for discriminating the presence or absence of dementia, and the discriminant formula was validated.

This resulted in a discriminant formula with an accuracy of 82%, a sensitivity of 94%, and a specificity of 51% in the validation cohort when the 4 miRNAs designated in Table 4 were used as discriminant markers (Table 4).

Example 1-5: Search for Lewy Body Dementia Markers—2

In order to sort as many samples as possible into a training cohort and search for markers with high accuracy, about ⅔ of samples from the respective Lewy body dementia patients or non-dementia subjects were sorted into a training cohort (J in Table 3-3) and the rest samples were sorted into a validation cohort (K in Table 3-3).

Like Example 1-1, a combination of 20 miRNAs was used to construct a discriminant formula for discriminating the presence or absence of dementia, and the discriminant formula was validated.

This resulted in a discriminant formula with an accuracy of 87%, a sensitivity of 96%, and a specificity of 72% in the validation cohort when the 20 miRNAs designated in Table 4 were used as discriminant markers (Table 4).

Sorting many samples into the training cohort resulted in the increased accuracy by 5%, the increased sensitivity by 2%, and the increased specificity by 21% compared to those in Example 1-4.

Example 1-6: Search for Frontotemporal Lobar Degeneration Markers

To search for markers that can discriminate between patients with frontotemporal lobar degeneration, a type of dementia and non-dementia subjects, 30 samples from the respective frontotemporal lobar degeneration patients or non-dementia subjects were sorted into a training cohort (L in Table 3-3) and the rest samples were sorted into a validation cohort (M in Table 3-3).

Like Example 1-1, a combination of 4 miRNAs was used to construct a discriminant formula for discriminating the presence or absence of dementia, and the discriminant formula was validated.

This resulted in a discriminant formula with an accuracy of 62%, a sensitivity of 90%, and a specificity of 59% in the validation cohort when the 4 miRNAs designated in Table 4 were used as discriminant markers (Table 4).

Example 1-7: Search for Normal Pressure Hydrocephalus Markers—1

To search for markers that can discriminate between patients with normal pressure hydrocephalus, a type of dementia and non-dementia subjects, 30 samples from the respective normal pressure hydrocephalus patients or non-dementia subjects were sorted into a training cohort (N in Table 3-4) and the rest samples were sorted into a validation cohort (0 in Table 3-4).

Like Example 1-1, a combination of 6 miRNAs was used to construct a discriminant formula for discriminating the presence or absence of dementia, and the discriminant formula was validated.

This resulted in a discriminant formula with an accuracy of 73%, a sensitivity of 75%, and a specificity of 72% in the validation cohort when the 6 miRNAs designated in Table 4 were used as discriminant markers (Table 4).

Example 1-8: Search for Normal Pressure Hydrocephalus Markers—2

In order to sort as many samples as possible into a training cohort and search for markers with high accuracy, about ⅔ of samples from the respective normal pressure hydrocephalus patients or non-dementia subjects were sorted into a training cohort (P in Table 3-4) and the rest samples were sorted into a validation cohort (Q in Table 3-4).

Like Example 1-1, a combination of 18 miRNAs was used to construct a discriminant formula for discriminating the presence or absence of dementia, and the discriminant formula was validated.

This resulted in a discriminant formula with an accuracy of 78%, a sensitivity of 65%, and a specificity of 86% in the validation cohort when the 18 miRNAs designated in Table 4 were used as discriminant markers (Table 4).

TABLE 4

| | | | Training cohort | | | Validation cohort | | |
|---|---|---|---|---|---|---|---|---|
| Example No. | Number of miRNAs | SEQ ID NOs: | Accuracy (%) | Sensitivity (%) | Specificity (%) | Accuracy (%) | Sensitivity (%) | Specificity (%) |
| Example 1-1 | 6 | 3, 26, 54, 91, 99, 206 | 76 | 81 | 71 | 76 | 77 | 49 |
| Example 1-2 | 13 | 4, 24, 25, 26, 28, 37, 45, 199, 201, 203, 204, 206, 216 | 87 | 90 | 84 | 79 | 87 | 75 |
| Example 1-3 | 17 | 3, 4, 23, 24, 26, 28, 32, 37, 45, 83, 88, 89, 199, 204, 206, 208, 216 | 84 | 78 | 89 | 84 | 73 | 92 |
| Example 1-4 | 4 | 3, 26, 90, 91 | 85 | 93 | 76 | 82 | 94 | 51 |
| Example 1-5 | 20 | 3, 4, 11, 26, 45, 55, 83, 91, 92, 93, 94, 95, 96, 97, 98, 196, 197, 204, 206, 210 | 87 | 99 | 70 | 87 | 96 | 72 |
| Example 1-6 | 4 | 26, 69, 135, 213 | 73 | 80 | 67 | 62 | 90 | 59 |
| Example 1-7 | 6 | 3, 26, 54, 203, 211, 212 | 79 | 90 | 68 | 73 | 75 | 72 |
| Example 1-8 | 18 | 3, 26, 45, 52, 54, 88, 94, 98, 140, 141, 142, 143, 144, 200, 203, 205, 211, 212 | 86 | 81 | 89 | 78 | 65 | 86 |

Sorting many samples into the training cohort resulted in the increased accuracy by 5% and the increased specificity by 14% compared to those in Example 1-7. However, because the number of positive samples was less than the number of negative samples in the training cohort, the sensitivity was decreased by 10%.

Figure 2:
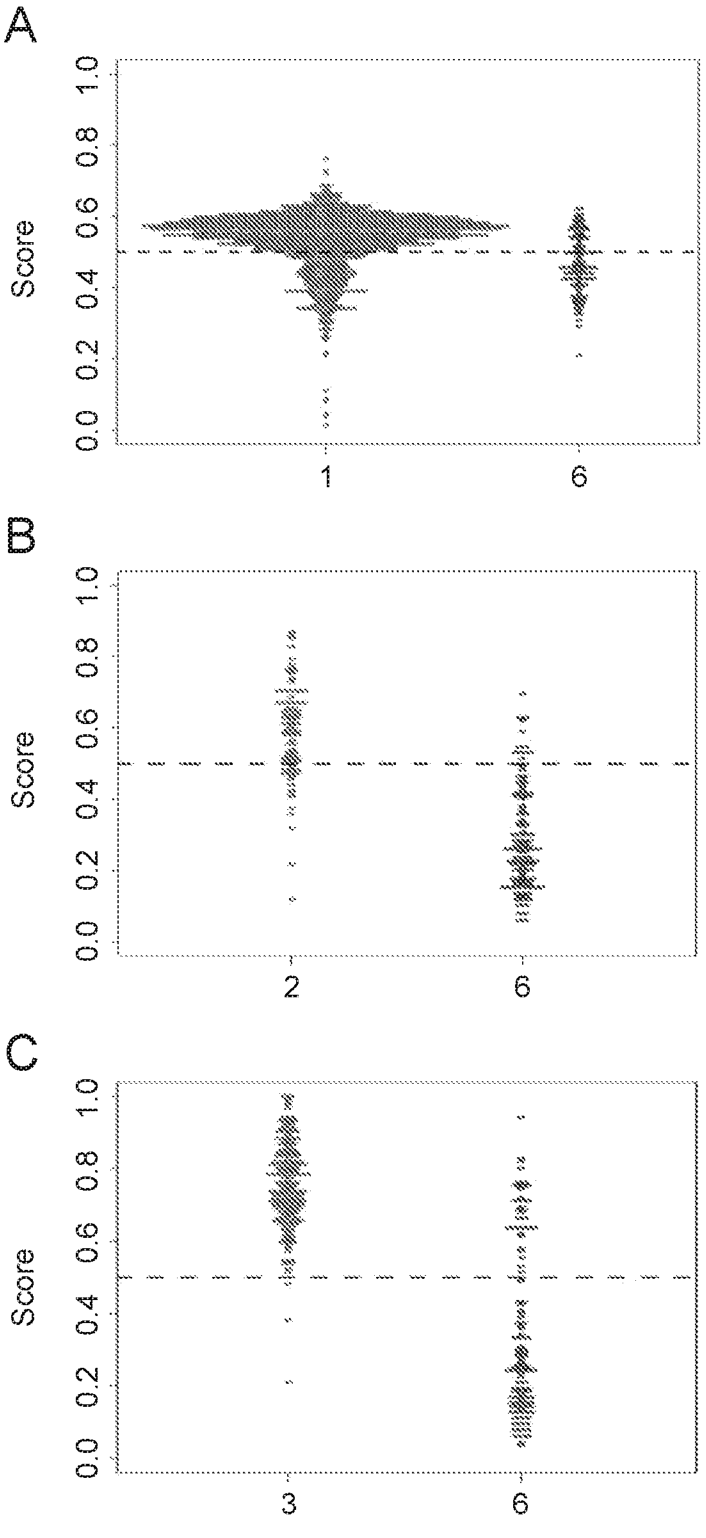
FIG. 2 shows plots of discriminant scores in each training cohort and each validation cohort as obtained in Example 1.

FIG. 2 shows plots of discriminant scores obtained in Examples 1-1, 1-3, and 1-5. FIG. 2A is a plot of discriminant scores for Alzheimer's dementia as described in Example 1-1; FIG. 2B is a plot of discriminant scores for vascular dementia as described in Example 1-3; and FIG. 2C is a plot of discriminant scores for Lewy body dementia as described in Example 1-5. The discriminant scores range from 0 to 1. The dotted line in each panel depicts a discriminant boundary (a discriminant score of 0.5) that discriminates the presence or absence of dementia. The measurement values for the expression levels of the above 6 (FIG. 2A), 17 (FIG. 2B), or 20 (FIG. 2C) miRNAs in sera from dementia patients or non-dementia subjects selected as each training cohort were used to prepare a discriminant formula by logistic regression analysis using the LASSO method. The ordinate represents a discriminant score obtained from the discriminant formula, and the abscissa represents each cohort.

On the abscissa of FIG. 2, the numeral 1 represents Alzheimer's dementia, the numeral 2 represents vascular dementia, the numeral 3 represents Lewy body dementia, and the numeral 6 represents non-dementia subjects (the disease type numbers in Table 2 and 3 are the same as the numerals on the abscissa in each panel).

Example 2

In Example 1, a plurality of marker sets having excellent discriminant performance having a sensitivity or a specificity of more than 80% were obtained. Thus, in Example 2, deepening Example 1, a goal was set to investigate whether or not any marker set having both sensitivity and specificity of more than 70% or 80% was obtained by varying the cohort sorting.

Accordingly, samples from each of the positive group or the negative group were divided into 5 groups, and ⅘ of the divided groups were assigned to a training cohort and ⅕ thereof was assigned to a validation cohort. The validation cohort was changed five times. Whenever the validation cohort was changed, a discriminant formula was constructed using the training cohort like Example 1-1 by logistic regression using the LASSO method. Then, the performance was evaluated on the validation cohort. Further, the dividing methods were changed five times.

Example 2-1: Search for Alzheimer's Dementia Markers

One thousand and one hundred forty seven (1,147) samples from patients with Alzheimer's dementia, a type of dementia, and 110 samples from non-dementia subjects were used for analysis. As a result, any discriminant formula with both sensitivity and specificity of more than 80% in the validation cohort was not obtained, but 3 different discriminant formulae with both sensitivity and specificity of more than 70% were obtained.

In the case of using, as the 1$^{st}$ discriminant markers, 10 miRNAs designated in Table 5, a discriminant formula with an AUC of 0.824 and a sensitivity of 81% and a specificity of 79% in the validation cohort was obtained.

In the case of using, as the 2$^{nd}$ discriminant markers, 12 miRNAs designated in Table 5, a discriminant formula with an AUC of 0.803 and a sensitivity of 80% and a specificity of 74% in the validation cohort was obtained.

In the case of using, as the 3$^{rd}$ discriminant markers, 19 miRNAs designated in Table 5, a discriminant formula with an AUC of 0.831 and a sensitivity of 76% and a specificity of 77% in the validation cohort was obtained (Table 5).

Varying the cohort made it possible to discover discriminant markers that made the sensitivity comparable or higher and the specificity improved by maximum 30% compared to that in Example 1-1.

Example 2-2: Search for Vascular Dementia Markers

Eighty (80) samples from patients with vascular dementia, a type of dementia, and 110 samples from non-dementia subjects were used for analysis. As a result, 8 different discriminant formulae with sensitivity and specificity of more than 80% in the validation cohort were obtained.

In the case of using, as the 4$^{th}$ discriminant markers, 8 miRNAs designated in Table 5, a discriminant formula with an AUC of 0.892 and a sensitivity of 83% and a specificity of 80% in the validation cohort was obtained.

In the case of using, as the 5$^{th}$ discriminant markers, 10 miRNAs designated in Table 5, a discriminant formula with an AUC of 0.939 and a sensitivity of 87% and a specificity of 91% in the validation cohort was obtained.

In the case of using, as the 6$^{th}$ discriminant markers, 18 miRNAs designated in Table 5, a discriminant formula with an AUC of 0.929 and a sensitivity of 80% and a specificity of 86% in the validation cohort was obtained.

In the case of using, as the 7$^{th}$ discriminant markers, 15 miRNAs designated in Table 5, a discriminant formula with an AUC of 0.898 and a sensitivity of 92% and a specificity of 80% in the validation cohort was obtained.

In the case of using, as the 8$^{th}$ discriminant markers, 14 miRNAs designated in Table 5, a discriminant formula with an AUC of 0.900 and a sensitivity of 83% and a specificity of 85% in the validation cohort was obtained.

In the case of using, as the 9$^{th}$ discriminant markers, 11 miRNAs designated in Table 5, a discriminant formula with an AUC of 0.950 and a sensitivity of 82% and a specificity of 91% in the validation cohort was obtained.

In the case of using, as the 10$^{th}$ discriminant markers, 11 miRNAs designated in Table 5, a discriminant formula with an AUC of 0.810 and a sensitivity of 82% and a specificity of 81% in the validation cohort was obtained.

In the case of using, as the 11$^{th}$ discriminant markers, 13 miRNAs designated in Table 5, a discriminant formula with an AUC of 0.884 and a sensitivity of 81% and a specificity of 86% in the validation cohort was obtained (Table 5).

In Examples 1-2 and 1-3, either the sensitivity or the specificity was 80% or less. However, varying the cohort made it possible to discover discriminant markers with both the sensitivity and the specificity more than 80%.

Example 2-3: Search for Lewy Body Dementia Markers

One hundred fifty nine (159) samples from patients with Lewy body dementia, a type of dementia, and 110 samples from non-dementia subjects were used for analysis. As a result, 6 different discriminant formulae with sensitivity and specificity of more than 80% in the validation cohort were obtained.

In the case of using, as the 12$^{th}$ discriminant markers, 17 miRNAs designated in Table 5, a discriminant formula with an AUC of 0.929 and a sensitivity of 94% and a specificity of 80% in the validation cohort was obtained.

In the case of using, as the 13$^{th}$ discriminant markers, 14 miRNAs designated in Table 5, a discriminant formula with an AUC of 0.927 and a sensitivity of 93% and a specificity of 85% in the validation cohort was obtained.

In the case of using, as the 14$^{th}$ discriminant markers, 18 miRNAs designated in Table 5, a discriminant formula with an AUC of 0.879 and a sensitivity of 87% and a specificity of 83% in the validation cohort was obtained.

In the case of using, as the 15$^{th}$ discriminant markers, 28 miRNAs designated in Table 5, a discriminant formula with an AUC of 0.885 and a sensitivity of 84% and a specificity of 83% in the validation cohort was obtained.

In the case of using, as the 16$^{th}$ discriminant markers, 18 miRNAs designated in Table 5, a discriminant formula with an AUC of 0.890 and a sensitivity of 88% and a specificity of 80% in the validation cohort was obtained.

In the case of using, as the 17$^{th}$ discriminant markers, 16 miRNAs designated in Table 5, a discriminant formula with an AUC of 0.872 and a sensitivity of 85% and a specificity of 82% in the validation cohort was obtained (Table 5).

In Examples 1-4 and 1-5, the specificity was 80% or less. However, varying the cohort made it possible to discover discriminant markers with both the sensitivity and the specificity more than 80%.

Example 2-4: Search for Frontotemporal Lobar Degeneration Markers

Forty (40) samples from patients with frontotemporal lobar degeneration, a type of dementia, and 110 samples from non-dementia subjects were used for analysis. As a result, any discriminant formula with both sensitivity and specificity of more than 80% in the validation cohort was not obtained, but 2 different discriminant formulae with both sensitivity and specificity of more than 70% were obtained.

In the case of using, as the 18$^{th}$ discriminant markers, 3 miRNAs designated in Table 5, a discriminant formula with an AUC of 0.886 and a sensitivity of 88% and a specificity of 77% in the validation cohort was obtained.

In the case of using, as the 19$^{th}$ discriminant markers, 12 miRNAs designated in Table 5, a discriminant formula with an AUC of 0.784 and a sensitivity of 75% and a specificity of 73% in the validation cohort was obtained (Table 5).

In Example 1-6, the specificity was as low as 59%. However, varying the cohort made it possible to discover discriminant markers with both the sensitivity and the specificity more than 70%.

Example 2-5: Search for Normal Pressure Hydrocephalus Markers

Seventy (70) samples from patients with frontotemporal lobar degeneration, a type of dementia, and 110 samples from non-dementia subjects were used for analysis. As a result, 3 different discriminant formulae with sensitivity and specificity of more than 80% in the validation cohort were obtained.

In the case of using, as the 20$^{th}$ discriminant markers, 6 miRNAs designated in Table 5, a discriminant formula with an AUC of 0.894 and a sensitivity of 88% and a specificity of 85% in the validation cohort was obtained.

In the case of using, as the 21$^{st}$ discriminant markers, 6 miRNAs designated in Table 5, a discriminant formula with an AUC of 0.903 and a sensitivity of 100% and a specificity of 82% in the validation cohort was obtained.

In the case of using, as the 22$^{nd}$ discriminant markers, 8 miRNAs designated in Table 5, a discriminant formula with an AUC of 0.816 and a sensitivity of 81% and a specificity of 80% in the validation cohort was obtained (Table 5).

TABLE 5

| Example | No. | Number of miRNAs | SEQ ID NOs | AUC | Sensitivity | Specificity |
|---|---|---|---|---|---|---|
| Example 2-1 | 1st | 10 | 1, 2, 3, 4, 5, 6, 7, 8, 200, 214 | 0.824 | 81 | 79 |
| | 2nd | 12 | 1, 2, 3, 4, 5, 9, 10, 11, 12, 13, 214, 215 | 0.803 | 80 | 74 |
| | 3rd | 19 | 3, 4, 5, 6, 7, 8, 10, 13, 14, 15, 16, 17, 18, 19, 20, 21, 22, 200, 214 | 0.831 | 76 | 77 |
| Example 2-2 | 4th | 8 | 4, 16, 23, 24, 25, 26, 197, 216 | 0.892 | 83 | 80 |
| | 5th | 10 | 3, 4, 16, 23, 26, 27, 28, 29, 214, 217 | 0.939 | 87 | 91 |
| | 6th | 18 | 4, 16, 24, 26, 29, 30, 31, 32, 33, 34, 35, 36, 37, 197, 201, 214, 217, 218 | 0.929 | 80 | 86 |
| | 7th | 15 | 3, 4, 16, 25, 26, 28, 34, 37, 38, 39, 40, 197, 207, 214, 218 | 0.898 | 92 | 80 |
| | 8th | 14 | 4, 16, 23, 24, 26, 28, 29, 32, 36, 37, 41, 42, 207, 214 | 0.900 | 83 | 85 |
| | 9th | 11 | 4, 16, 23, 24, 26, 36, 37, 42, 207, 214, 217 | 0.950 | 82 | 91 |
| | 10th | 11 | 3, 4, 23, 25, 26, 28, 36, 43, 214, 216, 218 | 0.810 | 82 | 81 |
| | 11th | 13 | 3, 4, 16, 25, 26, 28, 29, 36, 44, 45, 197, 217, 218 | 0.884 | 81 | 86 |
| Example 2-3 | 12th | 17 | 3, 4, 16, 26, 29, 45, 46, 47, 48, 49, 50, 51, 52, 53, 214, 216, 218 | 0.929 | 94 | 80 |
| | 13th | 14 | 3, 4, 11, 16, 26, 29, 45, 48, 49, 54, 55, 200, 214, 219 | 0.927 | 93 | 85 |
| | 14th | 18 | 3, 11, 16, 26, 29, 45, 46, 48, 49, 52, 55, 56, 57, 194, 209, 214, 216, 220 | 0.879 | 87 | 83 |
| | 15th | 28 | 3, 4, 11, 16, 26, 29, 30, 36, 46, 47, 48, 58, 59, 60, 61, 62, 63, 64, 65, 66, 197, 200, 207, 209, 216, 219, 220, 221 | 0.885 | 84 | 83 |

TABLE 5-continued

| Example No. | | Number of miRNAs | SEQ ID NOs | AUC | Sensitivity | Specificity |
|---|---|---|---|---|---|---|
| | 16th | 18 | 3, 13, 16, 26, 29, 45, 47, 48, 49, 54, 60, 64, 194, 214, 216, 219, 220, 222 | 0.890 | 88 | 80 |
| | 17th | 16 | 3, 8, 16, 26, 33, 45, 48, 49, 54, 55, 67, 68, 194, 214, 219, 220 | 0.872 | 85 | 82 |
| Example 2-4 | 18th | 3 | 26, 69, 70 | 0.886 | 88 | 77 |
| | 19th | 12 | 26, 30, 37, 53, 70, 71, 72, 73, 74, 223, 224, 225 | 0.784 | 75 | 73 |
| Example 2-5 | 20th | 6 | 3, 11, 16, 26, 75, 226 | 0.894 | 88 | 85 |
| | 21st | 6 | 3, 26, 34, 75, 76, 226 | 0.903 | 100 | 82 |
| | 22nd | 8 | 3, 11, 26, 34, 52, 75, 203, 220 | 0.816 | 81 | 80 |

In Examples 1-7 and 1-8, the sensitivity was 80% or less. However, varying the cohort made it possible to discover discriminant markers with both the sensitivity and the specificity more than 80%.

FIGS. 3 to 7 show plots of discriminant scores and ROC (Receiver Operating Characteristic) curves as obtained in Examples 2-1 to 2-5.

Figure 3:
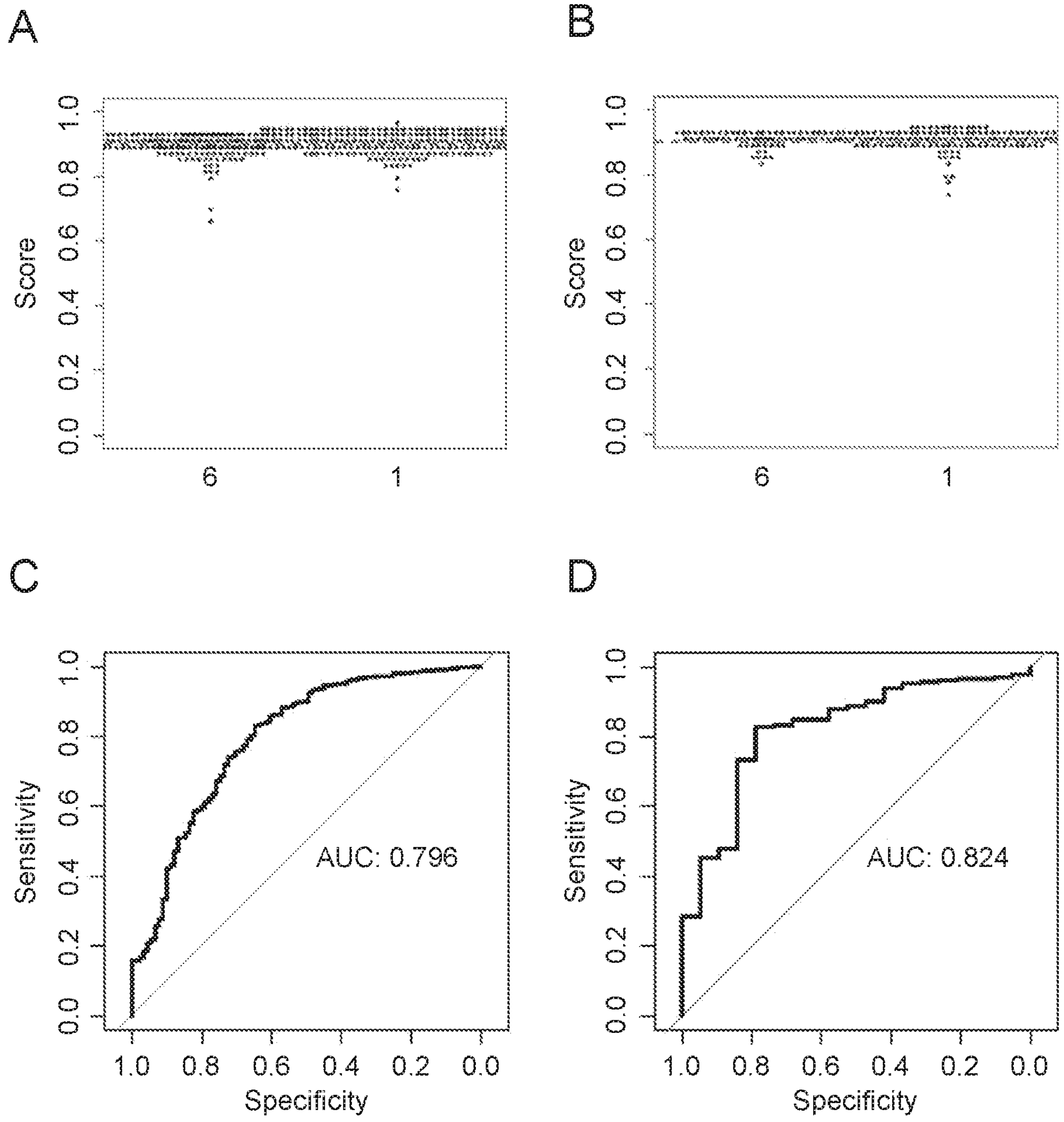
FIG. 3 shows plots of discriminant scores in a training cohort (A) and a validation cohort (B) and ROC curves for the training cohort (C) and the validation cohort (D) as obtained in Example 2-1.
Figure 4:
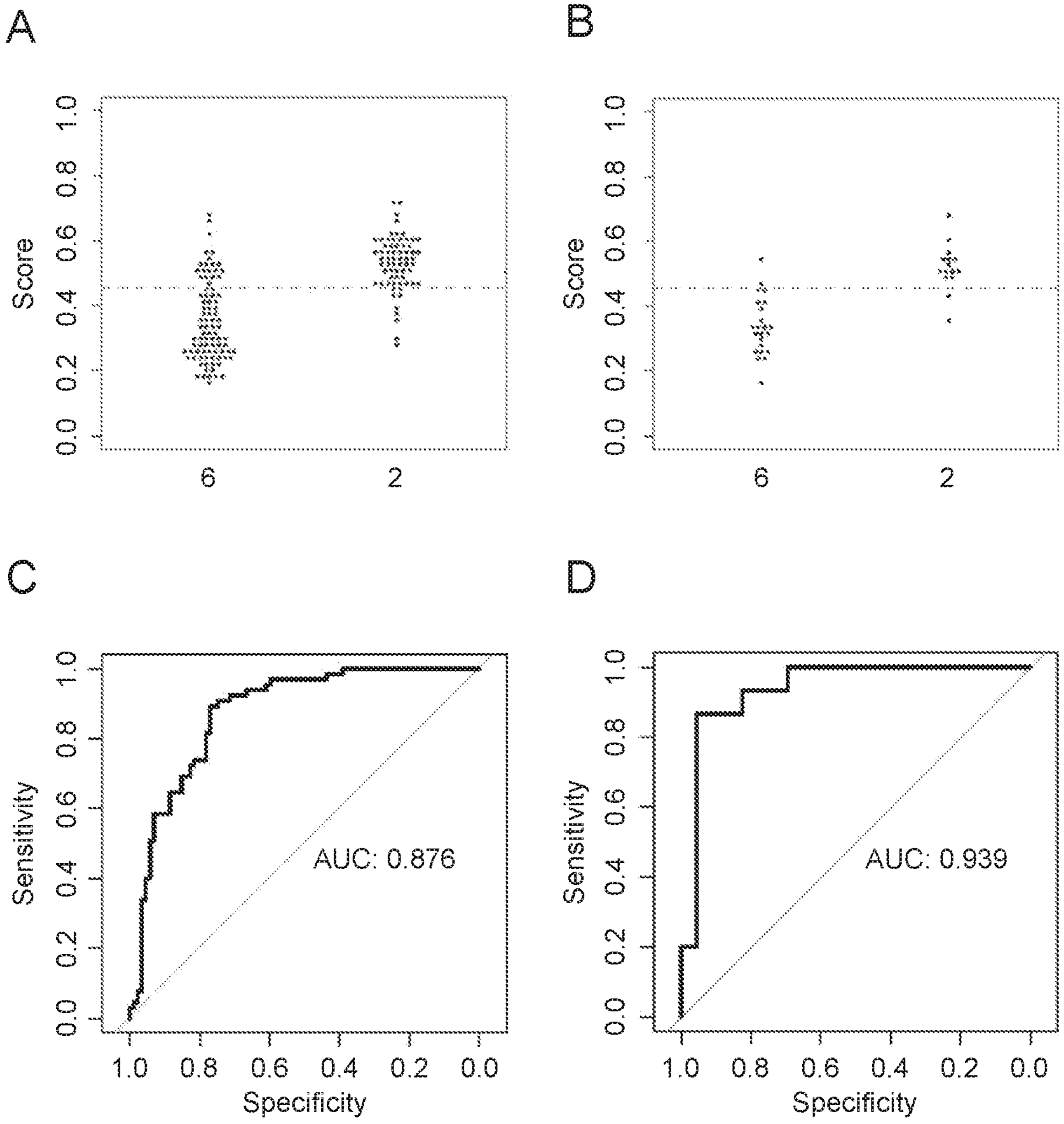
FIG. 4 shows plots of discriminant scores in a training cohort (A) and a validation cohort (B) and ROC curves for the training cohort (C) and the validation cohort (D) as obtained in Example 2-2.
Figure 5:
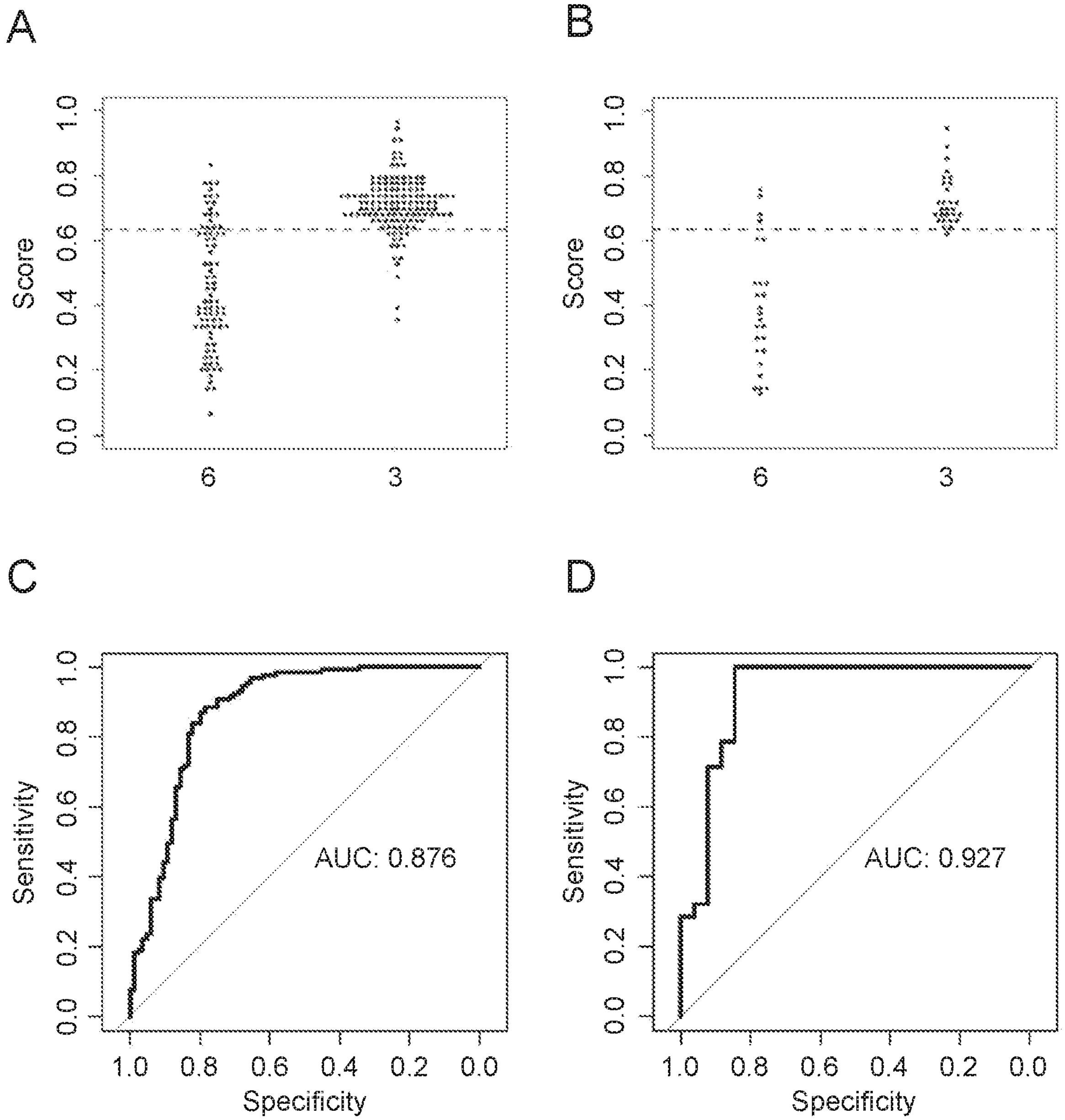
FIG. 5 shows plots of discriminant scores in a training cohort (A) and a validation cohort (B) and ROC curves for the training cohort (C) and the validation cohort (D) as obtained in Example 2-3.
Figure 6:
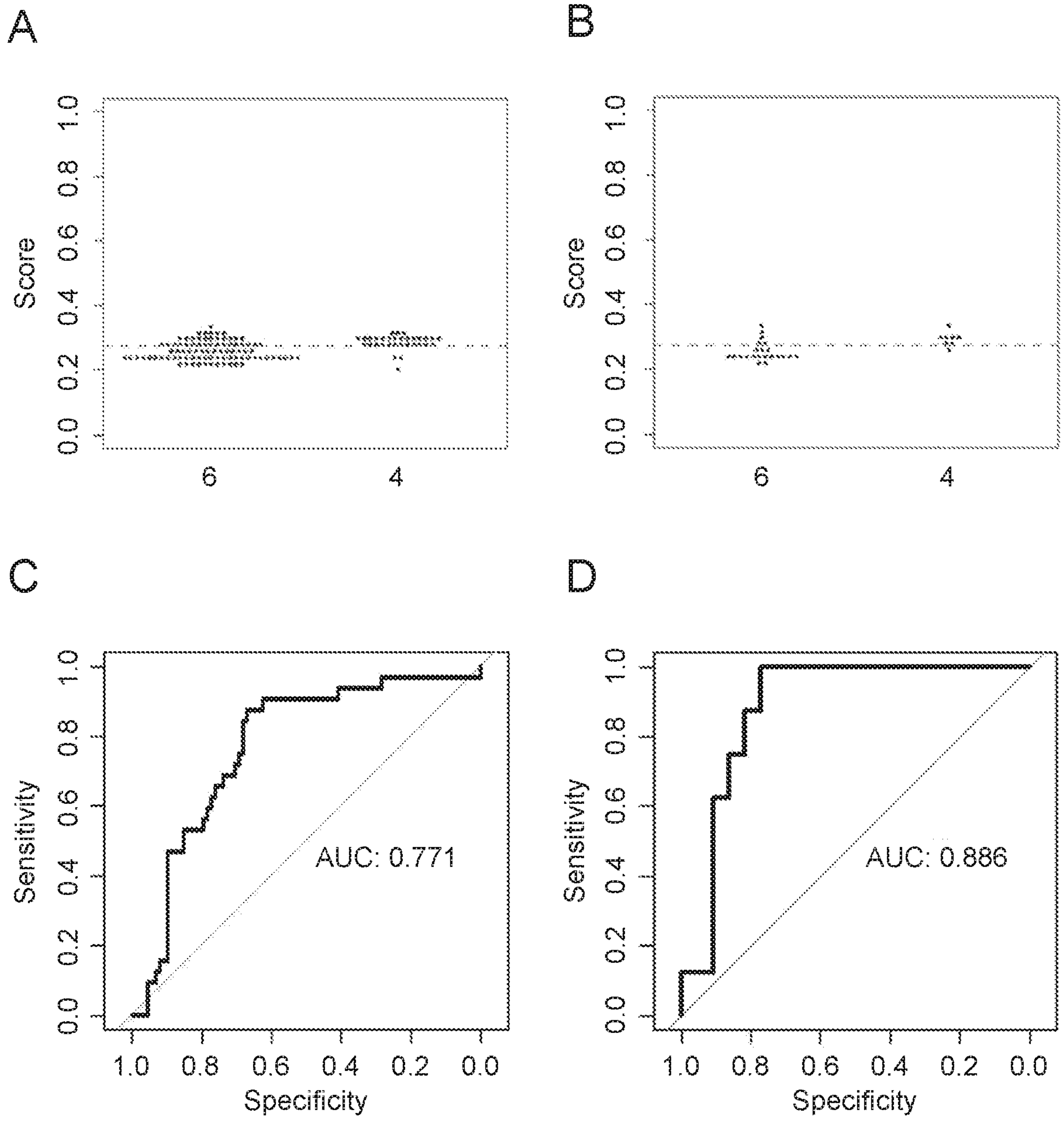
FIG. 6 shows plots of discriminant scores in a training cohort (A) and a validation cohort (B) and ROC curves for the training cohort (C) and the validation cohort (D) as obtained in Example 2-4.
Figure 7:
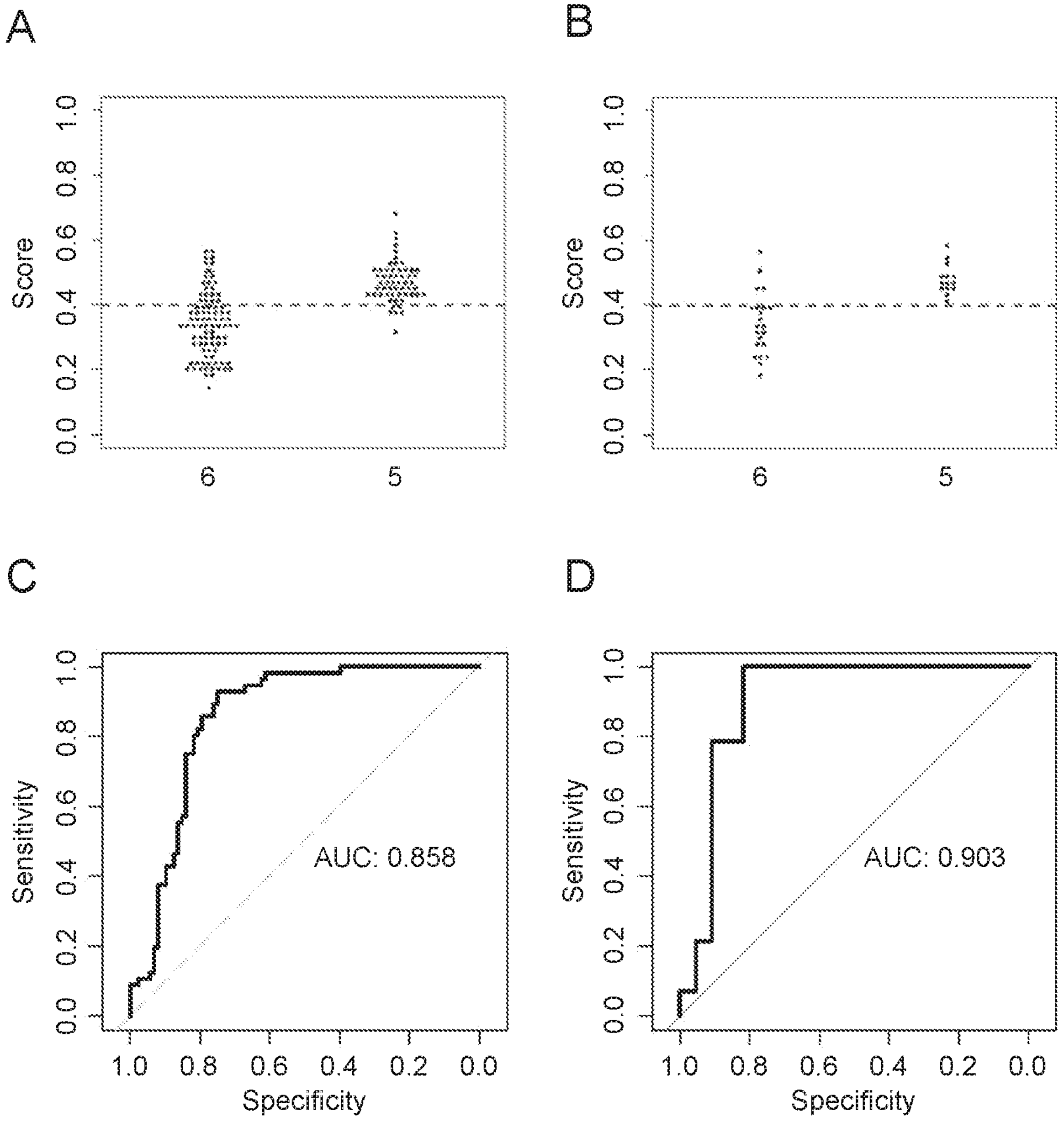
FIG. 7 shows plots of discriminant scores in a training cohort (A) and a validation cohort (B) and ROC curves for the training cohort (C) and the validation cohort (D) as obtained in Example 2-5.

FIG. 3 shows plots of discriminant scores and ROC curves for Alzheimer's dementia described in Example 2-1. FIG. 4 shows plots of discriminant scores and ROC curves for vascular dementia described in Example 2-2. FIG. 5 shows plots of discriminant scores and ROC curves for Lewy body dementia described in Example 2-3. FIG. 6 shows plots of discriminant scores and ROC curves for frontotemporal lobar degeneration described in Example 2-4. FIG. 7 shows plots of discriminant scores and ROC curves for normal pressure hydrocephalus described in Example 2-5. In each figure, panel A is a plot of discriminant scores in a training cohort; panel B is a plot of discriminant scores in a validation cohort; panel C is a ROC curve for the training cohort; and panel D is a ROC curve for the validation cohort.

The discriminant scores in each plot of discriminant scores range from 0 to 1. The dotted line in each panel depicts a discriminant boundary that discriminates the presence or absence of dementia. Logistic regression analysis using the LASSO method was used to prepare a discriminant formula from the measurement values for the expression levels of miRNAs that are the $1^{st}$ (FIG. 3), the $5^{th}$ (FIG. 4), the $13^{th}$ (FIG. 5), the $18^{th}$ (FIG. 6), or the $21^{st}$ (FIG. 7) discriminant markers in sera from dementia patients and non-dementia subjects selected as the training cohort. The ordinate represents a discriminant score obtained from the discriminant formula, and the abscissa represents each cohort.

MiRNA markers obtained in each Example were used to calculate the sensitivity as the ordinate and the specificity as the abscissa expressed in each ROC curve. Early detection and early treatment of dementia require diagnosis without misidentification. Meanwhile, once diagnosed as dementia, the disease patients receive a large social impact. Accordingly, it is also important to be able to give a diagnosis with good accuracy and without false positives. At the time of selection of a discriminant formula and markers for discriminating the presence or absence of dementia, a desired combination can be selected, depending on prioritized performance, from the ROC curves shown in FIGS. 3 to 7.

On the abscissa of FIGS. 3 to 7, the numeral 1 represents Alzheimer's dementia, the numeral 2 represents vascular dementia, the numeral 3 represents Lewy body dementia, the numeral 4 represents frontotemporal lobar degeneration, the numeral 5 represents normal pressure hydrocephalus, and the numeral 6 represents non-dementia subjects (the disease type numbers in Table 2 and 3 are the same as the numerals on the abscissa in each panel).

Example 3

Example 3 had the following two objects.

Object 1: To conduct analysis, as a supplement of Example 2, by deepening Example 1 by varying, like Example 2, the cohort sorting while the statistical technique was changed from that in Example 2.

Object 2: To examine whether a marker set with sensitivity and specificity of more than 70% or 80% was obtained even when the number of markers used in the discriminant formula was reduced to 5.

Specifically, using a training cohort, the resulting markers with high correlation were excluded. Next, every combination of 5 out of the top 20 markers ranked by the P value was analyzed by Fisher's discriminant analysis to construct a discriminant formula. Then, the performance was evaluated in a validation cohort. The P value was calculated as follows. First, miRNA expression levels in dementia patients and non-dementia subjects as obtained in the above Reference Example 1 were together normalized in accordance with quantile normalization. Next, in order to evaluate a more highly reliable diagnostic marker, only a gene having a gene expression level of $2^6$ or more in 50% or more samples in either one of a group of dementia patients or a group of non-dementia subjects was selected. Further, to evaluate a gene having a statistically significant difference in the gene expression level between the group of dementia patients and the group of non-dementia subjects, an equal-variance-assumed two-sided t test was conducted to calculate the P value, which was corrected by Bonferroni correction. Table 6 lists the top markers ranked by the P value and used in the discriminant formula (Table 6).

TABLE 6

| SEQ ID NO | Name of gene | Selection Count |
|---|---|---|
| 26 | hsa-miR-6088 | 53 |
| 3 | hsa-miR-4728-5p | 43 |
| 4 | hsa-miR-4443 | 39 |
| 214 | hsa-miR-211-5p | 34 |
| 49 | hsa-miR-5088-5p | 27 |
| 16 | hsa-miR-4539 | 26 |
| 11 | hsa-miR-6729-3p | 23 |
| 8 | hsa-miR-3184-3p | 20 |
| 37 | hsa-miR-4725-3p | 17 |
| 70 | hsa-miR-1470 | 14 |
| 75 | hsa-miR-1914-5p | 14 |

TABLE 6-continued

| SEQ ID NO | Name of gene | Selection Count |
|---|---|---|
| 30 | hsa-miR-4658 | 12 |
| 226 | hsa-miR-1915-5p | 12 |
| 30 | hsa-miR-4658 | 12 |
| 200 | hsa-miR-6743-5p | 10 |
| 52 | hsa-miR-4734 | 10 |
| 45 | hsa-miR-6729-5p | 10 |
| 34 | hsa-miR-6777-3p | 10 |
| 83 | hsa-miR-4488 | 9 |
| 5 | hsa-miR-4506 | 9 |
| 203 | hsa-miR-4651 | 9 |
| 54 | hsa-miR-1249-3p | 8 |
| 220 | hsa-miR-150-5p | 7 |
| 115 | hsa-miR-378d | 7 |
| 10 | hsa-miR-320d | 6 |
| 218 | hsa-miR-744-5p | 6 |
| 99 | hsa-miR-1202 | 5 |
| 32 | hsa-miR-1260b | 5 |
| 236 | hsa-miR-328-3p | 5 |
| 23 | hsa-miR-4486 | 5 |
| 116 | hsa-miR-4701-5p | 5 |
| 69 | hsa-miR-6087 | 5 |
| 85 | hsa-miR-6731-3p | 5 |
| 43 | hsa-miR-6766-5p | 5 |
| 121 | hsa-miR-6769b-3p | 5 |
| 36 | hsa-miR-6832-3p | 5 |
| 13 | hsa-miR-6853-5p | 5 |
| 228 | hsa-miR-137 | 4 |
| 227 | hsa-miR-204-5p | 4 |
| 98 | hsa-miR-3178 | 4 |
| 9 | hsa-miR-4281 | 4 |
| 207 | hsa-miR-6075 | 4 |
| 234 | hsa-miR-1224-3p | 3 |
| 78 | hsa-miR-1289 | 3 |
| 20 | hsa-miR-1539 | 3 |
| 219 | hsa-miR-345-5p | 3 |
| 80 | hsa-miR-3666 | 3 |
| 1 | hsa-miR-4274 | 3 |
| 28 | hsa-miR-4505 | 3 |
| 112 | hsa-miR-4716-5p | 3 |
| 24 | hsa-miR-1227-5p | 2 |
| 114 | hsa-miR-1268b | 2 |
| 126 | hsa-miR-143-5p | 2 |
| 217 | hsa-miR-149-5p | 2 |
| 136 | hsa-miR-193b-3p | 2 |
| 79 | hsa-miR-4433a-5p | 2 |
| 84 | hsa-miR-4474-3p | 2 |
| 25 | hsa-miR-4667-5p | 2 |
| 82 | hsa-miR-4725-5p | 2 |
| 101 | hsa-miR-4731-3p | 2 |
| 122 | hsa-miR-520a-3p | 2 |
| 89 | hsa-miR-638 | 2 |
| 129 | hsa-miR-6842-3p | 2 |
| 128 | hsa-miR-6889-3p | 2 |
| 104 | hsa-miR-8072 | 2 |
| 53 | hsa-miR-936 | 2 |
| 100 | hsa-miR-6790-5p | 1 |
| 102 | hsa-miR-2681-3p | 1 |
| 87 | hsa-miR-202-5p | 1 |
| 229 | hsa-miR-382-5p | 1 |
| 103 | hsa-miR-6758-5p | 1 |
| 230 | hsa-miR-517-5p | 1 |
| 47 | hsa-miR-519e-5p | 1 |
| 105 | hsa-miR-518d-3p | 1 |
| 231 | hsa-miR-532-5p | 1 |
| 72 | hsa-miR-3150a-5p | 1 |
| 106 | hsa-miR-3606-3p | 1 |
| 77 | hsa-miR-15b-5p | 1 |
| 41 | hsa-miR-4312 | 1 |
| 233 | hsa-miR-1237-3p | 1 |
| 109 | hsa-miR-6784-3p | 1 |
| 110 | hsa-miR-4450 | 1 |
| 29 | hsa-miR-548q | 1 |
| 111 | hsa-miR-6132 | 1 |
| 94 | hsa-miR-3928-3p | 1 |
| 42 | hsa-miR-4461 | 1 |
| 198 | hsa-miR-6781-5p | 1 |
| 201 | hsa-miR-6726-5p | 1 |
| 113 | hsa-miR-6860 | 1 |

TABLE 6-continued

| SEQ ID NO | Name of gene | Selection Count |
|---|---|---|
| 48 | hsa-miR-512-5p | 1 |
| 235 | hsa-miR-625-3p | 1 |
| 46 | hsa-miR-526b-3p | 1 |
| 237 | hsa-miR-122-5p | 1 |
| 117 | hsa-miR-4329 | 1 |
| 118 | hsa-miR-185-3p | 1 |
| 33 | hsa-miR-3677-5p | 1 |
| 119 | hsa-miR-552-3p | 1 |
| 120 | hsa-miR-1273g-5p | 1 |
| 123 | hsa-miR-4524b-5p | 1 |
| 238 | hsa-miR-202-3p | 1 |
| 124 | hsa-miR-4291 | 1 |
| 125 | hsa-miR-6734-3p | 1 |
| 239 | hsa-miR-4781-5p | 1 |
| 127 | hsa-miR-939-3p | 1 |
| 240 | hsa-miR-718 | 1 |
| 241 | hsa-miR-342-3p | 1 |
| 130 | hsa-miR-4511 | 1 |
| 131 | hsa-miR-4318 | 1 |
| 242 | hsa-miR-26b-3p | 1 |
| 81 | hsa-miR-3186-3p | 1 |
| 243 | hsa-miR-140-3p | 1 |
| 132 | hsa-miR-4653-5p | 1 |
| 133 | hsa-miR-6867-3p | 1 |
| 244 | hsa-miR-200a-3p | 1 |
| 134 | hsa-miR-133b | 1 |
| 245 | hsa-miR-378a-3p | 1 |
| 135 | hsa-miR-3196 | 1 |
| 137 | hsa-miR-3162-3p | 1 |
| 194 | hsa-miR-5698 | 1 |
| 66 | hsa-miR-6509-3p | 1 |
| 246 | hsa-miR-484 | 1 |
| 138 | hsa-miR-6819-3p | 1 |
| 139 | hsa-miR-1908-3p | 1 |
| 86 | hsa-miR-4640-3p | 1 |
| 215 | hsa-miR-1247-5p | 1 |

Example 3-1: Search for Alzheimer's Dementia Markers

One thousand and one hundred forty seven (1,147) samples from patients with Alzheimer's dementia, a type of dementia, and 110 samples from non-dementia subjects were used for analysis. As a result, any discriminant formula with both sensitivity and specificity of more than 80% in the validation cohort was not obtained, but 4 different discriminant formulae with both sensitivity and specificity of more than 70% were obtained.

In the case of using, as the 23$^{rd}$ discriminant markers, 5 miRNAs designated in Table 7, a discriminant formula with an AUC of 0.845 and a sensitivity of 76% and a specificity of 74% in the validation cohort was obtained.

In the case of using, as the 24$^{th}$ discriminant markers, 5 miRNAs designated in Table 7, a discriminant formula with an AUC of 0.763 and a sensitivity of 79% and a specificity of 76% in the validation cohort was obtained.

In the case of using, as the 25$^{th}$ discriminant markers, 5 miRNAs designated in Table 7, a discriminant formula with an AUC of 0.804 and a sensitivity of 76% and a specificity of 75% in the validation cohort was obtained.

In the case of using, as the 26$^{th}$ discriminant markers, 5 miRNAs designated in Table 7, a discriminant formula with an AUC of 0.755 and a sensitivity of 75% and a specificity of 74% in the validation cohort was obtained (Table 7).

In Example 1-1, the specificity was as low as 49%. However, varying the cohort made it possible to discover discriminant markers with both the sensitivity and the specificity more than 70% even when the number of markers was reduced to 5.

Example 3-2: Search for Vascular Dementia Markers

Eighty (80) samples from patients with vascular dementia, a type of dementia, and 110 samples from non-dementia subjects were used for analysis. As a result, 2 different discriminant formulae with sensitivity and specificity of more than 80% in the validation cohort were obtained.

In the case of using, as the $27^{th}$ discriminant markers, 5 miRNAs designated in Table 7, a discriminant formula with an AUC of 0.942 and a sensitivity of 89% and a specificity of 80% in the validation cohort was obtained.

In the case of using, as the $28^{th}$ discriminant markers, 5 miRNAs designated in Table 7, a discriminant formula with an AUC of 0.938 and a sensitivity of 88% and a specificity of 100% in the validation cohort was obtained (Table 7).

In Examples 1-2 and 1-3, either the sensitivity or the specificity was 80% or less. However, varying the cohort made it possible to discover discriminant markers with both the sensitivity and the specificity more than 80% even when the number of markers was reduced to 5.

Example 3-3: Search for Lewy Body Dementia Markers

One hundred fifty nine (159) samples from patients with Lewy body dementia, a type of dementia, and 110 samples from non-dementia subjects were used for analysis. As a result, 2 different discriminant formulae with sensitivity and specificity of more than 80% in the validation cohort were obtained.

In the case of using, as the $29^{th}$ discriminant markers, 5 miRNAs designated in Table 7, a discriminant formula with an AUC of 0.864 and a sensitivity of 87% and a specificity of 83% in the validation cohort was obtained.

In the case of using, as the $30^{th}$ discriminant markers, 5 miRNAs designated in Table 7, a discriminant formula with an AUC of 0.862 and a sensitivity of 85% and a specificity of 80% in the validation cohort was obtained (Table 7).

In Examples 1-4 and 1-5, the specificity was 80% or less. However, varying the cohort made it possible to discover discriminant markers with both the sensitivity and the specificity more than 80% even when the number of markers was reduced to 5.

Example 3-4: Search for Frontotemporal Lobar Degeneration Markers

Forty (40) samples from patients with frontotemporal lobar degeneration, a type of dementia, and 110 samples from non-dementia subjects were used for analysis. As a result, any discriminant formula with both sensitivity and specificity of more than 80% in the validation cohort was not obtained, but 2 different discriminant formulae with both sensitivity and specificity of more than 70% were obtained.

In the case of using, as the $31^{st}$ discriminant markers, 5 miRNAs designated in Table 7, a discriminant formula with an AUC of 0.801 and a sensitivity of 88% and a specificity of 73% in the validation cohort was obtained.

In the case of using, as the $32^{nd}$ discriminant markers, 5 miRNAs designated in Table 7, a discriminant formula with an AUC of 0.630 and a sensitivity of 70% and a specificity of 70% in the validation cohort was obtained (Table 7).

In Example 1-6, the specificity was as low as 59%. However, varying the cohort made it possible to discover discriminant markers with both the sensitivity and the specificity more than 70% even when the number of markers was reduced to 5.

Example 3-5: Search for Normal Pressure Hydrocephalus Markers

Seventy (70) samples from patients with normal pressure hydrocephalus, a type of dementia, and 110 samples from non-dementia subjects were used for analysis. As a result, 3 different discriminant formulae with sensitivity and specificity of more than 80% in the validation cohort were obtained.

In the case of using, as the $33^{rd}$ discriminant markers, 5 miRNAs designated in Table 7, a discriminant formula with an AUC of 0.897 and a sensitivity of 81% and a specificity of 95% in the validation cohort was obtained.

In the case of using, as the $34^{th}$ discriminant markers, 5 miRNAs designated in Table 7, a discriminant formula with an AUC of 0.867 and a sensitivity of 87% and a specificity of 86% in the validation cohort was obtained.

In the case of using, as the $35^{th}$ discriminant markers, 5 miRNAs designated in Table 7, a discriminant formula with an AUC of 0.948 and a sensitivity of 100% and a specificity of 94% in the validation cohort was obtained (Table 7).

TABLE 7

| Example | No. | Number of miRNAs | SEQ ID NOs | AUC | Sensitivity | Specificity |
|---|---|---|---|---|---|---|
| Example 3-1 | 23rd | 5 | 3, 4, 11, 16, 214 | 0.845 | 76 | 74 |
| | 24th | 5 | 3, 4, 11, 49, 214 | 0.763 | 79 | 76 |
| | 25th | 5 | 4, 5, 9, 11, 72 | 0.804 | 76 | 75 |
| | 26th | 5 | 1, 3, 49, 77, 78 | 0.755 | 75 | 74 |
| Example 3-2 | 27th | 5 | 8, 16, 26, 79, 218 | 0.942 | 89 | 80 |
| | 28th | 5 | 4, 16, 26, 36, 80 | 0.938 | 88 | 100 |
| Example 3-3 | 29th | 5 | 26, 37, 45, 46, 54 | 0.864 | 87 | 83 |
| | 30th | 5 | 26, 37, 45, 49, 54 | 0.862 | 85 | 80 |
| Example 3-4 | 31st | 5 | 10, 13, 37, 70, 227 | 0.801 | 88 | 73 |
| | 32nd | 5 | 10, 81, 82, 200, 228 | 0.630 | 70 | 70 |
| Example 3-5 | 33rd | 5 | 34, 49, 83, 203, 226 | 0.897 | 81 | 95 |
| | 34th | 5 | 3, 8, 75, 84, 226 | 0.867 | 87 | 86 |
| | 35th | 5 | 3, 8, 75, 85, 86 | 0.948 | 100 | 94 |

In Examples 1-7 and 1-8, the sensitivity was 80% or less. However, varying the cohort made it possible to discover discriminant markers with both the sensitivity and the specificity more than 80% even when the number of markers was reduced to 5.

Figure 8:
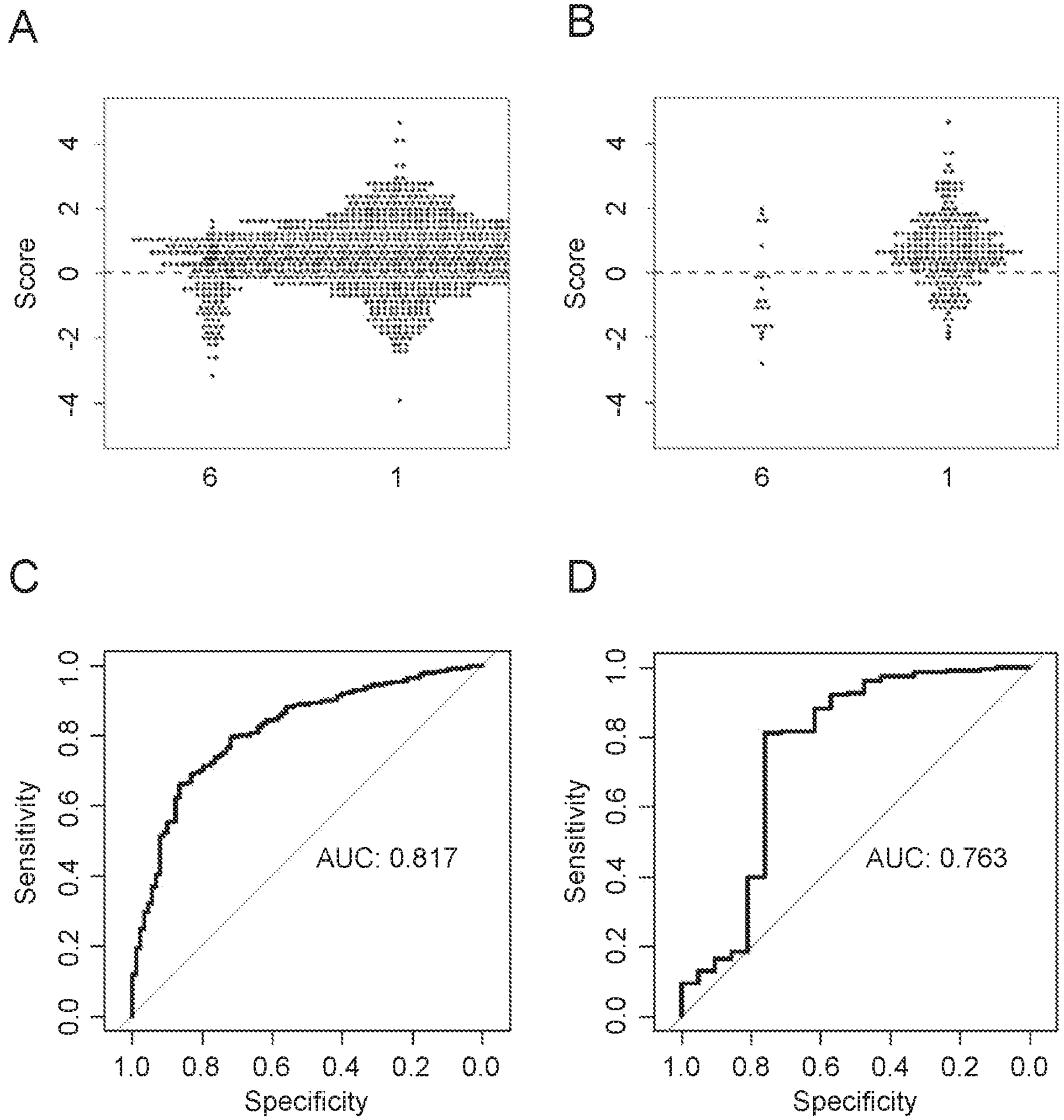
FIG. 8 shows plots of discriminant scores in a training cohort (A) and a validation cohort (B) and ROC curves for the training cohort (C) and the validation cohort (D) as obtained in Example 3-1.
Figure 9:
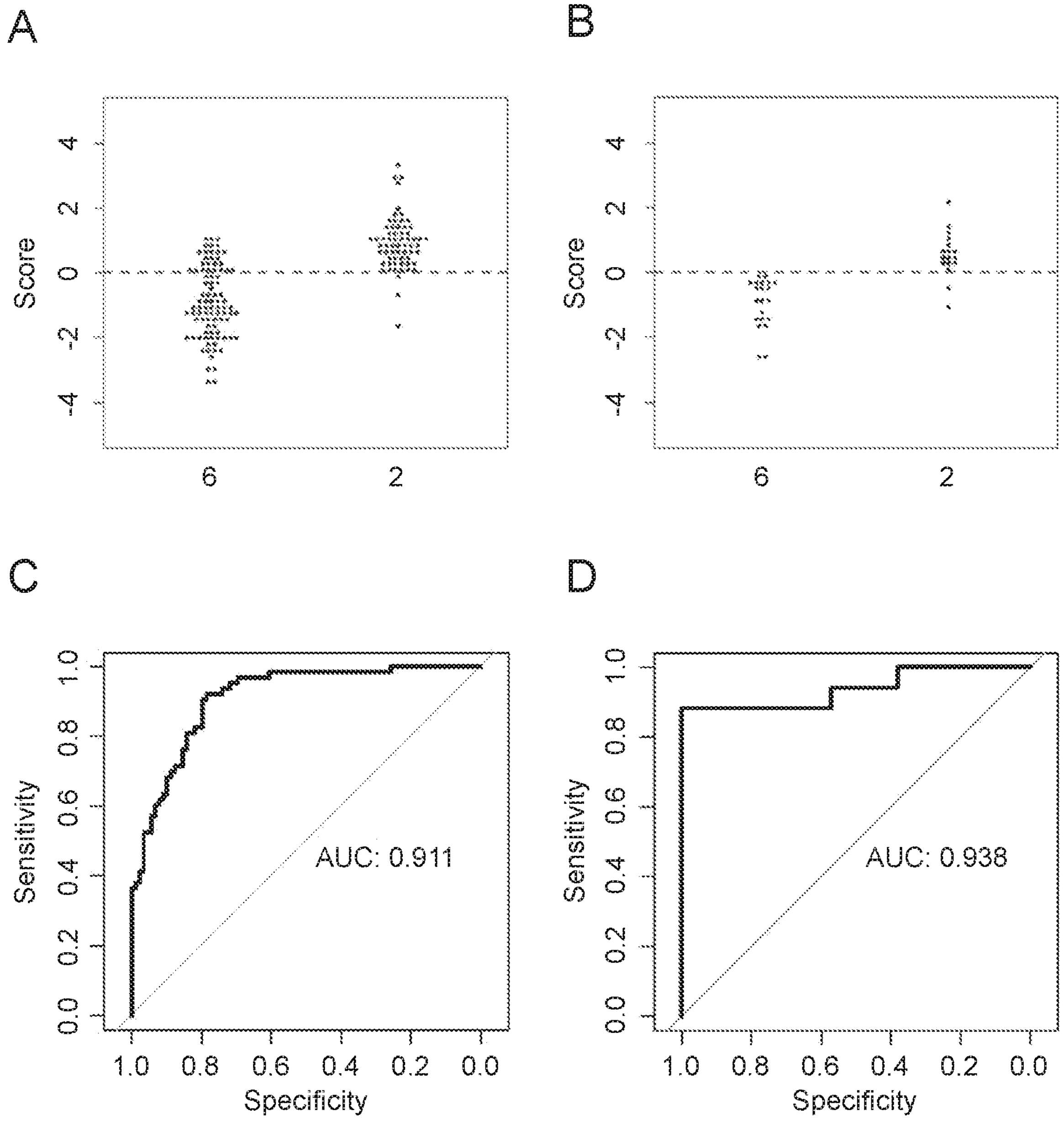
FIG. 9 shows plots of discriminant scores in a training cohort (A) and a validation cohort (B) and ROC curves for the training cohort (C) and the validation cohort (D) as obtained in Example 3-2.
Figure 10:
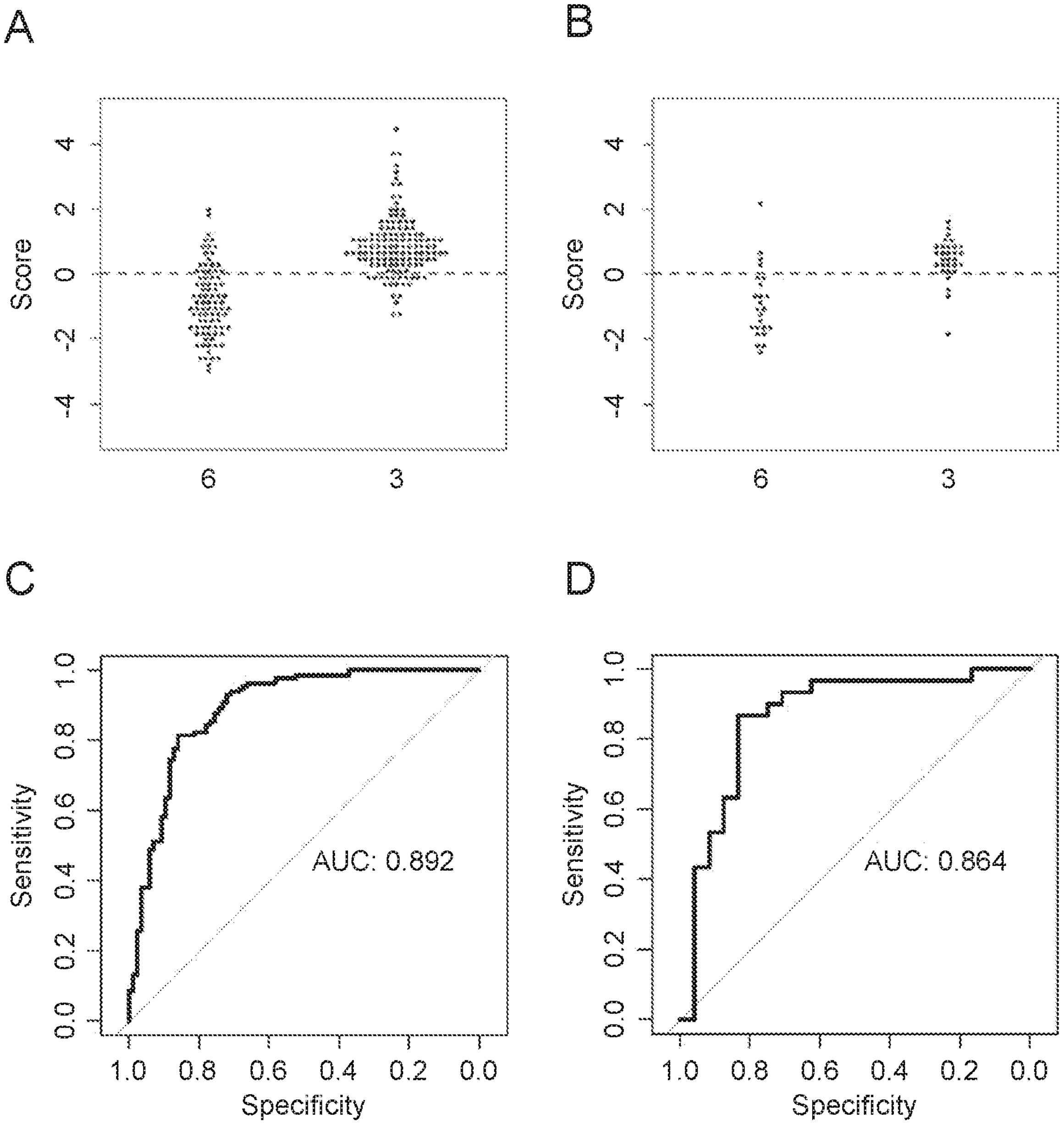
FIG. 10 shows plots of discriminant scores in a training cohort (A) and a validation cohort (B) and ROC curves for the training cohort (C) and the validation cohort (D) as obtained in Example 3-3.
Figure 11:
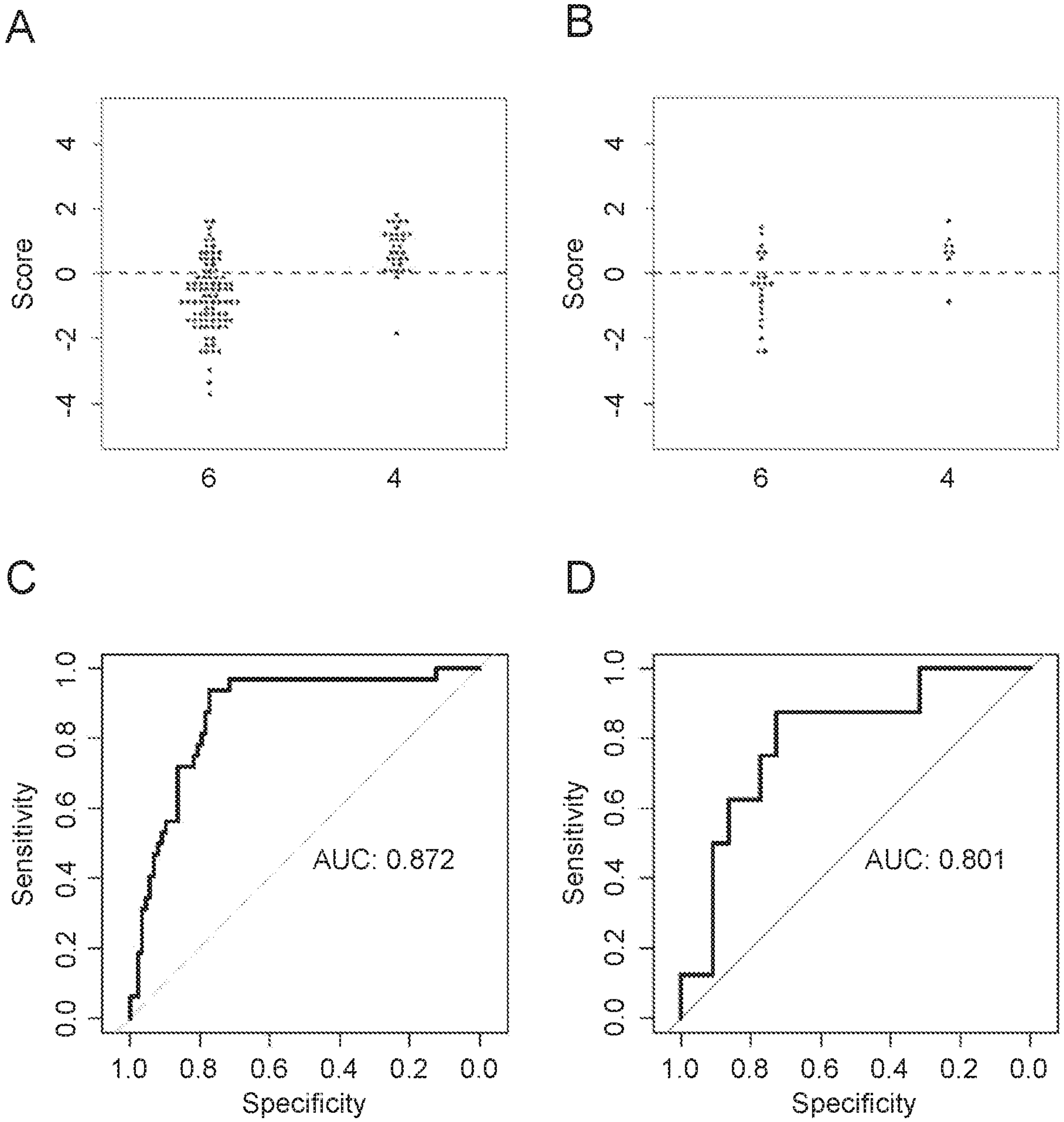
FIG. 11 shows plots of discriminant scores in a training cohort (A) and a validation cohort (B) and ROC curves for the training cohort (C) and the validation cohort (D) as obtained in Example 3-4.
Figure 12:
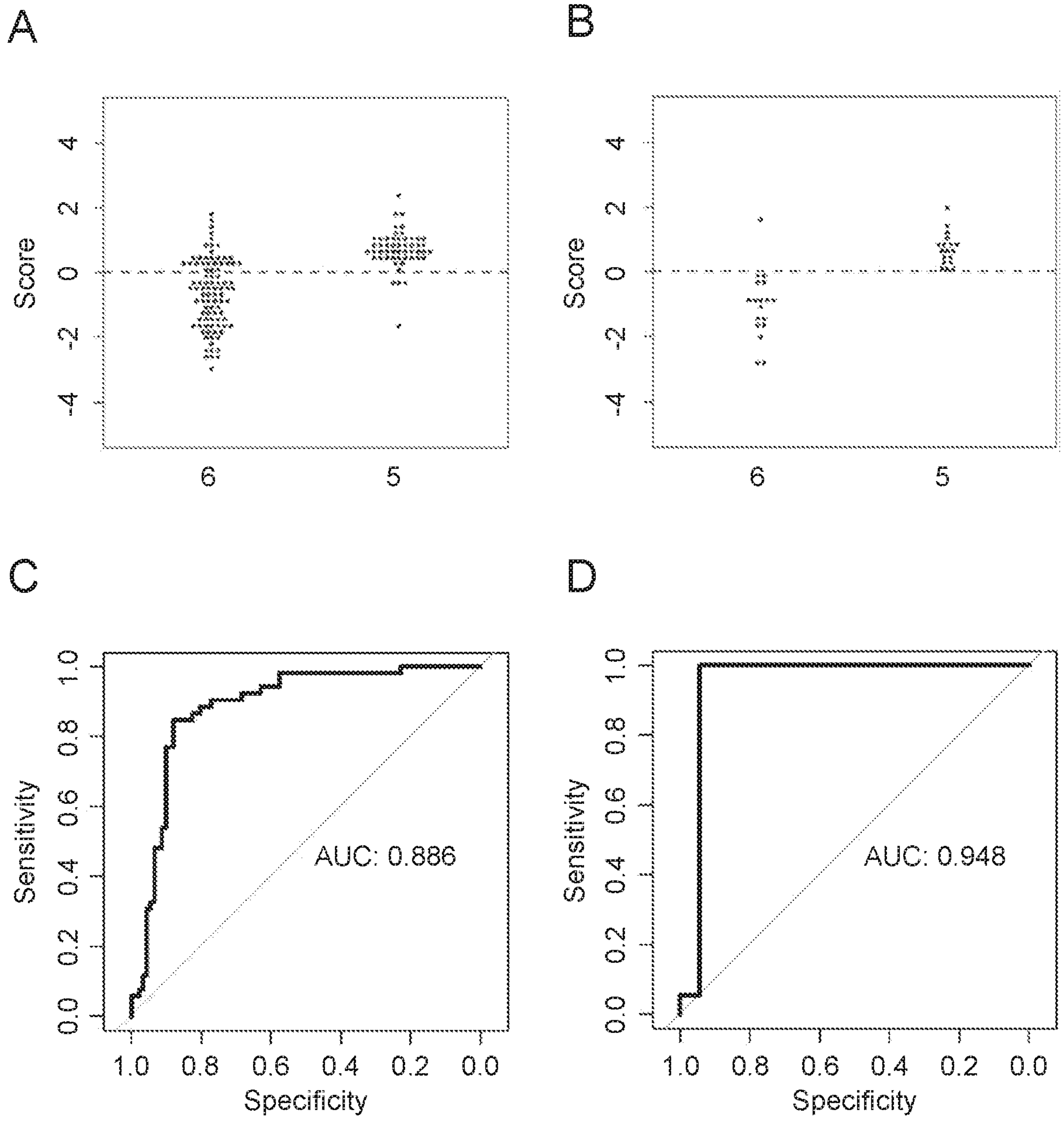
FIG. 12 shows plots of discriminant scores in a training cohort (A) and a validation cohort (B) and ROC curves for the training cohort (C) and the validation cohort (D) as obtained in Example 3-5.

FIGS. 8 to 12 show plots of discriminant scores and ROC curves as obtained in Examples 3-1 to 3-5. FIG. 8 shows plots of discriminant scores and ROC curves for Alzheimer's dementia described in Example 3-1. FIG. 9 shows plots of discriminant scores and ROC curves for vascular dementia described in Example 3-2. FIG. 10 shows plots of discriminant scores and ROC curves for Lewy body dementia described in Example 3-3. FIG. 11 shows plots of discriminant scores and ROC curves for frontotemporal lobar degeneration described in Example 3-4. FIG. 12 shows plots of discriminant scores and ROC curves for normal pressure hydrocephalus described in Example 3-5. In each figure, panel A is a plot of discriminant scores in a training cohort; panel B is a plot of discriminant scores in a validation cohort; panel C is a ROC curve for the training cohort; and panel D is a ROC curve for the validation cohort.

The discriminant scores in each plot of discriminant scores range from −5 to 5. The dotted line (a discriminant score of 0) in each panel depicts a discriminant boundary that discriminates the presence or absence of dementia. The discriminant scores were calculated by assigning the measurement values for the miRNA expression levels corresponding to each sample to a discriminant formula prepared using the above respective 5 miRNAs (the respective $24^{th}$, $28^{th}$, $29^{th}$, $31^{st}$, or $35^{th}$ discriminant markers in Examples 3-1 to 3-5). The ordinate represents a discriminant score obtained, and the abscissa represents each cohort. The numerals on the abscissa in FIGS. 8 to 12 indicate the dementia disease types, which are the same as in FIGS. 3 to 7 (the disease type numbers in Table 2 and 3 are the same as the numerals on the abscissa in each panel).

MiRNA markers obtained in each Example were used to calculate the sensitivity as the ordinate and the specificity as the abscissa expressed in each ROC curve. Early detection and early treatment of dementia require diagnosis without misidentification. Meanwhile, once diagnosed as dementia, the disease patients receive a large social impact. Accordingly, it is also important to be able to give a diagnosis with good accuracy and without false positives. At the time of selection of a discriminant formula and markers for discriminating the presence or absence of dementia, a desired combination can be selected, depending on prioritized performance, from the ROC curves shown in FIGS. 8 to 12.

Example 4

In Example 4, the examination of the object 2 in Example 3 was further deepened. The object is to examine the validation when the number of markers used in the discriminant formula was reduced to 3. Specifically, using a training cohort, the resulting markers with high correlation were excluded. Next, every combination of 3 out of the top 30 markers ranked by the P value was analyzed by Fisher's discriminant analysis to construct a discriminant formula. Then, the performance was evaluated in a validation cohort. Otherwise, the same procedure as in Example 3 was repeated.

Example 4-1: Search for Alzheimer's Dementia Markers

One thousand and one hundred forty seven (1,147) samples from patients with Alzheimer's dementia, a type of dementia, and 110 samples from non-dementia subjects were used for analysis. Table 8 shows the resulting various 25 different (the $36^{th}$ to the $60^{th}$) combinations and their discriminant performance. Note that only the $55^{th}$ combination gave a discriminant formula with sensitivity and specificity of more than 70% in the validation cohort (Table 8).

When combinations of 5 markers described in Example 3-1 were used, 4 different discriminant formulae with sensitivity and specificity of more than 70% in the validation cohort were obtained. Even when the number of markers was reduced to 3, some marker combination in the present invention was demonstrated to make it possible to exceed target performance.

Example 4-2: Search for Vascular Dementia Markers

Eighty (80) samples from patients with vascular dementia, a type of dementia, and 110 samples from non-dementia subjects were used for analysis. Table 8 shows the resulting various 25 different (the $61^{st}$ to the $85^{th}$) combinations and their discriminant performance. Note that the $80^{th}$ and $81^{st}$ combinations gave 2 discriminant formulae with sensitivity and specificity of more than 80% in the validation cohort (Table 8).

When combinations of 5 markers described in Example 3-2 were used, 2 different discriminant formulae with sensitivity and specificity of more than 80% in the validation cohort were obtained. Even when the number of markers was reduced to 3, some marker combination in the present invention was demonstrated to make it possible to exceed target performance.

Example 4-3: Search for Lewy Body Dementia Markers

One hundred fifty nine (159) samples from patients with Lewy body dementia, a type of dementia, and 110 samples from non-dementia subjects were used for analysis. Table 8 shows the resulting various 25 different (the $86^{th}$ to the $110^{th}$) combinations and their discriminant performance. Note that the $87^{th}$ and $101^{st}$ combinations gave 2 discriminant formulae with sensitivity and specificity of more than 80% in the validation cohort (Table 8).

When combinations of 5 markers described in Example 3-3 were used, 2 different discriminant formulae with sensitivity and specificity of more than 80% in the validation cohort were obtained. Even when the number of markers was reduced to 3, some marker combination in the present invention was demonstrated to make it possible to exceed target performance.

Example 4-4: Search for Frontotemporal Lobar Degeneration Markers

Forty (40) samples from patients with frontotemporal lobar degeneration, a type of dementia, and 110 samples from non-dementia subjects were used for analysis. Table 8 shows the resulting various 25 different (the $111^{5t}$ to the $135^{th}$) combinations and their discriminant performance. Note that only the $133^{rd}$ combination gave a discriminant formula with sensitivity and specificity of more than 70% in the validation cohort (Table 8).

When combinations of 5 markers described in Example 3-4 were used, 2 different discriminant formulae with sensitivity and specificity of more than 70% in the validation cohort were obtained. Even when the number of markers was reduced to 3, some marker combination in the present invention was demonstrated to make it possible to exceed target performance.

Example 4-5: Search for Normal Pressure Hydrocephalus Markers

Seventy (70) samples from patients with normal pressure hydrocephalus, a type of dementia, and 110 samples from non-dementia subjects were used for analysis. Table 8 shows the resulting various 25 different (the $136^{th}$ to the $160^{th}$) combinations and their discriminant performance. Note that the $139^{th}$, $145^{th}$, $147^{th}$, $153^{rd}$, and $158^{th}$ combinations gave 5 discriminant formulae with sensitivity and specificity of more than 80% in the validation cohort (Table 8).

TABLE 8

| Example | No. | Number of miRNAs | SEQ ID NOs | AUC | Sensi-tivity | Specific-ity |
|---|---|---|---|---|---|---|
| Example 4-1 | 36th | 3 | 26, 49, 101 | 0.673 | 74 | 62 |
| | 37th | 3 | 3, 4, 5 | 0.662 | 71 | 50 |
| | 38th | 3 | 3, 20, 49 | 0.679 | 76 | 48 |
| | 39th | 3 | 3, 16, 214 | 0.788 | 75 | 68 |
| | 40th | 3 | 3, 9, 11 | 0.683 | 79 | 37 |
| | 41st | 3 | 3, 16, 214 | 0.707 | 74 | 67 |
| | 42nd | 3 | 3, 49, 214 | 0.746 | 75 | 67 |
| | 43rd | 3 | 26, 49, 101 | 0.726 | 72 | 59 |
| | 44th | 3 | 3, 20, 49 | 0.705 | 77 | 60 |
| | 45th | 3 | 8, 145, 214 | 0.677 | 67 | 58 |
| | 46th | 3 | 3, 49, 215 | 0.753 | 76 | 68 |
| | 47th | 3 | 3, 20, 49 | 0.814 | 78 | 65 |
| | 48th | 3 | 26, 49, 101 | 0.683 | 71 | 56 |
| | 49th | 3 | 3, 49, 104 | 0.706 | 78 | 63 |
| | 50th | 3 | 8, 16, 20 | 0.610 | 72 | 47 |
| | 51st | 3 | 3, 49, 101 | 0.753 | 78 | 64 |
| | 52nd | 3 | 26, 49, 101 | 0.695 | 70 | 61 |
| | 53rd | 3 | 3, 16, 214 | 0.798 | 77 | 69 |
| | 54th | 3 | 23, 26, 214 | 0.664 | 69 | 67 |
| | 55th | 3 | 3, 11, 49 | 0.775 | 77 | 75 |
| | 56th | 3 | 3, 11, 49 | 0.737 | 78 | 64 |
| | 57th | 3 | 1, 3, 49 | 0.750 | 78 | 59 |
| | 58th | 3 | 8, 49, 214 | 0.664 | 76 | 68 |
| | 59th | 3 | 5, 8, 16 | 0.668 | 74 | 61 |
| | 60th | 3 | 11, 146, 200 | 0.672 | 68 | 63 |
| Example 4-2 | 61st | 3 | 26, 197, 218 | 0.886 | 78 | 90 |
| | 62nd | 3 | 16, 26, 32 | 0.832 | 81 | 77 |
| | 63rd | 3 | 26, 203, 218 | 0.745 | 87 | 57 |
| | 64th | 3 | 16, 26, 217 | 0.910 | 87 | 78 |
| | 65th | 3 | 26, 29, 111 | 0.872 | 81 | 73 |
| | 66th | 3 | 26, 28, 233 | 0.800 | 72 | 65 |
| | 67th | 3 | 4, 26, 34 | 0.867 | 78 | 75 |
| | 68th | 3 | 16, 26, 218 | 0.869 | 89 | 75 |
| | 69th | 3 | 16, 26, 218 | 0.907 | 90 | 75 |
| | 70th | 3 | 26, 203, 218 | 0.795 | 69 | 82 |
| | 71st | 3 | 16, 26, 218 | 0.859 | 95 | 74 |
| | 72nd | 3 | 16, 26, 111 | 0.788 | 93 | 57 |
| | 73rd | 3 | 16, 26, 30 | 0.818 | 71 | 79 |
| | 74th | 3 | 16, 26, 32 | 0.893 | 93 | 65 |
| | 75th | 3 | 16, 26, 197 | 0.835 | 59 | 86 |
| | 76th | 3 | 26, 203, 218 | 0.765 | 73 | 61 |
| | 77th | 3 | 26, 217, 218 | 0.832 | 77 | 67 |
| | 78th | 3 | 3, 4, 16 | 0.803 | 92 | 48 |
| | 79th | 3 | 16, 26, 45 | 0.888 | 71 | 91 |
| | 80th | 3 | 26, 28, 42 | 0.903 | 83 | 85 |
| | 81st | 3 | 16, 26, 42 | 0.924 | 88 | 81 |
| | 82nd | 3 | 26, 43, 141 | 0.716 | 73 | 69 |
| | 83rd | 3 | 16, 26, 32 | 0.810 | 88 | 64 |
| | 84th | 3 | 26, 203, 218 | 0.805 | 67 | 76 |
| | 85th | 3 | 26, 28, 217 | 0.864 | 88 | 64 |
| Example 4-3 | 86th | 3 | 11, 26, 49 | 0.753 | 86 | 52 |
| | 87th | 3 | 3, 16, 45 | 0.907 | 88 | 85 |
| | 88th | 3 | 3, 197, 219 | 0.722 | 70 | 71 |
| | 89th | 3 | 3, 16, 26 | 0.740 | 95 | 44 |
| | 90th | 3 | 3, 114, 220 | 0.775 | 79 | 64 |
| | 91st | 3 | 26, 87, 207 | 0.793 | 81 | 65 |
| | 92nd | 3 | 26, 32, 49 | 0.853 | 85 | 75 |
| | 93rd | 3 | 26, 214, 247 | 0.844 | 68 | 83 |
| | 94th | 3 | 26, 54, 220 | 0.815 | 92 | 63 |
| | 95th | 3 | 3, 4, 52 | 0.680 | 77 | 39 |
| | 96th | 3 | 3, 16, 26 | 0.841 | 89 | 68 |
| | 97th | 3 | 3, 29, 52 | 0.849 | 89 | 77 |
| | 98th | 3 | 26, 47, 52 | 0.681 | 71 | 53 |
| | 99th | 3 | 3, 45, 49 | 0.782 | 88 | 62 |
| | 100th | 3 | 3, 4, 116 | 0.772 | 76 | 68 |
| | 101st | 3 | 26, 32, 46 | 0.849 | 87 | 83 |
| | 102nd | 3 | 3, 49, 220 | 0.693 | 88 | 37 |
| | 103rd | 3 | 26, 45, 214 | 0.756 | 83 | 71 |
| | 104th | 3 | 26, 207, 221 | 0.850 | 77 | 78 |
| | 105th | 3 | 3, 16, 26 | 0.878 | 88 | 75 |
| | 106th | 3 | 26, 47, 207 | 0.803 | 69 | 63 |
| | 107th | 3 | 26, 214, 247 | 0.871 | 94 | 70 |
| | 108th | 3 | 3, 16, 45 | 0.857 | 85 | 74 |
| | 109th | 3 | 26, 45, 220 | 0.688 | 76 | 62 |
| | 110th | 3 | 26, 32, 49 | 0.878 | 83 | 74 |

TABLE 8-continued

| Example | No. | Number of miRNAs | SEQ ID NOs | AUC | Sensi-tivity | Specific-ity |
|---|---|---|---|---|---|---|
| Example 4-4 | 111th | 3 | 30, 70, 147 | 0.758 | 86 | 61 |
| | 112th | 3 | 26, 116, 117 | 0.646 | 46 | 63 |
| | 113th | 3 | 69, 148, 236 | 0.835 | 100 | 46 |
| | 114th | 3 | 3, 33, 70 | 0.566 | 56 | 62 |
| | 115th | 3 | 69, 121, 148 | 0.608 | 20 | 84 |
| | 116th | 3 | 69, 98, 236 | 0.704 | 80 | 64 |
| | 117th | 3 | 30, 69, 227 | 0.574 | 50 | 59 |
| | 118th | 3 | 3, 70, 217 | 0.693 | 56 | 86 |
| | 119th | 3 | 115, 121, 238 | 0.605 | 60 | 45 |
| | 120th | 3 | 26, 70, 125 | 0.631 | 50 | 73 |
| | 121st | 3 | 26, 120, 121 | 0.795 | 63 | 82 |
| | 122nd | 3 | 30, 70, 227 | 0.622 | 46 | 74 |
| | 123rd | 3 | 98, 99, 202 | 0.683 | 75 | 50 |
| | 124th | 3 | 3, 33, 121 | 0.661 | 67 | 57 |
| | 125th | 3 | 10, 30, 70 | 0.716 | 75 | 55 |
| | 126th | 3 | 37, 70, 128 | 0.503 | 57 | 52 |
| | 127th | 3 | 26, 30, 242 | 0.653 | 63 | 77 |
| | 128th | 3 | 82, 83, 120 | 0.600 | 60 | 70 |
| | 129th | 3 | 70, 99, 243 | 0.571 | 57 | 65 |
| | 130th | 3 | 43, 70, 121 | 0.659 | 63 | 73 |
| | 131st | 3 | 30, 37, 227 | 0.642 | 67 | 56 |
| | 132nd | 3 | 30, 70, 133 | 0.702 | 86 | 65 |
| | 133rd | 3 | 43, 70, 121 | 0.869 | 77 | 94 |
| | 134th | 3 | 37, 149, 227 | 0.761 | 50 | 77 |
| | 135th | 3 | 26, 43, 248 | 0.593 | 56 | 67 |
| Example 4-5 | 136th | 3 | 49, 99, 150 | 0.720 | 64 | 68 |
| | 137th | 3 | 34, 83, 226 | 0.841 | 75 | 75 |
| | 138th | 3 | 8, 75, 203 | 0.775 | 93 | 62 |
| | 139th | 3 | 3, 34, 49 | 0.906 | 86 | 82 |
| | 140th | 3 | 8, 49, 75 | 0.867 | 64 | 91 |
| | 141st | 3 | 26, 34, 49 | 0.850 | 81 | 70 |
| | 142nd | 3 | 3, 49, 85 | 0.756 | 93 | 59 |
| | 143rd | 3 | 3, 34, 226 | 0.708 | 83 | 58 |
| | 144th | 3 | 8, 75, 85 | 0.809 | 85 | 65 |
| | 145th | 3 | 8, 75, 83 | 0.870 | 93 | 81 |
| | 146th | 3 | 3, 10, 49 | 0.765 | 89 | 74 |
| | 147th | 3 | 3, 34, 49 | 0.884 | 80 | 88 |
| | 148th | 3 | 26, 75, 104 | 0.796 | 69 | 65 |
| | 149th | 3 | 8, 75, 203 | 0.829 | 87 | 67 |
| | 150th | 3 | 8, 75, 151 | 0.756 | 85 | 65 |
| | 151st | 3 | 26, 75, 104 | 0.833 | 73 | 68 |
| | 152nd | 3 | 3, 10, 246 | 0.741 | 75 | 65 |
| | 153rd | 3 | 3, 34, 49 | 0.897 | 94 | 80 |
| | 154th | 3 | 1, 49, 83 | 0.732 | 62 | 65 |
| | 155th | 3 | 8, 49, 75 | 0.873 | 57 | 86 |
| | 156th | 3 | 8, 75, 203 | 0.722 | 88 | 50 |
| | 157th | 3 | 34, 83, 226 | 0.724 | 93 | 50 |
| | 158th | 3 | 3, 34, 49 | 0.951 | 89 | 94 |
| | 159th | 3 | 3, 34, 49 | 0.854 | 90 | 62 |
| | 160th | 3 | 34, 37, 49 | 0.757 | 75 | 75 |

When combinations of 5 markers described in Example 3-5 were used, 3 different discriminant formulae with sensitivity and specificity of more than 80% in the validation cohort were obtained. Even when the number of markers was reduced to 3, some marker combination in the present invention was demonstrated to make it possible to give a large number of combinations exhibiting performance exceeding target discriminant performance.

Example 5

In Example 5, the examination in Examples 3 and 4 was further deepened in order to examine the variation when the number of markers used in the discriminant formula was increased to 8. Specifically, like Example 2, samples from each of the positive group or the negative group were divided into 5 groups. Then, ⅘ of the divided groups were assigned to a training cohort and ⅕ thereof was assigned to a validation cohort. The validation cohort was changed five times. Whenever the validation cohort was changed, a discriminant formula was constructed using the training cohort like Example 1-1 by logistic regression using the LASSO method. Then, the performance was evaluated on the validation cohort. Further, the dividing method was changed five times.

Example 5-1: Search for Lewy Body Dementia Markers

One hundred fifty nine (159) samples from patients with Lewy body dementia, a type of dementia, and 110 samples from non-dementia subjects were used for analysis. Table 9 shows the resulting 3 different (the $161^{st}$ to the $163^{rd}$) combinations and their discriminant performance. All the 3 combinations each gave a discriminant formula with sensitivity and specificity of more than 70% in the validation cohort (Table 9).

Example 5-2: Search for Frontotemporal Lobar Degeneration Markers

Forty (40) samples from patients with frontotemporal lobar degeneration, a type of dementia, and 110 samples from non-dementia subjects were used for analysis. Table 9 shows the resulting 6 different (the $164^{th}$ to the $169^{th}$) combinations and their discriminant performance. The $165^{th}$, $166^{th}$, and $167^{th}$ combinations gave 3 different discriminant formulae with sensitivity and specificity of more than 70% in the validation cohort (Table 9).

Example 5-3: Search for Normal Pressure Hydrocephalus Markers

Seventy (70) samples from patients with normal pressure hydrocephalus, a type of dementia, and 110 samples from non-dementia subjects were used for analysis. Table 9 shows the resulting 3 different (the $170^{th}$ to the $172^{nd}$) combinations and their discriminant performance. Only the $171^{st}$ combination gave a discriminant formula with sensitivity and specificity of more than 70% in the validation cohort (Table 9).

TABLE 9

| Example No. | | Number of miRNAs | SEQ ID NOs | AUC | Sensitivity | Specificity |
|---|---|---|---|---|---|---|
| Example 5-1 | 161st | 8 | 3, 4, 16, 26, 49, 54, 207, 219 | 0.854 | 77 | 84 |
| | 162nd | 8 | 3, 4, 16, 26, 49, 53, 194, 214 | 0.846 | 91 | 70 |
| | 163rd | 8 | 3, 4, 26, 49, 194, 214, 219, 220 | 0.858 | 90 | 74 |
| Example 5-2 | 164th | 8 | 26, 70, 117, 147, 160, 161, 197, 225 | 0.679 | 36 | 74 |
| | 165th | 8 | 30, 69, 70, 71, 73, 121, 248, 249 | 0.784 | 100 | 72 |
| | 166th | 8 | 26, 37, 69, 70, 71, 72, 171, 248 | 0.892 | 75 | 91 |
| | 167th | 8 | 26, 30, 70, 71, 72, 175, 193, 197 | 0.841 | 88 | 77 |
| | 168th | 8 | 3, 26, 37, 70, 72, 153, 176, 177 | 0.509 | 43 | 61 |
| | 169th | 8 | 13, 26, 69, 70, 71, 181, 197, 223 | 0.652 | 71 | 61 |
| Example 5-3 | 170th | 8 | 3, 8, 34, 66, 75, 136, 184/185, 203 | 0.806 | 69 | 83 |
| | 171st | 8 | 3, 8, 26, 75, 84, 186, 220, 226 | 0.879 | 73 | 86 |
| | 172nd | 8 | 3, 8, 11, 26, 75, 203, 220, 226 | 0.781 | 94 | 60 |

Example 6

In Example 6, the examination in Examples 3 to 5 was further deepened, in order to examine the variation when the number of markers used in the discriminant formula was increased to 9. Specifically, substantially the same procedure as in Example 5 was repeated.

Example 6-1: Search for Alzheimer's Dementia Markers

One thousand and one hundred forty seven (1,147) samples from patients with Alzheimer's dementia, a type of dementia, and 110 samples from non-dementia subjects were used for analysis. Table 10 shows the resulting 6 different (the $173^{rd}$ to the $178^{th}$) combinations and their discriminant performance. Regarding the 5 different $173^{rd}$, $175^{th}$, $176^{th}$, $177^{th}$, and $178^{th}$ combinations, some marker set variations with either sensitivity or specificity of more than 70% in the validation cohort were found (Table 10).

Example 6-2: Search for Vascular Dementia Markers

Eighty (80) samples from patients with vascular dementia, a type of dementia, and 110 samples from non-dementia subjects were used for analysis. Table 10 shows the resulting 4 different (the $179^{th}$ to the $182^{nd}$) combinations and their discriminant performance. Regarding the 2 different $179^{th}$ and $181^{st}$ combinations, marker set variations with either sensitivity or specificity of more than 80% in the validation cohort were found (Table 10).

Example 6-3: Search for Lewy Body Dementia Markers

One hundred fifty nine (159) samples from patients with Lewy body dementia, a type of dementia, and 110 samples from non-dementia subjects were used for analysis. Table 10 shows the resulting 8 different (the $183^{rd}$ to the $190^{th}$) combinations and their discriminant performance. Among them, regarding the 2 different $187^{th}$ and $190^{th}$ combinations, marker set variations with sensitivity and specificity of more than 80% in the validation cohort were found (Table 10).

Example 6-4: Search for Frontotemporal Lobar Degeneration Markers

Forty (40) samples from patients with frontotemporal lobar degeneration, a type of dementia, and 110 samples from non-dementia subjects were used for analysis. Table 10 shows the resulting 3 different (the $191^{st}$ to the $193^{rd}$) combinations and their discriminant performance. Regarding all the 3 different combinations, marker set variations with either sensitivity or specificity of more than 70% were found (Table 10).

Example 6-5: Search for Normal Pressure Hydrocephalus Markers

Seventy (70) samples from patients with normal pressure hydrocephalus, a type of dementia, and 110 samples from non-dementia subjects were used for analysis. Table 10 shows the resulting 8 different (the 194th to the 201st) combinations and their discriminant performance. Among them, regarding the 3 different 194th, 195th and 198th combinations, marker set variations with sensitivity and specificity of more than 80% in the validation cohort were found (Table 10).

TABLE 10

| Example No. | | Number of miRNAs | SEQ ID NOs | AUC | Sensitivity | Specificity |
|---|---|---|---|---|---|---|
| Example 6-1 | 173rd | 9 | 2, 3, 4, 5, 8, 9, 13, 49, 214 | 0.743 | 71 | 67 |
| | 174th | 9 | 4, 5, 8, 11, 20, 90, 155, 200, 214 | 0.634 | 65 | 65 |
| | 175th | 9 | 3, 4, 5, 7, 8, 9, 20, 200, 214 | 0.699 | 79 | 56 |
| | 176th | 9 | 3, 4, 5, 7, 8, 9, 10, 20, 214 | 0.782 | 80 | 63 |
| | 177th | 9 | 3, 4, 5, 7, 9, 13, 20, 49, 155 | 0.750 | 78 | 55 |
| | 178th | 9 | 1, 3, 4, 5, 8, 10, 11, 152, 200 | 0.714 | 75 | 61 |
| Example 6-2 | 179th | 9 | 3, 16, 23, 26, 32, 45, 89, 110, 218 | 0.833 | 89 | 75 |
| | 180th | 9 | 3, 4, 16, 23, 26, 34, 89, 111, 217 | 0.771 | 60 | 74 |
| | 181st | 9 | 16, 23, 25, 26, 28, 37, 203, 207, 218 | 0.885 | 65 | 95 |
| | 182nd | 9 | 4, 23, 26, 28, 45, 197, 203, 214, 218 | 0.745 | 67 | 74 |
| Example 6-3 | 183rd | 9 | 3, 11, 26, 49, 134, 194, 200, 214, 234 | 0.744 | 89 | 60 |
| | 184th | 9 | 3, 13, 16, 26, 49, 64, 68, 113, 214 | 0.709 | 90 | 56 |
| | 185th | 9 | 3, 16, 26, 29, 49, 52, 53, 214, 220 | 0.844 | 87 | 71 |
| | 186th | 9 | 1, 3, 13, 26, 49, 54, 200, 214, 220 | 0.858 | 96 | 70 |
| | 187th | 9 | 3, 4, 26, 29, 45, 49, 54, 55, 214 | 0.896 | 93 | 85 |
| | 188th | 9 | 3, 26, 36, 45, 49, 54, 60, 214, 219 | 0.811 | 88 | 67 |
| | 189th | 9 | 3, 4, 26, 49, 194, 200, 214, 219, 220 | 0.703 | 88 | 53 |
| | 190th | 9 | 3, 13, 16, 26, 45, 49, 194, 214, 219 | 0.881 | 94 | 80 |
| Example 6-4 | 191st | 9 | 69, 70, 72, 167, 173, 200, 202, 225, 248 | 0.654 | 75 | 65 |
| | 192nd | 9 | 37, 43, 70, 71, 121, 200, 225, 227, 249 | 0.653 | 50 | 73 |
| | 193rd | 9 | 24, 26, 43, 69, 70, 71, 163, 197, 248 | 0.720 | 78 | 48 |
| Example 6-5 | 194th | 9 | 3, 11, 16, 26, 34, 75, 104, 134, 226 | 0.891 | 81 | 85 |
| | 195th | 9 | 3, 26, 34, 75, 76, 104, 136, 215, 226 | 0.899 | 93 | 82 |
| | 196th | 9 | 3, 26, 34, 75, 84, 104, 203, 226, 230 | 0.799 | 77 | 78 |
| | 197th | 9 | 3, 8, 26, 75, 104, 151, 203, 220, 226 | 0.826 | 77 | 78 |
| | 198th | 9 | 3, 11, 26, 34, 45, 52, 75, 203, 220 | 0.806 | 81 | 80 |
| | 199th | 9 | 3, 16, 26, 41, 49, 75, 83, 136, 225 | 0.753 | 85 | 70 |
| | 200th | 9 | 3, 16, 26, 34, 45, 75, 104, 189, 190 | 0.935 | 72 | 94 |
| | 201st | 9 | 3, 26, 37, 49, 75, 84, 104, 203, 245 | 0.778 | 83 | 67 |

Example 7

In Example 7, the examination in Examples 3 to 6 was further deepened, in order to examine the validation when the number of markers used in the discriminant formula was increased to 10. Specifically, substantially the same procedure as in Example 5 was repeated.

Example 7-1: Search for Alzheimer's Dementia Markers

One thousand and one hundred forty seven (1,147) samples from patients with Alzheimer's dementia, a type of dementia, and 110 samples from non-dementia subjects were used for analysis. Table 11 shows the resulting 17 different (the 202nd to the 218th) combinations and their discriminant performance. Among them, regarding the 3 different 204th, 206th, and 209th combinations, marker set variations with sensitivity and specificity of more than 70% in the validation cohort were found (Table 11).

The number of discriminant formulae with sensitivity and specificity of more than 70% in the validation cohort was 1 for a combination of 3 markers (Example 4-1) and 4 for a combination of 5 markers (Example 3-1). In view of Examples 3 to 7, the discriminant performance of markers in the present invention is not necessarily improved as the number of markers in combination is increased. It can be said that any significant combination of at least 3, more preferably 5, and still more preferably about 10 different markers can elicit high discriminant performance.

Example 7-2: Search for Vascular Dementia Markers

Eighty (80) samples from patients with vascular dementia, a type of dementia, and 110 samples from non-dementia subjects were used for analysis. Table 11 shows the resulting 21 different (the 219th to the 239th) combinations and their discriminant performance. Among them, regarding the 9 different 219th, 222nd, 225th, 226th, 232nd, 234th, 235th, 236th, and 239th combinations, marker set variations with sensitivity and specificity of more than 80% in the validation cohort were found (Table 11).

The number of discriminant formulae with sensitivity and specificity of more than 80% in the validation cohort was 2 for a combination of 3 markers (Example 4-2) and 2 for a combination of 5 markers (Example 3-2). In view of Examples 3 to 7, the discriminant performance of markers in the present invention is not necessarily improved as the number of markers in combination is increased. It can be said that any significant combination of at least 3, more preferably 5, and still more preferably about 10 different markers can elicit high discriminant performance.

Example 7-3: Search for Lewy Body Dementia Markers

One hundred fifty nine (159) samples from patients with Lewy body dementia, a type of dementia, and 110 samples from non-dementia subjects were used for analysis. Table 11 shows the resulting 14 different (the 240th to the 253rd) combinations and their discriminant performance.

Among them, regarding the 5 different 240th, 243rd, 249th, 251st, and 252nd combinations, marker set variations with sensitivity and specificity of more than 80% in the validation cohort were found (Table 11).

The number of discriminant formulae with sensitivity and specificity of more than 80% in the validation cohort was 2 for a combination of 3 markers (Example 4-3), 2 for a combination of 5 markers (Example 3-3), and 2 for a combination of 9 markers (Example 6-3). In view of Examples 3 to 7, the discriminant performance of markers in the present invention is not necessarily improved as the number of markers in combination is increased. It can be said that any significant combination of at least 3, more preferably 5, and still more preferably about 10 different markers can elicit high discriminant performance.

Example 7-4: Search for Frontotemporal Lobar Degeneration Markers

Forty (40) samples from patients with frontotemporal lobar degeneration, a type of dementia, and 110 samples from non-dementia subjects were used for analysis. Table 11 shows the resulting 16 different (the 254$^{th}$ to the 269$^{th}$) combinations and their discriminant performance. Among them, regarding only the 269$^{th}$ combination, a marker set variation with sensitivity and specificity of more than 70% in the validation cohort were found (Table 11).

The number of discriminant formulae with sensitivity and specificity of more than 70% in the validation cohort was 1 for a combination of 3 markers (Example 4-4), 2 for a combination of 5 markers (Example 3-4), and 3 for a combination of 8 markers (Example 5-2). The discriminant performance of markers in the present invention is not necessarily improved as the number of markers in combination is increased. It can be said that any significant combination of at least 3, more preferably 5, and still more preferably about 10 different markers can elicit high discriminant performance.

Example 7-5: Search for Normal Pressure Hydrocephalus Markers

Seventy (70) samples from patients with normal pressure hydrocephalus, a type of dementia, and 110 samples from non-dementia subjects were used for analysis. Table 11 shows the resulting 14 different (the 270$^{th}$ to the 283$^{rd}$) combinations and their discriminant performance (Table 11).

TABLE 11

| Example No. | | Number of miRNAs | SEQ ID NOs | AUC | Sensitivity | Specificity |
|---|---|---|---|---|---|---|
| Example 7-1 | 202nd | 10 | 3, 4, 5, 7, 8, 10, 13, 20, 83, 214 | 0.686 | 72 | 56 |
| | 203rd | 10 | 3, 4, 5, 8, 9, 18, 20, 192, 200, 214 | 0.665 | 71 | 52 |
| | 204th | 10 | 1, 2, 3, 4, 5, 6, 7, 8, 200, 214 | 0.834 | 80 | 79 |
| | 205th | 10 | 2, 3, 4, 8, 9, 10, 13, 152, 200, 214 | 0.739 | 80 | 48 |
| | 206th | 10 | 1, 3, 4, 5, 8, 83, 152, 194, 200, 214 | 0.776 | 71 | 71 |
| | 207th | 10 | 3, 4, 5, 13, 20, 26, 63, 152, 153, 200 | 0.671 | 79 | 56 |
| | 208th | 10 | 4, 5, 7, 8, 10, 20, 83, 154, 200, 214 | 0.698 | 80 | 50 |
| | 209th | 10 | 1, 2, 3, 4, 5, 9, 10, 11, 214, 215 | 0.803 | 78 | 74 |
| | 210th | 10 | 2, 3, 5, 7, 8, 12, 18, 20, 200, 214 | 0.767 | 78 | 65 |
| | 211th | 10 | 3, 4, 5, 6, 8, 10, 152, 155, 200, 214 | 0.670 | 73 | 52 |
| | 212th | 10 | 3, 4, 5, 7, 9, 83, 152, 192, 194, 200 | 0.696 | 77 | 52 |
| | 213th | 10 | 1, 3, 5, 10, 11, 13, 18, 20, 156, 200 | 0.653 | 77 | 55 |
| | 214th | 10 | 3, 4, 5, 6, 8, 13, 18, 20, 200, 214 | 0.830 | 80 | 62 |
| | 215th | 10 | 4, 5, 9, 19, 23, 26, 47, 153, 200, 214 | 0.697 | 85 | 57 |
| | 216th | 10 | 2, 3, 4, 5, 9, 18, 20, 49, 200, 214 | 0.802 | 80 | 67 |
| | 217th | 10 | 3, 4, 5, 6, 8, 18, 20, 83, 200, 214 | 0.604 | 64 | 58 |
| | 218th | 10 | 3, 4, 5, 8, 11, 13, 152, 156, 200, 214 | 0.749 | 73 | 58 |
| Example 7-2 | 219th | 10 | 3, 4, 16, 23, 24, 25, 26, 197, 216, 218 | 0.894 | 83 | 85 |
| | 220th | 10 | 3, 4, 16, 26, 32, 37, 45, 140, 194, 218 | 0.810 | 63 | 82 |
| | 221st | 10 | 4, 16, 23, 25, 26, 28, 29, 32, 36, 218 | 0.736 | 73 | 70 |
| | 222nd | 10 | 3, 4, 16, 23, 26, 27, 28, 29, 214, 217 | 0.942 | 87 | 91 |
| | 223rd | 10 | 4, 16, 23, 24, 25, 26, 28, 29, 37, 214 | 0.864 | 81 | 68 |
| | 224th | 10 | 3, 4, 23, 25, 26, 28, 29, 125, 207, 216 | 0.831 | 61 | 85 |
| | 225th | 10 | 4, 8, 16, 25, 26, 34, 37, 59, 203, 214 | 0.892 | 89 | 80 |
| | 226th | 10 | 4, 16, 24, 26, 29, 30, 32, 36, 214, 218 | 0.932 | 80 | 86 |
| | 227th | 10 | 4, 23, 26, 28, 45, 88, 91, 203, 217, 218 | 0.810 | 75 | 77 |
| | 228th | 10 | 3, 4, 16, 23, 26, 28, 37, 45, 214, 218 | 0.845 | 90 | 74 |
| | 229th | 10 | 3, 4, 16, 26, 28, 29, 30, 36, 79, 214 | 0.881 | 79 | 79 |
| | 230th | 10 | 3, 4, 16, 25, 26, 28, 32, 37, 214, 218 | 0.893 | 87 | 74 |
| | 231st | 10 | 3, 4, 16, 26, 34, 36, 37, 45, 99, 218 | 0.770 | 65 | 86 |
| | 232nd | 10 | 3, 4, 16, 25, 26, 28, 37, 207, 214, 218 | 0.898 | 92 | 80 |
| | 233rd | 10 | 4, 16, 23, 25, 26, 29, 36, 45, 216, 218 | 0.882 | 71 | 86 |
| | 234th | 10 | 4, 16, 23, 24, 26, 28, 29, 32, 207, 214 | 0.906 | 83 | 85 |
| | 235th | 10 | 4, 16, 23, 24, 26, 37, 42, 207, 214, 217 | 0.941 | 88 | 86 |
| | 236th | 10 | 3, 4, 23, 25, 26, 28, 43, 214, 216, 218 | 0.810 | 82 | 81 |
| | 237th | 10 | 3, 4, 16, 26, 28, 32, 45, 201, 209, 214 | 0.798 | 75 | 73 |
| | 238th | 10 | 4, 16, 23, 26, 30, 34, 36, 37, 203, 218 | 0.812 | 67 | 83 |
| | 239th | 10 | 3, 4, 16, 26, 28, 29, 36, 45, 217, 218 | 0.866 | 81 | 82 |
| Example 7-3 | 240th | 10 | 3, 4, 16, 26, 45, 47, 49, 53, 194, 214 | 0.915 | 97 | 80 |
| | 241st | 10 | 3, 8, 11, 16, 26, 45, 49, 53, 197, 219 | 0.788 | 93 | 71 |
| | 242nd | 10 | 3, 4, 26, 45, 47, 194, 207, 214, 219, 220 | 0.834 | 83 | 76 |
| | 243rd | 10 | 3, 4, 16, 26, 49, 54, 157, 194, 207, 214 | 0.859 | 97 | 80 |
| | 244th | 10 | 3, 16, 26, 48, 55, 134, 194, 200, 214, 219 | 0.842 | 84 | 78 |

TABLE 11-continued

| Example No. | | Number of miRNAs | SEQ ID NOs | AUC | Sensitivity | Specificity |
|---|---|---|---|---|---|---|
| | 245th | 10 | 3, 4, 11, 26, 49, 52, 53, 64, 158, 219 | 0.707 | 81 | 57 |
| | 246th | 10 | 3, 16, 26, 49, 52, 53, 55, 194, 207, 214 | 0.803 | 89 | 74 |
| | 247th | 10 | 3, 16, 26, 47, 49, 53, 134, 200, 214, 219 | 0.720 | 94 | 42 |
| | 248th | 10 | 3, 4, 26, 45, 47, 49, 116, 134, 207, 220 | 0.789 | 86 | 68 |
| | 249th | 10 | 3, 11, 16, 26, 29, 46, 49, 53, 55, 214 | 0.850 | 87 | 83 |
| | 250th | 10 | 3, 4, 8, 26, 45, 47, 53, 159, 194, 214 | 0.788 | 97 | 63 |
| | 251st | 10 | 3, 16, 26, 29, 47, 54, 209, 214, 219, 220 | 0.860 | 94 | 83 |
| | 252nd | 10 | 3, 8, 16, 26, 49, 54, 194, 214, 219, 220 | 0.860 | 85 | 82 |
| | 253rd | 10 | 3, 4, 11, 26, 45, 47, 53, 60, 200, 220 | 0.698 | 88 | 57 |
| Example 7-4 | 254th | 10 | 26, 29, 37, 69, 70, 71, 72, 74, 147, 200 | 0.770 | 57 | 65 |
| | 255th | 10 | 26, 37, 69, 70, 71, 74, 162, 197, 248, 249 | 0.818 | 63 | 82 |
| | 256th | 10 | 3, 33, 69, 70, 72, 73, 163, 164, 225, 241 | 0.651 | 67 | 76 |
| | 257th | 10 | 13, 49, 69, 70, 71, 72, 120, 121, 148, 161 | 0.704 | 60 | 76 |
| | 258th | 10 | 26, 30, 37, 69, 70, 71, 74, 224, 227, 248 | 0.631 | 38 | 59 |
| | 259th | 10 | 37, 70, 71, 72, 121, 165, 166, 167, 223, 248 | 0.741 | 33 | 86 |
| | 260th | 10 | 26, 37, 69, 70, 72, 73, 74, 161, 168, 197 | 0.845 | 60 | 75 |
| | 261st | 10 | 26, 69, 70, 72, 125, 147, 169, 170, 241, 242 | 0.619 | 38 | 73 |
| | 262nd | 10 | 30, 69, 70, 71, 73, 121, 172, 197, 227, 249 | 0.632 | 18 | 63 |
| | 263rd | 10 | 3, 26, 37, 69, 70, 72, 73, 174, 191, 241 | 0.619 | 67 | 71 |
| | 264th | 10 | 26, 30, 69, 71, 73, 94, 121, 178, 236, 248 | 0.676 | 63 | 64 |
| | 265th | 10 | 69, 70, 72, 73, 98, 147, 162, 179/180, 248, 249 | 0.875 | 50 | 85 |
| | 266th | 10 | 13, 26, 30, 37, 70, 71, 72, 121, 227, 236 | 0.605 | 67 | 78 |
| | 267th | 10 | 30, 37, 69, 70, 72, 116, 166, 169, 176, 248 | 0.652 | 57 | 70 |
| | 268th | 10 | 24, 29, 69, 70, 71, 72, 73, 175, 182, 197 | 0.878 | 54 | 100 |
| | 269th | 10 | 26, 30, 37, 70, 71, 73, 74, 223, 224, 225 | 0.761 | 75 | 73 |
| Example 7-5 | 270th | 10 | 3, 8, 49, 75, 84, 94, 176, 203, 220, 226 | 0.753 | 73 | 72 |
| | 271st | 10 | 3, 11, 26, 34, 75, 84, 183, 203, 220, 240 | 0.702 | 87 | 62 |
| | 272nd | 10 | 3, 8, 16, 26, 41, 49, 75, 104, 226, 234 | 0.877 | 86 | 77 |
| | 273rd | 10 | 8, 16, 26, 49, 52, 75, 88, 104, 203, 226 | 0.844 | 63 | 85 |
| | 274th | 10 | 3, 26, 49, 75, 84, 85, 104, 184/185, 226, 230 | 0.740 | 71 | 73 |
| | 275th | 10 | 3, 8, 11, 26, 34, 41, 49, 75, 136, 214 | 0.688 | 83 | 67 |
| | 276th | 10 | 1, 3, 8, 26, 41, 43, 49, 75, 136, 176 | 0.827 | 78 | 70 |
| | 277th | 10 | 3, 26, 30, 34, 49, 66, 75, 140, 187, 245 | 0.881 | 75 | 94 |
| | 278th | 10 | 3, 8, 26, 49, 60, 75, 184/185, 203, 220, 226 | 0.860 | 67 | 81 |
| | 279th | 10 | 3, 8, 26, 34, 41, 60, 75, 84, 104, 226 | 0.829 | 73 | 84 |
| | 280th | 10 | 3, 16, 26, 75, 85, 104, 188, 195, 226, 234 | 0.816 | 75 | 75 |
| | 281st | 10 | 3, 8, 26, 30, 49, 53, 75, 104, 116, 226 | 0.883 | 71 | 91 |
| | 282nd | 10 | 3, 8, 16, 26, 60, 75, 94, 139, 186, 226 | 0.795 | 93 | 64 |
| | 283rd | 10 | 3, 8, 26, 34, 49, 75, 94, 104, 136, 140 | 0.842 | 90 | 69 |

The number of discriminant formulae with sensitivity and specificity of more than 80% in the validation cohort was 5 for a combination of 3 markers (Example 4-5), 3 for a combination of 5 markers (Example 3-5), 1 for a combination of 8 markers (Example 5-3), and 3 for a combination of 9 markers (Example 6-5). The discriminant performance of markers in the present invention is not necessarily improved as the number of markers is increased. As the number of markers is increased, information that supports any significant markers is increased. Thus, it can be said that any significant combination of at least 3, more preferably 5, and still more preferably about 10 different markers can elicit high discriminant performance.

Example 8

In Example 8, the object is to examine whether the sensitivity and specificity were improved, compared to those in Example 3, by increasing the number of markers to the top 30 ranked by the P value for Alzheimer's dementia in Example 3.

Specifically, a training cohort was used, and the resulting markers with high correlation were excluded. Next, every combination of 4 or 5 out of the top 30 markers ranked by the P value was analyzed by Fisher's discriminant analysis to construct a discriminant formula. Then, the performance was evaluated in a validation cohort. Otherwise, substantially the same procedure as in Example 3 was repeated.

Example 8-1: Search for Alzheimer's Dementia Markers

One thousand and one hundred forty seven (1,147) samples from patients with Alzheimer's dementia, a type of dementia, and 110 samples from non-dementia subjects were used for analysis. Four (4) out of the top 30 markers ranked by the P value were used. This resulted in 3 different (the 284$^{th}$ to the 286$^{th}$) discriminant formulae with both sensitivity and specificity of more than 70% in the validation cohort. Table 12 shows these combinations and their discriminant performance.

Example 8-2: Search for Alzheimer's Dementia Markers

One thousand and one hundred forty seven (1,147) samples from patients with Alzheimer's dementia, a type of dementia, and 110 samples from non-dementia subjects were used for analysis. Five (5) out of the top 30 markers ranked by the P value were used. This resulted in 3 different (the 287$^{th}$ to the 289$^{th}$) discriminant formulae with both sensitivity and specificity of more than 70% in the validation cohort. Table 12 shows these combinations and their discriminant performance.

TABLE 12

| Example No. | | Number of miRNAs | SEQ ID NOs | AUC | Sensi-tivity | Specific-ity |
|---|---|---|---|---|---|---|
| Example | 284th | 4 | 3, 16, 23, 214 | 0.825 | 75 | 74 |
| 8-1 | 285th | 4 | 3, 16, 23, 214 | 0.774 | 76 | 74 |
| | 286th | 4 | 1, 3, 49, 77 | 0.748 | 74 | 74 |
| Example | 287th | 5 | 3, 16, 23, 87, 214 | 0.832 | 75 | 79 |
| 8-2 | 288th | 5 | 1, 4, 26, 49, 214 | 0.766 | 79 | 71 |
| | 289th | 5 | 4, 5, 9, 11, 72 | 0.804 | 76 | 75 |

The discriminant performance was comparable even when the number of selected markers used in the discriminant formula was increased from the top 20 ranked by the P value (Example 3) to the top 30 ranked by the P value (Example 8).

From the results of Examples 1 to 8, for Alzheimer's dementia, SEQ ID NOs: 1 to 13, 15, 16, 18 to 20, 23, 26, 49, 72, 77, 83, 101, 152, 153, 155, 156, 192 and 194, 200, 214, and 215 are preferably included; for vascular dementia, SEQ ID NOs: 3, 4, 8, 16, 23 to 30, 32, 34, 36, 37, 42, 43, 45, 79, 88, 89, 99, 111, 125 and 194, 197, 199, 201, 203, 204, 206, 207, 214, and 216 to 218 are preferably included; for Lewy body dementia, SEQ ID NOs: 3, 4, 8, 11, 13, 16, 26, 29, 32, 36, 37, 45 to 49, 52 to 55, 60, 64, 68, 91, 116, 134 and 194, 197, 200, 207, 209, 214, 216, 219, 220, 221, and 247 are preferably included; for frontotemporal lobar degeneration, SEQ ID NOs: 3, 10, 13, 24, 26, 29, 30, 33, 37, 43, 69 to 74, 82, 98, 99, 116, 117, 120, 121, 125, 147, 148, 161 to 163, 166, 167, 169, 175, 176 and 197, 200, 202, 223 to 225, 227, 236, 241, 242, 248, and 249 are preferably included; and for normal pressure hydrocephalus, SEQ ID NOs: 1, 3, 8, 10, 11, 16, 26, 30, 34, 37, 41, 45, 49, 52, 54, 60, 66, 75, 76, 83 to 85, 88, 94, 104, 136, 140, 151, 176, 184 to 186 and 203, 211, 212, 220, 226, 230, 234, and 245 are preferably included.

Example 9

In Example 9, the object is to perform analysis while the other statistical technique than those in Examples 1 to 8 was used and to construct any marker set with high discriminant accuracy. Specifically, first, miRNA expression levels obtained in the above Reference Example 1 were together normalized in accordance with global normalization. Next, univariate logistic regression was used to calculate a test statistic (z value) for each miRNA, and any miRNA with a z value larger than a certain cut-off T value was selected. Only the selected miRNAs were used in principal component analysis to calculate principal component scores. A multivariate logistic regression formula was prepared using the top-ranked principal component scores as explanatory variables. All the miRNAs were retrieved while the T value and the principal component scores were changed in this operation, and 10-times cross validation was conducted to optimize the T value and the principal component scores. The optimized T value and principal component scores were used to select a prediction formula. This prediction formula was validated in other independent samples.

Example 9-1: Search for Alzheimer's Dementia Markers

In Example 9-1, 1,021 samples from patients with Alzheimer's dementia, a type of dementia, as described in Reference Example 1, and 288 samples from non-dementia subjects including non-dementia subjects described in Reference Example 1 and subjects with disease other than dementia as collected likewise in Reference Example 1 were used for analysis. Among them, 511 samples from Alzheimer's dementia patients and 144 samples from non-dementia subjects were assigned to a training cohort and the rest samples, i.e., 510 samples from Alzheimer's dementia patients and 144 samples from non-dementia subjects were assigned to a validation cohort. When 78 miRNAs represented by SEQ ID NOs: 8, 15, 34, 40, 133, 191, 212, 250 to 316, and 375 to 378 were used as discriminant markers, the T value was set to 4.5, and the 10 principal component scores were used, it was possible to predict Alzheimer's dementia in the validation cohort while the AUC value=0.874. When the cut-off of prediction index value was set to 0.281, the accuracy was 87%, the sensitivity was 93%, and the specificity was 66% (Table 13).

Example 9-2: Search for Vascular Dementia Markers

In Example 9-2, 91 samples including samples from vascular dementia patients described in Reference Example 1 and samples from other vascular dementia patients collected likewise in Reference Example 1, and 288 samples from non-dementia subjects same as those in Example 9-1 were used for analysis. Among them, 46 samples from vascular dementia patients and 144 samples from non-dementia subjects were assigned to a training cohort and the rest samples, i.e., 45 samples from vascular dementia patients and 144 samples from non-dementia subjects were assigned to a validation cohort. When 86 miRNAs represented by SEQ ID NOs: 3, 8, 15, 26, 34, 69, 99, 101, 109, 112, 125, 133, 191 to 194, 252, 255, 258, 261 to 264, 266, 267, 271, 277, 278, 282, 284, 287, 289, 290, 293, 294, 297, 298, 301, 303, 306, 307, 310, 312 to 314, 320, 321, 323, 327, 329, 335, 336, 338, 342, 343, 345, 348, 349, 351, 352, 354, 359, 361 to 373 and 375, 376, 380 to 383, 385, and 387 to 390 were used as discriminant markers, the T value was set to 4.0, and the 10 principal component scores were used, it was possible to predict vascular dementia in the validation cohort while the AUC value=0.867. When the cut-off of prediction index value was set to 0.761, the accuracy was 84%, the sensitivity was 73%, and the specificity was 87% (Table 13).

Example 9-3: Search for Lewy Body Dementia Markers

In Example 9-3, 169 samples including samples from Lewy body dementia patients described in Reference Example 1 and samples from other Lewy body dementia patients collected likewise in Reference Example 1, and 288 samples from non-dementia subjects same as those in Example 9-1 were used for analysis. Among them, 85 samples from Lewy body dementia patients and 144 samples from non-dementia subjects were assigned to a training cohort and the rest samples, i.e., 84 samples from Lewy body dementia patients and 144 samples from non-dementia subjects were assigned to a validation cohort. When 110 miRNAs represented by SEQ ID NOs: 3, 8, 15, 26, 34, 53, 99, 101, 107, 109, 112, 128, 133, 191, 192, 194, 250, 253 to 258, 261, 262, 264 to 267, 271, 277, 279, 282 to 284, 287, 289, 290, 293, 294, 298, 299, 301 to 303, 306, 308, 310, 312 to 314, 316 to 360, 374 to 377, and 379 to 388 were used as discriminant markers, the T value was set to 3.4, and the 9 principal component scores were used, it was possible to predict Lewy body dementia in the validation cohort while the AUC value=0.870. When the cut-off of prediction index value was set to 0.0392, the accuracy was 83%, the sensitivity was 76%, and the specificity was 86% (Table 13).

TABLE 13

| Example No | T value | Number of principal component scores | Number of miRNAs | AUC | Cut-off of prediction index | Accuracy (%) | Sensitivity (%) | Specificity (%) |
|---|---|---|---|---|---|---|---|---|
| Example 8-1 | 4.5 | 10 | 78 | 0.874 | 0.281 | 87 | 93 | 66 |
| Example 8-2 | 4 | 10 | 86 | 0.867 | −0.761 | 84 | 73 | 87 |
| Example 8-3 | 3.4 | 9 | 110 | 0.870 | 0.0392 | 83 | 76 | 86 |

Figure 13:
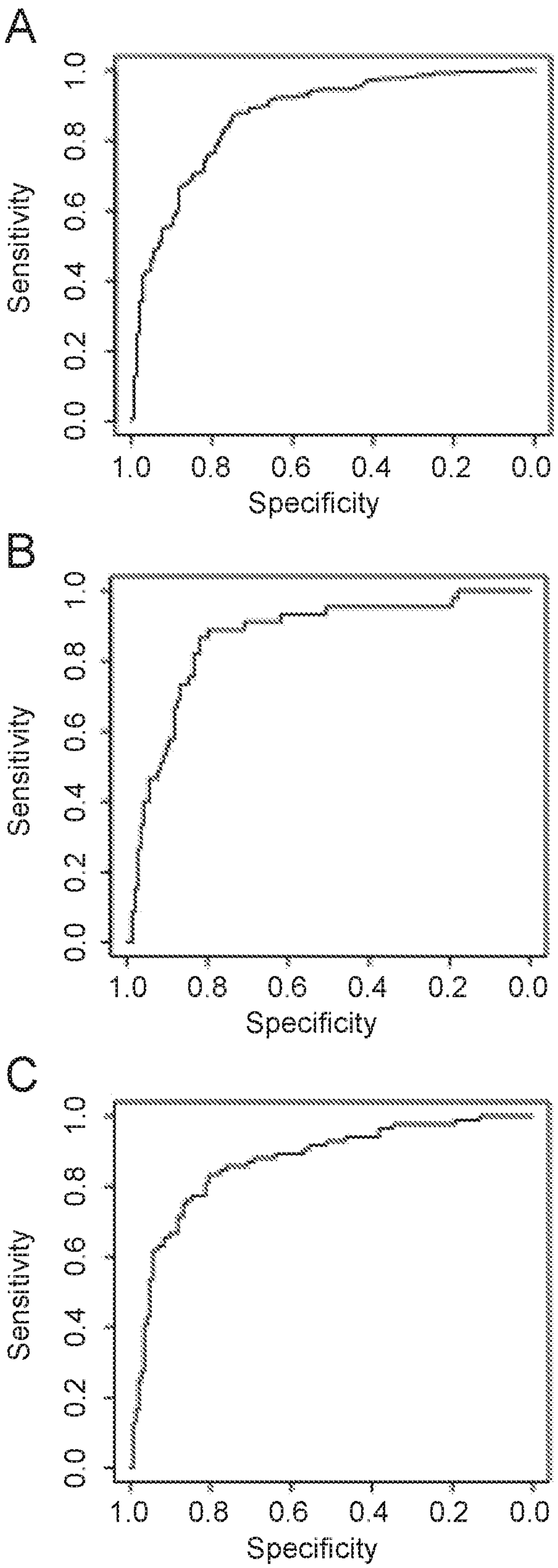
FIG. 13 shows ROC curves for validation cohorts as obtained in Example 9.

FIGS. 13A to 13C show ROC curves as obtained in Examples 9-1 to 9-3. FIG. 13A is for Alzheimer's dementia as described in Example 9-1; FIG. 13B is for vascular dementia as described in Example 9-2; and FIG. 13C is for Lewy body dementia as described in Example 9-3. MiRNA markers obtained in each Example were used to calculate the true positive rate as the ordinate and the false positive rate as the abscissa expressed in each ROC curve. Early detection and early treatment of dementia require diagnosis without misidentification. Meanwhile, once diagnosed as dementia, the disease patients receive a large social impact. Accordingly, it is also important to be able to give a diagnosis with good accuracy and without false positives. At the time of selection of a discriminant formula and markers for discriminating the presence or absence of dementia, a desired combination can be selected, depending on prioritized performance, from the ROC curves shown in FIGS. 13A to 13C.

Example 10

The discriminant formula prepared in Example 9-1 was used to carry out a progress prediction of whether or not 32 subjects with mild cognitive impairment at a pre-dementia stage progressed into dementia. Among them, 10 cases progressed into Alzheimer's dementia as clinically diagnosed after at least 6 months. When the cut-off of prediction index value was set to 0.281, all the 10 progressed cases were able to be predicted with a sensitivity of 100%. In addition, all the 4 cases that did not progress into Alzheimer's dementia were able to be predicted with a specificity of 100%. Meanwhile, the discriminant results predicted that the rest 18 cases would progress into Alzheimer's dementia. However, when clinically diagnosed, the cases were mild cognitive impairment and were still in follow-up.

Reference Example 2

<Collection of Samples>

Sera were collected using VENOJECT II vacuum blood collecting tube VP-AS109K60 (Terumo Corp. (Japan)) from a total of 2,978 people including 1,972 dementia patients (patients having diagnosed definitely as dementia by doctors) and 1,006 non-dementia subjects after obtainment of informed consent. The details of the disease types of dementia patients included; 1: 1,147 Alzheimer's dementia patients; 2: 151 patients with Alzheimer's dementia complicated by vascular dementia; 3: 240 patients suspected of Alzheimer's dementia and with Alzheimer's dementia complicated by dementia other than vascular dementia; 4: 80 vascular dementia patients; 5: 85 patients with "other dementia" (dementia resulting from other disease such as alcoholic dementia or vitamin induced dementia and type-unknown or unspecified dementia; the same applies to the following Examples); 6: 159 Lewy body dementia patients; 7: 40 frontotemporal lobar degeneration patients; and 8: 70 normal pressure hydrocephalus patients. In addition, the details of the non-dementia subjects included; 9: 110 subjects without a disease other than dementia; and 10: 896 subjects with a disease other than dementia (Table 14).

TABLE 14

| | | Subjects disease type | Number of samples | |
|---|---|---|---|---|
| Dementia patients | 1 | Alzheimer's dementia | 1147 | 1972 |
| | 2 | Alzheimer's dementia complicated by vascular dementia | 151 | |
| | 3 | Suspected of Alzheimer's dementia and Alzheimer's dementia complicated by dementia other than vascular dementia | 240 | |
| | 4 | Vascular dementia | 80 | |
| | 5 | "Other dementia" (Dementia resulting from another disease and type-unknown or unspecified dementia) | 85 | |
| | 6 | Lewy body dementia | 159 | |
| | 7 | Frontotemporal lobar degeneration | 40 | |
| | 8 | Normal pressure hydrocephalus | 70 | |
| Non-dementia subjects | 9 | Subjects without a disease other than dementia | 110 | 1006 |
| | 10 | Subjects with a disease other than dementia | 896 | |
| Total | | | | 2978 |

Figure 15:
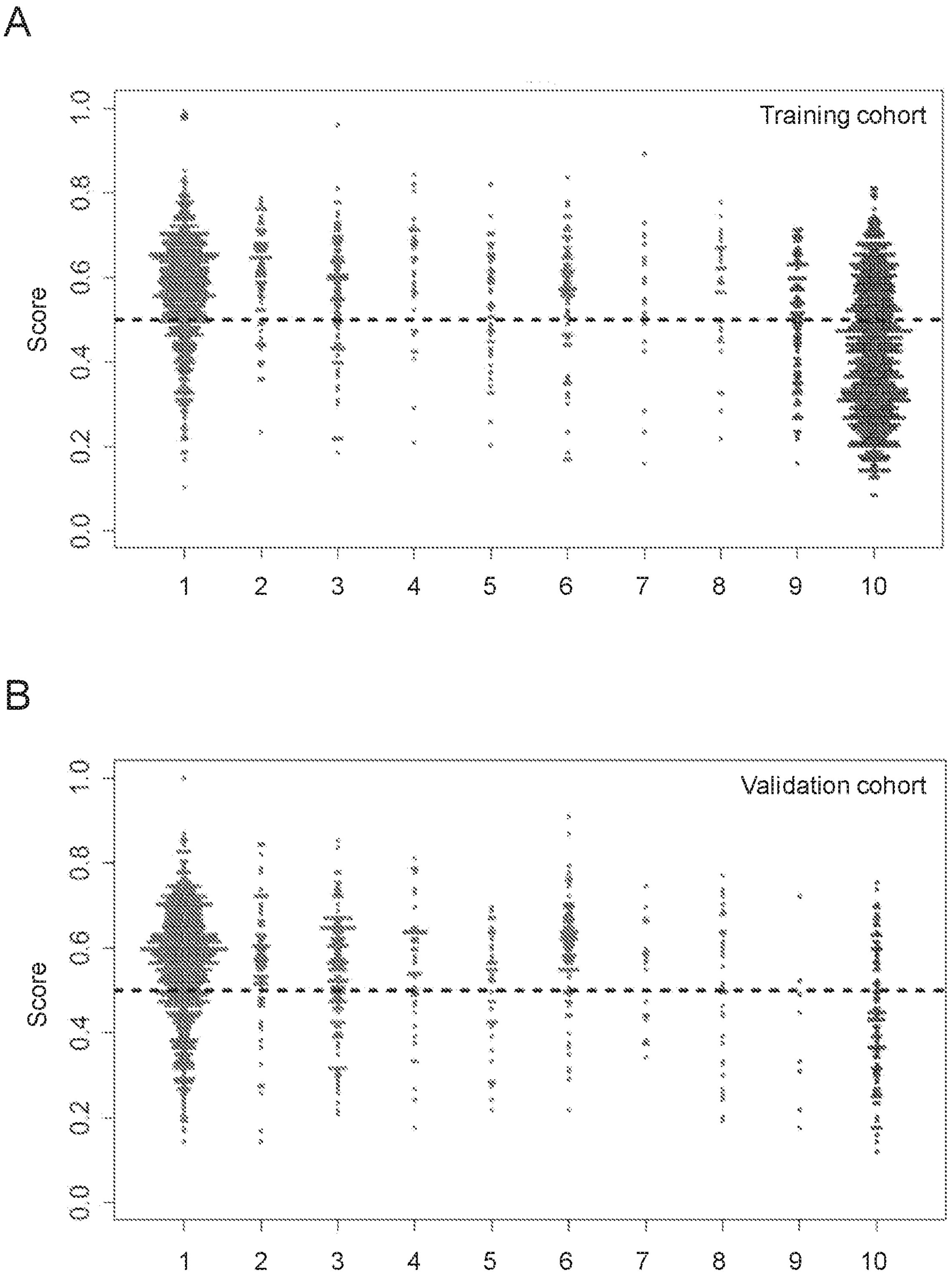
FIG. 15 shows plots of discriminant scores in training cohorts (A) and validation cohorts (B) as obtained in Example 15.
Figure 16:
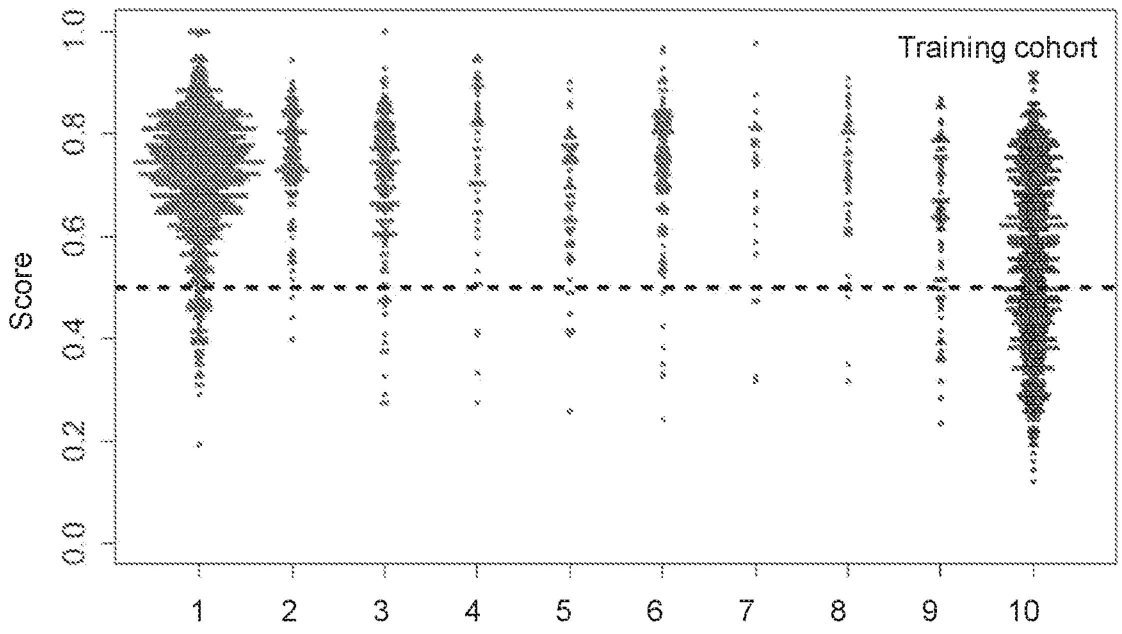
FIG. 16 shows plots of discriminant scores in training cohorts (A) and validation cohorts (B) as obtained in Example 20.
Figure 16:
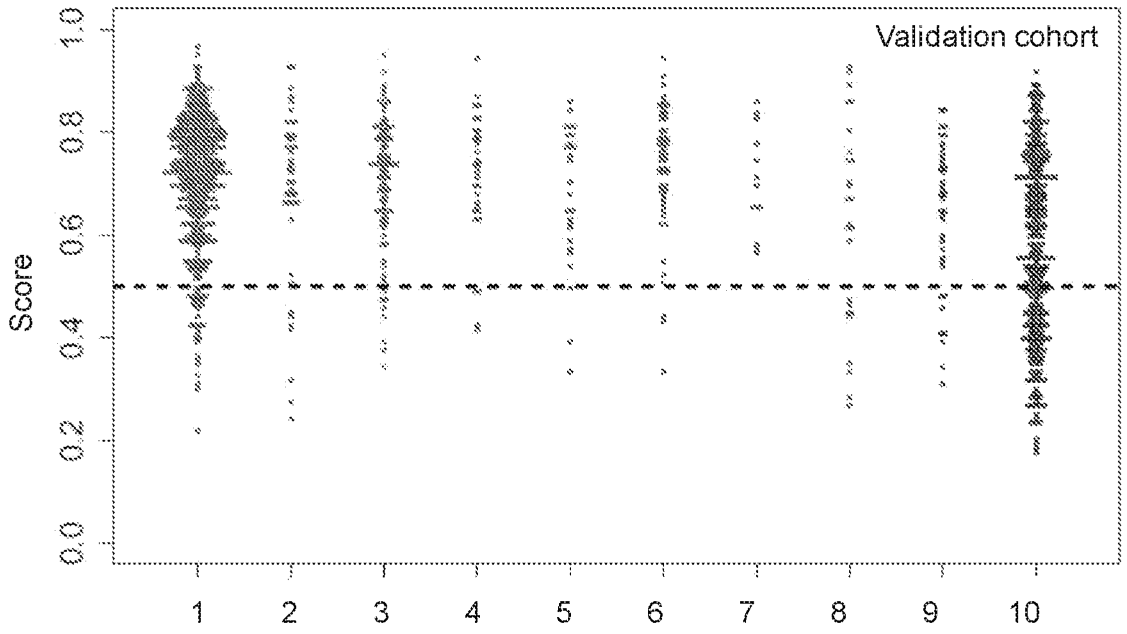

Each disease type number corresponds to the same numeral on the abscissa in FIG. 15 or 16.

<Extraction of Total RNA>

Total RNA was obtained, using a reagent for RNA extraction in 3D-Gene (registered trademark) RNA extraction reagent from liquid sample kit (Toray Industries, Inc. (Japan)) according to the protocol provided by the manufacturer, from 300 μL of the serum sample obtained from each of the total of 2,978 people.

<Measurement of Gene Expression Level>

First, miRNA in the total RNA, which was obtained from the serum sample of each of the total of 2,978 people was fluorescently labeled by use of 3D-Gene (registered trademark) miRNA Labeling kit (Toray Industries, Inc.) according to the protocol provided by the manufacturer. The oligo DNA chip used was 3D-Gene (registered trademark) Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene (registered trademark) scanner (Toray Industries, Inc.) to obtain images. Fluorescence intensity was digitized using 3D-Gene (registered trademark) Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for the above 2,978 people Subsequently, samples used for discriminant analysis of dementia were extracted. First, 1,972 dementia patients were assigned to a positive group. Further, 1,006 subjects without dementia (non-dementia subjects) were assigned to a negative group. Next, each group was sorted into a training cohort and a validation cohort as shown in each Example below. Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

Example 11

To search for markers that can discriminate, with a good balance, between dementia patients and non-dementia subjects, 900 samples from each of the dementia patients and the non-dementia subjects were sorted into a training cohort (B of Table 15), and the rest samples were sorted into a validation cohort (C of Table 15). Specifically, as listed in Table 15, 900 of all the samples from the dementia patients (1: 522 Alzheimer's dementia patients; 2: 73 patients with Alzheimer's dementia complicated by vascular dementia; 3: 99 patients suspected of Alzheimer's dementia and with Alzheimer's dementia complicated by dementia other than vascular dementia; 4: 34 vascular dementia patients; 5: 46 patients with "other dementia"; 6: 72 Lewy body dementia patients; 7: 20 frontotemporal lobar degeneration patients; and 8: 34 normal pressure hydrocephalus patients) and 900 of all the samples from the non-dementia subjects (9: 102 subjects without a disease other than dementia; and 10: 798 subjects with a disease other than dementia) were assigned to a training cohort, and 1072 of all the samples from the dementia patients (1: 625 Alzheimer's dementia patients; 2: 78 patients with Alzheimer's dementia complicated by vascular dementia; 3: 141 patients suspected of Alzheimer's dementia and with Alzheimer's dementia complicated by dementia other than vascular dementia; 4: 46 vascular dementia patients; 5: 39 patients with "other dementia"; 6: 87 Lewy body dementia patients; 7: 20 frontotemporal lobar degeneration patients; and 8: 36 normal pressure hydrocephalus patients) and 106 of all the samples from the non-dementia subjects (9: 8 subjects without a disease other than dementia; and 10: 98 subjects with a disease other than dementia) were assigned to a validation cohort.

TABLE 15

| | | Subject's disease type | A. All samples | | B. Training cohort | | C. Validation cohort | |
|---|---|---|---|---|---|---|---|---|
| Dementia patients | 1 | Alzheimer's dementia | 1972 | 1147 | 900 | 522 | 1072 | 625 |
| | 2 | Alzheimer's dementia complicated by vascular dementia | | 151 | | 73 | | 78 |
| | 3 | Suspected of Alzheimer's dementia and Alzheimer's dementia complicated by dementia other than vascular dementia | | 240 | | 99 | | 141 |
| | 4 | Vascular dementia | | 80 | | 34 | | 46 |
| | 5 | "Other dementia" (Dementia resulting from another disease and type-unknown or unspecified dementia) | | 85 | | 46 | | 39 |
| | 6 | Lewy body dementia | | 159 | | 72 | | 87 |
| | 7 | Frontotemporal lobar degeneration | | 40 | | 20 | | 20 |
| | 8 | Normal pressure hydrocephalus | | 70 | | 34 | | 36 |
| Non-dementia subjects | 9 | Subjects without a disease other than dementia | 1006 | 110 | 900 | 102 | 106 | 8 |
| | 10 | Subjects with a disease other than dementia | | 896 | | 798 | | 98 |

Each disease type number corresponds to the same numeral on the abscissa in FIG. 15 or 16.

Meanwhile, in this Example, a discriminant formula with three gene markers was prepared using the above training cohort, and discriminant performance was then evaluated in the above validation cohort.

Specifically, first, miRNA expression levels in the training cohort and the validation cohort obtained in the above Reference Example 2 were together normalized in accordance with quantile normalization. Further, in order to obtain a more highly reliable diagnostic marker, only 317 genes having gene expression levels of $2^6$ or more in 50% or more samples in either one of a group of dementia patients or a group of non-dementia subjects were selected as analytes Next, a combination of the measurement values for the gene expression levels of 3 out of 317 miRNAs was subjected to logistic regression to construct a discriminant formula for discriminating the presence or absence of dementia. Further, the above-prepared discriminant formula was used to calculate the accuracy, the sensitivity, and the specificity in the validation cohort. Then, discriminant performance was validated in independent samples.

This resulted in a discriminant formula with a sensitivity of 70% and a specificity of 56% in the validation cohort when the 3 miRNAs represented by SEQ ID NOs: 1315 to 1316 and 194 were used as discriminant markers (Table 17).

Example 12

Like Example 11, a combination of 11 miRNAs was used to construct a discriminant formula for discriminating the presence or absence of dementia, and the discriminant formula was validated.

This resulted in a discriminant formula with a sensitivity of 70% and a specificity of 60% in the validation cohort when the 11 miRNAs represented by SEQ ID NOs: 1315 to 1316, 194, 195, 1318, 1319, 1320 to 1322, and 1335 were used as discriminant markers (Table 17). When the number of miRNA markers was increased from 3 to 11, an increase in the specificity (a decrease in the false positive) was demonstrated.

Example 13

Like Example 1, a combination of 20 miRNAs was used to construct a discriminant formula for discriminating the presence or absence of dementia, and the discriminant formula was validated.

This resulted in a discriminant formula with a sensitivity of 70% and a specificity of 64% in the validation cohort when the 20 miRNAs represented by SEQ ID NOs: 1315, 1316, 194, 195, 1318, 1319, 197, 1320 to 1325, 199, 1331, 200, 1335, 1352, 1354, and 1356 were used as discriminant markers (Table 17). When the number of miRNA markers was increased from 11 to 20, a further increase in the specificity (a decrease in the false positive) was demonstrated.

Example 14

Like Example 11, a combination of 26 miRNAs was used to construct a discriminant formula for discriminating the presence or absence of dementia, and the discriminant formula was validated.

This resulted in a discriminant formula with a sensitivity of 70% and a specificity of 66% in the validation cohort when the 26 miRNAs represented by SEQ ID NOs: 1315 to 1325, 194 to 197, 199, 1328, 1331, 200, 201, 1335, 1338, 1352 to 1354, and 1356 were used as discriminant markers (Table 17). When the number of miRNA markers was increased from 20 to 26, a further increase in the specificity (a decrease in the false positive) was demonstrated.

Example 15

Like Example 11, a combination of 42 miRNAs was used to construct a discriminant formula for discriminating the presence or absence of dementia, and the discriminant formula was validated.

This resulted in a discriminant formula with a sensitivity of 70% and a specificity of 66% in the validation cohort when the 42 miRNAs represented by SEQ ID NOs: 194 to 205, 1315 to 1339, 1352 to 1355, and 1356 were used as discriminant markers (Table 17). When the number of miRNA markers was increased from 26 to 42, each of the accuracy, the sensitivity, or the specificity was slightly increased in the training cohort. However, the accuracy was slightly decreased in the validation cohort while the sensitivity and the specificity were kept at a high value. This demonstrated that about 26 miRNA markers were at a peak.

FIG. 15 shows plots of discriminant scores obtained at that time. FIG. 15A is a plot of discriminant scores for the training cohort and FIG. 15B is a plot of discriminant scores for the validation cohort. The discriminant scores range from 0 to 1. The dotted line in each panel depicts a discriminant boundary (a discriminant score of 0.5) that discriminates the presence or absence of dementia. In FIG. 15A, the measurement values for the expression levels of the above 42 miRNAs in sera from (900) dementia patients or (900) non-dementia subjects selected as the training cohort were used to prepare a discriminant formula by logistic regression analysis using the LASSO method. The ordinate represents a discriminant score obtained from the discriminant formula, and the abscissa represents each cohort. The measurement values for the expression levels of the 42 miRNAs in sera from (1072) dementia patients and (106) non-dementia subjects selected as the validation cohort were plugged into the discriminant formula prepared using the training cohort to give discriminant scores as the ordinate and each cohort as the abscissa expressed in FIG. 15B.

Here, regarding the abscissa in each of FIG. 15A or FIG. 15B, the numeral 1 represents Alzheimer's dementia, the numeral 2 represents Alzheimer's dementia complicated by vascular dementia, the numeral 3 represents cases suspected of Alzheimer's dementia and Alzheimer's dementia complicated by dementia other than vascular dementia, the numeral 4 represents vascular dementia, the numeral 5 represents "other dementia" (dementia caused by another disease and dementia of type-unknown or unspecified dementia), the numeral 6 represents Lewy body dementia, the numeral 7 represents frontotemporal lobar degeneration, the numeral 8 represents normal pressure hydrocephalus, the numeral 9 represents non-dementia subjects (subjects without a disease other than dementia), and the numeral 10 represents non-dementia subjects (subjects with a disease other than dementia).

Example 16

To search for markers that can discriminate, with good sensitivity, dementia patients in particular, about ⅔ of samples from each group were sorted into a training cohort (B of Table 16) and the rest samples were sorted into a validation cohort (C of Table 16). Specifically, as listed in Table 16, 1,315 of all the samples from the dementia patients (1: 774 Alzheimer's dementia patients; 2: 108 patients with Alzheimer's dementia complicated by vascular dementia; 3: 150 patients suspected of Alzheimer's dementia and with Alzheimer's dementia complicated by dementia other than vascular dementia; 4: 48 vascular dementia patients; 5: 58 patients with "other dementia"; 6: 106 Lewy body dementia patients: 7: 27 frontotemporal lobar degeneration patients; and 8: 44 normal pressure hydrocephalus patients) and 671 of all the samples from the non-dementia subjects (9: 71 subjects without a disease other than dementia; and 10: 600 subjects with a disease other than dementia) were assigned to a training cohort, and 657 of all the samples from the dementia patients (1: 373 Alzheimer's dementia patients; 2: 43 patients with Alzheimer's dementia complicated by vascular dementia; 3: 90 patients suspected of Alzheimer's dementia and with Alzheimer's dementia complicated by dementia other than vascular dementia; 4: 32 vascular dementia patients; 5: 27 patients with "other dementia"; 6: 53 Lewy body dementia patients; 7: 13 frontotemporal lobar degeneration patients; and 8:26 normal pressure hydrocephalus patients) and 335 of all the samples from the non-dementia subjects (9: 39 subjects without a disease other than dementia; and 10: 296 subjects with a disease other than dementia) were assigned to a validation cohort.

TABLE 16

| Subject's disease type | | | A. All samples | | B. Training cohort | | C. Validation cohort | |
|---|---|---|---|---|---|---|---|---|
| Dementia patients | 1 | Alzheimer's dementia | 1972 | 1147 | 1315 | 774 | 657 | 373 |
| | 2 | Alzheimer's dementia complicated by vascular dementia | | 151 | | 108 | | 43 |
| | 3 | Suspected of Alzheimer's dementia and Alzheimer's dementia complicated by dementia other than vascular dementia | | 240 | | 150 | | 90 |
| | 4 | Vascular dementia | | 80 | | 48 | | 32 |
| | 5 | "Other dementia" (Dementia resulting from another disease and type-unknown or unspecified dementia) | | 85 | | 58 | | 27 |
| | 6 | Lewy body dementia | | 159 | | 106 | | 53 |
| | 7 | Frontotemporal lobar degeneration | | | | | | |
| | 8 | Normal pressure hydrocephalus | | 40 | | 27 | | 13 |
| Non-dementia subjects | 9 | Subjects without a disease other | | 70 | | 44 | | 26 |
| | | than dementia | 1006 | 110 | 671 | 71 | 335 | 39 |
| | 10 | Subjects with a disease other than dementia | | 896 | | 600 | | 296 |

Each disease type number corresponds to the same numeral on the abscissa in FIG. 15 or 16.

Meanwhile, in this Example, a discriminant formula with three gene markers was prepared using the above training cohort, and discriminant performance was then evaluated in the above validation cohort.

Specifically, a discriminant formula for discriminating the presence or absence of dementia was constructed by logistic regression using a combination of the measurement values for the expression levels of 3 miRNAs included in the above 317 genes obtained as analytes like Example 11. Further, the above-prepared discriminant formula was used to calculate the accuracy, the sensitivity, and the specificity in the validation cohort. Then, discriminant performance was validated in independent samples.

This resulted in a discriminant formula with a sensitivity of 97% and a specificity of 11% in the validation cohort when the 3 miRNAs represented by SEQ ID NOs: 1315 to 1316 and 194 were used as discriminant markers (Table 17).

Example 17

Like Example 16, a combination of 10 miRNAs was used to construct a discriminant formula for discriminating the presence or absence of dementia, and the discriminant formula was validated.

This resulted in a discriminant formula with a sensitivity of 95% and a specificity of 21% in the validation cohort when the 10 miRNAs represented by SEQ ID NOs: 1315 to 1316, 194, 195, 1321, 1322, 1326, 1327, 202, and 1347 were used as discriminant markers (Table 17). When the number of miRNA markers was increased from 3 to 10, an increase in the specificity (a decrease in the false positive) was demonstrated.

Example 18

Like Example 16, a combination of 20 miRNAs was used to construct a discriminant formula for discriminating the presence or absence of dementia, and the discriminant formula was validated.

This resulted in a discriminant formula with a sensitivity of 92% and a specificity of 27% in the validation cohort when the 20 miRNAs represented by SEQ ID NOs: 1315, 1316, 194, 195, 197, 1321, 1322, 1326, 1327, 199, 1331, 200, 202, 1333, 1335, 206, 1349, 1352, 1355, and 212 were used as discriminant markers (Table 17). When the number of miRNA markers was increased from 10 to 20, a further increase in the specificity (a decrease in the false positive) was demonstrated.

Example 19

Like Example 16, a combination of 39 miRNAs was used to construct a discriminant formula for discriminating the presence or absence of dementia, and the discriminant formula was validated.

This resulted in a discriminant formula with a sensitivity of 90% and a specificity of 33% in the validation cohort when the 39 miRNAs represented by SEQ ID NOs: 1315, 1316, 194, 195, 1318, 1319, 197, 1321 to 1323, 1326, 1327, 198, 1331, 200, 202, 1333, 203, 1335, 1337 to 1339, 1340, 374, 1342, 1343, 208 to 209, 1345, 1347 to 1349, 1351, 1353 to 1356, and 211 to 212 were used as discriminant markers (Table 17). When the number of miRNA markers was increased from 20 to 39, a further increase in the specificity (a decrease in the false positive) was demonstrated.

Example 20

Like Example 16, a combination of 51 miRNAs was used to construct a discriminant formula for discriminating the presence or absence of dementia, and the discriminant formula was validated.

This resulted in a discriminant formula with a sensitivity of 90% and a specificity of 35% in the validation cohort when the 51 miRNAs represented by SEQ ID NOs: 1315, 1316, 194, 195, 1318, 1319, 197, 1321 to 1323, 1326, 1327, 198, 199, 1329, 1331, 200, 202, 1333, 203, 1335, 204 to 212, 374, and 1337 to 1356 were used as discriminant markers (Table 17). When the number of miRNA markers was increased from 39 to 51, a further increase in the specificity (a decrease in the false positive) was demonstrated.

FIG. 16 shows plots of discriminant scores obtained in this Example. FIG. 16A is a plot of discriminant scores for the training cohort and FIG. 16B is a plot of discriminant scores for the validation cohort. The discriminant scores range from 0 to 1. The dotted line in each panel depicts a discriminant boundary (a discriminant score of 0.5) that discriminates the presence or absence of dementia. In FIG. 16A, the measurement values for the expression levels of the above 51 miRNAs in sera from (1,315) dementia patients or (671) non-dementia subjects selected as the training cohort were used to prepare a discriminant formula by logistic regression analysis using the LASSO method. The ordinate represents a discriminant score obtained from the discriminant formula, and the abscissa represents each cohort. The measurement values for the expression levels of the 51 miRNAs in sera from (657) dementia patients and (335) non-dementia subjects selected as the validation cohort were plugged into the discriminant formula prepared using the training cohort to give discriminant scores as the ordinate and each cohort as the abscissa expressed in FIG. 16B.

Here, the numerals 1 to 10 on the abscissa in each of FIG. 16A or 16B denote the respective same dementia disease types as in FIG. 15 (Example 15).

TABLE 17

| Example No. | number of miRNAs | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|---|
| Example 11 | 3 | 64 | 71 | 56 | 69 | 70 | 56 |
| Example 12 | 11 | 65 | 71 | 58 | 69 | 70 | 60 |
| Example 13 | 20 | 67 | 71 | 62 | 69 | 70 | 64 |
| Example 14 | 26 | 68 | 72 | 63 | 70 | 70 | 66 |
| Example 15 | 42 | 69 | 73 | 64 | 69 | 70 | 66 |
| Example 16 | 3 | 68 | 97 | 10 | 68 | 97 | 11 |
| Example 17 | 10 | 70 | 94 | 22 | 70 | 95 | 21 |
| Example 18 | 20 | 72 | 93 | 29 | 70 | 92 | 27 |
| Example 19 | 39 | 73 | 92 | 36 | 71 | 90 | 33 |
| Example 20 | 51 | 75 | 93 | 39 | 71 | 90 | 35 |
| Example 22 | 2 | 62 | 70 | 54 | 68 | 70 | 52 |
| Example 23 | 1 | 62 | 69 | 54 | 67 | 69 | 53 |

Example 21

Early detection and early treatment of dementia require diagnosis without misidentification. Meanwhile, once diagnosed as dementia, the disease patients receive a large social impact. Accordingly, it is also important to be able to give a diagnosis with good accuracy and without false positives. In view of the above Examples 11 to 20, some combination of 1, 2 or more, preferably 20 to 60, and more preferably 40 to 55 polynucleotides from all the nucleotide sequences represented by SEQ ID NOs: 1 to 54, 55 to 62, and 127 to 178 can be said to be genes that can discriminate, with high accuracy, between dementia patients and subjects without dementia.

Figure 17:
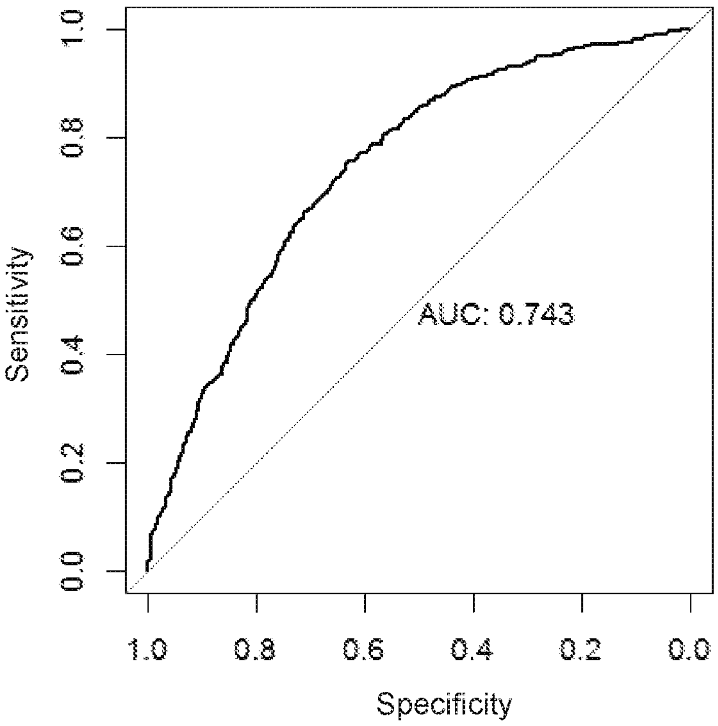
FIG. 17 shows ROC curves calculated in Example 21.
Figure 17:
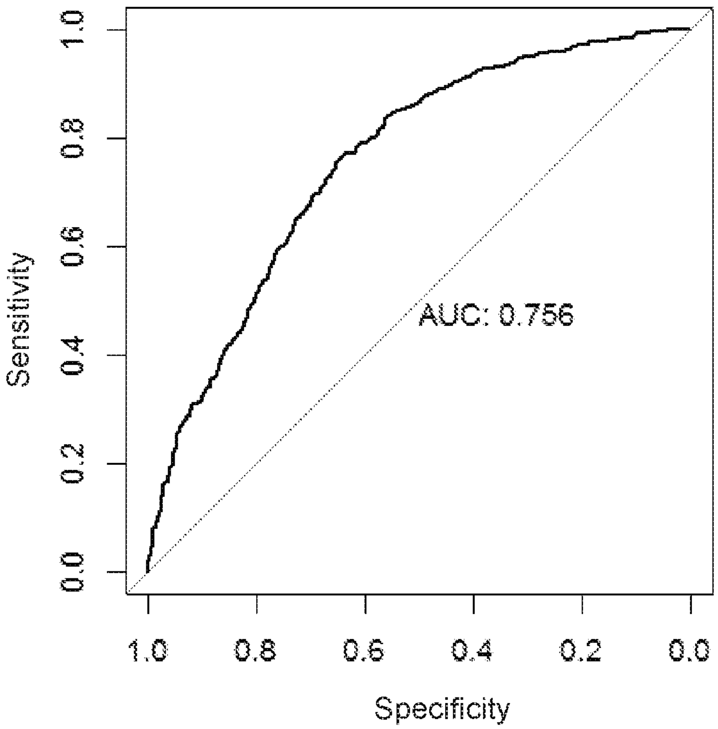

FIG. 17A is a ROC (Receiver Operating Characteristic) curve while the ordinate denotes the sensitivity and the abscissa denotes the specificity as calculated using 42 miRNA markers (SEQ ID NOs: 194 to 205, 1315 to 1339, 1352 to 1355, and 1356) obtained in Example 15. In FIG. 17B, 51 miRNA markers (SEQ ID NOs: 1315, and 1316, 194, 195, 1318, 1319, 197, 1321 to 1323, 1326, 1327, 198, 199, 1329, 1331, 200, 202, 1333, 203, 1335, 204 to 212, 374, 1337 to 1356) obtained in Example 20 were used to calculate the sensitivity as the ordinate and the specificity as the abscissa expressed in a ROC curve. At the time of selection of a discriminant formula and markers for discriminating the presence or absence of dementia, a desired combination can be selected, depending on prioritized performance, from the ROC curves shown in FIG. 17.

Example 22

Like Example 11, a combination of 2 miRNAs was used to construct a discriminant formula for discriminating the presence or absence of dementia, and the discriminant formula was validated.

This resulted in a discriminant formula with a sensitivity of 70% and a specificity of 52% in the validation cohort when the 2 miRNAs represented by SEQ ID NOs: 1317 and 195 were used as discriminant markers (Table 17).

Example 23

Like Example 11, one miRNA was used to construct a discriminant formula for discriminating the presence or absence of dementia, and the discriminant formula was validated.

This resulted in a discriminant formula with a sensitivity of 69% and a specificity of 53% in the validation cohort when the one miRNA represented by SEQ ID NO: 1315 was used as a discriminant marker (Table 17).

Example 24

In Example 24, in order to search for a statistical technique more fit to discriminate dementia, the statistical techniques used in Examples 11 to 23; the LASSO method, elastic net, and ridge regression were compared. For this comparison, analysis was conducted using 2,177 samples from dementia patients including samples from the dementia patients described in Reference Example 2 and samples from dementia patients newly collected like in Reference Example 2. In addition, 756 samples from non-dementia subjects including the samples from the non-dementia subjects described in Reference Example 2 and samples from non-dementia subjects newly collected like in Reference Example 2 were used. Specifically, first, miRNA expression levels obtained in the above Reference Example 2 were together normalized in accordance with global normalization. Next, the samples were divided, and ¾ of all the samples were assigned to a training cohort and the rest ¼ were assigned to a validation cohort. Further the training cohort was divided into 5 groups. Then, the p value for each miRNA was calculated by multivariate logistic regression using each of the LASSO method, elastic net, or ridge regression. After the number of variables was increased while each miRNA was included according to the order from the top-ranked p value, the optimal number of miRNAs was examined by cross validation between the 5 divided groups.

The results demonstrated that even when any of the analysis techniques was used, the case where the number of miRNAs used was 60 was optimal. Then, the 60 miRNAs with the top-ranked p-values were used to create each dementia discriminant model, and this model was validated in the validation cohort.

As a result, in the case of the LASSO method, the AUC value was 0.772, the accuracy was 73%, the sensitivity was 74%, and the specificity was 70%; in the case of elastic net, the AUC value was 0.773, the accuracy was 74%, the sensitivity was 76%, and the specificity was 68%; and in the case of ridge regression, the AUC value was 0.773, the accuracy was 73%, the sensitivity was 75%, and the specificity was 66%. When attention was paid to the accuracy and the sensitivity, elastic net exhibited the highest discriminant accuracy with a marginal difference (Table 18). In the discriminant model obtained using this elastic net, used were 44 miRNAs of SEQ ID NOs: 68, 99, 100, 194, 197, 200, 212, 255, 263, 265, 294, 302, 315, 342, 344, 1315, 1316, 1318, 1320, 1321, 1322, 1323, 1326, 1331, 1340, 1435, 1436, 1438, 1439, 1440, 1441, 1446, 1448, 1449, 1451, 1452, 1453, 1455, 1456, 1458, 1460, 1461, 1462, and 1463.

TABLE 18

| Example No. | Statistical technique | AUC | Accuracy (%) | Sensitivity (%) | Specificity (%) |
|---|---|---|---|---|---|
| Example 24 | LASSO method | 0.772 | 73 | 74 | 69 |
| | Elastic net | 0.773 | 74 | 76 | 68 |
| | Ridge regression | 0.773 | 73 | 75 | 66 |

Figure 18:
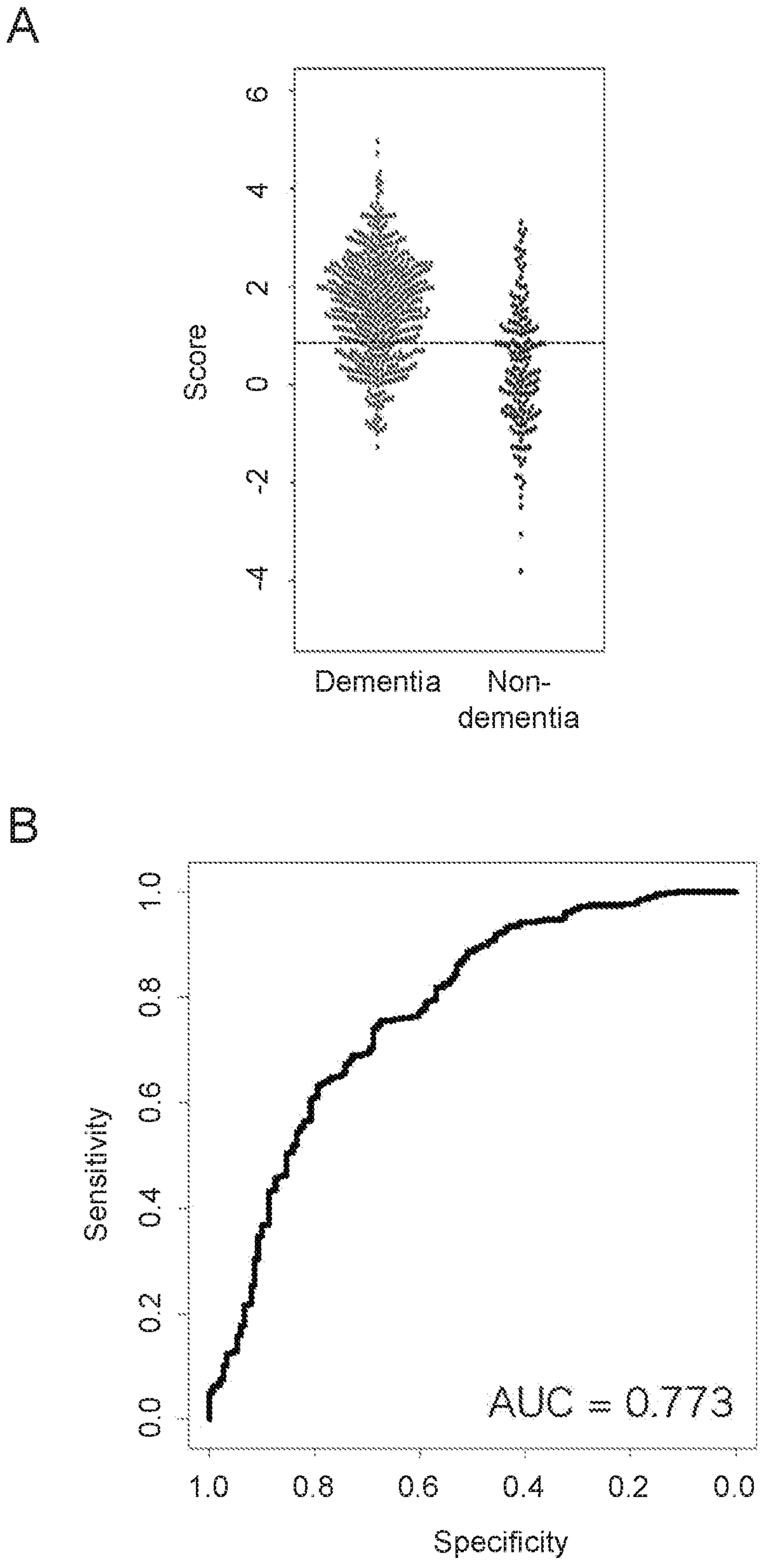

FIG. 18 shows a plot (FIG. 18A) of discriminant scores and a ROC curve (FIG. 18B) as obtained using elastic net. The dotted line in the panel of FIG. 18A depicts a discriminant boundary that discriminates the presence or absence of dementia. A discriminant formula was prepared from measurement values for the expression levels of the above 44 miRNAs by logistic regression analysis using elastic net. The ordinate represents a discriminant score obtained from the discriminant formula, and the abscissa represents each cohort. FIG. 18B is a ROC (Receiver Operating Characteristic) curve while the ordinate denotes the sensitivity and the abscissa denotes the specificity as calculated using the above 44 miRNAs. At the time of selection of a discriminant formula and markers for discriminating the presence or absence of dementia, a desired combination can be selected, depending on prioritized performance, from the ROC curve shown in FIG. 18B.

All the publications, patents, and patent applications cited herein are incorporated herein by reference in the entirety.

The invention claimed is:

1. A method for detecting dementia, comprising measuring expression levels of the polynucleotides of dementia markers: miR-6088 and miR-211-5p in a sample from a subject; and evaluating in vitro whether or not the subject has dementia using the measured expression levels of only miR-6088 and miR-211-5p.

2. The method according to claim 1, comprising plugging the gene expression levels of the polynucleotides in the sample from the subject into a discriminant formula capable of discriminating dementia or non-dementia distinctively, wherein the discriminant formula is created by using gene expression levels in samples from subjects known to have dementia and gene expression levels in samples from non-dementia subjects as training samples; and thereby evaluating whether or not the subject has dementia.

3. The method according to claim 1, wherein the expression levels of the target genes in the sample from the subject are measured by using a kit for detection of dementia, comprising nucleic acids capable of specifically binding polynucleotides of dementia markers: or to complementary strands of the polynucleotides.

4. The method according to claim 1, the subject is a human.

5. The method according to claim 1, the sample is blood, serum, or plasma.

* * * * *

SEQUENCE LISTING

```
<160> NUMBER OF SEQ ID NOS: 1505

<210> SEQ ID NO 1
<211> LENGTH: 18
<212> TYPE: RNA
<213> ORGANISM: Homo sapiens

<400> SEQUENCE: 1

cagcagucc uccccug                                               18


<210> SEQ ID NO 2
<211> LENGTH: 18
<212> TYPE: RNA
<213> ORGANISM: Homo sapiens

<400> SEQUENCE: 2

cauucaacua gugauugu                                             18


<210> SEQ ID NO 3
<211> LENGTH: 23
<212> TYPE: RNA
```

<213> ORGANISM: Homo sapiens

<400> SEQUENCE: 3
ugggagggga gaggcagcaa gca 23

<210> SEQ ID NO 4
<211> LENGTH: 17
<212> TYPE: RNA
<213> ORGANISM: Homo sapiens

<400> SEQUENCE: 4
uuggaggcgu ggguuuu 17

<210> SEQ ID NO 5
<211> LENGTH: 20
<212> TYPE: RNA
<213> ORGANISM: Homo sapiens

<400> SEQUENCE: 5
aaaugggugg ucugaggcaa 20

<210> SEQ ID NO 6
<211> LENGTH: 23
<212> TYPE: RNA
<213> ORGANISM: Homo sapiens

<400> SEQUENCE: 6
uugggcccag gaguaaacag gau 23

<210> SEQ ID NO 7
<211> LENGTH: 22
<212> TYPE: RNA
<213> ORGANISM: Homo sapiens

<400> SEQUENCE: 7
uuagccaauu guccaucuuu ag 22

<210> SEQ ID NO 8
<211> LENGTH: 23
<212> TYPE: RNA
<213> ORGANISM: Homo sapiens

<400> SEQUENCE: 8
aaagucucgc ucucugcccc uca 23

<210> SEQ ID NO 9
<211> LENGTH: 18
<212> TYPE: RNA
<213> ORGANISM: Homo sapiens

<400> SEQUENCE: 9
gggucccggg gaggggg 18

<210> SEQ ID NO 10
<211> LENGTH: 19
<212> TYPE: RNA
<213> ORGANISM: Homo sapiens

<400> SEQUENCE: 10
aaaagcuggg uugagagga 19

<210> SEQ ID NO 11
<211> LENGTH: 21

<212> TYPE: RNA
<213> ORGANISM: Homo sapiens

<400> SEQUENCE: 11
ucaucccccu cgcccucuca g 21

<210> SEQ ID NO 12
<211> LENGTH: 22
<212> TYPE: RNA
<213> ORGANISM: Homo sapiens

<400> SEQUENCE: 12
aggagagugg auuccaggug gu 22

<210> SEQ ID NO 13
<211> LENGTH: 24
<212> TYPE: RNA
<213> ORGANISM: Homo sapiens

<400> SEQUENCE: 13
agcgugggau guccaugaag ucag 24

<210> SEQ ID NO 14
<211> LENGTH: 22
<212> TYPE: RNA
<213> ORGANISM: Homo sapiens

<400> SEQUENCE: 14
ucggccugac cacccacccc ac 22

<210> SEQ ID NO 15
<211> LENGTH: 20
<212> TYPE: RNA
<213> ORGANISM: Homo sapiens

<400> SEQUENCE: 15
ugagcccugu ccuccccgcag 20

<210> SEQ ID NO 16
<211> LENGTH: 22
<212> TYPE: RNA
<213> ORGANISM: Homo sapiens

<400> SEQUENCE: 16
gcugaacugg gcugagcugg gc 22

<210> SEQ ID NO 17
<211> LENGTH: 22
<212> TYPE: RNA
<213> ORGANISM: Homo sapiens

<400> SEQUENCE: 17
aaggaaccag aaaaugagaa gu 22

<210> SEQ ID NO 18
<211> LENGTH: 22
<212> TYPE: RNA
<213> ORGANISM: Homo sapiens

<400> SEQUENCE: 18
accagcgcgu uuucaguuuc au 22

<210> SEQ ID NO 19

<211> LENGTH: 21
<212> TYPE: RNA
<213> ORGANISM: Homo sapiens

<400> SEQUENCE: 19
uggcaguuac uuuugcacca g 21

<210> SEQ ID NO 20
<211> LENGTH: 21
<212> TYPE: RNA
<213> ORGANISM: Homo sapiens

<400> SEQUENCE: 20
uccugcgcgu cccagaugcc c 21

<210> SEQ ID NO 21
<211> LENGTH: 21
<212> TYPE: RNA
<213> ORGANISM: Homo sapiens

<400> SEQUENCE: 21
ugcuuaaguu guaccaagua u 21

<210> SEQ ID NO 22
<211> LENGTH: 22
<212> TYPE: RNA
<213> ORGANISM: Homo sapiens

<400> SEQUENCE: 22
agggacuuuc aggggcagcu gu 22

<210> SEQ ID NO 23
<211> LENGTH: 17
<212> TYPE: RNA
<213> ORGANISM: Homo sapiens

<400> SEQUENCE: 23
gcugggcgag gcuggca 17

<210> SEQ ID NO 24
<211> LENGTH: 17
<212> TYPE: RNA
<213> ORGANISM: Homo sapiens

<400> SEQUENCE: 24
guggggccag gcggugg 17

<210> SEQ ID NO 25
<211> LENGTH: 22
<212> TYPE: RNA
<213> ORGANISM: Homo sapiens

<400> SEQUENCE: 25
acuggggagc agaaggagaa cc 22

<210> SEQ ID NO 26
<211> LENGTH: 20
<212> TYPE: RNA
<213> ORGANISM: Homo sapiens

<400> SEQUENCE: 26
agagaugaag cgggggggcg 20

<210> SEQ ID NO 27
<211> LENGTH: 19
<212> TYPE: RNA
<213> ORGANISM: Homo sapiens

<400> SEQUENCE: 27
ugcggcagag cugggguca 19

<210> SEQ ID NO 28
<211> LENGTH: 18
<212> TYPE: RNA
<213> ORGANISM: Homo sapiens

<400> SEQUENCE: 28
aggcugggcu gggacgga 18

<210> SEQ ID NO 29
<211> LENGTH: 22
<212> TYPE: RNA
<213> ORGANISM: Homo sapiens

<400> SEQUENCE: 29
gcuggugcaa aaguaauggc gg 22

<210> SEQ ID NO 30
<211> LENGTH: 23
<212> TYPE: RNA
<213> ORGANISM: Homo sapiens

<400> SEQUENCE: 30
gugagugugg auccuggagg aau 23

<210> SEQ ID NO 31
<211> LENGTH: 22
<212> TYPE: RNA
<213> ORGANISM: Homo sapiens

<400> SEQUENCE: 31
uuuugcgaug uguuccuaau au 22

<210> SEQ ID NO 32
<211> LENGTH: 19
<212> TYPE: RNA
<213> ORGANISM: Homo sapiens

<400> SEQUENCE: 32
aucccaccac ugccaccau 19

<210> SEQ ID NO 33
<211> LENGTH: 22
<212> TYPE: RNA
<213> ORGANISM: Homo sapiens

<400> SEQUENCE: 33
caguggccag agcccugcag ug 22

<210> SEQ ID NO 34
<211> LENGTH: 20
<212> TYPE: RNA
<213> ORGANISM: Homo sapiens

<400> SEQUENCE: 34
uccacucucc uggcccccag 20

<210> SEQ ID NO 35
<211> LENGTH: 22
<212> TYPE: RNA
<213> ORGANISM: Homo sapiens

<400> SEQUENCE: 35
cuccccucuc uuuccuguuc ag 22

<210> SEQ ID NO 36
<211> LENGTH: 20
<212> TYPE: RNA
<213> ORGANISM: Homo sapiens

<400> SEQUENCE: 36
acccuuuuuc ucuuucccag 20

<210> SEQ ID NO 37
<211> LENGTH: 22
<212> TYPE: RNA
<213> ORGANISM: Homo sapiens

<400> SEQUENCE: 37
uggggaaggc gucagugucg gg 22

<210> SEQ ID NO 38
<211> LENGTH: 28
<212> TYPE: RNA
<213> ORGANISM: Homo sapiens

<400> SEQUENCE: 38
uagaucuuug acucuggcag ucuccagg 28

<210> SEQ ID NO 39
<211> LENGTH: 24
<212> TYPE: RNA
<213> ORGANISM: Homo sapiens

<400> SEQUENCE: 39
agcgcgggcu gagcgcugcc aguc 24

<210> SEQ ID NO 40
<211> LENGTH: 22
<212> TYPE: RNA
<213> ORGANISM: Homo sapiens

<400> SEQUENCE: 40
ucucucuccc acuucccugc ag 22

<210> SEQ ID NO 41
<211> LENGTH: 19
<212> TYPE: RNA
<213> ORGANISM: Homo sapiens

<400> SEQUENCE: 41
ggccuuguuc cuguccccca 19

<210> SEQ ID NO 42
<211> LENGTH: 24
<212> TYPE: RNA
<213> ORGANISM: Homo sapiens

<400> SEQUENCE: 42
cgggugggag cagaucuuau ugag 24

<210> SEQ ID NO 43
<211> LENGTH: 22
<212> TYPE: RNA
<213> ORGANISM: Homo sapiens

<400> SEQUENCE: 43
cccuguucua ugcccugagg ga 22

<210> SEQ ID NO 44
<211> LENGTH: 22
<212> TYPE: RNA
<213> ORGANISM: Homo sapiens

<400> SEQUENCE: 44
ugggcgaggg cggcugagcg gc 22

<210> SEQ ID NO 45
<211> LENGTH: 22
<212> TYPE: RNA
<213> ORGANISM: Homo sapiens

<400> SEQUENCE: 45
gaaagugcuu ccuuuuagag gc 22

<210> SEQ ID NO 46
<211> LENGTH: 22
<212> TYPE: RNA
<213> ORGANISM: Homo sapiens

<400> SEQUENCE: 46
uucuccaaaa gggagcacuu uc 22

<210> SEQ ID NO 47
<211> LENGTH: 23
<212> TYPE: RNA
<213> ORGANISM: Homo sapiens

<400> SEQUENCE: 47
cacucagccu ugagggcacu uuc 23

<210> SEQ ID NO 48
<211> LENGTH: 23
<212> TYPE: RNA
<213> ORGANISM: Homo sapiens

<400> SEQUENCE: 48
cacucagccu ugagggcacu uuc 23

<210> SEQ ID NO 49
<211> LENGTH: 24
<212> TYPE: RNA
<213> ORGANISM: Homo sapiens

<400> SEQUENCE: 49
cagggcucag ggauuggaug gagg 24

<210> SEQ ID NO 50
<211> LENGTH: 22
<212> TYPE: RNA
<213> ORGANISM: Homo sapiens

<400> SEQUENCE: 50
cgcaggggcc gggugcucac cg 22

<210> SEQ ID NO 51
<211> LENGTH: 23
<212> TYPE: RNA
<213> ORGANISM: Homo sapiens

<400> SEQUENCE: 51
caggcagaag uggggcugac agg 23

<210> SEQ ID NO 52
<211> LENGTH: 22
<212> TYPE: RNA
<213> ORGANISM: Homo sapiens

<400> SEQUENCE: 52
gcugcgggcu gcggucaggg cg 22

<210> SEQ ID NO 53
<211> LENGTH: 22
<212> TYPE: RNA
<213> ORGANISM: Homo sapiens

<400> SEQUENCE: 53
acaguagagg gaggaaucgc ag 22

<210> SEQ ID NO 54
<211> LENGTH: 22
<212> TYPE: RNA
<213> ORGANISM: Homo sapiens

<400> SEQUENCE: 54
acgcccuucc cccccuucuu ca 22

<210> SEQ ID NO 55
<211> LENGTH: 23
<212> TYPE: RNA
<213> ORGANISM: Homo sapiens

<400> SEQUENCE: 55
acggggaguc aggcaguggu gga 23

<210> SEQ ID NO 56
<211> LENGTH: 19
<212> TYPE: RNA
<213> ORGANISM: Homo sapiens

<400> SEQUENCE: 56
agagcuggcu gaagggcag 19

<210> SEQ ID NO 57
<211> LENGTH: 21
<212> TYPE: RNA
<213> ORGANISM: Homo sapiens

<400> SEQUENCE: 57
ccaggcucug cagugggaac u 21

<210> SEQ ID NO 58
<211> LENGTH: 19
<212> TYPE: RNA
<213> ORGANISM: Homo sapiens

<400> SEQUENCE: 58
agguugacau acguuuccc 19

<210> SEQ ID NO 59
<211> LENGTH: 23
<212> TYPE: RNA
<213> ORGANISM: Homo sapiens

<400> SEQUENCE: 59
cgggcugucc ggaggggucg gcu 23

<210> SEQ ID NO 60
<211> LENGTH: 21
<212> TYPE: RNA
<213> ORGANISM: Homo sapiens

<400> SEQUENCE: 60
cugggagaag aguggugaag a 21

<210> SEQ ID NO 61
<211> LENGTH: 21
<212> TYPE: RNA
<213> ORGANISM: Homo sapiens

<400> SEQUENCE: 61
augucccacc cccacuccug u 21

<210> SEQ ID NO 62
<211> LENGTH: 22
<212> TYPE: RNA
<213> ORGANISM: Homo sapiens

<400> SEQUENCE: 62 agguggucg uggcgcguuc gc 22

<210> SEQ ID NO 63
<211> LENGTH: 22
<212> TYPE: RNA
<213> ORGANISM: Homo sapiens

<400> SEQUENCE: 63
augcaggccu guguacagca cu 22

<210> SEQ ID NO 64
<211> LENGTH: 23
<212> TYPE: RNA
<213> ORGANISM: Homo sapiens

<400> SEQUENCE: 64
ugggcagggg cuuauuguag gag 23

<210> SEQ ID NO 65
<211> LENGTH: 22
<212> TYPE: RNA
<213> ORGANISM: Homo sapiens

<400> SEQUENCE: 65
ugaggacagg gcaaauucac ga 22

<210> SEQ ID NO 66
<211> LENGTH: 22
<212> TYPE: RNA
<213> ORGANISM: Homo sapiens

<400> SEQUENCE: 66
uuccacugcc acuaccuaau uu 22

<210> SEQ ID NO 67
<211> LENGTH: 19
<212> TYPE: RNA
<213> ORGANISM: Homo sapiens

<400> SEQUENCE: 67
aagugugcag ggcacuggu 19

<210> SEQ ID NO 68
<211> LENGTH: 20
<212> TYPE: RNA
<213> ORGANISM: Homo sapiens

<400> SEQUENCE: 68
gcucggacug agcaggugggg 20

<210> SEQ ID NO 69
<211> LENGTH: 18
<212> TYPE: RNA
<213> ORGANISM: Homo sapiens

<400> SEQUENCE: 69
ugaggcgggg gggcgagc 18

<210> SEQ ID NO 70
<211> LENGTH: 21
<212> TYPE: RNA
<213> ORGANISM: Homo sapiens

<400> SEQUENCE: 70
gcccuccgcc cgugcacccc g 21

<210> SEQ ID NO 71
<211> LENGTH: 22
<212> TYPE: RNA
<213> ORGANISM: Homo sapiens

<400> SEQUENCE: 71
uaugcauugu auuuuuaggu cc 22

<210> SEQ ID NO 72
<211> LENGTH: 22
<212> TYPE: RNA
<213> ORGANISM: Homo sapiens

<400> SEQUENCE: 72
caaccucgac gaucuccuca gc 22

<210> SEQ ID NO 73
<211> LENGTH: 22
<212> TYPE: RNA
<213> ORGANISM: Homo sapiens

<400> SEQUENCE: 73
acggauguuu gagcaugugc ua 22

<210> SEQ ID NO 74
<211> LENGTH: 20
<212> TYPE: RNA
<213> ORGANISM: Homo sapiens

<400> SEQUENCE: 74
ugugacccua gaauaauuac 20

<210> SEQ ID NO 75
<211> LENGTH: 22
<212> TYPE: RNA
<213> ORGANISM: Homo sapiens

<400> SEQUENCE: 75
cccugugccc ggcccacuuc ug 22

<210> SEQ ID NO 76
<211> LENGTH: 20
<212> TYPE: RNA
<213> ORGANISM: Homo sapiens

<400> SEQUENCE: 76
cgccccuccu gcccccacag 20

<210> SEQ ID NO 77
<211> LENGTH: 22
<212> TYPE: RNA
<213> ORGANISM: Homo sapiens

<400> SEQUENCE: 77
uagcagcaca ucaugguuua ca 22

<210> SEQ ID NO 78
<211> LENGTH: 23
<212> TYPE: RNA
<213> ORGANISM: Homo sapiens

<400> SEQUENCE: 78
uggaguccag gaaucugcau uuu 23

<210> SEQ ID NO 79
<211> LENGTH: 21
<212> TYPE: RNA
<213> ORGANISM: Homo sapiens

<400> SEQUENCE: 79
cgucccaccc cccacuccug u 21

<210> SEQ ID NO 80
<211> LENGTH: 21
<212> TYPE: RNA
<213> ORGANISM: Homo sapiens

<400> SEQUENCE: 80
cagugcaagu guagaugccg a 21

<210> SEQ ID NO 81
<211> LENGTH: 21
<212> TYPE: RNA
<213> ORGANISM: Homo sapiens

<400> SEQUENCE: 81
ucacgcggag agauggcuuu g 21

<210> SEQ ID NO 82
<211> LENGTH: 21
<212> TYPE: RNA

<213> ORGANISM: Homo sapiens

<400> SEQUENCE: 82
agacccugca gccuucccac c 21

<210> SEQ ID NO 83
<211> LENGTH: 18
<212> TYPE: RNA
<213> ORGANISM: Homo sapiens

<400> SEQUENCE: 83
agggggcggg cuccggcg 18

<210> SEQ ID NO 84
<211> LENGTH: 22
<212> TYPE: RNA
<213> ORGANISM: Homo sapiens

<400> SEQUENCE: 84
uuguggcugg ucaugaggcu aa 22

<210> SEQ ID NO 85
<211> LENGTH: 21
<212> TYPE: RNA
<213> ORGANISM: Homo sapiens

<400> SEQUENCE: 85
ucuauucccc acucucccca g 21

<210> SEQ ID NO 86
<211> LENGTH: 22
<212> TYPE: RNA
<213> ORGANISM: Homo sapiens

<400> SEQUENCE: 86
cacccccugu uuccuggccc ac 22

<210> SEQ ID NO 87
<211> LENGTH: 22
<212> TYPE: RNA
<213> ORGANISM: Homo sapiens

<400> SEQUENCE: 87
uuccuaugca uauacuucuu ug 22

<210> SEQ ID NO 88
<211> LENGTH: 21
<212> TYPE: RNA
<213> ORGANISM: Homo sapiens

<400> SEQUENCE: 88
uggggcgggg cagguccoug c 21

<210> SEQ ID NO 89
<211> LENGTH: 25
<212> TYPE: RNA
<213> ORGANISM: Homo sapiens

<400> SEQUENCE: 89
agggaucgcg ggcggguggc ggccu 25

<210> SEQ ID NO 90
<211> LENGTH: 23

<212> TYPE: RNA
<213> ORGANISM: Homo sapiens

<400> SEQUENCE: 90
gugcguggug gcucgaggcg ggg 23

<210> SEQ ID NO 91
<211> LENGTH: 24
<212> TYPE: RNA
<213> ORGANISM: Homo sapiens

<400> SEQUENCE: 91
ccccgggaac gucgagacug gagc 24

<210> SEQ ID NO 92
<211> LENGTH: 25
<212> TYPE: RNA
<213> ORGANISM: Homo sapiens

<400> SEQUENCE: 92
gugaggcggg gccaggaggg ugugu 25

<210> SEQ ID NO 93
<211> LENGTH: 21
<212> TYPE: RNA
<213> ORGANISM: Homo sapiens

<400> SEQUENCE: 93
guaggugaca gucaggggcg g 21

<210> SEQ ID NO 94
<211> LENGTH: 22
<212> TYPE: RNA
<213> ORGANISM: Homo sapiens

<400> SEQUENCE: 94
ggaggaaccu uggagcuucg gc 22

<210> SEQ ID NO 95
<211> LENGTH: 20
<212> TYPE: RNA
<213> ORGANISM: Homo sapiens

<400> SEQUENCE: 95
guggguuggg gcgggcucug 20

<210> SEQ ID NO 96
<211> LENGTH: 20
<212> TYPE: RNA
<213> ORGANISM: Homo sapiens

<400> SEQUENCE: 96
ggcggcggcg gaggcggggg 20

<210> SEQ ID NO 97
<211> LENGTH: 25
<212> TYPE: RNA
<213> ORGANISM: Homo sapiens

<400> SEQUENCE: 97
ucggggcaug gggagggag gcugg 25

<210> SEQ ID NO 98

<211> LENGTH: 17
<212> TYPE: RNA
<213> ORGANISM: Homo sapiens

<400> SEQUENCE: 98
ggggcgcggc cggaucg 17

<210> SEQ ID NO 99
<211> LENGTH: 21
<212> TYPE: RNA
<213> ORGANISM: Homo sapiens

<400> SEQUENCE: 99
gugccagcug cagugggga g 21

<210> SEQ ID NO 100
<211> LENGTH: 23
<212> TYPE: RNA
<213> ORGANISM: Homo sapiens

<400> SEQUENCE: 100
gugagugugg auuuggcggg guu 23

<210> SEQ ID NO 101
<211> LENGTH: 22
<212> TYPE: RNA
<213> ORGANISM: Homo sapiens

<400> SEQUENCE: 101
cacacaagug gcccccaaca cu 22

<210> SEQ ID NO 102
<211> LENGTH: 22
<212> TYPE: RNA
<213> ORGANISM: Homo sapiens

<400> SEQUENCE: 102
uaucauggag uugguaaagc ac 22

<210> SEQ ID NO 103
<211> LENGTH: 23
<212> TYPE: RNA
<213> ORGANISM: Homo sapiens

<400> SEQUENCE: 103
uagagagggg aaggauguga ugu 23

<210> SEQ ID NO 104
<211> LENGTH: 20
<212> TYPE: RNA
<213> ORGANISM: Homo sapiens

<400> SEQUENCE: 104
ggcggcgggg agguaggcag 20

<210> SEQ ID NO 105
<211> LENGTH: 21
<212> TYPE: RNA
<213> ORGANISM: Homo sapiens

<400> SEQUENCE: 105
caaagcgcuu cccuuuggag c 21

<210> SEQ ID NO 106
<211> LENGTH: 21
<212> TYPE: RNA
<213> ORGANISM: Homo sapiens

<400> SEQUENCE: 106
aaaauuucuu ucacuacuua g 21

<210> SEQ ID NO 107
<211> LENGTH: 21
<212> TYPE: RNA
<213> ORGANISM: Homo sapiens

<400> SEQUENCE: 107
aguggaccga ggaaggaagg a 21

<210> SEQ ID NO 108
<211> LENGTH: 20
<212> TYPE: RNA
<213> ORGANISM: Homo sapiens

<400> SEQUENCE: 108
ucgcgccccg gcuccccguuc 20

<210> SEQ ID NO 109
<211> LENGTH: 22
<212> TYPE: RNA
<213> ORGANISM: Homo sapiens

<400> SEQUENCE: 109
ucucacccca acucugcccc ag 22

<210> SEQ ID NO 110
<211> LENGTH: 22
<212> TYPE: RNA
<213> ORGANISM: Homo sapiens

<400> SEQUENCE: 110
uggggauuug gagaaguggu ga 22

<210> SEQ ID NO 111
<211> LENGTH: 19
<212> TYPE: RNA
<213> ORGANISM: Homo sapiens

<400> SEQUENCE: 111
agcagggcug gggauugca 19

<210> SEQ ID NO 112
<211> LENGTH: 22
<212> TYPE: RNA
<213> ORGANISM: Homo sapiens

<400> SEQUENCE: 112
uccauguuuc cuucccccuu cu 22

<210> SEQ ID NO 113
<211> LENGTH: 22
<212> TYPE: RNA
<213> ORGANISM: Homo sapiens

<400> SEQUENCE: 113
acugggcagg gcugugguga gu 22

<210> SEQ ID NO 114
<211> LENGTH: 20
<212> TYPE: RNA
<213> ORGANISM: Homo sapiens

<400> SEQUENCE: 114
cgggcguggu ggugggggug 20

<210> SEQ ID NO 115
<211> LENGTH: 20
<212> TYPE: RNA
<213> ORGANISM: Homo sapiens

<400> SEQUENCE: 115
acuggacuug gagucagaaa 20

<210> SEQ ID NO 116
<211> LENGTH: 22
<212> TYPE: RNA
<213> ORGANISM: Homo sapiens

<400> SEQUENCE: 116
uuggccacca caccuacccc uu 22

<210> SEQ ID NO 117
<211> LENGTH: 19
<212> TYPE: RNA
<213> ORGANISM: Homo sapiens

<400> SEQUENCE: 117
ccugagaccc uaguuccac 19

<210> SEQ ID NO 118
<211> LENGTH: 22
<212> TYPE: RNA
<213> ORGANISM: Homo sapiens

<400> SEQUENCE: 118
aggggcuggc uuuccucugg uc 22

<210> SEQ ID NO 119
<211> LENGTH: 21
<212> TYPE: RNA
<213> ORGANISM: Homo sapiens

<400> SEQUENCE: 119
aacaggugac ugguuagaca a 21

<210> SEQ ID NO 120
<211> LENGTH: 22
<212> TYPE: RNA
<213> ORGANISM: Homo sapiens

<400> SEQUENCE: 120
ggugguugag gcugcaguaa gu 22

<210> SEQ ID NO 121
<211> LENGTH: 21
<212> TYPE: RNA
<213> ORGANISM: Homo sapiens

<400> SEQUENCE: 121
cccucucugu cccacccaua g 21

<210> SEQ ID NO 122
<211> LENGTH: 22
<212> TYPE: RNA
<213> ORGANISM: Homo sapiens

<400> SEQUENCE: 122
aaagugcuuc ccuuuggacu gu 22

<210> SEQ ID NO 123
<211> LENGTH: 21
<212> TYPE: RNA
<213> ORGANISM: Homo sapiens

<400> SEQUENCE: 123
auagcagcau aagccugucu c 21

<210> SEQ ID NO 124
<211> LENGTH: 16
<212> TYPE: RNA
<213> ORGANISM: Homo sapiens

<400> SEQUENCE: 124
uucagcagga acagcu 16

<210> SEQ ID NO 125
<211> LENGTH: 23
<212> TYPE: RNA
<213> ORGANISM: Homo sapiens

<400> SEQUENCE: 125
cccuucccuc acucuucucu cag 23

<210> SEQ ID NO 126
<211> LENGTH: 22
<212> TYPE: RNA
<213> ORGANISM: Homo sapiens

<400> SEQUENCE: 126
ggugcagugc ugcaucucug gu 22

<210> SEQ ID NO 127
<211> LENGTH: 21
<212> TYPE: RNA
<213> ORGANISM: Homo sapiens

<400> SEQUENCE: 127
cccugggccu cugcuccca g 21

<210> SEQ ID NO 128
<211> LENGTH: 20
<212> TYPE: RNA
<213> ORGANISM: Homo sapiens

<400> SEQUENCE: 128
ucugugcccc uacuucccag 20

<210> SEQ ID NO 129
<211> LENGTH: 22
<212> TYPE: RNA
<213> ORGANISM: Homo sapiens

<400> SEQUENCE: 129
uuggcugguc ucugcuccgc ag 22

<210> SEQ ID NO 130
<211> LENGTH: 22
<212> TYPE: RNA
<213> ORGANISM: Homo sapiens

<400> SEQUENCE: 130
gaagaacugu ugcauuugcc cu 22

<210> SEQ ID NO 131
<211> LENGTH: 17
<212> TYPE: RNA
<213> ORGANISM: Homo sapiens

<400> SEQUENCE: 131
cacugugggu acaugcu 17

<210> SEQ ID NO 132
<211> LENGTH: 22
<212> TYPE: RNA
<213> ORGANISM: Homo sapiens

<400> SEQUENCE: 132
ucucugagca aggcuuaaca cc 22

<210> SEQ ID NO 133
<211> LENGTH: 21
<212> TYPE: RNA
<213> ORGANISM: Homo sapiens

<400> SEQUENCE: 133
cucucccucu uuacccacua g 21

<210> SEQ ID NO 134
<211> LENGTH: 22
<212> TYPE: RNA
<213> ORGANISM: Homo sapiens

<400> SEQUENCE: 134
uuuggucccc uucaaccagc ua 22

<210> SEQ ID NO 135
<211> LENGTH: 18
<212> TYPE: RNA
<213> ORGANISM: Homo sapiens

<400> SEQUENCE: 135
cggggcggca ggggccuc 18

<210> SEQ ID NO 136
<211> LENGTH: 22
<212> TYPE: RNA
<213> ORGANISM: Homo sapiens

<400> SEQUENCE: 136
aacuggcccu caaagucccg cu 22

<210> SEQ ID NO 137
<211> LENGTH: 21
<212> TYPE: RNA
<213> ORGANISM: Homo sapiens

<400> SEQUENCE: 137
ucccuacccc uccacucccc a 21

<210> SEQ ID NO 138
<211> LENGTH: 21
<212> TYPE: RNA
<213> ORGANISM: Homo sapiens

<400> SEQUENCE: 138
aagccucugu ccccacccca g 21

<210> SEQ ID NO 139
<211> LENGTH: 21
<212> TYPE: RNA
<213> ORGANISM: Homo sapiens

<400> SEQUENCE: 139
ccggccgccg gcuccgcccc g 21

<210> SEQ ID NO 140
<211> LENGTH: 21
<212> TYPE: RNA
<213> ORGANISM: Homo sapiens

<400> SEQUENCE: 140 gcggugggc cggaggggcg u 21

<210> SEQ ID NO 141
<211> LENGTH: 21
<212> TYPE: RNA
<213> ORGANISM: Homo sapiens

<400> SEQUENCE: 141
agccgcgggg aucgccgagg g 21

<210> SEQ ID NO 142
<211> LENGTH: 22
<212> TYPE: RNA
<213> ORGANISM: Homo sapiens

<400> SEQUENCE: 142
agacugacgg cuggaggccc au 22

<210> SEQ ID NO 143
<211> LENGTH: 18
<212> TYPE: RNA
<213> ORGANISM: Homo sapiens

<400> SEQUENCE: 143
cggcuggagg ugugagga 18

<210> SEQ ID NO 144
<211> LENGTH: 23
<212> TYPE: RNA
<213> ORGANISM: Homo sapiens

<400> SEQUENCE: 144
ugggccaggg agcagcuggu ggg 23

<210> SEQ ID NO 145
<211> LENGTH: 22
<212> TYPE: RNA
<213> ORGANISM: Homo sapiens

<400> SEQUENCE: 145
caugggaguu cggggugguu gc 22

<210> SEQ ID NO 146
<211> LENGTH: 21
<212> TYPE: RNA
<213> ORGANISM: Homo sapiens

<400> SEQUENCE: 146
aagggacagg gagggucgug g 21

<210> SEQ ID NO 147
<211> LENGTH: 24
<212> TYPE: RNA
<213> ORGANISM: Homo sapiens

<400> SEQUENCE: 147
uguggacagu gagguagagg gagu 24

<210> SEQ ID NO 148
<211> LENGTH: 22
<212> TYPE: RNA
<213> ORGANISM: Homo sapiens

<400> SEQUENCE: 148
agaggcugag aaggugaugu ug 22

<210> SEQ ID NO 149
<211> LENGTH: 23
<212> TYPE: RNA
<213> ORGANISM: Homo sapiens

<400> SEQUENCE: 149
uggaguuaag gguugcuugg aga 23

<210> SEQ ID NO 150
<211> LENGTH: 23
<212> TYPE: RNA
<213> ORGANISM: Homo sapiens

<400> SEQUENCE: 150
ugugcuugcu cgucccgccc gca 23

<210> SEQ ID NO 151
<211> LENGTH: 22
<212> TYPE: RNA
<213> ORGANISM: Homo sapiens

<400> SEQUENCE: 151
guucuguuaa cccauccccu ca 22

<210> SEQ ID NO 152
<211> LENGTH: 21
<212> TYPE: RNA
<213> ORGANISM: Homo sapiens

<400> SEQUENCE: 152
ucaggguugg uaggggguugc u 21

<210> SEQ ID NO 153
<211> LENGTH: 22
<212> TYPE: RNA
<213> ORGANISM: Homo sapiens

<400> SEQUENCE: 153
gcugaugaug auggugcuga ag 22

<210> SEQ ID NO 154
<211> LENGTH: 21
<212> TYPE: RNA
<213> ORGANISM: Homo sapiens

<400> SEQUENCE: 154
uccagggaga caguguguga g 21

<210> SEQ ID NO 155
<211> LENGTH: 23
<212> TYPE: RNA
<213> ORGANISM: Homo sapiens

<400> SEQUENCE: 155
gaagacuucu uggauuacag ggg 23

<210> SEQ ID NO 156
<211> LENGTH: 20
<212> TYPE: RNA
<213> ORGANISM: Homo sapiens

<400> SEQUENCE: 156
aggaggacaa guugugggau 20

<210> SEQ ID NO 157
<211> LENGTH: 24
<212> TYPE: RNA
<213> ORGANISM: Homo sapiens

<400> SEQUENCE: 157
ucugggcaca ggcggaugga cagg 24

<210> SEQ ID NO 158
<211> LENGTH: 21
<212> TYPE: RNA
<213> ORGANISM: Homo sapiens

<400> SEQUENCE: 158
agagaagaag aucagccugc a 21

<210> SEQ ID NO 159
<211> LENGTH: 23
<212> TYPE: RNA
<213> ORGANISM: Homo sapiens

<400> SEQUENCE: 159
ucucuggagg gaagcacuuu cug 23

<210> SEQ ID NO 160
<211> LENGTH: 23
<212> TYPE: RNA
<213> ORGANISM: Homo sapiens

<400> SEQUENCE: 160
gauccaucuc ugccuguauu ggc 23

<210> SEQ ID NO 161
<211> LENGTH: 23
<212> TYPE: RNA

<213> ORGANISM: Homo sapiens

<400> SEQUENCE: 161
uagccuucag aucuuggugu uuu 23

<210> SEQ ID NO 162
<211> LENGTH: 21
<212> TYPE: RNA
<213> ORGANISM: Homo sapiens

<400> SEQUENCE: 162
aucugccagc uuccacagug g 21

<210> SEQ ID NO 163
<211> LENGTH: 22
<212> TYPE: RNA
<213> ORGANISM: Homo sapiens

<400> SEQUENCE: 163
cuacuucuac cuguguuauc au 22

<210> SEQ ID NO 164
<211> LENGTH: 23
<212> TYPE: RNA
<213> ORGANISM: Homo sapiens

<400> SEQUENCE: 164
ccggggcaga uugguguagg gug 23

<210> SEQ ID NO 165
<211> LENGTH: 22
<212> TYPE: RNA
<213> ORGANISM: Homo sapiens

<400> SEQUENCE: 165
cuccuauaug augccuuucu uc 22

<210> SEQ ID NO 166
<211> LENGTH: 21
<212> TYPE: RNA
<213> ORGANISM: Homo sapiens

<400> SEQUENCE: 166
cccagauaau ggcacucuca a 21

<210> SEQ ID NO 167
<211> LENGTH: 22
<212> TYPE: RNA
<213> ORGANISM: Homo sapiens

<400> SEQUENCE: 167
aacccguaga uccgaacuug ug 22

<210> SEQ ID NO 168
<211> LENGTH: 22
<212> TYPE: RNA
<213> ORGANISM: Homo sapiens

<400> SEQUENCE: 168
uuggacagaa aacacgcagg aa 22

<210> SEQ ID NO 169
<211> LENGTH: 23

<212> TYPE: RNA
<213> ORGANISM: Homo sapiens

<400> SEQUENCE: 169
gaagugcuuc gauuuugggg ugu 23

<210> SEQ ID NO 170
<211> LENGTH: 22
<212> TYPE: RNA
<213> ORGANISM: Homo sapiens

<400> SEQUENCE: 170
ucgggcgcaa gagcacugca gu 22

<210> SEQ ID NO 171
<211> LENGTH: 22
<212> TYPE: RNA
<213> ORGANISM: Homo sapiens

<400> SEQUENCE: 171
uguccucuag ggccugcagu cu 22

<210> SEQ ID NO 172
<211> LENGTH: 22
<212> TYPE: RNA
<213> ORGANISM: Homo sapiens

<400> SEQUENCE: 172
uauugcacau uacuaaguug ca 22

<210> SEQ ID NO 173
<211> LENGTH: 23
<212> TYPE: RNA
<213> ORGANISM: Homo sapiens

<400> SEQUENCE: 173
uaagugcuuc cauguuuugg uga 23

<210> SEQ ID NO 174
<211> LENGTH: 23
<212> TYPE: RNA
<213> ORGANISM: Homo sapiens

<400> SEQUENCE: 174
uaucugcugg gcuuucuggu guu 23

<210> SEQ ID NO 175
<211> LENGTH: 22
<212> TYPE: RNA
<213> ORGANISM: Homo sapiens

<400> SEQUENCE: 175
uuucuucuua gacauggcaa cg 22

<210> SEQ ID NO 176
<211> LENGTH: 19
<212> TYPE: RNA
<213> ORGANISM: Homo sapiens

<400> SEQUENCE: 176
ucucccuuga gggcacuuu 19

<210> SEQ ID NO 177

<211> LENGTH: 19
<212> TYPE: RNA
<213> ORGANISM: Homo sapiens

<400> SEQUENCE: 177
cgcucuaggc accgcagca 19

<210> SEQ ID NO 178
<211> LENGTH: 19
<212> TYPE: RNA
<213> ORGANISM: Homo sapiens

<400> SEQUENCE: 178
ugucucugcu gggguuucu 19

<210> SEQ ID NO 179
<211> LENGTH: 22
<212> TYPE: RNA
<213> ORGANISM: Homo sapiens

<400> SEQUENCE: 179
aucgugcauc ccuuuagagu gu 22

<210> SEQ ID NO 180
<211> LENGTH: 22
<212> TYPE: RNA
<213> ORGANISM: Homo sapiens

<400> SEQUENCE: 180
aucgugcauc ccuuuagagu gu 22

<210> SEQ ID NO 181
<211> LENGTH: 23
<212> TYPE: RNA
<213> ORGANISM: Homo sapiens

<400> SEQUENCE: 181
uguaguguuu ccuacuuuau gga 23

<210> SEQ ID NO 182
<211> LENGTH: 22
<212> TYPE: RNA
<213> ORGANISM: Homo sapiens

<400> SEQUENCE: 182
auauacaggg ggagacucuc au 22

<210> SEQ ID NO 183
<211> LENGTH: 23
<212> TYPE: RNA
<213> ORGANISM: Homo sapiens

<400> SEQUENCE: 183
gacacgggcg acagcugcgg ccc 23

<210> SEQ ID NO 184
<211> LENGTH: 20
<212> TYPE: RNA
<213> ORGANISM: Homo sapiens

<400> SEQUENCE: 184
cugcaaaggg aagcccuuuc 20

<210> SEQ ID NO 185
<211> LENGTH: 20
<212> TYPE: RNA
<213> ORGANISM: Homo sapiens

<400> SEQUENCE: 185
cugcaaaggg aagcccuuuc 20

<210> SEQ ID NO 186
<211> LENGTH: 23
<212> TYPE: RNA
<213> ORGANISM: Homo sapiens

<400> SEQUENCE: 186
ucugaguucc uggagccugg ucu 23

<210> SEQ ID NO 187
<211> LENGTH: 22
<212> TYPE: RNA
<213> ORGANISM: Homo sapiens

<400> SEQUENCE: 187
aaggagcuca cagucuauug ag 22

<210> SEQ ID NO 188
<211> LENGTH: 19
<212> TYPE: RNA
<213> ORGANISM: Homo sapiens

<400> SEQUENCE: 188
ggccacugag ucagcacca 19

<210> SEQ ID NO 189
<211> LENGTH: 22
<212> TYPE: RNA
<213> ORGANISM: Homo sapiens

<400> SEQUENCE: 189
aacuguuugc agaggaaacu ga 22

<210> SEQ ID NO 190
<211> LENGTH: 21
<212> TYPE: RNA
<213> ORGANISM: Homo sapiens

<400> SEQUENCE: 190
cuccagaggg augcacuuuc u 21

<210> SEQ ID NO 191
<211> LENGTH: 22
<212> TYPE: RNA
<213> ORGANISM: Homo sapiens

<400> SEQUENCE: 191
ucaccugacc ucccaugccu gu 22

<210> SEQ ID NO 192
<211> LENGTH: 21
<212> TYPE: RNA
<213> ORGANISM: Homo sapiens

<400> SEQUENCE: 192
aaccuuggcc ccucucccca g 21

<210> SEQ ID NO 193
<211> LENGTH: 22
<212> TYPE: RNA
<213> ORGANISM: Homo sapiens

<400> SEQUENCE: 193
ucugccaucc ucccuccccu ac 22

<210> SEQ ID NO 194
<211> LENGTH: 22
<212> TYPE: RNA
<213> ORGANISM: Homo sapiens

<400> SEQUENCE: 194
ugggggagug cagugauugu gg 22

<210> SEQ ID NO 195
<211> LENGTH: 20
<212> TYPE: RNA
<213> ORGANISM: Homo sapiens

<400> SEQUENCE: 195
ccccagggcg acgcggcggg 20

<210> SEQ ID NO 196
<211> LENGTH: 22
<212> TYPE: RNA
<213> ORGANISM: Homo sapiens

<400> SEQUENCE: 196
uggggagcgg cccccgggug gg 22

<210> SEQ ID NO 197
<211> LENGTH: 22
<212> TYPE: RNA
<213> ORGANISM: Homo sapiens

<400> SEQUENCE: 197
acuggguagg uggggcucca gg 22

<210> SEQ ID NO 198
<211> LENGTH: 21
<212> TYPE: RNA
<213> ORGANISM: Homo sapiens

<400> SEQUENCE: 198
cgggccggag gucaagggcg u 21

<210> SEQ ID NO 199
<211> LENGTH: 17
<212> TYPE: RNA
<213> ORGANISM: Homo sapiens

<400> SEQUENCE: 199
gcggggcugg gcgcgcg 17

<210> SEQ ID NO 200
<211> LENGTH: 22
<212> TYPE: RNA
<213> ORGANISM: Homo sapiens

<400> SEQUENCE: 200
aaggggcagg gacggguggc cc 22

<210> SEQ ID NO 201
<211> LENGTH: 21
<212> TYPE: RNA
<213> ORGANISM: Homo sapiens

<400> SEQUENCE: 201
cgggagcugg ggucugcagg u 21

<210> SEQ ID NO 202
<211> LENGTH: 21
<212> TYPE: RNA
<213> ORGANISM: Homo sapiens

<400> SEQUENCE: 202
ggggggaugu gcaugcuggu u 21

<210> SEQ ID NO 203
<211> LENGTH: 20
<212> TYPE: RNA
<213> ORGANISM: Homo sapiens

<400> SEQUENCE: 203
cggggugggu gaggucgggc 20

<210> SEQ ID NO 204
<211> LENGTH: 23
<212> TYPE: RNA
<213> ORGANISM: Homo sapiens

<400> SEQUENCE: 204
caggggcugg gguuucaggu ucu 23

<210> SEQ ID NO 205
<211> LENGTH: 20
<212> TYPE: RNA
<213> ORGANISM: Homo sapiens

<400> SEQUENCE: 205
gggcuggggc gcggggaggu 20

<210> SEQ ID NO 206
<211> LENGTH: 19
<212> TYPE: RNA
<213> ORGANISM: Homo sapiens

<400> SEQUENCE: 206
uggauuuuug gaucaggga 19

<210> SEQ ID NO 207
<211> LENGTH: 21
<212> TYPE: RNA
<213> ORGANISM: Homo sapiens

<400> SEQUENCE: 207
acggcccagg cggcauuggu g 21

<210> SEQ ID NO 208
<211> LENGTH: 23
<212> TYPE: RNA
<213> ORGANISM: Homo sapiens

<400> SEQUENCE: 208
gugaguggga gccggugggg cug 23

<210> SEQ ID NO 209
<211> LENGTH: 22
<212> TYPE: RNA
<213> ORGANISM: Homo sapiens

<400> SEQUENCE: 209
gagcaggcga ggcugggcug aa 22

<210> SEQ ID NO 210
<211> LENGTH: 22
<212> TYPE: RNA
<213> ORGANISM: Homo sapiens

<400> SEQUENCE: 210
ggggcugggg ccggggccga gc 22

<210> SEQ ID NO 211
<211> LENGTH: 22
<212> TYPE: RNA
<213> ORGANISM: Homo sapiens

<400> SEQUENCE: 211
ugagccccug ugccgccccc ag 22

<210> SEQ ID NO 212
<211> LENGTH: 24
<212> TYPE: RNA
<213> ORGANISM: Homo sapiens

<400> SEQUENCE: 212
ugaggggccu cagaccgagc uuuu 24

<210> SEQ ID NO 213
<211> LENGTH: 20
<212> TYPE: RNA
<213> ORGANISM: Homo sapiens

<400> SEQUENCE: 213
accaggaggc ugaggccccu 20

<210> SEQ ID NO 214
<211> LENGTH: 22
<212> TYPE: RNA
<213> ORGANISM: Homo sapiens

<400> SEQUENCE: 214
uucccuuugu cauccuucgc cu 22

<210> SEQ ID NO 215
<211> LENGTH: 22
<212> TYPE: RNA
<213> ORGANISM: Homo sapiens

<400> SEQUENCE: 215
acccgucccg uucguccccg ga 22

<210> SEQ ID NO 216
<211> LENGTH: 17
<212> TYPE: RNA
<213> ORGANISM: Homo sapiens

<400> SEQUENCE: 216
ggcgggugcg ggggugg 17

<210> SEQ ID NO 217
<211> LENGTH: 23
<212> TYPE: RNA
<213> ORGANISM: Homo sapiens

<400> SEQUENCE: 217
ucuggcuccg ugucuucacu ccc 23

<210> SEQ ID NO 218
<211> LENGTH: 22
<212> TYPE: RNA
<213> ORGANISM: Homo sapiens

<400> SEQUENCE: 218
ugcggggcua gggcuaacag ca 22

<210> SEQ ID NO 219
<211> LENGTH: 22
<212> TYPE: RNA
<213> ORGANISM: Homo sapiens

<400> SEQUENCE: 219
gcugacuccu aguccagggc uc 22

<210> SEQ ID NO 220
<211> LENGTH: 22
<212> TYPE: RNA
<213> ORGANISM: Homo sapiens

<400> SEQUENCE: 220
ucucccaacc cuuguaccag ug 22

<210> SEQ ID NO 221
<211> LENGTH: 22
<212> TYPE: RNA
<213> ORGANISM: Homo sapiens

<400> SEQUENCE: 221
gcugcgcuug gauuucgucc cc 22

<210> SEQ ID NO 222
<211> LENGTH: 22
<212> TYPE: RNA
<213> ORGANISM: Homo sapiens

<400> SEQUENCE: 222
uuuaggauaa gcuugacuuu ug 22

<210> SEQ ID NO 223
<211> LENGTH: 22
<212> TYPE: RNA
<213> ORGANISM: Homo sapiens

<400> SEQUENCE: 223
uggcaguguc uuagcugguu gu 22

<210> SEQ ID NO 224
<211> LENGTH: 23
<212> TYPE: RNA
<213> ORGANISM: Homo sapiens

<400> SEQUENCE: 224
agguuacccg agcaacuuug cau 23

<210> SEQ ID NO 225
<211> LENGTH: 22
<212> TYPE: RNA
<213> ORGANISM: Homo sapiens

<400> SEQUENCE: 225
agaucgaccg uguuauauuc gc 22

<210> SEQ ID NO 226
<211> LENGTH: 22
<212> TYPE: RNA
<213> ORGANISM: Homo sapiens

<400> SEQUENCE: 226
accuugccuu gcugcccggg cc 22

<210> SEQ ID NO 227
<211> LENGTH: 22
<212> TYPE: RNA
<213> ORGANISM: Homo sapiens

<400> SEQUENCE: 227
uucccuuugu cauccuaugc cu 22

<210> SEQ ID NO 228
<211> LENGTH: 23
<212> TYPE: RNA
<213> ORGANISM: Homo sapiens

<400> SEQUENCE: 228
uuauugcuua agaauacgcg uag 23

<210> SEQ ID NO 229
<211> LENGTH: 22
<212> TYPE: RNA
<213> ORGANISM: Homo sapiens

<400> SEQUENCE: 229
gaaguuguuc gugguggauu cg 22

<210> SEQ ID NO 230
<211> LENGTH: 22
<212> TYPE: RNA
<213> ORGANISM: Homo sapiens

<400> SEQUENCE: 230
ccucuagaug gaagcacugu cu 22

<210> SEQ ID NO 231
<211> LENGTH: 22
<212> TYPE: RNA
<213> ORGANISM: Homo sapiens

<400> SEQUENCE: 231
caugccuuga guguaggacc gu 22

<210> SEQ ID NO 232
<211> LENGTH: 22
<212> TYPE: RNA
<213> ORGANISM: Homo sapiens

<400> SEQUENCE: 232
aguucuucag uggcaagcuu ua 22

<210> SEQ ID NO 233
<211> LENGTH: 21
<212> TYPE: RNA
<213> ORGANISM: Homo sapiens

<400> SEQUENCE: 233
uccuucugcu ccguccccca g 21

<210> SEQ ID NO 234
<211> LENGTH: 21
<212> TYPE: RNA
<213> ORGANISM: Homo sapiens

<400> SEQUENCE: 234
ccccaccucc ucucuccuca g 21

<210> SEQ ID NO 235
<211> LENGTH: 22
<212> TYPE: RNA
<213> ORGANISM: Homo sapiens

<400> SEQUENCE: 235
gacuauagaa cuuucccccu ca 22

<210> SEQ ID NO 236
<211> LENGTH: 22
<212> TYPE: RNA
<213> ORGANISM: Homo sapiens

<400> SEQUENCE: 236
cuggcccucu cugcccuucc gu 22

<210> SEQ ID NO 237
<211> LENGTH: 22
<212> TYPE: RNA
<213> ORGANISM: Homo sapiens

<400> SEQUENCE: 237
uggaguguga caaugguguu ug 22

<210> SEQ ID NO 238
<211> LENGTH: 20
<212> TYPE: RNA
<213> ORGANISM: Homo sapiens

<400> SEQUENCE: 238
agagguauag ggcaugggaa 20

<210> SEQ ID NO 239
<211> LENGTH: 21
<212> TYPE: RNA
<213> ORGANISM: Homo sapiens

<400> SEQUENCE: 239
uagcggggau uccaauauug g 21

<210> SEQ ID NO 240
<211> LENGTH: 21
<212> TYPE: RNA

<213> ORGANISM: Homo sapiens

<400> SEQUENCE: 240
cuuccgcccc gccgggcguc g 21

<210> SEQ ID NO 241
<211> LENGTH: 23
<212> TYPE: RNA
<213> ORGANISM: Homo sapiens

<400> SEQUENCE: 241
ucucacacag aaaucgcacc cgu 23

<210> SEQ ID NO 242
<211> LENGTH: 21
<212> TYPE: RNA
<213> ORGANISM: Homo sapiens

<400> SEQUENCE: 242
ccuguucucc auuacuuggc u 21

<210> SEQ ID NO 243
<211> LENGTH: 21
<212> TYPE: RNA
<213> ORGANISM: Homo sapiens

<400> SEQUENCE: 243
uaccacaggg uagaaccacg g 21

<210> SEQ ID NO 244
<211> LENGTH: 22
<212> TYPE: RNA
<213> ORGANISM: Homo sapiens

<400> SEQUENCE: 244
uaacacuguc ugguaacgau gu 22

<210> SEQ ID NO 245
<211> LENGTH: 22
<212> TYPE: RNA
<213> ORGANISM: Homo sapiens

<400> SEQUENCE: 245
acuggacuug gagucagaag gc 22

<210> SEQ ID NO 246
<211> LENGTH: 22
<212> TYPE: RNA
<213> ORGANISM: Homo sapiens

<400> SEQUENCE: 246
ucaggcucag uccccucccg au 22

<210> SEQ ID NO 247
<211> LENGTH: 21
<212> TYPE: RNA
<213> ORGANISM: Homo sapiens

<400> SEQUENCE: 247
agggcccccc cucaauccug u 21

<210> SEQ ID NO 248
<211> LENGTH: 22

<212> TYPE: RNA
<213> ORGANISM: Homo sapiens

<400> SEQUENCE: 248
uccuucauuc caccggaguc ug 22

<210> SEQ ID NO 249
<211> LENGTH: 21
<212> TYPE: RNA
<213> ORGANISM: Homo sapiens

<400> SEQUENCE: 249
ugucuugcag gccgucaugc a 21

<210> SEQ ID NO 250
<211> LENGTH: 22
<212> TYPE: RNA
<213> ORGANISM: Homo sapiens

<400> SEQUENCE: 250
gcccgcgugu ggagccaggu gu 22

<210> SEQ ID NO 251
<211> LENGTH: 23
<212> TYPE: RNA
<213> ORGANISM: Homo sapiens

<400> SEQUENCE: 251
cggcccgggc ugcugcuguu ccu 23

<210> SEQ ID NO 252
<211> LENGTH: 22
<212> TYPE: RNA
<213> ORGANISM: Homo sapiens

<400> SEQUENCE: 252
cagccacaac uacccugcca cu 22

<210> SEQ ID NO 253
<211> LENGTH: 20
<212> TYPE: RNA
<213> ORGANISM: Homo sapiens

<400> SEQUENCE: 253
ccuccugccc uccuugcugu 20

<210> SEQ ID NO 254
<211> LENGTH: 21
<212> TYPE: RNA
<213> ORGANISM: Homo sapiens

<400> SEQUENCE: 254
ggcuccuccu cucaggaugu g 21

<210> SEQ ID NO 255
<211> LENGTH: 16
<212> TYPE: RNA
<213> ORGANISM: Homo sapiens

<400> SEQUENCE: 255
cucuccuccc ggcuuc 16

<210> SEQ ID NO 256

<211> LENGTH: 22
<212> TYPE: RNA
<213> ORGANISM: Homo sapiens

<400> SEQUENCE: 256
ucacccugca ucccgcaccc ag 22

<210> SEQ ID NO 257
<211> LENGTH: 23
<212> TYPE: RNA
<213> ORGANISM: Homo sapiens

<400> SEQUENCE: 257
uucgggcugg ccugcugcuc cgg 23

<210> SEQ ID NO 258
<211> LENGTH: 21
<212> TYPE: RNA
<213> ORGANISM: Homo sapiens

<400> SEQUENCE: 258
cucccacuuc cagaucuuuc u 21

<210> SEQ ID NO 259
<211> LENGTH: 23
<212> TYPE: RNA
<213> ORGANISM: Homo sapiens

<400> SEQUENCE: 259
ccugggcagc guguggcuga agg 23

<210> SEQ ID NO 260
<211> LENGTH: 22
<212> TYPE: RNA
<213> ORGANISM: Homo sapiens

<400> SEQUENCE: 260
ucucccuucc ugcccuggcu ag 22

<210> SEQ ID NO 261
<211> LENGTH: 22
<212> TYPE: RNA
<213> ORGANISM: Homo sapiens

<400> SEQUENCE: 261
ugaucucacc gcugccuccu uc 22

<210> SEQ ID NO 262
<211> LENGTH: 24
<212> TYPE: RNA
<213> ORGANISM: Homo sapiens

<400> SEQUENCE: 262
ugucagugac uccugccccu uggu 24

<210> SEQ ID NO 263
<211> LENGTH: 22
<212> TYPE: RNA
<213> ORGANISM: Homo sapiens

<400> SEQUENCE: 263
uucucccacu accaggcucc ca 22

<210> SEQ ID NO 264
<211> LENGTH: 22
<212> TYPE: RNA
<213> ORGANISM: Homo sapiens

<400> SEQUENCE: 264
cccucucugg cuccuccccca aa 22

<210> SEQ ID NO 265
<211> LENGTH: 23
<212> TYPE: RNA
<213> ORGANISM: Homo sapiens

<400> SEQUENCE: 265
aagugccccc acaguuugag ugc 23

<210> SEQ ID NO 266
<211> LENGTH: 20
<212> TYPE: RNA
<213> ORGANISM: Homo sapiens

<400> SEQUENCE: 266
ccugauccca cagcccaccu 20

<210> SEQ ID NO 267
<211> LENGTH: 21
<212> TYPE: RNA
<213> ORGANISM: Homo sapiens

<400> SEQUENCE: 267
cucugaucgc ccucucagcu c 21

<210> SEQ ID NO 268
<211> LENGTH: 21
<212> TYPE: RNA
<213> ORGANISM: Homo sapiens

<400> SEQUENCE: 268
ucucugcucu gcucuccccca g 21

<210> SEQ ID NO 269
<211> LENGTH: 21
<212> TYPE: RNA
<213> ORGANISM: Homo sapiens

<400> SEQUENCE: 269
ucagcuccuc ucuacccaca g 21

<210> SEQ ID NO 270
<211> LENGTH: 22
<212> TYPE: RNA
<213> ORGANISM: Homo sapiens

<400> SEQUENCE: 270
ugucuucucu ccucccaaac ag 22

<210> SEQ ID NO 271
<211> LENGTH: 22
<212> TYPE: RNA
<213> ORGANISM: Homo sapiens

<400> SEQUENCE: 271
ucggcucucu cccucacccu ag 22

<210> SEQ ID NO 272
<211> LENGTH: 23
<212> TYPE: RNA
<213> ORGANISM: Homo sapiens

<400> SEQUENCE: 272
agccgcucuu cucccugccc aca 23

<210> SEQ ID NO 273
<211> LENGTH: 21
<212> TYPE: RNA
<213> ORGANISM: Homo sapiens

<400> SEQUENCE: 273
uccugccuuc cucugcacca g 21

<210> SEQ ID NO 274
<211> LENGTH: 21
<212> TYPE: RNA
<213> ORGANISM: Homo sapiens

<400> SEQUENCE: 274
gaacucaccc ucugcuccca g 21

<210> SEQ ID NO 275
<211> LENGTH: 22
<212> TYPE: RNA
<213> ORGANISM: Homo sapiens

<400> SEQUENCE: 275
ucuucaccug ccucugccug ca 22

<210> SEQ ID NO 276
<211> LENGTH: 22
<212> TYPE: RNA
<213> ORGANISM: Homo sapiens

<400> SEQUENCE: 276
ugaccuuugc cucuccccuc ag 22

<210> SEQ ID NO 277
<211> LENGTH: 22
<212> TYPE: RNA
<213> ORGANISM: Homo sapiens

<400> SEQUENCE: 277
uccuacgcug cucucucacu cc 22

<210> SEQ ID NO 278
<211> LENGTH: 23
<212> TYPE: RNA
<213> ORGANISM: Homo sapiens

<400> SEQUENCE: 278
uggcugcuuc ccuuggucuc cag 23

<210> SEQ ID NO 279
<211> LENGTH: 21
<212> TYPE: RNA
<213> ORGANISM: Homo sapiens

<400> SEQUENCE: 279
gagccccucu cugcucucca g 21

<210> SEQ ID NO 280
<211> LENGTH: 23
<212> TYPE: RNA
<213> ORGANISM: Homo sapiens

<400> SEQUENCE: 280
caaccaccac ugucucuccc cag 23

<210> SEQ ID NO 281
<211> LENGTH: 21
<212> TYPE: RNA
<213> ORGANISM: Homo sapiens

<400> SEQUENCE: 281
ugccucccug acauuccaca g 21

<210> SEQ ID NO 282
<211> LENGTH: 21
<212> TYPE: RNA
<213> ORGANISM: Homo sapiens

<400> SEQUENCE: 282
aagcccuguc uccucccauc u 21

<210> SEQ ID NO 283
<211> LENGTH: 23
<212> TYPE: RNA
<213> ORGANISM: Homo sapiens

<400> SEQUENCE: 283
ugacgccccu ucugauucug ccu 23

<210> SEQ ID NO 284
<211> LENGTH: 22
<212> TYPE: RNA
<213> ORGANISM: Homo sapiens

<400> SEQUENCE: 284
ucucagcugc ugcccucucc ag 22

<210> SEQ ID NO 285
<211> LENGTH: 22
<212> TYPE: RNA
<213> ORGANISM: Homo sapiens

<400> SEQUENCE: 285
cuccuccaca gccccugcuc au 22

<210> SEQ ID NO 286
<211> LENGTH: 20
<212> TYPE: RNA
<213> ORGANISM: Homo sapiens

<400> SEQUENCE: 286
cucacucuca gucccucccu 20

<210> SEQ ID NO 287
<211> LENGTH: 20
<212> TYPE: RNA
<213> ORGANISM: Homo sapiens

<400> SEQUENCE: 287
accccugcca cucacuggcc 20

<210> SEQ ID NO 288
<211> LENGTH: 22
<212> TYPE: RNA
<213> ORGANISM: Homo sapiens

<400> SEQUENCE: 288
uucaccccuc ucaccuaagc ag 22

<210> SEQ ID NO 289
<211> LENGTH: 22
<212> TYPE: RNA
<213> ORGANISM: Homo sapiens

<400> SEQUENCE: 289 uccccucgccu ucucacccuc ag 22

<210> SEQ ID NO 290
<211> LENGTH: 22
<212> TYPE: RNA
<213> ORGANISM: Homo sapiens

<400> SEQUENCE: 290
cgcaccugcc ucucacccac ag 22

<210> SEQ ID NO 291
<211> LENGTH: 23
<212> TYPE: RNA
<213> ORGANISM: Homo sapiens

<400> SEQUENCE: 291
auggggacag ggaucagcau ggc 23

<210> SEQ ID NO 292
<211> LENGTH: 21
<212> TYPE: RNA
<213> ORGANISM: Homo sapiens

<400> SEQUENCE: 292
ugagccucuc cuucccucca g 21

<210> SEQ ID NO 293
<211> LENGTH: 22
<212> TYPE: RNA
<213> ORGANISM: Homo sapiens

<400> SEQUENCE: 293
gcgcugaccc gccuucuccg ca 22

<210> SEQ ID NO 294
<211> LENGTH: 20
<212> TYPE: RNA
<213> ORGANISM: Homo sapiens

<400> SEQUENCE: 294
ugccuccucc guggccucag 20

<210> SEQ ID NO 295
<211> LENGTH: 21
<212> TYPE: RNA
<213> ORGANISM: Homo sapiens

<400> SEQUENCE: 295
uuucucucuc cacuuccuca g 21

<210> SEQ ID NO 296
<211> LENGTH: 20
<212> TYPE: RNA
<213> ORGANISM: Homo sapiens

<400> SEQUENCE: 296
uaugucccau cccuccauca 20

<210> SEQ ID NO 297
<211> LENGTH: 21
<212> TYPE: RNA
<213> ORGANISM: Homo sapiens

<400> SEQUENCE: 297
ucccuugucu ccuuucccua g 21

<210> SEQ ID NO 298
<211> LENGTH: 21
<212> TYPE: RNA
<213> ORGANISM: Homo sapiens

<400> SEQUENCE: 298
ccucuccucc cugugcccca g 21

<210> SEQ ID NO 299
<211> LENGTH: 24
<212> TYPE: RNA
<213> ORGANISM: Homo sapiens

<400> SEQUENCE: 299
ccucacccag cucucuggcc cucu 24

<210> SEQ ID NO 300
<211> LENGTH: 21
<212> TYPE: RNA
<213> ORGANISM: Homo sapiens

<400> SEQUENCE: 300
acacccucuu ucccuaccgc c 21

<210> SEQ ID NO 301
<211> LENGTH: 22
<212> TYPE: RNA
<213> ORGANISM: Homo sapiens

<400> SEQUENCE: 301
gcucaucccc aucuccuuuc ag 22

<210> SEQ ID NO 302
<211> LENGTH: 22
<212> TYPE: RNA
<213> ORGANISM: Homo sapiens

<400> SEQUENCE: 302
auucuuccug cccuggcucc au 22

<210> SEQ ID NO 303
<211> LENGTH: 21
<212> TYPE: RNA
<213> ORGANISM: Homo sapiens

<400> SEQUENCE: 303
cagccucugc ccuuggccuc c 21

<210> SEQ ID NO 304
<211> LENGTH: 21
<212> TYPE: RNA
<213> ORGANISM: Homo sapiens

<400> SEQUENCE: 304
ugucacccgc uccuugccca g 21

<210> SEQ ID NO 305
<211> LENGTH: 24
<212> TYPE: RNA
<213> ORGANISM: Homo sapiens

<400> SEQUENCE: 305
ugcugccucu ccucuugccu gcag 24

<210> SEQ ID NO 306
<211> LENGTH: 21
<212> TYPE: RNA
<213> ORGANISM: Homo sapiens

<400> SEQUENCE: 306
cuuugcuucc ugcuccccua g 21

<210> SEQ ID NO 307
<211> LENGTH: 21
<212> TYPE: RNA
<213> ORGANISM: Homo sapiens

<400> SEQUENCE: 307
ugcccuucuc uccuccugcc u 21

<210> SEQ ID NO 308
<211> LENGTH: 21
<212> TYPE: RNA
<213> ORGANISM: Homo sapiens

<400> SEQUENCE: 308
uccccuccac uuuccuccua g 21

<210> SEQ ID NO 309
<211> LENGTH: 20
<212> TYPE: RNA
<213> ORGANISM: Homo sapiens

<400> SEQUENCE: 309
ccacugccua ugccccacag 20

<210> SEQ ID NO 310
<211> LENGTH: 22
<212> TYPE: RNA
<213> ORGANISM: Homo sapiens

<400> SEQUENCE: 310
cccugcugcc uucaccugcc ag 22

<210> SEQ ID NO 311
<211> LENGTH: 21
<212> TYPE: RNA
<213> ORGANISM: Homo sapiens

<400> SEQUENCE: 311
uugccugccc ucuuccucca g 21

<210> SEQ ID NO 312
<211> LENGTH: 23
<212> TYPE: RNA
<213> ORGANISM: Homo sapiens

<400> SEQUENCE: 312
agcucccuga aucccugucc cag 23

<210> SEQ ID NO 313
<211> LENGTH: 22
<212> TYPE: RNA
<213> ORGANISM: Homo sapiens

<400> SEQUENCE: 313
caagccucuc cugcccuucc ag 22

<210> SEQ ID NO 314
<211> LENGTH: 21
<212> TYPE: RNA
<213> ORGANISM: Homo sapiens

<400> SEQUENCE: 314
ugacccaccc cucuccacca g 21

<210> SEQ ID NO 315
<211> LENGTH: 19
<212> TYPE: RNA
<213> ORGANISM: Homo sapiens

<400> SEQUENCE: 315
ucuggggucu ugggccauc 19

<210> SEQ ID NO 316
<211> LENGTH: 21
<212> TYPE: RNA
<213> ORGANISM: Homo sapiens

<400> SEQUENCE: 316
ugcugagguc cgggcugugc c 21

<210> SEQ ID NO 317
<211> LENGTH: 22
<212> TYPE: RNA
<213> ORGANISM: Homo sapiens

<400> SEQUENCE: 317
uccgagccug ggucucccuc uu 22

<210> SEQ ID NO 318
<211> LENGTH: 20
<212> TYPE: RNA
<213> ORGANISM: Homo sapiens

<400> SEQUENCE: 318
ggggagcugu ggaagcagua 20

<210> SEQ ID NO 319
<211> LENGTH: 18
<212> TYPE: RNA

<213> ORGANISM: Homo sapiens

<400> SEQUENCE: 319
uccagugccc uccucucc 18

<210> SEQ ID NO 320
<211> LENGTH: 20
<212> TYPE: RNA
<213> ORGANISM: Homo sapiens

<400> SEQUENCE: 320
cuguaugccc ucaccgcuca 20

<210> SEQ ID NO 321
<211> LENGTH: 21
<212> TYPE: RNA
<213> ORGANISM: Homo sapiens

<400> SEQUENCE: 321
ccaguccugu gccugccgcc u 21

<210> SEQ ID NO 322
<211> LENGTH: 22
<212> TYPE: RNA
<213> ORGANISM: Homo sapiens

<400> SEQUENCE: 322
gagagcagug uguguugccu gg 22

<210> SEQ ID NO 323
<211> LENGTH: 22
<212> TYPE: RNA
<213> ORGANISM: Homo sapiens

<400> SEQUENCE: 323
cgccucuuca gcgcugucuu cc 22

<210> SEQ ID NO 324
<211> LENGTH: 22
<212> TYPE: RNA
<213> ORGANISM: Homo sapiens

<400> SEQUENCE: 324
guugggacaa gaggacgguc uu 22

<210> SEQ ID NO 325
<211> LENGTH: 21
<212> TYPE: RNA
<213> ORGANISM: Homo sapiens

<400> SEQUENCE: 325
gguggggcaa ugggaucagg u 21

<210> SEQ ID NO 326
<211> LENGTH: 22
<212> TYPE: RNA
<213> ORGANISM: Homo sapiens

<400> SEQUENCE: 326
cggggagaga acgcagugac gu 22

<210> SEQ ID NO 327
<211> LENGTH: 18

<212> TYPE: RNA
<213> ORGANISM: Homo sapiens

<400> SEQUENCE: 327
cagccccaca gccucaga 18

<210> SEQ ID NO 328
<211> LENGTH: 20
<212> TYPE: RNA
<213> ORGANISM: Homo sapiens

<400> SEQUENCE: 328
uguuccucug ucucccagac 20

<210> SEQ ID NO 329
<211> LENGTH: 18
<212> TYPE: RNA
<213> ORGANISM: Homo sapiens

<400> SEQUENCE: 329
gggcucacau caccccau 18

<210> SEQ ID NO 330
<211> LENGTH: 23
<212> TYPE: RNA
<213> ORGANISM: Homo sapiens

<400> SEQUENCE: 330
ccuccguguu accuguccuc uag 23

<210> SEQ ID NO 331
<211> LENGTH: 20
<212> TYPE: RNA
<213> ORGANISM: Homo sapiens

<400> SEQUENCE: 331
aggcauggga ggucagguga 20

<210> SEQ ID NO 332
<211> LENGTH: 22
<212> TYPE: RNA
<213> ORGANISM: Homo sapiens

<400> SEQUENCE: 332
aaaaugaaau gagcccagcc ca 22

<210> SEQ ID NO 333
<211> LENGTH: 21
<212> TYPE: RNA
<213> ORGANISM: Homo sapiens

<400> SEQUENCE: 333
ccugcagaga ggaagcccuu c 21

<210> SEQ ID NO 334
<211> LENGTH: 22
<212> TYPE: RNA
<213> ORGANISM: Homo sapiens

<400> SEQUENCE: 334
accugccagc accucccugc ag 22

<210> SEQ ID NO 335

<211> LENGTH: 25
<212> TYPE: RNA
<213> ORGANISM: Homo sapiens

<400> SEQUENCE: 335
caugcugacc ucccuccugc cccag 25

<210> SEQ ID NO 336
<211> LENGTH: 22
<212> TYPE: RNA
<213> ORGANISM: Homo sapiens

<400> SEQUENCE: 336
aaggcccggg cuuuccuccc ag 22

<210> SEQ ID NO 337
<211> LENGTH: 22
<212> TYPE: RNA
<213> ORGANISM: Homo sapiens

<400> SEQUENCE: 337
guccacuucu gccugcccug cc 22

<210> SEQ ID NO 338
<211> LENGTH: 21
<212> TYPE: RNA
<213> ORGANISM: Homo sapiens

<400> SEQUENCE: 338
ucauccucgu cucccuccca g 21

<210> SEQ ID NO 339
<211> LENGTH: 21
<212> TYPE: RNA
<213> ORGANISM: Homo sapiens

<400> SEQUENCE: 339
ggcugggugc ucuugugcag u 21

<210> SEQ ID NO 340
<211> LENGTH: 22
<212> TYPE: RNA
<213> ORGANISM: Homo sapiens

<400> SEQUENCE: 340
gcccugaacg aggggucugg ag 22

<210> SEQ ID NO 341
<211> LENGTH: 22
<212> TYPE: RNA
<213> ORGANISM: Homo sapiens

<400> SEQUENCE: 341
gguucccucu ccaaaugugu cu 22

<210> SEQ ID NO 342
<211> LENGTH: 22
<212> TYPE: RNA
<213> ORGANISM: Homo sapiens

<400> SEQUENCE: 342
uccgaacucu ccauuccucu gc 22

<210> SEQ ID NO 343
<211> LENGTH: 23
<212> TYPE: RNA
<213> ORGANISM: Homo sapiens

<400> SEQUENCE: 343
ccucaccacc ccuucugccu gca 23

<210> SEQ ID NO 344
<211> LENGTH: 22
<212> TYPE: RNA
<213> ORGANISM: Homo sapiens

<400> SEQUENCE: 344
gagcuuuugg cccggguuau ac 22

<210> SEQ ID NO 345
<211> LENGTH: 20
<212> TYPE: RNA
<213> ORGANISM: Homo sapiens

<400> SEQUENCE: 345
cucgcccugu cuccegcuag 20

<210> SEQ ID NO 346
<211> LENGTH: 19
<212> TYPE: RNA
<213> ORGANISM: Homo sapiens

<400> SEQUENCE: 346
uggaugacag uggaggccu 19

<210> SEQ ID NO 347
<211> LENGTH: 23
<212> TYPE: RNA
<213> ORGANISM: Homo sapiens

<400> SEQUENCE: 347
caccuuugug uccccauccu gca 23

<210> SEQ ID NO 348
<211> LENGTH: 21
<212> TYPE: RNA
<213> ORGANISM: Homo sapiens

<400> SEQUENCE: 348
cggcgcccgu gucuccucca g 21

<210> SEQ ID NO 349
<211> LENGTH: 22
<212> TYPE: RNA
<213> ORGANISM: Homo sapiens

<400> SEQUENCE: 349
ugcaugaccc uucccucccc ac 22

<210> SEQ ID NO 350
<211> LENGTH: 21
<212> TYPE: RNA
<213> ORGANISM: Homo sapiens

<400> SEQUENCE: 350
caccucuccu ggcaucgccc c 21

<210> SEQ ID NO 351
<211> LENGTH: 24
<212> TYPE: RNA
<213> ORGANISM: Homo sapiens

<400> SEQUENCE: 351
uguaggcaug aggcagggcc cagg 24

<210> SEQ ID NO 352
<211> LENGTH: 21
<212> TYPE: RNA
<213> ORGANISM: Homo sapiens

<400> SEQUENCE: 352
ucucuggucu ugccacccca g 21

<210> SEQ ID NO 353
<211> LENGTH: 21
<212> TYPE: RNA
<213> ORGANISM: Homo sapiens

<400> SEQUENCE: 353
accagggcca gcagggaaug u 21

<210> SEQ ID NO 354
<211> LENGTH: 21
<212> TYPE: RNA
<213> ORGANISM: Homo sapiens

<400> SEQUENCE: 354
ugaccccuuc ugucucccua g 21

<210> SEQ ID NO 355
<211> LENGTH: 22
<212> TYPE: RNA
<213> ORGANISM: Homo sapiens

<400> SEQUENCE: 355
cagccagccc cugcucaccc cu 22

<210> SEQ ID NO 356
<211> LENGTH: 23
<212> TYPE: RNA
<213> ORGANISM: Homo sapiens

<400> SEQUENCE: 356
ugacccccau gucgccucug uag 23

<210> SEQ ID NO 357
<211> LENGTH: 18
<212> TYPE: RNA
<213> ORGANISM: Homo sapiens

<400> SEQUENCE: 357
uggaccucuc cuccccag 18

<210> SEQ ID NO 358
<211> LENGTH: 21
<212> TYPE: RNA
<213> ORGANISM: Homo sapiens

<400> SEQUENCE: 358
ccgccuucuc uccuccccca g 21

<210> SEQ ID NO 359
<211> LENGTH: 22
<212> TYPE: RNA
<213> ORGANISM: Homo sapiens

<400> SEQUENCE: 359
auccucucuu cccucucccc ag 22

<210> SEQ ID NO 360
<211> LENGTH: 22
<212> TYPE: RNA
<213> ORGANISM: Homo sapiens

<400> SEQUENCE: 360
uuuccugucc uccaaccaga cc 22

<210> SEQ ID NO 361
<211> LENGTH: 22
<212> TYPE: RNA
<213> ORGANISM: Homo sapiens

<400> SEQUENCE: 361
gucccucucc aaaugugucu ug 22

<210> SEQ ID NO 362
<211> LENGTH: 23
<212> TYPE: RNA
<213> ORGANISM: Homo sapiens

<400> SEQUENCE: 362
ggcagguucu cacccucucu agg 23

<210> SEQ ID NO 363
<211> LENGTH: 22
<212> TYPE: RNA
<213> ORGANISM: Homo sapiens

<400> SEQUENCE: 363
ccucuucccc uugucucucc ag 22

<210> SEQ ID NO 364
<211> LENGTH: 22
<212> TYPE: RNA
<213> ORGANISM: Homo sapiens

<400> SEQUENCE: 364
gcaggugcuc acuuguccuc cu 22

<210> SEQ ID NO 365
<211> LENGTH: 18
<212> TYPE: RNA
<213> ORGANISM: Homo sapiens

<400> SEQUENCE: 365
cucugggaaa ugggacag 18

<210> SEQ ID NO 366
<211> LENGTH: 22
<212> TYPE: RNA
<213> ORGANISM: Homo sapiens

<400> SEQUENCE: 366
caucucuaag gaacuccccc aa 22

<210> SEQ ID NO 367
<211> LENGTH: 18
<212> TYPE: RNA
<213> ORGANISM: Homo sapiens

<400> SEQUENCE: 367
aggagaaguc gggaaggu 18

<210> SEQ ID NO 368
<211> LENGTH: 22
<212> TYPE: RNA
<213> ORGANISM: Homo sapiens

<400> SEQUENCE: 368
cucucuggcc gucuaccuuc ca 22

<210> SEQ ID NO 369
<211> LENGTH: 22
<212> TYPE: RNA
<213> ORGANISM: Homo sapiens

<400> SEQUENCE: 369
ccucaccauc ccuucugccu gc 22

<210> SEQ ID NO 370
<211> LENGTH: 21
<212> TYPE: RNA
<213> ORGANISM: Homo sapiens

<400> SEQUENCE: 370
cuucucuucu cuccuuccca g 21

<210> SEQ ID NO 371
<211> LENGTH: 23
<212> TYPE: RNA
<213> ORGANISM: Homo sapiens

<400> SEQUENCE: 371
uagguggcgc cggaggaguc auu 23

<210> SEQ ID NO 372
<211> LENGTH: 21
<212> TYPE: RNA
<213> ORGANISM: Homo sapiens

<400> SEQUENCE: 372
ugacugagcu ucuccccaca g 21

<210> SEQ ID NO 373
<211> LENGTH: 21
<212> TYPE: RNA
<213> ORGANISM: Homo sapiens

<400> SEQUENCE: 373
cuggccucuu cuuucuccua g 21

<210> SEQ ID NO 374
<211> LENGTH: 20
<212> TYPE: RNA
<213> ORGANISM: Homo sapiens

<400> SEQUENCE: 374
acucaaacug ugggggcacu 20

<210> SEQ ID NO 375
<211> LENGTH: 22
<212> TYPE: RNA
<213> ORGANISM: Homo sapiens

<400> SEQUENCE: 375
acuccagccc cacagccuca gc 22

<210> SEQ ID NO 376
<211> LENGTH: 23
<212> TYPE: RNA
<213> ORGANISM: Homo sapiens

<400> SEQUENCE: 376
cucucaccac ugcccuccca cag 23

<210> SEQ ID NO 377
<211> LENGTH: 22
<212> TYPE: RNA
<213> ORGANISM: Homo sapiens

<400> SEQUENCE: 377
ccaccucccc ugcaaacguc ca 22

<210> SEQ ID NO 378
<211> LENGTH: 22
<212> TYPE: RNA
<213> ORGANISM: Homo sapiens

<400> SEQUENCE: 378
agccccugcc caccgcacac ug 22

<210> SEQ ID NO 379
<211> LENGTH: 22
<212> TYPE: RNA
<213> ORGANISM: Homo sapiens

<400> SEQUENCE: 379
gguccagagg ggagauaggu uc 22

<210> SEQ ID NO 380
<211> LENGTH: 22
<212> TYPE: RNA
<213> ORGANISM: Homo sapiens

<400> SEQUENCE: 380
gucauacacg gcucuccucu cu 22

<210> SEQ ID NO 381
<211> LENGTH: 23
<212> TYPE: RNA
<213> ORGANISM: Homo sapiens

<400> SEQUENCE: 381
ugucacucgg cucggcccac uac 23

<210> SEQ ID NO 382
<211> LENGTH: 22
<212> TYPE: RNA
<213> ORGANISM: Homo sapiens

<400> SEQUENCE: 382
ccucccacac ccaaggcuug ca 22

<210> SEQ ID NO 383
<211> LENGTH: 21
<212> TYPE: RNA
<213> ORGANISM: Homo sapiens

<400> SEQUENCE: 383
uccucuucuc ccuccuccca g 21

<210> SEQ ID NO 384
<211> LENGTH: 20
<212> TYPE: RNA
<213> ORGANISM: Homo sapiens

<400> SEQUENCE: 384
cuuccucguc ugucugcccc 20

<210> SEQ ID NO 385
<211> LENGTH: 21
<212> TYPE: RNA
<213> ORGANISM: Homo sapiens

<400> SEQUENCE: 385
uacccagucu ccggugcagc c 21

<210> SEQ ID NO 386
<211> LENGTH: 22
<212> TYPE: RNA
<213> ORGANISM: Homo sapiens

<400> SEQUENCE: 386
cugggacagg aggaggaggc ag 22

<210> SEQ ID NO 387
<211> LENGTH: 19
<212> TYPE: RNA
<213> ORGANISM: Homo sapiens

<400> SEQUENCE: 387
ugcccuccuu ucuucccuc 19

<210> SEQ ID NO 388
<211> LENGTH: 23
<212> TYPE: RNA
<213> ORGANISM: Homo sapiens

<400> SEQUENCE: 388
uagcccccag gcuucacuug gcg 23

<210> SEQ ID NO 389
<211> LENGTH: 23
<212> TYPE: RNA
<213> ORGANISM: Homo sapiens

<400> SEQUENCE: 389
ugucugcccg caugccugcc ucu 23

<210> SEQ ID NO 390
<211> LENGTH: 23
<212> TYPE: RNA
<213> ORGANISM: Homo sapiens

<400> SEQUENCE: 390
ucugcucaua ccccaugguu ucu 23

<210> SEQ ID NO 391
<211> LENGTH: 18
<212> TYPE: RNA
<213> ORGANISM: Homo sapiens

<400> SEQUENCE: 391
cagcaguccc ucccccug 18

<210> SEQ ID NO 392
<211> LENGTH: 18
<212> TYPE: RNA
<213> ORGANISM: Homo sapiens

<400> SEQUENCE: 392
cauucaacua gugauugu 18

<210> SEQ ID NO 393
<211> LENGTH: 67
<212> TYPE: RNA
<213> ORGANISM: Homo sapiens

<400> SEQUENCE: 393
gugggagggg agaggcagca agcacacagg gccugggacu agcaugcuga ccucccuccu 60
gccccag 67

<210> SEQ ID NO 394
<211> LENGTH: 17
<212> TYPE: RNA
<213> ORGANISM: Homo sapiens

<400> SEQUENCE: 394
uuggaggcgu ggguuuu 17

<210> SEQ ID NO 395
<211> LENGTH: 20
<212> TYPE: RNA
<213> ORGANISM: Homo sapiens

<400> SEQUENCE: 395
aaaugggugg ucugaggcaa 20

<210> SEQ ID NO 396
<211> LENGTH: 74
<212> TYPE: RNA
<213> ORGANISM: Homo sapiens

<400> SEQUENCE: 396
gggaguuggg cccaggagua aacaggauua gugcuuaugc uaagaugucu ucacugucac 60
uucucugccc auag 74

<210> SEQ ID NO 397
<211> LENGTH: 67
<212> TYPE: RNA
<213> ORGANISM: Homo sapiens

<400> SEQUENCE: 397
ucuauuuagc caauugucca ucuuuagcua uucugaaugc cuaaagauag acaauuggcu 60
aaauaga 67

<210> SEQ ID NO 398
<211> LENGTH: 75
<212> TYPE: RNA
<213> ORGANISM: Homo sapiens

<400> SEQUENCE: 398
aagcaagacu gaggggccuc agaccgagcu uuuggaaaau agaaaagucu cgcucucugc 60
cccucagccu aacuu 75

<210> SEQ ID NO 399
<211> LENGTH: 18
<212> TYPE: RNA
<213> ORGANISM: Homo sapiens

<400> SEQUENCE: 399 ggguccc ggg gagggggg 18

<210> SEQ ID NO 400
<211> LENGTH: 72
<212> TYPE: RNA
<213> ORGANISM: Homo sapiens

<400> SEQUENCE: 400
aaaauguugg ccuucucguc ccaguucuuc ccaaaguuga gaaaagcugg guugagagga 60
ugaaaagaaa aa 72

<210> SEQ ID NO 401
<211> LENGTH: 72
<212> TYPE: RNA
<213> ORGANISM: Homo sapiens

<400> SEQUENCE: 401
uaucaauaag ccuucucuuc ccaguucuuc uuggagucag gaaaagcugg guugagagga 60
gcagaaaaga aa 72

<210> SEQ ID NO 402
<211> LENGTH: 65
<212> TYPE: RNA
<213> ORGANISM: Homo sapiens

<400> SEQUENCE: 402
gagggugggc gagggcggcu gagcggcucc aucccccggc cugcucaucc cccucgcccu 60
cucag 65

<210> SEQ ID NO 403
<211> LENGTH: 22
<212> TYPE: RNA
<213> ORGANISM: Homo sapiens

<400> SEQUENCE: 403
aggagagugg auuccaggug gu 22

<210> SEQ ID NO 404
<211> LENGTH: 74
<212> TYPE: RNA
<213> ORGANISM: Homo sapiens

<400> SEQUENCE: 404
gggaaagcgu gggaugucca ugaagucagg ugauggugau aaggucaagg ccuguucauu 60
ggaacccugc gcag 74

<210> SEQ ID NO 405
<211> LENGTH: 80
<212> TYPE: RNA
<213> ORGANISM: Homo sapiens

<400> SEQUENCE: 405
gugagugugg gguggcuggg gcgggggggg cccggggacg gcuugggccu gccuagucgg 60
ccugaccacc caccccacag 80

<210> SEQ ID NO 406
<211> LENGTH: 82
<212> TYPE: RNA
<213> ORGANISM: Homo sapiens

<400> SEQUENCE: 406
gugaguggga ggccagggca cggcaggggg agcugcaggg cuaugggagg ggccccagcg 60
ucugagcccu guccucccgc ag 82

<210> SEQ ID NO 407
<211> LENGTH: 82
<212> TYPE: RNA
<213> ORGANISM: Homo sapiens

<400> SEQUENCE: 407
gugaguggga ggccagggca cggcaggggg agcugcaggg cuaugggagg ggccccagcg 60
ucugagcccu guccucccgc ag 82

<210> SEQ ID NO 408
<211> LENGTH: 22
<212> TYPE: RNA
<213> ORGANISM: Homo sapiens

<400> SEQUENCE: 408
gcugaacugg gcugagcugg gc 22

<210> SEQ ID NO 409
<211> LENGTH: 99
<212> TYPE: RNA
<213> ORGANISM: Homo sapiens

<400> SEQUENCE: 409
uggacuucag auuuaacuuc ucauuuucug guuccuucua augaguaugc uuaacuuggu 60
agaaggaacc agaaaaugag aaguugagua ggaacucua 99

<210> SEQ ID NO 410
<211> LENGTH: 95
<212> TYPE: RNA
<213> ORGANISM: Homo sapiens

<400> SEQUENCE: 410
gaguuccuac ucaacuucuc auuuucuggu uccuucuacc aaguuaagca uacucauuag 60
aaggaaccag aaaaugagaa guuaaaucug aaguc 95

<210> SEQ ID NO 411
<211> LENGTH: 87
<212> TYPE: RNA
<213> ORGANISM: Homo sapiens

<400> SEQUENCE: 411
ggucgcauuu cuccuucuua ccagcgcguu uucaguuuca uagggaagcc uuuccaugaa 60
acuggagcgc cuggaggaga aggggcc 87

<210> SEQ ID NO 412
<211> LENGTH: 54
<212> TYPE: RNA
<213> ORGANISM: Homo sapiens

<400> SEQUENCE: 412
aaaaguaauu gcgguuuuug cuauugguuu uaauggcagu uacuuuugca ccag 54

<210> SEQ ID NO 413
<211> LENGTH: 21
<212> TYPE: RNA
<213> ORGANISM: Homo sapiens

<400> SEQUENCE: 413
uccugcgcgu cccagaugcc c 21

<210> SEQ ID NO 414
<211> LENGTH: 76
<212> TYPE: RNA
<213> ORGANISM: Homo sapiens

<400> SEQUENCE: 414
aagccuggca uauuugguau aacuuaagca ccagguaaaa ucuggugcuu aaguuguacc 60
aaguauagcc aaguuu 76

<210> SEQ ID NO 415
<211> LENGTH: 111
<212> TYPE: RNA
<213> ORGANISM: Homo sapiens

<400> SEQUENCE: 415
agaguguuca aggacagcaa gaaaaaugag ggacuuucag ggcagcugu guuuucugac 60 ucagucauaa ugccccuaaa aauccuuauu guucuugcag ugugcaucgg g 111

<210> SEQ ID NO 416
<211> LENGTH: 17
<212> TYPE: RNA
<213> ORGANISM: Homo sapiens

<400> SEQUENCE: 416
gcugggcgag gcuggca 17

<210> SEQ ID NO 417
<211> LENGTH: 88
<212> TYPE: RNA
<213> ORGANISM: Homo sapiens

<400> SEQUENCE: 417
guggggccag gcgguggugg gcacugcugg ggugggcaca gcagccaugc agagcgggca 60
uuugaccccg ugccacccuu uuccccag 88

<210> SEQ ID NO 418
<211> LENGTH: 66
<212> TYPE: RNA
<213> ORGANISM: Homo sapiens

<400> SEQUENCE: 418
ugacugggga gcagaaggag aacccaagaa aagcugacuu ggaggucccu ccuucugucc 60
ccacag 66

<210> SEQ ID NO 419
<211> LENGTH: 20
<212> TYPE: RNA
<213> ORGANISM: Homo sapiens

<400> SEQUENCE: 419
agagaugaag cgggggggcg 20

<210> SEQ ID NO 420
<211> LENGTH: 62
<212> TYPE: RNA
<213> ORGANISM: Homo sapiens

<400> SEQUENCE: 420
ccuucugcgg cagagcuggg gucaccagcc cucauguacu ugugacuucu ccccugccac 60
ag 62

<210> SEQ ID NO 421
<211> LENGTH: 18
<212> TYPE: RNA
<213> ORGANISM: Homo sapiens

<400> SEQUENCE: 421
aggcugggcu gggacgga 18

<210> SEQ ID NO 422
<211> LENGTH: 22
<212> TYPE: RNA
<213> ORGANISM: Homo sapiens

<400> SEQUENCE: 422
gcuggugcaa aaguaauggc gg 22

<210> SEQ ID NO 423
<211> LENGTH: 23
<212> TYPE: RNA
<213> ORGANISM: Homo sapiens

<400> SEQUENCE: 423
gugagugugg auccuggagg aau 23

<210> SEQ ID NO 424
<211> LENGTH: 91
<212> TYPE: RNA
<213> ORGANISM: Homo sapiens

<400> SEQUENCE: 424
aaacgauacu aaacuguuuu ugcgaugugu uccuaauaug cacuauaaau auauugggaa 60
cauuuugcau guauaguuuu guaucaauau a 91

<210> SEQ ID NO 425
<211> LENGTH: 100
<212> TYPE: RNA
<213> ORGANISM: Homo sapiens

<400> SEQUENCE: 425
ccaaagaaag augcuaaacu auuuuugcga uguguuccua auauguaaua uaaauguauu 60
ggggacauuu ugcauucaua guuuuguauc aauaauaugg 100

<210> SEQ ID NO 426
<211> LENGTH: 19
<212> TYPE: RNA
<213> ORGANISM: Homo sapiens

<400> SEQUENCE: 426
aucccaccac ugccaccau 19

<210> SEQ ID NO 427
<211> LENGTH: 60
<212> TYPE: RNA
<213> ORGANISM: Homo sapiens

<400> SEQUENCE: 427
ggcaguggcc agagcccugc agugcugggc augggcuucu cgugggcucu ggccacggcc 60

<210> SEQ ID NO 428
<211> LENGTH: 66
<212> TYPE: RNA
<213> ORGANISM: Homo sapiens

<400> SEQUENCE: 428
ucaagacggg gagucaggca guggguggaga uggagagccc ugagccucca cucuccuggc 60
ccccag 66

<210> SEQ ID NO 429
<211> LENGTH: 98
<212> TYPE: RNA
<213> ORGANISM: Homo sapiens

<400> SEQUENCE: 429
cuuggucaau aggaaagagg ugggaccucc uggcuuuucc ucugcagcau ggcucggacc 60
uagugcaaug uuuaagcucc ccucucuuuc cuguucag 98

<210> SEQ ID NO 430
<211> LENGTH: 72
<212> TYPE: RNA
<213> ORGANISM: Homo sapiens

<400> SEQUENCE: 430
gguggaguag agaggaaaag uuagggucag uggcagagcc aggcagaugc ugacccuuuu 60
ucucuuuccc ag 72

<210> SEQ ID NO 431
<211> LENGTH: 90
<212> TYPE: RNA
<213> ORGANISM: Homo sapiens

<400> SEQUENCE: 431
gugucucucu ggagacccug cagccuuccc acccaccagg gagcuuucca ugggcugugg 60
ggaaggcguc agugucgggu gagggaacac 90

<210> SEQ ID NO 432
<211> LENGTH: 84
<212> TYPE: RNA
<213> ORGANISM: Homo sapiens

<400> SEQUENCE: 432
uaaagacugu agaggcaacu gguguucuca cgcaaagugg ccagggugug ggagacuaga 60
ucuuugacuc uggcagucuc cagg 84

<210> SEQ ID NO 433
<211> LENGTH: 93
<212> TYPE: RNA
<213> ORGANISM: Homo sapiens

<400> SEQUENCE: 433
gugcuuccug cgggcugagc gcgggcugag cgcugccagu cagcgcucac auuaaggcug 60
acagcgcccu gccuggcucg gccggcgaag cuc 93

<210> SEQ ID NO 434
<211> LENGTH: 86
<212> TYPE: RNA
<213> ORGANISM: Homo sapiens

<400> SEQUENCE: 434
ggggcugggg gugugggggag agagagugca cagccagcuc agggauuaaa gcucuuucuc 60
ucucucucuc ucccacuucc cugcag 86

<210> SEQ ID NO 435
<211> LENGTH: 19
<212> TYPE: RNA
<213> ORGANISM: Homo sapiens

<400> SEQUENCE: 435
ggccuuguuc cuguccccca 19

<210> SEQ ID NO 436
<211> LENGTH: 74
<212> TYPE: RNA
<213> ORGANISM: Homo sapiens

<400> SEQUENCE: 436
gaguaggcuu agguuaugua cguagucuag gccauacgug uuggagauug agacuaguag 60
ggcuaggccu acug 74

<210> SEQ ID NO 437
<211> LENGTH: 72
<212> TYPE: RNA
<213> ORGANISM: Homo sapiens

<400> SEQUENCE: 437
augagcgggu gggagcagau cuuauugaga guuccuucuc cugcuccuga uugucuuccc 60
ccacccucac ag 72

<210> SEQ ID NO 438
<211> LENGTH: 84
<212> TYPE: RNA
<213> ORGANISM: Homo sapiens

<400> SEQUENCE: 438
acagguagug ucccucaggg cuguagaaca gggcugggau uacuaaagcc cuguucuaug 60
cccugaggga cacugagcau guca 84

<210> SEQ ID NO 439
<211> LENGTH: 83
<212> TYPE: RNA
<213> ORGANISM: Homo sapiens

<400> SEQUENCE: 439
ucaggcugug acccucuuga gggaagcacu uucuguuguc ugaaagaaga gaaagugcuu 60
ccuuuuagag gcuuacuguc uga 83

<210> SEQ ID NO 440
<211> LENGTH: 84
<212> TYPE: RNA
<213> ORGANISM: Homo sapiens

<400> SEQUENCE: 440
ucucaugcag ucauucucca aaagggagca cuuucuguuu gaaagaaaac aaagugccuc 60
cuuuuagagu guuacuguuu gaga 84

<210> SEQ ID NO 441
<211> LENGTH: 84
<212> TYPE: RNA
<213> ORGANISM: Homo sapiens

<400> SEQUENCE: 441
ucucagucug uggcacucag ccuugagggc acuuucuggu gccagaauga aagugcuguc 60
auagcugagg uccaaugacu gagg 84

<210> SEQ ID NO 442
<211> LENGTH: 98
<212> TYPE: RNA
<213> ORGANISM: Homo sapiens

<400> SEQUENCE: 442
gguacuucuc agucuguggc acucagccuu gagggcacuu ucuggugcca gaaugaaagu 60
gcugucauag cugaggucca augacugagg cgagcacc 98

<210> SEQ ID NO 443
<211> LENGTH: 79
<212> TYPE: RNA
<213> ORGANISM: Homo sapiens

<400> SEQUENCE: 443
cccaucaggg cucagggauu ggauggaggu gaugggggca ggggaugggu cucacccucc 60
cuucuuccug ggcccucag 79

<210> SEQ ID NO 444
<211> LENGTH: 80
<212> TYPE: RNA
<213> ORGANISM: Homo sapiens

<400> SEQUENCE: 444
cauccaggac aauggugagu gccggugccu gcccuggggc cgucccugcg caggggccgg 60
gugcucaccg caucugcccc 80

<210> SEQ ID NO 445
<211> LENGTH: 67
<212> TYPE: RNA
<213> ORGANISM: Homo sapiens

<400> SEQUENCE: 445
ccugcaggca gaaguggggc ugacagggca gaggguugcg cccccucacc aucccuucug 60
ccugcag 67

<210> SEQ ID NO 446
<211> LENGTH: 67
<212> TYPE: RNA
<213> ORGANISM: Homo sapiens

<400> SEQUENCE: 446
ccugcaggca gaaguggggc ugacagggca gaggguugcg cccccucacc aucccuucug 60
ccugcag 67

<210> SEQ ID NO 447
<211> LENGTH: 67
<212> TYPE: RNA
<213> ORGANISM: Homo sapiens

<400> SEQUENCE: 447
ccugcaggca gaaguggggc ugacagggca gaggguugcg cccccucacc aucccuucug 60
ccugcag 67

<210> SEQ ID NO 448
<211> LENGTH: 67
<212> TYPE: RNA
<213> ORGANISM: Homo sapiens

<400> SEQUENCE: 448
ccugcaggca gaaguggggc ugacagggca gaggguugcg cccccucacc aucccuucug 60
ccugcag 67

<210> SEQ ID NO 449
<211> LENGTH: 22
<212> TYPE: RNA
<213> ORGANISM: Homo sapiens

<400> SEQUENCE: 449
gcugcgggcu gcggucaggg cg 22

<210> SEQ ID NO 450
<211> LENGTH: 22
<212> TYPE: RNA
<213> ORGANISM: Homo sapiens

<400> SEQUENCE: 450
acaguagagg gaggaaucgc ag 22

<210> SEQ ID NO 451
<211> LENGTH: 66
<212> TYPE: RNA
<213> ORGANISM: Homo sapiens

<400> SEQUENCE: 451
gggaggaggg aggagauggg ccaaguuccc ucuggcugga acgcccuucc cccccuucuu 60
caccug 66

<210> SEQ ID NO 452
<211> LENGTH: 19
<212> TYPE: RNA
<213> ORGANISM: Homo sapiens

<400> SEQUENCE: 452
agagcuggcu gaagggcag 19

<210> SEQ ID NO 453

<211> LENGTH: 21
<212> TYPE: RNA
<213> ORGANISM: Homo sapiens

<400> SEQUENCE: 453
ccaggcucug caguggggaac u 21

<210> SEQ ID NO 454
<211> LENGTH: 19
<212> TYPE: RNA
<213> ORGANISM: Homo sapiens

<400> SEQUENCE: 454
agguugacau acguuuccc 19

<210> SEQ ID NO 455
<211> LENGTH: 23
<212> TYPE: RNA
<213> ORGANISM: Homo sapiens

<400> SEQUENCE: 455
cgggcugucc ggaggggucg gcu 23

<210> SEQ ID NO 456
<211> LENGTH: 66
<212> TYPE: RNA
<213> ORGANISM: Homo sapiens

<400> SEQUENCE: 456
gacggcuggg agaagagugg ugaagaagag uauugauugu gcuguucgcc acuucccucc 60
cugcag 66

<210> SEQ ID NO 457
<211> LENGTH: 102
<212> TYPE: RNA
<213> ORGANISM: Homo sapiens

<400> SEQUENCE: 457
uguguucccu auccuccuua ugucccaccc ccacuccugu uugaauauuu caccagaaac 60
aggagugggg ggugggacgu aaggaggaug ggggaaagaa ca 102

<210> SEQ ID NO 458
<211> LENGTH: 86
<212> TYPE: RNA
<213> ORGANISM: Homo sapiens

<400> SEQUENCE: 458
uugguacuug gagagaggug guccguggcg cguucgcuuu auuuauggcg cacauuacac 60
ggucgaccuc uuugcaguau cuaauc 86

<210> SEQ ID NO 459
<211> LENGTH: 58
<212> TYPE: RNA
<213> ORGANISM: Homo sapiens

<400> SEQUENCE: 459
uaugcaggcc uguguacagc acucaggcag ugccaugagc cugugcuugu cccugcag 58

<210> SEQ ID NO 460
<211> LENGTH: 87
<212> TYPE: RNA
<213> ORGANISM: Homo sapiens

<400> SEQUENCE: 460
cccucaucuc ugggcagggg cuuauuguag gagucucuga agagagcugu ggacugaccu 60
gcuuuaaccc uuccccaggu ucccauu 87

<210> SEQ ID NO 461
<211> LENGTH: 107
<212> TYPE: RNA
<213> ORGANISM: Homo sapiens

<400> SEQUENCE: 461
ggcacuugcu uggggguuag ugaggacagg gcaaauucac gagauugggu ugugcagagg 60
cugacacuug gauuuuccug ggccucagga cuuccuuuca gacaugg 107

<210> SEQ ID NO 462
<211> LENGTH: 85
<212> TYPE: RNA
<213> ORGANISM: Homo sapiens

<400> SEQUENCE: 462
uuuuugugug ugaaauuagg uaguggcagu ggaacacuau auuaaucagg uuuccacugc 60
cacuaccuaa uuucucagau ggaaa 85

<210> SEQ ID NO 463
<211> LENGTH: 19
<212> TYPE: RNA
<213> ORGANISM: Homo sapiens

<400> SEQUENCE: 463
aagugugcag ggcacuggu 19

<210> SEQ ID NO 464
<211> LENGTH: 20
<212> TYPE: RNA
<213> ORGANISM: Homo sapiens

<400> SEQUENCE: 464
gcucggacug agcagguggg 20

<210> SEQ ID NO 465
<211> LENGTH: 18
<212> TYPE: RNA
<213> ORGANISM: Homo sapiens

<400> SEQUENCE: 465
ugaggcgggg gggcgagc 18

<210> SEQ ID NO 466
<211> LENGTH: 21
<212> TYPE: RNA
<213> ORGANISM: Homo sapiens

<400> SEQUENCE: 466
gcccuccgcc cgugcacccc g 21

<210> SEQ ID NO 467
<211> LENGTH: 22
<212> TYPE: RNA
<213> ORGANISM: Homo sapiens

<400> SEQUENCE: 467
uaugcauugu auuuuuaggu cc 22

<210> SEQ ID NO 468
<211> LENGTH: 80
<212> TYPE: RNA
<213> ORGANISM: Homo sapiens

<400> SEQUENCE: 468
gggaagcagg ccaaccucga cgaucuccuc agcaccugaa cgccaaggcu ggggagaucc 60
ucgagguugg ccugcuuucc 80

<210> SEQ ID NO 469
<211> LENGTH: 81
<212> TYPE: RNA
<213> ORGANISM: Homo sapiens

<400> SEQUENCE: 469
ugugcaucgu ggucaaaugc ucagacuccu gugguggcug cucaugcacc acggauguuu 60
gagcaugugc uacggugucu a 81

<210> SEQ ID NO 470
<211> LENGTH: 81
<212> TYPE: RNA
<213> ORGANISM: Homo sapiens

<400> SEQUENCE: 470
ugugcaucgu ggucaaaugc ucagacuccu gugguggcug cuuaugcacc acggauguuu 60
gagcaugugc uauggugucu a 81

<210> SEQ ID NO 471
<211> LENGTH: 76
<212> TYPE: RNA
<213> ORGANISM: Homo sapiens

<400> SEQUENCE: 471
ugugacccua gaauaauuac ccaacgucuc ugagucucgg uuuugagagg gugaguaauu 60
auucuagggu cacaca 76

<210> SEQ ID NO 472
<211> LENGTH: 76
<212> TYPE: RNA
<213> ORGANISM: Homo sapiens

<400> SEQUENCE: 472
ugugacccua gaauaauuac ucacccucuc aaaaccgaga cucagagacg uuggguaauu 60
auucuagggu cacaca 76

<210> SEQ ID NO 473
<211> LENGTH: 80
<212> TYPE: RNA
<213> ORGANISM: Homo sapiens

<400> SEQUENCE: 473
cgugugagcc cgcccugugc ccggcccacu ucugcuuccu cuuagcgcag gaggggeccc 60 gcacugggag gggcccucac 80

<210> SEQ ID NO 474
<211> LENGTH: 61
<212> TYPE: RNA
<213> ORGANISM: Homo sapiens

<400> SEQUENCE: 474
ccugcgggga caggccaggg caucuaggcu gugcacagug acgccccucc ugcccccaca 60
g 61

<210> SEQ ID NO 475
<211> LENGTH: 98
<212> TYPE: RNA
<213> ORGANISM: Homo sapiens

<400> SEQUENCE: 475
uugaggccuu aaaguacugu agcagcacau caugguuuac augcuacagu caagaugcga 60
aucauuauuu gcugcucuag aaauuuaagg aaauucau 98

<210> SEQ ID NO 476
<211> LENGTH: 84
<212> TYPE: RNA
<213> ORGANISM: Homo sapiens

<400> SEQUENCE: 476
uucucaauuu uuaguaggaa uuaaaaacaa aacugguaaa ugcagacucu ugguuuccac 60
gggugauucu gauaauuggg aaca 84

<210> SEQ ID NO 477
<211> LENGTH: 111
<212> TYPE: RNA
<213> ORGANISM: Homo sapiens

<400> SEQUENCE: 477
ccacgguccu aguuaaaaag gcacauuccu agacccugcc ucagaacuac ugaacagagu 60
cacugggugu ggaguccagg aaucugcauu uuuaccccua ucgcccccgc c 111

<210> SEQ ID NO 478
<211> LENGTH: 81
<212> TYPE: RNA
<213> ORGANISM: Homo sapiens

<400> SEQUENCE: 478
cauccuccuu acgucccacc ccccacuccu guuucuggug aaauauucaa acaggagugg 60
gggugggaca uaaggaggau a 81

<210> SEQ ID NO 479
<211> LENGTH: 21
<212> TYPE: RNA
<213> ORGANISM: Homo sapiens

<400> SEQUENCE: 479
cagugcaagu guagaugccg a 21

<210> SEQ ID NO 480
<211> LENGTH: 85
<212> TYPE: RNA
<213> ORGANISM: Homo sapiens

<400> SEQUENCE: 480
agccugcggu uccaacaggc gucugucuac guggcuucaa ccaaguucaa agucacgcgg 60
agagauggcu uuggaaccag gggcu 85

<210> SEQ ID NO 481

<211> LENGTH: 18
<212> TYPE: RNA
<213> ORGANISM: Homo sapiens

<400> SEQUENCE: 481
agggggcggg cuccggcg 18

<210> SEQ ID NO 482
<211> LENGTH: 78
<212> TYPE: RNA
<213> ORGANISM: Homo sapiens

<400> SEQUENCE: 482
uugccuaccu uguuagucuc augaucagac acaaauaugg cucuuugugg cuggucauga 60
ggcuaacaag guaggcac 78

<210> SEQ ID NO 483
<211> LENGTH: 72
<212> TYPE: RNA
<213> ORGANISM: Homo sapiens

<400> SEQUENCE: 483
acagguggga gagcagggua uuguggaagc uccaggugcc aaccaccugc cucuauuccc 60
cacucucccc ag 72

<210> SEQ ID NO 484
<211> LENGTH: 90
<212> TYPE: RNA
<213> ORGANISM: Homo sapiens

<400> SEQUENCE: 484
cugugggcug ggccagggag cagcuggugg gugggaagua agaucugacc uggacuccau 60
cccacccacc cccuguuucc uggcccacag 90

<210> SEQ ID NO 485
<211> LENGTH: 110
<212> TYPE: RNA
<213> ORGANISM: Homo sapiens

<400> SEQUENCE: 485
cgccucagag ccgcccgccg uuccuuuuuc cuaugcauau acuucuuuga ggaucuggcc 60
uaaagaggua uagggcaugg gaaaacgggg cggucggguc cuccccagcg 110

<210> SEQ ID NO 486
<211> LENGTH: 66
<212> TYPE: RNA
<213> ORGANISM: Homo sapiens

<400> SEQUENCE: 486 ccgaguggggg cggggcaggu cccugcaggg acugugacac ugaaggaccu gcaccuucgc 60
ccacag 66

<210> SEQ ID NO 487
<211> LENGTH: 25
<212> TYPE: RNA
<213> ORGANISM: Homo sapiens

<400> SEQUENCE: 487
agggaucgcg ggcggguggc ggccu 25

<210> SEQ ID NO 488
<211> LENGTH: 74
<212> TYPE: RNA
<213> ORGANISM: Homo sapiens

<400> SEQUENCE: 488
gugcguggug gcucgaggcg ggggugggg ccucgcccug cuugggcccu cccugaccuc 60 uccgcucccgc acag 74

<210> SEQ ID NO 489
<211> LENGTH: 76
<212> TYPE: RNA
<213> ORGANISM: Homo sapiens

<400> SEQUENCE: 489
ccgcuugccu cgcccagcgc agccccggcc gcugggcgca cccgucccgu ucgucccccgg 60 gaccccgaga gcggcg 76

<210> SEQ ID NO 490
<211> LENGTH: 87
<212> TYPE: RNA
<213> ORGANISM: Homo sapiens

<400> SEQUENCE: 490
gugaggcggg gccaggaggg uguguggcgu gggugcugcg gggccgucag ggugccugcg 60
ggacgcucac cuggcuggcc cgcccag 87

<210> SEQ ID NO 491
<211> LENGTH: 82
<212> TYPE: RNA
<213> ORGANISM: Homo sapiens

<400> SEQUENCE: 491
accuguaggu gacagucagg ggcggggugu gguggggcug gggcuggccc ccuccucaca 60
ccucuccugg caucgccccc ag 82

<210> SEQ ID NO 492
<211> LENGTH: 58
<212> TYPE: RNA
<213> ORGANISM: Homo sapiens

<400> SEQUENCE: 492
gcugaagcuc uaagguuccg ccugcgggca ggaagcggag gaaccuugga gcuucggc 58

<210> SEQ ID NO 493
<211> LENGTH: 102
<212> TYPE: RNA
<213> ORGANISM: Homo sapiens

<400> SEQUENCE: 493
gcuuaucgag gaaaagaucg aggugggguug gggcgggcuc uggggauuug gucucacagc 60
ccggauccca gcccacuuac cuugguuacu cuccuuccuu cu 102

<210> SEQ ID NO 494
<211> LENGTH: 20
<212> TYPE: RNA
<213> ORGANISM: Homo sapiens

<400> SEQUENCE: 494
ggcggcggcg gaggcggggg 20

<210> SEQ ID NO 495
<211> LENGTH: 69
<212> TYPE: RNA
<213> ORGANISM: Homo sapiens

<400> SEQUENCE: 495
gaaccucggg gcauggggga gggaggcugg acaggagagg gcucacccag gcccuguccu 60
cugccccag 69

<210> SEQ ID NO 496
<211> LENGTH: 17
<212> TYPE: RNA
<213> ORGANISM: Homo sapiens

<400> SEQUENCE: 496
ggggcgcggc cggaucg 17

<210> SEQ ID NO 497
<211> LENGTH: 21
<212> TYPE: RNA
<213> ORGANISM: Homo sapiens

<400> SEQUENCE: 497
gugccagcug caguggggga g 21

<210> SEQ ID NO 498
<211> LENGTH: 63
<212> TYPE: RNA
<213> ORGANISM: Homo sapiens

<400> SEQUENCE: 498
gugagugugg auuuggcggg guucgggggu uccgacggcg accucggcga ccccucacuc 60
acc 63

<210> SEQ ID NO 499
<211> LENGTH: 70
<212> TYPE: RNA
<213> ORGANISM: Homo sapiens

<400> SEQUENCE: 499
cccugccagu gcugggggcc acaugagugu gcagucaucc acacacaagu ggcccccaac 60
acuggcaggg 70

<210> SEQ ID NO 500
<211> LENGTH: 105
<212> TYPE: RNA
<213> ORGANISM: Homo sapiens

<400> SEQUENCE: 500
gcccccuuuu cacgcauuug uguuuuacca ccuccaggag acugcccaaa gacucuucag 60
uaucauggag uugguaaagc acagaugcau gaauaauuca acgug 105

<210> SEQ ID NO 501
<211> LENGTH: 63
<212> TYPE: RNA
<213> ORGANISM: Homo sapiens

<400> SEQUENCE: 501
ugggcuagag aggggaagga ugugauguga gcagaugguu cucacucauu cuccucuguc 60
cag 63

<210> SEQ ID NO 502
<211> LENGTH: 20
<212> TYPE: RNA
<213> ORGANISM: Homo sapiens

<400> SEQUENCE: 502
ggcggcgggg agguaggcag 20

<210> SEQ ID NO 503
<211> LENGTH: 87
<212> TYPE: RNA
<213> ORGANISM: Homo sapiens

<400> SEQUENCE: 503
ucccaugcug ugacccucua gagggaagca cuuucuguug ucugaaagaa accaaagcgc 60
uucccuuugg agcguuacgg uuugaga 87

<210> SEQ ID NO 504
<211> LENGTH: 63
<212> TYPE: RNA
<213> ORGANISM: Homo sapiens

<400> SEQUENCE: 504
uuguugcuau cuagguuagu gaaggcuauu uuaauuuuuu uaaaauuucu uucacuacuu 60
agg 63

<210> SEQ ID NO 505
<211> LENGTH: 80
<212> TYPE: RNA
<213> ORGANISM: Homo sapiens

<400> SEQUENCE: 505
ggagaaagga guggaccgag gaaggaagga aggcaaggcu gucuguccau ccguccgucu 60
guccaccuac cugucagucc 80

<210> SEQ ID NO 506
<211> LENGTH: 66
<212> TYPE: RNA
<213> ORGANISM: Homo sapiens

<400> SEQUENCE: 506
ccugggaacg gguuccggca gacgcugagg uugcguugac gcucgcgccc cggcucccgu 60
uccagg 66

<210> SEQ ID NO 507
<211> LENGTH: 67
<212> TYPE: RNA
<213> ORGANISM: Homo sapiens

<400> SEQUENCE: 507
uacaggccgg ggcuuugggu gagggacccc cggagucugu cacggucuca ccccaacucu 60
gccccag 67

<210> SEQ ID NO 508
<211> LENGTH: 22
<212> TYPE: RNA
<213> ORGANISM: Homo sapiens

<400> SEQUENCE: 508
uggggauuug gagaagugu ga 22

<210> SEQ ID NO 509
<211> LENGTH: 19
<212> TYPE: RNA
<213> ORGANISM: Homo sapiens

<400> SEQUENCE: 509
agcagggcug gggauugca 19

<210> SEQ ID NO 510
<211> LENGTH: 84
<212> TYPE: RNA
<213> ORGANISM: Homo sapiens

<400> SEQUENCE: 510
cauacuuugu cuccauguuu ccuucccccu ucuguauaca uguauacagg aggaaggggg 60
aaggaaacau ggagacaaag ugug 84

<210> SEQ ID NO 511
<211> LENGTH: 22
<212> TYPE: RNA
<213> ORGANISM: Homo sapiens

<400> SEQUENCE: 511
acugggcagg gcugugguga gu 22

<210> SEQ ID NO 512
<211> LENGTH: 20
<212> TYPE: RNA
<213> ORGANISM: Homo sapiens

<400> SEQUENCE: 512
cgggcguggu ggugggggug 20

<210> SEQ ID NO 513
<211> LENGTH: 98
<212> TYPE: RNA
<213> ORGANISM: Homo sapiens

<400> SEQUENCE: 513
gaaugguuac aaggagagaa cacuggacuu ggagucagaa aacuuucauc caagucauuc 60
ccugcucuaa gucccauuuc uguuccauga gauuguuu 98

<210> SEQ ID NO 514
<211> LENGTH: 54
<212> TYPE: RNA
<213> ORGANISM: Homo sapiens

<400> SEQUENCE: 514
acuguuucug uccuuguucu uguuguuauu acuggacuug gagucagaaa cagg 54

<210> SEQ ID NO 515
<211> LENGTH: 63
<212> TYPE: RNA
<213> ORGANISM: Homo sapiens

<400> SEQUENCE: 515
ccuuggccac cacaccuacc ccuugugaau gucgggcaau gggugauggg uguggugucc 60
aca 63

<210> SEQ ID NO 516
<211> LENGTH: 19
<212> TYPE: RNA
<213> ORGANISM: Homo sapiens

<400> SEQUENCE: 516
ccugagaccc uaguuccac 19

<210> SEQ ID NO 517
<211> LENGTH: 82
<212> TYPE: RNA
<213> ORGANISM: Homo sapiens

<400> SEQUENCE: 517
agggggcgag ggauuggaga gaaaggcagu uccugauggu ccccucccca ggggcuggcu 60
uuccucuggu ccuucccucc ca 82

<210> SEQ ID NO 518
<211> LENGTH: 96
<212> TYPE: RNA
<213> ORGANISM: Homo sapiens

<400> SEQUENCE: 518
aaccauucaa auauaccaca guuuguuuaa ccuuuugccu guugguugaa gaugccuuuc 60
aacaggugac ugguuagaca aacuguggua uauaca 96

<210> SEQ ID NO 519
<211> LENGTH: 100
<212> TYPE: RNA
<213> ORGANISM: Homo sapiens

<400> SEQUENCE: 519
gaggugggag gauugcuuga gucagggugg uugaggcugc aguaaguugu gaucauacca 60
cugcacucca gccugaguga cagagcaaga ccuugucuca 100

<210> SEQ ID NO 520
<211> LENGTH: 62
<212> TYPE: RNA
<213> ORGANISM: Homo sapiens

<400> SEQUENCE: 520
cuuccuggug ggugggg agg agaagugccg uccucaugag ccccucucug ucccacccau 60
ag 62

<210> SEQ ID NO 521
<211> LENGTH: 85
<212> TYPE: RNA
<213> ORGANISM: Homo sapiens

<400> SEQUENCE: 521
cucaggcugu gacccuccag agggaaguac uuucuguugu cugagagaaa agaaagugcu 60
ucccuuugga cuguuucggu uugag 85

<210> SEQ ID NO 522
<211> LENGTH: 115
<212> TYPE: RNA
<213> ORGANISM: Homo sapiens

<400> SEQUENCE: 522
uagcugggug gauguguucu uuugaaggau agcagcauaa gccugucuca aaauaauucu 60
gcagugagac agguucaugc ugcuaucguu ccaaagagga aggguaauca cuguc 115

<210> SEQ ID NO 523
<211> LENGTH: 16
<212> TYPE: RNA
<213> ORGANISM: Homo sapiens

<400> SEQUENCE: 523
uucagcagga acagcu 16

<210> SEQ ID NO 524
<211> LENGTH: 68
<212> TYPE: RNA
<213> ORGANISM: Homo sapiens

<400> SEQUENCE: 524
agaacuugag gggagaauga gguggagaag cccagguucu gaauccccuu cccucacucu 60
ucucucag 68

<210> SEQ ID NO 525
<211> LENGTH: 106
<212> TYPE: RNA
<213> ORGANISM: Homo sapiens

<400> SEQUENCE: 525
gcgcagcgcc cugucuccca gccugaggug cagugcugca ucucugguca guugggaguc 60
ugagaugaag cacuguagcu caggaagaga gaaguuguuc ugcagc 106

<210> SEQ ID NO 526
<211> LENGTH: 82
<212> TYPE: RNA
<213> ORGANISM: Homo sapiens

<400> SEQUENCE: 526
ugugggcagg gcccugggga gcugaggcuc ugggggugge cggggcugac ccugggccuc 60
ugcuccccag ugucugaccg cg 82

<210> SEQ ID NO 527
<211> LENGTH: 59
<212> TYPE: RNA
<213> ORGANISM: Homo sapiens

<400> SEQUENCE: 527
cugugucggg gagucugggg uccggaauuc uccagagccu cugugccccu acuucccag 59

<210> SEQ ID NO 528
<211> LENGTH: 65
<212> TYPE: RNA
<213> ORGANISM: Homo sapiens

<400> SEQUENCE: 528
agcccugggg gugcucucua gccaaggcuc uggggucuca cccuuggcug gucucugcuc 60
cgcag 65

<210> SEQ ID NO 529
<211> LENGTH: 22
<212> TYPE: RNA
<213> ORGANISM: Homo sapiens

<400> SEQUENCE: 529
gaagaacugu ugcauuugcc cu 22

<210> SEQ ID NO 530
<211> LENGTH: 17
<212> TYPE: RNA
<213> ORGANISM: Homo sapiens

<400> SEQUENCE: 530
cacugugggu acaugcu 17

<210> SEQ ID NO 531
<211> LENGTH: 83
<212> TYPE: RNA
<213> ORGANISM: Homo sapiens

<400> SEQUENCE: 531
uuguccaauu cucugagcaa ggcuuaacac caaaggguua aggguuugcu cuggaguuaa 60
ggguugcuug gagaauugga gaa 83

<210> SEQ ID NO 532
<211> LENGTH: 67
<212> TYPE: RNA
<213> ORGANISM: Homo sapiens

<400> SEQUENCE: 532
cccggugugu guguagagga agaagggaag cugggaaccu gacugccucu cccucuuuac 60
ccacuag 67

<210> SEQ ID NO 533
<211> LENGTH: 22
<212> TYPE: RNA
<213> ORGANISM: Homo sapiens

<400> SEQUENCE: 533
uuuggucccc uucaaccagc ua 22

<210> SEQ ID NO 534
<211> LENGTH: 18
<212> TYPE: RNA
<213> ORGANISM: Homo sapiens

<400> SEQUENCE: 534
cggggcggca ggggccuc 18

<210> SEQ ID NO 535
<211> LENGTH: 83
<212> TYPE: RNA
<213> ORGANISM: Homo sapiens

<400> SEQUENCE: 535
guggucucag aaucgggguu uugagggcga gaugaguuua uguuuuaucc aacuggcccu 60
caaagucccg cuuuuggggu cau 83

<210> SEQ ID NO 536
<211> LENGTH: 82
<212> TYPE: RNA
<213> ORGANISM: Homo sapiens

<400> SEQUENCE: 536
cugacuuuuu uagggaguag aagggugggg agcaugaaca auguuucuca cucccuaccc 60
cuccacuccc caaaaaaguc ag 82

<210> SEQ ID NO 537
<211> LENGTH: 61
<212> TYPE: RNA
<213> ORGANISM: Homo sapiens

<400> SEQUENCE: 537
gaggguuggg guggagggcc aaggagcugg gugggggugcc aagccucugu ccccacccca 60
g 61

<210> SEQ ID NO 538
<211> LENGTH: 80
<212> TYPE: RNA
<213> ORGANISM: Homo sapiens

<400> SEQUENCE: 538
cgggaaugcc gcggcgggga cggcgauugg uccguaugug uggugccacc ggccgccggc 60
uccgccccgg cccccgcccc 80

<210> SEQ ID NO 539
<211> LENGTH: 113
<212> TYPE: RNA
<213> ORGANISM: Homo sapiens

<400> SEQUENCE: 539
gccggguggg gcggggcggc cucaggaggg gcccagcucc ccuggaugug cugcggnggg 60
gccggagggg cgucacgugc acccaaguga cgccccuucu gauucugccu cag 113

<210> SEQ ID NO 540
<211> LENGTH: 120
<212> TYPE: RNA
<213> ORGANISM: Homo sapiens

<400> SEQUENCE: 540
cgcgacugcg gcggcggugg uggggggagc cgcggggauc gccgagggcc ggucggccgc 60
gucggccgcg cucgaggggu ccccguggcg uccccuuccc cgccggccgc cuuucucgcg 120

<210> SEQ ID NO 541
<211> LENGTH: 120
<212> TYPE: RNA
<213> ORGANISM: Homo sapiens

<400> SEQUENCE: 541
cgcgacugcg gcggcggugg uggggggagc cgcggggauc gccgagggcc ggucggccgc 60
gucggccgcg cucgaggggu ccccguggcg uccccuuccc cgccggccgc cuuucucgcg 120

<210> SEQ ID NO 542
<211> LENGTH: 22
<212> TYPE: RNA
<213> ORGANISM: Homo sapiens

<400> SEQUENCE: 542
agacugacgg cuggaggccc au 22

<210> SEQ ID NO 543
<211> LENGTH: 18
<212> TYPE: RNA
<213> ORGANISM: Homo sapiens

<400> SEQUENCE: 543
cggcuggagg ugugagga 18

<210> SEQ ID NO 544
<211> LENGTH: 56
<212> TYPE: RNA
<213> ORGANISM: Homo sapiens

<400> SEQUENCE: 544
cuccucaugg gaguucgggg ugguugcugg aggucagcac ccuguggcuc ccacag 56

<210> SEQ ID NO 545
<211> LENGTH: 99
<212> TYPE: RNA
<213> ORGANISM: Homo sapiens

<400> SEQUENCE: 545
gcaagggaca gggagggucg uggcgacacu cgcgccagcu cccgggacgg cugggcucgg 60
gcuggucgcc gaccuccgac ccuccacuag augccuggc 99

<210> SEQ ID NO 546
<211> LENGTH: 24
<212> TYPE: RNA
<213> ORGANISM: Homo sapiens

<400> SEQUENCE: 546
uguggacagu gagguagagg gagu 24

<210> SEQ ID NO 547
<211> LENGTH: 78
<212> TYPE: RNA
<213> ORGANISM: Homo sapiens

<400> SEQUENCE: 547
cccgcagagg cugagaaggu gauguuggcu caagaaaggg agauagaugg uagcccauca 60
ccuuuccguc uccccuag 78

<210> SEQ ID NO 548
<211> LENGTH: 23
<212> TYPE: RNA
<213> ORGANISM: Homo sapiens

<400> SEQUENCE: 548
ugugcuugcu cgucccgccc gca 23

<210> SEQ ID NO 549
<211> LENGTH: 78
<212> TYPE: RNA
<213> ORGANISM: Homo sapiens

<400> SEQUENCE: 549
uauuggacga ggggacuggu uaauagaacu aacuaaccag aacuauuuug uucuguuaac 60 ccaucccuc aucuaaua 78

<210> SEQ ID NO 550
<211> LENGTH: 61
<212> TYPE: RNA
<213> ORGANISM: Homo sapiens

<400> SEQUENCE: 550
caaggucagg guugguaggg guugcuguug cugugaaagc ugagccucuc cuucccucca 60
g 61

<210> SEQ ID NO 551
<211> LENGTH: 22
<212> TYPE: RNA
<213> ORGANISM: Homo sapiens

<400> SEQUENCE: 551
gcugaugaug auggugcuga ag 22

<210> SEQ ID NO 552
<211> LENGTH: 59
<212> TYPE: RNA
<213> ORGANISM: Homo sapiens

<400> SEQUENCE: 552
cuccagggag acagugugug aggccucuug ccauggccuc ccugcccgcc ucucugcag 59

<210> SEQ ID NO 553
<211> LENGTH: 23
<212> TYPE: RNA
<213> ORGANISM: Homo sapiens

<400> SEQUENCE: 553
gaagacuucu uggauuacag ggg 23

<210> SEQ ID NO 554
<211> LENGTH: 73
<212> TYPE: RNA
<213> ORGANISM: Homo sapiens

<400> SEQUENCE: 554
uucaugaacu gggucuagcu uggagccuug guagggaagc aagcugagga gauaggagga 60
caaguugugg gau 73

<210> SEQ ID NO 555
<211> LENGTH: 114
<212> TYPE: RNA
<213> ORGANISM: Homo sapiens

<400> SEQUENCE: 555
ggcccgccuu uuaggggccu cgcugucugg gcacaggcgg auggacaggc uggccucugg 60
augaccugcc aaccgucaga gcccagaccc acguggccuc aguuggggac cagg 114

<210> SEQ ID NO 556
<211> LENGTH: 21
<212> TYPE: RNA
<213> ORGANISM: Homo sapiens

<400> SEQUENCE: 556
agagaagaag aucagccugc a 21

<210> SEQ ID NO 557
<211> LENGTH: 101
<212> TYPE: RNA
<213> ORGANISM: Homo sapiens

<400> SEQUENCE: 557
gcgagaagau cucaugcugu gacucucugg agggaagcac uuucuguugu cugaaagaaa 60
acaaagcgcu ucucuuuaga guguuacggu uugagaaaag c 101

<210> SEQ ID NO 558
<211> LENGTH: 60

<212> TYPE: RNA
<213> ORGANISM: Homo sapiens

<400> SEQUENCE: 558
gauccaucuc ugccuguauu ggcuuggauu cugcaaagcc uacaggcugg aaugggcuca 60

<210> SEQ ID NO 559
<211> LENGTH: 86
<212> TYPE: RNA
<213> ORGANISM: Homo sapiens

<400> SEQUENCE: 559
gguucugucu ugggccacuu ggaucugaag gcugccccuu ugcucucugg gguagccuuc 60
agaucuuggu guuuugaauu cuuacu 86

<210> SEQ ID NO 560
<211> LENGTH: 55
<212> TYPE: RNA
<213> ORGANISM: Homo sapiens

<400> SEQUENCE: 560
aaucugccag cuuccacagu ggcagauuuu cccauagugg gaagcuggca gauuc 55

<210> SEQ ID NO 561
<211> LENGTH: 84
<212> TYPE: RNA
<213> ORGANISM: Homo sapiens

<400> SEQUENCE: 561
uaaguuauau augucuacuu cuaccugugu uaucauaaua aaggugucau gaugauacag 60
guggagguag aaauauauaa cuua 84

<210> SEQ ID NO 562
<211> LENGTH: 23
<212> TYPE: RNA
<213> ORGANISM: Homo sapiens

<400> SEQUENCE: 562
ccggggcaga uugguguagg gug 23

<210> SEQ ID NO 563
<211> LENGTH: 93
<212> TYPE: RNA
<213> ORGANISM: Homo sapiens

<400> SEQUENCE: 563
guagucagua guugggggggu gggaacggcu ucauacagga guugaugcac aguuauccag 60
cuccuauaug augccuuucu ucauccccuu caa 93

<210> SEQ ID NO 564
<211> LENGTH: 83
<212> TYPE: RNA
<213> ORGANISM: Homo sapiens

<400> SEQUENCE: 564
gagaaucauc ucucccagau aauggcacuc ucaaacaagu uuccaaauug uuugaaaggc 60
uauuucuugg ucagaugacu cuc 83

<210> SEQ ID NO 565
<211> LENGTH: 80
<212> TYPE: RNA

<213> ORGANISM: Homo sapiens

<400> SEQUENCE: 565
ccuguugcca caaacccgua gauccgaacu ugugguauua guccgcacaa gcuuguaucu 60
auagguaugu gucuguuagg 80

<210> SEQ ID NO 566
<211> LENGTH: 70
<212> TYPE: RNA
<213> ORGANISM: Homo sapiens

<400> SEQUENCE: 566
gugugccacc ugcguguuuu cuguccaaau cagaaaagga uuuggacaga aaacacgcag 60
gaagaaggaa 70

<210> SEQ ID NO 567
<211> LENGTH: 69
<212> TYPE: RNA
<213> ORGANISM: Homo sapiens

<400> SEQUENCE: 567
gggauacuca aaaugggggc gcuuuccuuu uugucuguac ugggaagugc uucgauuuug 60 gggugucce 69

<210> SEQ ID NO 568
<211> LENGTH: 62
<212> TYPE: RNA
<213> ORGANISM: Homo sapiens

<400> SEQUENCE: 568
ucagucgggc gcaagagcac ugcaguucug uugggugaca gcaguguuug uuuugcccac 60
ag 62

<210> SEQ ID NO 569
<211> LENGTH: 22
<212> TYPE: RNA
<213> ORGANISM: Homo sapiens

<400> SEQUENCE: 569
uguccucuag ggccugcagu cu 22

<210> SEQ ID NO 570
<211> LENGTH: 70
<212> TYPE: RNA
<213> ORGANISM: Homo sapiens

<400> SEQUENCE: 570
ggagauauug cacauuacua aguugcaugu ugucacggcc ucaaugcaau uuagugugug 60
ugauauuuuc 70

<210> SEQ ID NO 571
<211> LENGTH: 69
<212> TYPE: RNA
<213> ORGANISM: Homo sapiens

<400> SEQUENCE: 571
ccaccacuua aacguggaug uacuugcuuu gaaacuaaag aaguaagugc uuccauguuu 60
uggugaugg 69

<210> SEQ ID NO 572
<211> LENGTH: 23
<212> TYPE: RNA
<213> ORGANISM: Homo sapiens

<400> SEQUENCE: 572
uaucugcugg gcuuucuggu guu 23

<210> SEQ ID NO 573
<211> LENGTH: 81
<212> TYPE: RNA
<213> ORGANISM: Homo sapiens

<400> SEQUENCE: 573
gaaacugcug aagcugccau gucuaagaag aaaacuuugg agaaaaauuu ucuucuuaga 60
cauggcaacg ucaacaguuu c 81

<210> SEQ ID NO 574
<211> LENGTH: 19
<212> TYPE: RNA
<213> ORGANISM: Homo sapiens

<400> SEQUENCE: 574
ucucccuuga gggcacuuu 19

<210> SEQ ID NO 575
<211> LENGTH: 82
<212> TYPE: RNA
<213> ORGANISM: Homo sapiens

<400> SEQUENCE: 575
ggauuguggg ggucgcucu aggcaccgca gcacugugcu ggggauguug cagcugccug 60
ggagugacuu cacacagucc uc 82

<210> SEQ ID NO 576
<211> LENGTH: 100
<212> TYPE: RNA
<213> ORGANISM: Homo sapiens

<400> SEQUENCE: 576
cccccagaau cugucaggca ccagccaggc auugcucagc ccguuucccu cugggggagc 60
aaggaguggu gcuggguuug ucucugcugg gguuucuccu 100

<210> SEQ ID NO 577
<211> LENGTH: 87
<212> TYPE: RNA
<213> ORGANISM: Homo sapiens

<400> SEQUENCE: 577
ucucaggcag ugacccucua gauggaagca cugucuguug uauaaaagaa aagaucgugc 60
aucccuuuag aguguuacug uuugaga 87

<210> SEQ ID NO 578
<211> LENGTH: 67
<212> TYPE: RNA
<213> ORGANISM: Homo sapiens

<400> SEQUENCE: 578
gugacccucu agauggaagc acugucuguu gucuaagaaa agaucgugca ucccuuuaga 60
guguuac 67

<210> SEQ ID NO 579
<211> LENGTH: 87
<212> TYPE: RNA
<213> ORGANISM: Homo sapiens

<400> SEQUENCE: 579
gacagugcag ucacccauaa aguagaaagc acuacuaaca gcacuggagg guguaguguu 60
uccuacuuua uggaugagug uacugug 87

<210> SEQ ID NO 580
<211> LENGTH: 86
<212> TYPE: RNA
<213> ORGANISM: Homo sapiens

<400> SEQUENCE: 580
uuugguacuu aaagagagga uacccuuugu auguucacuu gauuaauggc gaauauacag 60
ggggagacuc ucauuugcgu aucaaa 86

<210> SEQ ID NO 581
<211> LENGTH: 23
<212> TYPE: RNA
<213> ORGANISM: Homo sapiens

<400> SEQUENCE: 581
gacacgggcg acagcugcgg ccc 23

<210> SEQ ID NO 582
<211> LENGTH: 20
<212> TYPE: RNA
<213> ORGANISM: Homo sapiens

<400> SEQUENCE: 582
cugcaaaggg aagcccuuuc 20

<210> SEQ ID NO 583
<211> LENGTH: 85
<212> TYPE: RNA
<213> ORGANISM: Homo sapiens

<400> SEQUENCE: 583
ucucaagcug ugacugcaaa gggaagcccu uucuguuguc ugaaagaaga gaaagcgcuu 60
cccuuugcug gauuacgguu ugaga 85

<210> SEQ ID NO 584
<211> LENGTH: 87
<212> TYPE: RNA
<213> ORGANISM: Homo sapiens

<400> SEQUENCE: 584
ucucaagcug ugggucugca aagggaagcc cuuucuguug ucuaaaagaa gagaaagcgc 60
uucccuuugc uggauuacgg uuugaga 87

<210> SEQ ID NO 585
<211> LENGTH: 23
<212> TYPE: RNA
<213> ORGANISM: Homo sapiens

<400> SEQUENCE: 585
ucugaguucc uggagccugg ucu 23

<210> SEQ ID NO 586
<211> LENGTH: 86
<212> TYPE: RNA
<213> ORGANISM: Homo sapiens

<400> SEQUENCE: 586 ggucuugcc cucaaggagc ucacagucua uugaguuacc uuucugacuu ucccacuaga 60
uugugagcuc cuggagggca ggcacu 86

<210> SEQ ID NO 587
<211> LENGTH: 19
<212> TYPE: RNA
<213> ORGANISM: Homo sapiens

<400> SEQUENCE: 587
ggccacugag ucagcacca 19

<210> SEQ ID NO 588
<211> LENGTH: 85
<212> TYPE: RNA
<213> ORGANISM: Homo sapiens

<400> SEQUENCE: 588
gcuaagcacu uacaacuguu ugcagaggaa acugagacuu uguaacuaug ucucagucuc 60
aucugcaaag aaguaagugc uuugc 85

<210> SEQ ID NO 589
<211> LENGTH: 85
<212> TYPE: RNA
<213> ORGANISM: Homo sapiens

<400> SEQUENCE: 589
cucaagcugu gacucuccag agggaugcac uuucucuuau gugaaaaaaa agaaggcgcu 60
ucccuuuaga gcguuacggu uuggg 85

<210> SEQ ID NO 590
<211> LENGTH: 83
<212> TYPE: RNA
<213> ORGANISM: Homo sapiens

<400> SEQUENCE: 590
aauagagggu gcacaggcac gggagcucag gugaggcagg gagcugagcu caccugaccu 60
cccaugccug ugcacccucu auu 83

<210> SEQ ID NO 591
<211> LENGTH: 56
<212> TYPE: RNA
<213> ORGANISM: Homo sapiens

<400> SEQUENCE: 591
guaggcaggg gcugggguuu cagguucuca gucagaaccu uggccccucu ccccag 56

<210> SEQ ID NO 592
<211> LENGTH: 77
<212> TYPE: RNA
<213> ORGANISM: Homo sapiens

<400> SEQUENCE: 592
gaggagaggu gggauggaga gaagguauga gcuaaaaauc cccaagcucu gccauccucc 60
cuccccuacu ucucccc 77

<210> SEQ ID NO 593
<211> LENGTH: 22
<212> TYPE: RNA
<213> ORGANISM: Homo sapiens

<400> SEQUENCE: 593 uggggagug cagugauugu gg 22

<210> SEQ ID NO 594
<211> LENGTH: 80
<212> TYPE: RNA
<213> ORGANISM: Homo sapiens

<400> SEQUENCE: 594
ugagaggccg caccuugccu ugcugcccgg gccgugcacc cgugggcccc agggcgacgc 60
ggcgggggcg gcccuagcga 80

<210> SEQ ID NO 595
<211> LENGTH: 84
<212> TYPE: RNA
<213> ORGANISM: Homo sapiens

<400> SEQUENCE: 595
gcuggcgucg gugcugggga gcggcccccg ggugggccuc ugcucuggcc ccuccugggg 60
cccgcacucu cgcucugggc ccgc 84

<210> SEQ ID NO 596
<211> LENGTH: 64
<212> TYPE: RNA
<213> ORGANISM: Homo sapiens

<400> SEQUENCE: 596
gaggcacugg guaggugggg cuccagggcu ccugacaccu ggaccucucc uccccaggcc 60
caca 64

<210> SEQ ID NO 597
<211> LENGTH: 64
<212> TYPE: RNA
<213> ORGANISM: Homo sapiens

<400> SEQUENCE: 597
aaccccgggc cggaggucaa gggcgucgcu ucucccuaau guugccucuu uuccacggcc 60
ucag 64

<210> SEQ ID NO 598
<211> LENGTH: 17
<212> TYPE: RNA
<213> ORGANISM: Homo sapiens

<400> SEQUENCE: 598
gcggggcugg gcgcgcg 17

<210> SEQ ID NO 599
<211> LENGTH: 71
<212> TYPE: RNA
<213> ORGANISM: Homo sapiens

<400> SEQUENCE: 599
ggguaaaggg gcagggacgg guggccccag gaagaagggc cugguggagc cgcucuucuc 60
ccugcccaca g 71

<210> SEQ ID NO 600
<211> LENGTH: 61
<212> TYPE: RNA
<213> ORGANISM: Homo sapiens

<400> SEQUENCE: 600
gggggcggga gcuggggucu gcagguucgc acugaugccu gcucgcccug ucuccegcua 60 g 61

<210> SEQ ID NO 601
<211> LENGTH: 21
<212> TYPE: RNA
<213> ORGANISM: Homo sapiens

<400> SEQUENCE: 601
ggggggaugu gcaugcuggu u 21

<210> SEQ ID NO 602
<211> LENGTH: 20
<212> TYPE: RNA
<213> ORGANISM: Homo sapiens

<400> SEQUENCE: 602
cggggugggu gaggucgggc 20

<210> SEQ ID NO 603
<211> LENGTH: 20
<212> TYPE: RNA
<213> ORGANISM: Homo sapiens

<400> SEQUENCE: 603
gggcuggggc gcggggaggu 20

<210> SEQ ID NO 604
<211> LENGTH: 19
<212> TYPE: RNA
<213> ORGANISM: Homo sapiens

<400> SEQUENCE: 604
uggauuuuug gaucaggga 19

<210> SEQ ID NO 605
<211> LENGTH: 21
<212> TYPE: RNA
<213> ORGANISM: Homo sapiens

<400> SEQUENCE: 605
acggcccagg cggcauuggu g 21

<210> SEQ ID NO 606
<211> LENGTH: 71
<212> TYPE: RNA
<213> ORGANISM: Homo sapiens

<400> SEQUENCE: 606
ggugaguggg agccgguggg gcuggaguaa gggcacgccc ggggcugccc caccugcuga 60
ccacccuccc c 71

<210> SEQ ID NO 607
<211> LENGTH: 60
<212> TYPE: RNA

<213> ORGANISM: Homo sapiens

<400> SEQUENCE: 607
gagcaggcga ggcugggcug aacccguggg ugaggagugc agcccagcug aggccucugc 60

<210> SEQ ID NO 608
<211> LENGTH: 22
<212> TYPE: RNA
<213> ORGANISM: Homo sapiens

<400> SEQUENCE: 608
ggggcugggg ccggggccga gc 22

<210> SEQ ID NO 609
<211> LENGTH: 90
<212> TYPE: RNA
<213> ORGANISM: Homo sapiens

<400> SEQUENCE: 609
guggguacgg cccagugggg gggagaggga cacgcccugg gcucugccca gggugcagcc 60
ggacugacug agccccugug ccgcccccag 90

<210> SEQ ID NO 610
<211> LENGTH: 20
<212> TYPE: RNA
<213> ORGANISM: Homo sapiens

<400> SEQUENCE: 610
accaggaggc ugaggccccu 20

<210> SEQ ID NO 611
<211> LENGTH: 110
<212> TYPE: RNA
<213> ORGANISM: Homo sapiens

<400> SEQUENCE: 611
ucaccuggcc augugacuug ugggcuuccc uuugucaucc uucgccuagg gcucugagca 60
gggcagggac agcaaagggg ugcucaguug ucacuuccca cagcacggag 110

<210> SEQ ID NO 612
<211> LENGTH: 17
<212> TYPE: RNA
<213> ORGANISM: Homo sapiens

<400> SEQUENCE: 612
ggcgggugcg gggugg 17

<210> SEQ ID NO 613
<211> LENGTH: 89
<212> TYPE: RNA
<213> ORGANISM: Homo sapiens

<400> SEQUENCE: 613
gccggcgccc gagcucuggc uccgugucuu cacucccgug cuuguccgag gagggaggga 60
gggacggggg cugugcuggg gcagcugga 89

<210> SEQ ID NO 614
<211> LENGTH: 98
<212> TYPE: RNA
<213> ORGANISM: Homo sapiens

<400> SEQUENCE: 614
uugggcaagg ugcggggcua gggcuaacag cagucuuacu gaagguuucc uggaaaccac 60
gcacaugcug uugccacuaa ccucaaccuu acucgguc 98

<210> SEQ ID NO 615
<211> LENGTH: 98
<212> TYPE: RNA
<213> ORGANISM: Homo sapiens

<400> SEQUENCE: 615
acccaaaccc uaggucugcu gacuccuagu ccagggcucg ugauggcugg ugggcccuga 60 acgaggggguc uggaggccug gguuugaaua ucgacagc 98

<210> SEQ ID NO 616
<211> LENGTH: 84
<212> TYPE: RNA
<213> ORGANISM: Homo sapiens

<400> SEQUENCE: 616
cuccccaugg cccugucucc caacccuugu accagugcug ggcucagacc cugguacagg 60
ccugggggac agggaccugg ggac 84

<210> SEQ ID NO 617
<211> LENGTH: 92
<212> TYPE: RNA
<213> ORGANISM: Homo sapiens

<400> SEQUENCE: 617
cggcuggaca gcgggcaacg gaaucccaaa agcagcuguu gucuccagag cauuccagcu 60
gcgcuuggau uucgucccccu gcucuccugc cu 92

<210> SEQ ID NO 618
<211> LENGTH: 97
<212> TYPE: RNA
<213> ORGANISM: Homo sapiens

<400> SEQUENCE: 618
aaucuaucac ugcuuuuuag gauaagcuug acuuuuguuc aaauaaaaau gcaaaaggaa 60
aguguauccu aaaaggcaau gacaguuuaa uguguuu 97

<210> SEQ ID NO 619
<211> LENGTH: 110
<212> TYPE: RNA
<213> ORGANISM: Homo sapiens

<400> SEQUENCE: 619
ggccagcugu gaguguuucu uuggcagugu cuuagcuggu uguugugagc aauaguaagg 60
aagcaaucag caaguauacu gcccuagaag ugcugcacgu uguggggccc 110

<210> SEQ ID NO 620
<211> LENGTH: 79
<212> TYPE: RNA
<213> ORGANISM: Homo sapiens

<400> SEQUENCE: 620
ugguacucgg ggagagguua cccgagcaac uuugcaucug gacgacgaau guugcucggu 60
gaaccccuuu ucgguauca 79

<210> SEQ ID NO 621

<211> LENGTH: 70
<212> TYPE: RNA
<213> ORGANISM: Homo sapiens

<400> SEQUENCE: 621
uugaagggag aucgaccgug uuauauucgc uuuauugacu ucgaauaaua caugguugau 60
cuuuucucag 70

<210> SEQ ID NO 622
<211> LENGTH: 110
<212> TYPE: RNA
<213> ORGANISM: Homo sapiens

<400> SEQUENCE: 622
ggcuacaguc uuucuucaug ugacucgugg acuucccuuu gucauccuau gccugagaau 60
auaugaagga ggcugggaag gcaaagggac guucaauugu caucacuggc 110

<210> SEQ ID NO 623
<211> LENGTH: 23
<212> TYPE: RNA
<213> ORGANISM: Homo sapiens

<400> SEQUENCE: 623
uuauugcuua agaauacgcg uag 23

<210> SEQ ID NO 624
<211> LENGTH: 76
<212> TYPE: RNA
<213> ORGANISM: Homo sapiens

<400> SEQUENCE: 624
uacuugaaga gaaguuguuc gugguggauu cgcuuuacuu augacgaauc auucacggac 60
aacacuuuuu ucagua 76

<210> SEQ ID NO 625
<211> LENGTH: 95
<212> TYPE: RNA
<213> ORGANISM: Homo sapiens

<400> SEQUENCE: 625
gaagaucuca ggcagugacc cucuagaugg aagcacuguc uguugucuaa gaaaagaucg 60
ugcauccuuu uagaguguua cuguuugaga aaauc 95

<210> SEQ ID NO 626
<211> LENGTH: 91
<212> TYPE: RNA
<213> ORGANISM: Homo sapiens

<400> SEQUENCE: 626
cgacuugcuu ucucuccucc augccuugag uguaggaccg uuggcaucuu aauuacccuc 60
ccacacccaa ggcuugcaga agagcgagcc u 91

<210> SEQ ID NO 627
<211> LENGTH: 85
<212> TYPE: RNA
<213> ORGANISM: Homo sapiens

<400> SEQUENCE: 627
ggcugagccg caguaguucu ucaguggcaa gcuuuauguc cugacccagc uaaagcugcc 60
aguugaagaa cuguugcccu cugcc 85

<210> SEQ ID NO 628
<211> LENGTH: 102
<212> TYPE: RNA
<213> ORGANISM: Homo sapiens

<400> SEQUENCE: 628
gugggagggc ccaggcgcgg gcaggggugg ggguggcaga gcgcuguccc gggggcgggg 60
ccgaagcgcg gcgaccguaa cuccuucugc uccgucccccc ag 102

<210> SEQ ID NO 629
<211> LENGTH: 85
<212> TYPE: RNA
<213> ORGANISM: Homo sapiens

<400> SEQUENCE: 629
gugaggacuc gggaggugga ggguggugcc gccggggccg ggcgcuguuu cagcucgcuu 60 cucccccac cuccucucuc cucag 85

<210> SEQ ID NO 630
<211> LENGTH: 85
<212> TYPE: RNA
<213> ORGANISM: Homo sapiens

<400> SEQUENCE: 630
aggguagagg gaugaggggg aaaguucuau aguccuguaa uuagaucuca ggacuauaga 60
acuuuccccc ucaucccucu gcccu 85

<210> SEQ ID NO 631
<211> LENGTH: 75
<212> TYPE: RNA
<213> ORGANISM: Homo sapiens

<400> SEQUENCE: 631
uggagugggg gggcaggagg ggcucaggga gaaagugcau acagccccug gcccucucug 60
cccuuccguc cccug 75

<210> SEQ ID NO 632
<211> LENGTH: 85
<212> TYPE: RNA
<213> ORGANISM: Homo sapiens

<400> SEQUENCE: 632
ccuuagcaga gcuguggagu gugacaaugg uguuuguguc uaaacuauca aacgccauua 60
ucacacuaaa uagcuacugc uaggc 85

<210> SEQ ID NO 633
<211> LENGTH: 76
<212> TYPE: RNA
<213> ORGANISM: Homo sapiens

<400> SEQUENCE: 633
aggugcacgc ucuagcgggg auuccaauau ugggccaauu cccccaaugu uggaauccuc 60
gcuagagcgu gcacuu 76

<210> SEQ ID NO 634
<211> LENGTH: 21
<212> TYPE: RNA
<213> ORGANISM: Homo sapiens

<400> SEQUENCE: 634
cuuccgcccc gccgggcguc g 21

<210> SEQ ID NO 635
<211> LENGTH: 99
<212> TYPE: RNA
<213> ORGANISM: Homo sapiens

<400> SEQUENCE: 635
gaaacugggc ucaaggugag gggugcuauc ugugauugag ggacaugguu aauggaauug 60
ucucacacag aaaucgcacc cgucaccuug gccuacuua 99

<210> SEQ ID NO 636
<211> LENGTH: 77
<212> TYPE: RNA
<213> ORGANISM: Homo sapiens

<400> SEQUENCE: 636
ccgggaccca guucaaguaa uucaggauag guugugugcu guccagccug uucuccauua 60
cuuggcucgg ggaccgg 77

<210> SEQ ID NO 637
<211> LENGTH: 100
<212> TYPE: RNA
<213> ORGANISM: Homo sapiens

<400> SEQUENCE: 637
ugugucucuc ucuguguccu gccagugguu uuacccuaug guagguuacg ucaugcuguu 60
cuaccacagg guagaaccac ggacaggaua ccggggcacc 100

<210> SEQ ID NO 638
<211> LENGTH: 90
<212> TYPE: RNA
<213> ORGANISM: Homo sapiens

<400> SEQUENCE: 638
ccgggccccu gugagcaucu uaccggacag ugcuggauuu cccagcuuga cucuaacacu 60
gucugguaac gauguucaaa ggugacccgc 90

<210> SEQ ID NO 639
<211> LENGTH: 66
<212> TYPE: RNA
<213> ORGANISM: Homo sapiens

<400> SEQUENCE: 639
agggcuccug acuccagguc cuguguguua ccuagaaaua gcacuggacu uggagucaga 60
aggccu 66

<210> SEQ ID NO 640
<211> LENGTH: 22
<212> TYPE: RNA
<213> ORGANISM: Homo sapiens

<400> SEQUENCE: 640
ucaggcucag uccccucccg au 22

<210> SEQ ID NO 641
<211> LENGTH: 80
<212> TYPE: RNA
<213> ORGANISM: Homo sapiens

<400> SEQUENCE: 641
aggacccuuc cagagggccc ccccucaauc cuguugugcc uaauucagag gguugggugg 60
aggcucuccu gaagggcucu 80

<210> SEQ ID NO 642
<211> LENGTH: 110
<212> TYPE: RNA
<213> ORGANISM: Homo sapiens

<400> SEQUENCE: 642
aaagauccuc agacaaucca ugugcuucuc uuguccuuca uuccaccgga gucugucuca 60
uacccaacca gauuucagug gagugaaguu caggaggcau ggagcugaca 110

<210> SEQ ID NO 643
<211> LENGTH: 114
<212> TYPE: RNA
<213> ORGANISM: Homo sapiens

<400> SEQUENCE: 643
uccugcuugu ccugcgaggu gucuugcagg ccgucaugca ggccacacug acgguaacgu 60
ugcaggucgu cuugcagggc uucucgcaag acgacauccu caucaccaac gacg 114

<210> SEQ ID NO 644
<211> LENGTH: 22
<212> TYPE: RNA
<213> ORGANISM: Homo sapiens

<400> SEQUENCE: 644
gcccgcgugu ggagccaggu gu 22

<210> SEQ ID NO 645
<211> LENGTH: 23
<212> TYPE: RNA
<213> ORGANISM: Homo sapiens

<400> SEQUENCE: 645
cggcccgggc ugcugcuguu ccu 23

<210> SEQ ID NO 646
<211> LENGTH: 97
<212> TYPE: RNA
<213> ORGANISM: Homo sapiens

<400> SEQUENCE: 646
ugaccugaau cagguaggca guguauuguu agcuggcugc uugggucaag ucagcagcca 60
caacuacccu gccacuugcu ucuggauaaa uucuucu 97

<210> SEQ ID NO 647
<211> LENGTH: 20
<212> TYPE: RNA
<213> ORGANISM: Homo sapiens

<400> SEQUENCE: 647
ccuccugccc uccuugcugu 20

<210> SEQ ID NO 648
<211> LENGTH: 21
<212> TYPE: RNA
<213> ORGANISM: Homo sapiens

<400> SEQUENCE: 648
ggcuccuccu cucaggaugu g 21

<210> SEQ ID NO 649
<211> LENGTH: 16
<212> TYPE: RNA
<213> ORGANISM: Homo sapiens

<400> SEQUENCE: 649
cucuccuccc ggcuuc 16

<210> SEQ ID NO 650
<211> LENGTH: 79
<212> TYPE: RNA
<213> ORGANISM: Homo sapiens

<400> SEQUENCE: 650
gugagguggg ggccagcagg gagugggcug ggcugggcug ggccaaggua caaggccuca 60
cccugcaucc cgcacccag 79

<210> SEQ ID NO 651
<211> LENGTH: 108
<212> TYPE: RNA
<213> ORGANISM: Homo sapiens

<400> SEQUENCE: 651
uccacccagc aggcgcaggu ccugugcagc aggccaaccg agaagcgccu gcgucuccca 60
uuuucgggcu ggccugcugc uccggaccug ugccugaucu uaaugcug 108

<210> SEQ ID NO 652
<211> LENGTH: 75
<212> TYPE: RNA
<213> ORGANISM: Homo sapiens

<400> SEQUENCE: 652
gcagaagaaa gaucuggaag ugggagacac uuuuacuaua uauaguggcu cccacuucca 60
gaucuuucuc ucugu 75

<210> SEQ ID NO 653
<211> LENGTH: 77
<212> TYPE: RNA
<213> ORGANISM: Homo sapiens

<400> SEQUENCE: 653
ugcagaagaa agaucuggaa gugggagaca cuuucacuau auauaguggc ucccacuucc 60
agaucuuucu cucugua 77

<210> SEQ ID NO 654
<211> LENGTH: 70
<212> TYPE: RNA
<213> ORGANISM: Homo sapiens

<400> SEQUENCE: 654
gcuggcccug ggcagcgugu ggcugaaggu caccauguuc uccuuggcca uggggcugcg 60
cggggccagc 70

<210> SEQ ID NO 655
<211> LENGTH: 69
<212> TYPE: RNA
<213> ORGANISM: Homo sapiens

<400> SEQUENCE: 655
uagcccaggg cuuggagugg ggcaagguug uuggugauau ggcuuccucu cccuuccugc 60
ccuggcuag 69

<210> SEQ ID NO 656
<211> LENGTH: 74
<212> TYPE: RNA
<213> ORGANISM: Homo sapiens

<400> SEQUENCE: 656
ccugcaggag gcagugggcg agcaggcggg gcagcccaau gccaugggcc ugaucucacc 60
gcugccuccu uccc 74

<210> SEQ ID NO 657
<211> LENGTH: 78
<212> TYPE: RNA
<213> ORGANISM: Homo sapiens

<400> SEQUENCE: 657
gggcccagaa gggggcgcag ucacugacgu gaagggacca caucccgcuu caugucagug 60
acuccugccc cuuggucu 78

<210> SEQ ID NO 658
<211> LENGTH: 75
<212> TYPE: RNA
<213> ORGANISM: Homo sapiens

<400> SEQUENCE: 658
guccccauuu uucucccacu accaggcucc cauaagggug gaaugggauc cagacagugg 60
gagaaaaaug gggac 75

<210> SEQ ID NO 659
<211> LENGTH: 81
<212> TYPE: RNA
<213> ORGANISM: Homo sapiens

<400> SEQUENCE: 659 aguuggugggg ggagccauga gauaagagca ccuccuagag aauguugaac uaaaggugcc 60
cucucuggcu ccucccccaaa g 81

<210> SEQ ID NO 660
<211> LENGTH: 66
<212> TYPE: RNA
<213> ORGANISM: Homo sapiens

<400> SEQUENCE: 660
gguaacacuc aaaagauggc ggcacuuuca ccagagagca gaaagugccc ccacaguuug 60
agugcc 66

<210> SEQ ID NO 661
<211> LENGTH: 76
<212> TYPE: RNA
<213> ORGANISM: Homo sapiens

<400> SEQUENCE: 661
ggggugaugg guggggcaau gggaucaggu gccucaaagg gcaucccacc ugaucccaca 60
gcccaccugu cacccc 76

<210> SEQ ID NO 662
<211> LENGTH: 77
<212> TYPE: RNA
<213> ORGANISM: Homo sapiens

<400> SEQUENCE: 662
ggaagggauu cugggagguu guagcagugg aaaaaguucu uuucuuccuc ugaucgcccu 60
cucagcucuu uccuucu 77

<210> SEQ ID NO 663
<211> LENGTH: 89
<212> TYPE: RNA
<213> ORGANISM: Homo sapiens

<400> SEQUENCE: 663
cuagauuggg augguaggac cagaggggcu uacugcccug uggggcucuc uggacccagu 60
gccaugcuuc ucugcucugc ucuccccag 89

<210> SEQ ID NO 664
<211> LENGTH: 59
<212> TYPE: RNA
<213> ORGANISM: Homo sapiens

<400> SEQUENCE: 664
cugagcuggg ugagggcauc uguggguuugc uggcugccuc agcuccucuc uacccacag 59

<210> SEQ ID NO 665
<211> LENGTH: 113
<212> TYPE: RNA
<213> ORGANISM: Homo sapiens

<400> SEQUENCE: 665
gaaagaguuu gggauggaga gaggagaaac uugaggucuc ugggaguugc uuaaaccagu 60
ugaccguaac cuggccagag aauucugaua gugucuucuc uccucccaaa cag 113

<210> SEQ ID NO 666
<211> LENGTH: 63
<212> TYPE: RNA
<213> ORGANISM: Homo sapiens

<400> SEQUENCE: 666 aaugggugg ugcugguggg agccgugccc uggccacuca uucggcucuc ucccucaccc 60
uag 63

<210> SEQ ID NO 667
<211> LENGTH: 61
<212> TYPE: RNA
<213> ORGANISM: Homo sapiens

<400> SEQUENCE: 667
uuuggagggg uguggaaaga ggcagaacau ucguucacuu uccugccuuc cucugcacca 60
g 61

<210> SEQ ID NO 668
<211> LENGTH: 75
<212> TYPE: RNA
<213> ORGANISM: Homo sapiens

<400> SEQUENCE: 668
gcugucaggg aacagcuggg ugagcugcug ccccagaggc ccagcaggug uccagaacuc 60
acccucugcu cccag 75

<210> SEQ ID NO 669
<211> LENGTH: 66
<212> TYPE: RNA
<213> ORGANISM: Homo sapiens

<400> SEQUENCE: 669
ggcugccagg gaggcugguu uggaggaguc ugguggccug uucucuucac cugccucugc 60
cugcag 66

<210> SEQ ID NO 670
<211> LENGTH: 65
<212> TYPE: RNA
<213> ORGANISM: Homo sapiens

<400> SEQUENCE: 670
uauuguugug ggugggcaga agucuguuuu cuucaugguu uucugaccuu ugccucuccc 60
cucag 65

<210> SEQ ID NO 671
<211> LENGTH: 72
<212> TYPE: RNA
<213> ORGANISM: Homo sapiens

<400> SEQUENCE: 671
ucugcucuga gagagcucga uggcaggugc cuccguguug ccgaacccuc cuacgcugcu 60
cucucacucc ag 72

<210> SEQ ID NO 672
<211> LENGTH: 86
<212> TYPE: RNA
<213> ORGANISM: Homo sapiens

<400> SEQUENCE: 672
agagccgggg ccauggagca gccuguguag acggggaccu gcccugcaug ggcacccccu 60
cacuggcugc uucccuuggu cuccag 86

<210> SEQ ID NO 673
<211> LENGTH: 73
<212> TYPE: RNA
<213> ORGANISM: Homo sapiens

<400> SEQUENCE: 673
aggccaggug gguauggagg agcccucaua uggcaguugg cgagggccca gugagccccu 60
cucugcucuc cag 73

<210> SEQ ID NO 674
<211> LENGTH: 59
<212> TYPE: RNA
<213> ORGANISM: Homo sapiens

<400> SEQUENCE: 674
cgggcucugg gugcaguggg gguucccacg ccgcggcaac caccacuguc ucuccccag 59

<210> SEQ ID NO 675
<211> LENGTH: 73
<212> TYPE: RNA
<213> ORGANISM: Homo sapiens

<400> SEQUENCE: 675
guucaagugg gaggacagga ggcaggugug guuggaggaa gcagccugaa ccugccuccc 60
ugacauucca cag 73

<210> SEQ ID NO 676
<211> LENGTH: 64
<212> TYPE: RNA
<213> ORGANISM: Homo sapiens

<400> SEQUENCE: 676
gagcucuggg aggggcuggg uuuggcagga caguuuccaa gcccugucuc cucccaucuu 60
ccag 64

<210> SEQ ID NO 677
<211> LENGTH: 61
<212> TYPE: RNA
<213> ORGANISM: Homo sapiens

<400> SEQUENCE: 677
ucggcuggcg gggguagagc uggcugcagg cccggccccu cucagcugcu gcccucucca 60
g 61

<210> SEQ ID NO 678
<211> LENGTH: 67
<212> TYPE: RNA
<213> ORGANISM: Homo sapiens

<400> SEQUENCE: 678
guaagcaggg gcucugggug augugaggag caacaggcac ccuccuccac agccccugcu 60
cauuccu 67

<210> SEQ ID NO 679
<211> LENGTH: 68
<212> TYPE: RNA
<213> ORGANISM: Homo sapiens

<400> SEQUENCE: 679
gggcgcaggg ggacuggggg ugagcaggcc cagaacccag cucgugcuca cucucagucc 60
cuccccuag 68

<210> SEQ ID NO 680
<211> LENGTH: 79
<212> TYPE: RNA
<213> ORGANISM: Homo sapiens

<400> SEQUENCE: 680
uggccugguc agaggcagca ggaaaugaga guuagccagg agcuuugcau acucaccccu 60
gccacucacu ggccccccag 79

<210> SEQ ID NO 681
<211> LENGTH: 65
<212> TYPE: RNA
<213> ORGANISM: Homo sapiens

<400> SEQUENCE: 681
gagggcuagg uggggggcuu gaagccccga gaugccucac gucuucaccc cucucaccua 60
agcag 65

<210> SEQ ID NO 682
<211> LENGTH: 65
<212> TYPE: RNA
<213> ORGANISM: Homo sapiens

<400> SEQUENCE: 682
cuccucuggg ggugggggc ugggcguggu ggacagcgau gcaucccucg ccuucucacc 60
cucag 65

<210> SEQ ID NO 683
<211> LENGTH: 68
<212> TYPE: RNA
<213> ORGANISM: Homo sapiens

<400> SEQUENCE: 683
ggaugugagg gugucagcag gugacggugg gggccacgcu gacagccgca ccugccucuc 60
acccacag 68

<210> SEQ ID NO 684
<211> LENGTH: 70
<212> TYPE: RNA
<213> ORGANISM: Homo sapiens

<400> SEQUENCE: 684
cugggauggg gacagggauc agcauggcac agauccaaua ccuucugucc ccugcucccu 60
uguuccccag 70

<210> SEQ ID NO 685
<211> LENGTH: 66
<212> TYPE: RNA
<213> ORGANISM: Homo sapiens

<400> SEQUENCE: 685
gggcaugggg aggugugggag ucagcauggg gcuaggaggc cccgcgcuga cccgccuucu 60
ccgcag 66

<210> SEQ ID NO 686
<211> LENGTH: 67
<212> TYPE: RNA
<213> ORGANISM: Homo sapiens

<400> SEQUENCE: 686
cagcgugggc ugcugagaag ggcagggguc cuccagcuca uuccuccugc cuccuccgug 60
gccucag 67

<210> SEQ ID NO 687
<211> LENGTH: 61
<212> TYPE: RNA
<213> ORGANISM: Homo sapiens

<400> SEQUENCE: 687
aaacggugug gaagauggga ggagaaaaau cccuguuaac uuucucucuc cacuuccuca 60
g 61

<210> SEQ ID NO 688
<211> LENGTH: 81
<212> TYPE: RNA
<213> ORGANISM: Homo sapiens

<400> SEQUENCE: 688
gugagggacu gggauuugug gggcgaggag ggaccuguac uagccauggu ucugaucaca 60
uaugucccau cccuccauca g 81

<210> SEQ ID NO 689
<211> LENGTH: 79
<212> TYPE: RNA
<213> ORGANISM: Homo sapiens

<400> SEQUENCE: 689
cagccugggg aaggcuuggc agggaagaca caugagcagu gccuccacuu cacgccucuc 60
ccuugucucc uuucccuag 79

<210> SEQ ID NO 690
<211> LENGTH: 61
<212> TYPE: RNA
<213> ORGANISM: Homo sapiens

<400> SEQUENCE: 690
aacugcgggg ccagagcaga gagcccuugc acaccaccag ccucuccucc cugugcccca 60
g 61

<210> SEQ ID NO 691
<211> LENGTH: 70
<212> TYPE: RNA
<213> ORGANISM: Homo sapiens

<400> SEQUENCE: 691
cgaagcgggc augcugggag agacuuugug auuugucucc aaagccucac ccagcucucu 60
ggcccucuag 70

<210> SEQ ID NO 692
<211> LENGTH: 70
<212> TYPE: RNA
<213> ORGANISM: Homo sapiens

<400> SEQUENCE: 692
cgaagcgggc augcugggag agacuuugug auuugucucc aaagccucac ccagcucucu 60
ggcccucuag 70

<210> SEQ ID NO 693
<211> LENGTH: 65
<212> TYPE: RNA
<213> ORGANISM: Homo sapiens

<400> SEQUENCE: 693
auccauaggu ggcagaggag ggacuucaga ugcuucauga cacccucuuu cccuaccgcc 60
uacag 65

<210> SEQ ID NO 694
<211> LENGTH: 60
<212> TYPE: RNA
<213> ORGANISM: Homo sapiens

<400> SEQUENCE: 694
caaggugggg gagauggggg uugaacuuca uuucucaugc ucauccccau cuccuuucag 60

<210> SEQ ID NO 695
<211> LENGTH: 72
<212> TYPE: RNA
<213> ORGANISM: Homo sapiens

<400> SEQUENCE: 695
gagucugagg gacccaggac aggagaaggc cuauggugau uugcauucuu ccugcccugg 60
cuccauccuc ag 72

<210> SEQ ID NO 696
<211> LENGTH: 64
<212> TYPE: RNA
<213> ORGANISM: Homo sapiens

<400> SEQUENCE: 696
aguucagggc cgaagggugg aagcugcugg ugcucaucuc agccucugcc cuuggccucc 60
ccag 64

<210> SEQ ID NO 697
<211> LENGTH: 66
<212> TYPE: RNA
<213> ORGANISM: Homo sapiens

<400> SEQUENCE: 697
cagagcaggg cagggaaggu gggagagggg cccagcugac ccuccuguca cccgcuccuu 60
gcccag 66

<210> SEQ ID NO 698
<211> LENGTH: 66
<212> TYPE: RNA
<213> ORGANISM: Homo sapiens

<400> SEQUENCE: 698
ggcuuuacaa gucaggagcu gaagcagcug gaauucaagc ccugcugccu cuccucuugc 60
cugcag 66

<210> SEQ ID NO 699
<211> LENGTH: 66
<212> TYPE: RNA
<213> ORGANISM: Homo sapiens

<400> SEQUENCE: 699
ccuggagggg ggcacugcgc aagcaaagcc agggacccug agaggcuuug cuuccugcuc 60
cccuag 66

<210> SEQ ID NO 700
<211> LENGTH: 61
<212> TYPE: RNA
<213> ORGANISM: Homo sapiens

<400> SEQUENCE: 700
cuuggcccgc aggugagaug agggcuccug gcgcugaugc ccuucucucc uccugccuca 60
g 61

<210> SEQ ID NO 701
<211> LENGTH: 65
<212> TYPE: RNA
<213> ORGANISM: Homo sapiens

<400> SEQUENCE: 701
gagaaugggg ggacagaugg agaggacaca ggcuggcacu gagguccccu ccacuuuccu 60
ccuag 65

<210> SEQ ID NO 702
<211> LENGTH: 61
<212> TYPE: RNA
<213> ORGANISM: Homo sapiens

<400> SEQUENCE: 702
ugggccaugg gguagggcag aguagggcug gaugguaggg cccacugccu augccccaca 60
g 61

<210> SEQ ID NO 703
<211> LENGTH: 69
<212> TYPE: RNA
<213> ORGANISM: Homo sapiens

<400> SEQUENCE: 703
ccgggcaggc agguguaggg uggagcccac uguggcuccu gacucagccc ugcugccuuc 60
accugccag 69

<210> SEQ ID NO 704
<211> LENGTH: 57
<212> TYPE: RNA
<213> ORGANISM: Homo sapiens

<400> SEQUENCE: 704
caagaaggag gauggagagc ugggccagac augcucuugc cugcccucuu ccuccag 57

<210> SEQ ID NO 705
<211> LENGTH: 65
<212> TYPE: RNA
<213> ORGANISM: Homo sapiens

<400> SEQUENCE: 705
gcuucuggga ggaggggauc uugggaguga ucccaacagc ugagcucccu gaaucccugu 60
cccag 65

<210> SEQ ID NO 706
<211> LENGTH: 65
<212> TYPE: RNA
<213> ORGANISM: Homo sapiens

<400> SEQUENCE: 706
gucuccuggg gggaggagac ccugcucucc cuggcagcaa gccucuccug cccuuccaga 60
uuagc 65

<210> SEQ ID NO 707
<211> LENGTH: 61
<212> TYPE: RNA
<213> ORGANISM: Homo sapiens

<400> SEQUENCE: 707
uccgcucugu ggagugggu gccugucccc ugccacuggg ugacccaccc cucuccacca 60
g 61

<210> SEQ ID NO 708
<211> LENGTH: 56
<212> TYPE: RNA
<213> ORGANISM: Homo sapiens

<400> SEQUENCE: 708
ucuggggucu ugggccaucu gguugugaca ucacugaugg cccaagaccu cagacc 56

<210> SEQ ID NO 709
<211> LENGTH: 52
<212> TYPE: RNA
<213> ORGANISM: Homo sapiens

<400> SEQUENCE: 709
ugcugagguc cgggcugugc cccguaccgg acagggcccu ggcuuuagca ga 52

<210> SEQ ID NO 710
<211> LENGTH: 96
<212> TYPE: RNA
<213> ORGANISM: Homo sapiens

<400> SEQUENCE: 710
cucgggaggg gcgggagggg gguccccggu gcucggaucu cgagggugcu uauuguucgg 60
uccgagccug ggucucccuc uucccccaa cccccc 96

<210> SEQ ID NO 711
<211> LENGTH: 20
<212> TYPE: RNA
<213> ORGANISM: Homo sapiens

<400> SEQUENCE: 711
ggggagcugu ggaagcagua 20

<210> SEQ ID NO 712
<211> LENGTH: 18
<212> TYPE: RNA
<213> ORGANISM: Homo sapiens

<400> SEQUENCE: 712
uccagugccc uccucucc 18

<210> SEQ ID NO 713
<211> LENGTH: 73
<212> TYPE: RNA
<213> ORGANISM: Homo sapiens

<400> SEQUENCE: 713
cccagggucu ggugcggaga gggcccacag uggacuuggu gacgcuguau gcccucaccg 60
cucagccccu ggg 73

<210> SEQ ID NO 714
<211> LENGTH: 80
<212> TYPE: RNA
<213> ORGANISM: Homo sapiens

<400> SEQUENCE: 714
ugucccuuca gccaguccug ugccugccgc cuuugugcug uccuuggagg gaggcagaag 60
caggaugaca augagggcaa 80

<210> SEQ ID NO 715
<211> LENGTH: 22
<212> TYPE: RNA
<213> ORGANISM: Homo sapiens

<400> SEQUENCE: 715
gagagcagug uguguugccu gg 22

<210> SEQ ID NO 716

<211> LENGTH: 110
<212> TYPE: RNA
<213> ORGANISM: Homo sapiens

<400> SEQUENCE: 716
accuuccuga aagagguugg ggcaggcagu gacuguucag acguccaauc ucuuugggac 60
gccucuucag cgcugucuuc ccugccucug ccuuuaggac gagucucaaa 110

<210> SEQ ID NO 717
<211> LENGTH: 22
<212> TYPE: RNA
<213> ORGANISM: Homo sapiens

<400> SEQUENCE: 717
guugggacaa gaggacgguc uu 22

<210> SEQ ID NO 718
<211> LENGTH: 22
<212> TYPE: RNA
<213> ORGANISM: Homo sapiens

<400> SEQUENCE: 718
cggggagaga acgcagugac gu 22

<210> SEQ ID NO 719
<211> LENGTH: 18
<212> TYPE: RNA
<213> ORGANISM: Homo sapiens

<400> SEQUENCE: 719
cagccccaca gccucaga 18

<210> SEQ ID NO 720
<211> LENGTH: 20
<212> TYPE: RNA
<213> ORGANISM: Homo sapiens

<400> SEQUENCE: 720
uguuccucug ucucccagac 20

<210> SEQ ID NO 721
<211> LENGTH: 18
<212> TYPE: RNA
<213> ORGANISM: Homo sapiens

<400> SEQUENCE: 721
gggcucacau caccccau 18

<210> SEQ ID NO 722
<211> LENGTH: 100
<212> TYPE: RNA
<213> ORGANISM: Homo sapiens

<400> SEQUENCE: 722
acuuuauacg uguaauugug augaggaugg auagcaagga agccgcuccc accugacccu 60
cacggccucc guguuaccug uccucuaggu gggacgcucg 100

<210> SEQ ID NO 723
<211> LENGTH: 95
<212> TYPE: RNA
<213> ORGANISM: Homo sapiens

<400> SEQUENCE: 723
agugauauaa uagagggugc acaggcaugg gaggucaggu gagcucagcu cccugccuca 60
ccugagcucc cgugccugug cacccucuau uggcu 95

<210> SEQ ID NO 724
<211> LENGTH: 22
<212> TYPE: RNA
<213> ORGANISM: Homo sapiens

<400> SEQUENCE: 724
aaaaugaaau gagcccagcc ca 22

<210> SEQ ID NO 725
<211> LENGTH: 81
<212> TYPE: RNA
<213> ORGANISM: Homo sapiens

<400> SEQUENCE: 725
auucaggccg guccugcaga gaggaagccc uucugcuuac agguauugga agggcuuccu 60
cucugcagga ccggccugaa u 81

<210> SEQ ID NO 726
<211> LENGTH: 81
<212> TYPE: RNA
<213> ORGANISM: Homo sapiens

<400> SEQUENCE: 726
auucaggccg guccugcaga gaggaagccc uuccaauacc uguaagcaga agggcuuccu 60
cucugcagga ccggccugaa u 81

<210> SEQ ID NO 727
<211> LENGTH: 60
<212> TYPE: RNA
<213> ORGANISM: Homo sapiens

<400> SEQUENCE: 727
ggcaggaggg cugugccagg uuggcugggc caggccugac cugccagcac cucccugcag 60

<210> SEQ ID NO 728
<211> LENGTH: 54
<212> TYPE: RNA
<213> ORGANISM: Homo sapiens

<400> SEQUENCE: 728
agggaaggag gcuuggucuu agcacggggu cuaaggcccg ggcuuuccuc ccag 54

<210> SEQ ID NO 729
<211> LENGTH: 91
<212> TYPE: RNA
<213> ORGANISM: Homo sapiens

<400> SEQUENCE: 729
guguccucac uuguccacuu cugccugccc ugcccaaaug guggagcaga uucgaggggc 60
agggcaggaa gaaguggaca agugaggcca u 91

<210> SEQ ID NO 730
<211> LENGTH: 91
<212> TYPE: RNA
<213> ORGANISM: Homo sapiens

<400> SEQUENCE: 730
guguccucac uuguccacuu cugccugccc ugcccaaaug guggagcaga uucgaggggc 60
agggcaggaa gaaguggaca agugaggcca u 91

<210> SEQ ID NO 731
<211> LENGTH: 115
<212> TYPE: RNA
<213> ORGANISM: Homo sapiens

<400> SEQUENCE: 731
ucugaggaga ccugggcugu cagaggccag ggaaggggac gaggguuggg gaacaggugg 60
uuagcacuuc auccucgucu cccucccagg uuagaagggc cccccucucu gaagg 115

<210> SEQ ID NO 732
<211> LENGTH: 60
<212> TYPE: RNA
<213> ORGANISM: Homo sapiens

<400> SEQUENCE: 732
ggcugggugc ucuugugcag ugagcaaccu acacaacugc acauggcaac cuagcuccca 60

<210> SEQ ID NO 733
<211> LENGTH: 77
<212> TYPE: RNA
<213> ORGANISM: Homo sapiens

<400> SEQUENCE: 733
gaguugggag guucccucuc caaaugugc uugaucccc accccaagac acauuuggag 60
agggacccuc ccaacuc 77

<210> SEQ ID NO 734
<211> LENGTH: 80
<212> TYPE: RNA
<213> ORGANISM: Homo sapiens

<400> SEQUENCE: 734
gagaggccaa gaccuuggga augggguaa gggccuucug agcccagguc cgaacucucc 60
auuccucugc agagcgcucu 80

<210> SEQ ID NO 735
<211> LENGTH: 85
<212> TYPE: RNA
<213> ORGANISM: Homo sapiens

<400> SEQUENCE: 735
gggacggggc cugcaggcag aagugggcu gacagggcag aggguugcgc ccccucacca 60
ccccuucugc cugcagcggu gggcu 85

<210> SEQ ID NO 736
<211> LENGTH: 71
<212> TYPE: RNA
<213> ORGANISM: Homo sapiens

<400> SEQUENCE: 736
ggggccugca ggcagaagug gggcugacag ggcagagggu ugcgccccu caccaccccu 60 ucugccugca g 71

<210> SEQ ID NO 737
<211> LENGTH: 71
<212> TYPE: RNA
<213> ORGANISM: Homo sapiens

<400> SEQUENCE: 737
ugacgggcga gcuuuuggcc cggguuauac cugaugcuca cguauaagac gagcaaaaag 60
cuuguugguc a 71

<210> SEQ ID NO 738
<211> LENGTH: 66
<212> TYPE: RNA
<213> ORGANISM: Homo sapiens

<400> SEQUENCE: 738
ucacguggau gacaguggag gccuccugga ucucuagguc ucagggccuc ucuugucauc 60
cugcag 66

<210> SEQ ID NO 739
<211> LENGTH: 69
<212> TYPE: RNA
<213> ORGANISM: Homo sapiens

<400> SEQUENCE: 739
uggggtaggg gugggggaau ucaggggugu cgaacucaug gcugccaccu uugugucccc 60
auccugcag 69

<210> SEQ ID NO 740
<211> LENGTH: 98
<212> TYPE: RNA
<213> ORGANISM: Homo sapiens

<400> SEQUENCE: 740
cgagguaggg gcgucccggg cgcgcgggcg ggucccaggc ugggccccuc ggaggccggg 60
ugcucacugc cccgucccgg cgcccguguc uccuccag 98

<210> SEQ ID NO 741
<211> LENGTH: 72
<212> TYPE: RNA
<213> ORGANISM: Homo sapiens

<400> SEQUENCE: 741
cagccaggag ggaaggggcu gagaacagga ccugugcuca cuggggccug caugacccuu 60
cccuccccac ag 72

<210> SEQ ID NO 742
<211> LENGTH: 64
<212> TYPE: RNA
<213> ORGANISM: Homo sapiens

<400> SEQUENCE: 742
ugcucuguag gcaugaggca gggcccaggu uccaugugau gcugaagcuc ugacauuccu 60
gcag 64

<210> SEQ ID NO 743
<211> LENGTH: 63
<212> TYPE: RNA
<213> ORGANISM: Homo sapiens

<400> SEQUENCE: 743
gagguguagg ggagguuggg ccagggaugc cuucacugug ucucucuggu cuugccaccc 60
cag 63

<210> SEQ ID NO 744
<211> LENGTH: 64
<212> TYPE: RNA
<213> ORGANISM: Homo sapiens

<400> SEQUENCE: 744
gugggaccag ggccagcagg gaaugucagg gccaccccug accuucacug ugacucugcu 60
gcag 64

<210> SEQ ID NO 745
<211> LENGTH: 60
<212> TYPE: RNA
<213> ORGANISM: Homo sapiens

<400> SEQUENCE: 745
caggcugggg gcuggauggg guagaguagg agagcccacu gaccccuucu gucuccccuag 60

<210> SEQ ID NO 746
<211> LENGTH: 67
<212> TYPE: RNA
<213> ORGANISM: Homo sapiens

<400> SEQUENCE: 746
gugaggaggg gcuggcaggg accccuccaa guuggggacg gcagccagcc ccugcucacc 60
ccucgcc 67

<210> SEQ ID NO 747
<211> LENGTH: 68
<212> TYPE: RNA
<213> ORGANISM: Homo sapiens

<400> SEQUENCE: 747
ugugggagag gaacaugggc ucaggacagc gggugucagc uugccugacc cccaugucgc 60
cucuguag 68

<210> SEQ ID NO 748
<211> LENGTH: 68
<212> TYPE: RNA
<213> ORGANISM: Homo sapiens

<400> SEQUENCE: 748
ugugggagag gaacaugggc ucaggacagc gggugucagc uugccugacc cccaugucgc 60
cucuguag 68

<210> SEQ ID NO 749
<211> LENGTH: 68
<212> TYPE: RNA
<213> ORGANISM: Homo sapiens

<400> SEQUENCE: 749
ugugggagag gaacaugggc ucaggacagc gggugucagc uugccugacc cccaugucgc 60
cucuguag 68

<210> SEQ ID NO 750
<211> LENGTH: 68
<212> TYPE: RNA
<213> ORGANISM: Homo sapiens

<400> SEQUENCE: 750
ugugggagag gaacaugggc ucaggacagc gggugucagc uugccugacc cccaugucgc 60
cucuguag 68

<210> SEQ ID NO 751
<211> LENGTH: 62
<212> TYPE: RNA
<213> ORGANISM: Homo sapiens

<400> SEQUENCE: 751
gaggguggug gaggaagagg gcagcuccca ugacugccug accgccuucu cuccuccccc 60
ag 62

<210> SEQ ID NO 752
<211> LENGTH: 72
<212> TYPE: RNA
<213> ORGANISM: Homo sapiens

<400> SEQUENCE: 752
cugggggagg aaggacaggc caucugcuau ucguccacca accugacuug auccucucuu 60
cccuccuccc ag 72

<210> SEQ ID NO 753
<211> LENGTH: 54
<212> TYPE: RNA
<213> ORGANISM: Homo sapiens

<400> SEQUENCE: 753
uuuccugucc uccaaccaga ccaugccaca uccgucuggu ccuggacagg aggc 54

<210> SEQ ID NO 754
<211> LENGTH: 97
<212> TYPE: RNA
<213> ORGANISM: Homo sapiens

<400> SEQUENCE: 754
aucugaguug ggagggucccc ucuccaaaug ugucuugggg ugggggauca agacacauuu 60
ggagagggaa ccucccaacu cggccucugc caucauu 97

<210> SEQ ID NO 755
<211> LENGTH: 23
<212> TYPE: RNA
<213> ORGANISM: Homo sapiens

<400> SEQUENCE: 755
ggcagguucu cacccucucu agg 23

<210> SEQ ID NO 756
<211> LENGTH: 102
<212> TYPE: RNA
<213> ORGANISM: Homo sapiens

<400> SEQUENCE: 756
gugagugaca ggggaaaugg ggauggacug gaagugggca gcauggagcu gaccuucauc 60
auggcuuggc caacauaaug ccucuucccc uugucucucc ag 102

<210> SEQ ID NO 757
<211> LENGTH: 22
<212> TYPE: RNA
<213> ORGANISM: Homo sapiens

<400> SEQUENCE: 757
gcaggugcuc acuuguccuc cu 22

<210> SEQ ID NO 758
<211> LENGTH: 18
<212> TYPE: RNA
<213> ORGANISM: Homo sapiens

<400> SEQUENCE: 758
cucugggaaa ugggacag 18

<210> SEQ ID NO 759
<211> LENGTH: 73
<212> TYPE: RNA
<213> ORGANISM: Homo sapiens

<400> SEQUENCE: 759
ggaugauaag uuaugggggcu ucuguagaga uuucuaugag aacaucucua aggaacuccc 60
ccaaacugaa uuc 73

<210> SEQ ID NO 760
<211> LENGTH: 18
<212> TYPE: RNA
<213> ORGANISM: Homo sapiens

<400> SEQUENCE: 760
aggagaaguc gggaaggu 18

<210> SEQ ID NO 761
<211> LENGTH: 76
<212> TYPE: RNA
<213> ORGANISM: Homo sapiens

<400> SEQUENCE: 761
ggggucaccu cucuggccgu cuaccuucca cacugacaag ggccgugggg acguagcugg 60
ccagacaggu gacccc 76

<210> SEQ ID NO 762
<211> LENGTH: 116
<212> TYPE: RNA
<213> ORGANISM: Homo sapiens

<400> SEQUENCE: 762
aauguuggca aggaaagaag aggaucaugu uugccccccgu ggacagcucu cuggugugcu 60
ccuccugcca uccugcccac cccugcauaa ugcugcuucu cuucucuccu ucccag 116

<210> SEQ ID NO 763
<211> LENGTH: 61
<212> TYPE: RNA
<213> ORGANISM: Homo sapiens

<400> SEQUENCE: 763
cacuguaggu ggcgccggag gagucauuuc ccaucacuaa uggcuucucu ugcacaccca 60
g 61

<210> SEQ ID NO 764
<211> LENGTH: 93
<212> TYPE: RNA
<213> ORGANISM: Homo sapiens

<400> SEQUENCE: 764
gcuuguuggg gauuggguca ggccaguguu caagggcccc uccucuagua cucccuguuu 60
guguucugcc acugacugag cuucucccca cag 93

<210> SEQ ID NO 765
<211> LENGTH: 66
<212> TYPE: RNA
<213> ORGANISM: Homo sapiens

<400> SEQUENCE: 765
augagaggga gaaagcuaga agcugaagau ucugaaaauc acuaacuggc cucuucuuuc 60
uccuag 66

<210> SEQ ID NO 766
<211> LENGTH: 67
<212> TYPE: RNA
<213> ORGANISM: Homo sapiens

<400> SEQUENCE: 766
guggcacuca aacuguggg gcacuuucug cucucuggug aaagugccgc caucuuuuga 60
guguuac 67

<210> SEQ ID NO 767
<211> LENGTH: 111
<212> TYPE: RNA
<213> ORGANISM: Homo sapiens

<400> SEQUENCE: 767
gcauccucag gaccugggcu ugggugguag gaggaauugg ugcuggucuu ucauuuugga 60
uuugacucca gccccacagc cucagccacc ccagccaauu gucauaggag c 111

<210> SEQ ID NO 768
<211> LENGTH: 69
<212> TYPE: RNA
<213> ORGANISM: Homo sapiens

<400> SEQUENCE: 768
guggguaggg uuuggggag agcgugggcu gggguucagg gacacccucu caccacugcc 60
cucccacag 69

<210> SEQ ID NO 769
<211> LENGTH: 85
<212> TYPE: RNA
<213> ORGANISM: Homo sapiens

<400> SEQUENCE: 769
gugagcaguc uccaccaccu ccccugcaaa cguccagugg ugcagaggua auggacguug 60
gcucuggugg ugauggacag uccga 85

<210> SEQ ID NO 770
<211> LENGTH: 110
<212> TYPE: RNA
<213> ORGANISM: Homo sapiens

<400> SEQUENCE: 770
acccggcagu gccuccaggc gcagggcagc cccugcccac cgcacacugc gcugccccag 60
acccacugug cgugugacag cggcugaucu gugccugggc agcgcgaccc 110

<210> SEQ ID NO 771
<211> LENGTH: 22
<212> TYPE: RNA

<213> ORGANISM: Homo sapiens

<400> SEQUENCE: 771
gguccagagg ggagauaggu uc 22

<210> SEQ ID NO 772
<211> LENGTH: 73
<212> TYPE: RNA
<213> ORGANISM: Homo sapiens

<400> SEQUENCE: 772
acuuggagag aggcuggccg ugaugaauuc gauucaucaa agcgagucau acacggcucu 60
ccucucuuuu agu 73

<210> SEQ ID NO 773
<211> LENGTH: 66
<212> TYPE: RNA
<213> ORGANISM: Homo sapiens

<400> SEQUENCE: 773
gguaagugcg ccucggguga gcaugcacuu aaugugggug uaugucacuc ggcucggccc 60
acuacc 66

<210> SEQ ID NO 774
<211> LENGTH: 86
<212> TYPE: RNA
<213> ORGANISM: Homo sapiens

<400> SEQUENCE: 774
guagaggaga uggcgcaggg gacacgggca aagacuuggg gguuccuggg acccucagac 60
gugugucCuc uucucccucc ucccag 86

<210> SEQ ID NO 775
<211> LENGTH: 83
<212> TYPE: RNA
<213> ORGANISM: Homo sapiens

<400> SEQUENCE: 775
gugaguggga gccccagugu gugguugggg ccauggcggg ugggcagccc agccucugag 60
ccuuccucgu cugucugccc cag 83

<210> SEQ ID NO 776
<211> LENGTH: 75
<212> TYPE: RNA
<213> ORGANISM: Homo sapiens

<400> SEQUENCE: 776
cuugucaugu cuuacccagu cuccggugca gccuguuguc aaggcugcac cggagacugg 60
guaagacaug acaag 75

<210> SEQ ID NO 777
<211> LENGTH: 75
<212> TYPE: RNA
<213> ORGANISM: Homo sapiens

<400> SEQUENCE: 777
cuugucaugu cuuacccagu cuccggugca gccuugacaa caggcugcac cggagacugg 60
guaagacaug acaag 75

<210> SEQ ID NO 778
<211> LENGTH: 22
<212> TYPE: RNA
<213> ORGANISM: Homo sapiens

<400> SEQUENCE: 778
cugggacagg aggaggaggc ag 22

<210> SEQ ID NO 779
<211> LENGTH: 19
<212> TYPE: RNA
<213> ORGANISM: Homo sapiens

<400> SEQUENCE: 779
ugcccuccuu ucuucccuc 19

<210> SEQ ID NO 780
<211> LENGTH: 23
<212> TYPE: RNA
<213> ORGANISM: Homo sapiens

<400> SEQUENCE: 780
uagcccccag gcuucacuug gcg 23

<210> SEQ ID NO 781
<211> LENGTH: 23
<212> TYPE: RNA
<213> ORGANISM: Homo sapiens

<400> SEQUENCE: 781
ugucugcccg caugccugcc ucu 23

<210> SEQ ID NO 782
<211> LENGTH: 109
<212> TYPE: RNA
<213> ORGANISM: Homo sapiens

<400> SEQUENCE: 782
gcuuuuauau uguagguuuu ugcucaugca ccaugguugu cugagcaugc agcaugcuug 60
ucugcucaua ccccaugguu ucugagcagg aaccuucauu gucuacugc 109

<210> SEQ ID NO 783
<211> LENGTH: 22
<212> TYPE: RNA
<213> ORGANISM: Homo sapiens

<400> SEQUENCE: 783
ugggagggga gaggcagcaa gc 22

<210> SEQ ID NO 784
<211> LENGTH: 22
<212> TYPE: RNA
<213> ORGANISM: Homo sapiens

<400> SEQUENCE: 784
ugggagggga gaggcagcaa gc 22

<210> SEQ ID NO 785
<211> LENGTH: 21
<212> TYPE: RNA
<213> ORGANISM: Homo sapiens

<400> SEQUENCE: 785
guuggaggcg uggguuuuag a 21

<210> SEQ ID NO 786
<211> LENGTH: 15
<212> TYPE: RNA
<213> ORGANISM: Homo sapiens

<400> SEQUENCE: 786
guuggaggcg ugggu 15

<210> SEQ ID NO 787
<211> LENGTH: 21
<212> TYPE: RNA
<213> ORGANISM: Homo sapiens

<400> SEQUENCE: 787
aaaugggugg ucugaggcaa g 21

<210> SEQ ID NO 788
<211> LENGTH: 16
<212> TYPE: RNA
<213> ORGANISM: Homo sapiens

<400> SEQUENCE: 788
aaaugggugg ucugag 16

<210> SEQ ID NO 789
<211> LENGTH: 24
<212> TYPE: RNA
<213> ORGANISM: Homo sapiens

<400> SEQUENCE: 789
ugggcccagg aguaaacagg auua 24

<210> SEQ ID NO 790
<211> LENGTH: 16
<212> TYPE: RNA
<213> ORGANISM: Homo sapiens

<400> SEQUENCE: 790
gaguugggcc caggag 16

<210> SEQ ID NO 791
<211> LENGTH: 17
<212> TYPE: RNA
<213> ORGANISM: Homo sapiens

<400> SEQUENCE: 791
caauugucca ucuuuag 17

<210> SEQ ID NO 792
<211> LENGTH: 20
<212> TYPE: RNA
<213> ORGANISM: Homo sapiens

<400> SEQUENCE: 792
agucucgcuc ucugccccuc 20

<210> SEQ ID NO 793
<211> LENGTH: 22
<212> TYPE: RNA
<213> ORGANISM: Homo sapiens

<400> SEQUENCE: 793
aaaagcuggg uugagaggau ga 22

<210> SEQ ID NO 794
<211> LENGTH: 16
<212> TYPE: RNA
<213> ORGANISM: Homo sapiens

<400> SEQUENCE: 794
aaaagcuggg uugaga 16

<210> SEQ ID NO 795
<211> LENGTH: 22
<212> TYPE: RNA
<213> ORGANISM: Homo sapiens

<400> SEQUENCE: 795
ucccccggcc ugcucauccc cc 22

<210> SEQ ID NO 796
<211> LENGTH: 18
<212> TYPE: RNA
<213> ORGANISM: Homo sapiens

<400> SEQUENCE: 796
aggagagugg auuccagg 18

<210> SEQ ID NO 797
<211> LENGTH: 21
<212> TYPE: RNA
<213> ORGANISM: Homo sapiens

<400> SEQUENCE: 797
aagcguggga uguccaugaa g 21

<210> SEQ ID NO 798
<211> LENGTH: 21
<212> TYPE: RNA
<213> ORGANISM: Homo sapiens

<400> SEQUENCE: 798
cugagcccug uccucccgca g 21

<210> SEQ ID NO 799
<211> LENGTH: 18
<212> TYPE: RNA
<213> ORGANISM: Homo sapiens

<400> SEQUENCE: 799
ugagcccugu ccucccgc 18

<210> SEQ ID NO 800
<211> LENGTH: 16
<212> TYPE: RNA
<213> ORGANISM: Homo sapiens

<400> SEQUENCE: 800
cugaacuggg cugagc 16

<210> SEQ ID NO 801
<211> LENGTH: 19
<212> TYPE: RNA
<213> ORGANISM: Homo sapiens

<400> SEQUENCE: 801
aaggaaccag aaaaugaga 19

<210> SEQ ID NO 802
<211> LENGTH: 18
<212> TYPE: RNA
<213> ORGANISM: Homo sapiens

<400> SEQUENCE: 802
uggcaguuac uuuugcac 18

<210> SEQ ID NO 803
<211> LENGTH: 56
<212> TYPE: RNA
<213> ORGANISM: Homo sapiens

<400> SEQUENCE: 803
gagggacuuu caggggcagc uguguuuucu gacucaguca uaaugccccu aaaaau 56

<210> SEQ ID NO 804
<211> LENGTH: 16
<212> TYPE: RNA
<213> ORGANISM: Homo sapiens

<400> SEQUENCE: 804
agggacuuuc aggggc 16

<210> SEQ ID NO 805
<211> LENGTH: 19
<212> TYPE: RNA
<213> ORGANISM: Homo sapiens

<400> SEQUENCE: 805
gcugggcgag gcuggcauc 19

<210> SEQ ID NO 806
<211> LENGTH: 24
<212> TYPE: RNA
<213> ORGANISM: Homo sapiens

<400> SEQUENCE: 806
ugacugggga gcagaaggag aacc 24

<210> SEQ ID NO 807
<211> LENGTH: 15
<212> TYPE: RNA
<213> ORGANISM: Homo sapiens

<400> SEQUENCE: 807
gacuggggag cagaa 15

<210> SEQ ID NO 808
<211> LENGTH: 15
<212> TYPE: RNA
<213> ORGANISM: Homo sapiens

<400> SEQUENCE: 808
ugaagcgggg gggcg 15

<210> SEQ ID NO 809
<211> LENGTH: 15
<212> TYPE: RNA
<213> ORGANISM: Homo sapiens

<400> SEQUENCE: 809
ugaagcgggg gggcg 15

<210> SEQ ID NO 810
<211> LENGTH: 30
<212> TYPE: RNA
<213> ORGANISM: Homo sapiens

<400> SEQUENCE: 810
gcugggcugg gacggacacc cggccuccac 30

<210> SEQ ID NO 811
<211> LENGTH: 23
<212> TYPE: RNA
<213> ORGANISM: Homo sapiens

<400> SEQUENCE: 811
uuaggcuggu gcaaaaguaa ugg 23

<210> SEQ ID NO 812
<211> LENGTH: 16
<212> TYPE: RNA
<213> ORGANISM: Homo sapiens

<400> SEQUENCE: 812
uggugcaaaa guaaug 16

<210> SEQ ID NO 813
<211> LENGTH: 17
<212> TYPE: RNA
<213> ORGANISM: Homo sapiens

<400> SEQUENCE: 813
gugagugugg auccugg 17

<210> SEQ ID NO 814
<211> LENGTH: 23
<212> TYPE: RNA
<213> ORGANISM: Homo sapiens

<400> SEQUENCE: 814
uuuuugcgau guguuccuaa uau 23

<210> SEQ ID NO 815
<211> LENGTH: 16
<212> TYPE: RNA
<213> ORGANISM: Homo sapiens

<400> SEQUENCE: 815
uuuugcgaug uguucc 16

<210> SEQ ID NO 816
<211> LENGTH: 20
<212> TYPE: RNA
<213> ORGANISM: Homo sapiens

<400> SEQUENCE: 816
aucccaccac ugccaccauu 20

<210> SEQ ID NO 817
<211> LENGTH: 30
<212> TYPE: RNA

<213> ORGANISM: Homo sapiens

<400> SEQUENCE: 817
ccaccaccca ccacugccac caugccacca 30

<210> SEQ ID NO 818
<211> LENGTH: 16
<212> TYPE: RNA
<213> ORGANISM: Homo sapiens

<400> SEQUENCE: 818
caguggccag agcccu 16

<210> SEQ ID NO 819
<211> LENGTH: 16
<212> TYPE: RNA
<213> ORGANISM: Homo sapiens

<400> SEQUENCE: 819
cacucuccug gccccc 16

<210> SEQ ID NO 820
<211> LENGTH: 18
<212> TYPE: RNA
<213> ORGANISM: Homo sapiens

<400> SEQUENCE: 820
cuccccucuc uuuccugu 18

<210> SEQ ID NO 821
<211> LENGTH: 18
<212> TYPE: RNA
<213> ORGANISM: Homo sapiens

<400> SEQUENCE: 821
acccuuuuuc ucuuuccc 18

<210> SEQ ID NO 822
<211> LENGTH: 23
<212> TYPE: RNA
<213> ORGANISM: Homo sapiens

<400> SEQUENCE: 822
uggggaaggc gucagugucg ggu 23

<210> SEQ ID NO 823
<211> LENGTH: 16
<212> TYPE: RNA
<213> ORGANISM: Homo sapiens

<400> SEQUENCE: 823
uggggaaggc gucagu 16

<210> SEQ ID NO 824
<211> LENGTH: 25
<212> TYPE: RNA
<213> ORGANISM: Homo sapiens

<400> SEQUENCE: 824
agcgcgggcu gagcgcugcc aguca 25

<210> SEQ ID NO 825
<211> LENGTH: 16

<212> TYPE: RNA
<213> ORGANISM: Homo sapiens

<400> SEQUENCE: 825
agcgcgggcu gagcgc 16

<210> SEQ ID NO 826
<211> LENGTH: 22
<212> TYPE: RNA
<213> ORGANISM: Homo sapiens

<400> SEQUENCE: 826
cucucucucc cacuucccug ca 22

<210> SEQ ID NO 827
<211> LENGTH: 18
<212> TYPE: RNA
<213> ORGANISM: Homo sapiens

<400> SEQUENCE: 827
ucucucccac uucccugc 18

<210> SEQ ID NO 828
<211> LENGTH: 16
<212> TYPE: RNA
<213> ORGANISM: Homo sapiens

<400> SEQUENCE: 828
gagucaggcc uuguuc 16

<210> SEQ ID NO 829
<211> LENGTH: 18
<212> TYPE: RNA
<213> ORGANISM: Homo sapiens

<400> SEQUENCE: 829
cccuguucua ugcccuga 18

<210> SEQ ID NO 830
<211> LENGTH: 19
<212> TYPE: RNA
<213> ORGANISM: Homo sapiens

<400> SEQUENCE: 830
uucuccaaaa gggagcacu 19

<210> SEQ ID NO 831
<211> LENGTH: 18
<212> TYPE: RNA
<213> ORGANISM: Homo sapiens

<400> SEQUENCE: 831
acucagccuu gagggcac 18

<210> SEQ ID NO 832
<211> LENGTH: 71
<212> TYPE: RNA
<213> ORGANISM: Homo sapiens

<400> SEQUENCE: 832
cagggcucag ggauuggaug gaggugaugg gggcagggga ugggucucac ccucccuucu 60
uccugggccc u 71

<210> SEQ ID NO 833
<211> LENGTH: 16
<212> TYPE: RNA
<213> ORGANISM: Homo sapiens

<400> SEQUENCE: 833
cagggcucag ggauug 16

<210> SEQ ID NO 834
<211> LENGTH: 23
<212> TYPE: RNA
<213> ORGANISM: Homo sapiens

<400> SEQUENCE: 834
ugcgcagggg ccgggugcuc acc 23

<210> SEQ ID NO 835
<211> LENGTH: 19
<212> TYPE: RNA
<213> ORGANISM: Homo sapiens

<400> SEQUENCE: 835
cgcaggggcc gggugcuca 19

<210> SEQ ID NO 836
<211> LENGTH: 25
<212> TYPE: RNA
<213> ORGANISM: Homo sapiens

<400> SEQUENCE: 836
ugcaggcaga aguggggcug acagg 25

<210> SEQ ID NO 837
<211> LENGTH: 20
<212> TYPE: RNA
<213> ORGANISM: Homo sapiens

<400> SEQUENCE: 837
cugcaggcag aaguggggcu 20

<210> SEQ ID NO 838
<211> LENGTH: 20
<212> TYPE: RNA
<213> ORGANISM: Homo sapiens

<400> SEQUENCE: 838
gcugcgggcu gcggucaggg 20

<210> SEQ ID NO 839
<211> LENGTH: 24
<212> TYPE: RNA
<213> ORGANISM: Homo sapiens

<400> SEQUENCE: 839
acgcccuucc cccccuucuu cacc 24

<210> SEQ ID NO 840
<211> LENGTH: 17
<212> TYPE: RNA
<213> ORGANISM: Homo sapiens

<400> SEQUENCE: 840
acgcccuucc cccccuu 17

<210> SEQ ID NO 841
<211> LENGTH: 21
<212> TYPE: RNA
<213> ORGANISM: Homo sapiens

<400> SEQUENCE: 841
agccagagcu ggcugaaggg c 21

<210> SEQ ID NO 842
<211> LENGTH: 16
<212> TYPE: RNA
<213> ORGANISM: Homo sapiens

<400> SEQUENCE: 842
agcuggcuga agggca 16

<210> SEQ ID NO 843
<211> LENGTH: 22
<212> TYPE: RNA
<213> ORGANISM: Homo sapiens

<400> SEQUENCE: 843
ccaggcucug cagugggaac ug 22

<210> SEQ ID NO 844
<211> LENGTH: 16
<212> TYPE: RNA
<213> ORGANISM: Homo sapiens

<400> SEQUENCE: 844
ccaggcucug cagugg 16

<210> SEQ ID NO 845
<211> LENGTH: 26
<212> TYPE: RNA
<213> ORGANISM: Homo sapiens

<400> SEQUENCE: 845
gcgggcuguc cggaggggguc ggcuuu 26

<210> SEQ ID NO 846
<211> LENGTH: 16
<212> TYPE: RNA
<213> ORGANISM: Homo sapiens

<400> SEQUENCE: 846
gcuguccgga gggguc 16

<210> SEQ ID NO 847
<211> LENGTH: 21
<212> TYPE: RNA
<213> ORGANISM: Homo sapiens

<400> SEQUENCE: 847
gcugggagaa gaguggugaa g 21

<210> SEQ ID NO 848
<211> LENGTH: 17
<212> TYPE: RNA
<213> ORGANISM: Homo sapiens

<400> SEQUENCE: 848
ugggagaaga gugguga 17

<210> SEQ ID NO 849
<211> LENGTH: 22
<212> TYPE: RNA
<213> ORGANISM: Homo sapiens

<400> SEQUENCE: 849
ugucccaccc ccacuccugu uu 22

<210> SEQ ID NO 850
<211> LENGTH: 18
<212> TYPE: RNA
<213> ORGANISM: Homo sapiens

<400> SEQUENCE: 850
ugucccaccc ccacuccu 18

<210> SEQ ID NO 851
<211> LENGTH: 24
<212> TYPE: RNA
<213> ORGANISM: Homo sapiens

<400> SEQUENCE: 851
agguggtccg uggcgcguuc gcuu 24

<210> SEQ ID NO 852
<211> LENGTH: 17
<212> TYPE: RNA
<213> ORGANISM: Homo sapiens

<400> SEQUENCE: 852
agguggtccg uggcgcg 17

<210> SEQ ID NO 853
<211> LENGTH: 25
<212> TYPE: RNA
<213> ORGANISM: Homo sapiens

<400> SEQUENCE: 853
uaugcaggcc uguguacagc acuca 25

<210> SEQ ID NO 854
<211> LENGTH: 17
<212> TYPE: RNA
<213> ORGANISM: Homo sapiens

<400> SEQUENCE: 854
augcaggccu guguaca 17

<210> SEQ ID NO 855
<211> LENGTH: 25
<212> TYPE: RNA
<213> ORGANISM: Homo sapiens

<400> SEQUENCE: 855
ugggcagggg cuuauuguag gaguc 25

<210> SEQ ID NO 856
<211> LENGTH: 21
<212> TYPE: RNA
<213> ORGANISM: Homo sapiens

<400> SEQUENCE: 856
gggcaggggc uuauuguagg a 21

<210> SEQ ID NO 857
<211> LENGTH: 16
<212> TYPE: RNA
<213> ORGANISM: Homo sapiens

<400> SEQUENCE: 857
ugaggacagg gcaaau 16

<210> SEQ ID NO 858
<211> LENGTH: 16
<212> TYPE: RNA
<213> ORGANISM: Homo sapiens

<400> SEQUENCE: 858
uuccacugcc acuacc 16

<210> SEQ ID NO 859
<211> LENGTH: 16
<212> TYPE: RNA
<213> ORGANISM: Homo sapiens

<400> SEQUENCE: 859
gugcagggca cuggug 16

<210> SEQ ID NO 860
<211> LENGTH: 29
<212> TYPE: RNA
<213> ORGANISM: Homo sapiens

<400> SEQUENCE: 860
ggucaggcgg cucggacuga gcagguggg 29

<210> SEQ ID NO 861
<211> LENGTH: 15
<212> TYPE: RNA
<213> ORGANISM: Homo sapiens

<400> SEQUENCE: 861
agaguguggu caggc 15

<210> SEQ ID NO 862
<211> LENGTH: 26
<212> TYPE: RNA
<213> ORGANISM: Homo sapiens

<400> SEQUENCE: 862
gaggggcucu cgcuucuggc gccaag 26

<210> SEQ ID NO 863
<211> LENGTH: 15
<212> TYPE: RNA
<213> ORGANISM: Homo sapiens

<400> SEQUENCE: 863
ggugaggcgg ggggg 15

<210> SEQ ID NO 864
<211> LENGTH: 15
<212> TYPE: RNA
<213> ORGANISM: Homo sapiens

<400> SEQUENCE: 864
cccgcgggac gcgcc 15

<210> SEQ ID NO 865
<211> LENGTH: 18
<212> TYPE: RNA
<213> ORGANISM: Homo sapiens

<400> SEQUENCE: 865
uaugcauugu auuuuuag 18

<210> SEQ ID NO 866
<211> LENGTH: 22
<212> TYPE: RNA
<213> ORGANISM: Homo sapiens

<400> SEQUENCE: 866
ccaaccucga cgaucuccuc ag 22

<210> SEQ ID NO 867
<211> LENGTH: 16
<212> TYPE: RNA
<213> ORGANISM: Homo sapiens

<400> SEQUENCE: 867
aaccucgacg aucucc 16

<210> SEQ ID NO 868
<211> LENGTH: 23
<212> TYPE: RNA
<213> ORGANISM: Homo sapiens

<400> SEQUENCE: 868
ccacggaugu uugagcaugu gcu 23

<210> SEQ ID NO 869
<211> LENGTH: 16
<212> TYPE: RNA
<213> ORGANISM: Homo sapiens

<400> SEQUENCE: 869
cggauguuug agcaug 16

<210> SEQ ID NO 870
<211> LENGTH: 19
<212> TYPE: RNA
<213> ORGANISM: Homo sapiens

<400> SEQUENCE: 870
cccugugccc ggcccacuu 19

<210> SEQ ID NO 871
<211> LENGTH: 59
<212> TYPE: RNA
<213> ORGANISM: Homo sapiens

<400> SEQUENCE: 871
uagcagcaca ucaugguuua caugcuacag ucaagaugcg aaucauuauu ugcugcucu 59

<210> SEQ ID NO 872
<211> LENGTH: 16
<212> TYPE: RNA
<213> ORGANISM: Homo sapiens

<400> SEQUENCE: 872
cacaucaugg uuuaca 16

<210> SEQ ID NO 873
<211> LENGTH: 18
<212> TYPE: RNA
<213> ORGANISM: Homo sapiens

<400> SEQUENCE: 873
uggaguccag gaaucugc 18

<210> SEQ ID NO 874
<211> LENGTH: 19
<212> TYPE: RNA
<213> ORGANISM: Homo sapiens

<400> SEQUENCE: 874
cgucccaccc cccacuccu 19

<210> SEQ ID NO 875
<211> LENGTH: 22
<212> TYPE: RNA
<213> ORGANISM: Homo sapiens

<400> SEQUENCE: 875
cacgcggaga gauggcuuug ga 22

<210> SEQ ID NO 876
<211> LENGTH: 17
<212> TYPE: RNA
<213> ORGANISM: Homo sapiens

<400> SEQUENCE: 876
ucacgcggag agauggc 17

<210> SEQ ID NO 877
<211> LENGTH: 22
<212> TYPE: RNA
<213> ORGANISM: Homo sapiens

<400> SEQUENCE: 877
agacccugca gccuucccac cc 22

<210> SEQ ID NO 878
<211> LENGTH: 19
<212> TYPE: RNA
<213> ORGANISM: Homo sapiens

<400> SEQUENCE: 878
agggggcggg cuccggcgc 19

<210> SEQ ID NO 879
<211> LENGTH: 15
<212> TYPE: RNA
<213> ORGANISM: Homo sapiens

<400> SEQUENCE: 879
guagggggcg ggcuc 15

<210> SEQ ID NO 880
<211> LENGTH: 16
<212> TYPE: RNA

<213> ORGANISM: Homo sapiens

<400> SEQUENCE: 880
uuguggcugg ucauga 16

<210> SEQ ID NO 881
<211> LENGTH: 19
<212> TYPE: RNA
<213> ORGANISM: Homo sapiens

<400> SEQUENCE: 881
ucuauucccc acucucccc 19

<210> SEQ ID NO 882
<211> LENGTH: 17
<212> TYPE: RNA
<213> ORGANISM: Homo sapiens

<400> SEQUENCE: 882
cacccccugu uuccugg 17

<210> SEQ ID NO 883
<211> LENGTH: 22
<212> TYPE: RNA
<213> ORGANISM: Homo sapiens

<400> SEQUENCE: 883
uuuccuaugc auauacuucu uu 22

<210> SEQ ID NO 884
<211> LENGTH: 16
<212> TYPE: RNA
<213> ORGANISM: Homo sapiens

<400> SEQUENCE: 884
uuccuaugca uauacu 16

<210> SEQ ID NO 885
<211> LENGTH: 16
<212> TYPE: RNA
<213> ORGANISM: Homo sapiens

<400> SEQUENCE: 885
ggcgcggagg gcggac 16

<210> SEQ ID NO 886
<211> LENGTH: 15
<212> TYPE: RNA
<213> ORGANISM: Homo sapiens

<400> SEQUENCE: 886
ggcgcggagg gcgga 15

<210> SEQ ID NO 887
<211> LENGTH: 22
<212> TYPE: RNA
<213> ORGANISM: Homo sapiens

<400> SEQUENCE: 887
ccgggaacgu cgagacugga gc 22

<210> SEQ ID NO 888
<211> LENGTH: 15

<212> TYPE: RNA
<213> ORGANISM: Homo sapiens

<400> SEQUENCE: 888
cgggaacguc gagac 15

<210> SEQ ID NO 889
<211> LENGTH: 22
<212> TYPE: RNA
<213> ORGANISM: Homo sapiens

<400> SEQUENCE: 889
ggcaggaagc ggaggaaccu ug 22

<210> SEQ ID NO 890
<211> LENGTH: 17
<212> TYPE: RNA
<213> ORGANISM: Homo sapiens

<400> SEQUENCE: 890
ggaggaaccu uggagcu 17

<210> SEQ ID NO 891
<211> LENGTH: 19
<212> TYPE: RNA
<213> ORGANISM: Homo sapiens

<400> SEQUENCE: 891
guggguuggg gcgggcucu 19

<210> SEQ ID NO 892
<211> LENGTH: 19
<212> TYPE: RNA
<213> ORGANISM: Homo sapiens

<400> SEQUENCE: 892
guggguuggg gcgggcucu 19

<210> SEQ ID NO 893
<211> LENGTH: 18
<212> TYPE: RNA
<213> ORGANISM: Homo sapiens

<400> SEQUENCE: 893
ggcagcggcg gcggcggc 18

<210> SEQ ID NO 894
<211> LENGTH: 15
<212> TYPE: RNA
<213> ORGANISM: Homo sapiens

<400> SEQUENCE: 894
gcuccccgcg ccccc 15

<210> SEQ ID NO 895
<211> LENGTH: 24
<212> TYPE: RNA
<213> ORGANISM: Homo sapiens

<400> SEQUENCE: 895
gaucggucga gagcguccug gcug 24

<210> SEQ ID NO 896

<211> LENGTH: 15
<212> TYPE: RNA
<213> ORGANISM: Homo sapiens

<400> SEQUENCE: 896
gcugggcggg gcgcg 15

<210> SEQ ID NO 897
<211> LENGTH: 15
<212> TYPE: RNA
<213> ORGANISM: Homo sapiens

<400> SEQUENCE: 897
gcugcagugg gggag 15

<210> SEQ ID NO 898
<211> LENGTH: 19
<212> TYPE: RNA
<213> ORGANISM: Homo sapiens

<400> SEQUENCE: 898
gugagugugg auuuggcgg 19

<210> SEQ ID NO 899
<211> LENGTH: 19
<212> TYPE: RNA
<213> ORGANISM: Homo sapiens

<400> SEQUENCE: 899
cacacaagug gcccccaac 19

<210> SEQ ID NO 900
<211> LENGTH: 19
<212> TYPE: RNA
<213> ORGANISM: Homo sapiens

<400> SEQUENCE: 900
uaucauggag uugguaaag 19

<210> SEQ ID NO 901
<211> LENGTH: 25
<212> TYPE: RNA
<213> ORGANISM: Homo sapiens

<400> SEQUENCE: 901
uagagagggg aaggauguga uguga 25

<210> SEQ ID NO 902
<211> LENGTH: 16
<212> TYPE: RNA
<213> ORGANISM: Homo sapiens

<400> SEQUENCE: 902
agagagggga aggaug 16

<210> SEQ ID NO 903
<211> LENGTH: 20
<212> TYPE: RNA
<213> ORGANISM: Homo sapiens

<400> SEQUENCE: 903
caaagcgcuu cccuuuggag 20

<210> SEQ ID NO 904
<211> LENGTH: 16
<212> TYPE: RNA
<213> ORGANISM: Homo sapiens

<400> SEQUENCE: 904
gaggaaggaa ggaagg 16

<210> SEQ ID NO 905
<211> LENGTH: 20
<212> TYPE: RNA
<213> ORGANISM: Homo sapiens

<400> SEQUENCE: 905
ucucacccca acucugcccc 20

<210> SEQ ID NO 906
<211> LENGTH: 23
<212> TYPE: RNA
<213> ORGANISM: Homo sapiens

<400> SEQUENCE: 906
acagcagggc uggggauugc agu 23

<210> SEQ ID NO 907
<211> LENGTH: 22
<212> TYPE: RNA
<213> ORGANISM: Homo sapiens

<400> SEQUENCE: 907
auacuuuguc uccauguuuc cu 22

<210> SEQ ID NO 908
<211> LENGTH: 19
<212> TYPE: RNA
<213> ORGANISM: Homo sapiens

<400> SEQUENCE: 908
auacuuuguc uccauguuu 19

<210> SEQ ID NO 909
<211> LENGTH: 20
<212> TYPE: RNA
<213> ORGANISM: Homo sapiens

<400> SEQUENCE: 909
ugggcagggc uguggugagu 20

<210> SEQ ID NO 910
<211> LENGTH: 24
<212> TYPE: RNA
<213> ORGANISM: Homo sapiens

<400> SEQUENCE: 910
cgggcguggu ggugggggug ggug 24

<210> SEQ ID NO 911
<211> LENGTH: 15
<212> TYPE: RNA
<213> ORGANISM: Homo sapiens

<400> SEQUENCE: 911
cgggcguggu ggugg 15

<210> SEQ ID NO 912
<211> LENGTH: 20
<212> TYPE: RNA
<213> ORGANISM: Homo sapiens

<400> SEQUENCE: 912
uacuggacuu ggagucagaa 20

<210> SEQ ID NO 913
<211> LENGTH: 16
<212> TYPE: RNA
<213> ORGANISM: Homo sapiens

<400> SEQUENCE: 913
acuggacuug gaguca 16

<210> SEQ ID NO 914
<211> LENGTH: 22
<212> TYPE: RNA
<213> ORGANISM: Homo sapiens

<400> SEQUENCE: 914
cuuggccacc acaccuaccc cu 22

<210> SEQ ID NO 915
<211> LENGTH: 17
<212> TYPE: RNA
<213> ORGANISM: Homo sapiens

<400> SEQUENCE: 915
uuggccacca caccuac 17

<210> SEQ ID NO 916
<211> LENGTH: 32
<212> TYPE: RNA
<213> ORGANISM: Homo sapiens

<400> SEQUENCE: 916
gguccccucc ccaggggcug gcuuuccucu gg 32

<210> SEQ ID NO 917
<211> LENGTH: 16
<212> TYPE: RNA
<213> ORGANISM: Homo sapiens

<400> SEQUENCE: 917
caggggcugg cuuucc 16

<210> SEQ ID NO 918
<211> LENGTH: 18
<212> TYPE: RNA
<213> ORGANISM: Homo sapiens

<400> SEQUENCE: 918
acaggugacu gguuagac 18

<210> SEQ ID NO 919
<211> LENGTH: 18
<212> TYPE: RNA
<213> ORGANISM: Homo sapiens

<400> SEQUENCE: 919
ccucucuguc ccacccau 18

<210> SEQ ID NO 920
<211> LENGTH: 18
<212> TYPE: RNA
<213> ORGANISM: Homo sapiens

<400> SEQUENCE: 920
aaagugcuuc ccuuugga 18

<210> SEQ ID NO 921
<211> LENGTH: 17
<212> TYPE: RNA
<213> ORGANISM: Homo sapiens

<400> SEQUENCE: 921
cccuucccuc acucuuc 17

<210> SEQ ID NO 922
<211> LENGTH: 55
<212> TYPE: RNA
<213> ORGANISM: Homo sapiens

<400> SEQUENCE: 922
ggugcagugc ugcaucucug gucaguuggg agucugagau gaagcacugu agcuc 55

<210> SEQ ID NO 923
<211> LENGTH: 16
<212> TYPE: RNA
<213> ORGANISM: Homo sapiens

<400> SEQUENCE: 923
aggugcagug cugcau 16

<210> SEQ ID NO 924
<211> LENGTH: 22
<212> TYPE: RNA
<213> ORGANISM: Homo sapiens

<400> SEQUENCE: 924
cccugggccu cugcuccca gu 22

<210> SEQ ID NO 925
<211> LENGTH: 16
<212> TYPE: RNA
<213> ORGANISM: Homo sapiens

<400> SEQUENCE: 925
cugggccucu gcuccc 16

<210> SEQ ID NO 926
<211> LENGTH: 18
<212> TYPE: RNA
<213> ORGANISM: Homo sapiens

<400> SEQUENCE: 926
ucugugcccc uacuuccc 18

<210> SEQ ID NO 927
<211> LENGTH: 19
<212> TYPE: RNA
<213> ORGANISM: Homo sapiens

<400> SEQUENCE: 927
uuggcugguc ucugcuccg 19

<210> SEQ ID NO 928
<211> LENGTH: 23
<212> TYPE: RNA
<213> ORGANISM: Homo sapiens

<400> SEQUENCE: 928
agaagaacug uugcauuugc ccu 23

<210> SEQ ID NO 929
<211> LENGTH: 16
<212> TYPE: RNA
<213> ORGANISM: Homo sapiens

<400> SEQUENCE: 929
agaagaacug uugcau 16

<210> SEQ ID NO 930
<211> LENGTH: 19
<212> TYPE: RNA
<213> ORGANISM: Homo sapiens

<400> SEQUENCE: 930
cucucccucu uuacccacu 19

<210> SEQ ID NO 931
<211> LENGTH: 22
<212> TYPE: RNA
<213> ORGANISM: Homo sapiens

<400> SEQUENCE: 931
guuugguccc cuucaaccag cu 22

<210> SEQ ID NO 932
<211> LENGTH: 16
<212> TYPE: RNA
<213> ORGANISM: Homo sapiens

<400> SEQUENCE: 932 uuugguccccc uucaac 16

<210> SEQ ID NO 933
<211> LENGTH: 17
<212> TYPE: RNA
<213> ORGANISM: Homo sapiens

<400> SEQUENCE: 933
gcggggcggc aggggcc 17

<210> SEQ ID NO 934
<211> LENGTH: 15
<212> TYPE: RNA
<213> ORGANISM: Homo sapiens

<400> SEQUENCE: 934
gggggcgggg cggca 15

<210> SEQ ID NO 935
<211> LENGTH: 30
<212> TYPE: RNA
<213> ORGANISM: Homo sapiens

<400> SEQUENCE: 935
uuuuauccaa cuggcccuca aagucccgcu 30

<210> SEQ ID NO 936
<211> LENGTH: 16
<212> TYPE: RNA
<213> ORGANISM: Homo sapiens

<400> SEQUENCE: 936
aacuggcccu caaagu 16

<210> SEQ ID NO 937
<211> LENGTH: 18
<212> TYPE: RNA
<213> ORGANISM: Homo sapiens

<400> SEQUENCE: 937
ucccuacccc uccacucc 18

<210> SEQ ID NO 938
<211> LENGTH: 18
<212> TYPE: RNA
<213> ORGANISM: Homo sapiens

<400> SEQUENCE: 938
aagccucugu ccccaccc 18

<210> SEQ ID NO 939
<211> LENGTH: 20
<212> TYPE: RNA
<213> ORGANISM: Homo sapiens

<400> SEQUENCE: 939
accggccgcc ggcuccgccc 20

<210> SEQ ID NO 940
<211> LENGTH: 17
<212> TYPE: RNA
<213> ORGANISM: Homo sapiens

<400> SEQUENCE: 940
ccggccgccg gcuccgc 17

<210> SEQ ID NO 941
<211> LENGTH: 29
<212> TYPE: RNA
<213> ORGANISM: Homo sapiens

<400> SEQUENCE: 941
gggagccgcg gggaucgccg agggccggu 29

<210> SEQ ID NO 942
<211> LENGTH: 15
<212> TYPE: RNA
<213> ORGANISM: Homo sapiens

<400> SEQUENCE: 942
ggcggcggug guggg 15

<210> SEQ ID NO 943
<211> LENGTH: 18
<212> TYPE: RNA
<213> ORGANISM: Homo sapiens

<400> SEQUENCE: 943 ucuaggugggg gagacuga 18

<210> SEQ ID NO 944
<211> LENGTH: 16
<212> TYPE: RNA
<213> ORGANISM: Homo sapiens

<400> SEQUENCE: 944
guggggagac ugacgg 16

<210> SEQ ID NO 945
<211> LENGTH: 22
<212> TYPE: RNA
<213> ORGANISM: Homo sapiens

<400> SEQUENCE: 945
cggcuggagg ugugaggauc cg 22

<210> SEQ ID NO 946
<211> LENGTH: 16
<212> TYPE: RNA
<213> ORGANISM: Homo sapiens

<400> SEQUENCE: 946
gcuggaggug ugagga 16

<210> SEQ ID NO 947
<211> LENGTH: 25
<212> TYPE: RNA
<213> ORGANISM: Homo sapiens

<400> SEQUENCE: 947
cugggccagg gagcagcugg ugggu 25

<210> SEQ ID NO 948
<211> LENGTH: 20
<212> TYPE: RNA
<213> ORGANISM: Homo sapiens

<400> SEQUENCE: 948
ugggccaggg agcagcuggu 20

<210> SEQ ID NO 949
<211> LENGTH: 20
<212> TYPE: RNA
<213> ORGANISM: Homo sapiens

<400> SEQUENCE: 949
ucaugggagu ucgggguggu 20

<210> SEQ ID NO 950
<211> LENGTH: 16
<212> TYPE: RNA
<213> ORGANISM: Homo sapiens

<400> SEQUENCE: 950
augggaguuc ggggug 16

<210> SEQ ID NO 951
<211> LENGTH: 26
<212> TYPE: RNA
<213> ORGANISM: Homo sapiens

<400> SEQUENCE: 951
ccacaagacu guggacagug agguag 26

<210> SEQ ID NO 952
<211> LENGTH: 16
<212> TYPE: RNA
<213> ORGANISM: Homo sapiens

<400> SEQUENCE: 952
uguggacagu gaggua 16

<210> SEQ ID NO 953
<211> LENGTH: 27
<212> TYPE: RNA
<213> ORGANISM: Homo sapiens

<400> SEQUENCE: 953
gcagaggcug agaaggugau guuggcu 27

<210> SEQ ID NO 954
<211> LENGTH: 16
<212> TYPE: RNA
<213> ORGANISM: Homo sapiens

<400> SEQUENCE: 954
cagaggcuga gaaggu 16

<210> SEQ ID NO 955
<211> LENGTH: 22
<212> TYPE: RNA
<213> ORGANISM: Homo sapiens

<400> SEQUENCE: 955
gaguuaaggg uugcuuggag aa 22

<210> SEQ ID NO 956
<211> LENGTH: 19
<212> TYPE: RNA
<213> ORGANISM: Homo sapiens

<400> SEQUENCE: 956
gaguuaaggg uugcuugga 19

<210> SEQ ID NO 957
<211> LENGTH: 23
<212> TYPE: RNA
<213> ORGANISM: Homo sapiens

<400> SEQUENCE: 957
cugugcuugc ucgucccgcc cgc 23

<210> SEQ ID NO 958
<211> LENGTH: 16
<212> TYPE: RNA
<213> ORGANISM: Homo sapiens

<400> SEQUENCE: 958
ugugcuugcu cguccc 16

<210> SEQ ID NO 959
<211> LENGTH: 21
<212> TYPE: RNA

<213> ORGANISM: Homo sapiens

<400> SEQUENCE: 959
ucuguuaacc cauccccuca u 21

<210> SEQ ID NO 960
<211> LENGTH: 17
<212> TYPE: RNA
<213> ORGANISM: Homo sapiens

<400> SEQUENCE: 960
uucuguuaac ccauccc 17

<210> SEQ ID NO 961
<211> LENGTH: 22
<212> TYPE: RNA
<213> ORGANISM: Homo sapiens

<400> SEQUENCE: 961
ucaggguugg uaggggguugc ug 22

<210> SEQ ID NO 962
<211> LENGTH: 16
<212> TYPE: RNA
<213> ORGANISM: Homo sapiens

<400> SEQUENCE: 962
ucaggguugg uagggg 16

<210> SEQ ID NO 963
<211> LENGTH: 23
<212> TYPE: RNA
<213> ORGANISM: Homo sapiens

<400> SEQUENCE: 963
ggcugaugau gauggugcug aag 23

<210> SEQ ID NO 964
<211> LENGTH: 16
<212> TYPE: RNA
<213> ORGANISM: Homo sapiens

<400> SEQUENCE: 964
gaugaugaug gugcug 16

<210> SEQ ID NO 965
<211> LENGTH: 24
<212> TYPE: RNA
<213> ORGANISM: Homo sapiens

<400> SEQUENCE: 965
uccagggaga caguguguga ggcc 24

<210> SEQ ID NO 966
<211> LENGTH: 17
<212> TYPE: RNA
<213> ORGANISM: Homo sapiens

<400> SEQUENCE: 966
uccagggaga cagugug 17

<210> SEQ ID NO 967
<211> LENGTH: 23

<212> TYPE: RNA
<213> ORGANISM: Homo sapiens

<400> SEQUENCE: 967
ugggcacagg cggauggaca ggc 23

<210> SEQ ID NO 968
<211> LENGTH: 17
<212> TYPE: RNA
<213> ORGANISM: Homo sapiens

<400> SEQUENCE: 968
ugggcacagg cggaugg 17

<210> SEQ ID NO 969
<211> LENGTH: 18
<212> TYPE: RNA
<213> ORGANISM: Homo sapiens

<400> SEQUENCE: 969
agagaagaag aucagccu 18

<210> SEQ ID NO 970
<211> LENGTH: 17
<212> TYPE: RNA
<213> ORGANISM: Homo sapiens

<400> SEQUENCE: 970
cucuggaggg aagcacu 17

<210> SEQ ID NO 971
<211> LENGTH: 19
<212> TYPE: RNA
<213> ORGANISM: Homo sapiens

<400> SEQUENCE: 971
gguagccuuc agaucuugg 19

<210> SEQ ID NO 972
<211> LENGTH: 17
<212> TYPE: RNA
<213> ORGANISM: Homo sapiens

<400> SEQUENCE: 972
uagccuucag aucuugg 17

<210> SEQ ID NO 973
<211> LENGTH: 18
<212> TYPE: RNA
<213> ORGANISM: Homo sapiens

<400> SEQUENCE: 973
aucugccagc uuccacag 18

<210> SEQ ID NO 974
<211> LENGTH: 36
<212> TYPE: RNA
<213> ORGANISM: Homo sapiens

<400> SEQUENCE: 974
uguguuauca uaauaaaggu gucaugauga uacagg 36

<210> SEQ ID NO 975

<211> LENGTH: 19
<212> TYPE: RNA
<213> ORGANISM: Homo sapiens

<400> SEQUENCE: 975
cuacuucuac cuguguuau 19

<210> SEQ ID NO 976
<211> LENGTH: 24
<212> TYPE: RNA
<213> ORGANISM: Homo sapiens

<400> SEQUENCE: 976
cccggggcag auugguguag ggug 24

<210> SEQ ID NO 977
<211> LENGTH: 17
<212> TYPE: RNA
<213> ORGANISM: Homo sapiens

<400> SEQUENCE: 977
cggggcagau uggugua 17

<210> SEQ ID NO 978
<211> LENGTH: 23
<212> TYPE: RNA
<213> ORGANISM: Homo sapiens

<400> SEQUENCE: 978
cuccuauaug augccuuucu uca 23

<210> SEQ ID NO 979
<211> LENGTH: 16
<212> TYPE: RNA
<213> ORGANISM: Homo sapiens

<400> SEQUENCE: 979
cuauaugaug ccuuuc 16

<210> SEQ ID NO 980
<211> LENGTH: 17
<212> TYPE: RNA
<213> ORGANISM: Homo sapiens

<400> SEQUENCE: 980
cccagauaau ggcacuc 17

<210> SEQ ID NO 981
<211> LENGTH: 26
<212> TYPE: RNA
<213> ORGANISM: Homo sapiens

<400> SEQUENCE: 981
aacccguaga uccgaacuug ugguau 26

<210> SEQ ID NO 982
<211> LENGTH: 16
<212> TYPE: RNA
<213> ORGANISM: Homo sapiens

<400> SEQUENCE: 982
aacccguaga uccgaa 16

<210> SEQ ID NO 983
<211> LENGTH: 23
<212> TYPE: RNA
<213> ORGANISM: Homo sapiens

<400> SEQUENCE: 983
uuuggacaga aaacacgcag gaa 23

<210> SEQ ID NO 984
<211> LENGTH: 16
<212> TYPE: RNA
<213> ORGANISM: Homo sapiens

<400> SEQUENCE: 984
uggacagaaa acacgc 16

<210> SEQ ID NO 985
<211> LENGTH: 17
<212> TYPE: RNA
<213> ORGANISM: Homo sapiens

<400> SEQUENCE: 985
gaagugcuuc gauuuug 17

<210> SEQ ID NO 986
<211> LENGTH: 21
<212> TYPE: RNA
<213> ORGANISM: Homo sapiens

<400> SEQUENCE: 986
agucgggcgc aagagcacug c 21

<210> SEQ ID NO 987
<211> LENGTH: 16
<212> TYPE: RNA
<213> ORGANISM: Homo sapiens

<400> SEQUENCE: 987
ucgggcgcaa gagcac 16

<210> SEQ ID NO 988
<211> LENGTH: 22
<212> TYPE: RNA
<213> ORGANISM: Homo sapiens

<400> SEQUENCE: 988
uuguccucua gggccugcag uc 22

<210> SEQ ID NO 989
<211> LENGTH: 16
<212> TYPE: RNA
<213> ORGANISM: Homo sapiens

<400> SEQUENCE: 989
uuguccucua gggccu 16

<210> SEQ ID NO 990
<211> LENGTH: 59
<212> TYPE: RNA
<213> ORGANISM: Homo sapiens

<400> SEQUENCE: 990
uauugcacau uacuaaguug cauguuguca cggccucaau gcaauuuagu gugugugau 59

<210> SEQ ID NO 991
<211> LENGTH: 16
<212> TYPE: RNA
<213> ORGANISM: Homo sapiens

<400> SEQUENCE: 991
cacauuacua aguugc 16

<210> SEQ ID NO 992
<211> LENGTH: 22
<212> TYPE: RNA
<213> ORGANISM: Homo sapiens

<400> SEQUENCE: 992
aguaagugcu uccauguuuu gg 22

<210> SEQ ID NO 993
<211> LENGTH: 18
<212> TYPE: RNA
<213> ORGANISM: Homo sapiens

<400> SEQUENCE: 993
uaagugcuuc cauguuuu 18

<210> SEQ ID NO 994
<211> LENGTH: 23
<212> TYPE: RNA
<213> ORGANISM: Homo sapiens

<400> SEQUENCE: 994
uuuucuucuu agacauggca acg 23

<210> SEQ ID NO 995
<211> LENGTH: 16
<212> TYPE: RNA
<213> ORGANISM: Homo sapiens

<400> SEQUENCE: 995
uuucuucuua gacaug 16

<210> SEQ ID NO 996
<211> LENGTH: 21
<212> TYPE: RNA
<213> ORGANISM: Homo sapiens

<400> SEQUENCE: 996
ggucgcucua ggcaccgcag c 21

<210> SEQ ID NO 997
<211> LENGTH: 17
<212> TYPE: RNA
<213> ORGANISM: Homo sapiens

<400> SEQUENCE: 997
ggucgcucua ggcaccg 17

<210> SEQ ID NO 998
<211> LENGTH: 22
<212> TYPE: RNA
<213> ORGANISM: Homo sapiens

<400> SEQUENCE: 998
ucgugcaucc cuuuagagug uu 22

<210> SEQ ID NO 999
<211> LENGTH: 16
<212> TYPE: RNA
<213> ORGANISM: Homo sapiens

<400> SEQUENCE: 999
gugcaucccu uuagag 16

<210> SEQ ID NO 1000
<211> LENGTH: 22
<212> TYPE: RNA
<213> ORGANISM: Homo sapiens

<400> SEQUENCE: 1000
ucgugcaucc cuuuagagug uu 22

<210> SEQ ID NO 1001
<211> LENGTH: 16
<212> TYPE: RNA
<213> ORGANISM: Homo sapiens

<400> SEQUENCE: 1001
gugcaucccu uuagag 16

<210> SEQ ID NO 1002
<211> LENGTH: 32
<212> TYPE: RNA
<213> ORGANISM: Homo sapiens

<400> SEQUENCE: 1002
acuggagggu guaguguuuc cuacuuuaug ga 32

<210> SEQ ID NO 1003
<211> LENGTH: 16
<212> TYPE: RNA
<213> ORGANISM: Homo sapiens

<400> SEQUENCE: 1003
uaguguuucc uacuuu 16

<210> SEQ ID NO 1004
<211> LENGTH: 24
<212> TYPE: RNA
<213> ORGANISM: Homo sapiens

<400> SEQUENCE: 1004
auauacaggg ggagacucuc auuu 24

<210> SEQ ID NO 1005
<211> LENGTH: 15
<212> TYPE: RNA
<213> ORGANISM: Homo sapiens

<400> SEQUENCE: 1005
auauacaggg ggaga 15

<210> SEQ ID NO 1006
<211> LENGTH: 18
<212> TYPE: RNA
<213> ORGANISM: Homo sapiens

<400> SEQUENCE: 1006
cugcaaaggg aagcccuu 18

<210> SEQ ID NO 1007
<211> LENGTH: 25
<212> TYPE: RNA
<213> ORGANISM: Homo sapiens

<400> SEQUENCE: 1007
caaggagcuc acagucuauu gaguu 25

<210> SEQ ID NO 1008
<211> LENGTH: 16
<212> TYPE: RNA
<213> ORGANISM: Homo sapiens

<400> SEQUENCE: 1008
caaggagcuc acaguc 16

<210> SEQ ID NO 1009
<211> LENGTH: 61
<212> TYPE: RNA
<213> ORGANISM: Homo sapiens

<400> SEQUENCE: 1009
aacuguuugc agaggaaacu gagacuuugu aacuaugucu cagucucauc ugcaaagaag 60
u 61

<210> SEQ ID NO 1010
<211> LENGTH: 16
<212> TYPE: RNA
<213> ORGANISM: Homo sapiens

<400> SEQUENCE: 1010
aacuguuugc agagga 16

<210> SEQ ID NO 1011
<211> LENGTH: 17
<212> TYPE: RNA
<213> ORGANISM: Homo sapiens

<400> SEQUENCE: 1011
cuccagaggg augcacu 17

<210> SEQ ID NO 1012
<211> LENGTH: 23
<212> TYPE: RNA
<213> ORGANISM: Homo sapiens

<400> SEQUENCE: 1012
caccugaccu cccaugccug ugc 23

<210> SEQ ID NO 1013
<211> LENGTH: 19
<212> TYPE: RNA
<213> ORGANISM: Homo sapiens

<400> SEQUENCE: 1013
accugaccuc ccaugccug 19

<210> SEQ ID NO 1014
<211> LENGTH: 19
<212> TYPE: RNA
<213> ORGANISM: Homo sapiens

<400> SEQUENCE: 1014
aaccuuggcc ccucucccc 19

<210> SEQ ID NO 1015
<211> LENGTH: 24
<212> TYPE: RNA
<213> ORGANISM: Homo sapiens

<400> SEQUENCE: 1015
ugggggagug cagugauugu ggaa 24

<210> SEQ ID NO 1016
<211> LENGTH: 19
<212> TYPE: RNA
<213> ORGANISM: Homo sapiens

<400> SEQUENCE: 1016
ugggggagug cagugauug 19

<210> SEQ ID NO 1017
<211> LENGTH: 20
<212> TYPE: RNA
<213> ORGANISM: Homo sapiens

<400> SEQUENCE: 1017
ccccagggcg acgcggcggg 20

<210> SEQ ID NO 1018
<211> LENGTH: 15
<212> TYPE: RNA
<213> ORGANISM: Homo sapiens

<400> SEQUENCE: 1018
cgcggcgggg gcggc 15

<210> SEQ ID NO 1019
<211> LENGTH: 18
<212> TYPE: RNA
<213> ORGANISM: Homo sapiens

<400> SEQUENCE: 1019
cagcggggcu gggcgcgc 18

<210> SEQ ID NO 1020
<211> LENGTH: 15
<212> TYPE: RNA
<213> ORGANISM: Homo sapiens

<400> SEQUENCE: 1020
cggggcuggg cgcgc 15

<210> SEQ ID NO 1021
<211> LENGTH: 23
<212> TYPE: RNA
<213> ORGANISM: Homo sapiens

<400> SEQUENCE: 1021
ggggggaugu gcaugcuggu ugg 23

<210> SEQ ID NO 1022
<211> LENGTH: 15
<212> TYPE: RNA

<213> ORGANISM: Homo sapiens

<400> SEQUENCE: 1022
aucagcgugc acuuc 15

<210> SEQ ID NO 1023
<211> LENGTH: 23
<212> TYPE: RNA
<213> ORGANISM: Homo sapiens

<400> SEQUENCE: 1023
ggugggugag gucgggcccc aag 23

<210> SEQ ID NO 1024
<211> LENGTH: 15
<212> TYPE: RNA
<213> ORGANISM: Homo sapiens

<400> SEQUENCE: 1024
ggcgcgggga ggugc 15

<210> SEQ ID NO 1025
<211> LENGTH: 15
<212> TYPE: RNA
<213> ORGANISM: Homo sapiens

<400> SEQUENCE: 1025
ggcgcgggga ggugc 15

<210> SEQ ID NO 1026
<211> LENGTH: 20
<212> TYPE: RNA
<213> ORGANISM: Homo sapiens

<400> SEQUENCE: 1026
ggauuuuugg aucagggaug 20

<210> SEQ ID NO 1027
<211> LENGTH: 15
<212> TYPE: RNA
<213> ORGANISM: Homo sapiens

<400> SEQUENCE: 1027
uuuuuggauc aggga 15

<210> SEQ ID NO 1028
<211> LENGTH: 24
<212> TYPE: RNA
<213> ORGANISM: Homo sapiens

<400> SEQUENCE: 1028
gugaguggga gccggugggg cugg 24

<210> SEQ ID NO 1029
<211> LENGTH: 15
<212> TYPE: RNA
<213> ORGANISM: Homo sapiens

<400> SEQUENCE: 1029
ggggcuggag uaagg 15

<210> SEQ ID NO 1030
<211> LENGTH: 19

<212> TYPE: RNA
<213> ORGANISM: Homo sapiens

<400> SEQUENCE: 1030
gcaggcgagg cugggcuga 19

<210> SEQ ID NO 1031
<211> LENGTH: 16
<212> TYPE: RNA
<213> ORGANISM: Homo sapiens

<400> SEQUENCE: 1031
aggcgaggcu gggcug 16

<210> SEQ ID NO 1032
<211> LENGTH: 22
<212> TYPE: RNA
<213> ORGANISM: Homo sapiens

<400> SEQUENCE: 1032
accaggaggc ugaggccccu ca 22

<210> SEQ ID NO 1033
<211> LENGTH: 15
<212> TYPE: RNA
<213> ORGANISM: Homo sapiens

<400> SEQUENCE: 1033
accaggaggc ugagg 15

<210> SEQ ID NO 1034
<211> LENGTH: 24
<212> TYPE: RNA
<213> ORGANISM: Homo sapiens

<400> SEQUENCE: 1034
uucccuuugu cauccuucgc cuag 24

<210> SEQ ID NO 1035
<211> LENGTH: 16
<212> TYPE: RNA
<213> ORGANISM: Homo sapiens

<400> SEQUENCE: 1035
cuuugucauc cuucgc 16

<210> SEQ ID NO 1036
<211> LENGTH: 23
<212> TYPE: RNA
<213> ORGANISM: Homo sapiens

<400> SEQUENCE: 1036
cacccguccc guucgucccc gga 23

<210> SEQ ID NO 1037
<211> LENGTH: 16
<212> TYPE: RNA
<213> ORGANISM: Homo sapiens

<400> SEQUENCE: 1037
cacccguccc guucgu 16

<210> SEQ ID NO 1038

<211> LENGTH: 19
<212> TYPE: RNA
<213> ORGANISM: Homo sapiens

<400> SEQUENCE: 1038
uggcgggugc gggggguggg 19

<210> SEQ ID NO 1039
<211> LENGTH: 15
<212> TYPE: RNA
<213> ORGANISM: Homo sapiens

<400> SEQUENCE: 1039
uggcgggugc ggggg 15

<210> SEQ ID NO 1040
<211> LENGTH: 62
<212> TYPE: RNA
<213> ORGANISM: Homo sapiens

<400> SEQUENCE: 1040
ucuggcuccg ugucuucacu cccgugcuug uccgaggagg gagggaggga cgggggcugu 60
gc 62

<210> SEQ ID NO 1041
<211> LENGTH: 16
<212> TYPE: RNA
<213> ORGANISM: Homo sapiens

<400> SEQUENCE: 1041
ucuggcuccg ugucuu 16

<210> SEQ ID NO 1042
<211> LENGTH: 25
<212> TYPE: RNA
<213> ORGANISM: Homo sapiens

<400> SEQUENCE: 1042
ugcggggcua gggcuaacag caguc 25

<210> SEQ ID NO 1043
<211> LENGTH: 15
<212> TYPE: RNA
<213> ORGANISM: Homo sapiens

<400> SEQUENCE: 1043
ugcggggcua gggcu 15

<210> SEQ ID NO 1044
<211> LENGTH: 58
<212> TYPE: RNA
<213> ORGANISM: Homo sapiens

<400> SEQUENCE: 1044
gcugacuccu aguccagggc ucgugauggc uggugggccc ugaacgaggg gucuggag 58

<210> SEQ ID NO 1045
<211> LENGTH: 16
<212> TYPE: RNA
<213> ORGANISM: Homo sapiens

<400> SEQUENCE: 1045
ugacuccuag uccagg 16

<210> SEQ ID NO 1046
<211> LENGTH: 24
<212> TYPE: RNA
<213> ORGANISM: Homo sapiens

<400> SEQUENCE: 1046
gucucccaac ccuuguacca gugc 24

<210> SEQ ID NO 1047
<211> LENGTH: 16
<212> TYPE: RNA
<213> ORGANISM: Homo sapiens

<400> SEQUENCE: 1047
ugucucccaa cccuug 16

<210> SEQ ID NO 1048
<211> LENGTH: 22
<212> TYPE: RNA
<213> ORGANISM: Homo sapiens

<400> SEQUENCE: 1048
gcugcgcuug gauuucgucc cc 22

<210> SEQ ID NO 1049
<211> LENGTH: 16
<212> TYPE: RNA
<213> ORGANISM: Homo sapiens

<400> SEQUENCE: 1049
cagcugcgcu uggauu 16

<210> SEQ ID NO 1050
<211> LENGTH: 23
<212> TYPE: RNA
<213> ORGANISM: Homo sapiens

<400> SEQUENCE: 1050
uuuaggauaa gcuugacuuu ugu 23

<210> SEQ ID NO 1051
<211> LENGTH: 16
<212> TYPE: RNA
<213> ORGANISM: Homo sapiens

<400> SEQUENCE: 1051
uuuaggauaa gcuuga 16

<210> SEQ ID NO 1052
<211> LENGTH: 24
<212> TYPE: RNA
<213> ORGANISM: Homo sapiens

<400> SEQUENCE: 1052
uuggcagugu cuuagcuggu uguu 24

<210> SEQ ID NO 1053
<211> LENGTH: 16
<212> TYPE: RNA
<213> ORGANISM: Homo sapiens

<400> SEQUENCE: 1053
uuggcagugu cuuagc 16

<210> SEQ ID NO 1054
<211> LENGTH: 24
<212> TYPE: RNA
<213> ORGANISM: Homo sapiens

<400> SEQUENCE: 1054
agguuacccg agcaacuuug cauc 24

<210> SEQ ID NO 1055
<211> LENGTH: 16
<212> TYPE: RNA
<213> ORGANISM: Homo sapiens

<400> SEQUENCE: 1055
ccgagcaacu uugcau 16

<210> SEQ ID NO 1056
<211> LENGTH: 22
<212> TYPE: RNA
<213> ORGANISM: Homo sapiens

<400> SEQUENCE: 1056
agaucgaccg uguuauauuc gc 22

<210> SEQ ID NO 1057
<211> LENGTH: 16
<212> TYPE: RNA
<213> ORGANISM: Homo sapiens

<400> SEQUENCE: 1057
agaucgaccg uguuau 16

<210> SEQ ID NO 1058
<211> LENGTH: 23
<212> TYPE: RNA
<213> ORGANISM: Homo sapiens

<400> SEQUENCE: 1058
caccuugccu ugcugcccgg gcc 23

<210> SEQ ID NO 1059
<211> LENGTH: 22
<212> TYPE: RNA
<213> ORGANISM: Homo sapiens

<400> SEQUENCE: 1059
caccuugccu ugcugcccgg gc 22

<210> SEQ ID NO 1060
<211> LENGTH: 24
<212> TYPE: RNA
<213> ORGANISM: Homo sapiens

<400> SEQUENCE: 1060
uucccuuugu cauccuaugc cuga 24

<210> SEQ ID NO 1061
<211> LENGTH: 16
<212> TYPE: RNA
<213> ORGANISM: Homo sapiens

<400> SEQUENCE: 1061
uucccuuugu cauccu 16

<210> SEQ ID NO 1062
<211> LENGTH: 32
<212> TYPE: RNA
<213> ORGANISM: Homo sapiens

<400> SEQUENCE: 1062
cggauuacgu uguuauugcu uaagaauacg cg 32

<210> SEQ ID NO 1063
<211> LENGTH: 16
<212> TYPE: RNA
<213> ORGANISM: Homo sapiens

<400> SEQUENCE: 1063
uuguuauugc uuaaga 16

<210> SEQ ID NO 1064
<211> LENGTH: 23
<212> TYPE: RNA
<213> ORGANISM: Homo sapiens

<400> SEQUENCE: 1064
aguuguucgu gguggauucg cuu 23

<210> SEQ ID NO 1065
<211> LENGTH: 16
<212> TYPE: RNA
<213> ORGANISM: Homo sapiens

<400> SEQUENCE: 1065
gaaguuguuc guggug 16

<210> SEQ ID NO 1066
<211> LENGTH: 22
<212> TYPE: RNA
<213> ORGANISM: Homo sapiens

<400> SEQUENCE: 1066
ccucuagaug gaagcacugu cu 22

<210> SEQ ID NO 1067
<211> LENGTH: 48
<212> TYPE: RNA
<213> ORGANISM: Homo sapiens

<400> SEQUENCE: 1067
caugccuuga guguaggacc guuggcaucu uaauuacccu cccacacc 48

<210> SEQ ID NO 1068
<211> LENGTH: 16
<212> TYPE: RNA
<213> ORGANISM: Homo sapiens

<400> SEQUENCE: 1068
caugccuuga guguag 16

<210> SEQ ID NO 1069
<211> LENGTH: 60
<212> TYPE: RNA
<213> ORGANISM: Homo sapiens

<400> SEQUENCE: 1069
aguucuucag uggcaagcuu uauguccuga cccagcuaaa gcugccaguu gaagaacugu 60

<210> SEQ ID NO 1070
<211> LENGTH: 16
<212> TYPE: RNA
<213> ORGANISM: Homo sapiens

<400> SEQUENCE: 1070
aguucuucag uggcaa 16

<210> SEQ ID NO 1071
<211> LENGTH: 21
<212> TYPE: RNA
<213> ORGANISM: Homo sapiens

<400> SEQUENCE: 1071
uccuucugcu ccgucccccca g 21

<210> SEQ ID NO 1072
<211> LENGTH: 16
<212> TYPE: RNA
<213> ORGANISM: Homo sapiens

<400> SEQUENCE: 1072
uucugcuccg uccccc 16

<210> SEQ ID NO 1073
<211> LENGTH: 21
<212> TYPE: RNA
<213> ORGANISM: Homo sapiens

<400> SEQUENCE: 1073
ccccaccucc ucucuccuca g 21

<210> SEQ ID NO 1074
<211> LENGTH: 18
<212> TYPE: RNA
<213> ORGANISM: Homo sapiens

<400> SEQUENCE: 1074
ccccaccucc ucucuccu 18

<210> SEQ ID NO 1075
<211> LENGTH: 26
<212> TYPE: RNA
<213> ORGANISM: Homo sapiens

<400> SEQUENCE: 1075
gacuauagaa cuuucccccu cauccc 26

<210> SEQ ID NO 1076
<211> LENGTH: 15
<212> TYPE: RNA
<213> ORGANISM: Homo sapiens

<400> SEQUENCE: 1076
aacuuucccc cucau 15

<210> SEQ ID NO 1077
<211> LENGTH: 24
<212> TYPE: RNA
<213> ORGANISM: Homo sapiens

<400> SEQUENCE: 1077
cuggcccucu cugcccuucc gucc 24

<210> SEQ ID NO 1078
<211> LENGTH: 16
<212> TYPE: RNA
<213> ORGANISM: Homo sapiens

<400> SEQUENCE: 1078
cuggcccucu cugccc 16

<210> SEQ ID NO 1079
<211> LENGTH: 24
<212> TYPE: RNA
<213> ORGANISM: Homo sapiens

<400> SEQUENCE: 1079
guggagugug acaauggugu uugu 24

<210> SEQ ID NO 1080
<211> LENGTH: 18
<212> TYPE: RNA
<213> ORGANISM: Homo sapiens

<400> SEQUENCE: 1080
uggaguguga caauggug 18

<210> SEQ ID NO 1081
<211> LENGTH: 23
<212> TYPE: RNA
<213> ORGANISM: Homo sapiens

<400> SEQUENCE: 1081
aagagguaua gggcauggga aaa 23

<210> SEQ ID NO 1082
<211> LENGTH: 16
<212> TYPE: RNA
<213> ORGANISM: Homo sapiens

<400> SEQUENCE: 1082
agagguauag ggcaug 16

<210> SEQ ID NO 1083
<211> LENGTH: 22
<212> TYPE: RNA
<213> ORGANISM: Homo sapiens

<400> SEQUENCE: 1083
cuagcgggga uuccaauauu gg 22

<210> SEQ ID NO 1084
<211> LENGTH: 18
<212> TYPE: RNA
<213> ORGANISM: Homo sapiens

<400> SEQUENCE: 1084
ucuagcgggg auuccaau 18

<210> SEQ ID NO 1085
<211> LENGTH: 27
<212> TYPE: RNA

<213> ORGANISM: Homo sapiens

<400> SEQUENCE: 1085
gaauugucuc acacagaaau cgcaccc 27

<210> SEQ ID NO 1086
<211> LENGTH: 16
<212> TYPE: RNA
<213> ORGANISM: Homo sapiens

<400> SEQUENCE: 1086
ucucacacag aaaucg 16

<210> SEQ ID NO 1087
<211> LENGTH: 57
<212> TYPE: RNA
<213> ORGANISM: Homo sapiens

<400> SEQUENCE: 1087
uucaaguaau ucaggauagg uugugugcug uccagccugu ucuccauuac uuggcuc 57

<210> SEQ ID NO 1088
<211> LENGTH: 16
<212> TYPE: RNA
<213> ORGANISM: Homo sapiens

<400> SEQUENCE: 1088
gccuguucuc cauuac 16

<210> SEQ ID NO 1089
<211> LENGTH: 62
<212> TYPE: RNA
<213> ORGANISM: Homo sapiens

<400> SEQUENCE: 1089
cagugguuuu acccuauggu agguuacguc augcuguucu accacagggu agaaccacgg 60
ac 62

<210> SEQ ID NO 1090
<211> LENGTH: 16
<212> TYPE: RNA
<213> ORGANISM: Homo sapiens

<400> SEQUENCE: 1090
uaccacaggg uagaac 16

<210> SEQ ID NO 1091
<211> LENGTH: 24
<212> TYPE: RNA
<213> ORGANISM: Homo sapiens

<400> SEQUENCE: 1091
uaacacuguc ugguaacgau guuc 24

<210> SEQ ID NO 1092
<211> LENGTH: 16
<212> TYPE: RNA
<213> ORGANISM: Homo sapiens

<400> SEQUENCE: 1092
uaacacuguc ugguaa 16

<210> SEQ ID NO 1093
<211> LENGTH: 60
<212> TYPE: RNA
<213> ORGANISM: Homo sapiens

<400> SEQUENCE: 1093
cuccugacuc cagguccugu guguuaccua gaaauagcac uggacuugga gucagaaggc 60

<210> SEQ ID NO 1094
<211> LENGTH: 16
<212> TYPE: RNA
<213> ORGANISM: Homo sapiens

<400> SEQUENCE: 1094
cacuggacuu ggaguc 16

<210> SEQ ID NO 1095
<211> LENGTH: 25
<212> TYPE: RNA
<213> ORGANISM: Homo sapiens

<400> SEQUENCE: 1095
agccucguca ggcucagucc ccucc 25

<210> SEQ ID NO 1096
<211> LENGTH: 16
<212> TYPE: RNA
<213> ORGANISM: Homo sapiens

<400> SEQUENCE: 1096
ucaggcucag uccccu 16

<210> SEQ ID NO 1097
<211> LENGTH: 23
<212> TYPE: RNA
<213> ORGANISM: Homo sapiens

<400> SEQUENCE: 1097
gagggccccc ccucaauccu guu 23

<210> SEQ ID NO 1098
<211> LENGTH: 16
<212> TYPE: RNA
<213> ORGANISM: Homo sapiens

<400> SEQUENCE: 1098
agggcccccc cucaau 16

<210> SEQ ID NO 1099
<211> LENGTH: 36
<212> TYPE: RNA
<213> ORGANISM: Homo sapiens

<400> SEQUENCE: 1099
uccuucauuc caccggaguc ugucucauac ccaacc 36

<210> SEQ ID NO 1100
<211> LENGTH: 16
<212> TYPE: RNA
<213> ORGANISM: Homo sapiens

<400> SEQUENCE: 1100
uccuucauuc caccgg 16

<210> SEQ ID NO 1101
<211> LENGTH: 21
<212> TYPE: RNA
<213> ORGANISM: Homo sapiens

<400> SEQUENCE: 1101
ugucuugcag gccgucaugc a 21

<210> SEQ ID NO 1102
<211> LENGTH: 16
<212> TYPE: RNA
<213> ORGANISM: Homo sapiens

<400> SEQUENCE: 1102
ugucuugcag gccguc 16

<210> SEQ ID NO 1103
<211> LENGTH: 21
<212> TYPE: RNA
<213> ORGANISM: Homo sapiens

<400> SEQUENCE: 1103
cggcccgggc ugcugcuguu c 21

<210> SEQ ID NO 1104
<211> LENGTH: 18
<212> TYPE: RNA
<213> ORGANISM: Homo sapiens

<400> SEQUENCE: 1104
cggcccgggc ugcugcug 18

<210> SEQ ID NO 1105
<211> LENGTH: 23
<212> TYPE: RNA
<213> ORGANISM: Homo sapiens

<400> SEQUENCE: 1105
gcagccacaa cuacccugcc acu 23

<210> SEQ ID NO 1106
<211> LENGTH: 18
<212> TYPE: RNA
<213> ORGANISM: Homo sapiens

<400> SEQUENCE: 1106
cagccacaac uacccugc 18

<210> SEQ ID NO 1107
<211> LENGTH: 21
<212> TYPE: RNA
<213> ORGANISM: Homo sapiens

<400> SEQUENCE: 1107
uccuccugcc cuccuugcug u 21

<210> SEQ ID NO 1108
<211> LENGTH: 16
<212> TYPE: RNA
<213> ORGANISM: Homo sapiens

<400> SEQUENCE: 1108
ccuccugccc uccuug 16

<210> SEQ ID NO 1109
<211> LENGTH: 16
<212> TYPE: RNA
<213> ORGANISM: Homo sapiens

<400> SEQUENCE: 1109
ggagcugagg agcaga 16

<210> SEQ ID NO 1110
<211> LENGTH: 36
<212> TYPE: RNA
<213> ORGANISM: Homo sapiens

<400> SEQUENCE: 1110
caagguacaa ggccucaccc ugcaucccgc acccag 36

<210> SEQ ID NO 1111
<211> LENGTH: 17
<212> TYPE: RNA
<213> ORGANISM: Homo sapiens

<400> SEQUENCE: 1111
ucacccugca ucccgca 17

<210> SEQ ID NO 1112
<211> LENGTH: 23
<212> TYPE: RNA
<213> ORGANISM: Homo sapiens

<400> SEQUENCE: 1112
uucgggcugg ccugcugcuc cgg 23

<210> SEQ ID NO 1113
<211> LENGTH: 16
<212> TYPE: RNA
<213> ORGANISM: Homo sapiens

<400> SEQUENCE: 1113
uucgggcugg ccugcu 16

<210> SEQ ID NO 1114
<211> LENGTH: 60
<212> TYPE: RNA
<213> ORGANISM: Homo sapiens

<400> SEQUENCE: 1114
ccugggcagc guguggcuga aggucaccau guucuccuug gccaugggc ugcgcggggc 60

<210> SEQ ID NO 1115
<211> LENGTH: 16
<212> TYPE: RNA
<213> ORGANISM: Homo sapiens

<400> SEQUENCE: 1115
ccugggcagc guguggc 16

<210> SEQ ID NO 1116
<211> LENGTH: 22
<212> TYPE: RNA
<213> ORGANISM: Homo sapiens

<400> SEQUENCE: 1116
ucucccuucc ugcccuggcu ag 22

<210> SEQ ID NO 1117
<211> LENGTH: 17
<212> TYPE: RNA
<213> ORGANISM: Homo sapiens

<400> SEQUENCE: 1117
ucucccuucc ugcccug 17

<210> SEQ ID NO 1118
<211> LENGTH: 23
<212> TYPE: RNA
<213> ORGANISM: Homo sapiens

<400> SEQUENCE: 1118
ugaucucacc gcugccuccu ucc 23

<210> SEQ ID NO 1119
<211> LENGTH: 20
<212> TYPE: RNA
<213> ORGANISM: Homo sapiens

<400> SEQUENCE: 1119
cugaucucac cgcugccucc 20

<210> SEQ ID NO 1120
<211> LENGTH: 24
<212> TYPE: RNA
<213> ORGANISM: Homo sapiens

<400> SEQUENCE: 1120
ugucagugac uccugccccu uggu 24

<210> SEQ ID NO 1121
<211> LENGTH: 21
<212> TYPE: RNA
<213> ORGANISM: Homo sapiens

<400> SEQUENCE: 1121
ucaugucagu gacuccugcc c 21

<210> SEQ ID NO 1122
<211> LENGTH: 23
<212> TYPE: RNA
<213> ORGANISM: Homo sapiens

<400> SEQUENCE: 1122
uucucccacu accaggcucc cau 23

<210> SEQ ID NO 1123
<211> LENGTH: 16
<212> TYPE: RNA
<213> ORGANISM: Homo sapiens

<400> SEQUENCE: 1123
uucucccacu accagg 16

<210> SEQ ID NO 1124
<211> LENGTH: 28
<212> TYPE: RNA
<213> ORGANISM: Homo sapiens

<400> SEQUENCE: 1124
uaaaggugcc cucucuggcu ccucccca 28

<210> SEQ ID NO 1125
<211> LENGTH: 16
<212> TYPE: RNA
<213> ORGANISM: Homo sapiens

<400> SEQUENCE: 1125
ggugcccucu cuggcu 16

<210> SEQ ID NO 1126
<211> LENGTH: 22
<212> TYPE: RNA
<213> ORGANISM: Homo sapiens

<400> SEQUENCE: 1126
agugccccca caguuugagu gc 22

<210> SEQ ID NO 1127
<211> LENGTH: 19
<212> TYPE: RNA
<213> ORGANISM: Homo sapiens

<400> SEQUENCE: 1127
ucucugcucu gcucucccc 19

<210> SEQ ID NO 1128
<211> LENGTH: 20
<212> TYPE: RNA
<213> ORGANISM: Homo sapiens

<400> SEQUENCE: 1128
ccucagcucc ucucuaccca 20

<210> SEQ ID NO 1129
<211> LENGTH: 19
<212> TYPE: RNA
<213> ORGANISM: Homo sapiens

<400> SEQUENCE: 1129
ucagcuccuc ucuacccac 19

<210> SEQ ID NO 1130
<211> LENGTH: 20
<212> TYPE: RNA
<213> ORGANISM: Homo sapiens

<400> SEQUENCE: 1130
ugucuucucu ccucccaaac 20

<210> SEQ ID NO 1131
<211> LENGTH: 19
<212> TYPE: RNA
<213> ORGANISM: Homo sapiens

<400> SEQUENCE: 1131
gucuucucuc cucccaaac 19

<210> SEQ ID NO 1132
<211> LENGTH: 20
<212> TYPE: RNA
<213> ORGANISM: Homo sapiens

<400> SEQUENCE: 1132
ucggcucucu cccucacccu 20

<210> SEQ ID NO 1133
<211> LENGTH: 16
<212> TYPE: RNA
<213> ORGANISM: Homo sapiens

<400> SEQUENCE: 1133
ucggcucucu cccuca 16

<210> SEQ ID NO 1134
<211> LENGTH: 22
<212> TYPE: RNA
<213> ORGANISM: Homo sapiens

<400> SEQUENCE: 1134
agccgcucuu cucccugccc ac 22

<210> SEQ ID NO 1135
<211> LENGTH: 19
<212> TYPE: RNA
<213> ORGANISM: Homo sapiens

<400> SEQUENCE: 1135
gagccgcucu ucucccugc 19

<210> SEQ ID NO 1136
<211> LENGTH: 21
<212> TYPE: RNA
<213> ORGANISM: Homo sapiens

<400> SEQUENCE: 1136
uuuccugccu uccucugcac c 21

<210> SEQ ID NO 1137
<211> LENGTH: 17
<212> TYPE: RNA
<213> ORGANISM: Homo sapiens

<400> SEQUENCE: 1137
cugccuuccu cugcacc 17

<210> SEQ ID NO 1138
<211> LENGTH: 21
<212> TYPE: RNA
<213> ORGANISM: Homo sapiens

<400> SEQUENCE: 1138
gaacucaccc ucugcuccca g 21

<210> SEQ ID NO 1139
<211> LENGTH: 19
<212> TYPE: RNA
<213> ORGANISM: Homo sapiens

<400> SEQUENCE: 1139
gaacucaccc ucugcuccc 19

<210> SEQ ID NO 1140
<211> LENGTH: 21
<212> TYPE: RNA
<213> ORGANISM: Homo sapiens

<400> SEQUENCE: 1140
ucuucaccug ccucugccug c 21

<210> SEQ ID NO 1141
<211> LENGTH: 19
<212> TYPE: RNA
<213> ORGANISM: Homo sapiens

<400> SEQUENCE: 1141
ucuucaccug ccucugccu 19

<210> SEQ ID NO 1142
<211> LENGTH: 20
<212> TYPE: RNA
<213> ORGANISM: Homo sapiens

<400> SEQUENCE: 1142
ugaccuuugc cucuccccuc 20

<210> SEQ ID NO 1143
<211> LENGTH: 20
<212> TYPE: RNA
<213> ORGANISM: Homo sapiens

<400> SEQUENCE: 1143
ccuccuacgc ugcucucuca 20

<210> SEQ ID NO 1144
<211> LENGTH: 18
<212> TYPE: RNA
<213> ORGANISM: Homo sapiens

<400> SEQUENCE: 1144
cuccuacgcu gcucucuc 18

<210> SEQ ID NO 1145
<211> LENGTH: 22
<212> TYPE: RNA
<213> ORGANISM: Homo sapiens

<400> SEQUENCE: 1145
cuggcugcuu cccuuggucu cc 22

<210> SEQ ID NO 1146
<211> LENGTH: 18
<212> TYPE: RNA
<213> ORGANISM: Homo sapiens

<400> SEQUENCE: 1146
cugcuucccu uggucucc 18

<210> SEQ ID NO 1147
<211> LENGTH: 19
<212> TYPE: RNA
<213> ORGANISM: Homo sapiens

<400> SEQUENCE: 1147
gagccccucu cugcucucc 19

<210> SEQ ID NO 1148
<211> LENGTH: 21
<212> TYPE: RNA

<213> ORGANISM: Homo sapiens

<400> SEQUENCE: 1148
caaccaccac ugucucuccc c 21

<210> SEQ ID NO 1149
<211> LENGTH: 20
<212> TYPE: RNA
<213> ORGANISM: Homo sapiens

<400> SEQUENCE: 1149
caaccaccac ugucucuccc 20

<210> SEQ ID NO 1150
<211> LENGTH: 20
<212> TYPE: RNA
<213> ORGANISM: Homo sapiens

<400> SEQUENCE: 1150
cugccucccu gacauuccac 20

<210> SEQ ID NO 1151
<211> LENGTH: 19
<212> TYPE: RNA
<213> ORGANISM: Homo sapiens

<400> SEQUENCE: 1151
ugccucccug acauuccac 19

<210> SEQ ID NO 1152
<211> LENGTH: 22
<212> TYPE: RNA
<213> ORGANISM: Homo sapiens

<400> SEQUENCE: 1152
aagcccuguc uccucccauc uu 22

<210> SEQ ID NO 1153
<211> LENGTH: 19
<212> TYPE: RNA
<213> ORGANISM: Homo sapiens

<400> SEQUENCE: 1153
aagcccuguc uccucccau 19

<210> SEQ ID NO 1154
<211> LENGTH: 24
<212> TYPE: RNA
<213> ORGANISM: Homo sapiens

<400> SEQUENCE: 1154
acgccccuuc ugauucugcc ucag 24

<210> SEQ ID NO 1155
<211> LENGTH: 21
<212> TYPE: RNA
<213> ORGANISM: Homo sapiens

<400> SEQUENCE: 1155
ugacgccccu ucugauucug c 21

<210> SEQ ID NO 1156
<211> LENGTH: 22

<212> TYPE: RNA
<213> ORGANISM: Homo sapiens

<400> SEQUENCE: 1156
ucucagcugc ugcccucucc ag 22

<210> SEQ ID NO 1157
<211> LENGTH: 19
<212> TYPE: RNA
<213> ORGANISM: Homo sapiens

<400> SEQUENCE: 1157
cccggccccu cucagcugc 19

<210> SEQ ID NO 1158
<211> LENGTH: 23
<212> TYPE: RNA
<213> ORGANISM: Homo sapiens

<400> SEQUENCE: 1158
cccagcucgu gcucacucuc agu 23

<210> SEQ ID NO 1159
<211> LENGTH: 18
<212> TYPE: RNA
<213> ORGANISM: Homo sapiens

<400> SEQUENCE: 1159
cucacucuca gucccucc 18

<210> SEQ ID NO 1160
<211> LENGTH: 20
<212> TYPE: RNA
<213> ORGANISM: Homo sapiens

<400> SEQUENCE: 1160
accccugcca cucacuggcc 20

<210> SEQ ID NO 1161
<211> LENGTH: 19
<212> TYPE: RNA
<213> ORGANISM: Homo sapiens

<400> SEQUENCE: 1161
ucaccccugc cacucacug 19

<210> SEQ ID NO 1162
<211> LENGTH: 23
<212> TYPE: RNA
<213> ORGANISM: Homo sapiens

<400> SEQUENCE: 1162
cuucaccccu cucaccuaag cag 23

<210> SEQ ID NO 1163
<211> LENGTH: 17
<212> TYPE: RNA
<213> ORGANISM: Homo sapiens

<400> SEQUENCE: 1163
cuucaccccu cucaccu 17

<210> SEQ ID NO 1164

<211> LENGTH: 22
<212> TYPE: RNA
<213> ORGANISM: Homo sapiens

<400> SEQUENCE: 1164
ucccucgccu ucucacccuc ag 22

<210> SEQ ID NO 1165
<211> LENGTH: 17
<212> TYPE: RNA
<213> ORGANISM: Homo sapiens

<400> SEQUENCE: 1165
ucccucgccu ucucacc 17

<210> SEQ ID NO 1166
<211> LENGTH: 19
<212> TYPE: RNA
<213> ORGANISM: Homo sapiens

<400> SEQUENCE: 1166
cgcaccugcc ucucaccca 19

<210> SEQ ID NO 1167
<211> LENGTH: 25
<212> TYPE: RNA
<213> ORGANISM: Homo sapiens

<400> SEQUENCE: 1167
gauggggaca gggaucagca uggca 25

<210> SEQ ID NO 1168
<211> LENGTH: 16
<212> TYPE: RNA
<213> ORGANISM: Homo sapiens

<400> SEQUENCE: 1168
auggggacag ggauca 16

<210> SEQ ID NO 1169
<211> LENGTH: 19
<212> TYPE: RNA
<213> ORGANISM: Homo sapiens

<400> SEQUENCE: 1169
ugagccucuc cuucccucc 19

<210> SEQ ID NO 1170
<211> LENGTH: 22
<212> TYPE: RNA
<213> ORGANISM: Homo sapiens

<400> SEQUENCE: 1170
cgcgcugacc cgccuucucc gc 22

<210> SEQ ID NO 1171
<211> LENGTH: 17
<212> TYPE: RNA
<213> ORGANISM: Homo sapiens

<400> SEQUENCE: 1171
cccgcgcuga cccgccu 17

<210> SEQ ID NO 1172
<211> LENGTH: 21
<212> TYPE: RNA
<213> ORGANISM: Homo sapiens

<400> SEQUENCE: 1172
uuucucucuc cacuuccuca g 21

<210> SEQ ID NO 1173
<211> LENGTH: 17
<212> TYPE: RNA
<213> ORGANISM: Homo sapiens

<400> SEQUENCE: 1173
uucucucucc acuuccu 17

<210> SEQ ID NO 1174
<211> LENGTH: 75
<212> TYPE: RNA
<213> ORGANISM: Homo sapiens

<400> SEQUENCE: 1174
gugagggacu gggauuugug gggcgaggag ggaccuguac uagccauggu ucugaucaca 60
uaugucccau cccuc 75

<210> SEQ ID NO 1175
<211> LENGTH: 17
<212> TYPE: RNA
<213> ORGANISM: Homo sapiens

<400> SEQUENCE: 1175
uaugucccau cccucca 17

<210> SEQ ID NO 1176
<211> LENGTH: 21
<212> TYPE: RNA
<213> ORGANISM: Homo sapiens

<400> SEQUENCE: 1176
ucccuugucu ccuuucccua g 21

<210> SEQ ID NO 1177
<211> LENGTH: 18
<212> TYPE: RNA
<213> ORGANISM: Homo sapiens

<400> SEQUENCE: 1177
ucccuugucu ccuuuccc 18

<210> SEQ ID NO 1178
<211> LENGTH: 19
<212> TYPE: RNA
<213> ORGANISM: Homo sapiens

<400> SEQUENCE: 1178
caccaccagc cucuccucc 19

<210> SEQ ID NO 1179
<211> LENGTH: 24
<212> TYPE: RNA
<213> ORGANISM: Homo sapiens

<400> SEQUENCE: 1179
ccucacccag cucucuggcc cucu 24

<210> SEQ ID NO 1180
<211> LENGTH: 20
<212> TYPE: RNA
<213> ORGANISM: Homo sapiens

<400> SEQUENCE: 1180
ccucacccag cucucuggcc 20

<210> SEQ ID NO 1181
<211> LENGTH: 21
<212> TYPE: RNA
<213> ORGANISM: Homo sapiens

<400> SEQUENCE: 1181
acacccucuu ucccuaccgc c 21

<210> SEQ ID NO 1182
<211> LENGTH: 19
<212> TYPE: RNA
<213> ORGANISM: Homo sapiens

<400> SEQUENCE: 1182
acacccucuu ucccuaccg 19

<210> SEQ ID NO 1183
<211> LENGTH: 20
<212> TYPE: RNA
<213> ORGANISM: Homo sapiens

<400> SEQUENCE: 1183
gcucaucccc aucuccuuuc 20

<210> SEQ ID NO 1184
<211> LENGTH: 28
<212> TYPE: RNA
<213> ORGANISM: Homo sapiens

<400> SEQUENCE: 1184
auggugauuu gcauucuucc ugcccugg 28

<210> SEQ ID NO 1185
<211> LENGTH: 19
<212> TYPE: RNA
<213> ORGANISM: Homo sapiens

<400> SEQUENCE: 1185
auucuuccug cccuggcuc 19

<210> SEQ ID NO 1186
<211> LENGTH: 19
<212> TYPE: RNA
<213> ORGANISM: Homo sapiens

<400> SEQUENCE: 1186
cucugcccuu ggccucccc 19

<210> SEQ ID NO 1187
<211> LENGTH: 22
<212> TYPE: RNA
<213> ORGANISM: Homo sapiens

<400> SEQUENCE: 1187
uccugucacc cgcuccuugc cc 22

<210> SEQ ID NO 1188
<211> LENGTH: 19
<212> TYPE: RNA
<213> ORGANISM: Homo sapiens

<400> SEQUENCE: 1188
ugucacccgc uccuugccc 19

<210> SEQ ID NO 1189
<211> LENGTH: 21
<212> TYPE: RNA
<213> ORGANISM: Homo sapiens

<400> SEQUENCE: 1189
ugccucuccu cuugccugca g 21

<210> SEQ ID NO 1190
<211> LENGTH: 17
<212> TYPE: RNA
<213> ORGANISM: Homo sapiens

<400> SEQUENCE: 1190
gccucuccuc uugccug 17

<210> SEQ ID NO 1191
<211> LENGTH: 19
<212> TYPE: RNA
<213> ORGANISM: Homo sapiens

<400> SEQUENCE: 1191
cuuugcuucc ugcuccccu 19

<210> SEQ ID NO 1192
<211> LENGTH: 18
<212> TYPE: RNA
<213> ORGANISM: Homo sapiens

<400> SEQUENCE: 1192
uuugcuuccu gcuccccu 18

<210> SEQ ID NO 1193
<211> LENGTH: 21
<212> TYPE: RNA
<213> ORGANISM: Homo sapiens

<400> SEQUENCE: 1193
ugcccuucuc uccuccugcc u 21

<210> SEQ ID NO 1194
<211> LENGTH: 21
<212> TYPE: RNA
<213> ORGANISM: Homo sapiens

<400> SEQUENCE: 1194
uccccuccac uuuccuccua g 21

<210> SEQ ID NO 1195
<211> LENGTH: 19
<212> TYPE: RNA
<213> ORGANISM: Homo sapiens

<400> SEQUENCE: 1195
uccccuccac uuuccuccu 19

<210> SEQ ID NO 1196
<211> LENGTH: 18
<212> TYPE: RNA
<213> ORGANISM: Homo sapiens

<400> SEQUENCE: 1196
ccacugccua ugccccac 18

<210> SEQ ID NO 1197
<211> LENGTH: 20
<212> TYPE: RNA
<213> ORGANISM: Homo sapiens

<400> SEQUENCE: 1197
cccugcugcc uucaccugcc 20

<210> SEQ ID NO 1198
<211> LENGTH: 19
<212> TYPE: RNA
<213> ORGANISM: Homo sapiens

<400> SEQUENCE: 1198
uugccugccc ucuuccucc 19

<210> SEQ ID NO 1199
<211> LENGTH: 17
<212> TYPE: RNA
<213> ORGANISM: Homo sapiens

<400> SEQUENCE: 1199
ugccugcccu cuuccuc 17

<210> SEQ ID NO 1200
<211> LENGTH: 18
<212> TYPE: RNA
<213> ORGANISM: Homo sapiens

<400> SEQUENCE: 1200
ucccugaauc ccuguccc 18

<210> SEQ ID NO 1201
<211> LENGTH: 21
<212> TYPE: RNA
<213> ORGANISM: Homo sapiens

<400> SEQUENCE: 1201
caagccucuc cugcccuucc a 21

<210> SEQ ID NO 1202
<211> LENGTH: 20
<212> TYPE: RNA
<213> ORGANISM: Homo sapiens

<400> SEQUENCE: 1202
caagccucuc cugcccuucc 20

<210> SEQ ID NO 1203
<211> LENGTH: 19
<212> TYPE: RNA
<213> ORGANISM: Homo sapiens

<400> SEQUENCE: 1203
ugacccaccc cucuccacc 19

<210> SEQ ID NO 1204
<211> LENGTH: 16
<212> TYPE: RNA
<213> ORGANISM: Homo sapiens

<400> SEQUENCE: 1204
cccaccccuc uccacc 16

<210> SEQ ID NO 1205
<211> LENGTH: 20
<212> TYPE: RNA
<213> ORGANISM: Homo sapiens

<400> SEQUENCE: 1205
acugauggcc caagaccuca 20

<210> SEQ ID NO 1206
<211> LENGTH: 20
<212> TYPE: RNA
<213> ORGANISM: Homo sapiens

<400> SEQUENCE: 1206
cagggcccug gcuuuagcag 20

<210> SEQ ID NO 1207
<211> LENGTH: 18
<212> TYPE: RNA
<213> ORGANISM: Homo sapiens

<400> SEQUENCE: 1207
cagggcccug gcuuuagc 18

<210> SEQ ID NO 1208
<211> LENGTH: 22
<212> TYPE: RNA
<213> ORGANISM: Homo sapiens

<400> SEQUENCE: 1208
uccgagccug ggucucccuc uu 22

<210> SEQ ID NO 1209
<211> LENGTH: 16
<212> TYPE: RNA
<213> ORGANISM: Homo sapiens

<400> SEQUENCE: 1209
uccgagccug ggucuc 16

<210> SEQ ID NO 1210
<211> LENGTH: 23
<212> TYPE: RNA
<213> ORGANISM: Homo sapiens

<400> SEQUENCE: 1210
cuguaugccc ucaccgcuca gcc 23

<210> SEQ ID NO 1211
<211> LENGTH: 18
<212> TYPE: RNA

<213> ORGANISM: Homo sapiens

<400> SEQUENCE: 1211
cuguaugccc ucaccgcu 18

<210> SEQ ID NO 1212
<211> LENGTH: 23
<212> TYPE: RNA
<213> ORGANISM: Homo sapiens

<400> SEQUENCE: 1212
ccaguccugu gccugccgcc uuu 23

<210> SEQ ID NO 1213
<211> LENGTH: 16
<212> TYPE: RNA
<213> ORGANISM: Homo sapiens

<400> SEQUENCE: 1213
ccaguccugu gccugc 16

<210> SEQ ID NO 1214
<211> LENGTH: 23
<212> TYPE: RNA
<213> ORGANISM: Homo sapiens

<400> SEQUENCE: 1214
gagagcagug uguguugccu ggg 23

<210> SEQ ID NO 1215
<211> LENGTH: 17
<212> TYPE: RNA
<213> ORGANISM: Homo sapiens

<400> SEQUENCE: 1215
agcagugugu guugccu 17

<210> SEQ ID NO 1216
<211> LENGTH: 20
<212> TYPE: RNA
<213> ORGANISM: Homo sapiens

<400> SEQUENCE: 1216
cgccucuuca gcgcugucuu 20

<210> SEQ ID NO 1217
<211> LENGTH: 18
<212> TYPE: RNA
<213> ORGANISM: Homo sapiens

<400> SEQUENCE: 1217
acgccucuuc agcgcugu 18

<210> SEQ ID NO 1218
<211> LENGTH: 24
<212> TYPE: RNA
<213> ORGANISM: Homo sapiens

<400> SEQUENCE: 1218
guugggacaa gaggacgguc uucu 24

<210> SEQ ID NO 1219
<211> LENGTH: 20

<212> TYPE: RNA
<213> ORGANISM: Homo sapiens

<400> SEQUENCE: 1219
guugggacaa gaggacgguc 20

<210> SEQ ID NO 1220
<211> LENGTH: 21
<212> TYPE: RNA
<213> ORGANISM: Homo sapiens

<400> SEQUENCE: 1220 gggugggca augggaucag g 21

<210> SEQ ID NO 1221
<211> LENGTH: 17
<212> TYPE: RNA
<213> ORGANISM: Homo sapiens

<400> SEQUENCE: 1221
gguggggcaa ugggauc 17

<210> SEQ ID NO 1222
<211> LENGTH: 23
<212> TYPE: RNA
<213> ORGANISM: Homo sapiens

<400> SEQUENCE: 1222
gcggggagag aacgcaguga cgu 23

<210> SEQ ID NO 1223
<211> LENGTH: 16
<212> TYPE: RNA
<213> ORGANISM: Homo sapiens

<400> SEQUENCE: 1223
gggggcgggg agagaa 16

<210> SEQ ID NO 1224
<211> LENGTH: 16
<212> TYPE: RNA
<213> ORGANISM: Homo sapiens

<400> SEQUENCE: 1224
cagccccaca gccuca 16

<210> SEQ ID NO 1225
<211> LENGTH: 25
<212> TYPE: RNA
<213> ORGANISM: Homo sapiens

<400> SEQUENCE: 1225
uguuccucug ucucccagac ucugg 25

<210> SEQ ID NO 1226
<211> LENGTH: 16
<212> TYPE: RNA
<213> ORGANISM: Homo sapiens

<400> SEQUENCE: 1226
cucugucucc cagacu 16

<210> SEQ ID NO 1227

<211> LENGTH: 20
<212> TYPE: RNA
<213> ORGANISM: Homo sapiens

<400> SEQUENCE: 1227
gggcucacau caccccauca 20

<210> SEQ ID NO 1228
<211> LENGTH: 16
<212> TYPE: RNA
<213> ORGANISM: Homo sapiens

<400> SEQUENCE: 1228
aggggcucac aucacc 16

<210> SEQ ID NO 1229
<211> LENGTH: 23
<212> TYPE: RNA
<213> ORGANISM: Homo sapiens

<400> SEQUENCE: 1229
ccuccguguu accuguccuc uag 23

<210> SEQ ID NO 1230
<211> LENGTH: 18
<212> TYPE: RNA
<213> ORGANISM: Homo sapiens

<400> SEQUENCE: 1230
ccuccguguu accugucc 18

<210> SEQ ID NO 1231
<211> LENGTH: 22
<212> TYPE: RNA
<213> ORGANISM: Homo sapiens

<400> SEQUENCE: 1231
acaggcaugg gaggucaggu ga 22

<210> SEQ ID NO 1232
<211> LENGTH: 19
<212> TYPE: RNA
<213> ORGANISM: Homo sapiens

<400> SEQUENCE: 1232
uuggguucau uucauuuuc 19

<210> SEQ ID NO 1233
<211> LENGTH: 22
<212> TYPE: RNA
<213> ORGANISM: Homo sapiens

<400> SEQUENCE: 1233
uccugcagag aggaagcccu uc 22

<210> SEQ ID NO 1234
<211> LENGTH: 18
<212> TYPE: RNA
<213> ORGANISM: Homo sapiens

<400> SEQUENCE: 1234
ccugcagaga ggaagccc 18

<210> SEQ ID NO 1235
<211> LENGTH: 24
<212> TYPE: RNA
<213> ORGANISM: Homo sapiens

<400> SEQUENCE: 1235
caugcugacc ucccuccugc ccca 24

<210> SEQ ID NO 1236
<211> LENGTH: 20
<212> TYPE: RNA
<213> ORGANISM: Homo sapiens

<400> SEQUENCE: 1236
caugcugacc ucccuccugc 20

<210> SEQ ID NO 1237
<211> LENGTH: 21
<212> TYPE: RNA
<213> ORGANISM: Homo sapiens

<400> SEQUENCE: 1237
ucauccucgu cucccuccca g 21

<210> SEQ ID NO 1238
<211> LENGTH: 17
<212> TYPE: RNA
<213> ORGANISM: Homo sapiens

<400> SEQUENCE: 1238
ucauccucgu cucccuc 17

<210> SEQ ID NO 1239
<211> LENGTH: 58
<212> TYPE: RNA
<213> ORGANISM: Homo sapiens

<400> SEQUENCE: 1239
gcugacuccu aguccagggc ucgugauggc uggugggccc ugaacgaggg gucuggag 58

<210> SEQ ID NO 1240
<211> LENGTH: 17
<212> TYPE: RNA
<213> ORGANISM: Homo sapiens

<400> SEQUENCE: 1240
gcccugaacg aggggguc 17

<210> SEQ ID NO 1241
<211> LENGTH: 22
<212> TYPE: RNA
<213> ORGANISM: Homo sapiens

<400> SEQUENCE: 1241
uucccucucc aaaugugucu ug 22

<210> SEQ ID NO 1242
<211> LENGTH: 16
<212> TYPE: RNA
<213> ORGANISM: Homo sapiens

<400> SEQUENCE: 1242
uccaaaugug ucuuga 16

<210> SEQ ID NO 1243
<211> LENGTH: 22
<212> TYPE: RNA
<213> ORGANISM: Homo sapiens

<400> SEQUENCE: 1243
uccgaacucu ccauuccucu gc 22

<210> SEQ ID NO 1244
<211> LENGTH: 17
<212> TYPE: RNA
<213> ORGANISM: Homo sapiens

<400> SEQUENCE: 1244
acucuccauu ccucugc 17

<210> SEQ ID NO 1245
<211> LENGTH: 23
<212> TYPE: RNA
<213> ORGANISM: Homo sapiens

<400> SEQUENCE: 1245
ccucaccacc ccuucugccu gca 23

<210> SEQ ID NO 1246
<211> LENGTH: 17
<212> TYPE: RNA
<213> ORGANISM: Homo sapiens

<400> SEQUENCE: 1246
accaccccuu cugccug 17

<210> SEQ ID NO 1247
<211> LENGTH: 20
<212> TYPE: RNA
<213> ORGANISM: Homo sapiens

<400> SEQUENCE: 1247
cugcucgccc ugucuccgc 20

<210> SEQ ID NO 1248
<211> LENGTH: 16
<212> TYPE: RNA
<213> ORGANISM: Homo sapiens

<400> SEQUENCE: 1248
gcucgcccug ucuccc 16

<210> SEQ ID NO 1249
<211> LENGTH: 21
<212> TYPE: RNA
<213> ORGANISM: Homo sapiens

<400> SEQUENCE: 1249
caccuuugug uccccauccu g 21

<210> SEQ ID NO 1250
<211> LENGTH: 18
<212> TYPE: RNA
<213> ORGANISM: Homo sapiens

<400> SEQUENCE: 1250
accuuugugu ccccaucc 18

<210> SEQ ID NO 1251
<211> LENGTH: 19
<212> TYPE: RNA
<213> ORGANISM: Homo sapiens

<400> SEQUENCE: 1251
cggcgcccgu gucuccucc 19

<210> SEQ ID NO 1252
<211> LENGTH: 18
<212> TYPE: RNA
<213> ORGANISM: Homo sapiens

<400> SEQUENCE: 1252
ggcgcccgug ucuccucc 18

<210> SEQ ID NO 1253
<211> LENGTH: 22
<212> TYPE: RNA
<213> ORGANISM: Homo sapiens

<400> SEQUENCE: 1253
cugcaugacc cuucccuccc ca 22

<210> SEQ ID NO 1254
<211> LENGTH: 17
<212> TYPE: RNA
<213> ORGANISM: Homo sapiens

<400> SEQUENCE: 1254
cugcaugacc cuucccu 17

<210> SEQ ID NO 1255
<211> LENGTH: 15
<212> TYPE: RNA
<213> ORGANISM: Homo sapiens

<400> SEQUENCE: 1255
accucuccug gcauc 15

<210> SEQ ID NO 1256
<211> LENGTH: 20
<212> TYPE: RNA
<213> ORGANISM: Homo sapiens

<400> SEQUENCE: 1256
cucucugguc uugccacccc 20

<210> SEQ ID NO 1257
<211> LENGTH: 19
<212> TYPE: RNA
<213> ORGANISM: Homo sapiens

<400> SEQUENCE: 1257
ucucuggucu ugccacccc 19

<210> SEQ ID NO 1258
<211> LENGTH: 25
<212> TYPE: RNA
<213> ORGANISM: Homo sapiens

<400> SEQUENCE: 1258
ggaccagggc cagcagggaa uguca 25

<210> SEQ ID NO 1259
<211> LENGTH: 17
<212> TYPE: RNA
<213> ORGANISM: Homo sapiens

<400> SEQUENCE: 1259
gaccagggcc agcaggg 17

<210> SEQ ID NO 1260
<211> LENGTH: 21
<212> TYPE: RNA
<213> ORGANISM: Homo sapiens

<400> SEQUENCE: 1260
ugaccccuuc ugucucccua g 21

<210> SEQ ID NO 1261
<211> LENGTH: 21
<212> TYPE: RNA
<213> ORGANISM: Homo sapiens

<400> SEQUENCE: 1261
acggcagcca gccccugcuc a 21

<210> SEQ ID NO 1262
<211> LENGTH: 19
<212> TYPE: RNA
<213> ORGANISM: Homo sapiens

<400> SEQUENCE: 1262
gcagccagcc ccugcucac 19

<210> SEQ ID NO 1263
<211> LENGTH: 21
<212> TYPE: RNA
<213> ORGANISM: Homo sapiens

<400> SEQUENCE: 1263
ugacccccau gucgccucug u 21

<210> SEQ ID NO 1264
<211> LENGTH: 16
<212> TYPE: RNA
<213> ORGANISM: Homo sapiens

<400> SEQUENCE: 1264
gacccccaug ucgccu 16

<210> SEQ ID NO 1265
<211> LENGTH: 17
<212> TYPE: RNA
<213> ORGANISM: Homo sapiens

<400> SEQUENCE: 1265
uggaccucuc cucccca 17

<210> SEQ ID NO 1266
<211> LENGTH: 16
<212> TYPE: RNA
<213> ORGANISM: Homo sapiens

<400> SEQUENCE: 1266
uggaccucuc cucccc 16

<210> SEQ ID NO 1267
<211> LENGTH: 21
<212> TYPE: RNA
<213> ORGANISM: Homo sapiens

<400> SEQUENCE: 1267
auccucucuu cccuccuccc a 21

<210> SEQ ID NO 1268
<211> LENGTH: 17
<212> TYPE: RNA
<213> ORGANISM: Homo sapiens

<400> SEQUENCE: 1268
auccucucuu cccuccu 17

<210> SEQ ID NO 1269
<211> LENGTH: 22
<212> TYPE: RNA
<213> ORGANISM: Homo sapiens

<400> SEQUENCE: 1269
gucccucucc aaaugugucu ug 22

<210> SEQ ID NO 1270
<211> LENGTH: 17
<212> TYPE: RNA
<213> ORGANISM: Homo sapiens

<400> SEQUENCE: 1270
gucccucucc aaaugug 17

<210> SEQ ID NO 1271
<211> LENGTH: 19
<212> TYPE: RNA
<213> ORGANISM: Homo sapiens

<400> SEQUENCE: 1271
gcagguucuc acccucucu 19

<210> SEQ ID NO 1272
<211> LENGTH: 20
<212> TYPE: RNA
<213> ORGANISM: Homo sapiens

<400> SEQUENCE: 1272
ccucuucccc uugucucucc 20

<210> SEQ ID NO 1273
<211> LENGTH: 18
<212> TYPE: RNA
<213> ORGANISM: Homo sapiens

<400> SEQUENCE: 1273
ucuuccccuu gucucucc 18

<210> SEQ ID NO 1274
<211> LENGTH: 20
<212> TYPE: RNA
<213> ORGANISM: Homo sapiens

<400> SEQUENCE: 1274
aggagaaguc gggaaggugg 20

<210> SEQ ID NO 1275
<211> LENGTH: 16
<212> TYPE: RNA
<213> ORGANISM: Homo sapiens

<400> SEQUENCE: 1275
gaagucggga aggugg 16

<210> SEQ ID NO 1276
<211> LENGTH: 20
<212> TYPE: RNA
<213> ORGANISM: Homo sapiens

<400> SEQUENCE: 1276
ucucuggccg ucuaccuucc 20

<210> SEQ ID NO 1277
<211> LENGTH: 19
<212> TYPE: RNA
<213> ORGANISM: Homo sapiens

<400> SEQUENCE: 1277
ucuggccguc uaccuucca 19

<210> SEQ ID NO 1278
<211> LENGTH: 24
<212> TYPE: RNA
<213> ORGANISM: Homo sapiens

<400> SEQUENCE: 1278
ccucaccauc ccuucugccu gcag 24

<210> SEQ ID NO 1279
<211> LENGTH: 16
<212> TYPE: RNA
<213> ORGANISM: Homo sapiens

<400> SEQUENCE: 1279
ccucaccauc ccuucu 16

<210> SEQ ID NO 1280
<211> LENGTH: 22
<212> TYPE: RNA
<213> ORGANISM: Homo sapiens

<400> SEQUENCE: 1280
uguagguggc gccggaggag uc 22

<210> SEQ ID NO 1281
<211> LENGTH: 16
<212> TYPE: RNA
<213> ORGANISM: Homo sapiens

<400> SEQUENCE: 1281
uagguggcgc cggagg 16

<210> SEQ ID NO 1282
<211> LENGTH: 21
<212> TYPE: RNA
<213> ORGANISM: Homo sapiens

<400> SEQUENCE: 1282
ugacugagcu ucuccccaca g 21

<210> SEQ ID NO 1283
<211> LENGTH: 17
<212> TYPE: RNA
<213> ORGANISM: Homo sapiens

<400> SEQUENCE: 1283
ugacugagcu ucucccc 17

<210> SEQ ID NO 1284
<211> LENGTH: 19
<212> TYPE: RNA
<213> ORGANISM: Homo sapiens

<400> SEQUENCE: 1284
cuggccucuu cuuucuccu 19

<210> SEQ ID NO 1285
<211> LENGTH: 22
<212> TYPE: RNA
<213> ORGANISM: Homo sapiens

<400> SEQUENCE: 1285
acucaaacug ugggggcacu uu 22

<210> SEQ ID NO 1286
<211> LENGTH: 19
<212> TYPE: RNA
<213> ORGANISM: Homo sapiens

<400> SEQUENCE: 1286
acucaaacug ugggggcac 19

<210> SEQ ID NO 1287
<211> LENGTH: 36
<212> TYPE: RNA
<213> ORGANISM: Homo sapiens

<400> SEQUENCE: 1287
ucauuuugga uuugacucca gccccacagc cucagc 36

<210> SEQ ID NO 1288
<211> LENGTH: 16
<212> TYPE: RNA
<213> ORGANISM: Homo sapiens

<400> SEQUENCE: 1288
acuccagccc cacagc 16

<210> SEQ ID NO 1289
<211> LENGTH: 24
<212> TYPE: RNA
<213> ORGANISM: Homo sapiens

<400> SEQUENCE: 1289
cccucucacc acugcccucc caca 24

<210> SEQ ID NO 1290
<211> LENGTH: 18
<212> TYPE: RNA

<213> ORGANISM: Homo sapiens

<400> SEQUENCE: 1290
cucucaccac ugcccucc 18

<210> SEQ ID NO 1291
<211> LENGTH: 28
<212> TYPE: RNA
<213> ORGANISM: Homo sapiens

<400> SEQUENCE: 1291
caccuccccu gcaaacgucc aguggugc 28

<210> SEQ ID NO 1292
<211> LENGTH: 16
<212> TYPE: RNA
<213> ORGANISM: Homo sapiens

<400> SEQUENCE: 1292
ccaccucccc ugcaaa 16

<210> SEQ ID NO 1293
<211> LENGTH: 23
<212> TYPE: RNA
<213> ORGANISM: Homo sapiens

<400> SEQUENCE: 1293
agccccugcc caccgcacac ugc 23

<210> SEQ ID NO 1294
<211> LENGTH: 16
<212> TYPE: RNA
<213> ORGANISM: Homo sapiens

<400> SEQUENCE: 1294
agccccugcc caccgc 16

<210> SEQ ID NO 1295
<211> LENGTH: 19
<212> TYPE: RNA
<213> ORGANISM: Homo sapiens

<400> SEQUENCE: 1295
gguccagagg ggagauagg 19

<210> SEQ ID NO 1296
<211> LENGTH: 16
<212> TYPE: RNA
<213> ORGANISM: Homo sapiens

<400> SEQUENCE: 1296
cagaggggag auaggu 16

<210> SEQ ID NO 1297
<211> LENGTH: 23
<212> TYPE: RNA
<213> ORGANISM: Homo sapiens

<400> SEQUENCE: 1297
agucauacac ggcucuccuc ucu 23

<210> SEQ ID NO 1298
<211> LENGTH: 16

<212> TYPE: RNA
<213> ORGANISM: Homo sapiens

<400> SEQUENCE: 1298
gucauacacg gcucuc 16

<210> SEQ ID NO 1299
<211> LENGTH: 24
<212> TYPE: RNA
<213> ORGANISM: Homo sapiens

<400> SEQUENCE: 1299
uaugucacuc ggcucggccc acua 24

<210> SEQ ID NO 1300
<211> LENGTH: 18
<212> TYPE: RNA
<213> ORGANISM: Homo sapiens

<400> SEQUENCE: 1300
uaugucacuc ggcucggc 18

<210> SEQ ID NO 1301
<211> LENGTH: 26
<212> TYPE: RNA
<213> ORGANISM: Homo sapiens

<400> SEQUENCE: 1301
ccucccacac ccaaggcuug cagaag 26

<210> SEQ ID NO 1302
<211> LENGTH: 16
<212> TYPE: RNA
<213> ORGANISM: Homo sapiens

<400> SEQUENCE: 1302
ccucccacac ccaagg 16

<210> SEQ ID NO 1303
<211> LENGTH: 22
<212> TYPE: RNA
<213> ORGANISM: Homo sapiens

<400> SEQUENCE: 1303
uguccucuuc ucccuccucc ca 22

<210> SEQ ID NO 1304
<211> LENGTH: 17
<212> TYPE: RNA
<213> ORGANISM: Homo sapiens

<400> SEQUENCE: 1304
uccucuucuc ccuccuc 17

<210> SEQ ID NO 1305
<211> LENGTH: 23
<212> TYPE: RNA
<213> ORGANISM: Homo sapiens

<400> SEQUENCE: 1305
uacccagucu ccggugcagc cuu 23

<210> SEQ ID NO 1306

<211> LENGTH: 16
<212> TYPE: RNA
<213> ORGANISM: Homo sapiens

<400> SEQUENCE: 1306
uacccagucu ccggug 16

<210> SEQ ID NO 1307
<211> LENGTH: 15
<212> TYPE: RNA
<213> ORGANISM: Homo sapiens

<400> SEQUENCE: 1307
aggaggagga ggcag 15

<210> SEQ ID NO 1308
<211> LENGTH: 15
<212> TYPE: RNA
<213> ORGANISM: Homo sapiens

<400> SEQUENCE: 1308
aggaggagga ggcag 15

<210> SEQ ID NO 1309
<211> LENGTH: 22
<212> TYPE: RNA
<213> ORGANISM: Homo sapiens

<400> SEQUENCE: 1309
uagcccccag gcuucacuug gc 22

<210> SEQ ID NO 1310
<211> LENGTH: 19
<212> TYPE: RNA
<213> ORGANISM: Homo sapiens

<400> SEQUENCE: 1310
uagcccccag gcuucacuu 19

<210> SEQ ID NO 1311
<211> LENGTH: 23
<212> TYPE: RNA
<213> ORGANISM: Homo sapiens

<400> SEQUENCE: 1311
ugucugcccg caugccugcc ucu 23

<210> SEQ ID NO 1312
<211> LENGTH: 16
<212> TYPE: RNA
<213> ORGANISM: Homo sapiens

<400> SEQUENCE: 1312
ugucugcccg caugcc 16

<210> SEQ ID NO 1313
<211> LENGTH: 58
<212> TYPE: RNA
<213> ORGANISM: Homo sapiens

<400> SEQUENCE: 1313
ugcaccaugg uugucugagc augcagcaug cuugucugcu cauaccccau gguuucug 58

<210> SEQ ID NO 1314
<211> LENGTH: 18
<212> TYPE: RNA
<213> ORGANISM: Homo sapiens

<400> SEQUENCE: 1314
ucugcucaua ccccaugg 18

<210> SEQ ID NO 1315
<211> LENGTH: 21
<212> TYPE: RNA
<213> ORGANISM: Homo sapiens

<400> SEQUENCE: 1315
ucaccuggcu ggcccgccca g 21

<210> SEQ ID NO 1316
<211> LENGTH: 20
<212> TYPE: RNA
<213> ORGANISM: Homo sapiens

<400> SEQUENCE: 1316
gccggggcuu ugggugaggg 20

<210> SEQ ID NO 1317
<211> LENGTH: 22
<212> TYPE: RNA
<213> ORGANISM: Homo sapiens

<400> SEQUENCE: 1317
agugggagga caggaggcag gu 22

<210> SEQ ID NO 1318
<211> LENGTH: 21
<212> TYPE: RNA
<213> ORGANISM: Homo sapiens

<400> SEQUENCE: 1318
ugagggaccc aggacaggag a 21

<210> SEQ ID NO 1319
<211> LENGTH: 17
<212> TYPE: RNA
<213> ORGANISM: Homo sapiens

<400> SEQUENCE: 1319
ggauggagga ggggucu 17

<210> SEQ ID NO 1320
<211> LENGTH: 22
<212> TYPE: RNA
<213> ORGANISM: Homo sapiens

<400> SEQUENCE: 1320
ugagggcucc aggugacggu gg 22

<210> SEQ ID NO 1321
<211> LENGTH: 23
<212> TYPE: RNA
<213> ORGANISM: Homo sapiens

<400> SEQUENCE: 1321 agggugggc uggagguggg gcu 23

<210> SEQ ID NO 1322
<211> LENGTH: 22
<212> TYPE: RNA
<213> ORGANISM: Homo sapiens

<400> SEQUENCE: 1322
gggggucccc ggugcucgga uc 22

<210> SEQ ID NO 1323
<211> LENGTH: 23
<212> TYPE: RNA
<213> ORGANISM: Homo sapiens

<400> SEQUENCE: 1323
cucggggcag gcggcuggga gcg 23

<210> SEQ ID NO 1324
<211> LENGTH: 23
<212> TYPE: RNA
<213> ORGANISM: Homo sapiens

<400> SEQUENCE: 1324 ugggggaca gauggagagg aca 23

<210> SEQ ID NO 1325
<211> LENGTH: 22
<212> TYPE: RNA
<213> ORGANISM: Homo sapiens

<400> SEQUENCE: 1325
ucaaaaucag gagucggggc uu 22

<210> SEQ ID NO 1326
<211> LENGTH: 22
<212> TYPE: RNA
<213> ORGANISM: Homo sapiens

<400> SEQUENCE: 1326
ugguggagga agagggcagc uc 22

<210> SEQ ID NO 1327
<211> LENGTH: 23
<212> TYPE: RNA
<213> ORGANISM: Homo sapiens

<400> SEQUENCE: 1327
uugcucugcu cccccgcccc cag 23

<210> SEQ ID NO 1328
<211> LENGTH: 23
<212> TYPE: RNA
<213> ORGANISM: Homo sapiens

<400> SEQUENCE: 1328
agggccagag gagccuggag ugg 23

<210> SEQ ID NO 1329
<211> LENGTH: 18
<212> TYPE: RNA
<213> ORGANISM: Homo sapiens

<400> SEQUENCE: 1329
gggugagggc aggugguu 18

<210> SEQ ID NO 1330
<211> LENGTH: 22
<212> TYPE: RNA
<213> ORGANISM: Homo sapiens

<400> SEQUENCE: 1330 uggggggagga aggacaggcc au 22

<210> SEQ ID NO 1331
<211> LENGTH: 22
<212> TYPE: RNA
<213> ORGANISM: Homo sapiens

<400> SEQUENCE: 1331
gggaccaucc ugccugcugu gg 22

<210> SEQ ID NO 1332
<211> LENGTH: 24
<212> TYPE: RNA
<213> ORGANISM: Homo sapiens

<400> SEQUENCE: 1332 ugggggaca ggaugagagg cugu 24

<210> SEQ ID NO 1333
<211> LENGTH: 24
<212> TYPE: RNA
<213> ORGANISM: Homo sapiens

<400> SEQUENCE: 1333
agccuggaag cuggagccug cagu 24

<210> SEQ ID NO 1334
<211> LENGTH: 22
<212> TYPE: RNA
<213> ORGANISM: Homo sapiens

<400> SEQUENCE: 1334
agugggaggc cagggcacgg ca 22

<210> SEQ ID NO 1335
<211> LENGTH: 21
<212> TYPE: RNA
<213> ORGANISM: Homo sapiens

<400> SEQUENCE: 1335
augccucccc cggccccgca g 21

<210> SEQ ID NO 1336
<211> LENGTH: 21
<212> TYPE: RNA
<213> ORGANISM: Homo sapiens

<400> SEQUENCE: 1336
agguggguau ggaggagccc u 21

<210> SEQ ID NO 1337
<211> LENGTH: 17
<212> TYPE: RNA
<213> ORGANISM: Homo sapiens

<400> SEQUENCE: 1337
ccccggggag cccggcg 17

<210> SEQ ID NO 1338
<211> LENGTH: 23
<212> TYPE: RNA
<213> ORGANISM: Homo sapiens

<400> SEQUENCE: 1338
agggacuuuu gggggcagau gug 23

<210> SEQ ID NO 1339
<211> LENGTH: 20
<212> TYPE: RNA
<213> ORGANISM: Homo sapiens

<400> SEQUENCE: 1339
gugucugggc ggacagcugc 20

<210> SEQ ID NO 1340
<211> LENGTH: 21
<212> TYPE: RNA
<213> ORGANISM: Homo sapiens

<400> SEQUENCE: 1340
gugggcgggg gcaggugugu g 21

<210> SEQ ID NO 1341
<211> LENGTH: 18
<212> TYPE: RNA
<213> ORGANISM: Homo sapiens

<400> SEQUENCE: 1341
aggcuggagu gagcggag 18

<210> SEQ ID NO 1342
<211> LENGTH: 22
<212> TYPE: RNA
<213> ORGANISM: Homo sapiens

<400> SEQUENCE: 1342
gaggguuggg uggaggcucu cc 22

<210> SEQ ID NO 1343
<211> LENGTH: 21
<212> TYPE: RNA
<213> ORGANISM: Homo sapiens

<400> SEQUENCE: 1343
cgggggcggg gccgaagcgc g 21

<210> SEQ ID NO 1344
<211> LENGTH: 18
<212> TYPE: RNA
<213> ORGANISM: Homo sapiens

<400> SEQUENCE: 1344
gggugcgggc cggcgggg 18

<210> SEQ ID NO 1345
<211> LENGTH: 24
<212> TYPE: RNA
<213> ORGANISM: Homo sapiens

<400> SEQUENCE: 1345
guaggggcgu cccgggcgcg cggg 24

<210> SEQ ID NO 1346
<211> LENGTH: 23
<212> TYPE: RNA
<213> ORGANISM: Homo sapiens

<400> SEQUENCE: 1346
gagggcagcg ugggugugge gga 23

<210> SEQ ID NO 1347
<211> LENGTH: 23
<212> TYPE: RNA
<213> ORGANISM: Homo sapiens

<400> SEQUENCE: 1347
ugaguggggc ucccgggacg gcg 23

<210> SEQ ID NO 1348
<211> LENGTH: 23
<212> TYPE: RNA
<213> ORGANISM: Homo sapiens

<400> SEQUENCE: 1348
cugggggacg cgugagcgcg agc 23

<210> SEQ ID NO 1349
<211> LENGTH: 22
<212> TYPE: RNA
<213> ORGANISM: Homo sapiens

<400> SEQUENCE: 1349
gugagccagu ggaauggaga gg 22

<210> SEQ ID NO 1350
<211> LENGTH: 21
<212> TYPE: RNA
<213> ORGANISM: Homo sapiens

<400> SEQUENCE: 1350
ucuguggagu ggggugccug u 21

<210> SEQ ID NO 1351
<211> LENGTH: 22
<212> TYPE: RNA
<213> ORGANISM: Homo sapiens

<400> SEQUENCE: 1351
cugguacagg ccugggggac ag 22

<210> SEQ ID NO 1352
<211> LENGTH: 23
<212> TYPE: RNA
<213> ORGANISM: Homo sapiens

<400> SEQUENCE: 1352
ugaggggcag agagcgagac uuu 23

<210> SEQ ID NO 1353
<211> LENGTH: 19
<212> TYPE: RNA
<213> ORGANISM: Homo sapiens

<400> SEQUENCE: 1353
gagccaguug gacaggagc 19

<210> SEQ ID NO 1354
<211> LENGTH: 23
<212> TYPE: RNA
<213> ORGANISM: Homo sapiens

<400> SEQUENCE: 1354
aggaagcccu ggaggggcug gag 23

<210> SEQ ID NO 1355
<211> LENGTH: 24
<212> TYPE: RNA
<213> ORGANISM: Homo sapiens

<400> SEQUENCE: 1355
uggggagcug aggcucuggg ggug 24

<210> SEQ ID NO 1356
<211> LENGTH: 18
<212> TYPE: RNA
<213> ORGANISM: Homo sapiens

<400> SEQUENCE: 1356
agcaggugcg gggcggcg 18

<210> SEQ ID NO 1357
<211> LENGTH: 67
<212> TYPE: RNA
<213> ORGANISM: Homo sapiens

<400> SEQUENCE: 1357
uacaggccgg ggcuuugggu gagggacccc cggagucugu cacggucuca ccccaacucu 60
gccccag 67

<210> SEQ ID NO 1358
<211> LENGTH: 73
<212> TYPE: RNA
<213> ORGANISM: Homo sapiens

<400> SEQUENCE: 1358
guucaagugg gaggacagga ggcaggugug guuggaggaa gcagccugaa ccugccuccc 60
ugacauucca cag 73

<210> SEQ ID NO 1359
<211> LENGTH: 72
<212> TYPE: RNA
<213> ORGANISM: Homo sapiens

<400> SEQUENCE: 1359
gagucugagg gacccaggac aggagaaggc cuauggugau uugcauucuu ccugcccugg 60
cuccauccuc ag 72

<210> SEQ ID NO 1360
<211> LENGTH: 60
<212> TYPE: RNA
<213> ORGANISM: Homo sapiens

<400> SEQUENCE: 1360
ugugaaugac ccccuuccag agccaaaauc accagggaug gaggaggggu cuuggguacu 60

<210> SEQ ID NO 1361
<211> LENGTH: 89
<212> TYPE: RNA
<213> ORGANISM: Homo sapiens

<400> SEQUENCE: 1361
gggccugguc auggucaagc cagguuccau caagccccac cagaaggugg aggcccaggu 60
gagggcucca ggugacggug ggcaggguu 89

<210> SEQ ID NO 1362
<211> LENGTH: 63
<212> TYPE: RNA
<213> ORGANISM: Homo sapiens

<400> SEQUENCE: 1362
acccuagggu ggggcuggag guggggcuga ggcugagucu uccuccccuu ccucccugcc 60
cag 63

<210> SEQ ID NO 1363
<211> LENGTH: 96
<212> TYPE: RNA
<213> ORGANISM: Homo sapiens

<400> SEQUENCE: 1363
cucgggaggg gcgggagggg gguccccggu gcucggaucu cgagggugcu uauuguucgg 60
uccgagccug ggucucccuc uuccccccaa cccccc 96

<210> SEQ ID NO 1364
<211> LENGTH: 65
<212> TYPE: RNA
<213> ORGANISM: Homo sapiens

<400> SEQUENCE: 1364
gggugcucgg ggcaggcggc ugggagcggc ccucacauug auggcuccug ccaccuccuc 60
cgcag 65

<210> SEQ ID NO 1365
<211> LENGTH: 65
<212> TYPE: RNA
<213> ORGANISM: Homo sapiens

<400> SEQUENCE: 1365
gagaaugggg ggacagaugg agaggacaca ggcuggcacu gagguccccu ccacuuuccu 60
ccuag 65

<210> SEQ ID NO 1366
<211> LENGTH: 81
<212> TYPE: RNA
<213> ORGANISM: Homo sapiens

<400> SEQUENCE: 1366
uagaggcagu uucaacagau guguagacuu uugauaugag aaauugguuu caaaaucagg 60
agucggggcu uuacugcuuu u 81

<210> SEQ ID NO 1367
<211> LENGTH: 62
<212> TYPE: RNA
<213> ORGANISM: Homo sapiens

<400> SEQUENCE: 1367 gagggguggug gaggaagagg gcagcuccca ugacugccug accgccuucu cuccuccccc 60
ag 62

<210> SEQ ID NO 1368
<211> LENGTH: 62
<212> TYPE: RNA
<213> ORGANISM: Homo sapiens

<400> SEQUENCE: 1368
uggccuaggg ggcggcuugu ggaguguaug ggcugagccu ugcucugcuc ccccgccccc 60
ag 62

<210> SEQ ID NO 1369
<211> LENGTH: 58
<212> TYPE: RNA
<213> ORGANISM: Homo sapiens

<400> SEQUENCE: 1369
agggccagag gagccuggag uggucggguc gacugaaccc agguucccuc uggccgca 58

<210> SEQ ID NO 1370
<211> LENGTH: 56
<212> TYPE: RNA
<213> ORGANISM: Homo sapiens

<400> SEQUENCE: 1370
gaccgagugg ggugagggca ggugguucuu cccgaagcag cucucgccuc uucguc 56

<210> SEQ ID NO 1371
<211> LENGTH: 72
<212> TYPE: RNA
<213> ORGANISM: Homo sapiens

<400> SEQUENCE: 1371
cugggggagg aaggacaggc caucugcuau ucguccacca accugacuug auccucucuu 60
cccuccuccc ag 72

<210> SEQ ID NO 1372
<211> LENGTH: 83
<212> TYPE: RNA
<213> ORGANISM: Homo sapiens

<400> SEQUENCE: 1372
acggcaucuu ugcacucagc aggcaggcug gugcagcccg uggugggga ccauccugcc 60 ugcugugggg uaaggacggc ugu 83

<210> SEQ ID NO 1373
<211> LENGTH: 68
<212> TYPE: RNA
<213> ORGANISM: Homo sapiens

<400> SEQUENCE: 1373
aggguugggg ggacaggaug agaggcuguc uucauucccu cuugaccacc ccucguuucu 60
ucccccag 68

<210> SEQ ID NO 1374
<211> LENGTH: 97
<212> TYPE: RNA
<213> ORGANISM: Homo sapiens

<400> SEQUENCE: 1374
ggugggagga uugcuugagc cuggaagcug gagccugcag ugaacuauca uugugccacu 60
guacuccagc cuaggcaaca aaaugaaauc cugucua 97

<210> SEQ ID NO 1375
<211> LENGTH: 63
<212> TYPE: RNA
<213> ORGANISM: Homo sapiens

<400> SEQUENCE: 1375
cugagccugg aagcuggagc cugcagugag cuaugaucau gucccuguac ucuagccugg 60
gca 63

<210> SEQ ID NO 1376
<211> LENGTH: 82
<212> TYPE: RNA
<213> ORGANISM: Homo sapiens

<400> SEQUENCE: 1376
gugagyggga ggccagggca cggcaggggg agcugcaggg cuaugggagg ggccccagcg 60
ucugagcccu guccucccgc ag 82

<210> SEQ ID NO 1377
<211> LENGTH: 82
<212> TYPE: RNA
<213> ORGANISM: Homo sapiens

<400> SEQUENCE: 1377
gugaguggga ggccagggca cggcaggggg agcugcaggg cuaugggagg ggccccagcg 60
ucugagcccu guccucccgc ag 82

<210> SEQ ID NO 1378
<211> LENGTH: 63
<212> TYPE: RNA
<213> ORGANISM: Homo sapiens

<400> SEQUENCE: 1378
ggcuccgcag ggcccuggcg caggcaucca gacagcgggc gaaugccucc cccggccccg 60
cag 63

<210> SEQ ID NO 1379
<211> LENGTH: 73
<212> TYPE: RNA
<213> ORGANISM: Homo sapiens

<400> SEQUENCE: 1379
aggccaggug gguauggagg agcccucaua uggcaguugg cgagggccca gugagccccu 60
cucugcucuc cag 73

<210> SEQ ID NO 1380
<211> LENGTH: 51
<212> TYPE: RNA
<213> ORGANISM: Homo sapiens

<400> SEQUENCE: 1380
acagaccccg gggagcccgg cggugaagcu ccugguaucc ugggugucug a 51

<210> SEQ ID NO 1381

<211> LENGTH: 87
<212> TYPE: RNA
<213> ORGANISM: Homo sapiens

<400> SEQUENCE: 1381
accgcaggga aaaugaggga cuuuuggggg cagauguguu uccauuccac uaucauaaug 60
ccccuaaaaa uccuuauugc ucuugca 87

<210> SEQ ID NO 1382
<211> LENGTH: 92
<212> TYPE: RNA
<213> ORGANISM: Homo sapiens

<400> SEQUENCE: 1382
gucagugucu gggcggacag cugcaggaaa gggaagacca aggcuugcug ucuguccagu 60
cugccacccu acccugucug uucuugccac ag 92

<210> SEQ ID NO 1383
<211> LENGTH: 73
<212> TYPE: RNA
<213> ORGANISM: Homo sapiens

<400> SEQUENCE: 1383
gugggcgggg gcaggugugu gguggguggu ggccugcggu gagcagggcc cucacaccug 60
ccucgccccc cag 73

<210> SEQ ID NO 1384
<211> LENGTH: 49
<212> TYPE: RNA
<213> ORGANISM: Homo sapiens

<400> SEQUENCE: 1384
gugaggcugg agugagcgga gaucguacca cugcacucca accugguga 49

<210> SEQ ID NO 1385
<211> LENGTH: 80
<212> TYPE: RNA
<213> ORGANISM: Homo sapiens

<400> SEQUENCE: 1385
aggacccuuc cagagggccc ccccucaauc cuguugugcc uaauucagag gguugggugg 60
aggcucuccu gaagggcucu 80

<210> SEQ ID NO 1386
<211> LENGTH: 102
<212> TYPE: RNA
<213> ORGANISM: Homo sapiens

<400> SEQUENCE: 1386
gugggagggc ccaggcgcgg gcaggggugg ggguggcaga gcgcuguccc gggggcgggg 60
ccgaagcgcg gcgaccguaa cuccuucugc uccguccccc ag 102

<210> SEQ ID NO 1387
<211> LENGTH: 54
<212> TYPE: RNA
<213> ORGANISM: Homo sapiens

<400> SEQUENCE: 1387
acgcgggugc gggccggcgg gguagaagcc acccggcccg gcccggcccg gcga 54

<210> SEQ ID NO 1388
<211> LENGTH: 98
<212> TYPE: RNA
<213> ORGANISM: Homo sapiens

<400> SEQUENCE: 1388
cgagguaggg gcgucccggg cgcgcgggcg ggucccaggc ugggccccuc ggaggccggg 60
ugcucacugc cccgucccgg cgcccguguc ucccuccag 98

<210> SEQ ID NO 1389
<211> LENGTH: 61
<212> TYPE: RNA
<213> ORGANISM: Homo sapiens

<400> SEQUENCE: 1389
gagggcagcg ugggugugc ggaggcaggc gugaccguuu gccgcccucu cgcugcucua 60
g 61

<210> SEQ ID NO 1390
<211> LENGTH: 62
<212> TYPE: RNA
<213> ORGANISM: Homo sapiens

<400> SEQUENCE: 1390
gugagugggg cucccgggac ggcgcccgcc cuggcccugg cccggcgacg ucucacgguc 60
cc 62

<210> SEQ ID NO 1391
<211> LENGTH: 79
<212> TYPE: RNA
<213> ORGANISM: Homo sapiens

<400> SEQUENCE: 1391
cucgaggugc ugggggacgc gugagcgcga gccgcuuccu cacggcucgg ccgcggcgcg 60 uagccccgc cacaucggg 79

<210> SEQ ID NO 1392
<211> LENGTH: 92
<212> TYPE: RNA
<213> ORGANISM: Homo sapiens

<400> SEQUENCE: 1392
gugagccagu ggaauggaga ggcugugggc agggggagau gugaaggaaa gaacuaggac 60
ccauucaucc acugcauucc ugcuuggccc ag 92

<210> SEQ ID NO 1393
<211> LENGTH: 61
<212> TYPE: RNA
<213> ORGANISM: Homo sapiens

<400> SEQUENCE: 1393
uccgcucugu ggaguggggu gccuguccc ugccacuggg ugacccaccc cucuccacca 60
g 61

<210> SEQ ID NO 1394
<211> LENGTH: 84
<212> TYPE: RNA
<213> ORGANISM: Homo sapiens

<400> SEQUENCE: 1394
cuccccaugg cccugucucc caacccuugu accagugcug ggcucagacc cugguacagg 60
ccugggggac agggaccugg ggac 84

<210> SEQ ID NO 1395
<211> LENGTH: 94
<212> TYPE: RNA
<213> ORGANISM: Homo sapiens

<400> SEQUENCE: 1395
auaaaggaag uuaggcugag gggcagagag cgagacuuuu cuauuuucca aaagcucggu 60
cugaggcccc ucagucuugc uuccuaaccc gcgc 94

<210> SEQ ID NO 1396
<211> LENGTH: 94
<212> TYPE: RNA
<213> ORGANISM: Homo sapiens

<400> SEQUENCE: 1396
aauucagccc ugccacuggc uuaugucaug accuugggcu acucaggcug ucugcacaau 60
gagccaguug gacaggagca gugccacuca acuc 94

<210> SEQ ID NO 1397
<211> LENGTH: 118
<212> TYPE: RNA
<213> ORGANISM: Homo sapiens

<400> SEQUENCE: 1397
gcaggugaac uggcaggcca ggaagaggag gaagcccugg aggggcugga ggugauggau 60
guuuuccucc gguucucagg gcuccaccuc uuucgggccg uagagccagg gcuggugc 118

<210> SEQ ID NO 1398
<211> LENGTH: 82
<212> TYPE: RNA
<213> ORGANISM: Homo sapiens

<400> SEQUENCE: 1398
ugugggcagg gcccugggga gcugaggcuc ugggggu ggc cggggcugac ccugggccuc 60
ugcuccccag ugucugaccg cg 82

<210> SEQ ID NO 1399
<211> LENGTH: 105
<212> TYPE: RNA
<213> ORGANISM: Homo sapiens

<400> SEQUENCE: 1399
gcgggcggcg gcggcggcag cagcagcagg ugcggggcgg cggccgcgcu ggccgcucga 60
cuccgcagcu gcucguucug cuucuccagc uugcgcacca gcucc 105

<210> SEQ ID NO 1400
<211> LENGTH: 24
<212> TYPE: RNA
<213> ORGANISM: Homo sapiens

<400> SEQUENCE: 1400
ugagggcucc aggugacggu gggc 24

<210> SEQ ID NO 1401
<211> LENGTH: 23
<212> TYPE: RNA
<213> ORGANISM: Homo sapiens

<400> SEQUENCE: 1401
gggggucccc ggugcucgga ucu 23

<210> SEQ ID NO 1402
<211> LENGTH: 16
<212> TYPE: RNA
<213> ORGANISM: Homo sapiens

<400> SEQUENCE: 1402
ucgggagggg cgggag 16

<210> SEQ ID NO 1403
<211> LENGTH: 27
<212> TYPE: RNA
<213> ORGANISM: Homo sapiens

<400> SEQUENCE: 1403
agggccagag gagccuggag uggucgg 27

<210> SEQ ID NO 1404
<211> LENGTH: 23
<212> TYPE: RNA
<213> ORGANISM: Homo sapiens

<400> SEQUENCE: 1404
agggccagag gagccuggag ugg 23

<210> SEQ ID NO 1405
<211> LENGTH: 15
<212> TYPE: RNA
<213> ORGANISM: Homo sapiens

<400> SEQUENCE: 1405
gggugagggc aggug 15

<210> SEQ ID NO 1406
<211> LENGTH: 27
<212> TYPE: RNA
<213> ORGANISM: Homo sapiens

<400> SEQUENCE: 1406
agccuggaag cuggagccug cagugaa 27

<210> SEQ ID NO 1407
<211> LENGTH: 15
<212> TYPE: RNA
<213> ORGANISM: Homo sapiens

<400> SEQUENCE: 1407
ggugggagga uugcu 15

<210> SEQ ID NO 1408
<211> LENGTH: 19
<212> TYPE: RNA
<213> ORGANISM: Homo sapiens

<400> SEQUENCE: 1408
agugggaggc cagggcacg 19

<210> SEQ ID NO 1409
<211> LENGTH: 15
<212> TYPE: RNA

<213> ORGANISM: Homo sapiens

<400> SEQUENCE: 1409 aggggagcu gcagg 15

<210> SEQ ID NO 1410
<211> LENGTH: 20
<212> TYPE: RNA
<213> ORGANISM: Homo sapiens

<400> SEQUENCE: 1410
ccccggggag cccggcggug 20

<210> SEQ ID NO 1411
<211> LENGTH: 15
<212> TYPE: RNA
<213> ORGANISM: Homo sapiens

<400> SEQUENCE: 1411
accccgggga gcccg 15

<210> SEQ ID NO 1412
<211> LENGTH: 27
<212> TYPE: RNA
<213> ORGANISM: Homo sapiens

<400> SEQUENCE: 1412
ugagggacuu uugggggcag auguguu 27

<210> SEQ ID NO 1413
<211> LENGTH: 17
<212> TYPE: RNA
<213> ORGANISM: Homo sapiens

<400> SEQUENCE: 1413
ggacuuuugg gggcaga 17

<210> SEQ ID NO 1414
<211> LENGTH: 22
<212> TYPE: RNA
<213> ORGANISM: Homo sapiens

<400> SEQUENCE: 1414
gugggcgggg gcaggugugu gg 22

<210> SEQ ID NO 1415
<211> LENGTH: 15
<212> TYPE: RNA
<213> ORGANISM: Homo sapiens

<400> SEQUENCE: 1415
cgggggcagg ugugu 15

<210> SEQ ID NO 1416
<211> LENGTH: 19
<212> TYPE: RNA
<213> ORGANISM: Homo sapiens

<400> SEQUENCE: 1416
gaggcuggag ugagcggag 19

<210> SEQ ID NO 1417
<211> LENGTH: 15

<212> TYPE: RNA
<213> ORGANISM: Homo sapiens

<400> SEQUENCE: 1417
aggcuggagu gagcg 15

<210> SEQ ID NO 1418
<211> LENGTH: 15
<212> TYPE: RNA
<213> ORGANISM: Homo sapiens

<400> SEQUENCE: 1418
gaggguuggg uggag 15

<210> SEQ ID NO 1419
<211> LENGTH: 15
<212> TYPE: RNA
<213> ORGANISM: Homo sapiens

<400> SEQUENCE: 1419
uggcagagcg cuguc 15

<210> SEQ ID NO 1420
<211> LENGTH: 19
<212> TYPE: RNA
<213> ORGANISM: Homo sapiens

<400> SEQUENCE: 1420
gggugcgggc cggcggggu 19

<210> SEQ ID NO 1421
<211> LENGTH: 15
<212> TYPE: RNA
<213> ORGANISM: Homo sapiens

<400> SEQUENCE: 1421
ugcgggccgg cgggg 15

<210> SEQ ID NO 1422
<211> LENGTH: 21
<212> TYPE: RNA
<213> ORGANISM: Homo sapiens

<400> SEQUENCE: 1422
gagggcagcg ugggguggc g 21

<210> SEQ ID NO 1423
<211> LENGTH: 20
<212> TYPE: RNA
<213> ORGANISM: Homo sapiens

<400> SEQUENCE: 1423
ugaguggggc ucccgggacg 20

<210> SEQ ID NO 1424
<211> LENGTH: 21
<212> TYPE: RNA
<213> ORGANISM: Homo sapiens

<400> SEQUENCE: 1424
cugggggacg cgugagcgcg a 21

<210> SEQ ID NO 1425

<211> LENGTH: 24
<212> TYPE: RNA
<213> ORGANISM: Homo sapiens

<400> SEQUENCE: 1425
cugguacagg ccugggggac aggg 24

<210> SEQ ID NO 1426
<211> LENGTH: 18
<212> TYPE: RNA
<213> ORGANISM: Homo sapiens

<400> SEQUENCE: 1426
cugguacagg ccuggggg 18

<210> SEQ ID NO 1427
<211> LENGTH: 30
<212> TYPE: RNA
<213> ORGANISM: Homo sapiens

<400> SEQUENCE: 1427
ugaggggcag agagcgagac uuuucuauuu 30

<210> SEQ ID NO 1428
<211> LENGTH: 15
<212> TYPE: RNA
<213> ORGANISM: Homo sapiens

<400> SEQUENCE: 1428
ugaggggcag agagc 15

<210> SEQ ID NO 1429
<211> LENGTH: 25
<212> TYPE: RNA
<213> ORGANISM: Homo sapiens

<400> SEQUENCE: 1429
aggaagcccu ggaggggcug gaggu 25

<210> SEQ ID NO 1430
<211> LENGTH: 15
<212> TYPE: RNA
<213> ORGANISM: Homo sapiens

<400> SEQUENCE: 1430
aggaagagga ggaag 15

<210> SEQ ID NO 1431
<211> LENGTH: 24
<212> TYPE: RNA
<213> ORGANISM: Homo sapiens

<400> SEQUENCE: 1431
uggggagcug aggcucuggg ggug 24

<210> SEQ ID NO 1432
<211> LENGTH: 15
<212> TYPE: RNA
<213> ORGANISM: Homo sapiens

<400> SEQUENCE: 1432
ggcccugggg agcug 15

<210> SEQ ID NO 1433
<211> LENGTH: 18
<212> TYPE: RNA
<213> ORGANISM: Homo sapiens

<400> SEQUENCE: 1433
gcggcggcgg cggcagca 18

<210> SEQ ID NO 1434
<211> LENGTH: 15
<212> TYPE: RNA
<213> ORGANISM: Homo sapiens

<400> SEQUENCE: 1434
gcgggcggcg gcggc 15

<210> SEQ ID NO 1435
<211> LENGTH: 23
<212> TYPE: RNA
<213> ORGANISM: Homo sapiens

<400> SEQUENCE: 1435
uucucgagga aagaagcacu uuc 23

<210> SEQ ID NO 1436
<211> LENGTH: 23
<212> TYPE: RNA
<213> ORGANISM: Homo sapiens

<400> SEQUENCE: 1436
cugggaucuc cggggucuug guu 23

<210> SEQ ID NO 1437
<211> LENGTH: 24
<212> TYPE: RNA
<213> ORGANISM: Homo sapiens

<400> SEQUENCE: 1437
ccugcugguc aggaguggau acug 24

<210> SEQ ID NO 1438
<211> LENGTH: 23
<212> TYPE: RNA
<213> ORGANISM: Homo sapiens

<400> SEQUENCE: 1438
agggcauagg agaggguuga uau 23

<210> SEQ ID NO 1439
<211> LENGTH: 21
<212> TYPE: RNA
<213> ORGANISM: Homo sapiens

<400> SEQUENCE: 1439
acaggagugg gggugggaca u 21

<210> SEQ ID NO 1440
<211> LENGTH: 20
<212> TYPE: RNA
<213> ORGANISM: Homo sapiens

<400> SEQUENCE: 1440
uaacggccgc gguacccuaa 20

<210> SEQ ID NO 1441
<211> LENGTH: 24
<212> TYPE: RNA
<213> ORGANISM: Homo sapiens

<400> SEQUENCE: 1441
uagguagagu gugaggagga gguc 24

<210> SEQ ID NO 1442
<211> LENGTH: 22
<212> TYPE: RNA
<213> ORGANISM: Homo sapiens

<400> SEQUENCE: 1442
cucuagaggg aagcgcuuuc ug 22

<210> SEQ ID NO 1443
<211> LENGTH: 22
<212> TYPE: RNA
<213> ORGANISM: Homo sapiens

<400> SEQUENCE: 1443
gaaaucaagc gugggugaga cc 22

<210> SEQ ID NO 1444
<211> LENGTH: 22
<212> TYPE: RNA
<213> ORGANISM: Homo sapiens

<400> SEQUENCE: 1444
cuccuggggc ccgcacucuc gc 22

<210> SEQ ID NO 1445
<211> LENGTH: 17
<212> TYPE: RNA
<213> ORGANISM: Homo sapiens

<400> SEQUENCE: 1445
accccacucc ugguacc 17

<210> SEQ ID NO 1446
<211> LENGTH: 19
<212> TYPE: RNA
<213> ORGANISM: Homo sapiens

<400> SEQUENCE: 1446
cggcgcgacc ggcccgggg 19

<210> SEQ ID NO 1447
<211> LENGTH: 22
<212> TYPE: RNA
<213> ORGANISM: Homo sapiens

<400> SEQUENCE: 1447
ccaccagguc uagcauuggg au 22

<210> SEQ ID NO 1448
<211> LENGTH: 20
<212> TYPE: RNA
<213> ORGANISM: Homo sapiens

<400> SEQUENCE: 1448
ggagguuggg aagggcagag 20

<210> SEQ ID NO 1449
<211> LENGTH: 22
<212> TYPE: RNA
<213> ORGANISM: Homo sapiens

<400> SEQUENCE: 1449
uguaaacauc cccgacugga ag 22

<210> SEQ ID NO 1450
<211> LENGTH: 22
<212> TYPE: RNA
<213> ORGANISM: Homo sapiens

<400> SEQUENCE: 1450
cugggaggug gauguuuacu uc 22

<210> SEQ ID NO 1451
<211> LENGTH: 22
<212> TYPE: RNA
<213> ORGANISM: Homo sapiens

<400> SEQUENCE: 1451
uauugcacuu gucccggccu gu 22

<210> SEQ ID NO 1452
<211> LENGTH: 22
<212> TYPE: RNA
<213> ORGANISM: Homo sapiens

<400> SEQUENCE: 1452
acucaaaaga uggcggcacu uu 22

<210> SEQ ID NO 1453
<211> LENGTH: 22
<212> TYPE: RNA
<213> ORGANISM: Homo sapiens

<400> SEQUENCE: 1453
uccuguacug agcugccccg ag 22

<210> SEQ ID NO 1454
<211> LENGTH: 90
<212> TYPE: RNA
<213> ORGANISM: Homo sapiens

<400> SEQUENCE: 1454
ucucaggcug ugaccuucuc gaggaaagaa gcacuuucug uugucugaaa gaaaagaaag 60
ugcuuccuuu cagaggguua cgguuugaga 90

<210> SEQ ID NO 1455
<211> LENGTH: 118
<212> TYPE: RNA
<213> ORGANISM: Homo sapiens

<400> SEQUENCE: 1455
gccuuggugc ugauuccugg gcucugaccu gagaccucug gguucugagc ugugauguug 60
cucucgagcu gggaucuccg gggucuuggu ucagggccgg ggccucuggg uuccaagc 118

<210> SEQ ID NO 1456
<211> LENGTH: 69
<212> TYPE: RNA

<213> ORGANISM: Homo sapiens

<400> SEQUENCE: 1456
ccauuccugc uggucaggag uggauacugg agcaauagau acaguuccac acugacacug 60
cagaagugg 69

<210> SEQ ID NO 1457
<211> LENGTH: 98
<212> TYPE: RNA
<213> ORGANISM: Homo sapiens

<400> SEQUENCE: 1457
gauguugaug cacgugacgg ggagggcaua ggagaggguu gauauaaaau gcaauuacag 60
ccucuuaugc uuuccaaagu gggggaugau ucaaugau 98

<210> SEQ ID NO 1458
<211> LENGTH: 81
<212> TYPE: RNA
<213> ORGANISM: Homo sapiens

<400> SEQUENCE: 1458
cauccuccuu acgucccacc ccccacuccu guuucuggug aaauauucaa acaggagugg 60
gggugggaca uaaggaggau a 81

<210> SEQ ID NO 1459
<211> LENGTH: 57
<212> TYPE: RNA
<213> ORGANISM: Homo sapiens

<400> SEQUENCE: 1459
agaggcaccg ccugcccagu gacaugcguu uaacggccgc gguacccuaa cugugca 57

<210> SEQ ID NO 1460
<211> LENGTH: 81
<212> TYPE: RNA
<213> ORGANISM: Homo sapiens

<400> SEQUENCE: 1460
guagguagag ugugaggagg aggucugagc ccaugugugg accuaggucu gcuguuaaac 60
ugacuaacuc ccacucuaca g 81

<210> SEQ ID NO 1461
<211> LENGTH: 87
<212> TYPE: RNA
<213> ORGANISM: Homo sapiens

<400> SEQUENCE: 1461
ucucagccug ugacccucua gagggaagcg cuuucuguug ucugaaagaa aagaaagugc 60
aucuuuuuag aggauuacag uuugaga 87

<210> SEQ ID NO 1462
<211> LENGTH: 96
<212> TYPE: RNA
<213> ORGANISM: Homo sapiens

<400> SEQUENCE: 1462
agaugugcuc uccuggccca ugaaaucaag cgugggugag accuggugca gaacgggaag 60
gcgacccaua cuugguuuca gaggcuguga gaauaa 96

<210> SEQ ID NO 1463
<211> LENGTH: 84
<212> TYPE: RNA
<213> ORGANISM: Homo sapiens

<400> SEQUENCE: 1463
gcuggcgucg gugcugggga gcggcccccg ggugggccuc ugcucuggcc ccuccugggg 60
cccgcacucu cgcucugggc ccgc 84

<210> SEQ ID NO 1464
<211> LENGTH: 93
<212> TYPE: RNA
<213> ORGANISM: Homo sapiens

<400> SEQUENCE: 1464
uacuuauggc accccacucc ugguaccaua gucauaaguu aggagauguu agagcuguga 60
guaccaugac uuaagugugg uggcuuaaac aug 93

<210> SEQ ID NO 1465
<211> LENGTH: 54
<212> TYPE: RNA
<213> ORGANISM: Homo sapiens

<400> SEQUENCE: 1465
ggacaagggc ggcgcgaccg gcccggggcu cuugggcggc cgcguuuccc cucc 54

<210> SEQ ID NO 1466
<211> LENGTH: 76
<212> TYPE: RNA
<213> ORGANISM: Homo sapiens

<400> SEQUENCE: 1466
ggucgcuuaa aucccaaugc uagacccggu ggcaaucaag gucuagccac caggucuagc 60
auugggauuu aagccc 76

<210> SEQ ID NO 1467
<211> LENGTH: 55
<212> TYPE: RNA
<213> ORGANISM: Homo sapiens

<400> SEQUENCE: 1467
aggagguugg gaagggcaga gaugagcaua aaguuuuugc cuuguuuuuc uuuuu 55

<210> SEQ ID NO 1468
<211> LENGTH: 70
<212> TYPE: RNA
<213> ORGANISM: Homo sapiens

<400> SEQUENCE: 1468
guuguuguaa acauccccga cuggaagcug uaagacacag cuaagcuuuc agucagaugu 60
uugcugcuac 70

<210> SEQ ID NO 1469
<211> LENGTH: 88
<212> TYPE: RNA
<213> ORGANISM: Homo sapiens

<400> SEQUENCE: 1469
accaaguuuc aguucaugua aacauccuac acucagcugu aauacaugga uuggcuggga 60
gguggauguu uacuucagcu gacuugga 88

<210> SEQ ID NO 1470
<211> LENGTH: 78
<212> TYPE: RNA
<213> ORGANISM: Homo sapiens

<400> SEQUENCE: 1470
cuuucuacac agguugggau cgguugcaau gcuguguuuc uguaugguau ugcacuuguc 60
ccggccuguu gaguuugg 78

<210> SEQ ID NO 1471
<211> LENGTH: 66
<212> TYPE: RNA
<213> ORGANISM: Homo sapiens

<400> SEQUENCE: 1471
gguaacacuc aaaagauggc ggcacuuuca ccagagagca gaaagugccc ccacaguuug 60
agugcc 66

<210> SEQ ID NO 1472
<211> LENGTH: 68
<212> TYPE: RNA
<213> ORGANISM: Homo sapiens

<400> SEQUENCE: 1472
gcauccugua cugagcugcc ccgaggcccu ucaugcugcc cagcucgggg cagcucagua 60
caggauac 68

<210> SEQ ID NO 1473
<211> LENGTH: 23
<212> TYPE: RNA
<213> ORGANISM: Homo sapiens

<400> SEQUENCE: 1473
uucucgagga aagaagcacu uuc 23

<210> SEQ ID NO 1474
<211> LENGTH: 16
<212> TYPE: RNA
<213> ORGANISM: Homo sapiens

<400> SEQUENCE: 1474
uucucgagga aagaag 16

<210> SEQ ID NO 1475
<211> LENGTH: 23
<212> TYPE: RNA
<213> ORGANISM: Homo sapiens

<400> SEQUENCE: 1475
cugggaucuc cggggucuug guu 23

<210> SEQ ID NO 1476
<211> LENGTH: 16
<212> TYPE: RNA
<213> ORGANISM: Homo sapiens

<400> SEQUENCE: 1476
ugggaucucc gggguc 16

<210> SEQ ID NO 1477
<211> LENGTH: 22

<212> TYPE: RNA
<213> ORGANISM: Homo sapiens

<400> SEQUENCE: 1477
ccugcugguc aggaguggau ac 22

<210> SEQ ID NO 1478
<211> LENGTH: 19
<212> TYPE: RNA
<213> ORGANISM: Homo sapiens

<400> SEQUENCE: 1478
ccugcugguc aggagugga 19

<210> SEQ ID NO 1479
<211> LENGTH: 22
<212> TYPE: RNA
<213> ORGANISM: Homo sapiens

<400> SEQUENCE: 1479
gagggcauag gagaggguug au 22

<210> SEQ ID NO 1480
<211> LENGTH: 16
<212> TYPE: RNA
<213> ORGANISM: Homo sapiens

<400> SEQUENCE: 1480
uacagccucu uaugcu 16

<210> SEQ ID NO 1481
<211> LENGTH: 23
<212> TYPE: RNA
<213> ORGANISM: Homo sapiens

<400> SEQUENCE: 1481
acaggagugg gggugggaca uaa 23

<210> SEQ ID NO 1482
<211> LENGTH: 20
<212> TYPE: RNA
<213> ORGANISM: Homo sapiens

<400> SEQUENCE: 1482
acaggagugg gggugggaca 20

<210> SEQ ID NO 1483
<211> LENGTH: 24
<212> TYPE: RNA
<213> ORGANISM: Homo sapiens

<400> SEQUENCE: 1483
guuuaacggc cgcgguaccc uaac 24

<210> SEQ ID NO 1484
<211> LENGTH: 16
<212> TYPE: RNA
<213> ORGANISM: Homo sapiens

<400> SEQUENCE: 1484
uuuaacggcc gcggua 16

<210> SEQ ID NO 1485

<211> LENGTH: 22
<212> TYPE: RNA
<213> ORGANISM: Homo sapiens

<400> SEQUENCE: 1485
uagguagagu gugaggagga gg 22

<210> SEQ ID NO 1486
<211> LENGTH: 17
<212> TYPE: RNA
<213> ORGANISM: Homo sapiens

<400> SEQUENCE: 1486
uagguagagu gugagga 17

<210> SEQ ID NO 1487
<211> LENGTH: 23
<212> TYPE: RNA
<213> ORGANISM: Homo sapiens

<400> SEQUENCE: 1487
cucuagaggg aagcgcuuuc ugu 23

<210> SEQ ID NO 1488
<211> LENGTH: 18
<212> TYPE: RNA
<213> ORGANISM: Homo sapiens

<400> SEQUENCE: 1488
cucuagaggg aagcgcuu 18

<210> SEQ ID NO 1489
<211> LENGTH: 23
<212> TYPE: RNA
<213> ORGANISM: Homo sapiens

<400> SEQUENCE: 1489
gaaaucaagc gugggugaga ccu 23

<210> SEQ ID NO 1490
<211> LENGTH: 20
<212> TYPE: RNA
<213> ORGANISM: Homo sapiens

<400> SEQUENCE: 1490
gaaaucaagc gugggugaga 20

<210> SEQ ID NO 1491
<211> LENGTH: 23
<212> TYPE: RNA
<213> ORGANISM: Homo sapiens

<400> SEQUENCE: 1491
cuccuggggc ccgcacucuc gcu 23

<210> SEQ ID NO 1492
<211> LENGTH: 18
<212> TYPE: RNA
<213> ORGANISM: Homo sapiens

<400> SEQUENCE: 1492
cuccuggggc ccgcacuc 18

<210> SEQ ID NO 1493
<211> LENGTH: 20
<212> TYPE: RNA
<213> ORGANISM: Homo sapiens

<400> SEQUENCE: 1493
caccccacuc cugguaccau 20

<210> SEQ ID NO 1494
<211> LENGTH: 15
<212> TYPE: RNA
<213> ORGANISM: Homo sapiens

<400> SEQUENCE: 1494
ccccacuccu gguac 15

<210> SEQ ID NO 1495
<211> LENGTH: 19
<212> TYPE: RNA
<213> ORGANISM: Homo sapiens

<400> SEQUENCE: 1495
accaggucua gcauuggga 19

<210> SEQ ID NO 1496
<211> LENGTH: 52
<212> TYPE: RNA
<213> ORGANISM: Homo sapiens

<400> SEQUENCE: 1496
uguaaacauc cccgacugga agcuguaaga cacagcuaag cuuucaguca ga 52

<210> SEQ ID NO 1497
<211> LENGTH: 16
<212> TYPE: RNA
<213> ORGANISM: Homo sapiens

<400> SEQUENCE: 1497
uguaaacauc cccgac 16

<210> SEQ ID NO 1498
<211> LENGTH: 29
<212> TYPE: RNA
<213> ORGANISM: Homo sapiens

<400> SEQUENCE: 1498
cauggauugg cugggaggug gauguuuac 29

<210> SEQ ID NO 1499
<211> LENGTH: 16
<212> TYPE: RNA
<213> ORGANISM: Homo sapiens

<400> SEQUENCE: 1499
ggagguggau guuuac 16

<210> SEQ ID NO 1500
<211> LENGTH: 28
<212> TYPE: RNA
<213> ORGANISM: Homo sapiens

<400> SEQUENCE: 1500
guaugguauu gcacuugucc cggccugu 28

```
<210> SEQ ID NO 1501
<211> LENGTH: 15
<212> TYPE: RNA
<213> ORGANISM: Homo sapiens

<400> SEQUENCE: 1501

uauugcacuu guccc                                                  15


<210> SEQ ID NO 1502
<211> LENGTH: 21
<212> TYPE: RNA
<213> ORGANISM: Homo sapiens

<400> SEQUENCE: 1502

cacucaaaag auggcggcac u                                           21


<210> SEQ ID NO 1503
<211> LENGTH: 20
<212> TYPE: RNA
<213> ORGANISM: Homo sapiens

<400> SEQUENCE: 1503

acacucaaaa gauggcggca                                             20


<210> SEQ ID NO 1504
<211> LENGTH: 25
<212> TYPE: RNA
<213> ORGANISM: Homo sapiens

<400> SEQUENCE: 1504

uccuguacug agcugccccg aggcc                                       25


<210> SEQ ID NO 1505
<211> LENGTH: 15
<212> TYPE: RNA
<213> ORGANISM: Homo sapiens

<400> SEQUENCE: 1505

uccuguacug agcug                                                  15
```